United States Patent
Bernal Anchuela et al.

(10) Patent No.: US 9,340,547 B2
(45) Date of Patent: May 17, 2016

(54) PYRROLOTRIAZINONE DERIVATIVES AS INHIBITORS P13K

(75) Inventors: Francisco Javier Bernal Anchuela, Barcelona (ES); Marta Carrascal Riera, Barcelona (ES); Juan Francisco Caturla Javaloyes, Barcelona (ES); Jordi Gracia Ferrer, Barcelona (ES); Victor Giulio Matassa, Barcelona (ES); Emma Terricabras Belart, Barcelona (ES); Joan Taltavull Moll, Barcelona (ES); Montserrat Erra Sola, Barcelona (ES)

(73) Assignee: Almirall, S.A., Barcelona (ES)

( * ) Notice: Subject to any disclaimer, the term of this patent is extended or adjusted under 35 U.S.C. 154(b) by 169 days.

(21) Appl. No.: 14/114,541

(22) PCT Filed: Apr. 26, 2012

(86) PCT No.: PCT/EP2012/057671
§ 371 (c)(1),
(2), (4) Date: Jan. 27, 2014

(87) PCT Pub. No.: WO2012/146666
PCT Pub. Date: Nov. 1, 2012

(65) Prior Publication Data
US 2014/0163033 A1   Jun. 12, 2014
US 2015/0099752 A9   Apr. 9, 2015

Related U.S. Application Data

(60) Provisional application No. 61/502,550, filed on Jun. 29, 2011.

(30) Foreign Application Priority Data

Apr. 29, 2011 (EP) .................................. 11382124

(51) Int. Cl.
C07D 487/04 (2006.01)
A61K 31/53 (2006.01)
A61P 11/06 (2006.01)
A61P 11/00 (2006.01)
C07D 473/34 (2006.01)
A61K 45/06 (2006.01)

(52) U.S. Cl.
CPC .............. *C07D 487/04* (2013.01); *A61K 31/53* (2013.01); *A61K 45/06* (2013.01); *C07D 473/34* (2013.01)

(58) Field of Classification Search
CPC ..... C07D 491/04; C07D 487/04; A61K 31/53
USPC .................. 544/183, 184; 514/243
See application file for complete search history.

(56) References Cited

U.S. PATENT DOCUMENTS

| | | |
|---|---|---|
| 2002/0161014 A1 | 10/2002 | Sadhu et al. |
| 2003/0232832 A1 | 12/2003 | Lombardo et al. |
| 2010/0029693 A1 | 2/2010 | Douangpanya et al. |

FOREIGN PATENT DOCUMENTS

| | | |
|---|---|---|
| WO | WO 01/81346 | 11/2001 |
| WO | WO 03/035075 | 5/2003 |
| WO | WO 03/099286 | 12/2003 |
| WO | WO 2007/023186 | 3/2007 |
| WO | WO 2010/111432 | 9/2010 |
| WO | WO 2011/058109 | 5/2011 |
| WO | WO 2012/146666 | 11/2012 |
| WO | WO 2014/015523 | 1/2014 |

OTHER PUBLICATIONS

Klempner et al.Cancer Discov. Dec. 2013;3(12):1345-54.*
Massacesi et al. Ann. N.Y. Acad. Sci. 1280 (2013) 19-23.*
Gautschi et al., Clin. Cancer Res., 14(6), 1639-1648, 2008.*
Mountzios et al., Cancer Treatments Reviews, 34, 175-182, 2008.*
Mass, R. D., Int. J. Radiation Oncology Bio. Phys.vol. 58(3): 932-940, 2004.*
Fabbro et al. Pharmacology & therapeutics 93, 79-98, 2002.*
Cecil Textbook of Medicine, edited by Bennet, J.C., and Plum F., 20th edition,vol. 1, 1004-101 O, 1996.*
Cohen et al., Current Opinion in Chemical Biology, 3,459-465, 1999.*
Freshney et al.,Culture of Animal Cells, A Manual of Basic Technique, Alan R. Liss, Inc., 1983, New York, p. 4.*
Dermer et al., Bio/Technology, 1994, 12:320.*
Golub et al., Science, 286, 531-537, 1999.*
Hulikal, V. Deuterium Labeled Compounds in Drug Discovery Process—Abstract, www.hwb.gov.in/htmldocs/nahwd2010/L15.pdf.*
Kyoung Soon Kim et al., "Synthesis and SAR of pyrrolotriazine-4-one based Eg5 inhibitors," Bioorganic & Medicinal Chemistry Letters, vol. 26, No. 15, pp. 3937-3942, 2006.

(Continued)

*Primary Examiner* — Venkataraman Balasubramanian
(74) *Attorney, Agent, or Firm* — Finnegan, Henderson, Farabow, Garrett & Dunner, L.L.P.

(57) ABSTRACT

New pyrrolotriazinone derivatives having the chemical structure of formula (I) are disclosed; as well as process for their preparation, pharmaceutical compositions comprising them and their use in therapy as inhibitors of Phosphoinositide 3-Kinases (PI3Ks).

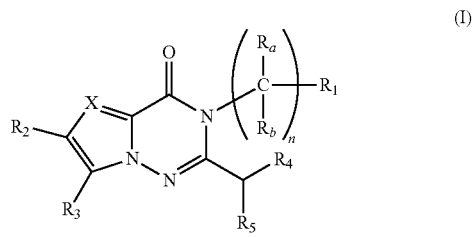

22 Claims, No Drawings

(56) References Cited

OTHER PUBLICATIONS

Helen McNeill et al., "When pathways collide: collaboration and connivance among signaling proteins in development," Nature Reviews Mollecular Cell Biology, Nature Publishing GB, vol. 11, No. 6, pp. 404-413, 2010.
International Search Report of International Application No. PCT/EP2012/057671, Jun. 8, 2012.
Liu, Xuesong et al., "Akt Inhibitor A-443654 Interferes with Mitotic Progression by Regulating Aurora A Kinase Expression" *Neoplasia* Aug. 2008 10(8) pp. 828-837 (2008).
Kumar, Amit at al., "New Functions for PI3K in the Control of Cell Division," *Cell Cycle*. vol. 6, issue 14, pp. 1696-1698 (2007).
Kok, Klaartje, et al., "Regulation of Phosphoinositide 3-kinase Expression in Health and Disease" *Trends Biochem Sci.*, vol. 34, No. 3, pp. 115-127 (2009).
Stearns, Ralph A. et al., "Evidence for a 1,3-Hydride Shift in the Microsomal Metabolism of the Heterocycle L-158,338, a NonPeptide Angiotensin II Receptor Antagonist", *Drug Metabolism and Disposition*, vol. 21, No. 4, pp. 670-676 (1993).
PCT International Search Report for International Application No. PCT/EP2013/071561, Nov. 22, 2013.
Pimlott SL., Radiotracer development in psychiatry, Nucl. Med. Commun. 26(3): 183-188, 2005 (PubMed Abstract provided).

* cited by examiner

PYRROLOTRIAZINONE DERIVATIVES AS INHIBITORS P13K

This application is a national stage filing under 35 U.S.C. §371 of International Application No. PCT/EP2012/057671 filed on 26 Apr. 2012, which claims priority of European Patent Application No. 11382124.3, filed on 29 Apr. 2011, and also claims priority of U.S. Provisional Patent Application No. 61/502,550, filed on 29 Jun. 2011. The contents of all three applications are incorporated herein by reference.

When cells are activated by extracellular stimuli, intracellular signalling cascades involving the regulation of second messengers are initiated that eventually produce a response of the cell to the stimuli. Phosphoinositide 3-Kinases (PI3Ks) are among the enzymes involved in early signalling events to a plethora of different types of stimuli. PI3Ks phosphorylate the 3-hydroxyl group of the inositol ring of phosphatidylinositol (PtdIns), PtdIns-4-phosphate (PtdIns4P), and PtdIns-4,5-bisphosphate (PtdIns(4,5)P2). The resulting 3-phosphoinositides mediate correct localization and subsequent activation of a number of downstream effector proteins that bind to the lipids via specific lipid binding sequences such as the pleckstrin homology (PH) domain (Vanhaesebroeck B, 2010, *Nat Rev Mol Cell Biol* 5:11381-6).

The PI3K family is divided into 3 different classes (PI3K class I, class II, and class III), depending on substrate preference and structural features.

The best characterized is the PI3K class I with the preferential substrate PtdIns-(4,5)P2. It englobes 4 different isoforms which originally were further subdivided into class IA (p110a, p110b, p110d), binding to a p85 type of regulatory subunit, and class IB (p110g) which is regulated by p101 and p87 subunits. Whereas p110a (PI3Ka or PI3Kα) and p110b (PI3 Kb or P13Kβ) isoforms are expressed ubiquitously, p110g (P13 Kg or PI3Kγ) and especially p110d (PI3 Kd or PI3Kδ) have a more restricted expression pattern and seem to play a major role in leukocytes (Kok K, *Trends Biochem Science* 34:115-127, 2009).

Both, PI3 Kd and PI3 Kg are involved in activation of immune cells by a large variety of different stimuli. Pharmacological inhibition or genetic deficiency in active p110d has been shown to inhibit T cell proliferation and cytokine production in response to different stimuli such as anti-CD3, anti-CD3/CD28, superantigen or antigen in vitro (Ji H, Blood 2007; Okkenhaug K, Science 2002; Garcon F, 2009; Soond D R, Blood 2010; Herman S E M, Blood Jun. 3, 2010; William O, Chemistry & Biology 17, 2010) and to suppress concanavalin A and anti-CD3 induced cytokine production as well as antigen-dependent tissue retention in vivo (Soond D R, Blood 2010; Jarmin S J, JCI 2008). In addition, B cell function is critically dependent on functional PI3 Kd activity as demonstrated by suppressed B cell proliferation and cytokine release in vitro in response to anti-IgM (Bilancio A, Blood 107, 2006), toll like receptor agonists such as LPS and oligodeoxynucleotides (Dil N, Mol Immunol 46, 2009) or impaired ability to stimulate antigen-specific T cells (Al-Alwan M, JI 2007) in the absence of functional p110d or pharmacological inhibition. In vivo, PI3 Kg deficient mice display partially suppressed antibody production upon immunization (Garcon F, 2009; Durand C A, J I 2009). Further studies have demonstrated an important role of PI3 Kd in inhibition of T cell apoptosis and in TH17 differentiation (Haylock-Jacobs S, J. Autoimmun 2010).

In addition, mast cell degranulation was reduced in cells from mice with inactivated PI3 Kd or by pharmacological inhibition of PI3 Kd (Ali K, Nature 431:1007-1011, 2004; Ali K, Journal of Immunology 180:2538-2544, 2008) and basophil activation via the FcE receptor is suppressed by pharmacological inhibition of PI3 Kd (Lannutti B J, Blood October 2010).

In terms of neutrophil function, PI3 Kd inhibition inhibits migration of mouse neutrophils to fMLP in an under-agarose migration assay by inhibiting cell polarization and directional movement (Sadhu C, JI 170, 2003) and mouse PI3 Kd deficient or inhibitor treated neutrophils show slightly (25%) reduced in vitro chemotaxis to LTB4, whereas in vivo accumulation in the lung in response to LPS was reduced by more than 80%, indicating an important role of PI3 Kd in endothelial cells for mediating PMN transendothelial migration (Puri K D, Blood 103, 2004). Furthermore, TNF induced neutrophil infiltration to an air pouch in mice and elastase release is partially inhibited by a PI3 Kd selective inhibitor (Sadhu C, Biochem Biophys Res Comm 308, 2003). In addition, TNF mediated priming of oxidative burst by human neutrophils depends on PI3 Kd activity (Condliffe A M, Blood 106, 2005).

In contrast to the dominant role of PI3 Kd in lymphocyte activation, PI3 Kg seems to affect primarily chemotaxis of different immune cells induced by various mediators and chemokines (Martin A L, JI 180, 2008; Thomas M S, J Leukoc Biol 84, 2008; Jarmin S J, JCI-2008; Matthew T, Immunology 126, 2008), as well as degranulation and oxidative burst of innate immuce cells induced by GPCR mediated stimuli such as fMLP, IL-8 or C5a (Condliffe A M, Blood 106, 2005; Yum H K, JI 167, 2001; Pinho V, JI 179, 2007

The above mentioned findings suggest that selective PI3 Kd or dual PI3 Kd/PI3 Kg pharmacological inhibition represents a promising approach for treating a variety of diseases such as respiratory diseases (asthma, chronic obstructive pulmonary disease (COPD), cystic fibrosis, idiopathic pulmonary fibrosis, sarcoidosis), allergic diseases (allergic rhinitis), inflammatory or autoimmune diseases (rheumatoid arthritis, multiple sclerosis, amyotrophic lateral sclerosis, Crohn's disease, ulcerative colitis, systemic lupus erythematosis, myastenia gravias, acute disseminated encephalomyelitis, idiopathic thromocytopenic purpura, Sjoegren's syndrome, autoimmune hemolytic anemia, type I diabetes, psoriasis, acrodermatitis, angiodermatitis, atopic dermatitis, contact dermatitis, eczema, acne, chronic urticaria, blistering diseases including but not limited to bullous pemphigoid, scleroderma, dermatomyositis, etc.), cardiovascular diseases; viral infection; metabolism/endocrine function disorders; neurological disorders and pain (such as pain associated with rheumatoid arthritis or osteoarthritis, back pain, general inflammatory pain, inflammatory neuropathic pain, trigeminal neuralgia or central pain) as well as in bone marrow and organ transplant rejection; myelo-dysplastic syndrome; myeloproliferative disorders (MPDs); cancer and hematologic malignancies, leukemia, lymphomas and solid tumors (such as pancreatic cancer; bladder cancer; colorectal cancer; breast cancer; prostate cancer; renal cancer; hepatocellular cancer; lung cancer; ovarian cancer; cervical cancer; gastric cancer; esophageal cancer; head and neck cancer; non-small cell lung cancer and small-cell lung cancer; melanoma; neuroendocrine cancers; central nervous system cancers; brain tumors; bone cancer; soft tissue sarcoma; chronic lymphocytic leukemia, B-cell acute lymphoblastic leukemia, T-cell acute lymphoblastic leukaemia, non-hodgkins lymphoma, B-cell lymphoma, acute myeloid leukaemia; cutaneous T cell lymphoma, premalignant and malignant skin conditions including but not limited to basal cell carcinoma (BCC), squamous cell carcinoma (SCC) or actinic keratosis (AK)).

There is substantial experimental evidence supporting this view. In rodent models of allergic lung inflammation, genetic or pharmacolocical inactivation of PI3 Kd or dual PI3 Kd/g dual inhibition reduces cell influx, mucus production, cytokine production and airway hyperreactivity (Nashed et al. 2007, *Eur J Immunol* 37:416; Lee et al. 2006, FASEB J 20:455 & Lee K S et al. 2006, J Allergy Clin Immunol 118:403; Doukas J, JPET 2009; 328:758; Par S J, ERJ 2010). Moreover, LPS induced lung neutrophil infiltration is blocked by PI3 Kd inhibition (Puri K D, Blood 2004; 103:3448) and inflammation in response to LPS or tobacco smoke exposure is suppressed by a dual PI3 Kd/g inhibitor (Doukas J, JPET 2009; 328:758). Moreover, PI3 Kd seems to be involved in the reduction of responsiveness to corticosteroid treatment associated with oxidative stress and chronic obstructive pulmonary disease (COPD). This notion is based on the findings that tobacco smoke induced inflammation remains responsive to treatment with budesonide, whereas wild type or PI3 Kg deficient mice develop resistance to corticosteroid treatment (Marwick J A, JRCCM 179:542-548, 2009). Similar results were obtained with a PI3 Kd selective inhibitor (To Y, AJRCCM 182:897-904, 2010). In addition, in vitro induction of corticosteroid resistance by oxidative stress is prevented by PI3 Kd inhibition (To Y, AJRCCM 2010). In COPD patients, lung macrophages display increased expression of PI3 Kd and phosphorylation of its downstream effector Akt and non-selective PI3K or PI3 Kd- selective inhibition restored the impaired inhibitory efficacy of dexamethasone in PBMC from COPD patients (To Y, AJRCCM 182:897-904, 2010; Marwick J A, JACI-125:1146-53, 2010).

Furthermore, PI3 Kd inhibition was effective in a model of contact hypersensitivity (Soond D R, Blood January 2010). In a model of experimental autoimmune encephalomyelitis, PI3 Kd deficiency or pharmacological inhibition of PI3 Kd attenuated T cell activation and function and reduced T cell numbers in the CNS, suggesting a therapeutic benefit of PI3 Kd inhibitor in multiple sclerosis and other Th17-mediated autoimmune diseases (Haylock-Jacobs S, J. Autoimmun 2010). In line with that, genetic deficiency or pharmacological inhibition of PI3 Kd diminished joint erosion in a mouse model of inflammatory arthritis (Randis T M, Eur J Immunol 38, 2008). Concerning metabolic diseases, PI3 Kd overexpression seems to contribute to excessive vascular contraction and PI3 Kd inhibition normalized vascular contractive responses in a mouse model of type I diabetes, suggesting a therapeutic potential of PI3 Kd blockade to treat vascular dysfunction in diabetic patients (Pinho J F, Br. J. Pharmacol 161, 2010).

There is also substantial experimental evidence supporting that genetic of pharmacolocical inactivation of PI3 Kd or dual PI3 Kd/g dual inhibition is effective in the treatment of cancers including but not restricted to leukemias, such as chronic lymphocytic leukemia, B-cell acute lymphoblastic leukemia, T-cell acute lymphoblastic leukaemia, non-hodgkins lymphoma, B-cell lymphoma, acute myeloid leukaemia, myelo-dysplastic syndrome or myelo-proliferative diseases. In this aspect, the selective PI3 Kd inhibitor CAL-101 demonstrated anti-proliferative properties on different tumor cells in vitro and efficacy in cancer patients with a dysregulated PI3 Kd activity, such as chronic lymphocytic leukemia (Hermann S E, Blood 116:2078-88, 2010; Lannutti B J, Blood October 2010).

Conditions in which targeting of the PI3K pathway or modulation of the PI3 Kinases, particularly PI3 Kd or PI3 Kd/g, are contemplated to be therapeutically useful for the treatment or prevention of diseases including: respiratory diseases (asthma, chronic obstructive pulmonary disease (COPD), cystic fibrosis, idiopathic pulmonary fibrosis, sarcoidosis), allergic diseases (allergic rhinitis), inflammatory or autoimmune-mediated diseases (rheumatoid arthritis, multiple sclerosis, amyotrophic lateral sclerosis, Crohn's disease, ulcerative colitis, systemic lupus erythematosis, myastenia gravias, acute disseminated encephalomyelitis, idiopathic thromocytopenic purpura, Sjoegren's syndrome, autoimmune hemolytic anemia, type I diabetes, psoriasis, acrodermatitis, angiodermatitis, atopic dermatitis, contact dermatitis, eczema, acne, chronic urticaria, scleroderma, dermatomyositis and blistering diseases including but not limited to bullous pemphigoid), cardiovascular diseases; viral infection; metabolism/endocrine function disorders; neurological disorders and pain (such as pain associated with rheumatoid arthritis or osteoarthritis, back pain, general inflammatory pain, inflammatory neuropathic pain, trigeminal neuralgia or central pain) as well as in bone marrow and organ transplant rejection; myelo-dysplastic syndrome; myeloproliferative disorders (MPDs); cancer and hematologic malignancies, leukemia, lymphomas and solid tumors (such as pancreatic cancer; bladder cancer; colorectal cancer; breast cancer; prostate cancer; renal cancer; hepatocellular cancer; lung cancer; ovarian cancer; cervical cancer; gastric cancer; esophageal cancer; head and neck cancer; non-small cell lung cancer and small-cell lung cancer; melanoma; neuroendocrine cancers; central nervous system cancers; brain tumors; bone cancer; soft tissue sarcoma; chronic lymphocytic leukemia, B-cell acute lymphoblastic leukemia, T-cell acute lymphoblastic leukaemia, non-hodgkins lymphoma, B-cell lymphoma, acute myeloid leukaemia; cutaneous T cell lymphoma, premalignant and malignant skin conditions including but not limited to basal cell carcinoma (BCC), squamous cell carcinoma (SCC) or actinic keratosis (AK)).

In view of the numerous conditions that are contemplated to benefit by treatment involving modulation of the PI3K pathway or modulation of the PI3 Kinases it is immediately apparent that new compounds that modulate PI3K pathways and use of these compounds should provide substantial therapeutic benefits to a wide variety of patients.

Provided herein are novel pyrrolotriazinone derivatives for use in the treatment of conditions in which targeting of the PI3K pathway or inhibition of PI3 Kinases can be therapeutically useful.

The compounds described in the present invention are potent PI3K inhibitors, particularly PI3 Kd or dual PK3 Kd/g inhibitors. This property makes them useful for the treatment or prevention of pathological conditions or diseases such as respiratory diseases (asthma, chronic obstructive pulmonary disease (COPD), cystic fibrosis, idiopathic pulmonary fibrosis, sarcoidosis), allergic diseases (allergic rhinitis), inflammatory or autoimmune diseases (rheumatoid arthritis, multiple sclerosis, amyotrophic lateral sclerosis, Crohn's disease, ulcerative colitis, systemic lupus erythematosis, myastenia gravias, acute disseminated encephalomyelitis, idiopathic thromocytopenic purpura, Sjoegren's syndrome, autoimmune hemolytic anemia, type I diabetes, psoriasis, acrodermatitis, angiodermatitis, atopic dermatitis, contact dermatitis, eczema, acne, chronic urticaria, scleroderma, cutaneous vasculitis, cutaneous lupus erythematosus, dermatomyositis and blistering diseases including but not limited to pemphigus vulgaris, bullous pemphigoid and epidermolysis bullosa), cardiovascular diseases; viral infection; metabolism/endocrine function disorders; neurological disorders and pain (such as pain associated with rheumatoid arthritis or osteoarthritis, back pain, general inflammatory pain, inflammatory neuropathic pain, trigeminal neuralgia or central pain) as well as in bone marrow and organ transplant rejection; myelodysplastic syndrome; myeloproliferative disorders (such as polycythemia vera, essential thrombocythemia or mielofibrosis); cancer and hematologic malignancies, leukemia, lymphomas and solid tumors (such as pancreatic cancer; bladder cancer; colorectal cancer; breast cancer; prostate cancer; renal cancer; hepatocellular cancer; lung cancer; ovarian cancer; cervical cancer; gastric cancer; esophageal cancer; head and neck cancer; non-small cell lung cancer and small-cell lung cancer; melanoma; neuroendocrine cancers; central nervous system cancers; brain tumors; bone cancer; soft tissue sarcoma; chronic lymphocytic leukemia, B-cell acute lymphoblastic leukemia, T-cell acute lymphoblastic leukaemia, non-hodgkins lymphoma, B-cell lymphoma, acute myeloid leukaemia; cutaneous T cell lymphoma, premalignant and malignant skin conditions including but not limited to basal cell carcinoma (BCC), squamous cell carcinoma (SCC) or actinic keratosis (AK)).

The compounds described in the present invention are particularly useful for the treatment or prevention of pathological conditions or diseases such as neoplastic diseases (e.g. leukemia, lymphomas, solid tumors); transplant rejection, bone marrow transplant applications (e.g., graft—versus-host disease); autoimmune diseases (e.g. rheumatoid arthritis, multiple sclerosis, amyotrophic lateral sclerosis, Crohn's disease, ulcerative colitis, systemic lupus erythematosis, autoimmune hemolytic anemia, type I diabetes, cutaneous vasculitis, cutaneous lupus erythematosus, dermatomyositis and blistering diseases including but not limited to pemphigus vulgaris, bullous pemphigoid and epidermolysis bullosa; respiratory inflammation diseases (e.g. asthma, chronic obstructive pulmonary disease, cystic fibrosis, idiopathic pulmonary fibrosis, sarcoidosis); skin inflammatory diseases (e.g., atopic dermatitis, contact dermatitis, eczema or psoriasis); premalignant and malignant skin conditions (e.g. basal cell carcinoma (BCC), squamous cell carcinoma (SCC) or actinic keratosis (AK)); neurological disorders and pain (such as pain associated with rheumatoid arthritis or osteoarthritis, back pain, general inflammatory pain, inflammatory neuropathic pain, trigeminal neuralgia or central pain)

The compounds described in the present invention are particularly useful for the treatment or prevention of pathological conditions or diseases selected from leukemia, lymphomas and solid tumors, rheumatoid arthritis, multiple sclerosis, amyotrophic lateral sclerosis, Crohn's disease, ulcerative colitis, systemic lupus erythematosis, autoimmune hemolytic anemia, type I diabetes, cutaneous vasculitis, cutaneous lupus erythematosus, dermatomyositis, blistering diseases including but not limited to pemphigus vulgaris, bullous pemphigoid and epidermolysis bullosa, asthma, chronic obstructive pulmonary disease, cystic fibrosis, idiopathic pulmonary fibrosis, sarcoidosis, allergic rhinitis, atopic dermatitis, contact dermatitis, eczema, psoriasis, basal cell carcinoma, squamous cell carcinoma and actinic keratosis.

In an embodiment, the compounds described in the present invention are particularly useful for the treatment or prevention of pathological conditions or diseases selected from leukemia, lymphomas and solid tumors, rheumatoid arthritis, multiple sclerosis, amyotrophic lateral sclerosis, Crohn's disease, ulcerative colitis, systemic lupus erythematosis, autoimmune hemolytic anemia, type I diabetes, asthma, chronic obstructive pulmonary disease, cystic fibrosis, idiopathic pulmonary fibrosis, sarcoidosis, allergic rhinitis, atopic dermatitis, contact dermatitis, eczema, psoriasis, basal cell carcinoma, squamous cell carcinoma and actinic keratosis.

It has now been found that certain pyrrolotriazinone derivatives are novel and potent PI3K inhibitors and can therefore be used in the treatment or prevention of these diseases.

Thus the present invention is directed to compounds of formula (I), or a pharmaceutically acceptable salt, or solvate, or N-oxide, or stereoisomer or deuterated derivative thereof:

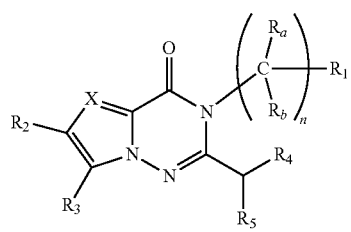

Formula (I)

X represents a nitrogen atom or a —$CR_6$ group;

n represents 0, 1, 2 or 3;

$R_a$ and $R_b$ each independently represent a hydrogen atom, a $C_1$-$C_4$ haloalkyl group, a $C_1$-$C_4$ hydroxyalkyl group or a linear or branched $C_1$-$C_4$ alkyl group;

$R_1$ represents a hydrogen atom, a linear or branched $C_1$-$C_4$ alkyl group, a $C_1$-$C_4$ haloalkyl group, a $C_3$-$C_{10}$ cycloalkyl group, a $C_3$-$C_{10}$ cycloalkenyl group, a monocyclic or bicyclic $C_6$-$C_{14}$ aryl group, a 5- to 14-membered monocyclic or bicyclic heteroaryl group containing at least one heteroatom selected from O, S and N, or a 5- to 14-membered monocyclic or bicyclic heterocyclyl group containing at least one heteroatom selected from O, S and N, wherein the cycloalkyl, cycloalkenyl, aryl, heteroaryl, and heterocyclyl groups are unsubstituted or substituted by one or more substituents selected from a halogen atom, a hydroxy group, a cyano group, a linear or branched $C_1$-$C_4$ alkyl group, a $C_1$-$C_4$ haloalkyl group, a $C_1$-$C_4$ hydroxyalkyl group, a $C_3$-$C_4$ cycloalkyl group, a —$(CH_2)_{1-3}CN$ group, a —$(CH_2)_{0-3}OR_8$ group, a —$(CH_2)_{0-3}NR_7R_8$ group, a —$C(O)$—$(CH_2)_{1-3}$—$CN$ group, a —$C(O)$—$(CH_2)_{0-3}$—$R_8$ group, a —$C(O)$—$(CH_2)_{0-3}$—$NR_7R_8$ group, a —$S(O)_2(CH_2)_{0-3}R_8$ group, a —$S(O)_2(CH_2)_{0-3}NR_7R_8$ group or a —$(CH_2)_{0-3}$(phenyl)-$OR_8$ group;

$R_2$ and $R_3$ each independently represent a hydrogen atom, a halogen atom, a hydroxyl group, a cyano group, a $C_1$-$C_4$ alkoxy group, a $C_1$-$C_4$ haloalkyl group, a $C_1$-$C_4$ hydroxyalkyl group, a $C_3$-$C_7$ cycloalkyl group, a —NR'R" group, or a linear or branched $C_1$-$C_6$ alkyl group, which alkyl group is unsubstituted or substituted by one or more substituents selected from a $C_1$-$C_4$ alkoxy group, a cyano group or a $C_3$-$C_7$ cycloalkyl group;

$R_4$ represents a hydrogen atom, a $C_1$-$C_4$ alkoxy group, a $C_1$-$C_4$ haloalkyl group, a $C_1$-$C_4$ hydroxyalkyl group, a $C_3$-$C_7$ cycloalkyl group, a —$(CH_2)_{1-4}NR'R''$ group, or a linear or branched $C_1$-$C_4$ alkyl group, which alkyl group is unsubstituted or substituted by one or more substituents selected from a $C_1$-$C_4$ alkoxy group, a cyano group, a $C_3$-$C_4$ cycloalkyl group, a —$C(O)$—$(CH_2)_{0-3}$—$R'$ group or a —$C(O)$—$(CH_2)_{0-3}$—$NR'R''$ group;

$R_6$ represents a hydrogen atom; a halogen atom; a hydroxyl group; a cyano group; a $C_1$-$C_4$ alkoxy group; a $C_1$-$C_4$ haloalkyl group; a linear or branched $C_1$-$C_4$ hydroxyalkyl group; a $C_3$-$C_7$ cycloalkyl group; a —$(CH_2)_{0-3}NR'R''$ group; a —$(CH_2)_{9-3}O(C_1$-$C_4$ alkyl group); a —$(CH_2)_{0-3}OC(O)$-$(C_1$-$C_4$ alkyl group); a —$(CH_2)_{0-3}C(O)O$—$(C_1$-$C_4$ alkyl group); a —$C(O)$—$(CH_2)_{0-3}$—$NR'R''$ group; a —$(CH_2)_{0-3}C(O)OH$ group; a —$(CH_2)_{0-3}$-(5- to 14-membered monocyclic or bicyclic heteroaryl group containing at least one heteroatom selected from O, S and N); a —(CH$_2$)$_{0-3}$-(5- to 14-membered monocyclic or bicyclic heterocyclyl group containing at least one heteroatom selected from O, S and N); or a linear or branched C$_1$-C$_4$ alkyl group, which alkyl group is unsubstituted or substituted by one or more substituents selected from a C$_1$-C$_4$ alkoxy group, a cyano group or a C$_3$-C$_4$ cycloalkyl group;
wherein the heteroaryl and heterocyclyl groups are unsubstituted or substituted by one or more substituents selected from a halogen atom, a hydroxy group, a cyano group, a linear or branched C$_1$-C$_4$ alkyl group or a C$_1$-C$_4$ haloalkyl group, R$_7$ and R$_8$ each independently represent a hydrogen atom, a C$_1$-C$_4$ haloalkyl group, a C$_1$-C$_4$ hydroxyalkyl group or a linear or branched C$_1$-C$_4$ alkyl group, which alkyl group is unsubstituted or substituted by one or more substituents selected from a C$_1$-C$_4$ alkoxy group, a cyano group or a C$_3$-C$_4$ cycloalkyl group;

R' and R" each independently represent a hydrogen atom, a hydroxyl group, a C$_1$-C$_4$ alkoxy group or a linear or branched C$_1$-C$_4$ alkyl group.

R$_5$ represents a group selected from:
  i) a group of formula (IIa)

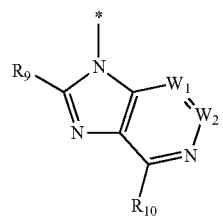

formula (IIa)

ii) a group of formula (IIb)

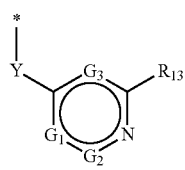

formula (IIb)

and
  iii) a group of formula (IIc)

formula (IIc)

wherein
Y represents a linker selected from a —NR'— group, —O— or —S—; wherein R' is as defined above;
(*) represents where R$_5$ is bonded to the carbon atom attached to R$_4$ and to the pyrrolotriazinone group;
W$_1$ represents a —CR$^{11}$ group and W$_2$ represents a nitrogen atom, or W$_1$ represents a nitrogen atom and W$_2$ represents a —CR$_{12}$ group;
G$_1$ represents a —CR$_{14}$ group and G$_2$ represents a nitrogen atom, or G$_1$ represents a nitrogen atom and G$_2$ represents a —CR$_{15}$ group, or G$_1$ represents a —CR$_{14}$ group and G$_2$ represents a —CR$_{15}$ group;

G$_3$ represents a nitrogen atom or a —CR$_{16}$ group;
R$_9$, R$_{10}$, R$_{11}$, R$_{12}$, R$_{13}$, R$_{14}$, R$_{15}$ and R$_{16}$ each independently represent a hydrogen atom; a halogen atom; a C$_1$-C$_4$ alkoxy group; a C$_1$-C$_4$ haloalkyl group; a C$_1$-C$_4$ hydroxyalkyl group; a C$_3$-C$_4$ cycloalkyl group; a —(CH$_2$)$_{0-3}$CN group; a —C(O)—(CH$_2$)$_{1-3}$—CN group; a —C(O)—(CH$_2$)$_{0-3}$—R' group; a —C(O)—(CH$_2$)$_{0-3}$—NR'R''; a —(CH$_2$)$_{0-3}$NR'R'' group; or a linear or branched C$_1$-C$_4$ alkyl group, which alkyl group is unsubstituted or substituted by one or more substituents selected from a C$_1$-C$_4$ alkoxy group, a cyano group or a C$_3$-C$_4$ cycloalkyl group;
wherein R' and R" are as defined above;
R$_{17}$ represents a group selected from
a) a group of formula (IIIa),

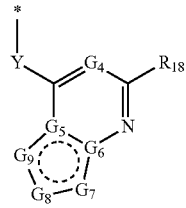

formula (IIIa)

b) a group of formula (IIIb),

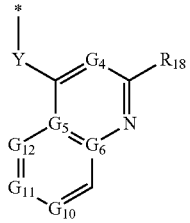

formula (IIIb)

c) a group of formula (IIIc), and

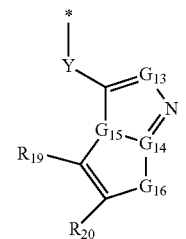

formula (IIIc)

d) a group of formula (IIId), and

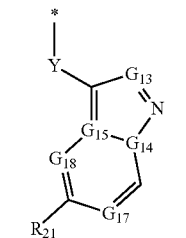

formula (IIId)

wherein
G$_4$ represents a nitrogen atom or a —CR$_{22}$ group;
G$_5$ and G$_6$ each independently represents a nitrogen atom or a carbon atom, wherein when one of G$_5$ and G$_6$ represents a nitrogen atom the remaining represents a carbon atom;

$G_7$ represents a —NH group or a —CH group;
$G_8$ represents a nitrogen atom or a —$CR_{23}$ group;
$G_9$ represents a nitrogen atom or a —$CR_{24}$ group;
$G_{10}$ represents a nitrogen atom or a —$CR_{25}$ group;
$G_{11}$ represents a nitrogen atom or a —$CR_{26}$ group;
$G_{12}$ represents a nitrogen atom or a —$CR_{27}$ group;
$G_{13}$ represents a nitrogen atom or a —$CR_{28}$ group;
$G_{14}$ and $G_{15}$ each independently represents a nitrogen atom or a carbon atom, wherein when one of $G_{14}$ and $G_{15}$ represents a nitrogen atom the remaining represents a carbon atom;
$G_{16}$ represents a —NH group or a —CH group;
$G_{17}$ represents a nitrogen atom or a —$CR_{29}$ group;
$G_{18}$ represents a nitrogen atom or a —$CR_{30}$ group;
$R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_{29}$, and $R_{30}$ each independently represent a hydrogen atom, a halogen atom, a $C_1$-$C_4$ alkoxy group, a $C_1$-$C_4$ haloalkyl group, a $C_1$-$C_4$ hydroxyalkyl group, a $C_3$-$C_4$ cycloalkyl group, a —$(CH_2)_{0-3}CN$ group, a —$C(O)$—$(CH_2)_{1-3}$—$CN$ group, a —$C(O)$—$(CH_2)_{0-3}$—$R'$ group, a —$C(O)$—$(CH_2)_{0-3}$—$NR'R''$, a —$(CH_2)_{0-3}NR'R''$ group, or a linear or branched $C_1$-$C_4$ alkyl group, which alkyl group is unsubstituted or substituted by one or more substituents selected from a $C_1$-$C_4$ alkoxy group, a cyano group or a $C_3$-$C_4$ cycloalkyl group; wherein R' and R" are as defined above; and wherein Y is as defined above;

or in the case that Y represents a —NR'— group, $R_4$ together with the —NR'— group and the carbon atom to which both $R_4$ and the —NR'— group are bonded form a 4- to 7-membered, saturated N-containing heterocyclyl group, which heterocyclyl group is unsubstituted or substituted by one or more substituents selected from a halogen atom, a hydroxyl group, a cyano group, a —$CHF_2$ group or a —$CF_3$ group.

The dotted line in the group of formula (IIIa)

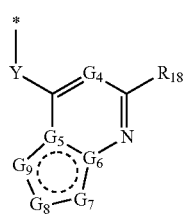

formula (IIIa)

denotes that there are two double bounds in the $C_5$ heteroaryl ring, whose position may vary depending on which $G_5$, $G_6$, $G_7$, $G_8$ or $G_9$ represents a nitrogen atom or a carbon atom.

The invention further provides synthetic processes and intermediates described herein, which are useful for preparing said compounds.

The invention is also directed to a compound of the invention as described herein for use in the treatment of the human or animal body by therapy.

The invention also provides a pharmaceutical composition comprising the compounds of the invention and a pharmaceutically-acceptable diluent or carrier.

The invention is also directed to the compounds of the invention as described herein, for use in the treatment of a pathological condition or disease susceptible to amelioration by inhibiton of Phosphoinositide 3-Kinases (PI3Ks), in particular wherein the pathological condition or disease is selected from respiratory diseases; allergic diseases; inflammatory or autoimmune-mediated diseases; function disorders and neurological disorders; cardiovascular diseases; viral infection; metabolism/endocrine function disorders; neurological disorders and pain; bone marrow and organ transplant rejection; myelo-dysplastic syndrome; myeloproliferative disorders (MPDs); cancer and hematologic malignancies, leukemia, lymphomas and solid tumors; more in particular wherein the pathological condition or disease is selected from leukemia, lymphomas and solid tumors, rheumatoid artritis (RA), multiple sclerosis (MS), amyotrophic lateral sclerosis, Crohn's disease, ulcerative colitis, systemic lupus erythematosis, autoimmune hemolytic anemia, type I diabetes, cutaneous vasculitis, cutaneous lupus erythematosus, dermatomyositis, blistering diseases including but not limited to pemphigus vulgaris, bullous pemphigoid and epidermolysis bullosa, asthma, chronic obstructive pulmonary disease (COPD), cystic fibrosis (CF), idiopathic pulmonary fibrosis, sarcoidosis, atopic dermatitis, allergic rhinitis, contact dermatitis, eczema, psoriasis, basal cell carcinoma (BCC), squamous cell carcinoma (SCC) and actinic keratosis (AK); preferably wherein the pathological condition or disease is selected from respiratory diseases; allergic diseases; inflammatory or autoimmune-mediated diseases; function disorders and neurological disorders; cardiovascular diseases; viral infection; metabolism/endocrine function disorders; neurological disorders and pain; bone marrow and organ transplant rejection; myelo-dysplastic syndrome; myeloproliferative disorders (MPDs); cancer and hematologic malignancies, leukemia, lymphomas and solid tumors; more in particular wherein the pathological condition or disease is selected from leukemia, lymphomas and solid tumors, rheumatoid artritis (RA), multiple sclerosis (MS), amyotrophic lateral sclerosis, Crohn's disease, ulcerative colitis, systemic lupus erythematosis, autoimmune hemolytic anemia, type I diabetes, dermatomyositis, blistering diseases including but not limited to asthma, chronic obstructive pulmonary disease (COPD), cystic fibrosis (CF), idiopathic pulmonary fibrosis, sarcoidosis, atopic dermatitis, allergic rhinitis, contact dermatitis, eczema, psoriasis, basal cell carcinoma (BCC), squamous cell carcinoma (SCC) and actinic keratosis (AK); even more in particular wherein the pathological condition or disease is leukemia, lymphomas and solid tumors, rheumatoid artritis (RA), multiple sclerosis (MS), amyotrophic lateral sclerosis, Crohn's disease, ulcerative colitis, systemic lupus erythematosis, autoimmune hemolytic anemia, type I diabetes, asthma, chronic obstructive pulmonary disease (COPD), cystic fibrosis (CF), idiopathic pulmonary fibrosis, sarcoidosis, atopic dermatitis, allergic rhinitis, contact dermatitis, eczema, psoriasis, basal cell carcinoma (BCC), squamous cell carcinoma (SCC) and actinic keratosis (AK).

The invention is also directed to use of the compounds of the invention as described herein, in the manufacture of a medicament for treatment of a pathological condition or disease susceptible to amelioration by inhibiton of Phosphoinositide 3-Kinases (PI3Ks), in particular wherein the pathological condition or disease is as defined above. The invention also provides a method of treatment of a pathological condition or disease susceptible to amelioration by inhibiton of Phosphoinositide 3-Kinases (PI3Ks), in particular wherein the pathological condition or disease is as defined above.

The invention also provides a combination product comprising (i) the compounds of the invention as described herein; and (ii) one or more additional active substances which are known to be useful in the treatment of respiratory diseases; allergic diseases; inflammatory or autoimmune-mediated diseases; function disorders and neurological disorders; cardiovascular diseases; viral infection; metabolism/ endocrine function disorders; neurological disorders and pain; bone marrow and organ transplant rejection; myelodysplastic syndrome; myeloproliferative disorders (MPDS); cancer and hematologic malignancies, leukemia, lymphomas and solid tumors; more in particular wherein the pathological condition or disease is selected from leukemia, lymphomas and solid tumors, rheumatoid artritis (RA), multiple sclerosis (MS), amyotrophic lateral sclerosis, Crohn's disease, ulcerative colitis, systemic lupus erythematosis, autoimmune hemolytic anemia, type I diabetes, cutaneous vasculitis, cutaneous lupus erythematosus, dermatomyositis, blistering diseases including but not limited to pemphigus vulgaris, bullous pemphigoid and epidermolysis bullosa, asthma, chronic obstructive pulmonary disease (COPD), cystic fibrosis (CF), idiopathic pulmonary fibrosis, sarcoidosis, atopic dermatitis, allergic rhinitis, contact dermatitis, eczema, psoriasis, basal cell carcinoma (BCC), squamous cell carcinoma (SCC) and actinic keratosis (AK); even more in particular wherein the pathological condition or disease is leukemia, lymphomas and solid tumors, rheumatoid artritis (RA), multiple sclerosis (MS), amyotrophic lateral sclerosis, Crohn's disease, ulcerative colitis, systemic lupus erythematosis, autoimmune hemolytic anemia, type I diabetes, asthma, chronic obstructive pulmonary disease (COPD), cystic fibrosis (CF), idiopathic pulmonary fibrosis, sarcoidosis, atopic dermatitis, allergic rhinitis, contact dermatitis, eczema, psoriasis, basal cell carcinoma (BCC), squamous cell carcinoma (SCC) and actinic keratosis (AK).

As used herein the term $C_1$-$C_6$ alkyl embraces linear or branched radicals having 1 to 6 carbon atoms, preferably 1 to 4 carbon atoms. Examples include methyl, ethyl, n-propyl, i-propyl, n-butyl, sec-butyl, t-butyl, n-pentyl, 1-methylbutyl, 2-methylbutyl, isopentyl, 1-ethylpropyl, 1,1-dimethylpropyl, 1,2-dimethylpropyl, n-hexyl, 1-ethylbutyl, 2-ethylbutyl, 1,1-dimethylbutyl, 1,2-dimethylbutyl, 1,3-dimethylbutyl, 2,2-dimethylbutyl, 2,3-dimethylbutyl, 2-methylpentyl, 3-methylpentyl and iso-hexyl radicals.

When it is mentioned that the alkyl radical may be optionally substituted it is meant to include linear or branched alkyl radical as defined above, which may be unsubstituted or substituted in any position by one or more substituents, for example by 1, 2 or 3 substituents. When two or more substituents are present, each substituent may be the same or different.

As used herein, the term $C_1$-$C_4$ haloalkyl group is an alkyl group, for example a $C_1$-$C_4$ or $C_1$-$C_2$ alkyl group, which is bonded to one or more, preferably 1, 2 or 3 halogen atoms. Preferably, said haloakyl group is chosen from —$CCl_3$, —$CHF_2$ and $CF_3$.

As used herein, the term $C_1$-$C_4$ hydroxyalkyl embraces linear or branched alkyl radicals having 1 to 4 carbon atoms, any one of which may be substituted by one or more, preferably 1 or 2, more preferably 1 hydroxyl radicals. Examples of such radicals include hydroxymethyl, hydroxyethyl, hydroxypropyl, and hydroxybutyl.

As used herein, the term $C_1$-$C_4$ alkoxy (or alkyloxy) embraces linear or branched oxy-containing radicals each having alkyl portions of 1 to 4 carbon atoms.

As used herein, the term $C_3$-$C_{10}$ cycloalkyl embraces saturated monocyclic or polycyclic carbocyclic radicals having from 3 to 10 carbon atoms, preferably from 3 to 7 carbon atoms. An optionally substituted $C_3$-$C_{10}$ cycloalkyl radical is typically unsubstituted or substituted by 1, 2 or 3 substituents which may be the same or different. When a $C_3$-$C_{10}$ cycloalkyl radical carries 2 or more substituents, the substituents may be the same or different. Typically the substituents on a $C_3$-$C_{10}$ cycloalkyl group are themselves unsubstituted. Polycyclic cycloalkyl radicals contains two or more fused cycloalkyl groups, preferably two cycloalkyl groups. Typically, polycyclic cycloalkyl radicals are selected from decahydronaphthyl (decalyl), bicyclo[2.2.2]octyl, adamantly, camphyl or bornyl groups.

Examples of monocyclic cycloalkyl groups include cyclopropyl, cyclobutyl, cyclopentyl, cyclohexyl, cycloheptyl, cyclooctyl, cyclononyl and cyclodecyl.

As used herein, the term $C_3$-$C_{10}$ cycloalkenyl embraces partially unsaturated carbocyclic radicals having from 3 to 10 carbon atoms, preferably from 3 to 7 carbon atoms. A $C_3$-$C_{10}$ cycloalkenyl radical is typically unsubstituted or substituted by 1, 2 or 3 substituents which may be the same or different. When a $C_3$-$C_{10}$ cycloalkenyl radical carries 2 or more substituents, the substituents may be the same or different. Typically, the substituents on a cycloalkenyl group are themselves unsubstituted.

Examples include cyclobutenyl, cyclopentenyl, cyclohexenyl, cycloheptenyl, cyclooctenyl, cyclononenyl and cyclodecenyl.

As used herein, the term $C_6$-$C_{14}$ aryl radical embraces typically a $C_6$-$C_{14}$, more preferably $C_6$-$C_{10}$ monocyclic or bicyclic aryl radical such as phenyl, naphthyl, anthranyl and phenanthryl. Phenyl is preferred. A said optionally substituted $C_6$-$C_{14}$ aryl radical is typically unsubstituted or substituted by 1, 2 or 3 substituents which may be the same or different. When a $C_6$-$C_{14}$ aryl radical carries 2 or more substituents, the substituents may be the same or different. Unless otherwise specified, the substituents on a $C_6$-$C_{14}$ aryl group are typically themselves unsubstituted.

As used herein, the term 5- to 14-membered heteroaryl radical embraces typically a 5- to 14-membered ring system, preferably a 5- to 10-membered ring system, more preferably a 5- to 6-membered ring system, comprising at least one heteroaromatic ring and containing at least one heteroatom selected from O, S and N. A 5- to 14-membered heteroaryl radical may be a single ring or two fused rings wherein at least one ring contains a heteroatom.

A said optionally substituted 5- to 14-membered heteroaryl radical is typically unsubstituted or substituted by 1, 2 or 3 substituents which may be the same or different. When a 5- to 14-membered heteroaryl radical carries 2 or more substituents, the substituents may be the same or different. Unless otherwise specified, the substituents on a 5- to 14-membered heteroaryl radical are typically themselves unsubstituted.

Examples include pyridyl, pyrazinyl, pyrimidinyl, pyridazinyl, furyl, benzofuranyl, oxadiazolyl, oxazolyl, isoxazolyl, benzoxazolyl, imidazolyl, benzimidazolyl, thiazolyl, thiadiazolyl, thienyl, pyrrolyl, benzothiazolyl, indolyl, indazolyl, purinyl, quinolyl, isoquinolyl, phthalazinyl, naphthyridinyl, quinoxalinyl, quinazolinyl, quinolizinyl, cinnolinyl, triazolyl, indolizinyl, indolinyl, isoindolinyl, isoindolyl, imidazolidinyl, pteridinyl, thianthrenyl, pyrazolyl, 2H-pyrazolo[3,4-d]pyrimidinyl, 1H-pyrazolo[3,4-d]pyrimidinyl, thieno[2,3-d]pyrimidinyl and the various pyrrolopyridyl radicals.

As used herein, the term 5- to 14-membered heterocyclyl radical embraces typically a non-aromatic, saturated or unsaturated $C_5$-$C_{14}$ carbocyclic ring system, preferably $C_5$-$C_{10}$ carbocyclic ring system, more preferably $C_5$-$C_6$-carbocyclic ring system, in which one or more, for example 1, 2, 3 or 4 of the carbon atoms preferably 1 or 2 of the carbon atoms are replaced by a heteroatom selected from N, O and S. A heterocyclyl radical may be a single ring or two fused rings wherein at least one ring contains a heteroatom. When a 5 to 14-membered heterocyclyl radical carries 2 or more substituents, the substituents may be the same or different.

A said optionally substituted 5- to 14-membered heterocyclyl radical is typically unsubstituted or substituted by 1, 2 or 3 substituents which may be the same or different. Typically, the substituents on a 5 to 14-membered heterocyclyl radical are themselves unsubstituted.

Examples of 5- to 14-membered heterocyclyl radicals include piperidyl, pyrrolidyl, pyrrolinyl, piperazinyl, morpholinyl, thiomorpholinyl, pyrrolyl, pyrazolinyl, pirazolidinyl, quinuclidinyl, triazolyl, pyrazolyl, tetrazolyl, imidazolidinyl, imidazolyl, oxiranyl, thiaranyl, aziridinyl, oxetanyl, thiatanyl, azetidinyl, 4,5-dihydro-oxazolyl, 2-benzofuran-1(3H)-one, 1,3-dioxol-2-one, tetrahydrofuranyl, 3-aza-tetrahydrofuranyl, tetrahydrothiophenyl, tetrahydropyranyl, tetrahydrothiopyranyl, 1,4-azathianyl, oxepanyl, thiephanyl, azepanyl, 1,4-dioxepnayl, 1,4-oxathiepanyl, 1,4-oxaazepanyl, 1,4-dithiepanyl, 1,4-thiezepanyl, 1,4-diazepanyl, tropanyl, (1S,5R)-3-aza-bicyclo[3.1.0]hexyl, 3,4-dihydro-2H-pyranyl, 5,6-dihydro-2H-pyranyl, 2H-pyranyl, 2,3-hydrobenzofuranyl, 1,2,3,4-tetrahydropyridinyl, 1,2,5,6-tetrahydropyridinyl, isoindolinyl and indolinyl.

Where a 5- to 14-membered heterocyclyl radical carries 2 or more substituents, the substituents may be the same or different.

As used herein, the bicyclic N-containing heteroaryl group is a $C_8$-$C_{10}$ membered ring system where two rings have been fused and wherein at least in one ring one of the carbon atoms is replaced by N and optionally in which 1, 2, 3, or 4, preferably 1, 2, or 3 further carbon atoms of any ring which form the group are replaced by N.

Examples include indolyl, benzimidazolyl, indazolyl, benzotriazolyl, pyrrolo[2,3-b]pyridinyl, pyrrolo[2,3-c]pyridinyl, pyrrolo[3,2-c]pyridinyl, pyrrolo[3,2-b]pyridinyl, imidazo[4,5-b]pyridinyl, imidazo[4,5-c]pyridinyl, pyrazolo[4,3-d]pyridinyl, pyrazolo[4,3-d]pyridinyl, pyrazolo[3,4-c]pyridinyl, pyrazolo[3,4-b]pyridinyl, isoindolinyl, indazolyl, purinyl, indolinyl, imidazo[1,2-a]pyridinyl, imidazo[1,5-a]pyridinyl, pyrazolo[1,5-a]pyridinyl, pyrrolo[1,2-b]pyridazinyl, imidazo[1,2-c]pyrimidinyl, quinolyl, isoquinolyl, cinnolinyl, azaquinazolinyl, quinoxalinyl, phthalazinyl, naphthyridinyl, pyrido[3,2-d]pyrimidinyl, pyrido[4,3-d]pyrimidinyl, pyrido[3,4-d]pyrimidinyl, pyrido[2,3-d]pyrimidinyl, pyrazolo[1,5-a]pyrimidinyl, pyrido[2,3-b]pyrazinyl, pyrido[3,4-b]pyrazinyl, pyrimido[5,4-d]pyrimidinyl, pyrazino[2,3-b]pyrazinyl and pyrimido[4,5-d]pyrimidinyl.

As used herein, some of the atoms, radicals, moieties, chains and cycles present in the general structures of the invention are "optionally substituted". This means that these atoms, radicals, moieties, chains and cycles can be either unsubstituted or substituted in any position by one or more, for example 1, 2, 3 or 4, substituents, whereby the hydrogen atoms bound to the unsubstituted atoms, radicals, moieties, chains and cycles are replaced by chemically acceptable atoms, radicals, moieties, chains and cycles. When two or more substituents are present, each substituent may be the same or different. The substituents are typically themselves unsubstituted.

As used herein, the term halogen atom embraces chlorine, fluorine, bromine and iodine atoms. A halogen atom is typically a fluorine, chlorine or bromine atom, most preferably chlorine or fluorine. The term halo when used as a prefix has the same meaning.

Compounds containing one or more chiral centre may be used in enantiomerically or diastereoisomerically pure form, in the form of racemic mixtures and in the form of mixtures enriched in one or more stereoisomer. The scope of the invention as described and claimed encompasses the racemic forms of the compounds as well as the individual enantiomers, diastereomers, and stereoisomer-enriched mixtures.

Conventional techniques for the preparation/isolation of individual enantiomers include chiral synthesis from a suitable optically pure precursor or resolution of the racemate using, for example, chiral high pressure liquid chromatography (HPLC). Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereomehc mixture may be separated by chromatography and/or fractional crystallization and one or both of the diastereoisomers converted to the corresponding pure enantiomer(s) by means well known to one skilled in the art. Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture. Stereoisomer conglomerates may be separated by conventional techniques known to those skilled in the art. See, e.g. "Stereochemistry of Organic Compounds" by Ernest L. Eliel (Wiley, New York, 1994).

Atropisomers are stereoisomers resulting from hindered rotation about single bonds where the steric strain barrier to rotation is high enough to allow for the isolation of the conformers. Oki (Oki, M; *Topics in Stereochemistry* 1983, 1) defined atropisomers as conformers that interconvert with a half-life of more than 1000 seconds at a given temperature. The scope of the invention as described and claimed encompasses the racemic forms of the compounds as well as the individual atropisomers (an atropisomer "substantially free" of tis corresponding enantionmer) and stereoisomer-enriched mixtures, i.e. mixtures of atropisomers.

Separation of atropisomers is possibly by chiral resolution methods such as selective crystallization. In an atropo-enantioselective or atroposelective synthesis one atropisomer is formed at the expense of the other. Atroposelective synthesis may be carried out by use of chiral auxiliaries like a Corey-Bakshi-Shibata (CBS) catalyst (asymmetric catalyst derived from proline) in the total synthesis of knipholone or by approaches based on thermodynamic equilibration when an isomerization reaction favors one atropisomer over the other.

As used herein, the term pharmaceutically acceptable salt refers to a salt prepared from a base or acid which is acceptable for administration to a patient, such as a mammal. Such salts can be derived from pharmaceutically-acceptable inorganic or organic bases and from pharmaceutically-acceptable inorganic or organic acids.

Pharmaceutically acceptable acids include both inorganic acids, for example hydrochloric, sulphuric, phosphoric, diphosphoric, hydrobromic, hydroiodic and nitric acid; and organic acids, for example citric, fumaric, gluconic, glutamic, lactic, maleic, malic, mandelic, mucic, ascorbic, oxalic, pantothenic, succinic, tartaric, benzoic, acetic, methanesulphonic, ethanesulphonic, benzenesulphonic, p-toluenesulphonic acid, xinafoic (1-hydroxy-2-naphthoic acid), napadisilic (1,5-naphthalenedisulfonic acid) and the like. Particularly preferred are salts derived from fumaric, hydrobromic, hydrochloric, acetic, sulfuric, methanesulfonic, xinafoic, and tartaric acids.

Salts derived from pharmaceutically-acceptable inorganic bases include aluminum, ammonium, calcium, copper, ferric, ferrous, lithium, magnesium, manganic, manganous, potassium, sodium, zinc and the like. Particularly preferred are ammonium, calcium, magnesium, potassium and sodium salts.

Salts derived from pharmaceutically-acceptable organic bases include salts of primary, secondary and tertiary amines, including alkyl amines, arylalkyl amines, heterocyclyl amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

Other preferred salts according to the invention are quaternary ammonium compounds wherein an equivalent of an anion ($X^-$) is associated with the positive charge of the N atom. $X^-$ may be an anion of various mineral acids such as, for example, chloride, bromide, iodide, sulphate, nitrate, phosphate, or an anion of an organic acid such as, for example, acetate, maleate, fumarate, citrate, oxalate, succinate, tartrate, malate, mandelate, trifluoroacetate, methanesulphonate and p-toluenesulphonate. $X^-$ is preferably an anion selected from chloride, bromide, iodide, sulphate, nitrate, acetate, maleate, oxalate, succinate or trifluoroacetate. More preferably $X^-$ is chloride, bromide, trifluoroacetate or methanesulphonate.

As used herein, an N-oxide is formed from the tertiary basic amines or imines present in the molecule, using a convenient oxidising agent.

The present invention also embraces tautomeric forms of the compounds of formula (I), or pharmaceutically acceptable salts, solvates, N-oxides, stereoisomers or deuterated derivatives thereof.

The compounds of the invention may exist in both unsolvated and solvated forms. The term solvate is used herein to describe a molecular complex comprising a compound of the invention and an amount of one or more pharmaceutically acceptable solvent molecules. The term hydrate is employed when said solvent is water. Examples of solvate forms include, but are not limited to, compounds of the invention in association with water, acetone, dichloromethane, 2-propanol, ethanol, methanol, dimethylsulfoxide (DMSO), ethyl acetate, acetic acid, ethanolamine, or mixtures thereof. It is specifically contemplated that in the present invention one solvent molecule can be associated with one molecule of the compounds of the present invention, such as a hydrate.

Furthermore, it is specifically contemplated that in the present invention, more than one solvent molecule may be associated with one molecule of the compounds of the present invention, such as a dihydrate. Additionally, it is specifically contemplated that in the present invention less than one solvent molecule may be associated with one molecule of the compounds of the present invention, such as a hemihydrate. Furthermore, solvates of the present invention are contemplated as solvates of compounds of the present invention that retain the biological effectiveness of the non-solvate form of the compounds.

The invention also includes isotopically-labeled compounds of the invention, wherein one or more atoms is replaced by an atom having the same atomic number, but an atomic mass or mass number different from the atomic mass or mass number usually found in nature. Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S. Certain isotopically-labeled compounds of the invention, for example, those incorporating a radioactive isotope, are useful in drug and/or substrate tissue distribution studies. The radioactive isotopes tritium, $^3$H, and carbon-14, $^{14}$C, are particularly useful for this purpose in view of their ease of incorporation and ready means of detection. Substitution with heavier isotopes such as deuterium, $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Preferred isotopically-labeled compounds include deuterated derivatives of the compounds of the invention. As used herein, the term deuterated derivative embraces compounds of the invention where in a particular position at least one hydrogen atom is replaced by deuterium. Deuterium (D or $^2$H) is a stable isotope of hydrogen which is present at a natural abundance of 0.015 molar %.

Hydrogen deuterium exchange (deuterium incorporation) is a chemical reaction in which a covalently bonded hydrogen atom is replaced by a deuterium atom. Said exchange (incorporation) reaction can be total or partial.

Typically, a deuterated derivative of a compound of the invention has an isotopic enrichment factor (ratio between the isotopic abundance and the natural abundance of that isotope, i.e. the percentage of incorporation of deuterium at a given position in a molecule in the place of hydrogen) for each deuterium present at a site designated as a potential site of deuteration on the compound of at least 3500 (52.5% deuterium incorporation).

In a preferred embodiment, the isotopic enrichment factor is at least 5000 (75% deuterium). In a more preferred embodiment, the isotopic enrichment factor is at least 6333.3 (95% deuterium incorporation). In a most preferred embodiment, the isotopic enrichment factor is at least 6633.3 (99.5% deuterium incorporation). It is understood that the isotopic enrichment factor of each deuterium present at a site designated as a site of deuteration is independent from the other deuteration sites.

The isotopic enrichment factor can be determined using conventional analytical methods known too en ordinary skilled in the art, including mass spectrometry (MS) and nuclear magnetic resonance (NMR).

Prodrugs of the compounds described herein are also within the scope of the invention. Thus certain derivatives of the compounds of the present invention, which derivatives may have little or no pharmacological activity themselves, when administered into or onto the body may be converted into compounds of the present invention having the desired activity, for example, by hydrolytic cleavage. Such derivatives are referred to as 'prodrugs'. Further information on the use of prodrugs may be found in Pro-drugs as Novel Delivery Systems, Vol. 14, ACS Symposium Series (T. Higuchi and W. Stella) and Bioreversible Carriers in Drug Design, Pergamon Press, 1987 (ed. E. B. Roche, American Pharmaceutical Association).

Prodrugs in accordance with the invention can, for example, be produced by replacing appropriate functionalities present in the compounds of the present invention with certain moieties known to those skilled in the art as 'pro-moieties' as described, for example, in Design of Prodrugs by H. Bundgaard (Elsevier, 1985).

In the case of compounds that are solids, it is understood by those skilled in the art that the inventive compounds and salts may exist in different crystalline or polymorphic forms, or in an amorphous form, all of which are intended to be within the scope of the present invention.

As used herein, the term PI3 Kd inhibitor generally refers to a compound that inhibits the activity of the PI3 Kd isoform more effectively than other isoforms of the PI3K family.

As used herein, the term PI3 Kd/g inhibitor generally refers to a compound that inhibits the activity of both the PI3 Kd isoform and the PI3 Kg isoform more effectively than other isoforms of the PI3K family.

The relative efficacies of compounds as inhibitors of an enzyme activity (or other biological activity) can be established by determining the concentrations at which each compound inhibits the activity to a predefined extent and then comparing the results. Typically, the preferred determination is the concentration that inhibits 50% of the activity in a biochemical assay, i.e., the 50% inhibitory concentration or "$IC_{50}$." $IC_{50}$ determinations can be accomplished using conventional techniques known in the art. In general, an $IC_{50}$ can be determined by measuring the activity of a given enzyme in the presence of a range of concentrations of the inhibitor under study. The experimentally obtained values of enzyme activity then are plotted against the inhibitor concentrations used. The concentration of the inhibitor that shows 50% enzyme activity (as compared to the activity in the absence of any inhibitor) is taken as the $IC_{50}$ value.

Accordingly, a PI3 Kd inhibitor alternatively can be understood to refer to a compound that exhibits a 50% inhibitory concentration ($IC_{50}$) with respect to PI3 Kd that is at least of less than about 100 μM, preferably of less than about 50 μM, more preferably of less than about 20 μM, even more preferably of less than about 10 μM PI3K HTRF assay (as described in Gray et al. *Anal Biochem*, 2003; 313: 234-45)

Typically, in the compound of formula (I), X represents a nitrogen atom or a —$CR_6$ group.

Typically, in the compound of formula (I), $R_a$ and $R_b$ each independently represent a hydrogen atom or a linear or branched $C_1$-$C_3$ alkyl group.

Preferably, $R_a$ and $R_b$ each independently represent a hydrogen atom, a methyl group or an ethyl group.

Typically, n represents 0, 1 or 2, preferably 0 or 1, more preferably 0.

Typically, in the compound of formula (I) $R_1$ represents a hydrogen atom, a linear or branched $C_1$-$C_4$ alkyl group, a $C_1$-$C_4$ haloalkyl group, a $C_3$-$C_{10}$ cycloalkyl group, a $C_3$-$C_{10}$ cycloalkenyl group, a monocyclic or bicyclic $C_6$-$C_{14}$ aryl group, a 5- to 14-membered monocyclic or bicyclic heteroaryl group containing at least one heteroatom selected from O, S and N, or a 5- to 14-membered monocyclic or bicyclic heterocyclyl group containing at least one heteroatom selected from O, S and N; wherein the cycloalkyl, cycloalkenyl, aryl, heteroaryl, and heterocyclyl groups are unsubstituted or substituted by one or more substituents selected from a halogen atom, a hydroxy group, a cyano group, a linear or branched $C_1$-$C_4$ alkyl group, a $C_1$-$C_4$ haloalkyl group, a $C_1$-$C_4$ hydroxyalkyl group, a $C_3$-$C_4$ cycloalkyl group, a —$(CH_2)_{1-3}CN$ group, a —$(CH_2)_{0-3}OR_8$ group, a —$(CH_2)_{0-3}NR_7R_8$ group, a —$C(O)$—$(CH_2)_{1-3}$—$CN$ group, a —$C(O)$—$(CH_2)_{0-3}$—$R_8$ group, a —$C(O)$—$(CH_2)_{0-3}$—$NR_7R_8$ group, a —$S(O)_2(CH_2)_{0-3}R_8$ group, a —$S(O)_2(CH_2)_{0-3}NR_7R_8$ group or a —$(CH_2)_{0-3}$(phenyl)-$OR_3$ group; wherein $R_7$ and $R_8$ are as defined above.

Preferably, $R_1$ represents a hydrogen atom, $C_1$-$C_3$ alkyl group, a $C_1$-$C_3$ haloalkyl group, a $C_3$-$C_7$ cycloalkyl group, a phenyl group, a naphthyl group, a 5- to 10-membered monocyclic or bicyclic heteroaryl group containing one, two or three heteroatoms selected from O, S and N, or a 5- to 10-membered monocyclic or bicyclic heterocyclyl group containing containing one, two or three heteroatoms selected from O, S and N, wherein the cycloalkyl, phenyl, naphthyl, heteroaryl and heterocyclyl groups are unsubstituted or substituted by one or more substituents selected from a halogen atom, a hydroxy group, a cyano group, a linear or branched $C_1$-$C_4$ alkyl group, a $C_1$-$C_4$ haloalkyl group, a $C_1$-$C_4$ hydroxyalkyl group, a $C_3$-$C_4$ cycloalkyl group, a —$(CH_2)_{0-3}OR_8$ group, a —$(CH_2)_{0-3}NR_7R_8$ group, a —$C(O)$—$(CH_2)_{0-3}$—$R_8$ group, a —$C(O)$—$(CH_2)_{0-3}$—$NR_7R_8$ group or a —$(CH_2)_{0-3}$(phenyl)-$OR_8$ group; wherein $R_7$ and $R_8$ are as defined above.

More preferably $R_1$ represents a phenyl group or a pyridinyl group, which phenyl or pyridinyl is unsubstituted or substituted by one, two or three substituents selected from a halogen atom, a hydroxyl group, a linear or branched $C_1$-$C_3$ alkyl group, a $C_1$-$C_3$ haloalkyl group, or a —$(CH_2)_{0-3}OCH_3$ group; for example from a halogen atom, a linear or branched $C_1$-$C_3$ alkyl group or a —$(CH_2)_{0-3}OCH_3$ group.

Preferably, when $R_1$ represents a phenyl group or a pyridinyl group, said phenyl and pyridinyl groups are directly bonded to the pyrrolotriazinone group. In other words, the linker —$(R_a$—$C$—$R_b)_n$— is not present. More preferably, $R_1$ represents a phenyl group.

Preferably, when $R_1$ is a phenyl group, it is unsubstituted or substituted by one, two or three substituents selected from a halogen atom (preferably a fluorine atom or a chlorine atom), a hydroxyl group, a linear or branched $C_1$-$C_3$ alkyl group (preferably a methyl group), a $C_1$-$C_3$ haloalkyl group, or a —$OCH_3$ group; for example when $R_1$ is a phenyl group, it is unsubstituted or substituted by one, two or three substituents selected from a halogen atom (preferably a fluorine atom or a chlorine atom), a linear or branched $C_1$-$C_3$ alkyl group (preferably a methyl group) or a —$OCH_3$ group.

Preferably, when $R_1$ is a pyridinyl or pyperidinyl group, said groups are linked to the rest of the molecule via a ring carbon atom, in other words they are linked to the pyrrolotriazinone group via a ring carbon atom. Substituents on a pyridinyl group may be present on any ring atom but are preferably present on a carbon atom. Substituents on a piperidinyl group may be present on any ring atom but are preferably present on the nitrogen atom.

In one embodiment, in the compound of formula (I) $R_1$ represents a $C_1$-$C_3$ alkyl group, a $C_3$-$C_7$ cycloalkyl group, a phenyl group, a naphtyl group, a 5- to 10-membered monocyclic or bicyclic heteroaryl group containing one, two or three heteroatoms selected from O, S and N, or a 5- to 10-membered monocyclic or bicyclic heterocyclyl group containing one, two or three heteroatoms selected from O, S and N; wherein the cycloalkyl, phenyl, naphtyl, heteroaryl and heterocyclyl groups are unsubstituted or substituted by one or more substituents selected from a halogen atom, a hydroxyl group, a cyano group, a linear or branched $C_1$-$C_4$ alkyl group, a $C_1$-$C_4$ haloalkyl group, a $C_1$-$C_4$ hydroxyalkyl group, a $C_3$-$C_4$ cycloalkyl group, a —$(CH_2)_{0-3}OR_8$ group, a —$(CH_2)_{0-3}NR_7R_8$ group, a —$C(O)$—$(CH_2)_{0-3}$—$R_8$ group or a —$C(O)$—$(CH_2)_{0-3}$—$NR_7R_8$ group; wherein $R_7$ and $R_8$ are as defined above.

In this embodiment $R_1$ preferably represents a $C_3$-$C_7$ cycloalkyl group, a phenyl group, a 5- to 10-membered monocyclic or bicyclic heteroaryl group containing one, two or three heteroatoms selected from O, S and N, a pyrrolidinyl group, a piperidinyl group, a piperazinyl group, a tetrahydropyranyl group or a morpholinyl group; wherein the cycloalkyl, phenyl, heteroaryl, pyrrolidinyl, piperidinyl, piperazinyl, tetrahydropyranyl or morpholinyl groups are unsubstituted or substituted by one or more substituents selected from a halogen atom, a linear or branched $C_1$-$C_4$ alkyl group, a $C_1$-$C_4$ haloalkyl group, a $C_1$-$C_4$ hydroxyalkyl group, a $C_3$-$C_4$ cycloalkyl group, a —$(CH_2)_{0-3}OR_8$ group, a —$(CH_2)_{0-3}NR_7R_8$ group, a —C(O)—$(CH_2)_{0-3}$—$R_8$ group or a —C(O)—$(CH_2)_{0-3}$—$NR_7R_8$ group; wherein $R_7$ and $R_8$ each independently represent a hydrogen atom or a $C_1$-$C_4$ alkyl group.

Typically, in the compound of formula (I) $R_2$ represents a hydrogen atom, a halogen atom, a hydroxyl group, a cyano group, a $C_1$-$C_4$ alkoxy group, a $C_1$-$C_4$ haloalkyl group, a $C_1$-$C_4$ hydroxyalkyl group, a $C_3$-$C_4$ cycloalkyl group, a —$(CH_2)_{0-3}NR'R''$ group, or a linear or branched $C_1$-$C_4$ alkyl group, which alkyl group is unsubstituted or substituted by a $C_1$-$C_3$ alkoxy group; wherein R' and R'' each independently represent a hydrogen atom, a hydroxyl group, or a linear or branched $C_1$-$C_3$ alkyl group.

Preferably $R_2$ represents a hydrogen atom, a halogen atom, a hydroxyl group, a $C_1$-$C_3$ alkoxy group, a $C_1$-$C_3$ haloalkyl group, a $C_3$-$C_4$ cycloalkyl group, a —$NH_2$ group, a —$N(CH_3)H$ group, a —$N(CH_3)_2$ group, or a linear or branched $C_1$-$C_4$ alkyl group, which alkyl group is unsubstituted or substituted by a $C_1$-$C_2$ alkoxy group.

More preferably $R_2$ represents a hydrogen atom, a halogen atom, —$NH_2$ group, a —$N(CH_3)H$ group, a —$N(CH_3)_2$ group, or a linear or branched $C_1$-$C_3$ alkyl group. Most preferably $R_2$ represents a hydrogen atom or a methyl group.

Typically, in the compound of formula (I) $R_3$ represents a hydrogen atom, a halogen atom, a hydroxyl group, a cyano group, a $C_1$-$C_4$ alkoxy group, a $C_1$-$C_4$ haloalkyl group, a $C_1$-$C_4$ hydroxyalkyl group, a $C_3$-$C_4$ cycloalkyl group, a —$(CH_2)_{0-3}NR'R''$ group, or a linear or branched $C_1$-$C_4$ alkyl group, which alkyl group is unsubstituted or substituted by a $C_1$-$C_3$ alkoxy group; wherein R' and R'' each independently represent a hydrogen atom, a hydroxyl group, or a linear or branched $C_1$-$C_3$ alkyl group.

Preferably, in the compound of formula (I) $R_3$ represents a hydrogen atom, a halogen atom, a hydroxyl group, a cyano group, a $C_1$-$C_3$ alkoxy group, a $C_1$-$C_3$ haloalkyl group, a $C_3$-$C_4$ cycloalkyl group, a —$NH_2$ group, a —$N(CH_3)H$ group, a —$N(CH_3)_2$ group, or a linear or branched $C_1$-$C_4$ alkyl group, which alkyl group is unsubstituted or substituted by a $C_1$-$C_2$ alkoxy group.

More preferably $R_3$ represents a hydrogen atom, a halogen atom, a cyano group, a $C-C_3$ alkoxy group, a $C_1$-$C_3$ haloalkyl group, a —$NH_2$ group, a —$N(CH_3)H$ group, a —$N(CH_3)_2$ group, or a linear or branched $C_1$-$C_3$ alkyl group;

In one embodiment, in the compound of formula (I) $R_3$ represents a hydrogen atom, a halogen atom, a hydroxyl group, a $C_1$-$C_3$ alkoxy group, a $C_1$-$C_3$ haloalkyl group, a $C_3$-$C_4$ cycloalkyl group, a —$NH_2$ group, a —$N(CH_3)H$ group, a —$N(CH_3)_2$ group, or a linear or branched $C_1$-$C_4$ alkyl group, which alkyl group is unsubstituted or substituted by a $C_1$-$C_2$ alkoxy group. In this embodiment, more preferably $R_3$ represents a hydrogen atom, a halogen atom, a —$NH_2$ group, a —$N(CH_3)H$ group, a —$N(CH_3)_2$ group, or a linear or branched $C_1$-$C_3$ alkyl group. Most preferably $R_3$ represents a hydrogen atom or a methyl group.

Typically, in the compound of formula (I), $R_4$ represents a hydrogen atom, a $C_1$-$C_4$ haloalkyl group, a $C_1$-$C_4$ hydroxyalkyl group, a $C_3$-$C_4$ cycloalkyl group, a —$(CH_2)_{1-4}NR'R''$ group, or a linear or branched $C_1$-$C_4$ alkyl group, which alkyl group is unsubstituted or substituted by a $C_1$-$C_3$ alkoxy group, a —C(O)—$(CH_2)_{0-3}$—R' a group or a —C(O)—$(CH_2)_{0-3}$—NR'R'' group; wherein R' and R'' each independently represent a hydrogen atom, a hydroxyl group, or a linear or branched $C_1$-$C_3$ alkyl group. More preferably, $R_4$ represents a hydrogen atom, a $C_1$-$C_3$ haloalkyl group, a $C_1$-$C_3$ hydroxyalkyl group, a $C_3$-$C_4$ cycloalkyl group, or a linear or branched $C_1$-$C_3$ alkyl group.

In one embodiment, in the compound of formula (I), $R_4$ represents a $R_4$ represents a hydrogen atom, a $C_1$-$C_4$ alkoxy group, a $C_1$-$C_4$ haloalkyl group, a $C_1$-$C_4$ hydroxyalkyl group, a $C_3$-$C_4$ cycloalkyl group, a —$(CH_2)_{1-4}NR'R''$ group, or a linear or branched $C_1$-$C_4$ alkyl group, which alkyl group is unsubstituted or substituted by a $C_1$-$C_3$ alkoxy group, a —C(O)—$(CH_2)_{0-3}R'$ group or a —C(O)—$(CH_2)_{0-3}$—NR'R'' group; wherein R' and R'' each independently represent a hydrogen atom, a hydroxy group, or a linear or branched $C_1$-$C_3$ alkyl group. In this embodiment, more preferably, $R_4$ represents a hydrogen atom, a $C_1$-$C_3$ alkoxy group, a $C_1$-$C_3$ haloalkyl group, a $C_3$-$C_4$ cycloalkyl group, or a linear or branched $C_1$-$C_3$ alkyl group. In this embodiment, most preferably $R_4$ represents a hydrogen atom, a $C_1$-$C_3$ haloalkyl group or a linear or branched $C_1$-$C_3$ alkyl group.

Typically, in the compound of formula (I), $R_6$ represents a hydrogen atom; a halogen atom; a hydroxy group; a cyano group; a $C_1$-$C_4$ alkoxy group; a $C_1$-$C_4$ haloalkyl group; a linear or branched $C_1$-$C_4$ hydroxyalkyl group; a $C_3$-$C_7$ cycloalkyl group; a —$(CH_2)_{0-3}NR'R''$ group; a —$(CH_2)_{1-3}O$ ($C_1$-$C_4$ alkyl group); a —$(CH_2)_{0-3}OC(O)$—($C_1$-$C_4$ alkyl group); a —$(CH_2)_{0-3}C(O)O$—($C_1$-$C_4$ alkyl group); a —C(O)—$(OH_2)_{0-3}$—NR'R'' group; a —$(CH_2)_{0-3}C(O)OH$ group; a —$(CH_2)_{0-3}$-(5- to 10-membered monocyclic or bicyclic heteroaryl group containing at least one heteroatom selected from O, S and N); a —$(CH_2)_{0-3}$-(5- to 10-membered monocyclic or bicyclic heterocyclyl group containing at least one heteroatom selected from O, S and N);

or a linear or branched $C_1$-$C_3$ alkyl group, which alkyl group is unsubstituted or substituted by one or more substituents selected from a $C_1$-$C_4$ alkoxy group, a cyano group or a $C_3$-$C_4$ cycloalkyl group; wherein R' and R'' each independently represent a hydrogen atom, a hydroxyl group, or a linear or branched $C_1$-$C_3$ alkyl group; and wherein the heteroaryl and heterocyclyl groups are unsubstituted or substituted by one or more substituents selected from a halogen atom, a hydroxyl group, a cyano group, a linear or branched $C_1$-$C_3$ alkyl group or a $C_1$-$C_3$ haloalkyl group.

Preferably, in the compound of formula (I), $R_6$ represents a hydrogen atom, a halogen atom, a hydroxyl group, a cyano group, a $C_1$-$C_4$ alkoxy group, a $C_1$-$C_4$ haloalkyl group, a $C_1$-$C_4$ hydroxyalkyl group, a $C_3$-$C_4$ cycloalkyl group, a —$(CH_2)_{0-3}NR'R''$ group, or a linear or branched $C_1$-$C_4$ alkyl group, which alkyl group is unsubstituted or substituted by a $C_1$-$C_3$ alkoxy group; wherein R' and R'' each independently represent a hydrogen atom, a hydroxyl group, or a linear or branched $C_1$-$C_3$ alkyl group.

More preferably, $R_6$ represents a hydrogen atom, a halogen atom, a $C_1$-$C_3$ alkoxy group, a $C_1$-$C_3$ haloalkyl group, a $C_3$-$C_4$ cycloalkyl group, a —$NH_2$ group, a —$N(CH_3)H$ group, a —$N(CH_3)_2$ group, or a linear or branched $C_1$-$C_4$ alkyl group, which alkyl group is unsubstituted or substituted by a $C_1$-$C_2$ alkoxy group. Even more preferably, $R_6$ represents a hydrogen atom, a halogen atom, a $C_1$-$C_3$ haloalkyl group (preferably a —$CHF_2$ group or a —$CF_3$ group), or a linear or branched $C_1$-$C_3$ alkyl group.

In one embodiment, in the compound of formula (I), $R_6$ represents a hydrogen atom, a halogen atom, a hydroxy group, a cyano group, a $C_1$-$C_4$ alkoxy group, a $C_1$-$C_4$ haloalkyl group, a $C_1$-$C_4$ hydroxyalkyl group, a $C_3$-$C_4$ cycloalkyl group, a —$(CH_2)_{0-3}$NR'R" group, or a linear or branched $C_1$-$C_4$ alkyl group, which alkyl group is unsubstituted or substituted by a $C_1$-$C_3$ alkoxy group; wherein R' and R" each independently represent a hydrogen atom, a hydroxyl group, or a linear or branched $C_1$-$C_3$ alkyl group. In this embodiment, preferably, $R_6$ represents a hydrogen atom, a halogen atom, a $C_1$-$C_3$ alkoxy group, a $C_1$-$C_3$ haloalkyl group, a $C_3$-$C_4$ cycloalkyl group, a —$NH_2$ group, a —$N(CH_3)H$ group, a —$N(CH_3)_2$ group, or a linear or branched $C_1$-$C_4$ alkyl group, which alkyl group is unsubstituted or substituted by a $C_1$-$C_2$ alkoxy group. In this embodiment, more preferably, $R_6$ represents a hydrogen atom, a halogen atom, a $C_1$-$C_3$ haloalkyl group (preferably a —$CHF_2$ group or a —$CF_3$ group), or a linear or branched $C_1$-$C_3$ alkyl group.

In a particular embodiment, $R_5$ represents a group selected from
i) a group of formula (IIa-1), and

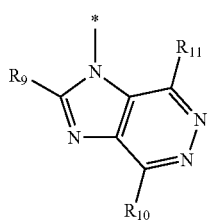

formula (IIa-1)

ii) a group of formula (IIa-2)

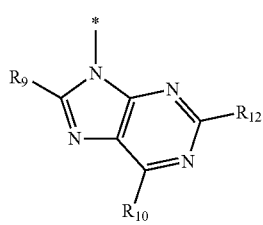

formula (IIa-2)

wherein
$R_9$, $R_{10}$, $R_{11}$ and $R_{12}$ each independently represent a hydrogen atom, a $C_1$-$C_4$ alkoxy group, a $C_1$-$C_4$ haloalkyl group, a $C_1$-$C_4$ hydroxyalkyl group, a $C_3$-$C_4$ cycloalkyl group, a —$(CH_2)_{0-3}$CN group, a —$C(O)$—$(CH_2)_{1-3}$—CN group, a —$C(O)$—$(CH_2)_{0-3}$—R' group, a —$C(O)$—$(CH_2)_{0-3}$—NR'R", a —$(CH_2)_{0-3}$NR'R" group, or a linear or branched $C_1$-$C_4$ alkyl group, which alkyl group is unsubstituted or substituted by one or more substituents selected from a $C_1$-$C_4$ alkoxy group, a cyano group or a $C_3$-$C_4$ cycloalkyl group; wherein R' and R" each independently represent a hydrogen atom, a hydroxyl group, a $C_1$-$C_4$ alkoxy group or a linear or branched $C_1$-$C_4$ alkyl group.

In this particular embodiment, preferably $R_5$ represents a group of formula (IIa-2) wherein $R_9$, $R_{10}$ and $R_{12}$ each independently represent a hydrogen atom, a —$(CH_2)_{0-3}$CN group, a —$C(O)$—$(CH_2)_{1-3}$—CN group, a —$C(O)$—$(CH_2)_{0-3}$—R' group, a —$C(O)$—$(CH_2)_{0-3}$—NR'R", a —$(CH_2)_{0-3}$NR'R" group, or a linear or branched $C_1$-$C_4$ alkyl group; wherein R' and R" each independently represent a hydrogen atom, a hydroxyl group, a $C_1$-$C_4$ alkoxy group or a linear or branched $C_1$-$C_4$ alkyl group. More preferably, $R_9$ and $R_{12}$ each independently represent a hydrogen atom and $R_{10}$ represents a —$(CH_2)_{0-3}$NR'R" group wherein R' and R" each independently represent a hydrogen atom or methyl group. Even more preferably, $R_9$ and $R_{12}$ each independently represent a hydrogen atom and $R_{10}$ represents a —$NH_2$ group.

In another particular embodiment, $R_5$ represents a group selected from
i) a group of formula (IIb-1),

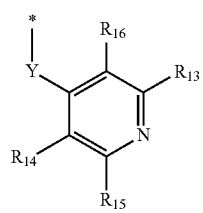

formula (IIb-1)

ii) a group of formula (IIb-2),

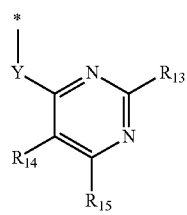

formula (IIb-2)

iii) a group of formula (IIb-3),

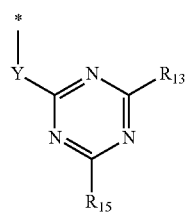

formula (IIb-3)

iv) a group of formula (IIb-4), and

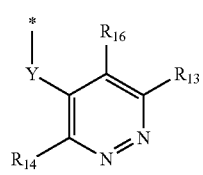

formula (IIb-4)

v) a group of formula (IIb-5),

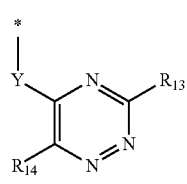

formula (IIb-5)

wherein
$R_{13}$, $R_{14}$, $R_{15}$ and $R_{16}$ each independently represent a hydrogen atom, a halogen atom; a $C_1$-$C_4$ alkoxy group;

a $C_1$-$C_4$ haloalkyl group; a $C_1$-$C_4$ hydroxyalkyl group; a $C_3$-$C_4$ cycloalkyl group, a —$(CH_2)_{0-3}CN$ group, a —C(O)—$(CH_2)_{1-3}$—CN group; a —C(O)—$(CH_2)_{0-3}$—R' group; a —C(O)—$(CH_2)_{0-3}$—NR'R"; a —$(CH_2)_{0-3}$NR'R" group; or a linear or branched $C_1$-$C_4$ alkyl group, which alkyl group is unsubstituted or substituted by one or more substituents selected from a $C_1$-$C_4$ alkoxy group, a cyano group or a $C_3$-$C_4$ cycloalkyl group;

wherein R' and R" each independently represent a hydrogen atom, a hydroxy group, a $C_1$-$C_4$ alkoxy group or a linear or branched $C_1$-$C_4$ alkyl group; and wherein Y represents a linker selected from a —NR'— group, —O— or —S—; wherein R' is as defined above;

or in the case that Y represents a —NR'— group, $R_4$ together with the —NR'— group and the carbon atom to which both $R_4$ and the —NR'— group are bonded form a 4- to 7-membered, saturated N-containing heterocyclyl group, which heterocyclyl group is unsubstituted or substituted by one or more substituents selected from a halogen atom, a hydroxyl group, a cyano group, a —$CHF_2$ group or a —$CF_3$ group.

In this particular embodiment, preferably $R_5$ represents a group selected from a group of formula (IIb-1), group of formula (IIb-2) and a group of formula (IIb-3) wherein $R_{13}$, $R_{14}$, $R_{15}$ and $R_{16}$ each independently represent a hydrogen atom, a halogen atom, a —$(CH_2)_{0-3}CN$ group, a —C(O)—$(CH_2)_{0-3}$—NR'R" or a —$(CH_2)_{0-3}$NR'R" group;

wherein R' and R" each independently represent a hydrogen atom or a linear or branched $C_1$-$C_4$ alkyl group; and wherein Y represents a —NR'— group, wherein R' is as defined before.

Preferably, when $R_5$ is a group of formula (IIb-1) $R_{14}$ and $R_{16}$ each independently represent a hydrogen atom, and $R_{13}$ and $R_{15}$ each independently represent a hydrogen atom, a —C(O)—$(CH_2)_{0-3}$—NR'R" or a —$(CH_2)_{0-3}$NR'R" group; wherein R' and R" each independently represent a hydrogen atom, a hydroxyl group, or a linear or branched $C_1$-$C_3$ alkyl group; wherein Y represents a —NR'— group, wherein R' is as defined before. Even more preferably, $R_{14}$ and $R_{16}$ each independently represent a hydrogen atom, and $R_{13}$ and $R_{15}$ each independently represent a hydrogen atom, a —C(O)—NR'R' group or a —NR'R" group; wherein R' and R" each independently represent a hydrogen atom or a methyl group; wherein Y represents a —NH— group.

Preferably, when $R_5$ is a group of formula (IIb-2) $R_{13}$ represents a hydrogen atom, and $R_{14}$ and $R_{15}$ each independently represent a hydrogen atom, a halogen atom, a —$(CH_2)_{0-3}CN$ group, a —C(O)—$(CH_2)_{0-3}$—NR'R" or a —$(CH_2)_{0-3}$NR'R" group; wherein R' and R" each independently represent a hydrogen atom, a hydroxy group, or a linear or branched $C_1$-$C_3$ alkyl group; wherein Y represents a —NR'— group, wherein R' is as defined before. Even more preferably, $R_{13}$ represents a hydrogen atom, and $R_{14}$ and $R_{15}$ each independently represent a hydrogen atom, a halogen atom, a —CN group or a —NR'R" group; wherein R' and R" each independently represent a hydrogen atom or a methyl group; and wherein Y represents a —NH— group. Still more preferably, $R_{13}$ represents a hydrogen atom, and $R_{14}$ and $R_{15}$ each independently represent a hydrogen atom, a —CN group or a —$NH_2$ group.

In a particular embodiment, when $R_5$ is a group of formula (IIb-2) $R_{13}$ represents a hydrogen atom, and $R_{14}$ and $R_{15}$ each independently represent a hydrogen atom, a halogen atom, a —$(CH_2)_{0-3}CN$ group, a —C(O)—$(CH_2)_{0-3}$—NR'R" or a —$(CH_2)_{0-3}$NR'R" group; wherein R' and R" each independently represent a hydrogen atom, a hydroxyl group, or a linear or branched $C_1$-$C_3$ alkyl group; wherein Y represents a —NR'— group, wherein R' is as defined before.

Even more preferably, when $R_5$ is a group of formula (IIb-2) $R_{13}$ represents a hydrogen atom, and $R_{14}$ and $R_{15}$ each independently represent a hydrogen atom, a halogen atom, a —CN group or a —NR'R" group; wherein R' and R" each independently represent a hydrogen atom or a methyl group; and wherein Y represents a —NH— group. Still more preferably, when $R_5$ is a group of formula (IIb-2) $R_{13}$ represents a hydrogen atom, and $R_{14}$ and $R_{15}$ each independently represent a hydrogen atom, a —CN group or a —$NH_2$ group.

Preferably, when $R_5$ is a group of formula (IIb-3) $R_{13}$ and $R_{15}$ each independently represent a hydrogen atom, a —C(O)—$(CH_2)_{0-3}$—NR'R" or a —$(CH_2)_{0-3}$NR'R" group; wherein R' and R" each independently represent a hydrogen atom, a hydroxyl group, or a linear or branched $C_1$-$C_3$ alkyl group; wherein Y represents a —NR'— group, wherein R' is as defined before. Even more preferably $R_{13}$ and $R_{15}$ each independently represent a hydrogen atom, a —C(O)—NR'R' group or a —NR'R" group; wherein R' and R" each independently represent a hydrogen atom or a methyl group; wherein Y represents a a —NH— group. Still more preferably, $R_{13}$ and $R_{15}$ each independently represent a hydrogen atom, a —CN group or a —$NH_2$ group.

In a particular embodiment, when $R_5$ represents a group selected from a group of formula (IIb-1), a group of formula (IIb-2), a group of formula (IIb-3), a group of formula (IIb-4), and a group of formula (IIb-3) as described above, $R_{13}$, $R_{14}$, $R_{15}$ and $R_{16}$ each independently represent a hydrogen atom, a $C_1$-$C_4$ alkoxy group, a $C_1$-$C_4$ haloalkyl group, a $C_1$-$C_4$ hydroxyalkyl group, a $C_3$-$C_4$ cycloalkyl group, a —$(CH_2)_{0-3}CN$ group, a —C(O)—$(CH_2)_{1-3}$—CN group, a —C(O)—$(CH_2)_{0-3}$—R' group, a —C(O)—$(CH_2)_{0-3}$—NR'R", a —$(CH_2)_{0-3}$NR'R" group, or a linear or branched $C_1$-$C_4$ alkyl group, which alkyl group is unsubstituted or substituted by one or more substituents selected from a $C_1$-$C_4$ alkoxy group, a cyano group or a $C_3$-$C_4$ cycloalkyl group; wherein R' and R" each independently represent a hydrogen atom, a hydroxy group, a $C_1$-$C_4$ alkoxy group or a linear or branched $C_1$-$C_4$ alkyl group; and wherein Y represents a linker selected from a —NR'— group, —O— or —S—; wherein R' is as defined above;

or in the case that Y represents a —NR'— group, $R_4$ together with the —NR'— group and the carbon atom to which both $R_4$ and the —NR'— group are bonded form a 4- to 7-membered, saturated N-containing heterocyclyl group, which heterocyclyl group is unsubstituted or substituted by one or more substituents selected from a halogen atom, a hydroxyl group, a cyano group, a —$CHF_2$ group or a —$CF_3$ group.

In this particular embodiment, preferably $R_5$ represents a group selected from a group of formula (IIb-1) and a group of formula (IIb-2) wherein $R_{13}$, $R_{14}$, $R_{15}$ and $R_{16}$ each independently represent a hydrogen atom, a —$(CH_2)_{0-3}CN$ group, a —C(O)—$(CH_2)_{0-3}$—NR'R" or a —$(CH_2)_{0-3}$NR'R" group; wherein R' and R" each independently represent a hydrogen atom or a linear or branched $C_1$-$C_4$ alkyl group; and wherein Y represents a —NR'— group, wherein R' is as defined before.

In this particular embodiment, preferably, when $R_5$ is a group of formula (IIb-1) $R_{14}$ and $R_{16}$ each independently represent a hydrogen atom, and $R_{13}$ and $R_{15}$ each independently represent a hydrogen atom, a —C(O)—$(CH_2)_{0-3}$—NR'R" or a —$(CH_2)_{0-3}$NR'R" group; wherein R' and R" each independently represent a hydrogen atom, a hydroxy group, or a linear or branched $C_1$-$C_3$ alkyl group; wherein Y represents a —NR'— group, wherein R' is as defined before. Even more preferably, $R_{14}$ and $R_{16}$ each independently represent a hydrogen atom, and $R_{13}$ and $R_{15}$ each independently represent a hydrogen atom, a —C(O)—NR'R' group or a —NR'R" group; wherein R' and R" each independently represent a hydrogen atom or a methyl group; wherein Y represents a —NH— group. In this particular embodiment, preferably, when $R_5$ is a group of formula (IIb-2) $R_{13}$ represents a hydrogen atom, and $R_{14}$ and $R_{15}$ each independently represent a hydrogen atom, a —(CH$_2$)$_{0-3}$CN group, a —C(O)—(CH$_2$)$_{0-3}$—NR'R" or a —(CH$_2$)$_{0-3}$NR'R" group; wherein R' and R" each independently represent a hydrogen atom, a hydroxy group, or a linear or branched $C_1$-$C_3$ alkyl group; wherein Y represents a —NR'— group, wherein R' is as defined before. Even more preferably, $R_{13}$ represents a hydrogen atom, and $R_{14}$ and $R_{15}$ each independently represent a hydrogen atom, a —CN group or a —NR'R" group; wherein R' and R" each independently represent a hydrogen atom or a methyl group; and wherein Y represents a —NH— group. Still more preferably, $R_{13}$ represents a hydrogen atom, and $R_{14}$ and $R_{15}$ each independently represent a hydrogen atom, a —CN group or a —NH$_2$ group.

In a further particular embodiment, $R_5$ represents a group selected from i) a group of formula (IIIa-1),

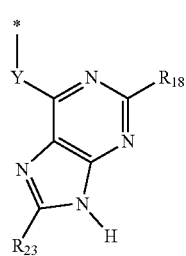

formula (IIIa-1)

ii) a group of formula (IIIa-2),

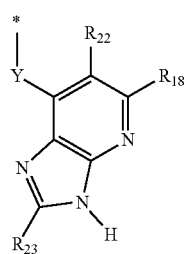

formula (IIIa-2)

iii) a group of formula (IIIa-3),

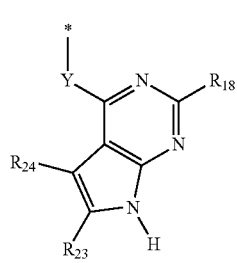

formula (IIIa-3)

iv) a group of formula (IIIa-4),

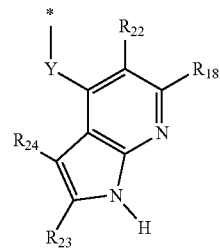

formula (IIIa-4)

v) a group of formula (IIIa-5),

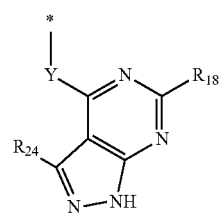

formula (IIIa-5)

vi) a group of formula (IIIa-6),

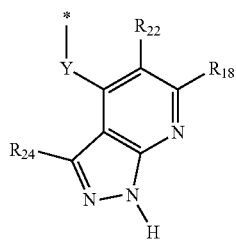

formula (IIIa-6)

vii) a group of formula (IIIa-7),

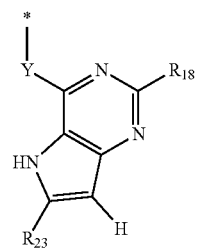

formula (IIIa-7)

viii) a group of formula (IIIa-8),

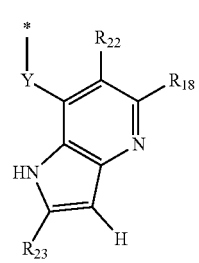

formula (IIIa-8)

ix) a group of formula (IIIa-9),

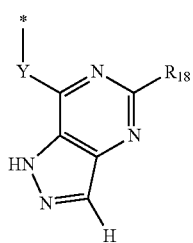

formula (IIIa-9)

x) a group of formula (IIIa-10),

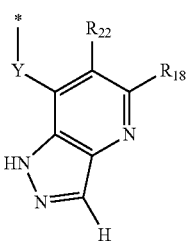

formula (IIIa-10)

xi) a group of formula (IIIa-11),

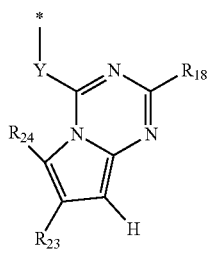

formula (IIIa-11)

xii) a group of formula (IIIa-12),

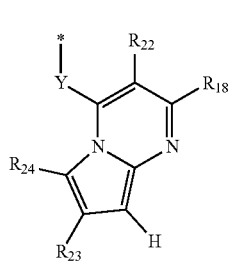

formula (IIIa-12)

xiii) a group of formula (IIIa-13),

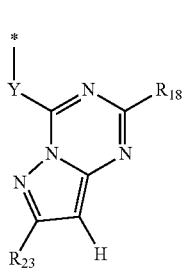

formula (IIIa-13)

xiv) a group of formula (IIIa-14),

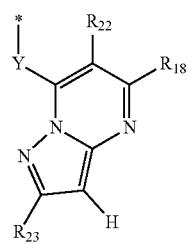

formula (IIIa-14)

xv) a group of formula (IIIa-15),

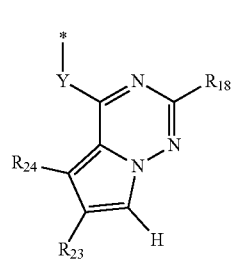

formula (IIIa-15)

xvi) a group of formula (IIIa-16),

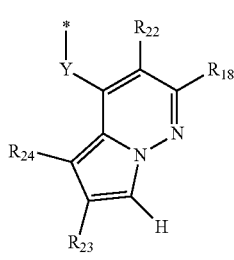

formula (IIIa-16)

xvii) a group of formula (IIIa-17),

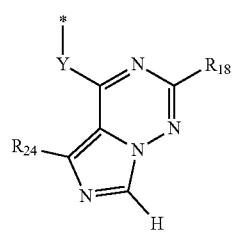

formula (IIIa-17)

xviii) a group of formula (IIIa-18),

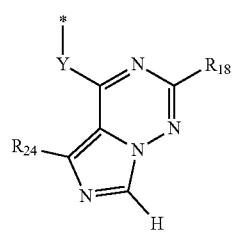

formula (IIIa-18)

xix) a group of formula (IIIa-19),

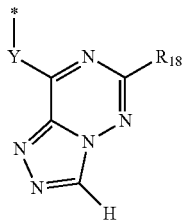

formula (IIIa-19)

xx) a group of formula (IIIa-20),

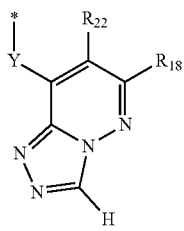

formula (IIIa-20)

xxi) a group of formula (IIIa-21), and

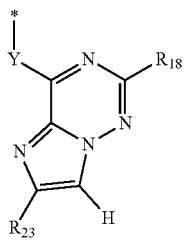

formula (IIIa-21)

xxii) a group of formula (IIIa-22),

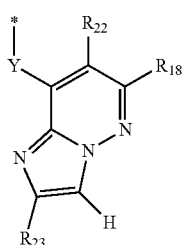

formula (IIIa-22)

wherein
$R_{18}$, $R_{22}$, $R_{23}$, and $R_{24}$ each independently represent a hydrogen atom, a halogen atom, a $C_1$-$C_4$ alkoxy group, a $C_1$-$C_4$ haloalkyl group, a $C_1$-$C_4$ hydroxyalkyl group, a $C_3$-$C_4$ cycloalkyl group, a —$(CH_2)_{0-3}$CN group, a —C(O)—$(CH_2)_{1-3}$—CN group, a —C(O)—$(CH_2)_{0-3}$—R' group, a —C(O)—$(CH_2)_{0-3}$—NR'R", a —$(CH_2)_{0-3}$NR'R" group, or a linear or branched $C_1$-$C_4$ alkyl group, which alkyl group is unsubstituted or substituted by one or more substituents selected from a $C_1$-$C_4$ alkoxy group, a cyano group or a $C_3$-$C_4$ cycloalkyl group; wherein R' and R" each independently represent a hydrogen atom, a hydroxy group, a $C_1$-$C_4$ alkoxy group or a linear or branched $C_1$-$C_4$ alkyl group; and wherein Y represents a linker selected from a —NR'— group, —O— or —S—; wherein R' is as defined above;

or in the case that Y represents a —NR'— group, $R_4$ together with the —NR'— group and the carbon atom to which both $R_4$ and the —NR'— group are bonded form a 4- to 7-membered, saturated N-containing heterocyclyl group, which heterocyclyl group is unsubstituted or substituted by one or more substituents selected from a halogen atom, a hydroxyl group, a cyano group, a —$CHF_2$ group or a —$CF_3$ group.

In this particular embodiment, preferably $R_5$ represents a group selected from a group of formula (IIIa-1), a group of formula (IIIa-3), a group of formula (IIIa-5) and a group of formula (IIIa-14) wherein $R_{18}$, $R_{22}$, $R_{23}$ and $R_{24}$ each independently represent a hydrogen atom, a halogen atom, a —$(CH_2)_{0-3}$CN group, a —C(O)—$(OH_2)_{1-3}$—CN group, a —C(O)—$(OH_2)_{0-3}$—R' group, a —C(O)—$(CH_2)_{0-3}$—NR'R", a —$(CH_2)_{0-3}$NR'R" group, or a linear or branched $C_1$-$C_4$ alkyl group; wherein R' and R" each independently represent a hydrogen atom, a hydroxyl group, a $C_1$-$C_4$ alkoxy group or a linear or branched $C_1$-$C_4$ alkyl group; and wherein Y is as defined above;

and wherein more preferably, $R_{18}$, $R_{22}$, $R_{23}$ and $R_{24}$ each independently represent a hydrogen atom, a halogen atom, a —CN group or a —$NH_2$ group;

or in the case that Y represents a —NR'— group, $R_4$ together with the —NR'— group and the carbon atom to which both $R_4$ and the —NR'— group are bonded form a 4- to 7-membered, saturated N-containing heterocyclyl group, which heterocyclyl group is unsubstituted or substituted by one or more substituents selected from a halogen atom, a hydroxyl group, a cyano group, a —$CHF_2$ group or a —$CF_3$ group.

In a particular embodiment, preferably $R_5$ represents a group of formula (IIIa-1), wherein $R_{18}$ and $R_{23}$ each independently represent a hydrogen atom, a —$(CH_2)_{0-3}$CN group, a —C(O)—$(CH_2)_{1-3}$—CN group, a —C(O)—$(CH_2)_{0-3}$—R' group, a —C(O)—$(CH_2)_{0-3}$—NR'R", a —$(CH_2)_{0-3}$NR'R" group, or a linear or branched $C_1$-$C_4$ alkyl group; wherein R' and R" each independently represent a hydrogen atom, a hydroxyl group, a $C_1$-$C_4$ alkoxy group or a linear or branched $C_1$-$C_4$ alkyl group; and wherein Y is as defined above;

or in the case that Y represents a —NR'— group, $R_4$ together with the —NR'— group and the carbon atom to which both $R_4$ and the —NR'— group are bonded form a 4- to 7-membered, saturated N-containing heterocyclyl group, which heterocyclyl group is unsubstituted or substituted by one or more substituents selected from a halogen atom, a hydroxyl group, a cyano group, a —$CHF_2$ group or a —$CF_3$ group.

In a particular embodiment, when $R_5$ is a group of formula (IIIa-1) $R_{18}$ and $R_{23}$ each independently represent a hydrogen atom, a —C(O)—$(CH_2)_{0-3}$—NR'R" or a —$(CH_2)_{0-3}$NR'R" group; wherein R' and R" each independently represent a hydrogen atom, a hydroxyl group, or a linear or branched $C_1$-$C_3$ alkyl group; wherein Y represents a —NR'— group or —S—, wherein R' is as defined before. Even more preferably, $R_{18}$ and $R_{23}$ each independently represent a hydrogen atom or a —NR'R" group; wherein R' and R" each independently represent a hydrogen atom or a methyl group; wherein Y represents a —NR'— group or —S—, wherein R' is as defined before.

Preferably, when $R_5$ is a group of formula (IIIa-1) wherein Y represents a —NR'— group, wherein R' is a linear or branched $C_1$-$C_4$ alkyl group; $R_4$ together with the —NR'— group and the carbon atom to which both $R_4$ and the —NR'— group are bonded form a 4- to 7-membered, saturated N-containing heterocyclyl group, which heterocyclyl group is unsubstituted or substituted by one or more substituents selected from a halogen atom, a hydroxyl group, a cyano group, a —$CHF_2$ group or a —$CF_3$ group. More preferably, $R_4$ together with the —NR'— group of $R_5$ and the carbon atom to which both $R_4$ and the —NR'— group are bonded form an azetidinyl group, a pyrrolidinyl group, a piperidinyl group or a piperazinyl group; even more preferably a pyrrolidinyl group or a piperidinyl group.

In a particular embodiment, $R_5$ represents a group of formula (IIIa-1), wherein $R_{18}$ and $R_{23}$ each independently represent a hydrogen atom, a —$(CH_2)_{0-3}CN$ group, a —$C(O)$—$(CH_2)_{1-3}$—CN group, a —$C(O)$—$(CH_2)_{0-3}$—R' group, a —$C(O)$—$(CH_2)_{0-3}$—NR'R'', a —$(CH_2)_{0-3}NR'R''$ group, or a linear or branched $C_1$-$C_4$ alkyl group; wherein R' and R'' each independently represent a hydrogen atom, a hydroxyl group, a $C_1$-$C_4$ alkoxy group or a linear or branched $C_1$-$C_4$ alkyl group; and wherein Y is as defined above;

or in the case that Y represents a —NR'— group, $R_4$ together with the —NR'— group and the carbon atom to which both $R_4$ and the —NR'— group are bonded form a 4- to 7-membered, saturated N-containing heterocyclyl group, which heterocyclyl group is unsubstituted or substituted by one or more substituents selected from a halogen atom, a hydroxyl group, a cyano group, a —$CHF_2$ group or a —$CF_3$ group.

In a particular embodiment, when $R_5$ represents a group selected from a group of formula (IIIa-1), a group of formula ((IIIa-2), a group of formula ((IIIa-3), a group of formula (IIIa-4), a group of formula (IIIa-5), a group of formula (IIIa-6), a group of formula ((IIIa-7), a group of formula (IIIa-8), a group of formula (IIIa-9), a group of formula (IIIa-10), a group of formula (IIIa-11), a group of formula (IIIa-12), a group of formula (IIIa-13), a group of formula (IIIa-14), a group of formula (IIIa-15), a group of formula (IIIa-16), a group of formula (IIIa-17), a group of formula (IIIa-18), a group of formula (IIIa-19), a group of formula (IIIa-20), a group of formula (IIIa-21), and a group of formula (IIIa-22), as described above, $R_{18}$, $R_{22}$, $R_{23}$, and $R_{24}$ each independently represent a hydrogen atom, a $C_1$-$C_4$ alkoxy group, a $C_1$-$C_4$ haloalkyl group, a $C_1$-$C_4$ hydroxyalkyl group, a $C_3$-$C_4$ cycloalkyl group, a —$(CH_2)_{0-3}CN$ group, a —$C(O)$—$(CH_2)_{1-3}$—CN group, a —$C(O)$—$(CH_2)_{0-3}$—R' group, a —$C(O)$—$(CH_2)_{0-3}$—NR'R'', a —$(CH_2)_{0-3}NR'R''$ group, or a linear or branched $C_1$-$C_4$ alkyl group, which alkyl group is unsubstituted or substituted by one or more substituents selected from a $C_1$-$C_4$ alkoxy group, a cyano group or a $C_3$-$C_4$ cycloalkyl group; wherein R' and R'' each independently represent a hydrogen atom, a hydroxy group, a $C_1$-$C_4$ alkoxy group or a linear or branched $C_1$-$C_4$ alkyl group; and wherein Y represents a linker selected from a —NR'— group, —O— or —S—; wherein R' is as defined above;

or in the case that Y represents a —NR'— group, $R_4$ together with the —NR'— group and the carbon atom to which both $R_4$ and the —NR'— group are bonded form a 4- to 7-membered, saturated N-containing heterocyclyl group, which heterocyclyl group is unsubstituted or substituted by one or more substituents selected from a halogen atom, a hydroxyl group, a cyano group, a —$CHF_2$ group or a —$CF_3$ group.

In this particular embodiment, preferably $R_5$ represents a group of formula (IIIa-1) wherein $R_{18}$ and $R_{23}$ each independently represent a hydrogen atom, a —$(CH_2)_{0-3}CN$ group, a —$C(O)$—$(CH_2)_{1-3}$—CN group, a —$C(O)$—$(CH_2)_{0-3}$—R' group, a —$C(O)$—$(CH_2)_{0-3}$—NR'R'', a —$(CH_2)_{0-3}NR'R''$ group, or a linear or branched $C_1$-$C_4$ alkyl group; wherein R' and R'' each independently represent a hydrogen atom, a hydroxy group, a $C_1$-$C_4$ alkoxy group or a linear or branched $C_1$-$C_4$ alkyl group; and wherein Y is as defined above;

or in the case that Y represents a —NR'— group, $R_4$ together with the —NR'— group and the carbon atom to which both $R_4$ and the —NR'— group are bonded form a 4- to 7-membered, saturated N-containing heterocyclyl group, which heterocyclyl group is unsubstituted or substituted by one or more substituents selected from a halogen atom, a hydroxyl group, a cyano group, a —$CHF_2$ group or a —$CF_3$ group.

In this embodiment, preferably, when $R_5$ is a group of formula (IIIa-1) $R_{18}$ and $R_{23}$ each independently represent a hydrogen atom, a —$C(O)$—$(CH_2)_{0-3}$—NR'R'' or a —$(CH_2)_{0-3}NR'R''$ group; wherein R' and R'' each independently represent a hydrogen atom, a hydroxy group, or a linear or branched $C_1$-$C_3$ alkyl group; wherein Y represents a —NR'— group or —S—, wherein R' is as defined before. Even more preferably, $R_{18}$ and $R_{23}$ each independently represent a hydrogen atom or a —NR'R'' group; wherein R' and R'' each independently represent a hydrogen atom or a methyl group; wherein Y represents a —NR'— group or —S—, wherein R' is as defined before.

In this embodiment, preferably, when $R_5$ is a group of formula (IIIa-1) wherein Y represents a —NR'— group, wherein R' is a linear or branched $C_1$-$C_4$ alkyl group; $R_4$ together with the —NR'— group and the carbon atom to which both $R_4$ and the —NR'— group are bonded form a 4- to 7-membered, saturated N-containing heterocyclyl group, which heterocyclyl group is unsubstituted or substituted by one or more substituents selected from a halogen atom, a hydroxyl group, a cyano group, a —$CHF_2$ group or a —$CF_3$ group. More preferably, $R_4$ together with the —NR'— group of $R_5$ and the carbon atom to which both $R_4$ and the —NR'— group are bonded form an azetidinyl group, a pyrrolidinyl group, a piperidinyl group or a piperazinyl group; even more preferably a pyrrolidinyl group or a piperidinyl group.

In another particular embodiment, $R_5$ represents a group selected from
i) a group of formula (IIIb-1),

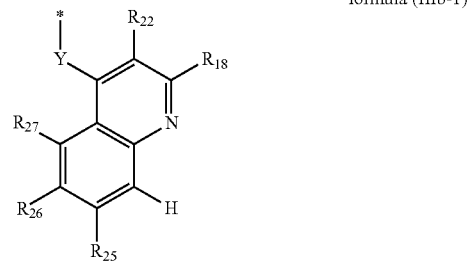

formula (IIIb-1)

ii) a group of formula (IIIb-2),

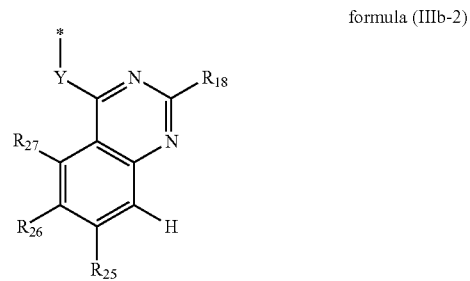

formula (IIIb-2)

iii) a group of formula (IIIb-3), formula (IIIb-3)

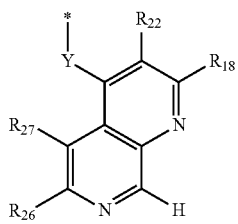

iv) a group of formula (IIIb-4), formula (IIIb-4)

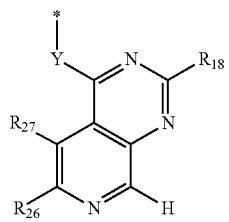

v) a group of formula (IIIb-5), formula (IIIb-5)

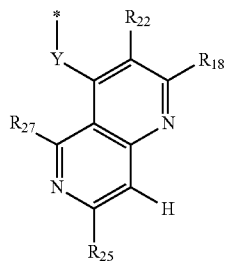

vi) a group of formula (IIIb-6), formula (IIIb-6)

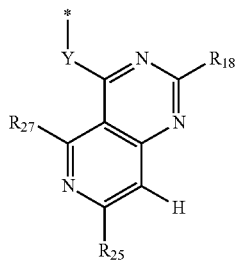

vii) a group of formula (IIIb-7), and formula (IIIb-7)

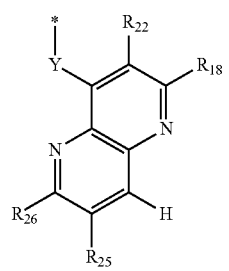

viii) a group of formula (IIIb-8), formula (IIIb-8)

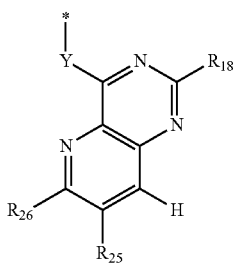

wherein $R_{18}$, $R_{22}$, $R_{25}$, $R_{26}$, and $R_{27}$ each independently represent a hydrogen atom, a $C_1$-$C_4$ alkoxy group, a $C_1$-$C_4$ haloalkyl group, a $C_1$-$C_4$ hydroxyalkyl group, a $C_3$-$C_4$ cycloalkyl group, a —$(CH_2)_{0-3}$CN group, a —C(O)—$(CH_2)_{1-3}$—CN group, a —C(O)—$(CH_2)_{0-3}$—R' group, a —C(O)—$(CH_2)_{0-3}$—NR'R", a —$(CH_2)_{0-3}$NR'R" group, or a linear or branched $C_1$-$C_4$ alkyl group, which alkyl group is unsubstituted or substituted by one or more substituents selected from a $C_1$-$C_4$ alkoxy group, a cyano group or a $C_3$-$C_4$ cycloalkyl group; wherein R' and R" each independently represent a hydrogen atom, a hydroxyl group, a $C_1$-$C_4$ alkoxy group or a linear or branched $C_1$-$C_4$ alkyl group; and wherein Y represents a linker selected from a —NR'— group, —O— or —S—; wherein R' is as defined above;

or in the case that Y represents a —NR'— group, $R_4$ together with the —NR'— group and the carbon atom to which both $R_4$ and the —NR'— group are bonded form a 4- to 7-membered, saturated N-containing heterocyclyl group, which heterocyclyl group is unsubstituted or substituted by one or more substituents selected from a halogen atom, a hydroxyl group, a cyano group, a —$CHF_2$ group or a —$CF_3$ group.

In a further particular embodiment, $R_5$ represents a group selected from i) a group of formula (IIIc-1), and formula (IIIc-1)

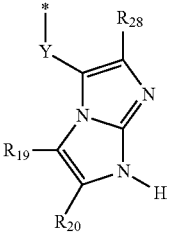

ii) a group of formula (IIIc-2), formula IIIc-2)

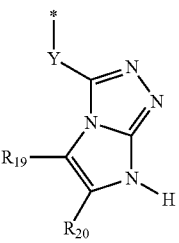

wherein

R$_{19}$, R$_{20}$, and R$_{28}$ each independently represent a hydrogen atom, a C$_1$-C$_4$ alkoxy group, a C$_1$-C$_4$ haloalkyl group, a C$_1$-C$_4$ hydroxyalkyl group, a C$_3$-C$_4$ cycloalkyl group, a —(CH$_2$)$_{0-3}$CN group, a —C(O)—(CH$_2$)$_{1-3}$—CN group, a —C(O)—(CH$_2$)$_{0-3}$—R' group, a —C(O)—(CH$_2$)$_{0-3}$—NR'R", a —(CH$_2$)$_{0-3}$NR'R" group, or a linear or branched C$_1$-C$_4$ alkyl group, which alkyl group is unsubstituted or substituted by one or more substituents selected from a C$_1$-C$_4$ alkoxy group, a cyano group or a C$_3$-C$_4$ cycloalkyl group; wherein R' and R" each independently represent a hydrogen atom, a hydroxyl group, a C$_1$-C$_4$ alkoxy group or a linear or branched C$_1$-C$_4$ alkyl group; and wherein Y represents a linker selected from a —NR'— group, —O— or —S—; wherein R' is as defined above;

or in the case that Y represents a —NR'— group, R$_4$ together with the —NR'— group and the carbon atom to which both R$_4$ and the —NR'— group are bonded form a 4- to 7-membered, saturated N-containing heterocyclyl group, which heterocyclyl group is unsubstituted or substituted by one or more substituents selected from a halogen atom, a hydroxyl group, a cyano group, a —CHF$_2$ group or a —CF$_3$ group.

In another particular embodiment, R$_5$ represents a group selected from i) a group of formula (IIId-1),

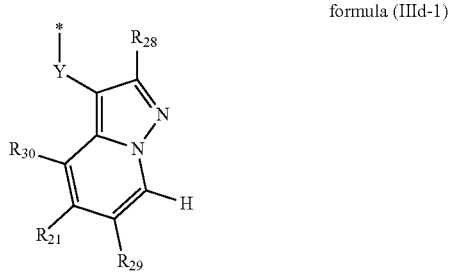

formula (IIId-1)

ii) a group of formula (IIId-2), and

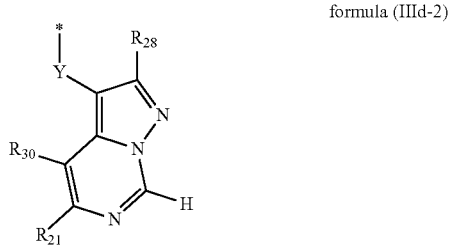

formula (IIId-2)

ii) a group of formula (IIId-3),

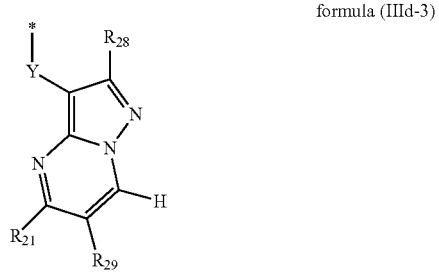

formula (IIId-3)

wherein

R$_{21}$, R$_{28}$, R$_{29}$, and R$_{30}$ each independently represent a hydrogen atom, a C$_1$-C$_4$ alkoxy group, a C$_1$-C$_4$ haloalkyl group, a C$_1$-C$_4$ hydroxyalkyl group, a C$_3$-C$_4$ cycloalkyl group, a —(CH$_2$)$_{0-3}$CN group, a —C(O)—(CH$_2$)$_{1-3}$—CN group, a —C(O)—(CH$_2$)$_{0-3}$—R' group, a —C(O)—(CH$_2$)$_{0-3}$—NR'R", a —(CH$_2$)$_{0-3}$NR'R" group, or a linear or branched C$_1$-C$_4$ alkyl group, which alkyl group is unsubstituted or substituted by one or more substituents selected from a C$_1$-C$_4$ alkoxy group, a cyano group or a C$_3$-C$_4$ cycloalkyl group; wherein R' and R" each independently represent a hydrogen atom, a hydroxyl group, C$_1$-C$_4$ alkoxy group or a linear or branched C$_1$-C$_4$ alkyl group; and wherein Y represents a linker selected from a —NR'— group, —O— or —S—; wherein R' is as defined above;

or in the case that Y represents a —NR'— group, R$_4$ together with the —NR'— group and the carbon atom to which both R$_4$ and the —NR'— group are bonded form a 4- to 7-membered, saturated N-containing heterocyclyl group, which heterocyclyl group is unsubstituted or substituted by one or more substituents selected from a halogen atom, a hydroxyl group, a cyano group, a —CHF$_2$ group or a —CF$_3$ group.

Typically, in the compound of formula (I), Y represents a linker selected from a —NR'— group, —O— or —S—; wherein R' represents a hydrogen atom, a hydroxyl group, a C$_1$-C$_4$ alkoxy group or a linear or branched C$_1$-C$_4$ alkyl group. Preferably Y represents a linker selected from a —NR'— group or —S—; wherein R' represents a hydrogen atom, a hydroxyl group, a C$_1$-C$_4$ alkoxy group or a linear or branched C$_1$-C$_4$ alkyl group. More preferably Y represents a linker selected from a —NR'— group or —S—; wherein R' represents a hydrogen atom or a linear or branched C$_1$-C$_3$ alkyl group. Most preferably Y represents a —NR'— group; wherein R' represents a hydrogen atom or a linear or branched C$_1$-C$_3$ alkyl group.

When R' and/or R" are attached to a nitrogen atom, preferably R' and/or R" do not represent a hydroxyl group or alkoxy group.

Where any of the above moieties represent —C(O)—(CH$_2$)$_{0-3}$—R$_8$ or —C(O)—(CH$_2$)$_{0-3}$—R', it is preferable that R$_8$ and R' do not represent a hydrogen atom if the alkylene spacer moiety is absent.

Preferably in the compound of formula (I):

R$_a$ and R$_b$ each independently represent a hydrogen atom or a linear or branched C$_1$-C$_3$ alkyl group;

n represents 0, 1 or 2;

R$_1$ represents a hydrogen atom, a linear or branched C$_1$-C$_4$ alkyl group, a C$_1$-C$_4$ haloalkyl group, a C$_3$-C$_7$ cycloalkyl group, a phenyl group, a 5- to 10-membered monocyclic or bicyclic heteroaryl group containing one, two or three heteroatoms selected from O, S and N, a pyrrolidinyl group, a piperidinyl group, a piperazinyl group, a tetrahydropyranyl group or a morpholinyl group;

wherein the cycloalkyl, phenyl, heteroaryl, pyrrolidinyl, piperidinyl, piperazinyl, tetrahydropyranyl or morpholinyl groups are unsubstituted or substituted by one or more substituents selected from a halogen atom, a hydroxyl group, a linear or branched C$_1$-C$_4$ alkyl group, a C$_1$-C$_4$ haloalkyl group, a C$_1$-C$_4$ hydroxyalkyl group, a C$_3$-C$_4$ cycloalkyl group, a —(CH$_2$)$_{0-3}$OR$_8$ group, a —(CH$_2$)$_{0-3}$NR$_7$R$_8$ group, a —C(O)—(OH$_2$)$_{0-3}$—R$_8$ group, a —C(O)—(OH$_2$)$_{0-3}$—NR$_7$R$_0$ group or a —(CH$_2$)$_{0-3}$(phenyl)-OR$_8$ group; wherein R$_7$ and R$_8$ each independently represent a hydrogen atom or a C$_1$-C$_4$ alkyl group;

R$_2$ represents a hydrogen atom, a halogen atom, a hydroxyl group, a C$_1$-C$_3$ alkoxy group, a C$_1$-C$_3$ haloalkyl group, a C$_3$-C$_4$ cycloalkyl group, a —NH$_2$ group, a —N(CH$_3$)H group, a —N(CH$_3$)$_2$ group, or a linear or branched C$_1$-C$_4$ alkyl group, which alkyl group is unsubstituted or substituted by a $C_1$-$C_2$ alkoxy group;

$R_3$ represents a hydrogen atom, a halogen atom, a hydroxyl group, a cyano group, a $C_1$-$C_3$ alkoxy group, a $C_1$-$C_3$ haloalkyl group, a $C_3$-$C_4$ cycloalkyl group, a —$NH_2$ group, a —$N(CH_3)H$ group, a —$N(CH_3)_2$ group, or a linear or branched $C_1$-$C_4$ alkyl group, which alkyl group is unsubstituted or substituted by a $C_1$-$C_2$ alkoxy group;

$R_4$ represents a hydrogen atom, a $C_1$-$C_3$ alkoxy group, a $C_1$-$C_3$ haloalkyl group, a $C_1$-$C_4$ hydroxyalkyl group, a $C_3$-$C_4$ cycloalkyl group, or a linear or branched $C_1$-$C_3$ alkyl group;

$R_6$ represents a hydrogen atom; a halogen atom; a hydroxyl group; a cyano group; a $C_1$-$C_3$ alkoxy group; a $C_1$-$C_3$ haloalkyl group; a linear or branched $C_1$-$C_4$ hydroxyalkyl group; a $C_3$-$C_4$ cycloalkyl group; a —$(CH_2)_{0-3}NR'R''$ group; a —$(CH_2)_{1-3}O(C_1$-$C_4$ alkyl group); a —$(CH_2)_{0-3}$OC(O)—($C_1$-$C_4$ alkyl group); a —$(CH_2)_{0-3}C(O)O$—($C_1$-$C_4$ alkyl group); a —C(O)—$(CH_2)_{0-3}$—$NR'R''$ group; a —$(CH_2)_{0-3}C(O)OH$ group; a —$(CH_2)_{0-3}$-(5- to 14-membered monocyclic or bicyclic heteroaryl group containing at least one heteroatom selected from O, S and N); a —$(CH_2)_{0-3}$-(5- to 14-membered monocyclic or bicyclic heterocyclyl group containing at least one heteroatom selected from O, S and N);

or a linear or branched $C_1$-$C_4$ alkyl group, which alkyl group is unsubstituted or substituted by a $C_1$-$C_2$ alkoxy group;

wherein the heteroaryl and heterocyclyl groups are unsubstituted or substituted by one or more substituents selected from a halogen atom, a hydroxyl group, a cyano group, a linear or branched $C_1$-$C_4$ alkyl group or a $C_1$-$C_4$ haloalkyl group, $R_5$ represents a moiety of formula (II-a2), (IIb-1), (IIb-2), (IIb-3), (IIIa-1), (IIIa-3), (IIIa-5) or (IIIa-14):

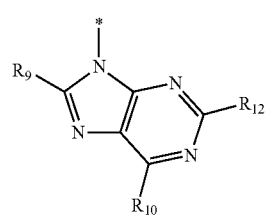

formula (IIa-2)

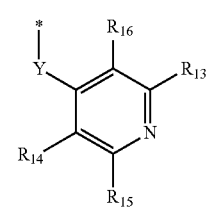

formula (IIb-1)

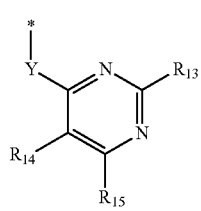

formula (IIb-2)

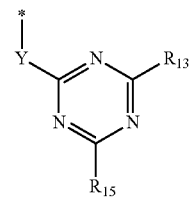

formula (IIb-3)

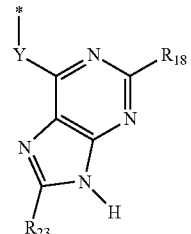

formula (IIIa-1)

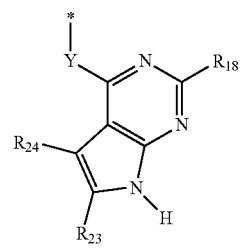

formula (IIIa-3)

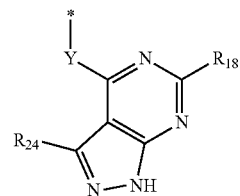

formula (IIIa-5)

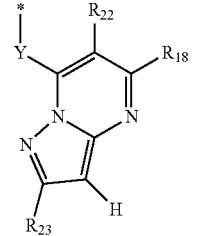

formula (IIIa-14)

wherein:

$R_9$, $R_{10}$, and $R_{12}$ each independently represent a hydrogen atom, a —$(CH_2)_{0-3}CN$ group, a —C(O)—$(CH_2)_{1-3}$—CN group, a —C(O)—$(CH_2)_{0-3}$—R' group, a —C(O)—$(CH_2)_{0-3}$—$NR'R''$, a —$(CH_2)_{0-3}NR'R''$ group, or a linear or branched $C_1$-$C_4$ alkyl group; wherein R' and R'' each independently represent a hydrogen atom, a hydroxyl group, a $C_1$-$C_4$ alkoxy group or a linear or branched $C_1$-$C_4$ alkyl group;

$R_{13}$, $R_{14}$, $R_{15}$ and $R_{16}$ each independently represent a hydrogen atom, a halogen atom, a $C_1$-$C_4$ haloalkyl group, a —$(CH_2)_{0-3}CN$ group, a —C(O)—$(CH_2)_{0-3}$—$NR'R''$, a —$(CH_2)_{0-3}NR'R''$ group; a phenyl group, which phenyl group is unsubstituted or substituted by one or more substituents selected from a halogen atom or a hydroxyl group; a 5- to 7-membered monocyclic heteroaryl group containing at least one heteroatom selected from O, S and N, which heteroaryl group is unsubstituted or substituted by one or more substituents selected from a halogen atom, a linear or branched $C_1$-$C_4$ alkyl group, a $C_1$-$C_4$ haloalkyl group, a $C_1$-$C_4$ hydroxyalkyl group or a —$(CH_2)_{0-3}$NR'R" group; wherein R' and R" each independently represent a hydrogen atom or a linear or branched $C_1$-$C_4$ alkyl group;

$R_{18}$, $R_{22}$, $R_{23}$ and $R_{24}$ each independently represent a hydrogen atom, a halogen atom, a —$(CH_2)_{0-3}$CN group, a —C(O)—$(CH_2)_{1-3}$—CN group, a —C(O)—$(CH_2)_{0-3}$—R' group, a —C(O)—$(CH_2)_{0-3}$—NR'R", a —$(CH_2)_{0-3}$NR'R" group, or a linear or branched $C_1$-$C_4$ alkyl group; wherein R' and R" each independently represent a hydrogen atom, a hydroxyl group, a $C_1$-$C_4$ alkoxy group or a linear or branched $C_1$-$C_4$ alkyl group;

Y represents a —NR'— group, —O— or —S—; wherein R' represents hydrogen or a linear or branched $C_1$-$C_4$ alkyl group; or in the case that Y represents a —NR'— group, $R_4$ together with the —NR'— group and the carbon atom to which both $R_4$ and the —NR'— group are bonded form a 4- to 7-membered, saturated N-containing heterocyclyl group, which heterocyclyl group is unsubstituted or substituted by one or more substituents selected from a halogen atom, a hydroxyl group, a cyano group, a —$CHF_2$ group or a —$CF_3$ group.

In a particular preferred embodiment, in the compound of formula (I)

X represents a nitrogen atom or a —$CR_6$ group;

$R_a$ and $R_b$ each independently represent a hydrogen atom or a methyl group;

$R_1$ represents a hydrogen atom, a halogen atom, a $C_1$-$C_3$ haloalkyl group, a methyl group, a $C_3$-$C_7$ cycloalkyl group, a phenyl group, a pyridinyl group, a pyrazolyl group, an isoxazolyl group, a piperidinyl group or a tetrahydropyranyl group;

wherein the cycloalkyl, phenyl, pyridinyl, pyrazolyl, isoxazolyl, piperidinyl or tetrahydropyranyl groups are unsubstituted or substituted by one or more substituents selected from a halogen atom, a hydroxyl group, a $C_1$-$C_3$ haloalkyl group, a linear or branched $C_1$-$C_3$ alkyl group, a —$(CH_2)$-(phenyl)-O—$(C_1$-$C_3$ alkyl group), a —$NR_7R_8$ group or a —$OR_8$ group; wherein $R_7$ and $R_8$ each independently represent a hydrogen atom or a linear or branched $C_1$-$C_3$ alkyl group;

$R_2$ and $R_3$ each independently represent a hydrogen atom, a halogen atom, a cyano group, a $C_1$-$C_3$ haloalkyl group or a linear or branched $C_1$-$C_3$ alkyl group;.

$R_4$ represents a hydrogen atom, a $C_1$-$C_3$ haloalkyl group, a $C_1$-$C_3$ hydroxyalkyl group or a linear or branched $C_1$-$C_3$ alkyl group;

$R_6$ represents a hydrogen atom, a halogen atom, a $C_1$-$C_3$ haloalkyl group, a linear or branched $C_1$-$C_3$ hydroxyalkyl group, a linear or branched $C_1$-$C_3$ alkyl group or a cyclopropyl group;

$R_6$ represents a hydrogen atom; a halogen atom; a hydroxyl group; a cyano group; a $C_1$-$C_4$ alkoxy group; a $C_1$-$C_4$ haloalkyl group; a linear or branched $C_1$-$C_4$ hydroxyalkyl group; a $C_3$-$C_7$ cycloalkyl group; a linear or branched $C_1$-$C_3$ alkyl group; a —$(CH_2)_{0-3}$NR'R" group; a —$(CH_2)_{1-3}$O($C_1$-$C_3$ alkyl group); a —$(CH_2)_{0-3}$OC(O)—($C_1$-$C_3$ alkyl group); a —$(CH_2)_{0-3}$C(O)O—($C_1$-$C_3$ alkyl group); a —C(O)—NR'R" group; a —$(CH_2)_{0-3}$C(O)OH group; a —$(OH_2)_{0-3}$-(imidazolyl group); a —$(CH_2)_{0-3}$-(oxazolylgroup); a —$(CH_2)_{0-3}$-(oxadiazolylgroup); a —$(CH_2)_{0-3}$-(pyrazolylgroup) or a —$(CH_2)_{0-3}$-(morpholinyl group); wherein R' and R" each independently represent a hydrogen atom, a hydroxyl group, or a linear or branched $C_1$-$C_3$ alkyl group; and wherein the imidazolyl, oxazolyl, oxadiazolyl, pyrazolyl and morpholinyl groups are unsubstituted or substituted by one or more substituents selected from a halogen atom, a linear or branched $C_1$-$C_3$ alkyl group or a $C_1$-$C_3$ haloalkyl group;

$R_5$ represents a group selected from:
i) a group of formula (IIa), which group is a purinyl group unsubstituted or substituted by a —NR'R" group;
ii) a group of formula (IIb), which group is selected from a —NR'-pyridinyl group, a —S-pyridinyl group, a —NR'-pyrimidinyl group, a —S-pyrimidinyl group or a —NR'-triazinyl group; wherein the pyridinyl, pyrimidinyl and triazinyl groups are unsubstituted or substituted by one, two or three substituents selected from a halogen atom, a $C_1$-$C_3$ haloalkyl group, a —$(CH_2)_{0-3}$CN group, a —C(O)—$(CH_2)_{0-3}$—NR'R", a —$(CH_2)_{0-3}$NR'R" group; and
iii) a group of formula (IIc), which group is selected from a —NR'-purinyl group, a —S-purinyl group, a —NR'-7H-pyrrolo[2,3-d]pyrimidinyl group, a —NR'-1H-pyrazolo[3,4-d]pyrimidinyl group or a —NR'-pyrazolo[1,5-a]pyrimidinyl group;

wherein the purinyl, 7H-pyrrolo[2,3-d]pyrimidinyl, 1H-pyrazolo[3,4-d]pyrimidinyl pyrazolo[1,5-a]pyrimidinyl and groups are unsubstituted or substituted by a halogen atom or a —$(CH_2)_{0-3}$NR'R" group; or $R_4$ and $R_5$ together with the carbon atom to which they are attached form a pyrrolidinyl-purinyl group or a pyrrolidinyl-pyrimidinyl; wherein the pyrrolidinyl group is unsubstituted or substituted by one or more substituents selected from a halogen atom or a hydroxyl group; and wherein the purinyl group is unsubstituted or substituted by a —$(CH_2)_{0-3}$NR'R" group; and wherein the pyrimidinyl group is unsubstituted or substituted by one, two or three substituents selected from a —$(CH_2)_{0-3}$CN group or a —$(CH_2)_{0-3}$NR'R" group; and R' and R" each independently represent a hydrogen atom, a $C_1$-$C_3$ alkoxy group or a linear or branched $C_1$-$C_3$ alkyl group.

In another particularly preferred embodiment, in the compound of formula (I)

X represents a nitrogen atom or a —$CR_6$ group;

$R_a$ and $R_b$ each independently represent a hydrogen atom or a methyl group;

n represents 0 or 1;

$R_1$ represents a methyl group, a $C_3$-$C_7$ cycloalkyl group, a phenyl group, a pyridinyl group, a piperidinyl group or a tetrahydropyranyl group;

wherein the cycloalkyl, phenyl, pyridinyl, piperidinyl or tetrahydropyranyl groups are unsubstituted or substituted by one or more substituents selected from a halogen atom, a linear or branched $C_1$-$C_3$ alkyl group, a —$NR_7R_8$ group or a —$OR_8$ group; wherein $R_7$ and $R_8$ each independently represent a hydrogen atom or a linear or branched $C_1$-$C_3$ alkyl group;

$R_2$ and $R_3$ each independently represent a hydrogen atom or a linear or branched $C_1$-$C_3$ alkyl group;

$R_4$ represents a hydrogen atom, a $C_1$-$C_3$ haloalkyl group, or a linear or branched $C_1$-$C_3$ alkyl group;

$R_6$ represents a hydrogen atom, a halogen atom, a $C_1$-$C_3$ haloalkyl group, a linear or branched $C_1$-$C_3$ alkyl group or a cyclopropyl group;

$R_6$ represents a moiety of formula (II-a2), (IIb-1), (IIb-2), (IIb-3), (IIIa-1), (IIIa-3), (IIIa-5) or (IIIa-14):

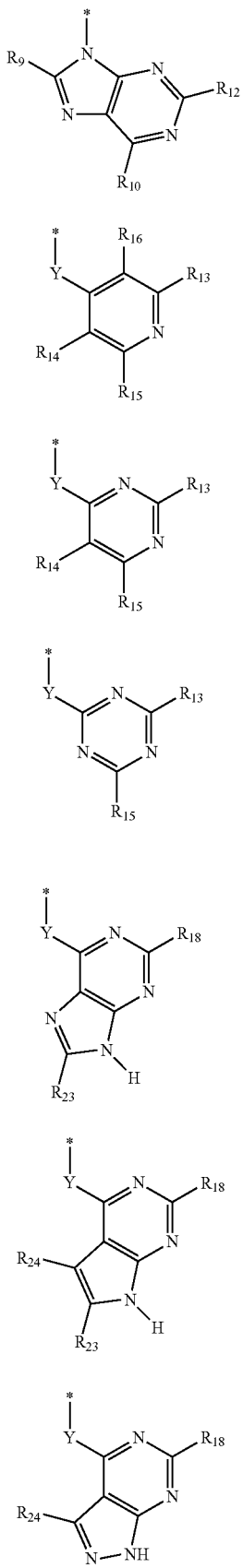

formula (IIa-2)

formula (IIb-1)

formula (IIb-2)

formula (IIb-3)

formula (IIIa-1)

formula (IIIa-3)

formula (IIIa-5)

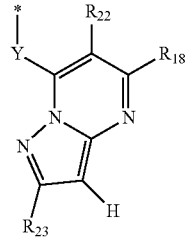

formula (IIIa-14)

wherein:
$R_9$, $R_{10}$ and $R_{12}$ independently represent a hydrogen atom or a —NR'R" group;
$R_{13}$ to $R_{16}$ independently represent a hydrogen atom, a halogen atom, a —CN group, a —C(O)—NR'R" group or a —NR'R" group;
$R_{18}$, $R_{22}$, $R_{23}$ and $R_{24}$ represent a hydrogen atom, a halogen atom or a —NR'R" group;
R' and R" each independently represent a hydrogen atom or a linear or branched $C_1$-$C_3$ alkyl group; and
Y represents —NH— or —S—; or
Y represents a nitrogen atom and Y, $R_4$ and the carbon atom to which both $R_4$ and Y are bonded form a pyrrolidinyl ring, which pyrrolidinyl group is unsubstituted or substituted by one or more substituents selected from a halogen atom or a hydroxyl group.

In one embodiment, in the compound of formula (I)
X represents a nitrogen atom or a —CR$_6$ group;
$R_a$ and $R_b$ each independently represent a hydrogen atom, a $C_1$-$C_4$ haloalkyl group, a $C_1$-$C_4$ hydroxyalkyl group or a linear or branched $C_1$-$C_4$ alkyl group;
n represents 0, 1, 2 or 3;
$R_1$ represents a linear or branched $C_1$-$C_4$ alkyl group, a $C_3$-$C_{10}$ cycloalkyl group, a $C_3$-$C_{10}$ cycloalkenyl group, a monocyclic or bicyclic $C_6$-$C_{14}$ aryl group, a 5- to 14-membered monocyclic or bicyclic heteroaryl group containing at least one heteroatom selected from O, S and N, or a 5- to 14-membered monocyclic or bicyclic heterocyclyl group containing at least one heteroatom selected from O, S and N,
wherein the cycloalkyl, cycloalkenyl, aryl, heteroaryl, and heterocyclyl groups are unsubstituted or substituted by one or more substituents selected from a halogen atom, a hydroxyl group, a cyano group, a linear or branched $C_1$-$C_4$ alkyl group, a $C_1$-$C_4$ haloalkyl group, a $C_1$-$C_4$ hydroxyalkyl group, a $C_3$-$C_4$ cycloalkyl group, a —(CH$_2$)$_{1-3}$CN group, a —(CH$_2$)$_{0-3}$OR$_8$ group, a —(CH$_2$)$_{0-3}$NR$_7$R$_8$ group, a —C(O)—(CH$_2$)$_{1-3}$—CN group, a —C(O)—(CH$_2$)$_{0-3}$—R$_8$ group, a —C(O)—(CH$_2$)$_{0-3}$—NR$_7$R$_8$ group, a —S(O)$_2$(CH$_2$)$_{0-3}$R$_8$ group or a —S(O)$_2$(CH$_2$)$_{0-3}$NR$_7$R$_8$ group;
$R_2$ and $R_3$ each independently represent a hydrogen atom, a halogen atom, a hydroxyl group, a cyano group, a $C_1$-$C_4$ alkoxy group, a $C_1$-$C_4$ haloalkyl group, a $C_1$-$C_4$ hydroxyalkyl group, a $C_3$-$C_7$ cycloalkyl group, a —NR'R" group, or a linear or branched $C_1$-$C_6$ alkyl group, which alkyl group is unsubstituted or substituted by one or more substituents selected from a $C_1$-$C_4$ alkoxy group, a cyano group or a $C_3$-$C_7$ cycloalkyl group;
$R_4$ represents a hydrogen atom, a $C_1$-$C_4$ alkoxy group, a $C_1$-$C_4$ haloalkyl group, a $C_1$-$C_4$ hydroxyalkyl group, a $C_3$-$C_7$ cycloalkyl group, a —(CH$_2$)$_{1-4}$NR'R" group, or a linear or branched $C_1$-$C_4$ alkyl group, which alkyl group is unsubstituted or substituted by one or more substituents selected from a $C_1$-$C_4$ alkoxy group, a cyano group, a $C_3$-$C_4$ cycloalkyl group, a —C(O)—(CH$_2$)$_{0-3}$—R group or a —C(O)—(CH$_2$)$_{0-3}$—NR'R" group;

$R_6$ represents a hydrogen atom, a halogen atom, a hydroxyl group, a cyano group, a $C_1$-$C_4$ alkoxy group, a $C_1$-$C_4$ haloalkyl group, a $C_1$-$C_4$ hydroxyalkyl group, a $C_3$-$C_7$ cycloalkyl group, a —(CH$_2$)$_{0-3}$NR'R" group, or a linear or branched $C_1$-$C_4$ alkyl group, which alkyl group is unsubstituted or substituted by one or more substituents selected from a $C_1$-$C_4$ alkoxy group, a cyano group or a $C_3$-$C_4$ cycloalkyl group;

$R_7$ and $R_8$ each independently represent a hydrogen atom, a $C_1$-$C_4$ haloalkyl group, a $C_1$-$C_4$ hydroxyalkyl group or a linear or branched $C_1$-$C_4$ alkyl group, which alkyl group is unsubstituted or substituted by one or more substituents selected from a $C_1$-$C_4$ alkoxy group, a cyano group or a $C_3$-$C_4$ cycloalkyl group;

R' and R" each independently represent a hydrogen atom, a hydroxyl group, a $C_1$-$C_4$ alkoxy group or a linear or branched $C_1$-$C_4$ alkyl group;

$R_5$ represents a group selected from:
i) a group of formula (IIa)

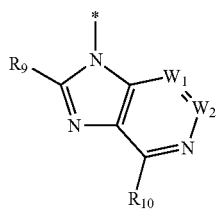

formula (IIa)

ii) a group of formula (IIb)

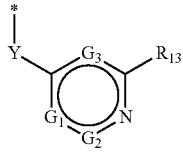

formula (IIb)

and
iii) a group of formula (IIc)

formula (IIc)

wherein
Y represents a linker selected from a —NR'— group, —O— or —S—; wherein R' is as defined above;
(*) represents where $R_5$ is bonded to the carbon atom attached to $R_4$ and to the pyrrolotriazinone group;
$W_1$ represents a —CR$_{11}$ group and $W_2$ represents a nitrogen atom, or $W_1$ represents a nitrogen atom and $W_2$ represents a —CR$_{12}$ group;
$G_1$ represents a —CR$_{14}$ group and $G_2$ represents a nitrogen atom, or $G_1$ represents a nitrogen atom and $G_2$ represents a —CR$_{15}$ group, or $G_1$ represents a —CR$_{14}$ group and $G_2$ represents a —CR$_{15}$ group;

$G_3$ represents a nitrogen atom or a —CR$_{16}$ group;
$R_9$, $R_{10}$, $R_{11}$, $R_{12}$, $R_{13}$, $R_{14}$, $R_{15}$ and $R_{16}$ each independently represent a hydrogen atom, a $C_1$-$C_4$ alkoxy group, a $C_1$-$C_4$ haloalkyl group, a $C_1$-$C_4$ hydroxyalkyl group, a $C_3$-$C_4$ cycloalkyl group, a —(CH$_2$)$_{0-3}$ON group, a —C(O)—(CH$_2$)$_{1-3}$—CN group, a —C(O)—(CH$_2$)$_{0-3}$—R' group, a —C(O)—(CH$_2$)$_{0-3}$—NR'R", a —(CH$_2$)$_{0-3}$NR'R" group, or a linear or branched $C_1$-$C_4$ alkyl group, which alkyl group is unsubstituted or substituted by one or more substituents selected from a $C_1$-$C_4$ alkoxy group, a cyano group or a $C_3$-$C_4$ cycloalkyl group; wherein R' and R" are as defined above;

$R_{17}$ represents a group selected from
a) a group of formula (IIa),

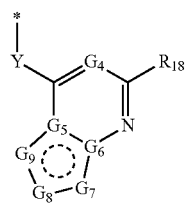

formula (IIIa)

b) a group of formula (IIb),

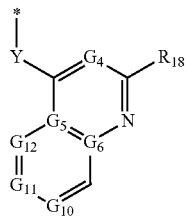

formula (IIIb)

c) a group of formula (IIc), and

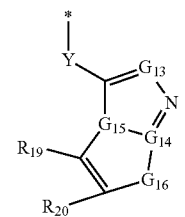

formula (IIIc)

d) a group of formula (IId),

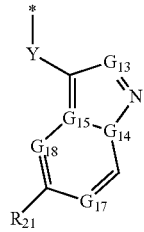

formula (IIId)

wherein
$G_4$ represents a nitrogen atom or a —$CR_{22}$ group;
$G_5$ and $G_6$ each independently represents a nitrogen atom or a-carbon atom, wherein when one of $G_5$ and $G_6$ represents a nitrogen atom the remaining represents a carbon atom;
$G_7$ represents a —NH group or a —CH group;
$G_8$ represents a nitrogen atom or a —$CR_{23}$ group;
$G_9$ represents a nitrogen atom or a —$CR_{24}$ group;
$G_{10}$ represents a nitrogen atom or a —$CR_{25}$ group;
$G_{11}$ represents a nitrogen atom or a —$CR_{26}$ group;
$G_{12}$ represents a nitrogen atom or a —$CR_{27}$ group;
$G_{13}$ represents a nitrogen atom or a —$CR_{28}$ group;
$G_{14}$ and $G_{15}$ each independently represents a nitrogen atom or a carbon atom, wherein when one of $G_{14}$ and $G_{15}$ represents a nitrogen atom the remaining represents a carbon atom;
$G_{16}$ represents a —NH group or a —CH group;
$G_{17}$ represents a nitrogen atom or a —$CR_{26}$ group;
$G_{18}$ represents a nitrogen atom or a —$CR_{30}$ group;
$R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_{29}$, and $R_{30}$ each independently represent a hydrogen atom, a $C_1$-$C_4$ alkoxy group, a $C_1$-$C_4$ haloalkyl group, a $C_1$-$C_4$ hydroxyalkyl group, a $C_3$-$C_4$ cycloalkyl group, a —$(CH_2)_{0-3}$CN group, a —C(O)—$(CH_2)_{1-3}$—CN group, a —C(O)—$(CH_2)_{0-3}$—R' group, a —C(O)—$(CH_2)_{0-3}$—NR'R'', a —$(CH_2)_{0-3}$NR'R'' group, or a linear or branched $C_1$-$C_4$ alkyl group, which alkyl group is unsubstituted or substituted by one or more substituents selected from a $C_1$-$C_4$ alkoxy group, a cyano group or a $C_3$-$C_4$ cycloalkyl group; wherein R' and R'' are as defined above; and wherein Y is as defined above;
or in the case that Y represents a —NR'— group, $R_4$ together with the —NR'— group and the carbon atom to which both $R_4$ and the —NR'— group are bonded form a 4- to 7-membered, saturated N-containing heterocyclyl group, which heterocyclyl group is unsubstituted or substituted by one or more substituents selected from a halogen atom, a hydroxyl group, a cyano group, a —$CHF_2$ group or a —$CF_3$ group.

In this embodiment, it is preferred that in the compound of formula (I):
$R_a$, and $R_b$ each independently represent a hydrogen atom or a linear or branched $C_1$-$C_3$ alkyl group;
n represents 0, 1 or 2;
$R_1$ represents a linear or branched $C_1$-$C_4$ alkyl group, a $C_3$-$C_7$ cycloalkyl group, a phenyl group, a 5- to 10-membered monocyclic or bicyclic heteroaryl group containing containing one, two or three heteroatoms selected from O, S and N, a pyrrolidinyl group, a piperidinyl group, a piperazinyl group, a tetrahydropyranyl group or a morpholinyl group;
wherein the cycloalkyl, phenyl, heteroaryl, pyrrolidinyl, piperidinyl, piperazinyl, tetrahydropyranyl or morpholinyl groups are unsubstituted or substituted by one or more substituents selected from a halogen atom, a linear or branched $C_1$-$C_4$ alkyl group, a $C_1$-$C_4$ haloalkyl group, a $C_1$-$C_4$ hydroxyalkyl group, a $C_3$-$C_4$ cycloalkyl group, a —$(CH_2)_{0-3}OR_8$ group, a —$(CH_2)_{0-3}NR_7R_8$ group, a —C(O)—$(CH_2)_{0-3}$—$R_8$ group or a —C(O)—$(OH_2)_{0-3}$—$NR_7R_8$ group; wherein $R_7$ and $R_8$ each independently represent a hydrogen atom or a $C_1$-$C_4$ alkyl group;
$R_2$ represents a hydrogen atom, a halogen atom, a hydroxyl group, a $C_1$-$C_3$ alkoxy group, a $C_1$-$C_3$ haloalkyl group, a $C_3$-$C_4$ cycloalkyl group, a —$NH_2$ group, a —$N(CH_3)H$ group, a —$N(CH_3)_2$ group, or a linear or branched $C_1$-$C_4$ alkyl group, which alkyl group is unsubstituted or substituted by a $C_1$-$C_2$ alkoxy group;
$R_3$ represents a hydrogen atom, a halogen atom, a hydroxyl group, a $C_1$-$C_3$ alkoxy group, a $C_1$-$C_3$ haloalkyl group, a $C_3$-$C_4$ cycloalkyl group, a —$NH_2$ group, a —$N(CH_3)H$ group, a —$N(CH_3)_2$ group, or a linear or branched $C_1$-$C_4$ alkyl group, which alkyl group is unsubstituted or substituted by a $C_1$-$C_2$ alkoxy group;
$R_4$ represents a hydrogen atom, a $C_1$-$C_3$ alkoxy group, a $C_1$-$C_3$ haloalkyl group, a $C_3$-$C_4$ cycloalkyl group, or a linear or branched $C_1$-$C_3$ alkyl group;
$R_6$ represents a hydrogen atom, a halogen atom, a $C_1$-$C_3$ alkoxy group, a $C_1$-$C_3$ haloalkyl group, a $C_3$-$C_4$ cycloalkyl group, a —$NH_2$ group, a —$N(CH_3)H$ group, a —$N(CH_3)_2$ group, or a linear or branched $C_1$-$C_4$ alkyl group, which alkyl group is unsubstituted or substituted by a $C_1$-$C_2$ alkoxy group;
$R_5$ represents a moiety of formula (II-a2), (IIb-1), (IIb-2) or (IIIa-1):

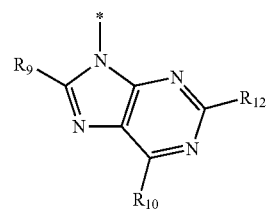

formula (IIa-2)

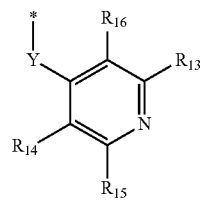

formula (IIb-1)

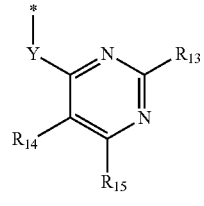

formula (IIb-2)

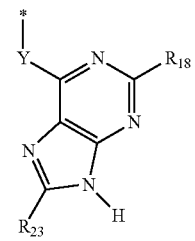

formula (IIIa-1)

wherein:
$R_9$, $R_{10}$, and $R_{12}$ each independently represent a hydrogen atom, a —$(CH_2)_{0-3}$CN group, a —C(O)—$(CH_2)_{1-3}$—CN group, a —C(O)—$(CH_2)_{0-3}$—R' group, a —C(O)—$(CH_2)_{0-3}$—NR'R'', a —$(CH_2)_{0-3}$NR'R'' group, or a linear or branched $C_1$-$C_4$ alkyl group; wherein R' and R'' each independently represent a hydrogen atom, a hydroxyl group, a $C_1$-$C_4$ alkoxy group or a linear or branched $C_1$-$C_4$ alkyl group;

$R_{13}$, $R_{14}$, $R_{15}$ and $R_{16}$ each independently represent a hydrogen atom, a —$(CH_2)_{0-3}$CN group, a —C(O)—$(CH_2)_{0-3}$—NR'R" or a —$(CH_2)_{0-3}$NR'R" group; wherein R' and R" each independently represent a hydrogen atom or a linear or branched $C_1$-$C_4$ alkyl group;

$R_{18}$ and $R_{23}$ each independently represent a hydrogen atom, a —$(CH_2)_{0-3}$CN group, a —C(O)—$(CH_2)_{1-3}$—CN group, a —C(O)—$(CH_2)_{0-3}$—R' group, a —C(O)—$(CH_2)_{0-3}$—NR'R", a —$(CH_2)_{0-3}$NR'R" group, or a linear or branched $C_1$-$C_4$ alkyl group; wherein R' and R" each independently represent a hydrogen atom, a hydroxyl group, a $C_1$-$C_4$ alkoxy group or a linear or branched $C_1$-$C_4$ alkyl group;

Y represents a —NR'— group, —O— or —S—; wherein R' represents hydrogen or a linear or branched $C_1$-$C_4$ alkyl group; or in the case that Y represents a —NR'— group, $R_4$ together with the —NR'— group and the carbon atom to which both $R_4$ and the —NR'— group are bonded form a 4- to 7-membered, saturated N-containing heterocyclyl group.

In a particularly preferred embodiment, in the compound of formula (I)

X represents a nitrogen atom or a —$CR_6$ group;

$R_a$ and $R_b$ each independently represent a hydrogen atom or a methyl group;

n represents 0 or 1;

$R_1$ represents a methyl group, a $C_3$-$C_7$ cycloalkyl group, a phenyl group, a pyridinyl group, a piperidinyl group or a tetrahydropyranyl group;
  wherein the cycloalkyl, phenyl, pyridinyl, piperidinyl or tetrahydropyranyl groups are unsubstituted or substituted by one or more substituents selected from a halogen atom, a linear or branched $C_1$-$C_3$ alkyl group, a —$NR_7R_8$ group or a —$OR_8$ group; wherein $R_7$ and $R_8$ each independently represent a hydrogen atom or a linear or branched $C_1$-$C_3$ alkyl group;

$R_2$ and $R_3$ each independently represent a hydrogen atom or a linear or branched $C_1$-$C_3$ alkyl group;

$R_4$ represents a hydrogen atom, a $C_1$-$C_3$ haloalkyl group, or a linear or branched $C_1$-$C_3$ alkyl group;

$R_6$ represents a hydrogen atom, a halogen atom, a $C_1$-$C_3$ haloalkyl group, a linear or branched $C_1$-$C_3$ alkyl group or a cyclopropyl group;

$R_5$ represents a group selected from:
  i) a group of formula (IIa), which group is a purinyl group unsubstituted or substituted by a —NR'R" group;
  ii) a group of formula (IIb), which group is selected from a —NH-pyridinyl group, a —S-pyridinyl group, a —NH-pyrimidinyl group or a —S-pyrimidinyl group and preferably from a —NH-pyridinyl group and a —NH-pyrimidinyl group; wherein the pyridinyl or pyrimidinyl groups are unsubstituted or substituted by one, two or three substituents selected from a —$(CH_2)_{0-3}$CN group, a —C(O)—$(CH_2)_{0-3}$—NR'R" or a —$(CH_2)_{0-3}$NR'R" group and preferably from a —CN group, a —C(O)$NH_2$ or a —$NH_2$ group; and
  iii) a group of formula (IIc), which group is selected from a —NH-purinyl group or a —S-purinyl group; wherein the purinyl group is unsubstituted or substituted by a —$(CH_2)_{0-3}$NR'R" group; or $R_4$ and $R_5$ together with the carbon atom to which they are attached form a pyrrolidinyl-purinyl group, wherein the purinyl group is unsubstituted or substituted by a —$(CH_2)_{0-3}$NR'R" group;

R' and R" each independently represent a hydrogen atom, a $C_1$-$C_3$ alkoxy group or a linear or branched $C_1$-$C_3$ alkyl group, preferably a a hydrogen atom or a linear or branched $C_1$-$C_3$ alkyl group.

In another particularly preferred embodiment, in the compound of formula (I)

X represents a nitrogen atom or a —$CR_6$ group;

$R_a$ and $R_b$ each independently represent a hydrogen atom or a methyl group;

n represents 0 or 1;

$R_1$ represents a methyl group, a $C_3$-$C_7$ cycloalkyl group, a phenyl group, a pyridinyl group, a piperidinyl group or a tetrahydropyranyl group;
  wherein the cycloalkyl, phenyl, pyridinyl, piperidinyl or tetrahydropyranyl groups are unsubstituted or substituted by one or more substituents selected from a halogen atom, a linear or branched $C_1$-$C_3$ alkyl group, a —$NR_7R_8$ group or a —$OR_B$ group; wherein $R_7$ and $R_8$ each independently represent a hydrogen atom or a linear or branched $C_1$-$C_3$ alkyl group;

$R_2$ and $R_3$ each independently represent a hydrogen atom or a linear or branched $C_1$-$C_3$ alkyl group;

$R_4$ represents a hydrogen atom, a $C_1$-$C_3$ haloalkyl group, or a linear or branched $C_1$-$C_3$ alkyl group;

$R_6$ represents a hydrogen atom, a halogen atom, a $C_1$-$C_3$ haloalkyl group, a linear or branched $C_1$-$C_3$ alkyl group or a cyclopropyl group;

$R_5$ represents a moiety of formula (II-a2), (IIb-1), (IIb-2) or (IIIa-1):

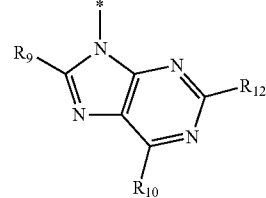

formula (IIa-2)

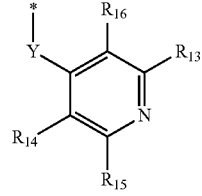

formula (IIb-1)

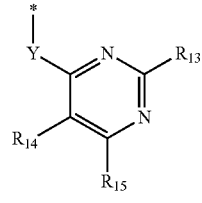

formula (IIb-2)

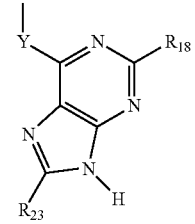

formula (IIIa-1)

wherein:
$R_9$, $R_{10}$ and $R_{12}$ independently represent a hydrogen atom or a —NR'R" group;
$R_{13}$ to $R_{16}$ independently represent a hydrogen atom, a —CN group, a —C(O)—NR'R" or a —NR'R" group;
$R_{18}$ and $R_{23}$ represent hydrogen or a —NR'R" group;
R' and R" each independently represent a hydrogen atom or a linear or branched $C_1$-$C_3$ alkyl group; and
Y represents —NH— or —S—; or
Y represents a nitrogen atom and Y, $R_4$ and the carbon atom to which both $R_4$ and Y are bonded form a pyrrolidinyl ring.

In a particularly preferred embodiment, the compound of the invention is of formula (Ia)

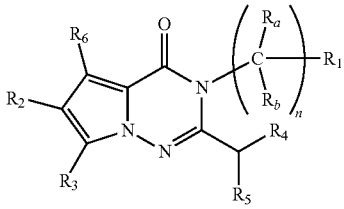

Formula (Ia)

wherein $R_1$, $R_2$, $R_3$, $R_4$, $R_5$, $R_6$, $R_a$, $R_b$ and n are as defined above.

In an alternative particularly preferred embodiment, the compound is of formula (Ib):

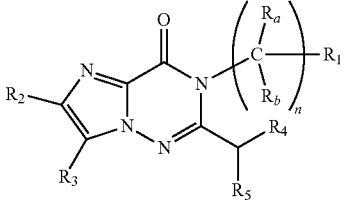

Formula (Ib)

wherein $R_1$, $R_2$, $R_3$, $R_4$, $R_5$, $R_a$, $R_b$ and n are as defined above.

Particular individual compounds of the invention include:
2-((6-Amino-9H-purin-9-yl)methyl)-5-chloro-3-o-tolylpyrrolo[1,2-f][1,2,4]triazin-4(3H)-one;
2-((6-Aminopyrimidin-4-ylamino)methyl)-5-chloro-3-o-tolylpyrrolo[1,2-f][1,2,4]triazin-4(3H)-one;
2-((6-Amino-9H-purin-9-yl)methyl)-5-cyclopropyl-3-o-tolylpyrrolo[1,24][1,2,4]triazin-4(3H)-one;
2-((6-amino-9H-purin-9-yl)methyl)-3-o-tolylpyrrolo[1,2-f][1,2,4]triazin-4(3H)-one;
2-((6-aminopyrimidin-4-ylamino)methyl)-3-o-tolylpyrrolo[1,2-f][1,2,4]triazin-4(3H)-one;
4-((4-Oxo-3-o-tolyl-3,4-dihydropyrrolo[1,2-f][1,2,4]triazin-2-yl)methylamino)picolinamide;
2-((2-aminopyridin-4-ylamino)methyl)-3-o-tolylpyrrolo[1,2-f][1,2,4]triazin-4(3H)-one;
2-(9H-purin-6-ylamino)methyl)-3-o-tolylpyrrolo[1,2-f][1,2,4]triazin-4(3H)-one;
2-((6-Amino-9H-purin-9-yl)methyl)-3-cyclohexylpyrrolo[1,2-f][1,2,4]triazin-4(3H)-one;
2-((6-amino-9H-purin-9-yl)methyl)-5-methyl-3-o-tolylpyrrolo[1,2-f][1,2,4]triazin-4(3H)-one;
2-((9H-purin-6-ylthio)methyl)-5-methyl-3-o-tolylpyrrolo[1,2-f][1,2,4]triazin-4(3H)-one;
2-((6-amino-9H-purin-9-yl)methyl)-6-methyl-3-o-tolylpyrrolo[1,2-f][1,2,4]triazin-4(3H)-one;
2-((9H-purin-6-ylthio)methyl)-6-methyl-3-o-tolylpyrrolo[1,2-f][1,2,4]triazin-4(3H)-one;
2-(1-(6-amino-9H-purin-9-yl)ethyl)-3-phenylpyrrolo[1,2-f][1,2,4]triazin-4(3H)-one;
(S)-2-(1-(9H-purin-6-ylamino)propyl)-3-phenylpyrrolo[1,2-f][1,2,4]triazin-4(3H)-one;
(S)-2-(1-(6-aminopyrimidin-4-ylamino)propyl)-3-phenylpyrrolo[1,2-f][1,2,4]triazin-4(3H)-one;
(S)-2-(1-(2-amino-9H-purin-6-ylamino)propyl)-3-phenylpyrrolo[1,2-f][1,2,4]triazin-4(3H)-one;
(S)-4-amino-6-(1-(4-oxo-3-phenyl-3,4-dihydropyrrolo[1,2-f][1,2,4]triazin-2-yl)propylamino)pyrimidine-5-carbonitrile;
(R)-2-(1-(9H-purin-6-ylamino)propyl)-3-phenylpyrrolo[1,2-f][1,2,4]triazin-4(3H)-one;
(S)-2-(1-(9H-purin-6-ylamino)ethyl)-3-phenylpyrrolo[1,2-f][1,2,4]triazin-4(3H)-one;
(S)-2-(1-(2-amino-9H-purin-6-ylamino)ethyl)-3-phenylpyrrolo[1,2-f][1,2,4]triazin-4(3H)-one;
(S)-2-(1-(6-aminopyrimidin-4-ylamino)ethyl)-3-phenylpyrrolo[1,2-f][1,2,4]triazin-4(3H)-one;
(S)-4-amino-6-(1-(4-oxo-3-phenyl-3,4-dihydropyrrolo[1,2-f][1,2,4]triazin-2-yl)ethylamino)pyrimidine-5-carbonitrile;
2-(1-(6-amino-9H-purin-9-yl)ethyl)-5-methyl-3-phenylpyrrolo[1,2-f][1,2,4]triazin-4(3H)-one;
2-((6-Amino-9H-purin-9-yl)methyl)-3-o-tolyl-5-(trifluoromethyl)pyrrolo[1,2-f][1,2,4]triazin-4(3H)-one;
2-((6-Amino-9H-purin-9-yl)methyl)-5-chloro-3-phenylpyrrolo[1,2-f][1,2,4]triazin-4(3H)-one;
2-((6-Amino-9H-purin-9-yl)methyl)-5-chloro-3-(3-methoxyphenyl)pyrrolo[1,2-f][1,2,4]triazin-4(3H)-one;
2-((6-Amino-9H-purin-9-yl)methyl)-5-chloro-3-(2,4-difluorophenyl)pyrrolo-[1,2-f][1,2,4]triazin-4(3H)-one;
2-((6-Amino-9H-purin-9-yl)methyl)-3-benzyl-5-chloropyrrolo[1,2-f][1,2,4]-triazin-4(3H)-one;
2-((6-amino-9H-purin-9-yl)methyl)-3-phenylimidazo[1,2-f][1,2,4]triazin-4(3H)-one;
2-((6-amino-9H-purin-9-yl)methyl)-3-o-tolylimidazo[1,2-f][1,2,4]triazin-4(3H)-one;
2-((6-Amino-9H-purin-9-yl)methyl)-5-chloro-3-(pyridin-4-yl)pyrrolo[1,2-f][1,2,4]triazin-4(3H)-one;
2-((6-Amino-9H-purin-9-yl)methyl)-5-chloro-3-(tetrahydro-2H-pyran-4-yl)pyrrolo-[1,2-f][1,2,4]triazin-4(3H)-one;
2-((6-Amino-9H-purin-9-yl)methyl)-5-chloro-3-(1-methylpiperidin-4-yl)pyrrolo[1,2-f][1,2,4]triazin-4(3H)-one;
(S)-2-(1-(9H-Purin-6-ylamino)ethyl)-3-(3-fluorophenyl)pyrrolo[1,2-f][1,2,4]triazin-4(3H)-one;
(S)-4-Amino-6-(1-(3-(3-fluorophenyl)-4-oxo-3,4-dihydropyrrolo[1,2-f][1,2,4]triazin-2-yl)ethylamino)pyrimidine-5-carbonitrile;
(S)-2-(1-(9H-Purin-6-ylamino)ethyl)-3-(3,5-difluorophenyl)pyrrolo[1,2-f][1,2,4]triazin-4(3H)-one;
(S)-4-Amino-6-(1-(3-(3,5-difluorophenyl)-4-oxo-3,4-dihydropyrrolo[1,2-f][1,2,4]triazin-2-yl)ethylamino)pyrimidine-5-carbonitrile;
2-((6-Amino-9H-purin-9-yl)methyl)-5-chloro-3-methylpyrrolo[1,2-f][1,2,4]triazin-4(3H)-one;
2-((6-Amino-9H-purin-9-yl)methyl)-3-((1r,4r)-4-aminocyclohexyl)-5-chloropyrrolo[1,2-f][1,2,4]triazin-4(3H)-one;
(R)-2-((6-Amino-9H-purin-9-yl)methyl)-5-chloro-3-(1-phenylethyl)pyrrolo[1,2-f][1,2,4]triazin-4(3H)-one;
(S)-2-((6-Amino-9H-purin-9-yl)methyl)-5-chloro-3-(1-phenylethyl)pyrrolo[1,2-f][1,2,4]triazin-4(3H)-one;

(S)-4-amino-6-(1-(4-oxo-3-(pyridin-2-yl)-3,4-dihydropyrrolo[1,2-f][1,2,4]triazin-2-yl)ethylamino)pyrimidine-5-carbonitrile;

(S)-2-(1-(9H-purin-6-yl)pyrrolidin-2-yl)-3-phenylpyrrolo[1,2-f][1,2,4]triazin-4(3H)-one;

(S)-4-amino-6-(1-(4-oxo-3-phenyl-5-(trifluoromethyl)-3,4-dihydropyrrolo[1,2-f][1,2,4]triazin-2-yl)ethylamino)pyrimidine-5-carbonitrile;

(S)-2-(1-(9H-purin-6-ylamino)ethyl)-3-phenyl-5-(trifluoromethyl)pyrrolo[1,2-f][1,2,4]triazin-4(3H)-one;

(S)-4-amino-6-(1-(5-(difluoromethyl)-4-oxo-3-phenyl-3,4-dihydropyrrolo[1,2-f][1,2,4]triazin-2-yl)ethylamino)pyrimidine-5-carbonitrile;

(S)-2-(1-(9H-purin-6-ylamino)ethyl)-5-(difluoromethyl)-3-phenylpyrrolo[1,2-f][1,2,4]triazin-4(3H)-one;

(S)-2-(1-(9H-purin-6-ylamino)ethyl)-3-phenylimidazo[1,2-f][1,2,4]triazin-4(3H)-one;

(S)-4-amino-6-(1-(4-oxo-3-phenyl-3,4-dihydroimidazo[1,2-f][1,2,4]triazin-2-yl)ethylamino)pyrimidine-5-carbonitrile;

2-(1-(9H-purin-6-ylamino)-3,3,3-trifluoropropyl)-3-phenylpyrrolo[1,2-f][1,2,4]triazin-4(3H)-one;

4-amino-6-(3,3,3-trifluoro-1-(4-oxo-3-phenyl-3,4-dihydropyrrolo[1,2-f][1,2,4]triazin-2-yl)propylamino)pyrimidine-5-carbonitrile;

(S)-4-amino-6-(2-(4-oxo-3-phenyl-3,4-dihydropyrrolo[1,2-f][1,2,4]triazin-2-yl)pyrrolidin-1-yl)pyrimidine-5-carbonitrile;

(S)-3-phenyl-2-(1-(pyrazolo[1,5-a]pyrimidin-7-ylamino)ethyl)pyrrolo[1,2-f][1,2,4]triazin-4(3H)-one;

2-((6-amino-9H-purin-9-yl)methyl)-5-(difluoromethyl)-3-phenylpyrrolo[1,2-f][1,2,4]triazin-4(3H)-one;

(S)-2-(1-(2-amino-9H-purin-6-yl)pyrrolidin-2-yl)-3-phenylpyrrolo[1,2-f][1,2,4]triazin-4(3H)-one;

(S)-2-(1-(4,6-diamino-1,3,5-triazin-2-ylamino)ethyl)-3-phenylpyrrolo[1,2-f][1,2,4]triazin-4(3H)-one;

(S)-2-((6-amino-9H-purin-9-yl)methyl)-5-chloro-3-(1-(5-fluoropyridin-2-yl)ethyl)pyrrolo[1,2-f][1,2,4]triazin-4(3H)-one;

(S)-2-(1-(2-amino-9H-purin-6-ylamino)ethyl)-3-(3,5-difluorophenyl)pyrrolo[1,2-f][1,2,4]triazin-4(3H)-one;

(S)-2-(1-(6-amino-5-cyanopyrimidin-4-ylamino)ethyl)-4-oxo-3-phenyl-3,4-dihydropyrrolo[1,2-f][1,2,4]triazine-5-carbonitrile;

(S)-2-(1-(9H-purin-6-ylamino)ethyl)-4-oxo-3-phenyl-3,4-dihydropyrrolo[1,2-f][1,2,4]triazine-5-carbonitrile;

(R)-2-(1-(9H-purin-6-ylamino)-2-hydroxyethyl)-3-phenylpyrrolo[1,2-f][1,2,4]triazin-4(3H)-one;

(R)-4-amino-6-(2-hydroxy-1-(4-oxo-3-phenyl-3,4-dihydropyrrolo[1,2-f][1,2,4]triazin-2-yl)ethylamino)pyrimidine-5-carbonitrile;

(S)-2-(1-(2-amino-9H-purin-6-ylamino)ethyl)-3-phenylimidazo[1,2-f][1,2,4]triazin-4(3H)-one;

(S)-2-(1-(7H-pyrrolo[2,3-d]pyrimidin-4-ylamino)ethyl)-3-phenylpyrrolo[1,2-f][1,2,4]triazin-4(3H)-one;

(S)-4-amino-6-(methyl(1-(4-oxo-3-phenyl-3,4-di hydropyrrolo[1,2-f][1,2,4]triazin-2-yl)ethyl)amino)pyrimidine-5-carbonitrile;

(S)-2-(1-(methyl(9H-purin-6-yl)amino)ethyl)-3-phenylpyrrolo[1,2-f][1,2,4]triazin-4(3H)-one;

(S)-2-(1-(9H-purin-6-ylamino)ethyl)-5-methyl-3-phenylpyrrolo[1,2-f][1,2,4]triazin-4(3H)-one;

(S)-4-amino-6-(1-(5-methyl-4-oxo-3-phenyl-3,4-dihydropyrrolo[1,2-f][1,2,4]triazin-2-yl)ethylamino)pyrimidine-5-carbonitrile;

(S)-2-(1-(9H-purin-6-ylamino)ethyl)-7-methyl-3-phenylpyrrolo[1,2-f][1,2,4]triazin-4(3H)-one;

(S)-4-amino-6-(1-(7-methyl-4-oxo-3-phenyl-3,4-dihydropyrrolo[1,2-f][1,2,4]triazin-2-yl)ethylamino)pyrimidine-5-carbonitrile;

(S)-2-(4,4-difluoro-1-(9H-purin-6-yl)pyrrolidin-2-yl)-3-phenylpyrrolo[1,2-f][1,2,4]triazin-4(3H)-one;

(S)-4-amino-6-(4,4-difluoro-2-(4-oxo-3-phenyl-3,4-dihydropyrrolo[1,2-f][1,2,4]triazin-2-yl)pyrrolidin-1-yl)pyrimidine-5-carbonitrile;

(S)-2-(1-(9H-purin-6-ylamino)ethyl)-6-fluoro-3-phenylpyrrolo[1,2-f][1,2,4]triazin-4(3H)-one;

(S)-4-amino-6-(1-(6-fluoro-4-oxo-3-phenyl-3,4-dihydropyrrolo[1,2-f][1,2,4]triazin-2-yl)ethylamino)pyrimidine-5-carbonitrile;

2-((S)-1-(9H-purin-6-ylamino)ethyl)-3-((S)-1-phenylethyl)pyrrolo[1,2-f][1,2,4]triazin-4(3H)-one;

4-amino-6-((S)-1-(4-oxo-3-((S)-1-phenylethyl)-3,4-dihydropyrrolo[1,2-f][1,2,4]triazin-2-yl)ethylamino)pyrimidine-5-carbonitrile;

(S)-4-amino-6-(1-(3-(2,6-dimethylphenyl)-4-oxo-3,4-dihydropyrrolo[1,2-f][1,2,4]triazin-2-yl)ethylamino)pyrimidine-5-carbonitrile;

(S)-2-((9H-purin-6-ylamino)methyl)-3-(1-phenylethyl)pyrrolo[1,2-f][1,2,4]triazin-4(3H)-one;

(S)-4-amino-6-((4-oxo-3-(1-phenylethyl)-3,4-dihydropyrrolo[1,2-f][1,2,4]triazin-2-yl)methylamino)pyrimidine-5-carbonitrile;

(S)-2-(1-(5-fluoro-7H-pyrrolo[2,3-d]pyrimidin-4-ylamino)ethyl)-3-phenylpyrrolo[1,2-f][1,2,4]triazin-4(3H)-one;

(S)-2-(1-(9H-purin-6-ylamino)ethyl)-3-(2,6-dimethylphenyl)pyrrolo[1,2-f][1,2,4]triazin-4(3H)-one;

(S)-4-amino-6-(1-(5-fluoro-4-oxo-3-phenyl-3,4-dihydropyrrolo[1,2-f][1,2,4]triazin-2-yl)ethylamino)pyrimidine-5-carbonitrile;

(S)-2-(1-(9H-purin-6-ylamino)ethyl)-5-fluoro-3-phenylpyrrolo[1,2-f][1,2,4]triazin-4(3H)-one;

(S)-2-(1-(6-amino-5-cyanopyrimidin-4-ylamino)ethyl)-3-(3,5-difluorophenyl)-4-oxo-3,4-dihydropyrrolo[1,2-f][1,2,4]triazine-5-carbonitrile;

(S)-4-amino-6-(1-(3-(3,5-difluorophenyl)-4-oxo-3,4-dihydroimidazo[1,2-f][1,2,4]triazin-2-yl)ethylamino)pyrimidine-5-carbonitrile;

(S)-2-(1-(9H-purin-6-ylamino)ethyl)-3-(3,5-difluorophenyl)-4-oxo-3,4-dihydropyrrolo[1,2-f][1,2,4]triazine-5-carbonitrile;

4-amino-6-((1S)-1-(5-(1,2-dihydroxyethyl)-4-oxo-3-phenyl-3,4-dihydropyrrolo[1,2-f][1,2,4]triazin-2-yl)ethylamino)pyrimidine-5-carbonitrile;

(S)-4-amino-6-(1-(3-(3,5-difluorophenyl)-4-oxo-5-(trifluoromethyl)-3,4-dihydropyrrolo[1,2-f][1,2,4]triazin-2-yl)ethylamino)pyrimidine-5-carbonitrile;

(S)-2-(1-(9H-Purin-6-ylamino)ethyl)-3-(3,5-difluorophenyl)-5-(trifluoromethyl)pyrrolo[1,2-f][1,2,4]triazin-4(3H)-one;

(S)-4-Amino-6-(1-(5-(hydroxymethyl)-4-oxo-3-phenyl-3,4-dihydropyrrolo[1,2-f][1,2,4]triazin-2-yl)ethylamino)pyrimidine-5-carbonitrile;

(S)-2-(1-(6-Amino-5-(trifluoromethyl)pyrimidin-4-ylamino)ethyl)-3-phenylpyrrolo[1,2-f][1,2,4]triazin-4(3H)-one;

(S)-2-(1-(6-Amino-5-cyanopyrimidin-4-ylamino)ethyl)-4-oxo-3-(pyridin-2-ylmethyl)-3,4-dihydropyrrolo[1,2-f][1,2,4]triazine-5-carbonitrile;

(S)-2-(1-(9H-Purin-6-ylamino)ethyl)-5-(difluoromethyl)-3-(3,5-difluorophenyl)pyrrolo[1,2-f][1,2,4]triazin-4(3H)-one;

(S)-2-(1-(9H-Purin-6-ylamino)ethyl)-3-(3,5-difluorophenyl)imidazo[1,2-f][1,2,4]triazin-4(3H)-one;

(S)-4-Amino-6-(1-(5-(diffluoromethyl)-3-(3,5-difluorophenyl)-4-oxo-3,4-dihydropyrrolo[1,2-f][1,2,4]triazin-2-yl)ethylamino)pyrimidine-5-carbonitrile;

(S)-2-(1-(2-Amino-9H-purin-6-ylamino)ethyl)-5-(difluoromethyl)-3-(3,5-difluorophenyl)pyrrolo[1,2-f][1,2,4]triazin-4(3H)-one;

(S)-2-(1-(2-Amino-9H-purin-6-ylamino)ethyl)-3-(3,5-difluorophenyl)-4-oxo-3,4-dihydropyrrolo[1,2-f][1,2,4]triazine-5-carbonitrile;

2-(1-(9H-Purin-6-ylamino)-2,2,2-trifluoroethyl)-3-phenylpyrrolo[1,2-f][1,2,4]triazin-4(3H)-one;

(S)-4-Amino-6-(1-(3-benzyl-4-oxo-3,4-dihydropyrrolo[1,2-f][1,2,4]triazin-2-yl)ethylamino)pyrimidine-5-carbonitrile;

(S)-2-(1-(6-Amino-5-fluoropyrimidin-4-ylamino)ethyl)-3-phenylpyrrolo[1,2-f][1,2,4]triazin-4(3H)-one;

(S)-2-(1-(6-Amino-5-fluoropyrimidin-4-ylamino)ethyl)-5-(difluoromethyl)-3-(3,5-difluorophenyl)pyrrolo[1,2-f][1,2,4]triazin-4(3H)-one;

(S)-2-(1-(6-Amino-5-cyanopyrimidin-4-ylamino)propyl)-3-(3,5-difluorophenyl)-4-oxo-3,4-dihydropyrrolo[1,2-f][1,2,4]triazine-5-carbonitrile;

(S)-2-(1-(6-Amino-5-cyanopyrimidin-4-ylamino)ethyl)-3-(3,5-dichlorophenyl)-4-oxo-3,4-dihydropyrrolo[1,2-f][1,2,4]triazine-5-carbonitrile;

(S)-2-(1-(6-Amino-5-fluoropyrimidin-4-ylamino)ethyl)-3-(3,5-difluorophenyl)-4-oxo-3,4-dihydropyrrolo[1,2-f][1,2,4]triazine-5-carbonitrile;

(S)-2-(1-(6-Amino-5-(trifluoromethyl)pyrimidin-4-ylamino)ethyl)-4-oxo-3-phenyl-3,4-dihydropyrrolo[1,2-f][1,2,4]triazine-5-carbonitrile;

(R)-2-(1-(6-Amino-5-cyanopyrimidin-4-ylamino)-2-hydroxyethyl)-3-(3,5-difluorophenyl)-4-oxo-3,4-dihydropyrrolo[1,2-f][1,2,4]triazine-5-carbonitrile;

(S)-2-(1-(6-Amino-5-carbamoylpyrimidin-4-ylamino)ethyl)-3-(3,5-difluorophenyl)-4-oxo-3,4-dihydropyrrolo[1,2-f][1,2,4]triazine-5-carboxamide;

(S)-2-(1-(6-Amino-5-cyanopyrimidin-4-ylamino)ethyl)-3-(3,5-difluorophenyl)-4-oxo-3,4-dihydropyrrolo[1,2-f][1,2,4]triazine-5-carboxamide;

(S)-2-(1-(6-Amino-5-cyanopyrimidin-4-ylamino)ethyl)-3-(2-chlorobenzyl)-4-oxo-3,4-dihydropyrrolo[1,2-f][1,2,4]triazine-5-carbonitrile;

2-((S)-1-(6-amino-5-cyanopyrimidin-4-ylamino)ethyl)-4-oxo-3-((S)-tetrahydro-2H-pyran-3-yl)-3,4-dihydropyrrolo[1,2-f][1,2,4]triazine-5-carbonitrile;

(R)-4-Amino-6-(1-(3-(3,5-difluorophenyl)-4-oxo-5-(trifluoromethyl)-3,4-dihydropyrrolo[1,2-f][1,2,4]triazin-2-yl)-2-hydroxyethylamino)pyrimidine-5-carbonitrile;

(S)-2-(1-(2-Amino-5-fluoropyrimidin-4-ylamino)ethyl)-3-(3,5-difluorophenyl)-4-oxo-3,4-dihydropyrrolo[1,2-f][1,2,4]triazine-5-carbonitrile;

(S)-2-(1-(2-Amino-5-cyanopyrimidin-4-ylamino)ethyl)-3-(3,5-difluorophenyl)-4-oxo-3,4-dihydropyrrolo[1,2-f][1,2,4]triazine-5-carbonitrile;

((S)-2-(1-(9H-Purin-6-ylamino)ethyl)-3-(3,5-difluorophenyl)-5-(2H-tetrazol-5-yl)pyrrolo[1,2-f][1,2,4]triazin-4(3H)-one;

(S)-4-Amino-6-(1-(3-((5-methylisoxazol-3-yl)methyl)-4-oxo-3,4-dihydropyrrolo[1,2-f][1,2,4]triazin-2-yl)ethylamino)pyrimidine-5-carbonitrile;

(S)-4-Amino-6-(1-(4-oxo-3-phenyl-7-(trifluoromethyl)-3,4-dihydropyrrolo[1,2-f][1,2,4]triazin-2-yl)ethylamino)pyrimidine-5-carbonitrile;

(S)-2-(1-(6-Amino-5-cyanopyrimidin-4-ylamino)ethyl)-4-oxo-3-phenyl-3,4-dihydropyrrolo[1,2-f][1,2,4]triazine-7-carbonitrile;

(S)-2-(1-(6-Amino-5-cyanopyrimidin-4-ylamino)ethyl)-3-(1-(4-methoxybenzyl)-1H-pyrazol-4-yl)-4-oxo-3,4-dihydropyrrolo[1,2-f][1,2,4]triazine-5-carbonitrile;

(S)-4-amino-6-(1-(4-oxo-3-phenyl-5-(thiazol-2-yl)-3,4-dihydropyrrolo[1,2-f][1,2,4]triazin-2-yl)ethylamino)pyrimidine-5-carbonitrile;

(S)-2-(1-(2,6-Diamino-5-cyanopyrimidin-4-ylamino)ethyl)-3-(3,5-difluorophenyl)-4-oxo-3,4-dihydropyrrolo[1,2-f][1,2,4]triazine-5-carbonitrile;

(S)-4-Amino-6-(1-(5-(morpholinomethyl)-4-oxo-3-phenyl-3,4-dihydropyrrolo[1,2-f][1,2,4]triazin-2-yl)ethylamino)pyrimidine-5-carbonitrile;

2-((S)-1-(6-Amino-5-cyanopyrimidin-4-ylamino)ethyl)-4-oxo-3-((R)-1-phenylethyl)-3,4-dihydropyrrolo[1,2-f][1,2,4]triazine-5-carbonitrile;

(S)-4-Amino-6-(1-(4-oxo-3-(1H-pyrazol-4-yl)-3,4-dihydropyrrolo[1,2-f][1,2,4]triazin-2-yl)ethylamino)pyrimidine-5-carbonitrile;

(S)-2-(1-(9H-Purin-6-ylamino)ethyl)-3-(3,5-difluorophenyl)-5-(5-methyl-1,2,4-oxadiazol-3-yl)pyrrolo[1,2-f][1,2,4]triazin-4(3H)-one;

4-amino-6-((S)-1-(4-oxo-3-((S)-tetrahydro-2H-pyran-3-yl)-5-(trifluoromethyl)-3,4-dihydropyrrolo[1,2-f][1,2,4]triazin-2-yl)ethylamino)pyrimidine-5-carbonitrile;

(S)-4-Amino-6-(1-(3-(5-methyl-1H-pyrazol-3-yl)-4-oxo-3,4-dihydropyrrolo[1,2-f][1,2,4]triazin-2-yl)ethylamino)pyrimidine-5-carbonitrile;

(S)-2-(1-(6-Amino-5-cyanopyrimidin-4-ylamino)ethyl)-4-oxo-3-phenyl-3,4-dihydropyrrolo[1,2-f][1,2,4]triazine-5-carboxylic acid;

2-((S)-1-(6-amino-5-cyanopyrimidin-4-ylamino)ethyl)-4-oxo-3-((R)-tetrahydro-2H-pyran-3-yl)-3,4-dihydropyrrolo[1,2-f][1,2,4]triazine-5-carbonitrile;

(S)-4-Amino-6-(1-(3-(5-fluoropyridin-3-yl)-4-oxo-3,4-dihydropyrrolo[1,2-f][1,2,4]triazin-2-yl)ethylamino)pyrimidine-5-carbonitrile;

(S)-4-Amino-6-(1-(4-oxo-3-(1H-pyrazol-3-yl)-3,4-dihydropyrrolo[1,2-f][1,2,4]triazin-2-yl)ethylamino)pyrimidine-5-carbonitrile;

(S)-4-Amino-6-(1-(4-oxo-3-(pyrimidin-5-yl)-3,4-dihydropyrrolo[1,2-f][1,2,4]triazin-2-yl)ethylamino)pyrimidine-5-carbonitrile;

4-amino-6-((S)-1-(4-oxo-3-((R)-tetrahydro-2H-pyran-3-yl)-5-(trifluoromethyl)-3,4-dihydropyrrolo[1,2-f][1,2,4]triazin-2-yl)ethylamino)pyrimidine-5-carbonitrile;

(S)-2,4-Diamino-6-(1-(4-oxo-3-phenyl-3,4-dihydropyrrolo[1,2-f][1,2,4]triazin-2-yl)ethylamino)pyrimidine-5-carbonitrile;

(S)-4-(1-(3-((1H-Pyrazol-3-yl)methyl)-4-oxo-3,4-dihydropyrrolo[1,2-f][1,2,4]triazin-2-yl)ethylamino)-6-aminopyrimidine-5-carbonitrile;

(S)-4-Amino-6-(1-(4-oxo-3-(tetrahydro-2H-pyran-4-yl)-3,4-dihydropyrrolo[1,2-f][1,2,4]triazin-2-yl)ethylamino)pyrimidine-5-carbonitrile;

(S)-4-Amino-6-(1-(4-oxo-3-(2,2,2-trifluoroethyl)-3,4-dihydropyrrolo[1,2-f][1,2,4]triazin-2-yl)ethylamino)pyrimidine-5-carbonitrile;

(S)-4-Amino-6-(1-(3-cyclobutyl-4-oxo-3,4-dihydropyrrolo[1,2-f][1,2,4]triazin-2-yl)ethylamino)pyrimidine-5-carbonitrile;

(S)-2-Amino-4-(1-(4-oxo-3-phenyl-3,4-dihydropyrrolo[1,2-f][1,2,4]triazin-2-yl)ethylamino)pyrimidine-5-carbonitrile;

4-Amino-6-(1-(5-(1-methyl-1H-pyrazol-4-yl)-4-oxo-3-phenyl-3,4-dihydropyrrolo[1,2-f][1,2,4]triazin-2-yl)ethylamino)pyrimidine-5-carbonitrile;

(S)-4-Amino-6-(1-(3-cyclopropyl-4-oxo-3,4-dihydropyr-rolo[1,2-f][1,2,4]triazin-2-yl)ethylamino)pyrimidine-5-carbonitrile;

(S)-4-Amino-6-(1-(5-bromo-4-oxo-3,4-dihydropyrrolo[1,2-f][1,2,4]triazin-2-yl)ethylamino)pyrimidine-5-carbonitrile;

4-amino-6-((S)-1-(4-oxo-3-((R)-tetrahydro-2H-pyran-3-yl)-3,4-di hydropyrrolo[1,2-f][1,2,4]triazin-2-yl)ethylamino) pyrimidine-5-carbonitrile;

(S)-4-Amino-6-(1-(5-bromo-4-oxo-3-phenyl-3,4-di hydropyrrolo[1,2-f][1,2,4]triazin-2-yl)ethylamino)pyrimidine-5-carbonitrile;

2-((3-Iodo-1H-pyrazolo[3,4-d]pyrimidin-4-ylamino)methyl)-5-methyl-3-o-tolylpyrrolo[1,2-f][1,2,4]triazin-4(3H)-one;

(S)-2-(1-(6-Amino-5-cyanopyrimidin-4-ylamino)ethyl)-3-(5-fluoropyridin-3-yl)-4-oxo-3,4-dihydropyrrolo[1,2-f][1,2,4]triazine-5-carbonitrile;

4-amino-6-((S)-1-(4-oxo-3-((S)-tetrahydro-2H-pyran-3-yl)-3,4-di hydropyrrolo[1,2-f][1,2,4]triazin-2-yl)ethylamino) pyrimidine-5-carbonitrile;

(S)-4-Amino-6-(1-(4-oxo-3-phenyl-5-(1H-pyrazol-4-yl)-3,4-dihydropyrrolo[1,2-f][1,2,4]triazin-2-yl)ethylamino) pyrimidine-5-carbonitrile;

(S)-4-Amino-6-(1-(3-(isoxazol-3-yl)-4-oxo-3,4-di hydropyrrolo[1,2-f][1,2,4]triazin-2-yl)ethylamino)pyrimidine-5-carbonitrile;

(S)-2-(1-(6-Amino-5-cyanopyrimidin-4-ylamino)ethyl)-N,N-dimethyl-4-oxo-3-phenyl-3,4-dihydropyrrolo[1,2-f][1,2,4]triazine-5-carboxamide;

(S)-4-Amino-6-(1-(3-(1-methyl-1H-pyrazol-3-yl)-4-oxo-3,4-dihydropyrrolo[1,2-f][1,2,4]triazin-2-yl)ethylamino) pyrimidine-5-carbonitrile (S)-2-(1-(6-Amino-5-cyanopyrimidin-4-ylamino)ethyl)-4-oxo-3-phenyl-N-propyl-3,4-dihydropyrrolo[1,2-f][1,2,4]triazine-5-carboxamide;

2-((S)-1-(9H-Purin-6-ylamino)ethyl)-3-(tetrahydro-2H-pyran-3-yl)pyrrolo[1,2-f][1,2,4]triazin-4(3H)-one;

2-((S)-1-(9H-purin-6-ylamino)ethyl)-3-((S)-tetrahydro-2H-pyran-3-yl)pyrrolo[1,2-f][1,2,4]triazin-4(3H)-one;

(S)-4-Amino-6-(3-hydroxy-1-(4-oxo-3-phenyl-3,4-dihydropyrrolo[1,2-f][1,2,4]triazin-2-yl)propylamino)pyrimidine-5-carbonitrile;

(S)-2-(1-(9H-Purin-6-ylamino)-3-hydroxypropyl)-3-phenylpyrrolo[1,2-f][1,2,4]triazin-4(3H)-one;

(R)-4-Amino-6-(1-(3-(3,5-difluorophenyl)-4-oxo-3,4-dihydropyrrolo[1,2-f][1,2,4]triazin-2-yl)-2-hydroxyethylamino)pyrimidine-5-carbonitrile;

4-Amino-6-((4-oxo-3-o-tolyl-3,4-dihydropyrrolo[1,2-f][1,2,4]triazin-2-yl)methylamino)pyrimidine-5-carbonitrile;

(S)-4-Amino-6-(1-(5-(2-hydroxyethyl)-4-oxo-3-phenyl-3,4-dihydropyrrolo[1,2-f][1,2,4]triazin-2-yl)ethylamino)pyrimidine-5-carbonitrile;

S)-2-(1-(6-amino-5-cyanopyrimidin-4-ylamino)-3-hydroxypropyl)-3-(3,5-difluorophenyl)-4-oxo-3,4-dihydropyrrolo[1,2-f][1,2,4]triazine-5-carbonitrile;

(S)-2-(1-(9H-Purin-6-ylamino)ethyl)-3-(5-fluoropyridin-3-yl)-4-oxo-3,4-dihydropyrrolo[1,2-f][1,2,4]triazine-5-carbonitrile;

(S)-4-Amino-6-(1-(5-(2-methyloxazol-5-yl)-4-oxo-3-phenyl-3,4-dihydropyrrolo[1,2-f][1,2,4]triazin-2-yl)ethylamino)pyrimidine-5-carbonitrile;

(S)-4-Amino-6-(1-(5-(2-methoxyethyl)-4-oxo-3-phenyl-3,4-dihydropyrrolo[1,2-f][1,2,4]triazin-2-yl)ethylamino) pyrimidine-5-carbonitrile;

(S)-Propyl 2-(1-(6-amino-5-cyanopyrimidin-4-ylamino) ethyl)-4-oxo-3-phenyl-3,4-dihydropyrrolo[1,2-f][1,2,4] triazine-5-carboxylate;

(S)-4-Amino-6-(3-hydroxy-1-(4-oxo-3,4-dihydropyrrolo[1,2-f][1,2,4]triazin-2-yl)propylamino)pyrimidine-5-carbonitrile;

(S)-2-(1-(9H-Purin-6-ylamino)-3-hydroxypropyl)pyrrolo[1,2-f][1,2,4]triazin-4(3H)-one;

(S)-4-amino-6-(1-(3-(3,5-difluorophenyl)-4-oxo-5-(trifluoromethyl)-3,4-dihydropyrrolo[1,2-f][1,2,4]triazin-2-yl)-3-hydroxypropylamino)pyrimidine-5-carbonitrile;

(S)-4-Amino-6-(1-(4-oxo-3-(6-(trifluoromethyl)pyridin-2-yl)-3,4-dihydropyrrolo[1,2-f][1,2,4]triazin-2-yl)ethylamino)pyrimidine-5-carbonitrile;

(S)-4-Amino-6-(1-(5-bromo-4-oxo-3-(3-(trifluoromethyl) phenyl)-3,4-dihydropyrrolo[1,2-f][1,2,4]triazin-2-yl) ethylamino)pyrimidine-5-carbonitrile;

(S)-2-(2-(1-(6-Amino-5-cyanopyrimidin-4-ylamino)ethyl)-4-oxo-3-phenyl-3,4-dihydropyrrolo[1,2-f][1,2,4]triazin-5-yl)ethyl acetate;

(S)-2-(1-(9H-Purin-6-ylamino)ethyl)-3-(6-(trifluoromethyl) pyridin-2-yl)pyrrolo[1,2-f][1,2,4]triazin-4(3H)-one;

2-((2S,4R)-1-(6-Amino-5-cyanopyrimidin-4-yl)-4-hydroxypyrrolidin-2-yl)-3-(3,5-difluorophenyl)-4-oxo-3,4-dihydropyrrolo[1,2-f][1,2,4]triazine-5-carbonitrile;

4-Amino-6-((2S,4R)-2-(5-(aminomethyl)-3-(3,5-difluorophenyl)-4-oxo-3,4-dihydropyrrolo[1,2-f][1,2,4]triazin-2-yl)-4-hydroxypyrrolidin-1-yl)pyrimidine-5-carbonitrile;

(S)-4-Amino-6-(1-(5-(4-methyl-1H-imidazol-1-yl)-4-oxo-3-phenyl-3,4-dihydropyrrolo[1,2-f][1,2,4]triazin-2-yl) ethylamino)pyrimidine-5-carbonitrile;

(S)-4-Amino-6-(1-(5-bromo-3-(3-methoxyphenyl)-4-oxo-3,4-dihydropyrrolo[1,2-f][1,2,4]triazin-2-yl)ethylamino) pyrimidine-5-carbonitrile;

(S)-2-(1-(6-Amino-5-cyanopyrimidin-4-ylamino)ethyl)-4-oxo-3-(3-(trifluoromethyl)phenyl)-3,4-dihydropyrrolo[1,2-f][1,2,4]triazine-5-carbonitrile;

(S)-4-Amino-6-(1-(5-bromo-3-(3-hydroxyphenyl)-4-oxo-3,4-dihydropyrrolo[1,2-f][1,2,4]triazin-2-yl)ethylamino) pyrimidine-5-carbonitrile;

(S)-4-Amino-6-(1-(3-(3-methoxyphenyl)-4-oxo-3,4-dihydropyrrolo[1,2-f][1,2,4]triazin-2-yl)ethylamino)pyrimidine-5-carbonitrile;

(S)-4-Amino-6-(1-(3-(3-hydroxyphenyl)-4-oxo-3,4-dihydropyrrolo[1,2-f][1,2,4]triazin-2-yl)ethylamino)pyrimidine-5-carbonitrile;

(S)-2-(1-(6-Amino-5-cyanopyrimidin-4-ylamino)ethyl)-3-(3-methoxyphenyl)-4-oxo-3,4-dihydropyrrolo[1,2-f][1,2,4]triazine-5-carbonitrile;

4-Amino-6-(1-(4-oxo-3-phenyl-3,4-dihydropyrrolo[1,2-f][1,2,4]triazin-2-yl)cyclopropylamino)pyrimidine-5-carbonitrile;

2-(1-(9H-Purin-6-ylamino)cyclopropyl)-3-phenylpyrrolo[1,2-f][1,2,4]triazin-4(3H)-one;

(S)-4-Amino-6-(1-(4-oxo-3-(3-(trifluoromethyl)phenyl)-3,4-dihydropyrrolo[1,2-f][1,2,4]triazin-2-yl)ethylamino) pyrimidine-5-carbonitrile;

(S)-2-(1-(6-Amino-5-cyanopyrimidin-4-ylamino)ethyl)-3-(3-hydroxyphenyl)-4-oxo-3,4-dihydropyrrolo[1,2-f][1,2,4]triazine-5-carbonitrile;

(S)-2-(1-(9H-purin-6-ylamino)ethyl)-3-(pyridin-2-yl)pyrrolo[1,2-f][1,2,4]triazin-4(3H)-one;

(S)-2-(1-(9H-purin-6-ylamino)propyl)-3-phenylimidazo[1,2-f][1,2,4]triazin-4(3H)-one;

(S)-4-amino-6-(1-(4-oxo-3-phenyl-3,4-dihydroimidazo[1,2-f][1,2,4]triazin-2-yl)propylamino)pyrimidine-5-carbonitrile;

or a pharmaceutically acceptable salt, or solvate, or N-oxide, or stereoisomer or deuterated derivative thereof.

Examples of the Preferred Compounds are:

(S)-2-(1-(9H-purin-6-ylamino)propyl)-3-phenylpyrrolo[1,2-f][1,2,4]triazin-4(3H)-one;

(S)-2-(1-(2-amino-9H-purin-6-ylamino)propyl)-3-phenylpyrrolo[1,2-f][1,2,4]triazin-4(3H)-one;

(S)-4-amino-6-(1-(4-oxo-3-phenyl-3,4-dihydropyrrolo[1,2-f][1,2,4]triazin-2-yl)propylamino)pyrimidine-5-carbonitrile;

(S)-2-(1-(9H-purin-6-ylamino)ethyl)-3-phenylpyrrolo[1,2-f][1,2,4]triazin-4(3H)-one;

(S)-2-(1-(2-amino-9H-purin-6-ylamino)ethyl)-3-phenylpyrrolo[1,2-f][1,2,4]triazin-4(3H) one;

(S)-4-amino-6-(1-(4-oxo-3-phenyl-3,4-dihydropyrrolo[1,2-f][1,2,4]triazin-2-yl)ethylamino)pyrimidine-5-carbonitrile;

(S)-2-(1-(9H-Purin-6-ylamino)ethyl)-3-(3-fluorophenyl)pyrrolo[1,2-f][1,2,4]triazin-4(3H)-one;

(S)-4-Amino-6-(1-(3-(3-fluorophenyl)-4-oxo-3,4-dihydropyrrolo[1,2-f][1,2,4]triazin-2-yl)ethylamino)pyrimidine-5-carbonitrile;

(S)-2-(1-(9H-Purin-6-ylamino)ethyl)-3-(3,5-difluorophenyl)pyrrolo[1,2-f][1,2,4]triazin-4(3H)-one;

(S)-4-amino-6-(1-(4-oxo-3-(pyridin-2-yl)-3,4-dihydropyrrolo[1,2-f][1,2,4]triazin-2-yl)ethylamino)pyrimidine-5-carbonitrile;

(S)-2-(1-(9H-purin-6-yl)pyrrolidin-2-yl)-3-phenylpyrrolo[1,2-f][1,2,4]triazin-4(3H)-one;

(S)-4-amino-6-(1-(4-oxo-3-phenyl-5-(trifluoromethyl)-3,4-dihydropyrrolo[1,2-f][1,2,4]triazin-2-yl)ethylamino)pyrimidine-5-carbonitrile;

(S)-2-(1-(9H-purin-6-ylamino)ethyl)-3-phenyl-5-(trifluoromethyl)pyrrolo[1,2-f][1,2,4]triazin-4(3H)-one;

(S)-4-amino-6-(1-(5-(difluoromethyl)-4-oxo-3-phenyl-3,4-dihydropyrrolo[1,2-f][1,2,4]triazin-2-yl)ethylamino)pyrimidine-5-carbonitrile;

(S)-2-(1-(9H-purin-6-ylamino)ethyl)-5-(difluoromethyl)-3-phenylpyrrolo[1,2-f][1,2,4]triazin-4(3H)-one;

(S)-4-amino-6-(2-(4-oxo-3-phenyl-3,4-dihydropyrrolo[1,2-f][1,2,4]triazin-2-yl)pyrrolidin-1-yl)pyrimidine-5-carbonitrile;

(S)-2-(1-(2-amino-9H-purin-6-yl)pyrrolidin-2-yl)-3-phenylpyrrolo[1,2-f][1,2,4]triazin-4(3H)-one;

(S)-2-(1-(2-amino-9H-purin-6-ylamino)ethyl)-3-(3,5-difluorophenyl)pyrrolo[1,2-f][1,2,4]triazin-4(3H)-one;

(S)-2-(1-(6-amino-5-cyanopyrimidin-4-ylamino)ethyl)-4-oxo-3-phenyl-3,4-dihydropyrrolo[1,2-f][1,2,4]triazine-5-carbonitrile;

(S)-2-(1-(9H-purin-6-ylamino)ethyl)-4-oxo-3-phenyl-3,4-dihydropyrrolo[1,2-f][1,2,4]triazine-5-carbonitrile;

(R)-4-amino-6-(2-hydroxy-1-(4-oxo-3-phenyl-3,4-dihydropyrrolo[1,2-f][1,2,4]triazin-2-yl)ethylamino)pyrimidine-5-carbonitrile;

(S)-2-(1-(7H-pyrrolo[2,3-d]pyrimidin-4-ylamino)ethyl)-3-phenylpyrrolo[1,2-f][1,2,4]triazin-4(3H)-one;

(S)-2-(1-(9H-purin-6-ylamino)ethyl)-5-methyl-3-phenylpyrrolo[1,2-f][1,2,4]triazin-4(3H)-one;

(S)-4-amino-6-(1-(5-methyl-4-oxo-3-phenyl-3,4-dihydropyrrolo[1,2-f][1,2,4]triazin-2-yl)ethylamino)pyrimidine-5-carbonitrile;

(S)-2-(1-(9H-purin-6-ylamino)ethyl)-7-methyl-3-phenylpyrrolo[1,2-f][1,2,4]triazin-4(3H)-one;

(S)-4-amino-6-(1-(7-methyl-4-oxo-3-phenyl-3,4-dihydropyrrolo[1,2-f][1,2,4]triazin-2-yl)ethylamino)pyrimidine-5-carbonitrile;

(S)-4-amino-6-(4,4-difluoro-2-(4-oxo-3-phenyl-3,4-dihydropyrrolo[1,2-f][1,2,4]triazin-2-yl)pyrrolidin-1-yl)pyrimidine-5-carbonitrile;

(S)-2-(1-(9H-purin-6-ylamino)ethyl)-6-fluoro-3-phenylpyrrolo[1,2-f][1,2,4]triazin-4(3H)-one;

(S)-4-amino-6-(1-(6-fluoro-4-oxo-3-phenyl-3,4-dihydropyrrolo[1,2-f][1,2,4]triazin-2-yl)ethylamino)pyrimidine-5-carbonitrile;

4-amino-6-((S)-1-(4-oxo-3-((S)-1-phenylethyl)-3,4-dihydropyrrolo[1,2-f][1,2,4]triazin-2-yl)ethylamino)pyrimidine-5-carbonitrile;

(S)-4-amino-6-(1-(3-(2,6-dimethylphenyl)-4-oxo-3,4-dihydropyrrolo[1,2-f][1,2,4]triazin-2-yl)ethylamino)pyrimidine-5-carbonitrile;

(S)-4-amino-6-((4-oxo-3-(1-phenylethyl)-3,4-dihydropyrrolo[1,2-f][1,2,4]triazin-2-yl)methylamino)pyrimidine-5-carbonitrile;

(S)-2-(1-(5-fluoro-7H-pyrrolo[2,3-d]pyrimidin-4-ylamino)ethyl)-3-phenylpyrrolo[1,2-f][1,2,4]triazin-4(3H)-one;

(S)-4-amino-6-(1-(5-fluoro-4-oxo-3-phenyl-3,4-dihydropyrrolo[1,2-f][1,2,4]triazin-2-yl)ethylamino)pyrimidine-5-carbonitrile;

(S)-2-(1-(9H-purin-6-ylamino)ethyl)-5-fluoro-3-phenylpyrrolo[1,2-f][1,2,4]triazin-4(3H)-one;

(S)-2-(1-(6-amino-5-cyanopyrimidin-4-ylamino)ethyl)-3-(3,5-difluorophenyl)-4-oxo-3,4-dihydropyrrolo[1,2-f][1,2,4]triazine-5-carbonitrile;

(S)-2-(1-(9H-purin-6-ylamino)ethyl)-3-(3,5-difluorophenyl)-4-oxo-3,4-dihydropyrrolo[1,2-f][1,2,4]triazine-5-carbonitrile;

(S)-4-amino-6-(1-(3-(3,5-difluorophenyl)-4-oxo-5-(trifluoromethyl)-3,4-dihydropyrrolo[1,2-f][1,2,4]triazin-2-yl)ethylamino)pyrimidine-5-carbonitrile;

(S)-2-(1-(9H-Purin-6-ylamino)ethyl)-3-(3,5-difluorophenyl)-5-(trifluoromethyl)pyrrolo[1,2-f][1,2,4]triazin-4(3H)-one;

(S)-4-Amino-6-(1-(5-(hydroxymethyl)-4-oxo-3-phenyl-3,4-dihydropyrrolo[1,2-f][1,2,4]triazin-2-yl)ethylamino)pyrimidine-5-carbonitrile;

(S)-2-(1-(6-Amino-5-(trifluoromethyl)pyrimidin-4-ylamino)ethyl)-3-phenylpyrrolo[1,2-f][1,2,4]triazin-4(3H)-one;

(S)-2-(1-(9H-Purin-6-ylamino)ethyl)-5-(difluoromethyl)-3-(3,5-difluorophenyl)pyrrolo[1,2-f][1,2,4]triazin-4(3H)-one;

(S)-4-Amino-6-(1-(5-(diffluoromethyl)-3-(3,5-difluorophenyl)-4-oxo-3,4-dihydropyrrolo[1,2-f][1,2,4]triazin-2-yl)ethylamino)pyrimidine-5-carbonitrile;

(S)-2-(1-(2-Amino-9H-purin-6-ylamino)ethyl)-5-(difluoromethyl)-3-(3,5-difluorophenyl)pyrrolo[1,2-f][1,2,4]triazin-4(3H)-one;

(S)-2-(1-(2-Amino-9H-purin-6-ylamino)ethyl)-3-(3,5-difluorophenyl)-4-oxo-3,4-dihydropyrrolo[1,2-f][1,2,4]triazine-5-carbonitrile;

(S)-2-(1-(6-Amino-5-fluoropyrimidin-4-ylamino)ethyl)-5-(difluoromethyl)-3-(3,5-difluorophenyl)pyrrolo[1,2-f][1,2,4]triazin-4(3H)-one;

(S)-2-(1-(6-Amino-5-cyanopyrimidin-4-ylamino)propyl)-3-(3,5-difluorophenyl)-4-oxo-3,4-dihydropyrrolo[1,2-f][1,2,4]triazine-5-carbonitrile;

(S)-2-(1-(6-Amino-5-cyanopyrimidin-4-ylamino)ethyl)-3-(3,5-dichlorophenyl)-4-oxo-3,4-dihydropyrrolo[1,2-f][1,2,4]triazine-5-carbonitrile;

(S)-2-(1-(6-Amino-5-(trifluoromethyl)pyrimidin-4-ylamino)ethyl)-4-oxo-3-phenyl-3,4-dihydropyrrolo[1,2-f][1,2,4]triazine-5-carbonitrile;

(R)-2-(1-(6-Amino-5-cyanopyrimidin-4-ylamino)-2-hydroxyethyl)-3-(3,5-difluorophenyl)-4-oxo-3,4-dihydropyrrolo[1,2-f][1,2,4]triazine-5-carbonitrile;

2-(((S)-1-(6-amino-5-cyanopyrimidin-4-ylamino)ethyl)-4-oxo-3,4(S)-tetrahydro-2H-pyran-3-yl)-3,4-dihydropyrrolo[1,2-f][1,2,4]triazine-5-carbonitrile;

(R)-4-Amino-6-(1-(3-(3,5-difluorophenyl)-4-oxo-5-(trifluoromethyl)-3,4-dihydropyrrolo[1,2-f][1,2,4]triazin-2-yl)-2-hydroxyethylamino)pyrimidine-5-carbonitrile;

(S)-2-(1-(2-Amino-5-cyanopyrimidin-4-ylamino)ethyl)-3-(3,5-difluorophenyl)-4-oxo-3,4-dihydropyrrolo[1,2-f][1,2,4]triazine-5-carbonitrile;

(S)-2-(1-(6-Amino-5-cyanopyrimidin-4-ylamino)ethyl)-4-oxo-3-phenyl-3,4-dihydropyrrolo[1,2-f][1,2,4]triazine-7-carbonitrile;

(S)-2-(1-(6-Amino-5-cyanopyrimidin-4-ylamino)ethyl)-3-(1-(4-methoxybenzyl)-1H-pyrazol-4-yl)-4-oxo-3,4-dihydropyrrolo[1,2-f][1,2,4]triazine-5-carbonitrile;

(S)-2-(1-(2,6-Diamino-5-cyanopyrimidin-4-ylamino)ethyl)-3-(3,5-difluorophenyl)-4-oxo-3,4-dihydropyrrolo[1,2-f][1,2,4]triazine-5-carbonitrile;

2-((S)-1-(6-Amino-5-cyanopyrimidin-4-ylamino)ethyl)-4-oxo-3-((R)-1-phenylethyl)-3,4-dihydropyrrolo[1,2-f][1,2,4]triazine-5-carbonitrile;

(S)-4-Amino-6-(1-(4-oxo-3-(1H-pyrazol-4-yl)-3,4-dihydropyrrolo[1,2-f][1,2,4]triazin-2-yl)ethylamino)pyrimidine-5-carbonitrile;

4-amino-6-((S)-1-(4-oxo-3-((S)-tetrahydro-2H-pyran-3-yl)-5-(trifluoromethyl)-3,4-dihydropyrrolo[1,2-f][1,2,4]triazin-2-yl)ethylamino)pyrimidine-5-carbonitrile;

2-((S)-1-(6-amino-5-cyanopyrimidin-4-ylamino)ethyl)-4-oxo-3-((R)-tetrahydro-2H-pyran-3-yl)-3,4-di hydropyrrolo[1,2-f][1,2,4]triazine-5-carbonitrile;

(S)-4-Amino-6-(1-(3-(5-fluoropyridin-3-yl)-4-oxo-3,4-dihydropyrrolo[1,2-f][1,2,4]triazin-2-yl)ethylamino)pyrimidine-5-carbonitrile;

(S)-4-Amino-6-(1-(4-oxo-3-(1H-pyrazol-3-yl)-3,4-dihydropyrrolo[1,2-f][1,2,4]triazin-2-yl)ethylamino)pyrimidine-5-carbonitrile;

4-amino-6-((S)-1-(4-oxo-3-((R)-tetrahydro-2H-pyran-3-yl)-5-(trifluoromethyl)-3,4-dihydropyrrolo[1,2-f][1,2,4]triazin-2-yl)ethylamino)pyrimidine-5-carbonitrile;

(S)-2,4-Diamino-6-(1-(4-oxo-3-phenyl-3,4-dihydropyrrolo[1,2-f][1,2,4]triazin-2-yl)ethylamino)pyrimidine-5-carbonitrile;

(S)-4-Amino-6-(1-(4-oxo-3-(tetrahydro-2H-pyran-4-yl)-3,4-dihydropyrrolo[1,2-f][1,2,4]triazin-2-yl)ethylamino)pyrimidine-5-carbonitrile;

(S)-4-Amino-6-(1-(4-oxo-3-(2,2,2-trifluoroethyl)-3,4-dihydropyrrolo[1,2-f][1,2,4]triazin-2-yl)ethylamino)pyrimidine-5-carbonitrile;

(S)-4-Amino-6-(1-(3-cyclobutyl-4-oxo-3,4-di hydropyrrolo[1,2-f][1,2,4]triazin-2-yl)ethylamino)pyrimidine-5-carbonitrile;

(S)-2-Amino-4-(1-(4-oxo-3-phenyl-3,4-dihydropyrrolo[1,2-f][1,2,4]triazin-2-yl)ethylamino)pyrimidine-5-carbonitrile;

(S)-4-Amino-6-(1-(3-cyclopropyl-4-oxo-3,4-dihydropyrrolo[1,2-f][1,2,4]triazin-2-yl)ethylamino)pyrimidine-5-carbonitrile;

(S)-4-Amino-6-(1-(5-bromo-4-oxo-3,4-dihydropyrrolo[1,2-f][1,2,4]triazin-2-yl)ethylamino)pyrimidine-5-carbonitrile;

4-amino-6-((S)-1-(4-oxo-3-((R)-tetrahydro-2H-pyran-3-yl)-3,4-di hydropyrrolo[1,2-f][1,2,4]triazin-2-yl)ethylamino)pyrimidine-5-carbonitrile;

(S)-4-Amino-6-(1-(5-bromo-4-oxo-3-phenyl-3,4-dihydropyrrolo[1,2-f][1,2,4]triazin-2-yl)ethylamino)pyrimidine-5-carbonitrile;

(S)-2-(1-(6-Amino-5-cyanopyrimidin-4-ylamino)ethyl)-3-(5-fluoropyridin-3-yl)-4-oxo-3,4-dihydropyrrolo[1,2-f][1,2,4]triazine-5-carbonitrile;

4-amino-6-((S)-1-(4-oxo-3-((S)-tetrahydro-2H-pyran-3-yl)-3,4-di hydropyrrolo[1,2-f][1,2,4]triazin-2-yl)ethylamino)pyrimidine-5-carbonitrile;

(S)-4-Amino-6-(1-(3-(isoxazol-3-yl)-4-oxo-3,4-dihydropyrrolo[1,2-f][1,2,4]triazin-2-yl)ethylamino)pyrimidine-5-carbonitrile;

(S)-4-Amino-6-(1-(3-(1-methyl-1H-pyrazol-3-yl)-4-oxo-3,4-dihydropyrrolo[1,2-f][1,2,4]triazin-2-yl)ethylamino)pyrimidine-5-carbonitrile;

2-((S)-1-(9H-Purin-6-ylamino)ethyl)-3-(tetrahydro-2H-pyran-3-yl)pyrrolo[1,2-f][1,2,4]triazin-4(3H)-one;

(S)-4-Amino-6-(3-hydroxy-1-(4-oxo-3-phenyl-3,4-dihydropyrrolo[1,2-f][1,2,4]triazin-2-yl)propylamino)pyrimidine-5-carbonitrile;

(S)-2-(1-(9H-Purin-6-ylamino)-3-hydroxypropyl)-3-phenylpyrrolo[1,2-f][1,2,4]triazin-4(3H)-one;

4-Amino-6-((4-oxo-3-o-tolyl-3,4-dihydropyrrolo[1,2-f][1,2,4]triazin-2-yl)methylamino)pyrimidine-5-carbonitrile;

(S)-4-Amino-6-(1-(5-(2-hydroxyethyl)-4-oxo-3-phenyl-3,4-dihydropyrrolo[1,2-f][1,2,4]triazin-2-yl)ethylamino)pyrimidine-5-carbonitrile;

(S)-2-(1-(9H-Purin-6-ylamino)ethyl)-3-(5-fluoropyridin-3-yl)-4-oxo-3,4-dihydropyrrolo[1,2-f][1,2,4]triazine-5-carbonitrile;

(S)-4-Amino-6-(1-(5-(2-methoxyethyl)-4-oxo-3-phenyl-3,4-dihydropyrrolo[1,2-f][1,2,4]triazin-2-yl)ethylamino)pyrimidine-5-carbonitrile;

(S)-4-Amino-6-(1-(4-oxo-3-(6-(trifluoromethyl)pyridin-2-yl)-3,4-dihydropyrrolo[1,2-f][1,2,4]triazin-2-yl)ethylamino)pyrimidine-5-carbonitrile;

(S)-4-Amino-6-(1-(5-bromo-4-oxo-3-(3-(trifluoromethyl)phenyl)-3,4-dihydropyrrolo[1,2-f][1,2,4]triazin-2-yl)ethylamino)pyrimidine-5-carbonitrile;

(S)-2-(2-(1-(6-Amino-5-cyanopyrimidin-4-ylamino)ethyl)-4-oxo-3-phenyl-3,4-dihydropyrrolo[1,2-f][1,2,4]triazin-5-yl)ethyl acetate;

(S)-4-Amino-6-(1-(5-bromo-3-(3-methoxyphenyl)-4-oxo-3,4-dihydropyrrolo[1,2-f][1,2,4]triazin-2-yl)ethylamino)pyrimidine-5-carbonitrile (S)-2-(1-(6-Amino-5-cyanopyrimidin-4-ylamino)ethyl)-4-oxo-3-(3-(trifluoromethyl)phenyl)-3,4-dihydropyrrolo[1,2-f][1,2,4]triazine-5-carbonitrile;

(S)-4-Amino-6-(1-(5-bromo-3-(3-hydroxyphenyl)-4-oxo-3,4-dihydropyrrolo[1,2-f][1,2,4]triazin-2-yl)ethylamino)pyrimidine-5-carbonitrile;

(S)-4-Amino-6-(1-(3-(3-methoxyphenyl)-4-oxo-3,4-dihydropyrrolo[1,2-f][1,2,4]triazin-2-yl)ethylamino)pyrimidine-5-carbonitrile;

(S)-4-Amino-6-(1-(3-(3-hydroxyphenyl)-4-oxo-3,4-dihydropyrrolo[1,2-f][1,2,4]triazin-2-yl)ethylamino)pyrimidine-5-carbonitrile;

(S)-2-(1-(6-Amino-5-cyanopyrimidin-4-ylamino)ethyl)-3-(3-methoxyphenyl)-4-oxo-3,4-dihydropyrrolo[1,2-f][1,2,4]triazine-5-carbonitrile;

(S)-2-(1-(6-Amino-5-cyanopyrimidin-4-ylamino)ethyl)-3-(3-hydroxyphenyl)-4-oxo-3,4-dihydropyrrolo[1,2-f][1,2,4]triazine-5-carbonitrile;

or a pharmaceutically acceptable salt, or solvate, or N-oxide, or stereoisomer or deuterated derivative thereof.

In one embodiment, particular compounds of the invention include:

2-((6-Amino-9H-purin-9-yl)methyl)-5-chloro-3-o-tolylpyrrolo[1,2-f][1,2,4]triazin-4(3H)-one;
2-((6-Aminopyrimidin-4-ylamino)methyl)-5-chloro-3-o-tolylpyrrolo[1,2-f][1,2,4]triazin-4(3H)-one;
2-((6-Amino-9H-purin-9-yl)methyl)-5-cyclopropyl-3-o-tolylpyrrolo[1,2-f][1,2,4]triazin-4(3H)-one;
2-((6-amino-9H-purin-9-yl)methyl)-3-o-tolylpyrrolo[1,2-f][1,2,4]triazin-4(3H)-one;
2-((6-aminopyrimidin-4-ylamino)methyl)-3-o-tolylpyrrolo[1,2-f][1,2,4]triazin-4(3H)-one;
4-((4-oxo-3-o-tolyl-3,4-dihydropyrrolo[1,2-f][1,2,4]triazin-2-yl)methylamino)picolinamide;
2-((2-aminopyridin-4-ylamino)methyl)-3-o-tolylpyrrolo[1,2-f][1,2,4]triazin-4(3H)-one;
2-((9H-purin-6-ylamino)methyl)-3-o-tolylpyrrolo[1,2-f][1,2,4]triazin-4(3H)-one;
2-((6-Amino-9H-purin-9-yl)methyl)-3-cyclohexylpyrrolo[1,2-f][1,2,4]triazin-4(3H)-one;
2-((6-amino-9H-purin-9-yl)methyl)-5-methyl-3-o-tolylpyrrolo[1,2-f][1,2,4]triazin-4(3H)-one;
24(9H-purin-6-ylthio)methyl)-5-methyl-3-o-tolylpyrrolo[1,2-f][1,2,4]triazin-4(3H)-one;
24(6-amino-9H-purin-9-yl)methyl)-6-methyl-3-o-tolylpyrrolo[1,2-f][1,2,4]triazin-4(3H)-one;
2-((9H-purin-6-ylthio)methyl)-6-methyl-3-o-tolylpyrrolo[1,2-f][1,2,4]triazin-4(3H)-one;
2-(1-(6-amino-9H-purin-9-yl)ethyl)-3-phenylpyrrolo[1,2-f][1,2,4]triazin-4(3H)-one;
(S)-2-(1-(9H-purin-6-ylamino)propyl)-3-phenylpyrrolo[1,2-f][1,2,4]triazin-4(3H)-one;
(S)-2-(1-(6-aminopyrimidin-4-ylamino)propyl)-3-phenylpyrrolo[1,2-f][1,2,4]triazin-4(3H)-one;
(S)-2-(1-(2-amino-9H-purin-6-ylamino)propyl)-3-phenylpyrrolo[1,2-f][1,2,4]triazin-4(3H)-one;
(S)-4-amino-6-(1-(4-oxo-3-phenyl-3,4-dihydropyrrolo[1,2-f][1,2,4]triazin-2-yl)propylamino)pyrimidine-5-carbonitrile;
(R)-2-(1-(9H-purin-6-ylamino)propyl)-3-phenylpyrrolo[1,2-f][1,2,4]triazin-4(3H)-one;
(S)-2-(1-(9H-purin-6-ylamino)ethyl)-3-phenylpyrrolo[1,2-f][1,2,4]triazin-4(3H)-one;
(S)-2-(1-(2-amino-9H-purin-6-ylamino)ethyl)-3-phenylpyrrolo[1,2-f][1,2,4]triazin-4(3H)-one;
(S)-2-(1-(6-aminopyrimidin-4-ylamino)ethyl)-3-phenylpyrrolo[1,2-f][1,2,4]triazin-4(3H)-one;
(S)-4-amino-6-(1-(4-oxo-3-phenyl-3,4-dihydropyrrolo[1,2-f][1,2,4]triazin-2-yl)ethylamino)pyrimidine-5-carbonitrile;
2-(1-(6-amino-9H-purin-9-yl)ethyl)-5-methyl-3-phenylpyrrolo[1,2-f][1,2,4]triazin-4(3H)-one;
2-((6-Amino-9H-purin-9-yl)methyl)-3-o-tolyl-5-(trifluoromethyl)pyrrolo[1,2-f][1,2,4]triazin-4(3H)-one;
2-((6-Amino-9H-purin-9-yl)methyl)-5-chloro-3-phenylpyrrolo[1,2-f][1,2,4]triazin-4(3H)-one;
2-((6-Amino-9H-purin-9-yl)methyl)-5-chloro-3-(3-methoxyphenyl)pyrrolo[1,2-f][1,2,4]triazin-4(3H)-one;
2-((6-Amino-9H-purin-9-yl)methyl)-5-chloro-3-(2,4-difluorophenyl)pyrrolo-[1,2-f][1,2,4]triazin-4(3H)-one;
2-((6-Amino-9H-purin-9-yl)methyl)-3-benzyl-5-chloropyrrolo[1,2-f][1,2,4]-triazin-4(3H)-one;
2-((6-amino-9H-purin-9-yl)methyl)-3-phenylimidazo[1,2-f][1,2,4]triazin-4(3H)-one;
2-((6-amino-9H-purin-9-yl)methyl)-3-o-tolylimidazo[1,2-f][1,2,4]triazin-4(3H)-one;
2-((6-Amino-9H-purin-9-yl)methyl)-5-chloro-3-(pyridin-4-yl)pyrrolo[1,2-f][1,2,4]triazin-4(3H)-one;
2-((6-Amino-9H-purin-9-yl)methyl)-5-chloro-3-(tetrahydro-2H-pyran-4-yl)pyrrolo-[1,2-f][1,2,4]triazin-4(3H)-one;
2-((6-Amino-9H-purin-9-yl)methyl)-5-chloro-3-(1-methylpiperidin-4-yl)pyrrolo[1,2-f][1,2,4]triazin-4(3H)-one;
(S)-2-(1-(9H-Purin-6-ylamino)ethyl)-3-(3-fluorophenyl)pyrrolo[1,2-f][1,2,4]triazin-4(3H)-one;
(S)-4-Amino-6-(1-(3-(3-fluorophenyl)-4-oxo-3,4-dihydropyrrolo[1,2-f][1,2,4]triazin-2-yl)ethylamino)pyrimidine-5-carbonitrile;
(S)-2-(1-(9H-Purin-6-ylamino)ethyl)-3-(3,5-difluorophenyl)pyrrolo[1,2-f][1,2,4]triazin-4(3H)-one;
(S)-4-Amino-6-(1-(3-(3,5-difluorophenyl)-4-oxo-3,4-dihydropyrrolo[1,2-f][1,2,4]triazin-2-yl)ethylamino)pyrimidine-5-carbonitrile;
2-((6-Amino-9H-purin-911)methyl)-5-chloro-3-methylpyrrolo[1,2-f][1,2,4]triazin-4(3H)-one;
2-((6-Amino-9H-purin-9-yl)methyl)-3-((1r,4r)-4-aminocyclohexyl)-5-chloropyrrolo[1,2-f][1,2,4]triazin-4(3H)-one;
(R)-2-((6-Amino-9H-purin-9-yl)methyl)-5-chloro-3-(1-phenylethyl)pyrrolo[1,2-f][1,2,4]triazin-4(3H)-one;
(S)-2-((6-Amino-9H-purin-9-yl)methyl)-5-chloro-3-(1-phenylethyl)pyrrolo[1,2-f][1,2,4]triazin-4(3H)-one;
(S)-2-(1-(9H-purin-6-yl)pyrrolidin-2-yl)-3-phenylpyrrolo[1,2-f][1,2,4]triazin-4(3H)-one;
(S)-2-(1-(9H-purin-6-ylamino)ethyl)-3-(pyridin-2-yl)pyrrolo[1,2-f][1,2,4]triazin-4(3H)-one;
(S)-4-amino-6-(1-(4-oxo-3-(pyridin-2-yl)-3,4-dihydropyrrolo[1,2-f][1,2,4]triazin-2-yl)ethylamino)pyrimidine-5-carbonitrile;
(S)-4-amino-6-(1-(4-oxo-3-phenyl-5-(trifluoromethyl)-3,4-dihydropyrrolo[1,2-f][1,2,4]triazin-2-yl)ethylamino)pyrimidine-5-carbonitrile;
(S)-2-(1-(9H-purin-6-ylamino)ethyl)-3-phenyl-5-(trifluoromethyl)pyrrolo[1,2-f][1,2,4]triazin-4(3H)-one;
(S)-4-amino-6-(1-(5-(difluoromethyl)-4-oxo-3-phenyl-3,4-dihydropyrrolo[1,2-f][1,2,4]triazin-2-yl)ethylamino)pyrimidine-5-carbonitrile;
(S)-2-(1-(9H-purin-6-ylamino)ethyl)-5-(difluoromethyl)-3-phenylpyrrolo[1,2-f][1,2,4]triazin-4(3H)-one;
(S)-2-(1-(9H-purin-6-ylamino)ethyl)-3-phenylimidazo[1,2-f][1,2,4]triazin-4(3H)-one;
(S)-4-amino-6-(1-(4-oxo-3-phenyl-3,4-dihydroimidazo[1,2-f][1,2,4]triazin-2-yl)ethylamino)pyrimidine-5-carbonitrile;
(S)-2-(1-(9H-purin-6-ylamino)propyl)-3-phenylimidazo[1,2-f][1,2,4]triazin-4(3H)-one;
(S)-4-amino-6-(1-(4-oxo-3-phenyl-3,4-dihydroimidazo[1,2-f][1,2,4]triazin-2-yl)propylamino)pyrimidine-5-carbonitrile;
2-(1-(9H-purin-6-ylamino)-3,3,3-trifluoropropyl)-3-phenylpyrrolo[1,2-f][1,2,4]triazin-4(3H)-one;
4-amino-6-(3,3,3-trifluoro-1-(4-oxo-3-phenyl-3,4-dihydropyrrolo[1,2-f][1,2,4]triazin-2-yl)propylamino)pyrimidine-5-carbonitrile;

or a pharmaceutically acceptable salt, or solvate, or N-oxide, or stereoisomer or deuterated derivative thereof.

Examples of the preferred compounds in this embodiment are:

(S)-2-(1-(9H-purin-6-ylamino)propyl)-3-phenylpyrrolo[1,2-f][1,2,4]triazin-4(3H)-one;
(S)-2-(1-(2-amino-9H-purin-6-ylamino)propyl)-3-phenylpyrrolo[1,2-f][1,2,4]triazin-4(3H)-one;

(S)-4-amino-6-(1-(4-oxo-3-phenyl-3,4-dihydropyrrolo[1,2-f][1,2,4]triazin-2-yl)propylamino)pyrimidine-5-carbonitrile;
(S)-2-(1-(9H-purin-6-ylamino)ethyl)-3-phenylpyrrolo[1,2-f][1,2,4]triazin-4(3H)-one
(S)-2-(1-(2-amino-9H-purin-6-ylamino)ethyl)-3-phenylpyrrolo[1,2-f][1,2,4]triazin-4(3H)-one;
(S)-4-amino-6-(1-(4-oxo-3-phenyl-3,4-dihydropyrrolo[1,2-f][1,2,4]triazin-2-yl)ethylamino)pyrimidine-5-carbonitrile;
(S)-2-(1-(9H-purin-6-ylamino)ethyl)-3-(3-fluorophenyl)pyrrolo[1,2-f][1,2,4]triazin-4(3H)-one;
(S)-4-amino-6-(1-(3-(3-fluorophenyl)-4-oxo-3,4-dihydropyrrolo[1,2-f][1,2,4]triazin-2-yl)ethylamino)pyrimidine-5-carbonitrile;
(S)-2-(1-(9H-purin-6-ylamino)ethyl)-3-(3,5-difluorophenyl)pyrrolo[1,2-f][1,2,4]triazin-4(3H)-one;
(S)-4-amino-6-(1-(3-(3,5-difluorophenyl)-4-oxo-3,4-dihydropyrrolo[1,2-f][1,2,4]triazin-2-yl)ethylamino)pyrimidine-5-carbonitrile;
(S)-2-((6-amino-9H-purin-9-yl)methyl)-5-chloro-3-(1-phenylethyl)pyrrolo[1,2-f][1,2,4]triazin-4(3H)-one;
(S)-2-(1-(9H-purin-6-yl)pyrrolidin-2-yl)-3-phenylpyrrolo[1,2-f][1,2,4]triazin-4(3H)-one;
(S)-2-(1-(9H-purin-6-ylamino)ethyl)-3-(pyridin-2-yl)pyrrolo[1,2-f][1,2,4]triazin-4(3H)-one;
(S)-4-amino-6-(1-(4-oxo-3-(pyridin-2-yl)-3,4-dihydropyrrolo[1,2-f][1,2,4]triazin-2-yl)ethylamino)pyrimidine-5-carbonitrile;
or a pharmaceutically acceptable salt, or solvate, or N-oxide, or stereoisomer or deuterated derivative thereof.

The compounds of the invention can be prepared using the methods and procedures described herein, or using similar methods and procedures. It will be appreciated that where typical or preferred process conditions (i.e., reaction temperatures, times, mole ratios of reactants, solvents, pressures, etc.) are given; other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group, as well as suitable conditions for protection and deprotection, are well known in the art. For example, numerous protecting groups, and their introduction and removal are described in T. W. Greene and G. M. Wuts, *Protecting Groups in Organic Synthesis, Third Edition*, Wiley, New York, 1999, and references cited therein.

The term amino-protecting group refers to a protecting group suitable for preventing undesired reactions at amino nitrogen. Representative amino-protecting groups include, but are not limited to, formyl; acyl groups, for example alkanoyl groups such as acetyl; alkoxycarbonyl groups such as tert-butoxycarbonyl (Boc); arylmethoxycarbonyl groups such as benzyloxycarbonyl (Cbz) and 9-fluorenylmethoxycarbonyl (Fmoc); arylmethyl groups such as benzyl (Bn), trityl (Tr), and 1,1-di-(4'-methoxyphenyl)methyl; silyl groups such as trimethylsilyl (TMS) and tert-butyldimethylsilyl (TBS); and the like.

The term hydroxy-protecting group refers to a protecting group suitable for preventing undesired reactions at a hydroxy group. Representative hydroxy-protecting groups include, but are not limited to, alkyl groups, such as methyl, ethyl, and tert-butyl; acyl groups, for example alkanoyl groups, such as acetyl; arylmethyl groups, such as benzyl (Bn), p-methoxybenzyl (PMB), 9-fluorenylmethyl (Fm), and diphenylmethyl (benzhydryl, DPM); silyl groups, such as trimethylsilyl (TMS) and tert-butyldimethylsilyl (TBS); and the like.

According to one embodiment of the present invention, compounds of general Formula (I) may be prepared by the synthetic route illustrated in Scheme 1, from compounds of Formula (Va), where the group $Z_1$ represents a halogen atom such as chlorine, bromine and iodine or another suitable leaving group such as methanesulfonate or trifluoromethanesulfonate or other groups such as hydroxyl, that can be converted to suitable leaving groups by standard methods described in the literature, such as the Mitsunobu reaction and others.

Compounds of Formula (I) can be obtained directly from compounds of Formula (Va) by treatment of (Va) with compounds of Formula (IVa), (IVb) or (IVc) in the presence of a suitable base such as potassium carbonate, diisopropylethylamine or sodium hydride in an appropriate solvent such as tert-butanol, N,N-dimethylformamide or tetrahydrofurane at temperatures ranging from room temperature to 160° C., with or without the use of microwaves irradiation.

When $Z_1$ is a halogen atom such as chlorine, it can be converted to another more reactive halogen atom such as iodine by treating the compound with the chlorine atom with sodium iodide in acetone at a temperature from room temperature to reflux.

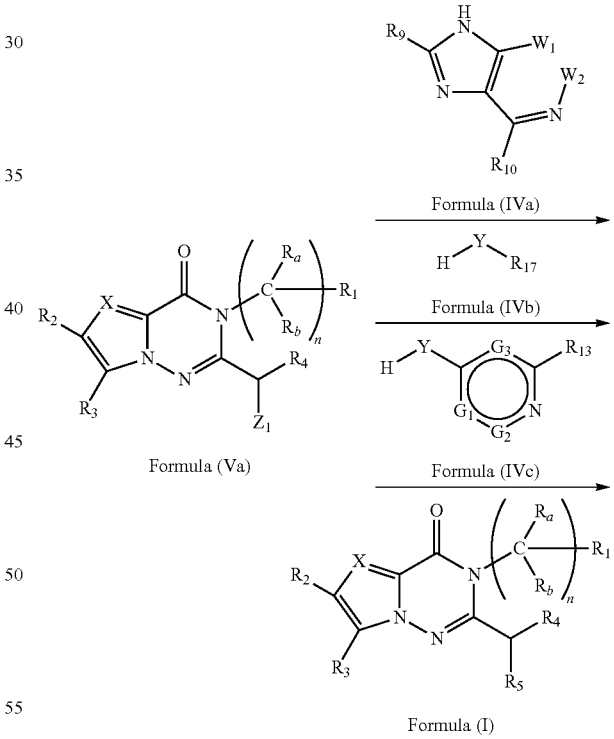

Scheme 1

Alternatively, compounds of general Formula (I) can be obtained directly from compounds of Formula (Vb), where the group Y represents a —NR'— group, wherein R' is a hydrogen atom, as illustrated in Scheme 2.

Thus, compounds of Formula (Vb) can be treated with electrophiles of Formula (IVd) or (IVe), where the group $Z_1$ represents a leaving group such as a halogen atom, methanesulphonate or trifluoromethanesulphonate, in the presence of a suitable base such as potassium carbonate, diisopropylethylamine or sodium hydride in an appropriate solvent such as tert-butanol, N,N-dimethylformamide or tetrahydrofurane at temperatures ranging from room temperature to 220° C., with or without the use of microwaves irradiation.

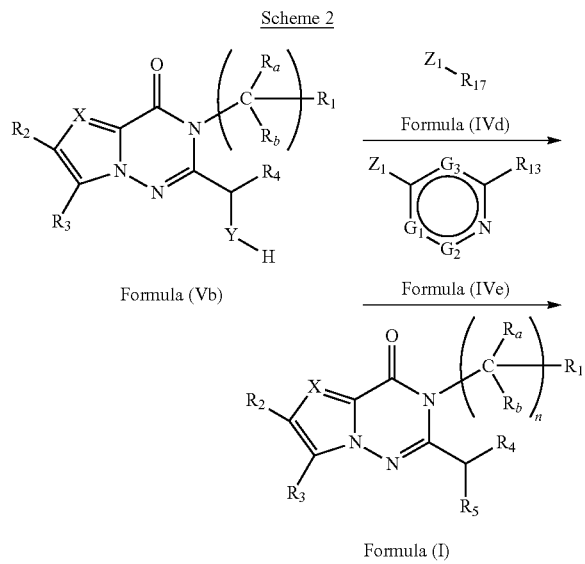

Scheme 2

Formula (Vb)

Formula (IVd)

Formula (IVe)

Formula (I)

Alternatively, compounds of Formula (Va) where $Z_1$ is for instance a halogen atom can be converted to compounds of Formula (Vb) where Y is a —NR'— group, wherein R' is as defined above, by treating compounds (Va) with a solution of ammonia in a solvent such as methanol at a temperature between 60 to 120° C.

Compounds of general Formula (V), which comprises compounds of subFormula (Va) and subFormula (Vb), can be prepared directly from compounds of Formula (VII) as illustrated in Scheme 3 by treatment of compounds with Formula (VII) with the appropriate acid chlorides of Formula (VIII) in a solvent such as acetic acid at a temperature ranging from room temperature to 150° C. with or without the use of microwaves irradiation.

In the particular case where $Z_2$ is a chlorine atom, the compounds of Formula (V) can also be prepared by treating the compounds of Formula (VII) with 2-chloro-1,1,1-trimethoxyethane in the presence of pyridinium p-toluenesulfonate at a temperature between 50° C. and 150° C.

Alternatively, compounds of Formula (V) can be obtained in two steps from compounds of Formula (VII), isolating the intermediate amides of Formula (VI).

Compounds of Formula (VII) can be transformed in amides of Formula (VI) by treatment with carboxylic acids of Formula (IX), where $Z_2$ represents a leaving group of Formula $Z_1$ or a nucleophile of Formula Y unprotected or protected by known protecting groups described in the literature, in the presence of an activating agent by methods and conditions well described in the literature, for example using EDC or HATU as an activating agent in a solvent such as tetrahydrofurane or dichloromethane or mixtures of these solvents at temperatures ranging from room temperature to 80° C.

Alternatively, amides of Formula (VI) can be obtained from compounds of Formula (VII) by treatement with acid chlorides of Formula (VIII) at room temperature in a suitable solvent such as acetic acid or 1,4-dioxane or alternatively in the presence of a base such as triethylamine in a suitable solvent such as dichloromethane.

In a second step, compounds of Formula (VI) can yield compounds of Formula (V) by treatment with phosphorous oxychloride at temperatures ranging from room temperature to 100° C., with or without a subsequent treatment with a solution of a base such as ammonia, pirrolidine, piperidine, potassium carbonate or sodium methanethiolate in a solvent such as methanol, ethyl acetate or N,N-dimethylformamide at a temperature between room temperature and 100° C.

Alternatively, amides of Formula (VI) can yield compounds of Formula (V) by heating these amides in a solvent such as xylene or toluene with the presence of pyridinium p-toluenesulfonate or p-toluenesulfonic acid at a temperature between 80° C. and 160° C.

Alternatively, compounds of Formula (VI) can yield compounds of Formula (V) by treatment of compounds of Formula (VI) with the complex resulting from the treatment of triphenylphosphine with bromine in a solvent such as dichloromethane in the presence of a base such as triethylamine at a temperature from room temperature to reflux, with or without a subsequent treatment with a base such as ammonia, pirrolidine, piperidine, potassium carbonate or sodium methanethiolate in a solvent such as methanol, ethyl acetate or N,N-dimethylformamide at a temperature between room temperature and 100° C.

Scheme 3

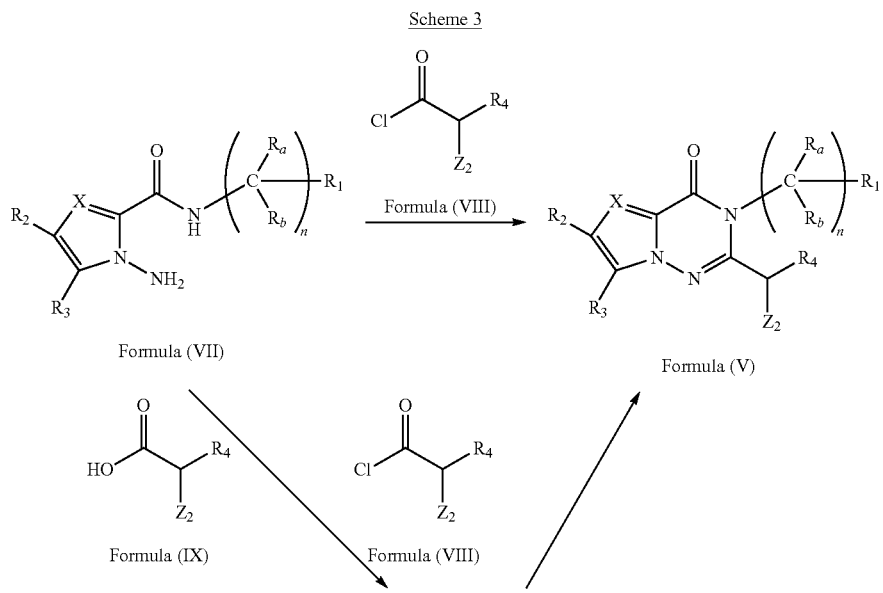

Formula (VII)

Formula (VIII)

Formula (V)

Formula (IX)

Formula (VIII)

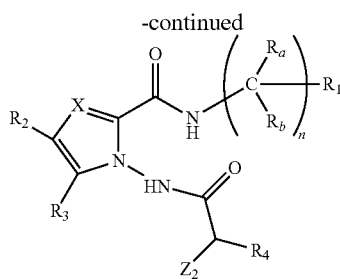

Formula (VI)

The acid chlorides of Formula (VIII) and the carboxylic acids of Formula (IX) can be used in a protected form to prevent certain functional groups from undergoing undesired reactions. In these cases, standard methods for the removal of these protecting groups can be used at the suitable step of the synthesis. Numerous protecting groups, their introduction and their removal are described in T. W. Greene and G. M. Wuts, Protecting Groups in Organic Synthesis, Third Edition, Wiley, New York, 1999, and references cited therein.

Compounds of Formula (VII) can be prepared from carboxylic acids of Formula (XII) following the Scheme described in Scheme 4.

Carboxylic acids (XII) can be activated with any activating reagent described in the literature such as thionyl chloride, oxalyl chloride, phosphorous oxychloride, 2-(3H-[1,2,3]triazolo[4,5-b]pyridin-3-yl)-1,1,3,3-tetramethylisouronium hexafluorophosphate(V), 3-((ethylimino)methyleneamino)-N,N-dimethylpropan-1-aminium chloride, 2,4,6-tripropyl-1,3,5,2,4,6-trioxatriphosphorinane-2,4,6-trioxide and treated with amines of Formula (XI) in the presence of a base such as diisopropylethylamine when needed in a suitable solvent such as dioxane, dichloromethane, N,N-dimethylformamide, ethyl acetate or tetrahydrofurane at temperatures ranging from 0° C. to reflux to give amides of Formula (X).

Subsequently, amides of Formula (X) can be aminated on the nitrogen atom in position 1 by any of the aminating reagents described in the literature, such as O-(mesitylenesulfonyl)hydroxylamine, O-(p-nitrobenzoyl)-hydroxylamine, O-(diphenyl-phosphinyl)-hydroxylamine, O-(2,4-dinitrophenyl)-hydroxylamine, hydroxylamine-O-sulfonic acid using a suitable base such as triethylamine, potassium carbonate, sodium hydride or butyl lithium in an appropriate solvent such as N,N'-dimethylformamide, tetrahydrofurane, 1,4-dioxane at temperatures ranging from −78 to 100° C.

Alternatively, the amination reaction can be carried out in a biphasic system using an aqueous solution of ammonia, sodium hydroxide, ammonium chloride and sodium hypochlorite and a suitable organic solvent such as dialkyl ethers and adding a phase transfer catalyst such as Aliquat 336® at temperatures ranging from 0° C. to room temperature.

Scheme 4

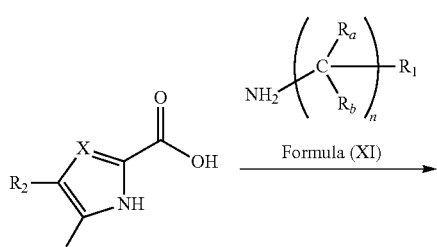

Formula (XII)

Formula (XI)

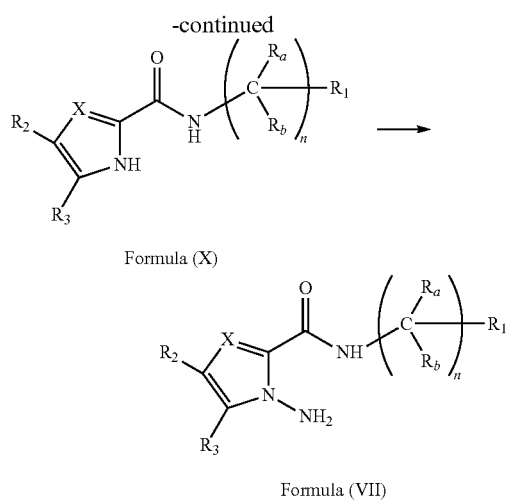

Formula (X)

Formula (VII)

In another embodiment of the present invention, compounds of general Formula (I) may be prepared by the synthetic route illustrated in Scheme 5, from compounds of Formula (XV), where the group $Z_1$ represents a halogen atom such as chlorine, bromine and iodine or another suitable leaving group such as methanesulfonate or trifluoromethanesulfonate or other groups such as hydroxyl, that can be converted to suitable leaving groups by standard methods described in the literature, such as the Mitsunobu reaction and others.

Compounds of Formula (I) can be obtained from compounds of Formula (XIV) by treatment of (XIV) with the corresponding amines of Formula (XI) in the presence or not of a suitable base such as sodium hexamethyldisilazide or a Lewis acid such as trimethyl aluminium at a temperature ranging from room temperature to 150° C. in an appropriate solvent such as 1,4-dioxane, tetrahydrofurane or dichloromethane. The intermediate diamides of Formula (XIII) obtained were subsequently cyclizated to afford compounds of Formula (I) by treatment with phosphorous oxychloride at temperatures ranging from room temperature to 100° C., with or without a subsequent treatment with a solution of a base such as ammonia, pyrrolidine, piperidine or sodium methanethiolate in a solvent such as methanol, tetrahydrofurane or ethyl acetate at a temperature between room temperature and 100° C.

Alternatively, compounds of Formula (XIII) can yield compounds of Formula (I) by treatment of compounds of Formula (XIII) with the complex resulting from the treatment of triphenylphosphine with bromine in a solvent such as dichloromethane in the presence of a base such as triethylamine at a temperature from room temperature to reflux, with or without a subsequent treatment with a base such as ammonia, pirrolidine, piperidine or sodium methanethiolate in a solvent such as methanol or ethyl acetate at a temperature between room temperature and 100° C.

Compounds of Formula (XIV) can be obtained directly from compounds of Formula (XV) by treatment of (XV) with compounds of Formula (IVa), (IVb) or (IVc) in the presence of a suitable base such as potassium carbonate, diisopropylethylamine or sodium hydride in an appropriate solvent such as tert-butanol, N,N-dimethylformamide or tetrahydrofurane at temperatures ranging from room temperature to 160° C., with or without the use of microwaves irradiation.

When $Z_1$ is a halogen atom such as chlorine, it can be converted to another more reactive halogen atom such as iodine by treating the compound with the chlorine atom with sodium iodide in acetone at a temperature from room temperature to reflux.

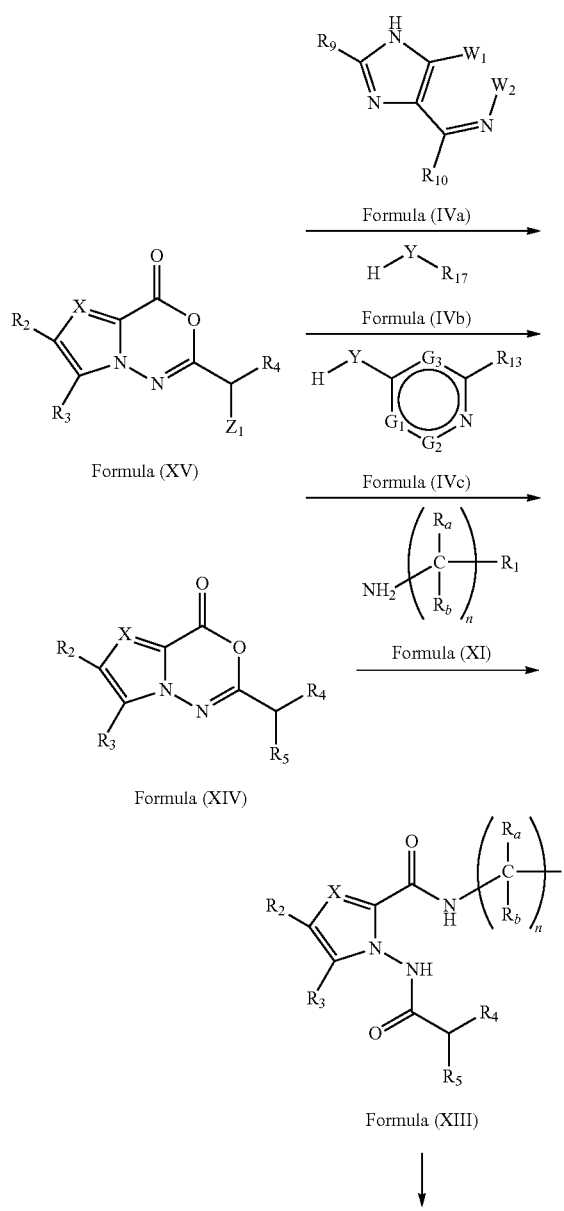

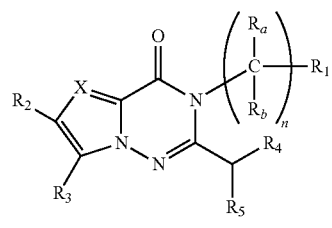

Formula (I)

Compounds of general Formula (XV) can be prepared directly from compounds of Formula (XVI) as illustrated in Scheme 6 by treatment of compounds with Formula (XVI) with the appropriate acid chlorides of Formula (VIII) in a solvent such as acetic acid at a temperature ranging from room temperature to 150° C. with or without the use of microwaves irradiation.

Alternatively, compounds of Formula (XV) can be obtained in two steps from compounds of Formula (XVI), isolating the intermediate amides of Formula (XVII).

Compounds of Formula (XVI) can be transformed in amides of Formula (XVII) by treatment with acid chlorides of Formula (VIII) at a temperature ranging from 0° C. to room temperature in a suitable solvent such as acetic acid or 1,4-dioxane.

In a second step, compounds of Formula (XVII) can yield compounds of Formula (XV) by treatment with phosphorous oxychloride at temperatures ranging from room temperature to 100° C. in a suitable solvent such as 1,4-dioxane. Alternatively, compounds of Formula (XVII) can yield compounds of Formula (XV) by treatment of compounds of Formula (XVII) with the complex resulting from the treatment of triphenylphosphine with bromine in a solvent such as dichloromethane in the presence of a base such as triethylamine at a temperature from room temperature to reflux, with or without a subsequent treatment with a base such as ammonia, pyrrolidine, piperidine or sodium methanethiolate or potassium carbonate in a solvent such as methanol, ethyl acetate or N,N-dimethylformamide at a temperature between room temperature and 100° C.

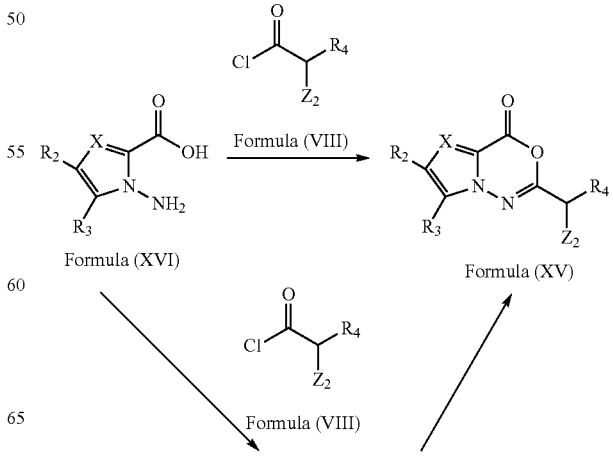

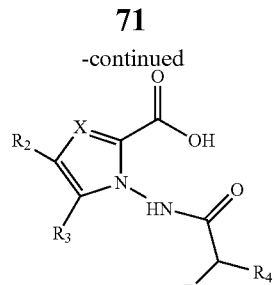

Formula (XVII)

Compounds of Formula (XVI) may be obtained from compounds of Formula (XII) as illustrated in Scheme 7 by treatment with benzyl bromide and a suitable base such as triethylamine or cesium carbonate in an appropriate solvent such as N,N-dimethyl-formamide or acetonitrile at temperatures ranging from 0 to 60° C. following the protocol described elsewhere in the literature. Alternatively, compounds of Formula (XII) may be coupled with benzyl alcohol activating the carboxylic group of (XII) through the formation of the corresponding acid chloride or any other activated ester.

Subsequently, esters of Formula (XIX) can be aminated on the nitrogen atom in position 1 by any of the aminating reagents described in the literature, such as O-(mesitylene-sulfonyl)hydroxylamine, O-(p-nitrobenzoyl)-hydroxylamine, O-(diphenyl-phosphinyl)-hydroxylamine, O-(2,4-dinitrophenyl)-hydroxylamine, hydroxylamine-O-sulfonic acid using a suitable base such as triethylamine, potassium carbonate, sodium hydride or butyl lithium in an appropriate solvent such as N,N'-dimethylformamide, tetrahydrofurane, 1,4-dioxane at temperatures ranging from −78 to 100° C.

Alternatively, the amination reaction can be carried out in a biphasic system using an aqueous solution of ammonia, sodium hydroxide, ammonium chloride and sodium hypochlorite and a suitable organic solvent such as dialkyl ethers and adding a phase transfer catalyst such as Aliquat 336® at temperatures ranging from 0° C. to room temperature.

Preparation of compounds of Formula (XVI) can be done by hydrogenolysis using an appropriate catalyst such as 10% palladium on charcoal in a suitable solvent such as an alkyl alcohol under a hydrogen atmosphere at pressures ranging from atmospheric pressure to 60 psi and at temperatures ranging from room temperature to 60° C.

Alternatively, it is also possible to add an acid to the reaction media such as hydrochloric acid to favour the hydrogenolysis process. Also, compounds of Formula (XVI) can be obtained by saponification of esters (XVIII) using an acid such as hydrochloric acid or sulphuric acid or a base such as sodium hydroxide in an appropriate solvent such as water or alkyl alcohols at temperatures ranging from room temperature to 100° C.

Scheme 7

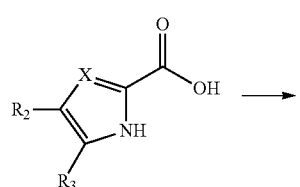

Formula (XII)

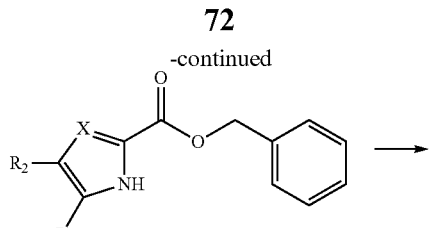

Formula (XIX)

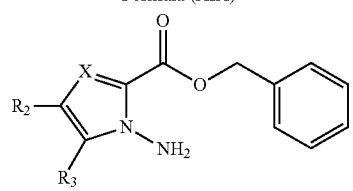

Formula (XVIII)

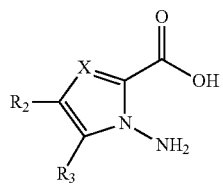

Formula (XVI)

Compounds (XII) can either be commercially available compounds or can be prepared by the synthetic Schemes illustrated in Schemes 8 and 9. In the particular case when X represents $CR_6$ being $R_6$ a $C_3$-$C_7$ cycloalkyl group, or a linear or branched $C_1$-$C_4$ alkyl group, saturated or unsaturated $C_1$-$C_4$ alkyl group compounds of Formula XIIa can be prepared, as illustrated in Scheme 8, from bromopyrrolof Formula (XXIa)[2] by Suzuki or Stille coupling with the corresponding boronic acids or organotin compound in the presence of a palladium catalyst such as tetrakis(triphenylphosphane) palladium(0) or palladium acetate with or without an appropriate base such as potassium carbonate or cesium carbonate and in a suitable solvent such as toluene or dioxane or N,N-dimethylformamide at temperatures ranging from 60° C. to 150° C.

In the particular case where X represents $CR_6$, being $R_6$ a trifluoromethyl group, the bromine atom of compound of Formula (XXIa) can be converted into a iodine atom by treatment of (XXIa) with sodium iodide in the presence of a catalysts such as copper (I) iodide and a chelating amine such as trans-1,2-bis(methylamino)cyclohexane in an appropriate solvent such as 1,4-dioxane at a temperature ranging from 60° C. to reflux. Next, treatment of the iodine intermediate with methyl 2,2-difluoro-2-(fluorosulfonyl)acetate or any other trifluoro methylating agent using a suitable catalyst such as copper (I) iodide in the presence or not of a chelating agent such as hexamethylphosphoramide and in an appropriate solvent such as N,N' dimethylformamide afforded intermediate compound of Formula (XXa).

In the particular case where $R_6$ is a cyano group, the bromine atom of compound of Formula (XXIa) can be converted first into a iodine with the methods previously described or treated directly with dicyanozinc in the presence of a palladium catalyst such as tetrakis(triphenylphoshane) palladium (0) in an appropriate solvent such as N,N'-dimethylformamide at a temperature ranging from 60° C. to 150° C. or by using copper cyanide in a solvent such pyridine at temperatures ranging from 60° C. to 150° C.

In the particular case where $R_6$ is a difluoromethyl group, vinyl intermediates synthesized by Stille reaction previously described can be treated with diethylaminosulfur trifluoride (DAST) in an appropriate solvent such as dichloromethane at a temperature between −78° C. and room temperature to yield the compounds of Formula (XXa).

Finally, compounds of Formula (XIIa) can be obtained by simultaneous cleavage of the sulphone and ester groups of compounds of Formula (XXa) by means of a base such as lithium hydroxide in a suitable solvent or mixture of solvents such as water or tetrahydrofurane at temperatures ranging from room temperature to 220° C., with or without the use of microwaves irradiation. Alternatively, the cleavage of the sulphone and ester groups of compounds of Formula (XXa) can be done sequentially by treatment of compounds (XXa) with tetrabutylammonium fluoride in an appropriate solvent such as tetrahydrofurane at a temperature from room temperature to reflux and subsequent hydrolysis of the ester group by any of the methods well known in the literature.

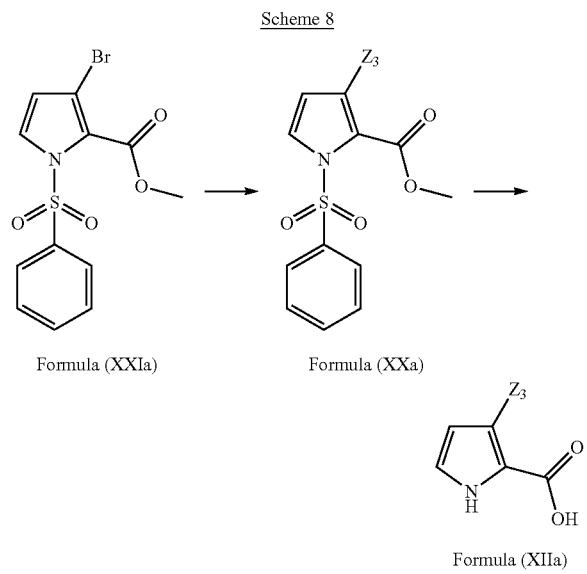

In the particular case when X represents $CR_6$ being $R_6$ hydrogen or $C_3$-$C_7$ cycloalkyl group, or a linear or branched $C_1$-$C_4$ alkyl group, and $R_2$ independently represents hydrogen or $C_3$-$C_7$ cycloalkyl group, or a linear or branched $C_1$-$C_4$ alkyl group, compounds Xa can be prepared, as illustrated in Scheme 9, from pyrroles of Formula (XXIIIa). Pyrroles of Formula (XXIIIa) can be reacted with 2,2,2-trichloroacetyl chloride in a suitable solvent such as diethyl ether at a temperature ranging from room temperature to reflux affording ketones of Formula (XXIIa). These intermediate compounds of Formula (XXIIa) can be reacted with the corresponding amines of Formula (XI) with or without solvent in the presence of a base such as triethylamine at a temperature ranging from room temperature to 150° C. to afford compounds of Formula (Xa).

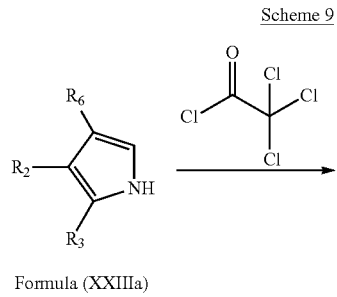

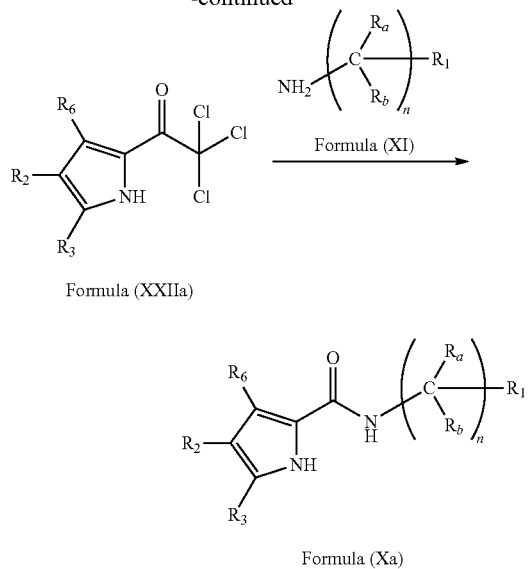

In another embodiment of the present invention compounds of Formula (X) may be prepared by the synthetic route illustrated in Scheme 10 from treating compounds of Formula (XXV) with amines of Formula (XI) in the presence or not of a Lewis acid such as trimethyl aluminium in an appropriate solvent such as toluene and a temperature ranging from room temperatures to 120° C.

Compounds of general Formula (XXV) can be obtained from commercial sources or prepared as described in the literature[2]. Additionaly, conventionaly protecting groups may be necessary to prevent NH group from pyrrole from undergoing undesired reactions such as phenylsulphonyl group.

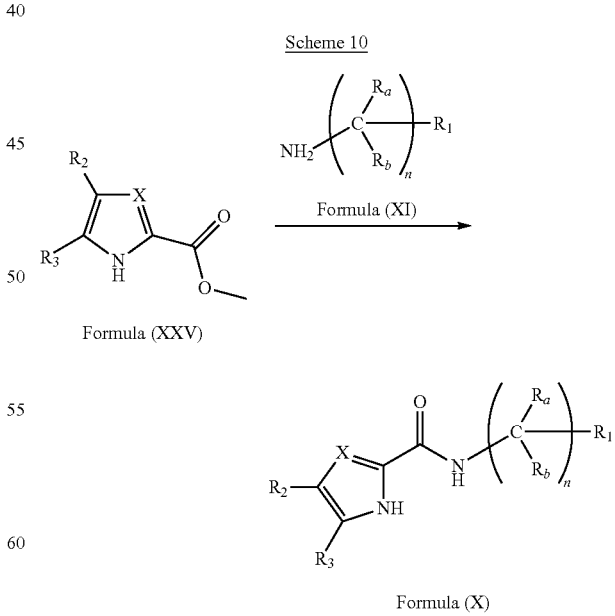

Alternatively, compounds of general Formula (VI) may be prepared by the synthetic route illustrated in Scheme 11. Thus, compounds of Formula (VI) can be prepared from compounds of Formula (XXVII) by known amide formation methods such as those described above. Compounds of Formula (XXVII) can be prepared by the known coupling methods previously described. Compounds of Formula (XXVI) can be obtained by amination of compounds of Formula (XXV) by the methods already described.

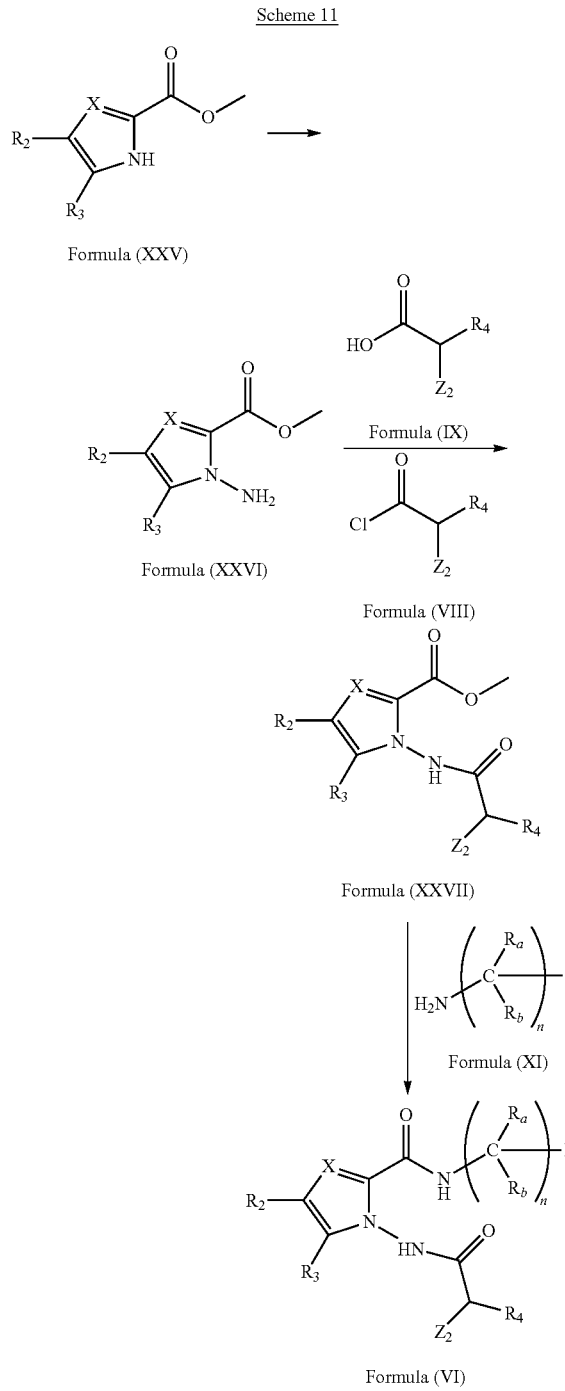

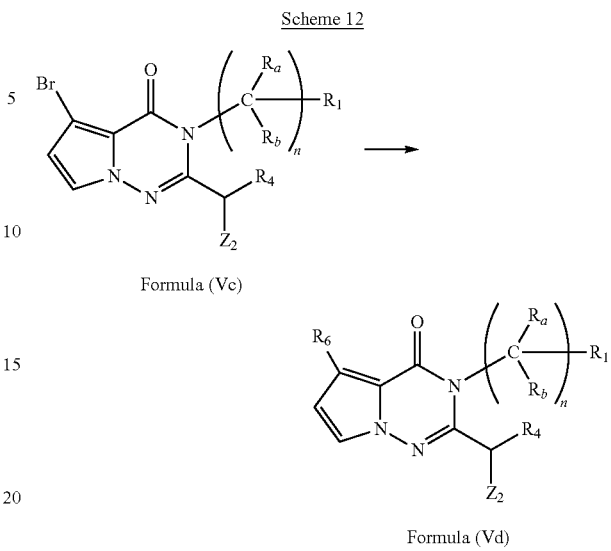

Compounds of general Formula (V) where X represents $CR_6$ being $R_6$ as defined in claim 1 can also be synthesized from compounds of Formula (Vc) as shown in Scheme 12 by the general methods described as it follows.

In the particular case where $R_6$ is a trifluoromethyl group, the bromine atom of compound of Formula (Vc) can be converted first into a iodine and subsequently transformed to a trifluoromethyl group following the general methods previously described.

In the particular case where $R_6$ is a cyano group, the bromine atom of compound of Formula (Vc) can be converted first into a iodine with the methods previously described or treated directly with dicyanozinc in the presence of a palladium catalyst such as tetrakis(triphenylphoshane) palladium (0) in an appropriate solvent such as N,N' dimethylformamide at a temperature ranging from 60° C. to 150° C. or by using copper cyanide in a solvent such pyridine at temperatures ranging from 60° C. to 150° C.

In the particular case where $R_6$ is a alkyl or cycloalkyl group, or an aromatic or heteroaromatic ring compounds of Formula (V) can be obtained by standard Suzuki or Stille couplings with the corresponding boronic acid or organotin compound in the presence of a palladium catalyst such as tetrakis(triphenylphosphane) palladium(0) or palladium acetate with or without an appropriate base such as potassium carbonate or cesium carbonate and in a suitable solvent such as toluene or dioxane or N,N-dimethylformamide at temperatures ranging from 60° C. to 150° C.

Alternatively, non commercial heteroaromatic rings can be prepared from compounds of Formula (V) where X is $CR_6$ being $R_6$ a cyano groups or a carboxylic acid with the standard methods described in the literature.

In the particular case where $R_6$ is a fluorine, compound of Formula (Vc) can be treated with a lithiated agent such as n-BuLi, in a non protic solvent such as hexanes and at a temperature between −78° C. and 0° C. and subsequently treated with a suitable fluorine source such as N-fluoro-N-(phenylsulfonyl)-benzenesulfonamide at a temperature between −78° C. and room temperature.

Compounds of general Formula (Vf) to (Vk) can be synthesized by the general methods illustrated in Scheme 13.

Scheme 13

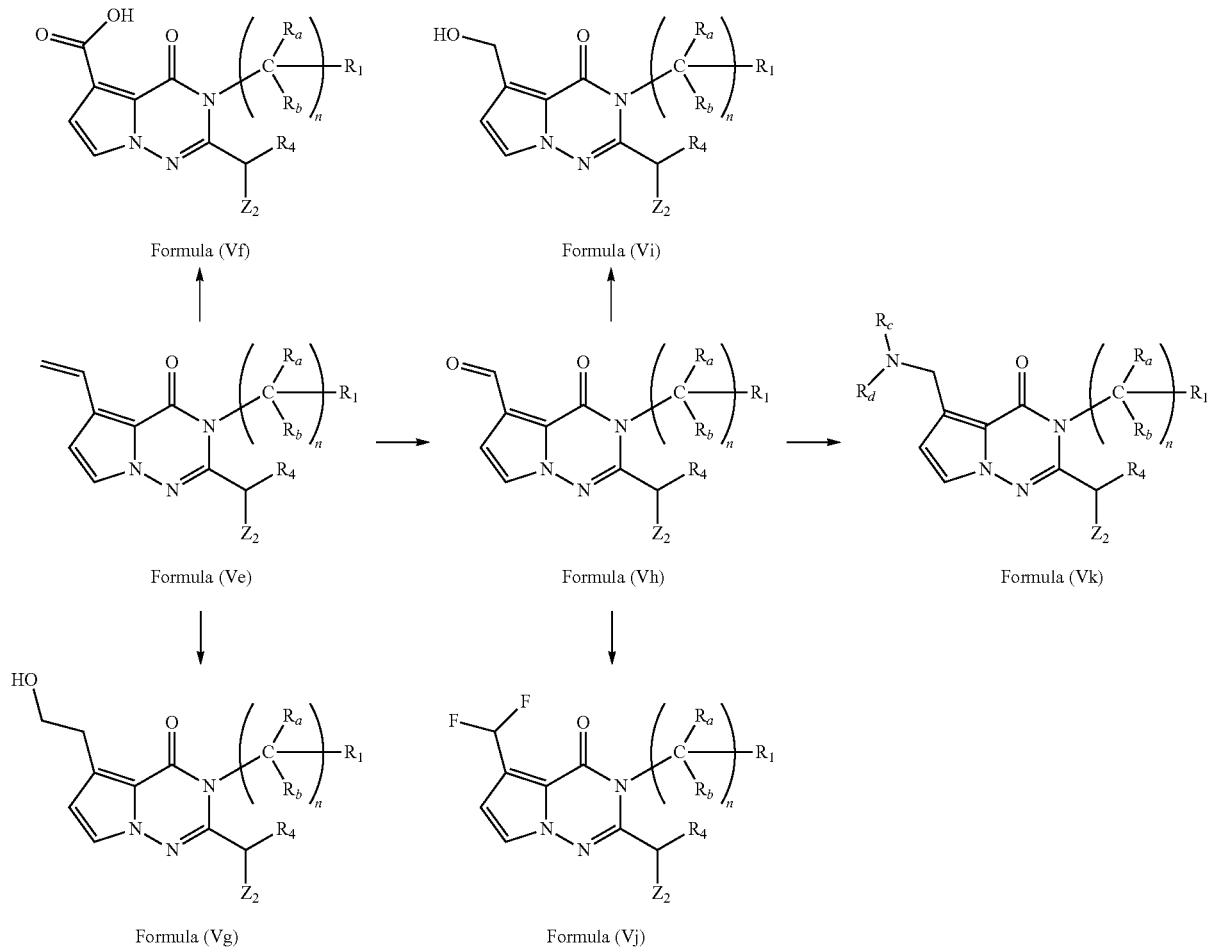

Compounds of Formula (Vi) can be prepared by treating compounds of general Formula (Vh) with a reducing reagent such as $NaBH_4$ in a protic solvent such as methanol at room temperature. Compound of Formula (Vi) can then be further derivatized by treating those compounds with haloalkanes or carboxylic acids to obtain the corresponding ethers or esters.

Compounds of Formula (Vj) can be synthesized by treating compounds of Formula (Vh) with diethylaminosulfur trifluoride (DAST) in an appropriate solvent such as dichloromethane at a temperature between $-78°$ C. and room temperature.

Compounds of Formula (Vk) can be prepared by treating compounds of Formula (Vh) with an amine of Formula $NHR_cR_d$ in an appropriate solvent such as acetic acid at room temperature and subsequently adding a reducing agent such as sodium cyanoborohydride.

Compounds of Formula (Vh) can be prepared by treating compounds of Formula (Ve) with osmium tetroxide and 4-methylmorpholine-4-oxide in an appropriate solvent such as tetrahydrofurane at room temperature obtaining the 1,2-dihydroxyethylderivative and then by treatment with sodium periodate in an appropriate solvent such as tetrahydrofurane at room temperature.

Alternatively, compounds of general Formula (Vh) may be prepared by ozonolisys of compounds of Formula (Ve) in a mixture of acetone and water at temperatures ranging from $-25°$ C. to $0°$ C.

Compounds of Formula (Ve) can be prepared by treating compounds of Formula (Vc) with ethenyl(tributyl)tin in the presence of a palladium catalyst such as tetrakis(triphenylphosphane) palladium(0) in a suitable solvent such as N,N-dimethylformamide at temperatures ranging from $60°$ C. to $150°$ C.

Compounds of Formula (Vf) can be prepared by ozonolysis of compounds of Formula (Ve) in a mixture of solvents such as ethyl acetate and pyridine at temperatures ranging from $-25°$ C. to $0°$ C. In the particular case where $R_6$ is an ester, compounds of Formula (Vf) can be treated with the corresponding haloalkane in the presence of a base such as potassium carbonate in a solvent such as N,N-dimethylformamide at temperatures ranging from $0°$ C. to $150°$ C.

In the particular case of compounds of (Vd) where $R_6$ is an amide, compounds can be obtained by treating compounds of Formula (Vf) with the corresponding amine with a coupling reagent such as N-(3-dimethylaminopropyl)-N'-ethylcarbodiimide hydrochloride in the presence of 1-hydroxybenzotriazole in a solvent such as N,N' dimethylformamide at temperatures ranging from $0°$ C. to $150°$ C.

In the particular case of the primary amide it can be obtained from compounds where $R_6$ is a cyanogroup by treating with concentrated sulphuric acid at room temperature.

Compounds of Formula (Vg) can be prepared by treating compounds of Formula (Ve) with an hidroborating agent such as 9-borabicyclo[3.3.1]nonane in an appropiate solvent such as tetrahydrofurane at temperatures beetween −5° C. and room temperature and subsequently treating with an oxidative reagent such as hydrogen peroxide in the presence of a base such as sodium hydroxide at temperatures ranging from −5° C. to room temperature.

Compounds of formula (Vg) can be treated with haloalkanes in the presence of a base such as sodium hydride in an aprotic solvent such as tetrahydrofurane to obtain the corresponding ethers. In another embodiment compounds of formula (Vg) can also be treated with carboxylic acids at temperatures ranging from 25° C. to 150° C. to obtain the corresponding esters.

In the particular case of compounds of Formula (Vd) where $R_6$ is hydrogen, compounds can alternatively be obtained by hydrogenolysis of compounds of Formula (Vc) using an appropriate catalyst such as 10% palladium on charcoal in a suitable solvent such as an alkyl alcohol under a hydrogen atmosphere at pressures ranging from atmospheric pressure to 60 psi and at temperatures ranging from room temperature to 60° C.

In another embodiment of the present invention, compounds of Formula (V) can alternatively be prepared from compounds of Formula (Vm) as shown in Scheme 14 using the derivatization methods described above. In some particular cases the bromine atom of compound of Formula (Vm) can be converted first into a iodine of Formula (Vn) and subsequently derivatized following the general methods previously described.

Reagents, starting materials, and solvents were purchased from commercial suppliers and used as received. Concentration or evaporation refers to evaporation under vacuum using a Büchi rotatory evaporator.

Reaction products were purified, when necessary, by flash chromatography on silica gel (40-63 μm) with the solvent system indicated. Purifications in reverse phase were made in a Biotage SP1® automated purification system equipped with a $C_{18}$ column and using a gradient of water-acetonitrile/MeOH (1:1) (0.1% v/v ammonium formate both phases) from 0% to 100% acetonitrile/MeOH (1:1) in 40 column volumes. The appropriate fractions were collected and the solvents evaporated under reduced pressure and/or liofilized.

Preparative HPLC-MS were performed on a Waters instrument equipped with a 2767 injector/collector, a 2525 binary gradient pump, a 2996 PDA detector, a 515 pump as a make-up pump and a ZQ4000 Mass spectrometer detector or on a Agilent 1200 Series coupled to an Agilent 6120 Mass spectrometer detector. Both systems were equipped with a Symmetry Prep $C_{18}$ (19×300 mm, 7 μm) column or a XBridge Prep $C_{18}$ (19×100 mm, 5 μm) column. The mobile phase was formic acid (0.4 mL), ammonia (0.1 mL), methanol (500 mL) and acetonitrile (500 mL) (B) and formic acid (0.5 mL), ammonia (0.125 mL) and water (1000 mL) (A), the specific gradients used are specified in each particular case. The flow rate was 20 mL/min.

Purity and MS identification was performed in a Waters 2795 system coupled to a 2996 Diode array detector and to a Waters ZQ mass spectrometer detector or in a Waters Acquity

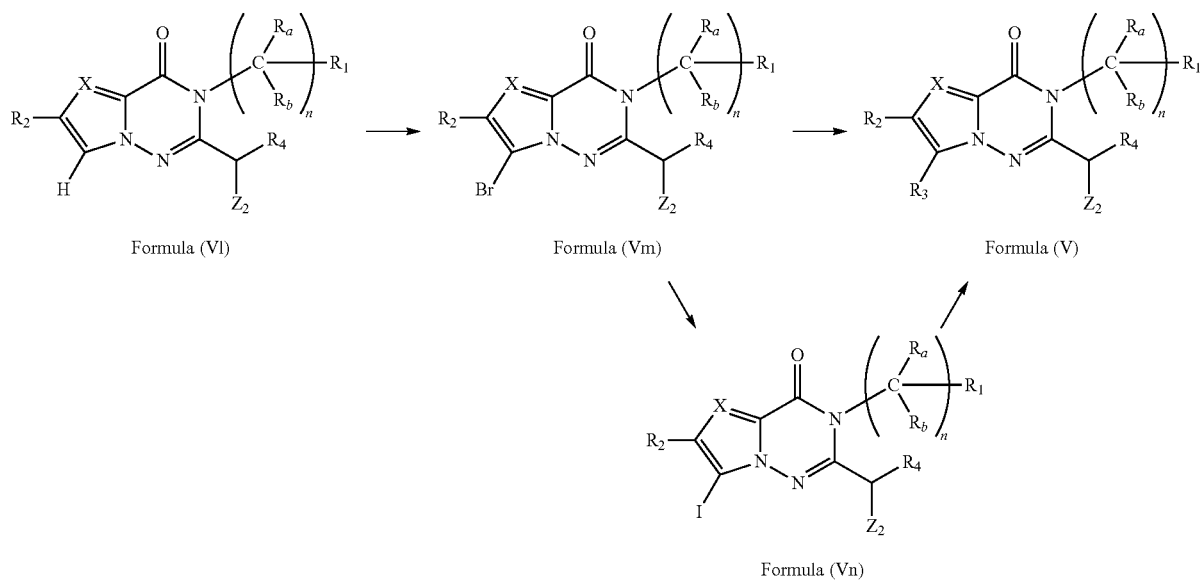

Scheme 14

Formula (VI)   Formula (Vm)   Formula (V)

Formula (Vn)

EXAMPLES

General

The syntheses of the compounds of the invention and of the intermediates for use therein are illustrated by the following Examples (1-187) (including Preparation Examples (Preparations 1-146)) are given in order to provide a person skilled in the art with a sufficiently clear and complete explanation of the present invention, but should not be considered as limiting of the essential aspects of its subject, as set out in the preceding portions of this description.

UPLC system coupled to a SQD mass spectrometer detector. The injection volume was 5 microliter on the HPLC and 0.5 microliter on the UPLC. Chromatograms were processed at 210 nM or 254 nM. Mass spectra of the chromatograms were acquired using positive and negative electrospray ionization. The mobile phase was formic acid (0.4 mL), ammonia (0.1 mL), methanol (500 mL) and acetonitrile (500 mL) (B) and formic acid (0.5 mL), ammonia (0.125 mL) and water (1000 mL) (A) and a gradient between 0 to 95% of B was used. Columns: HPLC: Waters Symmetry (2.1×50 mm, 3.5 □m); UPLC: ACQUITY UPLC BEH C-18 (2.1×50 mm, 1.7 □m)

¹H Nuclear Magnetic Resonance Spectra were recorded on a Varian Gemini-2000 spectrometer operating at a frequency of 300 MHz for the ¹H spectra or in a Varian Mercury plus operating at a frequency of 400 MHz for the ¹H spectra. Samples were dissolved in the specified deuterated solvent. Tetramethylsilane was used as reference.

Abbreviations
DMF Dimethylformamide
DMSO Dimethylsulfoxide
CDCl3 Deuterated chloroform
NMR Nuclear magnetic resonance
Singlet
d Doublet
dd Doublet doublet
td Triple doublet
br Broad
q Quarted
t Triplet
m Multiplet
LRMS Low resolution mass spectrometry
h hour
min minutes
NMM N-methylmorpholine
DMF N,N-dimethylformamide
DCM dichloromethane, methylene chloride
AcOEt ethyl acetate
DMSO dimethylsufoxide
EDC.HCl 3-((ethylimino)methyleneamino)-N,N-dimethyl-propan-1-aminium chloride
THF tetrahydrofurane
DIEA diisopropylethyamine
HOBt 1-Hydroxybenzotriazole hydrate
MeOH methanol
DPPONH$_2$ P,P-diphenylphosphinic amide
PPTS pyridinium p-toluenesulphonate
Pd(PPh$_3$)$_4$ Tetrakis(triphenylphosphane) palladium(0)
HMPA hexamethylphosphoramide
Celite® diatomaceous earth
BINAP 2,2'-Bis(diphenylphosphino)-1,1'-binaphthyl
T3P® 2,4,6-Tripropyl-1,3,5,2,4,6-trioxatriphosphorinane-2,4,6-trioxide
HATU 2-(1H-7-azabenzotriazol-1-yl)-1,1,3,3-tetramethyl uronium hexafluorophosphate Preparation 1

1-Amino-3-chloro-N-o-tolyl-1H-pyrrole-2-carboxamide a) 3-Chloro-N-o-tolyl-1H-pyrrole-2-carboxamide A suspension of the 3-chloro-1H-pyrrole-2-carboxylic acid[1] (1.2 g, 8.3 mmol) in thionyl chloride (6 ml) was heated to reflux during 30 minutes. At the end of this period, volatiles were removed by distillation under reduced pressure coevaporating with tetrahydrofurane a couple of times. The residue obtained after evaporation was dissolved in a small amount of dry dioxane and was added to a solution of o-toluidine (1.33 g, 12.4 mmol) and DIEA (4.32 mL, 25 mmol) in 70 mL of dry 1,4-dioxane at 0° C. Once the addition was finished, the reaction crude was heated to 60° C. during 2 hours. Afterwards, this crude was evaporated under vacuum and the residue was taken up with ethyl acetate and washed successively with water, saturated solution of sodium carbonate, water, hydrochloric acid 2N, water and brine. The organic phase was separated, dried (sodium sulphate, Na$_2$SO$_4$) and concentrated under vacuum to give a residue that was triturated with hexane affording 950 mg (88% yield) of a solid after filtration.

LRMS (m/z): 235 (M+1)$^+$.

b) 1-Amino-3-chloro-N-o-tolyl-1H-pyrrole-2-carboxamide

In a 100 mL three-necked flask it was placed 11 mL of a 28% aqueous solution of sodium hydroxide, 4.1 mL of a 28% ammonium hydroxide solution, 1.23 g of ammonium chloride and 0.12 mL of Aliquat 336. Afterwards, a solution of 3-chloro-N-o-tolyl-1H-pyrrole-2-carboxamide (0.9 g, 3.84 mmol) in 30 mL of diethyl ether and 30 mL of methyl tert-butyl ether was added and placed at 0° C. affording a suspension. Over this suspension, a 10% aqueous solution of sodium hypochlorite (26 mL) was added drop wise with vigorous stirring maintaining the temperature during 20 min. more. Subsequently, the reaction mixture was stirred at room temperature during a further 1.5 h producing the consumption of the starting material. Next, the reaction crude was diluted with ethyl acetate until no suspended material was observed. The layers were separated and the organic phase was washed with a 25% aqueous solution of sodium thiosulphate, water and brine, dried (Na$_2$SO$_4$) and concentrated under vacuum to give a residue that was triturated with hexane to produce a solid (870 mg, 86% yield) after filtration.

LRMS (m/z): 250 (M+1)$^+$.

¹H NMR (400 MHz, DMSO) δ 11.05 (s, 1H), 8.04 (d, J=7.5 Hz, 1H), 7.28-7.13 (m, 2H), 7.07-6.96 (m, 2H), 6.82 (s, 2H), 6.16 (d, J=3.0 Hz, 1H), 2.29 (s, 3H).

Preparation 2

5-Chloro-2-(chloromethyl)-3-o-tolylpyrrolo[1,2-f][1,2,4]triazin-4(3H)-one

To a suspension of 1-amino-3-chloro-N-phenyl-1H-pyrrole-2-carboxamide (0.56 g, 2.24 mmol) in glacial acetic acid (19 mL) was added 0.93 mL (11,7 mmol) of chloroacetyl chloride getting a solution. The reaction mixture was stirred during 2 hours to produce the desired compound. Then, the reaction mixture was poured into ice-water precipitating a solid that was filtered and washed with more water. This solid was taken up with ethyl acetate and the organic phase was washed with 4% aqueous solution of sodium bicarbonate and water, dried and evaporated under vacuum to yield 650 mg (89% yield) of 3-chloro-1-(2-chloroacetamido)-N-o-tolyl-1H-pyrrole-2-carboxamide as a solid.

This intermediate compound was dissolved in toluene (40 mL) and 50 mg of pyridinium p-toluenesulphonate (PPTS) were added heating the reaction to reflux with a Dean-Stark to remove the water from the reaction media. After 40 hours, the starting material has disappeared and then, the reaction was elaborated by cooling down to room temperature and adding ethyl acetate. This organic phase was washed with water, 4% aqueous solution of sodium bicarbonate and brine and dried (Na$_2$SO$_4$). Removal of the volatiles under vacuum produced a residue of 580 mg of the desired product (85% yield).

LRMS (m/z): 308 (M+1)$^+$.

¹H NMR (400 MHz, CDCl$_3$) δ 7.48-7.32 (m, 4H), 7.23 (d, J=7.8 Hz, 1H), 6.56 (d, J=3.0 Hz, 1H), 4.21 (d, J=12.1 Hz, 1H), 4.04 (d, J=12.1 Hz, 1H), 2.22 (s, 3H).

Preparation 3

2-(Aminomethyl)-5-chloro-3-o-tolylpyrrolo[1,2-f][1,2,4]triazin-4(3H)-one

A solution of the starting 5-chloro-2-(chloromethyl)-3-o-tolylpyrrolo[1,2-f][1,2,4]triazin-4(3H)-one (200 mg, 0.65 mmol) in a 7M ammonia solution in methanol was heated at 85° C. with stirring in a sealed tub during 4 h. At the end of this period, the volatiles were removed under vacuum and the residue was taken-up with ethyl acetate and washed with a 4% aqueous solution of sodium bicarbonate, water and brine. The organic layer was dried ($Na_2SO_4$) and concentrated to dryness giving 140 mg of a residue corresponding to the title compound of the preparation (76% yield).

LRMS (m/z): 289 $(M+1)^+$.

Preparation 4

3-Cyclopropyl-1H-pyrrole-2-carboxylic acid a) Methyl 3-cyclopropyl-1-(phenylsulfonyl)-1H-pyrrole-2-carboxylate

In a schlenk flask, a mixture of methyl 3-bromo-1-(phenylsulfonyl)-1H-pyrrole-2-carboxylate[2] (1.45 g, 4.2 mmol), cyclopropylboronic acid (1.09 g, 12.6 mmol) and potassium carbonate (1.75 g, 12.7 mmol) was suspended in toluene and the system was degassed doing 3 cycles of vacuum-Ar. Next, tetrakis(triphenylphosphane) palladium(0) ($Pd(PPh_3)_4$) was added as a solid and 3 new cycles of vacuum-Ar were done stirring the reaction at 100° C. overnight. At the end of this period, the starting material was consumed and the reaction was worked-up pouring the crude over water and extracting the resulting mixture with ethyl acetate (3×50 mL). The organic solution was washed with water and brine, dried over $Na_2SO_4$ and concentrated under vacuum to give a residue that was purified by flash chromatography silica (hexane/ethyl acetate). After the purification were obtained 976 mg of the title compound (76% yield).

LRMS (m/z): 306 $(M+1)^+$.

b) 3-Cyclopropyl-1H-pyrrole-2-carboxylic acid

To a suspension of the starting methyl 3-cyclopropyl-1-(phenylsulfonyl)-1H-pyrrole-2-carboxylate (0.9 g, 3 mmol) in tetrahydrofurane (4.6 mL) and water (2.3 mL) was added lithium hydroxide (0.29 g, 12 mmol) and this mixture was heated to 100° C. in a microwave vial during 4 hours. Next, the reaction mixture was poured into water (50 mL) and this aqueous phase was washed with diethyl ether (2×). Afterwards, the aqueous layer was acidified until pH=3 by adding solid phosphoric acid and extracted with ethyl acetate (3×). The organic solution was washed with water and brine, dried ($Na_2SO_4$) and concentrated in vacuum to give 370 mg of the title compound.

LRMS (m/z): 150 $(M-1)^-$.

Preparation 5

1-Amino-3-cyclopropyl-N-o-tolyl-1H-pyrrole-2-carboxamide a) 3-Cyclopropyl-N-o-tolyl-1H-pyrrole-2-carboxamide

To a suspension of the 3-cyclopropyl-1H-pyrrole-2-carboxylic acid (50 mg, 0,33 mmol) in dry dichloromethane (0.4 mL) was added a solution of oxalyl chloride (0.04 mL, 0,37 mmol) in 0.3 mL of dichloromethane at room temperature and 3 drops of N,N-dimethylformamide. After 1.5 h at this temperature, the mixture was concentrated under vacuum and the residue was redissolved in dichloromethane (1 mL). To this solution was added a solution of o-toluidine in dichloromethane (0,2 mL) and the mixture was stirred at room temperature overnight. The reaction was worked-up diluting with dichloromethane and washing with sodium bicarbonate (2×) and brine. The organic phase was dried and concentrated to give 74 mg of the title compound (88% yield).

LRMS (m/z): 241 $(M+1)^+$.

b) 1-Amino-3-cyclopropyl-N-o-tolyl-1H-pyrrole-2-carboxamide

This compound was prepared starting from 3-cyclopropyl-N-o-tolyl-1H-pyrrole-2-carboxamide (106 mg, 0.44 mmol) and following the experimental procedure described in Preparation 1b to afford 113 mg (93% yield) of the title compound.

LRMS (m/z): 256 $(M+1)^+$.

Preparation 6

2-(Chloromethyl)-5-cyclopropyl-3-o-tolylpyrrolo[1,2-f][1,2,4]triazin-4(3H)-one This compound was prepared starting from 1-amino-3-cyclopropyl-N-o-tolyl-1H-pyrrole-2-carboxamide (130 mg, 0.4 mmol) and following the experimental procedure described in Preparation 2 to afford 107 mg (73% yield) of the title compound.

LRMS (m/z): 314 $(M+1)^+$.

Preparation 7

1-Amino-N-o-tolyl-1H-pyrrole-2-carboxamide a) N-o-Tolyl-1H-pyrrole-2-carboxamide 15.0 g (135 mmol) of 1H-pyrrol 2-carboxylic acid (purchased from Aldrich®, cat. no. P7, 360-9) were suspended in a mixture of DMF (1.2 mL) and dichloromethane (150 mL). To this solution, 18 mL (207 mmol) of oxalyl chloride in dichloromethane (105 mL) were added dropwise over 30 minutes. The reaction was stirred two hours and then concentrated under reduced pressure to dryness.

The residual black oil was redissolved in dichloromethane (150 mL) and a solution of 15.9 g (148 mmol) of o-toluidine in dichloromethane (16 mL) was added dropwise. The reaction was stirred overnight then the solution was washed with a saturated aqueous solution of sodium bicarbonate. The organic phase was concentrated in vacuum. The product was purified by flash chromatography (30% AcOEt in hexane) to give 15.45 g (100% yield) of the title compound.

LRMS (m/z): 201 $(M+1)^+$.

b) 1-Amino-N-o-tolyl-1H-pyrrole-2-carboxamide

Prepared from 14.25 g (71.2 mmol) of N-o-tolyl-1H-pyrrole-2-carboxamide following the experimental procedure described in preparation 1b. The crude product was suspended in diisopropyl ether and sonicated and the solid was filtered and washed with diethylether to give 10.04 g (66% yield) of the title compound.

LRMS (m/z): 216 $(M+1)^+$.

¹H NMR (400 MHz, DMSO) δ 11.15 (s, 1H), 8.06 (d, J=7.7 Hz, 1H), 7.26-7.15 (m, 2H), 7.02 (t, J=6.8 Hz, 1H), 6.96 (t, J=2.3 Hz, 1H), 6.79-6.72 (m, 3H), 6.05 (dd, J=4.2, 2.7 Hz, 1H), 2.29 (s, 3H).

Preparation 8

2-(Chloromethyl)-3-o-tolylpyrrolo[1,2-f][1,2,4]triazin-4(3H)-one 9.5 mL (119 mmol) of 2-chloroacetyl chloride were added to a suspension of 5.14 g (23.9 mmol) of 1-amino-N-o-tolyl-1H-pyrrole-2-carboxamide in 188 mL of glacial acetic acid, and the mixture was stirred at 120° C. for 3.5 hours. Then, the reaction mixture was cooled down to room temperature and it was concentrated in vacuum. The residue obtained was dissolved in ethyl acetate, washed with a saturated aqueous solution of sodium bicarbonate, water and brine. It was dried over magnesium sulphate, filtered and concentrated in vacuum. 4.99 g (65% yield) of the title compound were obtained.

LRMS (m/z): 274 (M+1)$^+$.
¹H NMR (400 MHz, DMSO) δ 7.66-7.83 (m, 1H), 7.29-7.60 (m, 4H), 7.05 (d, J=4.30 Hz, 1H), 6.59-6.78 (m, 1H), 4.31 (dd, J=10.55 Hz, 2H), 2.10 (s, 3H).

Preparation 9

2-(Aminomethyl)-3-o-tolylpyrrolo[1,2-f][1,2,4]triazin-4(3H)-one

A solution of 450 mg (1.64 mmol) of 2-(chloromethyl)-3-o-tolylpyrrolo[1,2-f][1,2,4]triazin-4(3H)-one in 20 mL of a 7M solution of ammonia in methanol was heated at 85° C. in a sealed tube overnight, then cooled to room temperature and concentrated in vacuum to afford the title 491 mg (100% yield) of the title compound.

LRMS (m/z): 255 (M+1)$^+$.
¹H NMR (400 MHz, DMSO) δ 7.65-7.75 (m, 1 H), 7.32-7.52 (m, 4 H), 7.03 (d, J=3.91 Hz, 1 H), 6.42-6.97 (m, 3 H), 2.09 (s, 3 H).

Preparation 10

1-Amino-N-cyclohexyl-1H-pyrrole-2-carboxamide a) N-Cyclohexyl-1H-pyrrole-2-carboxamide The mixture of methyl 1H-pyrrole-2-carboxylate (2.5 g, 20 mmol) and cyclohexylamine (13.8 mL, 120 mmol) was heated at 160° C. in a sealed tub overnight with stirring. Next day, volatiles were removed under reduced pressure and the residue was taken-up with ethyl acetate and washed water, acidic water (pH=1) and brine. The organic layer was dried (Na$_2$SO$_4$) and concentrated in vacuum to give 1.88 g of a residue that was purified by flash chromatography silica (hexane/ethyl acetate) to obtain 0.88 g of the title compound (23% yield).

LRMS (m/z): 193 (M+1)$^+$.

b)
1-Amino-N-cyclohexyl-1H-pyrrole-2-carboxamide

This compound was prepared starting from N-cyclohexyl-1H-pyrrole-2-carboxamide (880 mg, 4.6 mmol) and following the experimental procedure described in Preparation 1b to afford 700 mg (74% yield) of the title compound that was used in the next step without any further purification.

LRMS (m/z): 208 (M+1)$^+$.
¹H NMR (400 MHz, DMSO) δ 8.53 (d, J=7.8 Hz, 1H), 6.84-6.77 (m, 1H), 6.61 (dd, J=4.2, 2.0 Hz, 1H), 6.55 (s, 2H), 5.91 (dd, J=4.2, 2.6 Hz, 1H), 3.80-3.64 (m, 1H), 1.87-1.48 (m, 5H), 1.39-1.20 (m, 5H).

Preparation 11

2-(Chloromethyl)-3-cyclohexylpyrrolo[1,2-f][1,2,4]triazin-4(3H)-one

To a solution of 1-amino-N-cyclohexyl-1H-pyrrole-2-carboxamide (160 mg, 0.77 mmol) in 1,4-dioxane (10 mL) was added 77 μL (0.97 mmol) of chloroacetyl chloride and the reaction mixture was stirred at 100° C. during 1 h. Afterwards, the mixture was concentrated to dryness and the residue was dissolved in phosphorous oxychloride (3 mL) and heated to 50° C. with stirring overnight. Next day, the cooled reaction mixture was poured slowly into an aqueous solution of potassium carbonate. The resulting mixture was extracted with ethyl acetate and the organic layer was washed with water (2×), dried (Na$_2$SO$_4$) and concentrated to afford 120 mg of a residue that was used in the next step without further purification.

LRMS (m/z): 266 (M+1)$^+$.

Preparation 12

3-Methyl-1H-pyrrole-2-carboxylic acid 2.0 g (14.37 mmol) of methyl 3-methyl-1H-pyrrole-2-carboxylate (purchased from Otava Chemicals®, cat. no. 1056278) were dissolved in 50 mL of methanol and 21.5 mL of a 2N aqueous solution of sodium hydroxide were added. The mixture was stirred at room temperature overnight and then at 60° C. for 20 hours. Then the methanol was evaporated in vacuum and the remaining aqueous solution was neutralized with 21.5 mL of a 2N solution of hydrochloric acid. The product was extracted with a 95:5 mixture of chloroform/methanol and the organic phase was washed with brine, dried over magnesium sulphate, filtered and evaporated under vacuum. 1.38 g (77% yield) of the title compound was obtained as a brown solid.

LRMS (m/z): 126 (M+1)$^+$.
¹H NMR (400 MHz, DMSO) δ 12.06 (s, 1H), 11.30 (s, 1H), 6.84-6.75 (m, 1H), 6.02-5.93 (m, 1H), 2.24 (s, 3H).

Preparation 13

1-Amino-3-methyl-N-o-tolyl-1H-pyrrole-2-carboxamide a) 3-Methyl-N-o-tolyl-1H-pyrrole-2-carboxamide 2.0 g (15.98 mmol) of 3-methyl-1H-pyrrole-2-carboxylic acid were dissolved in 50 mL of dichloromethane. 5.60 mL (63.9 mmol) of oxalyl chloride were added, followed by 5 drops of DMF. The reaction mixture was stirred at room temperature for 2 hours and then the solvents were evaporated. The black oil residue was dissolved in 50 mL of dichloromethane and 6.85 g (63.9 mmol) of o-toluidine were added dropwise. The reaction was stirred at room temperature for 1 hour and then the solvent was evaporated. The crude product was purified by flash chromatography (dichloromethane to dichloromethane/methanol 95:5) and then triturated in diisopropylether to give 2.97 g (87% yield) of the title compound as a brown solid.
LRMS (m/z): 215 (M+1)$^+$.

b) 1-Amino-3-methyl-N-o-tolyl-1H-pyrrole-2-carboxamide

3-Methyl-N-o-tolyl-1H-pyrrole-2-carboxamide (1.5 g, 7.00 mmol) was dissolved in 60 mL of DMF. 294 mg (7.35 mmol) of sodium hydride (60 wt % dispersion in mineral oil) were added and the reaction mixture was stirred at room temperature for 1 hour. Then O-(mesitylsulfonyl)hydroxylamine (1.658 g, 7.70 mmol) was added and the reaction mixture was stirred for 30 minutes. The solvent was evaporated to dryness and the crude product was purified by flash chromatography (0 to 50% heptane/AcOEt) to give 1.17 g (73% yield) of the title compound as a yellow solid.
LRMS (m/z): 230 (M+1)$^+$.

Preparation 14

2-(Chloromethyl)-5-methyl-3-o-tolylpyrrolo[1,2-f][1,2,4]triazin-4(3H)-one 140 mg (0.61 mmol) of 1-amino-3-methyl-N-o-tolyl-1H-pyrrole-2-carboxamide were dissolved in 3 mL of acetic acid. Chloroacetyl chloride (0.245 mL, 3.05 mmol) was added under vigorous stirring and the reaction mixture was then heated at 120° C. for 30 minutes. Then the mixture was allowed to cool to room temperature, poured into a mixture of water/ice and extracted twice with ethyl acetate. The organic layer was washed with a saturated aqueous solution of sodium bicarbonate, dried over magnesium sulphate, filtered and evaporated to dryness. The crude product was purified by flash chromatography (0 to 40% heptane/ethyl acetate) to give 125 mg (71% yield) of the title compound as a white solid.
LRMS (m/z): 288 (M+1)$^+$.

Preparation 15

2,2,2-Trichloro-1-(4-methyl-1H-pyrrol-2-yl)ethanone

To a solution of 2,2,2-trichloroacetyl chloride (5.05 mL, 45.3 mmol) in dry diethyl ether (12 mL) was slowly added a solution of 3-methyl-1H-pyrrole (3.15 g, 39.37 mmol) in 30 mL of dry diethyl ether during 1 h 15 min. Once the addition was finished, the reaction mixture was stirred at 45° C. during 1 hour 30 minutes more. Next, more diethyl ether was added and the organic phase was washed with an aqueous solution of potassium carbonate to neutralize de media, water and brine. The organic phase was dried (Na$_2$SO$_4$) and concentrated to dryness to give a residue that was purified by flash chromatography silica (hexane/dichloromethane) to afford 4.7 g of the title compound (55% yield).
LRMS (m/z): 224 (M−1)$^−$.

Preparation 16

1-Amino-4-methyl-N-o-tolyl-1H-pyrrole-2-carboxamide a) 4-Methyl-N-o-tolyl-1H-pyrrole-2-carboxamide A solution of 2,2,2-trichloro-1-(4-methyl-1H-pyrrol-2-yl)ethanone (2 g, 8.8 mmol) in a mixture of o-toluidine (1.76 mL, 16.5 mmol) and triethylamine (2.1 mL, 15.07 mmol) under argon was heated to 80° C. with stirring during 75 h. Afterwards, the reaction mixture was concentrated to dryness giving a residue that was treated with hexane and the resulting solid filtered to afford 848 mg of the title compound (45% yield).
LRMS (m/z): 215 (M+1)$^+$.

b) 1-Amino-4-methyl-N-o-tolyl-1H-pyrrole-2-carboxamide

This compound was prepared starting from 4-methyl-N-o-tolyl-1H-pyrrole-2-carboxamide (845 mg, 3.9 mmol) and following the experimental procedure described in Preparation 1b to afford 516 mg (54% yield) of the title compound that was used in the next step without any further purification.
LRMS (m/z): 230 (M+1)$^+$.

Preparation 17

2-(Chloromethyl)-6-methyl-3-o-tolylpyrrolo[1,2-f][1,2,4]triazin-4(3H)-one 465 mg (2.03 mmol) of 1-amino-4-methyl-N-o-tolyl-1H-pyrrole-2-carboxamide were dissolved in 10 mL of acetic acid and 759 μL (9.53 mmol) of chloroacetyl chloride were added. The mixture was stirred at 120° C. for 4 hours and the solvent was removed under vacuum. The residue was dissolved in AcOEt and washed with a saturated aqueous solution of sodium bicarbonate and brine, dried over magnesium sulphate, filtered and evaporated under vacuum. 660 mg (69% yield) of the title compound were obtained as a beige solid.
LRMS (m/z): 288 (M+1)$^+$.

Preparation 18

1-Amino-N-phenyl-1H-pyrrole-2-carboxamide a) N-Phenyl-1H-pyrrole-2-carboxamide

Prepared following the experimental method described in preparation 1a starting from 10.0 g (90.0 mmol) of 1H-pyrrole-2-carboxylic acid (purchased from Aldrich®, cat. no. P7,360-9) and 9.22 g (99.0 mmol) of aniline. 13.0 g (78% yield) of the title compound were obtained as a brownish solid.
LRMS (m/z): 187 (M+1)$^+$.

b) 1-Amino-N-phenyl-1H-pyrrole-2-carboxamide

The title compound was prepared from 12.9 g (69.8 mmol) of N-phenyl-1H-pyrrole-2-carboxamide following the experimental procedure described in preparation 1b. 10.3 g (73% yield) of the title compound were obtained as a solid.
LRMS (m/z): 202 (M+1)$^+$.
$^1$H NMR (400 MHz, DMSO) δ 10.74 (s, 1H), 7.67 (d, J=7.7 Hz, 2H), 7.33 (t, J=7.9 Hz, 2H), 7.06 (t, J=7.4 Hz, 1H), 6.95 (t, J=2.2 Hz, 1H), 6.83 (dd, J=4.2, 1.9 Hz, 1H), 6.64 (s, 2H), 6.02 (dd, J=4.2, 2.7 Hz, 1H).

Preparation 19

2-(1-Chloroethyl)-3-phenylpyrrolo[1,2-f][1,2,4]triazin-4(3H)-one 2.50 mL (25.75 mmol) of 2-chloropropanoyl chloride was added to a solution of 1-amino-N-phenyl-1H-pyrrole-2-carboxamide in glacial acetic acid and it was stirred at room temperature for 1 hour. Then it was concentrated in vacuum and the remaining acetic acid was co-evaporated with cyclohexane. 20 mL (218 mmol) of phosphorous oxychloride were added to the residue obtained and the resulting solution was heated at 125° C. After 10 hours it was allowed to cool down to room temperature and the reaction mixture was carefully poured into a cold over-saturated aqueous solution of sodium bicarbonate. The aqueous solution was extracted with ethyl acetate, and the organic phases were collected together and washed with brine and then concentrated in vacuum. The residue obtained was dissolved in a mixture of hexane and ethyl acetate (10:1), filtered through silica and concentrated in vacuum. This residue was dissolved in 4 mL of a 7M solution of ammonia in methanol and then was heated to 60° C. overnight. The reaction mixture was concentrated in vacuum to obtain 75 mg (6% yield) of the title compound.

LRMS (m/z): 274 (M+1)+.

Preparation 20

(S)-2-(1-Aminopropyl)-3-phenylpyrrolo[1,2-f][1,2,4]triazin-4(3H)-one a) (S)-tert-Butyl 1-oxo-1-(2-(phenylcarbamoyl)-1H-pyrrol-1-ylamino)butan-2-ylcarbamate 2.0 g (9.94 mmol) of 1-amino-N-phenyl-1H-pyrrole-2-carboxamide, 2.45 g (12.05 mmol) of (S)-2-(tert-butoxycarbonylamino)butanoic acid (purchased from Aldrich®, cat. no. 15533) and 1.90 g (12.24 mmol) of EDC.HCl were dissolved in a mixture of 90 mL of THF and 30 mL of dichloromethane. The resulting solution was heated at 55° C. overnight. Then the solvents were evaporated and the crude residue was taken up in dichloromethane and washed with an aqueous solution of sodium bicarbonate and brine. The organic layer was dried over magnesium sulphate, filtered and the solvent was evaporated. The solid obtained was triturated in diethyl ether to furnish 2.47 g (64% yield) of the title compound.

LRMS (m/z): 387 (M+1)+.

b) (S)-2-(1-Aminopropyl)-3-phenylpyrrolo[1,2-f][1,2,4]triazin-4(3H)-one 1.0 g (2.59 mmol) of (S)-tert-butyl 1-oxo-1-(2-(phenylcarbamoyl)-1H-pyrrol-1-ylamino)butan-2-ylcarbamate were suspended in 13 mL of phosphorous oxychloride and heated to 80° C. for 6 hours. Then the excess reagent was removed under vacuum and the residue was taken up in AcOEt and treated with an aqueous solution of sodium bicarbonate. The two layers were separated and the aqueous phase was extracted with more AcOEt. The combined organic extracts were washed with brine, dried and the solvent was evaporated to give 1.2 g of a black oil. This intermediate was purified by flash chromatography (0-100% AcOEt in hexane) to give 421 mg of a yellow syrup that was treated with 50 mL of a 7M methanolic solution of ammonia at 80° C. in a sealed vessel. The solvent was then evaporated and the final product was purified by flash chromatography (0-100% AcOEt in hexane) to give 125 mg (11% yield) of the title compound.

LRMS (m/z): 269 (M+1)+.
$^1$H NMR (400 MHz, DMSO) δ 8.23 (s, 1H), 7.71-7.37 (m, 5H), 6.94 (dd, J=4.3, 1.7 Hz, 1H), 6.60 (dd, J=4.3, 2.7 Hz, 1H), 3.14 (dd, J=7.5, 5.6 Hz, 1H), 1.81-1.64 (m, 1H), 1.48-1.32 (m, 1H), 0.72 (t, J=7.4 Hz, 3H).

Preparation 21

2-(1-Aminoethyl)-3-phenylpyrrolo[1,2-f][1,2,4]triazin-4(3H)-one a) tert-Butyl 1-oxo-1-(2-(phenylcarbamoyl)-1H-pyrrol-1-ylamino)propan-2-ylcarbamate The title compound was prepared following the experimental procedure described in preparation 20a from 1.50 g (7.45 mmol) of 1-amino-N-phenyl-1H-pyrrole-2-carboxamide and 1.82 g (8.95 mmol) of racemic 2-(tert-butoxycarbonylamino)butanoic acid (purchased from ABCR, cat. no. AB154485). After recristallysation of the crude product in diethylether, 2.43 g (84% yield) of the title compound were obtained.

LRMS (m/z): 387 (M+1)+.

b) 2-(1-Aminopropyl)-3-phenylpyrrolo[1,2-f][1,2,4]triazin-4(3H)-one 1.0 g (2.59 mmol) of tert-butyl 1-oxo-1-(2-(phenylcarbamoyl)-1H-pyrrol-1-ylamino)butan-2-ylcarbamate were suspended in 16 mL of phosphorous oxychloride and heated to 80° C. for 6 hours. Then the mixture was evaporated to dryness under vacuum the residue was taken up in chloroform and treated with an aqueous solution of sodium bicarbonate. The two layers were separated and the aqueous phase was extracted with more chloroform. The combined organic extracts were washed with brine, dried and the solvent was evaporated. This intermediate was treated with a solution of 0.72 g (5.18 mmol) of potassium carbonate in DMF at 60° C. for 2.5 hours. Then the mixture was evaporated to dryness and the crude product was purified by reverse phase chromatography (C-18 silica from Waters®, water/1:1 acetonitrile-methanol as eluents [0.1% v/v formic acid buffered] 0% to 100%) to obtain the title compound (70 mg, 10% yield) as a solid.

LRMS (m/z): 269 (M+1)+.

Preparation 22

(S)-2-(1-Aminoethyl)-3-phenylpyrrolo[1,2-f][1,2,4]triazin-4(3H)-one a) (S)-tert-Butyl 1-oxo-1-(2-(phenylcarbamoyl)-1H-pyrrol-1-ylamino)propan-2-ylcarbamate 2.00 g (9.94 mmol) of 1-amino-N-phenyl-1H-pyrrole-2-carboxamide were dissolved in 50 mL of DMF. To this solution, 2.07 g (10.94 mmol) of (S)-2-(tert-butoxycarbonylamino)propanoic acid (purchased from Aldrich®, cat. no. 13, 451-1) and 2.10 g (10.95 mmol) of EDC.HCl were added and the resulting reaction mixture was stirred at room temperature overnight. The solvent was then evaporated under vacuum, the residue was taken up in ethyl acetate and the organic solution was washed with an aqueous solution of sodium bicarbonate and brine, it was dried over magnesium sulphate, filtered and the solvent was evaporated. The product was purified by flash chromatography (0-5% methanol in dichloromethane). 2.21 g (60% yield) of the final product were obtained as a white solid.

LRMS (m/z): 373 (M+1)+.
$^1$H NMR (400 MHz, CDCl$_3$) δ 10.11 (s, 1H), 7.74 (s, 1H), 7.55-7.48 (m, 2H), 7.36-7.28 (m, 2H), 7.15-7.07 (m, 1H), 7.03 (dd, J=2.9, 1.7 Hz, 1H), 6.67 (dd, J=4.3, 1.7 Hz, 1H), 6.15 (dd, J=4.2, 2.9 Hz, 1H), 5.08 (d, J=7.5 Hz, 1H), 4.40 (s, 1H), 1.46 (s, 9H), 1.44 (d, J=7.1 Hz, 3H).

b) (S)-2-(1-Aminoethyl)-3-phenylpyrrolo[1,2-f][1,2,4]triazin-4(3H)-one 2.21 g (5.93 mmol) of (S)-tert-butyl 1-oxo-1-(2-(phenylcarbamoyl)-1H-pyrrol-1-ylamino)propan-2-ylcarbamate were treated with 27 mL of phosphorous oxychloride at 80° C. for 6 hours and then it was evaporated under vacuum until a dark solid formed. This residue was dissolved with chloroform and then treated with an aqueous solution of sodium bicarbonate. After stirring the mixture for 1 hour, the two layers were separated and the organic phase was washed with water and brine, dried over magnesium sulphate and the solvent was evaporated under vacuum. The residue was then treated in a sealed vessel with 30 mL of a 7M methanolic solution of ammonia at 80° C. overnight. The solvent was then evaporated and the product was purified by reverse phase chromatography (C-18 silica from Waters®, water/1:1 acetonitrile-methanol as eluents [0.1% v/v formic acid buffered] 0% to 100%) to obtain the title compound (350 mg, 23%) as a white solid.

LRMS (m/z): 255 (M+1)$^+$.

$^1$H NMR (400 MHz, CDCl$_3$) δ 7.58-7.49 (m, 3H), 7.41 (dd, J=2.6, 1.7 Hz, 1H), 7.32-7.26 (m, 2H), 7.07 (dd, J=4.3, 1.7 Hz, 1H), 6.56 (dd, J=4.3, 2.7 Hz, 1H), 3.67 (q, J=6.6 Hz, 1H), 1.30 (d, J=6.6 Hz, 3H).

Preparation 23

1-Amino-3-methyl-N-phenyl-1H-pyrrole-2-carboxamide a) 3-Methyl-N-phenyl-1H-pyrrole-2-carboxamide Prepared following the experimental method described in preparation 1a starting from 1.38 g (11.3 mmol) of 3-methyl-1H-pyrrole-2-carboxylic acid and 1.13 g (12.13 mmol) of aniline. After purification by flash chromatography (0-40% AcOEt in hexane), 1.08 g (49% yield) of the title compound were obtained as a white solid.

LRMS (m/z): 202 (1M+1)$^+$.

b) 1-Amino-3-methyl-N-phenyl-1H-pyrrole-2-carboxamide

The title compound was prepared from 1.08 g (5.39 mmol) of 3-methyl-N-phenyl-1H-pyrrole-2-carboxamide following the experimental procedure described in preparation 1b. 1.16 g (47% yield) of the title compound was obtained as a solid.

LRMS (m/z): 216 (M+1)$^+$.

$^1$H NMR (400 MHz, CDCl$_3$) δ 9.24 (s, 1H), 7.63-7.56 (m, 2H), 7.37-7.30 (m, 2H), 7.14-7.06 (m, 1H), 6.79 (d, J=2.7 Hz, 1H), 5.94 (d, J=2.3 Hz, 1H), 5.49 (s, 2H), 2.44 (s, 3H).

Preparation 24

2-(1-Chloroethyl)-5-methyl-3-phenylpyrrolo[1,2-f][1,2,4]triazin-4(3H)-one

To a solution of 1.13 g (5.25 mmol) of 1-amino-3-methyl-N-phenyl-1H-pyrrole-2-carboxamide in 45 mL of acetic acid were added 2.54 mL (26.21 mmol) of 2-chloropropanoyl chloride. The reaction was stirred at room temperature for 1 hour and then the solvent was removed in vacuum. The dark oil residue was treated with 20 mL of phosphorous oxychloride, and the mixture was heated to reflux for 16 hours and then it was evaporated under vacuum to dryness. The resulting residue was redissolved in dichloromethane and the organic solution was treated with a saturated aqueous solution of sodium bicarbonate. This mixture was vigorously stirred until the gas release stopped and the two layers were separated. The organic layer was washed with water and brine, dried over magnesium sulphate and the solvent was evaporated. The dark oil that resulted was treated with 40 mL of a 7M ammonia solution in methanol in a sealed vessel at 60° C. overnight. The solution was then evaporated to dryness and the product was purified by flash chromatography (0-5% methanol in dichloromethane) to furnish 0.28 g (18% yield) of the title compound as a white solid.

LRMS (m/z): 288 (M+1)$^+$.

Preparation 25

2-(1-Iodoethyl)-5-methyl-3-phenylpyrrolo[1,2-f][1,2,4]triazin-4(3H)-one 276 mg (0.96 mmol) of 2-(1-chloroethyl)-5-methyl-3-phenylpyrrolo[1,2-f][1,2,4]triazin-4(3H)-one were dissolved in 10 mL of acetone and 287 mg (1.91 mmol) of sodium iodide were added. The reaction was stirred at 65° C. for 8 hours and at room temperature overnight. The solvent was evaporated to dryness under vacuum and the residue was dissolved in ethyl acetate. This solution was washed twice with water and brine, dried over magnesium sulphate and the solvent was evaporated. 340 mg (94% yield) of the title product were obtained as a brownish solid.

LRMS (m/z): 380 (M+1)$^+$.

$^1$H NMR (400 MHz, CDCl$_3$) δ 7.68-7.62 (m, 1H), 7.59-7.45 (m, 3H), 7.33-7.28 (m, 1H), 7.15-7.10 (m, 1H), 6.41-6.32 (m, 1H), 4.49 (q, J=6.9 Hz, 1H), 2.50 (s, 3H), 2.16 (d, J=7.0 Hz, 3H).

Preparation 26

Methyl 1-(phenylsulfonyl)-3-(trifluoromethyl)-1H-pyrrole-2-carboxylate a) Methyl 3-iodo-1-(phenylsulfonyl)-1H-pyrrole-2-carboxylate A solution of methyl 3-bromo-1-(phenylsulfonyl)-1H-pyrrole-2-carboxylate[2] (2.0 g, 5.8 mmol), sodium iodide (3.5 g, 23 mmol), trans-1,2-bis(methylamino)cyclohexane (0.83 g, 5.84 mmol) and copper iodide (0.55 g, 2.9 mmol) in 1,4-dioxane (23 mL) was stirred under reflux during 3 days. At the end of this period, the crude was allowed to reach room temperature and filtered thought Celite® washing with ethyl acetate. The filtrate was concentrated to dryness, suspended in 80 mL of HCl 1N and extracted with ethyl acetate (3×). The organic mixture was washed with water and brine, dried (Mg$_2$SO$_4$) and concentrated to give an oily residue that was purified by flash chromatography silica (hexane/ethyl acetate). Concentration of the fractions containing the compound afforded 1.72 g (50%) of the title compound.

LRMS (m/z): 392 (M+1)$^+$.

b) Methyl 1-(phenylsulfonyl)-3-(trifluoromethyl)-1H-pyrrole-2-carboxylate

In a schlenk flask were placed methyl 3-iodo-1-(phenylsulfonyl)-1H-pyrrole-2-carboxylate (2.44 g, 6.24 mmol) and copper iodide (1.46 g, 7.7 mmol) and it was established an inert atmosphere doing 3 cycles of vacuum-Ar. Subsequently, were added dimethyl formamide (44 mL) as solvent, hexamethylphosphoramide (HMPA) (5.4 mL, 31 mmol) and methyl 2,2-difluoro-2-(fluorosulfonyl)acetate (3.9 mL, 30.7 mmol) and the reaction mixture was heated to 80° C. during 24 hours. Having consumed the starting material, the crude was poured into abundant ice-water an extracted with ethyl acetate (3×). The organic mixture was washed with water (2×) and brine, dried (Na2SO4) and concentrated in vacuum to give 2.58 g of a residue that was purified by flash chromatography silica (hexane/ethyl ether). Concentration of the fractions containing the compound afforded 370 mg (18%) of the title compound.

LRMS (m/z): 334 (M+1)+.

$^1$H NMR (400 MHz, CDCl$_3$) δ 8.07-7.99 (m, 2H), 7.69 (m, 1H), 7.62-7.55 (m, 2H), 7.48 (d, J=3.4 Hz, 1H), 6.51 (d, J=3.4 Hz, 1H), 3.91 (s, 3H).

Preparation 27

1-Amino-N-o-tolyl-3-(trifluoromethyl)-1H-pyrrole-2-carboxamide a) 1-(Phenylsulfonyl)-N-o-tolyl-3-(trifluoromethyl)-1H-pyrrole-2-carboxamide In a three-necked round-bottom flask o-toluidine (0.53 g, 5 mmol) was dissolved in 15 mL of toluene under inert atmosphere. To this solution was added trimethy aluminium (2.5 mL, 5 mmol) and the mixture was stirred at room temperature during 10 minutes. Afterwards, a solution of methyl 1-(phenylsulfonyl)-3-(trifluoromethyl)-1H-pyrrole-2-carboxylate (207 mg, 0.62 mmol) in 15 mL of toluene were added and the reaction mixtures was heated at 80° C. over night. Next, the mixture was allowed to cool to room temperature and 2-3 mL of water were added to hydrolyze unreacted trimethyl aluminium and a 0,5M aqueous solution of disodium tartrate dihydrate were added stirring for a while. Afterwards, the two layers were separated and the aqueous phase was extracted with ethyl acetate. The organic mixture was washed with the same 0,5M aqueous solution of disodium tartrate dihydrate (25 mL), water and brine, dried and concentrated in vacuum to afford 560 mg of a residue that was used in the following step without further purification.

LRMS (m/z): 409 (M+1)+.

b) N-o-Tolyl-3-(trifluoromethyl)-1H-pyrrole-2-carboxamide

To a solution of 1-(phenylsulfonyl)-N-o-tolyl-3-(trifluoromethyl)-1H-pyrrole-2-carboxamide (560 mg of crude material) in 12 mL of methanol was added 2 mL of an aqueous 1N solution of sodium hydroxide and the mixture was stirred at room temperature during 1 h. At the end of this period, no starting material was detected and the reaction was elaborated in the following way: methanol was evaporated and water was added basifying the mixture with saturated aqueous solution of potassium carbonate. This mixture was extracted with ethyl acetate and this organic phase was washed with water and brine, dried (Na$_2$SO$_4$) and concentrated to dryness affording a reddish residue. This residue was purified by flash chromatography silica (hexane/ethyl ether). Concentration of the fractions containing the compound afforded 120 mg (50%) of the title compound.

LRMS (m/z): 269 (M+1)+.

c) 1-Amino-N-o-tolyl-3-(trifluoromethyl)-1H-pyrrole-2-carboxamide

This compound was prepared starting from N-o-tolyl-3-(trifluoromethyl)-1H-pyrrole-2-carboxamide (120 mg, 0.35 mmol) and following the experimental procedure described in Preparation 1b to afford 44 mg (31% purity, 14% yield) of the title compound that was used in the next step without any further purification.

LRMS (m/z): 284 (M+1)+.

Preparation 28

2-(Chloromethyl)-3-o-tolyl-5-(trifluoromethyl)pyrrolo[1,2-f][1,2,4]triazin-4(3H)-one This compound was prepared starting from 1-amino-N-o-tolyl-3-(trifluoromethyl)-1H-pyrrole-2-carboxamide (44 mg, 31% purity, 0.05 mmol) and following the experimental procedure described in Preparation 2 to afford 2 mg (67% purity, 8% yield) of the title compound that was used in the following step without further purification.

LRMS (m/z): 342 (M+1)+.

Preparation 29

1-Amino-3-chloro-1H-pyrrole-2-carboxylic acid a) Benzyl 3-chloro-1H-pyrrole-2-carboxylate To a solution of 3-chloro-1H-pyrrole-2-carboxylic acid (15 g, 0.1 mol) in N,N-dimethylformamide (300 mL) and triethylamine (72 mL, 0.52 mmol) under argon atmosphere was added benzyl bromide (61 mL, 0.52 mmol) at 0-5° C. and the reaction was stirred mechanically overnight at room temperature. Next day, the reaction mixture was concentrated in vacuum and the residue was suspended in 4% aqueous solution of sodium bicarbonate (300 mL) and extracted with ethyl acetate (2×250 mL). The organic layers were mixed and washed with more 4% aqueous solution of sodium bicarbonate, water and brine, and were dried (magnesium sulphate, MgSO$_4$) and concentrated under reduced pressure to give 21.4 g of a residue corresponding to the title compound (88% yield).

LRMS (m/z): 236 (M+1)+.

b) Benzyl 1-amino-3-chloro-1H-pyrrole-2-carboxylate

This compound was prepared starting from benzyl 3-chloro-1H-pyrrole-2-carboxylate (21.3 g, 0.09 mol) and following the experimental procedure described in Preparation 1b to afford 22.19 g (92% yield) of the title compound that was used in the next step without any further purification.

LRMS (m/z): 251 (M+1)+.

c) 1-Amino-3-chloro-1H-pyrrole-2-carboxylic acid

To a solution of benzyl 1-amino-3-chloro-1H-pyrrole-2-carboxylate (20.56 g, 0.08 mol) in methanol (205 mL) was added 32.1 mL of a 3M methanolic solution of HCl (0.1 mol) and 7.7 g (0.07 mol) of 10% palladium on charcoal and this mixture was submitted to hydrogenation in a Parr apparatus working at 25 psi and room temperature during 21 hours. At the end of this period, the reaction was stopped filtering palladium catalyst through a pad of Celite® and the filtrate was concentrated in vacuum to give a light brown solid that was macerated with 40 mL of diethyl ether. This solid was filtrated and washed with petroleum ether to yield 13.32 g of the title compound with a purity of 55% (59% yield) being the dehalogenated compound the main impurity. No further purifications were done proceeding to the next step.

LRMS (m/z): 159 (M−1)⁻.

¹H NMR (400 MHz, DMSO) δ 7.51 (s, 2H), 7.05 (d, J=2.9 Hz, 1H), 6.10 (d, J=2.9 Hz, 1H).

Preparation 30

5-Chloro-2-(iodomethyl)-4H-pyrrolo[1,2-d][1,3,4]oxadiazin-4-one a) 3-Chloro-1-(2-chloroacetamido)-1H-pyrrole-2-carboxylic acid To a solution of 1-amino-3-chloro-1H-pyrrole-2-carboxylic acid (12.51 g, 55% purity, 0.04 mol) in 500 mL of glacial acetic acid were added under argon 17 mL of chloroacetyl chloride (0.21 mol) and the mixture was stirred at room temperature during 1.5 hours. Afterwards, the reaction mixture was poured into ice-water and extracted with ethyl acetate (2×400 mL). The organic layers were washed with water and brine, dried (MgSO₄) and concentrated in vacuum giving a dark oil that was crystallized from a 1/1 diethyl ether/petroleum ether mixture. Filtration of the solid obtained afforded 7.28 g of a white solid corresponding to the title compound (61% yield, 85% purity). This solid was used in the next step without further purifications.

LRMS (m/z): 237 (M+1)⁺.

b) 5-Chloro-2-(chloromethyl)-4H-pyrrolo[1,2-d][1,3,4]oxadiazin-4-one

To a solution of 3-chloro-1-(2-chloroacetamido)-1H-pyrrole-2-carboxylic acid (7.22 g, 25.9 mmol) in 110 mL of 1,4-dioxane was added phosphorous oxychloride (23.6 mL, 259 mmol) solved in 35 mL of 1,4-dioxane at room temperature. Then, the reaction mixture was stirred to reflux during 2 hours. At the end of this period, the reaction mixture was poured into 500 mL of a 4% aqueous solution of sodium bicarbonate and extracted with ethyl acetate (2×400 mL). The organic layers were mixed and washed with more 4% aqueous solution of sodium bicarbonate, water and brine, and were dried (MgSO₄) and concentrated under reduced pressure to give 6.97 g of a dark oil that was purified by flash chromatography silica (hexane/ethyl acetate). After purification were obtained 2.85 g of the title compound (57% yield).

LRMS (m/z): 219 (M+1)⁺.

c) 5-Chloro-2-(iodomethyl)-4H-pyrrolo[1,2-d][1,3,4]oxadiazin-4-one

To a solution of 5-chloro-2-(chloromethyl)-4H-pyrrolo[1,2-d][1,3,4]oxadiazin-4-one (2.87 g, 13.1 mmol) in 57 mL of dry acetone under inert atmosphere was added 3.93 g (26.2 mmol) of sodium iodide and this mixture was stirred at room temperature overnight. Next day, the reaction mixture was poured into a 1/1 mixture of water/brine (100 mL) and extracted with diethyl ether (2×75 mL). The organic layers were washed with water and brine, dried (MgSO₄) and concentrated in vacuum to afford 3.95 g of the title compound (95% yield).

LRMS (m/z): 311 (M+1)⁺.

¹H NMR (400 MHz, CDCl₃) δ 7.26 (d, J=3.0 Hz, 1H), 6.52 (d, J=3.0 Hz, 1H), 4.10 (s, 2H).

Preparation 31

Di-tert-butyl 9-((5-chloro-4-oxo-4H-pyrrolo[1,2-d][1,3,4]oxadiazin-2-yl)methyl)-9H-purin-6-ylimidodicarbonate To a solution of 5-chloro-2-(iodomethyl)-4H-pyrrolo[1,2-d][1,3,4]oxadiazin-4-one (0.93 g, 3 mmol) in 18.6 mL of dry N,N-dimethylformamide under argon atmosphere were added di-tert-butyl 9H-purin-6-ylimidodicarbonate (1.41 g, 4.2 mmol) and sodium bicarbonate (0,35 g, 4,2 mmol) and the reaction mixture was stirred overnight at room temperature. At the end of this period, the reaction mixture was poured into 50 mL of a 4% aqueous solution of sodium bicarbonate and extracted with ethyl acetate (2×40 mL). The organic layers were mixed and washed with more 4% aqueous solution of sodium bicarbonate, water and brine, and were dried (MgSO₄) and concentrated under reduced pressure to give 1.73 g of a solid that was purified by flash chromatography silica (hexane/ethyl acetate). After purification were obtained 0.81 g of the title compound (51% yield).

LRMS (m/z): 517 (M+1)⁺.

¹H NMR (400 MHz, CDCl₃) δ 8.89 (s, 1H), 8.23 (s, 1H), 7.16 (d, J=3.0 Hz, 1H), 6.49 (d, J=3.0 Hz, 1H), 5.37 (s, 2H), 1.48 (s, 18H).

Preparation 32

1H-Imidazole-2-carboxylic acid 21.75 mL (43.5 mmol) of a 2M solution of lithium hydroxide in water were added to a solution of 1.22 g (8.71 mmol) of ethyl 1H-imidazole-2-carboxylate (ref) in a mixture of tetrahydrofurane (20 mL) and water (20 mL). The reaction mixture was warmed up to reflux, and stirred for 1.5 hours. The reaction mixture was cooled to room temperature and the solvent was evaporated under vacuum. The crude residue (3.0 g) was used in next step without further purification.

LRMS (m/z): 113 (M+1)⁺.

Preparation 33

1-Amino-N-phenyl-1H-imidazole-2-carboxamide a) N-Phenyl-1H-imidazole-2-carboxamide To a solution of 1H-imidazole-2-carboxylic acid (0.975 g, 8.7 mmol) in DMF (30 mL) were added aniline (0.67 mL, 8.7 mmol), EDC.HCl (2.54 g, 13.05 mmol) and HOBt (1.76 g, 13.05 mmol). The reaction mixture was stirred at room temperature for 21 hours. Then, it was poured into water and extracted with ethyl acetate. The combined organic layer was dried over sodium sulphate, filtered and concentrated. The crude residue was purified by flash chromatography (2% to 3% methanol in dichloromethane) to yield 1.55 g (96% yield) of the title compound.

LRMS (m/z): 188 (M+1)⁺.

b) 1-Amino-N-phenyl-1H-imidazole-2-carboxamide 0.430 g (10.75 mmol) of sodium hydride (60% dispersion in mineral oil) was added to a 0° C. cooled solution of N-phenyl-1H-imidazole-2-carboxamide (1.55 g, 8.27 mmol) in DMF (50 mL). The mixture was stirred at 0° C. for 30 minutes and 2.70 g (11.57 mmol) of DPPONH₂ (P,P-diphenylphosphinic amide, available from Sigma Aldrich®, cat. no. 5994-87-6) were added portionwise. A thick suspension formed and additional 100 mL of DMF were added. The mixture was stirred at room temperature for 3 hours and then it was poured into 150 mL of a saturated aqueous solution of sodium thiosulphate and extracted with ethyl acetate. The combined organic layer was dried over sodium sulphate, filtered and concentrated. The crude product was purified by flash chromatography (20% to 40% AcOEt/Hexanes) to yield 1.27 g (76% yield) of the title compound as a pale yellow solid.

LRMS (m/z): 203 (M+1)$^+$.

Preparation 34

2-(Chloromethyl)-3-phenylimidazo[1,2-f][1,2,4]triazin-4(3H)-one 62 mg (0.25 mmol) of pyridinium p-toluenesulfonate were added to a suspension of 500 mg (2.47 mmol) of 1-amino-N-phenyl-1H-imidazole-2-carboxamide in 3.3 mL of 2-chloro-1,1,1-trimethoxyethane. The mixture was stirred at 100° C. for 5 hours and the solvent was evaporated. The crude product was purified by flash chromatography (1% to 3% MeOH/DCM) to yield 0.227 g (35%) of the title compound as a beige solid.

LRMS (m/z): 261 (M+1)$^+$.

Preparation 35

1-Amino-N-o-tolyl-1H-imidazole-2-carboxamide a) N-o-Tolyl-1H-imidazole-2-carboxamide To a solution of 1H-imidazole-2-carboxylic acid (0.52 g, 4.64 mmol) in DMF (20 mL) was added o-toluidine (0.50 mL, 4.64 mmol), EDCHCl (1.35 g, 6.96 mmol) and HOBt (0.94 g, 6.96 mmol). The reaction mixture was stirred at room temperature for 16 hours. Then, it was poured into water and extracted with ethyl acetate. The combined organic layer was dried over sodium sulphate, filtered and concentrated to dryness. The crude product was purified by flash chromatography (2% to 3% MeOH/DCM) to yield 0.93 g (99%) of the title compound as a beige solid.

LRMS (m/z): 202 (M+1)$^+$.

b) 1-Amino-N-o-tolyl-1H-imidazole-2-carboxamide 240 mg (6.02 mmol) of sodium hydride (60% dispersion in mineral oil) were added to a 0° C. cooled solution of N-o-tolyl-1H-imidazole-2-carboxamide (0.93 g, 4.63 mmol) in DMF (120 mL). The mixture was stirred at 0° C. for 30 minutes and DPPONH$_2$ (1.51 g, 6.49 mmol, available from Sigma Aldrich®, cat. no. 5994-87-6) was added portionwise. The mixture was stirred at room temperature for 2 hours and then it was poured into 200 mL of a saturated aqueous solution of sodium thiosulphate and extracted with ethyl acetate. The combined organic layer was dried over sodium sulphate, filtered and concentrated. The crude product was purified by flash chromatography (20% to 50% AcOEt/Hexanes) to yield 0.55 g (55%) of the title compound as a beige solid.

LRMS (m/z): 217 (M+1)$^+$.

Preparation 36

2-(Chloromethyl)-3-o-tolylimidazo[1,2-f][1,2,4]triazin-4(3H)-one

Pyridinium p-toluenesulfonate (0.067 g, 0.27 mmol) was added to a suspension of 1-amino-N-o-tolyl-1H-imidazole-2-carboxamide (0.58 g, 2.68 mmol) in 2-chloro-1,1,1-trimethoxyethane (3.62 mL). The mixture was stirred at 100° C. for 5 hours. The solvent was evaporated to dryness and the residue was purified by flash chromatography (10% to 50% AcOEt/hexanes) to yield 0.360 g (49% yield) of the title compound.

LRMS (m/z): 275 (M+1)$^+$.

Preparation 37

1-Amino-N-(3-fluorophenyl)-1H-pyrrole-2-carboxamide

This compound was prepared starting from 1H-pyrrole-2-carboxylic acid (0.67 g, 6 mmol) and following the experimental procedure described in Preparation 1 to afford 0.525 g (39% yield) of the title compound that was used in the next step without any further purification.

LRMS (m/z): 220 (M+1)$^+$.

Preparation 38

1-Amino-N-(3,5-difluorophenyl)-1H-pyrrole-2-carboxamide

This compound was prepared starting from 1H-pyrrole-2-carboxylic acid (0.67 g, 6 mmol) and following the experimental procedure described in Preparation 1 to afford 0.393 g (26% yield) of the title compound that was used in the next step without any further purification.

LRMS (m/z): 238 (M+1)$^+$.

Preparation 39

(S)-2-(1-Aminoethyl)-3-(3-fluorophenyl)pyrrolo[1,2-f][1,2,4]triazin-4(3H)-one

This compound was prepared starting from 1-amino-N-(3-fluorophenyl)-1H-pyrrole-2-carboxamide (525 mg, 2.39 mmol) and following the experimental procedure described in Preparation 22 to afford 42 mg (7% yield) of the title compound.

LRMS (m/z): 273 (M+1)$^+$.

Preparation 40

(S)-2-(1-Aminoethyl)-3-(3,5-difluorophenyl)pyrrolo[1,2-f][1,2,4]triazin-4(3H)-one This compound was prepared starting from 1-Amino-N-(3,5-difluorophenyl)-1H-pyrrole-2-carboxamide (393 mg, 1.66 mmol) and following the experimental procedure described in Preparation 22 to afford 36 mg (7% yield) of the title compound.

LRMS (m/z): 291 (M+1)$^+$.

Preparation 41

1-Amino-N-(pyridin-2-yl)-1H-pyrrole-2-carboxamide

This compound was prepared starting from 1H-pyrrole-2-carboxylic acid (2 g, 18 mmol) and 2-aminopyridine (3.40 g, 36 mmol), following the experimental procedure described in Preparation 1 to afford 0,34 g (9% yield) of the title compound that was used in the next step without any further purification.

LRMS (m/z): 203 (M+1)$^+$.

Preparation 42

(S)-2-(1-Aminoethyl)-3-(pyridin-2-yl)pyrrolo[1,2-f][1,2,4]triazin-4(3H)-one dihydrochloride a) (S)-tert-Butyl 1-oxo-1-(2-(pyridin-2-ylcarbamoyl)-1H-pyrrol-1-ylamino)propan-2-ylcarbamate This compound was prepared starting from 1-amino-N-(pyridin-2-yl)-1H-pyrrole-2-carboxamide (340 mg, 1.68 mmol) and following the experimental procedure described in Preparation 22a to afford 440 mg (56% yield) of the title compound of preparation 42a.

b) (S)-2-(1-Aminoethyl)-3-(pyridin-2-yl)pyrrolo[1,2-f][1,2,4]triazin-4(3H)-one dihydrochloride A solution of bromine (113 μL, 2.21 mmol) in dichloromethane (2 mL) was added dropwise to a solution of triphenylphosphine (558 mg, 2.13 mmol) in dichloromethane (5 mL) under nitrogen. The solution was stirred for 30 min, and triethylamine (494 μL, 3.51 mmol) and a solution of (S)-tert-butyl 1-oxo-1-(2-(pyridin-2-ylcarbamoyl)-1H-pyrrol-1-ylamino)propan-2-ylcarbamate (440 mg, 0.94 mmol) in 3 ml of dichloromethane were added. The reaction mixture was stirred at room temperature for 3.5 h, and then, volatiles were removed under reduced pressure and the residue was triturated with toluene affording a solid that was removed by filtration. The filtrate was concentrated to dryness under reduced pressure and the residue was redissolved in 20 mL of a 7M methanolic solution of ammonia and stirred overnight at 80° C. in a sealed vessel. The solvent was then evaporated and the residue was purified by flash chromatography (0% to 50% AcOEt/hexanes) to yield 0.19 g (57% yield) of (S)-tert-butyl 1-(4-oxo-3-(pyridin-2-yl)-3,4-dihydropyrrolo[1,2-f][1,2,4]triazin-2-yl)ethylcarbamate. This compound (190 mg, 0.43 mmol) was dissolved in 2 ml of dioxane and 2 ml of a 4M hydrogen chloride solution in dioxane were added. The mixture was stirred at room temperature overnight. Then, the solid present in the reaction media was filtered-off and washed with hexane to afford 127 mg of the title compound of preparation 42 (90% yield).

LRMS (m/z): 256 (M+1)$^+$.

Preparation 43

(S)-3-Phenyl-2-(pyrrolidin-2-yl)pyrrolo[1,2-f][1,2,4]triazin-4(3H)-one a) (S)-tert-Butyl 2-(2-(phenylcarbamoyl)-1H-pyrrol-1-ylcarbamoyl)pyrrolidine-1-carboxylate (S)-1-(tert-Butoxycarbonyl)pyrrolidine-2-carboxylic acid (1.80 g, 8.36 mmol) were dissolved in 20 ml of N,N-dimethylformamide and HATU (3.40 g, 8.95 mmol), DIEA (2.60 ml, 14.89 mmol) and 1-amino-N-phenyl-1H-pyrrole-2-carboxamide were added. The resulting solution was stirred at room temperature overnight and the solvent was removed in vacuum. The residue was taken up in ethyl acetate and the organic solution was washed with water and brine, dried over magnesium sulphate, filtered and evaporated to dryness. The crude product was purified by flash chromatography (0% to 30% hexane/AcOEt) to yield 1.90 g (62%) of the title compound as a white solid.

LRMS (m/z): 399 (M+1)$^+$.

b) (S)-tert-Butyl 2-(4-oxo-3-phenyl-3,4-dihydropyrrolo[1,2-f][1,2,4]triazin-2-yl)pyrrolidine-1-carboxylate To a solution of 2.50 g (9.54 mmol) of triphenylphosphine in 20 ml of methylene chloride was added a solution of 1.52 g (9.54 mmol) of bromine in 10 ml of dichloromethane dropwise under nitrogen atmosphere. At the end of the addition the colourless solution was stirred for 5 minutes and then 3.32 ml (23.84 mmol) of triethylamine and 1.90 g (4.77 mmol) of (S)-tert-butyl 2-(2-(phenylcarbamoyl)-1H-pyrrol-1-ylcarbamoyl)pyrrolidine-1-carboxylate were added. The reaction mixture was then stirred at reflux for 3 hours and then cooled and the solvent was evaporated. The residue was taken up in cold toluene and the insoluble salts were filtered. The filtrate was evaporated and the residue was then redissolved in a mixture of tetrahydrofurane (30 ml) and methanol (10 ml) and 1.00 g (14.31 mmol) of sodium methanethiolate was added. The solution was stirred at 60° C. for 3 hours. Then the solvents were evaporated and the residue was partitioned between water and ethyl acetate. The organic layer was washed with water and brine, dried over magnesium sulphate, filtered and evaporated under vacuum. The product was purified by flash chromatography (20% to 40% hexane/AcOEt) to yield 1.20 g (66%) of the title compound.

LRMS (m/z): 381 (M+1)$^+$.

c) (S)-3-Phenyl-2-(pyrrolidin-2-yl)pyrrolo[1,2-f][1,2,4]triazin-4(3H)-one 1.20 g (3.16 mmol) of (S)-tert-butyl 2-(4-oxo-3-phenyl-3,4-dihydropyrrolo[1,2-f][1,2,4]triazin-2-yl)pyrrolidine-1-carboxylate were dissolved in 2 ml of methylene chloride and 2 ml of trifluoroacetic acid were added. The resulting solution was stirred at room temperature for 1 hour and the reaction mixture was evaporated to dryness. The residue was then redissolved in dichloromethane and the solution was washed with an aqueous solution of sodium bicarbonate and brine, dried over magnesium sulphate, filtered and the solvent was removed under vacuum to yield 0.80 g (91%) of the title compound.

LRMS (m/z): 281 (M+1)$^+$.
$^1$H NMR (400 MHz, DMSO-d6) δ δ 7.56 (dd, 1H), 7.55-7.42 (m, 4H), 7.41-7.37 (m, 1H), 6.93 (dd, 1H), 6.57 (dd, 1H), 3.14-2.97 (m, 1H), 2.39 (dd, 2H), 2.07-1.93 (m, 1H), 2.00 (s, 1H), 1.91-1.78 (m, 1H), 1.69 (tt, 1H), 1.60-1.49 (m, 1H).

Preparation 44

1-Amino-3-bromo-N-phenyl-1H-pyrrole-2-carboxamide a) 3-Bromo-N-phenyl-1-(phenylsulfonyl)-1H-pyrrole-2-carboxamide

In a three-necked round-bottom flask aniline (1.57 mL, 17.20 mmol) was dissolved in 80 mL of toluene under inert atmosphere. To this solution was added trimethy aluminium (7.82 mL, 15.64 mmol) and the mixture was stirred at room temperature during 10 minutes. Afterwards, a solution methyl 3-bromo-1-(phenylsulfonyl)-1H-pyrrole-2-carboxylate (2.0 g, 5.81 mmol) in 20 mL of toluene were added and the reaction mixtures was heated at 80° C. for 3 h. Next, the mixture was allowed to cool to room temperature and 20-30 mL of water was added to hydrolyze unreacted trimethyl aluminium and a 0,5M aqueous solution of disodium tartrate dihydrate was also added. After stirring for a while, the two layers were separated and the aqueous phase was extracted with ethyl acetate. The organic mixture was washed with the same 0,5M aqueous solution of disodium tartrate dehydrate (200 mL), water and brine, dried and concentrated in vacuum to afford 2.7 g of a residue that was used in the following step without further purification.

LRMS (m/z): 405, 407 (M+1)$^+$.

b) 3-Bromo-N-phenyl-1H-pyrrole-2-carboxamide

To a solution of 3-bromo-N-phenyl-1-(phenylsulfonyl)-1H-pyrrole-2-carboxamide
(2.70 g of crude material) in 50 mL of methanol was added 15 mL of an aqueous 1N solution of sodium hydroxide and the mixture was stirred at room temperature during 1.5 h. At the end of this period, no starting material was detected and the reaction was elaborated in the following way: methanol was evaporated and a precipitate was formed which was filtered off and washed several times with water. The solid was dried in the vacuum oven to afford 1.14 g and used in the following step without further purification.

LRMS (m/z): 265, 267 (M+1)$^+$.

c)
1-Amino-3-bromo-N-phenyl-M-pyrrole-2-carboxamide

This compound was prepared starting from 3-bromo-N-phenyl-1H-pyrrole-2-carboxamide (1.11 g, 4.19 mmol) and following the experimental procedure described in Preparation 1b to afford 0.78 g (67% yield) of the title compound that was used in the next step without any further purification.

LRMS (m/z): 280, 282 (M+1)$^+$.

Preparation 45

(S)-tert-Butyl 1-(5-bromo-4-oxo-3-phenyl-3,4-dihydropyrrolo[1,2-f][1,2,4]triazin-2-yl)ethylcarbamate a) (S)-tert-Butyl 1-(3-bromo-2-(phenylcarbamoyl)-1H-pyrrol-1-ylamino)-1-oxopropan-2-ylcarbamate The title compound was prepared following the experimental procedure described in preparation 20a from 810 mg (2.89 mmol) of 1-amino-3-bromo-N-phenyl-1H-pyrrole-2-carboxamide and 656 mg (3.47 mmol) of (S)-2-(tert-butoxycarbonylamino)propanoic acid (purchased from Aldrich). The crude product was purified by flash chromatography in hexane/ethyl acetate to afford 670 mg (49% yield) of the title compound.

LRMS (m/z): 306, 308 (M+1)$^+$.

b) (S)-tert-Butyl 1-(5-bromo-4-oxo-3-phenyl-3,4-di hydropyrrolo[1,2-f][1,2,4]triazin-2-yl)ethylcarbamate This compound was prepared starting from (S)-tert-butyl 1-(3-bromo-2-(phenylcarbamoyl)-1H-pyrrol-1-ylamino)-1-oxopropan-2-ylcarbamate (670 mg, 1.48 mmol) and following the experimental procedure described in Preparation 42b. The residue was purified by flash chromatography in hexane/ethyl acetate to afford 500 mg (78% yield) of the title compound were obtained.

LRMS (m/z): 433, 435 (M+1)$^+$.

Preparation 46

(S)-2-(1-Aminoethyl)-3-phenyl-5-(trifluoromethyl)pyrrolo[1,2-f][1,2,4]triazin-4(3H)-one a) (S)-tert-Butyl 1-(5-iodo-4-oxo-3-phenyl-3,4-di hydropyrrolo[1,2-f][1,2,4]triazin-2-yl)ethylcarbamate A solution of (S)-tert-butyl 1-(5-bromo-4-oxo-3-phenyl-3,4-dihydropyrrolo[1,2-f][1,2,4]triazin-2-yl)ethylcarbamate (254 mg, 0.59 mmol), trans-1,2-bis(methylamino)cyclohexane (53 mg, 0.37 mmol) and copper iodide (50 mg, 0.26 mmol) in 1,4-dioxane (5 mL) was stirred at 120° C. overnight. The crude was allowed to reach room temperature and filtered thought Celite® washing with ethyl acetate. The filtrate was concentrated to dryness, suspended in 10 mL of HCl 1N and extracted with ethyl acetate (3×). The organic mixture was washed with water and brine, dried (Mg$_2$SO$_4$) and concentrated to give 259 mg (92% yield) of the title compound that was used without further purification.

LRMS (m/z): 481 (M+1)$^+$.

b) (S)-tert-Butyl 1-(4-oxo-3-phenyl-5-(trifluoromethyl)-3,4-dihydropyrrolo[1,2-f][1,2,4]triazin-2-yl)ethylcarbamate The title compound was prepared from (S)-tert-butyl 1-(5-iodo-4-oxo-3-phenyl-3,4-dihydropyrrolo[1,2-f][1,2,4]triazin-2-yl)ethylcarbamate (259 mg, 0.47 mmol) following the experimental procedure described in Preparation 26b. 185 mg (98% yield) of the desired compound were obtained.

LRMS (m/z): 423 (M+1)$^+$.

c) (S)-2-(1-Aminoethyl)-3-phenyl-5-(trifluoromethyl)pyrrolo[1,2-f][1,2,4]triazin-4(3H)-one (S)-tert-Butyl 1-(4-oxo-3-phenyl-5-(trifluoromethyl)-3,4-dihydropyrrolo[1,2-f][1,2,4]triazin-2-yl)ethylcarbamate (180 mg, 0.43 mmol) was dissolved in 2 ml of dioxane and 2 ml of a 4M hydrogen chloride solution were added. The mixture was stirred at room temperature overnight. Reaction mixture was then concentrated and the residue dissolved in ethyl acetate and a 2N solution of NaOH. The organic layer was separated and the aqueous layer extracted with more ethyl acetate. The combined organic layer was dried over magnesium sulphate and concentrated to dryness. The title compound was obtained (146 mg, 97% yield) as colourless oil.

LRMS (m/z): 323 (M+1)$^+$.

Preparation 47

(S)-2-(1-Aminoethyl)-4-oxo-3-phenyl-3,4-dihydropyrrolo[1,2-f][1,2,4]triazine-5-carbonitrile a) (S)-tert-butyl 1-(5-cyano-4-oxo-3-phenyl-3,4-dihydropyrrolo[1,2-f][1,2,4]triazin-2-yl)ethylcarbamate A mixture of methyl (S)-tert-butyl 1-(5-bromo-4-oxo-3-phenyl-3,4-dihydropyrrolo[1,2-f][1,2,4]triazin-2-yl)ethylcarbamate (238 mg, 0.55 mmol), dicyanozinc (129 mg, 1.10 mmol) and Tetrakis(triphenylphosphine)palladium(0) (64 mg, 0.06 mmol) in DMF, was heated at 120° C. in a sealed tub overnight with stirring. Next day, ethyl acetate was added and filtered thought Celite®. Phases were separated and the aqueous layer extracted with more ethyl acetate. The combined organic layer was dried (Na$_2$SO$_4$) and concentrated in vacuum to give 580 mg of a residue that was purified by flash chromatography silica (hexane/ethyl acetate) to obtain 119 mg (57% yield) of the title compound.

LRMS (m/z): 380 (M+1)$^+$.

b) (S)-2-(1-Aminoethyl)-4-oxo-3-phenyl-3,4-dihydropyrrolo[1,2-f][1,2,4]triazine-5-carbonitrile The title compound was prepared from (S)-tert-butyl 1-(5-cyano-4-oxo-3-phenyl-3,4-dihydropyrrolo[1,24/1,2,4]triazin-2-yl)ethylcarbamate (119 mg, 0.31 mmol) following the experimental procedure described in Preparation 46c. 67 mg (77% yield) of the desired compound were obtained.

LRMS (m/z): 280 (M+1)$^+$.

Preparation 48

1-(4-methoxybenzyl)-4-nitro-1H-pyrazole

4-Nitro-1H-pyrazole (1 g, 8.84 mmol) was dissolved in dimethylformamide (40 ml). Potassium carbonate (1.2 g, 8.68 mmol) and 1-(chloromethyl)-4-methoxybenzene (1.2 g, 8.96 mmol) were added and the mixture was heated with stirring at 80° C. for 3 h. Once at room temperature, the reaction mixture was poured onto water and extracted with ethyl acetate (x3). The organic phase was washed with water and brine, dried over magnesium sulphate, filtered and the solvent evaporated under reduced pressure to yield 2.27 g of the final compound as an oil. The product was used in the next synthetic step without further purification.

LRMS (m/z): 234 (M+1)$^+$.

Preparation 49

1-(4-Methoxybenzyl)-1H-pyrazol-4-amine 1-(4-Methoxybenzyl)-4-nitro-1H-pyrazole (2.17 g, 9.30 mmol) was dissolved in ethanol (20 ml). Ammonium chloride (50 mg, 0.93 mmol) and iron (powder, 2.60 g, 46.56 mmol) were added and the mixture was refluxed for 1 h. The reaction mixture was filtered through Celite® and the solvent was evaporated to dryness under reduced pressure. Usual work-up with water and ethyl acetate afforded 1.77 g (94% yield) of the title compound as an oil, which was used in the next synthetic step without further purification.

LRMS (m/z): 204 (M+1)$^+$.

Preparation 50

(S)-Methyl 3-bromo-1-(2-(tert-butoxycarbonylamino)propanamido)-1H-pyrrole-2-carboxylate The title compound was prepared following the experimental procedure described in preparation 20a from 6.1 g (18.38 mmol) of methyl 1-amino-3-bromo-1H-pyrrole-2-carboxylate and 3.5 g (28.50 mmol) of (S)-2-(tert-butoxycarbonylamino)propanoic acid (purchased from Aldrich). The crude product was purified by flash chromatography in hexane/ethyl acetate (0 to 25%) to afford 4.34 g (61% yield) of the title compound.

LRMS (m/z): 389, 391 (M+1)$^+$.

Preparation 51

(S)-tert-Butyl 1-(3-bromo-2-(1-(4-methoxybenzyl)-1H-pyrazol-4-ylcarbamoyl)-1H-pyrrol-1-ylamino)-1-oxopropan-2-ylcarbamate This compound was prepared starting from (S)-methyl 3-bromo-1-(2-(tert-butoxycarbonylamino)propanamido)-1H-pyrrole-2-carboxylate (300 mg, 0.77 mmol) and 1-(4-methoxybenzyl)-1H-pyrazol-4-amine (469 mg, 2.31 mmol) following the experimental procedure described in Preparation 27a to afford 271 mg (96% purity, 60% yield) of the title compound after purification by flash chromatography (0% to 70% AcOEt/hexanes).

LRMS (m/z): 562 (M+1)$^+$.

Preparation 52

(S)-tert-Butyl 1-(5-bromo-3-(1-(4-methoxybenzyl)-1H-pyrazol-4-yl)-4-oxo-3,4-dihydropyrrolo[1,2-f][1,2,4]triazin-2-yl)ethylcarbamate Bromine (35 µL, 0.68 mmol) was added dropwise to a solution of triphenylphosphine (177 mg, 0.67 mmol) in dichloromethane (3 mL) under nitrogen. The solution was stirred for 30 min, and triethylamine (269 µL, 1.93 mmol) and a solution of (S)-tert-butyl 1-(3-bromo-2-(1-(4-methoxybenzyl)-1H-pyrazol-4-ylcarbamoyl)-1H-pyrrol-1-ylamino)-1-oxopropan-2-ylcarbamate (271 mg, 0.48 mmol) in 7 ml of dichloromethane were added. The reaction mixture was stirred at 60° C. for 1,5 h, and then, volatiles were removed under reduced pressure and the residue was redissolved in 10 mL of a 7M methanolic solution of ammonia and stirred overnight at 80° C. in a sealed vessel. The solvent was then evaporated and the residue was purified by flash chromatography (0% to 50% AcOEt/hexanes) to yield 154 mg (59% yield) of the title compound.

LRMS (m/z): 544 (M+1)$^+$.

Preparation 53

(S)-2-(1-Aminoethyl)-3-(1-(4-methoxybenzyl)-1H-pyrazol-4-yl)-4-oxo-3,4-dihydropyrrolo[1,2-f][1,2,4]triazine-5-carbonitrile a) (S)-tert-Butyl 1-(5-iodo-3-(1-(4-methoxybenzyl)-1H-pyrazol-4-yl)-4-oxo-3,4-dihydropyrrolo[1,2-f][1,2,4]triazin-2-yl)ethyl carbamate A solution of (S)-tert-butyl 1-(5-bromo-3-(1-(4-methoxybenzyl)-1H-pyrazol-4-yl)-4-oxo-3,4-dihydropyrrolo[1,2-f][1,2,4]triazin-2-yl)ethylcarbamate (154 mg, 0.28 mmol), trans-1,2-bis(methylamino)cyclohexane (24 mg, 0.17 mmol) and copper iodide (27 mg, 0.14 mmol) in 1,4-dioxane (15 mL) was stirred in a sealed tube at 120° C. overnight. The crude was allowed to reach room temperature and filtered thought Celite® washing with ethyl acetate. The filtrate was concentrated to dryness, suspended in 10 mL of HCl 1N and extracted with ethyl acetate (3x). The organic mixture was washed with water and brine, dried (Mg$_2$SO$_4$) and concentrated to give 131 mg (69% yield) of the title compound that was used without further purification.

LRMS (m/z): 591(M+1)$^+$.

b) (S)-tert-Butyl 1-(5-cyano-3-(1-(4-methoxybenzyl)-1H-pyrazol-4-yl)-4-oxo-3,4-dihydropyrrolo[1,2-f][1,2,4]triazin-2-yl)ethylcarbamate In a sealed tube provided with magnetic stirring were placed (S)-tert-butyl 1-(5-iodo-3-(1-(4-methoxybenzyl)-1H-pyrazol-4-yl)-4-oxo-3,4-dihydropyrrolo[1,2-f][1,2,4]triazin-2-yl)ethylcarbamate (131 mg, 0.20 mmol) and copper cyanide (210 mg, 2.34 mmol). Subsequently, pyridine was added (10 mL) as solvent, and the reaction mixture was heated to 120° C. during 18 hours in a microwave apparatus. Having consumed the starting material, the crude was filtered through Celite® and washed with ethyl acetate. The organic mixture was washed with water (2×) and brine, dried ($Na_2SO_4$) and concentrated in vacuum to give 132 mg of a residue that was used in the next synthetic step without further purification.

LRMS (m/z): 490 (M+1)$^+$.

c) (S)-2-(1-Aminoethyl)-3-(1-(4-methoxybenzyl)-1H-pyrazol-4-yl)-4-oxo-3,4-dihydropyrrolo[1,2-f][1,2,4]triazine-5-carbonitrile The title compound was prepared from (S)-tert-butyl 1-(5-cyano-3-(1-(4-methoxybenzyl)-1H-pyrazol-4-yl)-4-oxo-3,4-dihydropyrrolo[1,2-f][1,2,4]triazin-2-yl)ethylcarbamate (132 mg, 0.27 mmol) following the experimental procedure described in Preparation 46c. 90 mg (81% yield) of the desired compound were obtained.

LRMS (m/z): 390 (M+1)$^+$.

Preparation 54 tert-Butyl (S)-1-(5-bromo-4-oxo-3-((R)-1-phenylethyl)-3,4-dihydropyrrolo[1,2-f][1,2,4]triazin-2-yl)ethylcarbamate a) tert-Butyl (S)-1-(3-bromo-2-((R)-1-phenylethylcarbamoyl)-1H-pyrrol-1-ylamino)-1-oxopropan-2-ylcarbamate The title compound was prepared from (S)-methyl 3-bromo-1-(2-(tert-butoxycarbonylamino)propanamido)-1H-pyrrole-2-carboxylate (1.27 g, 3.25 mmol) following the experimental procedure described in Preparation 27a. 600 mg (39% yield) of the desired compound were obtained.

LRMS (m/z): 480 (M+1)$^+$.

b) tert-Butyl (S)-1-(5-bromo-4-oxo-3-((R)-1-phenylethyl)-3,4-dihydropyrrolo[1,2-f][1,2,4]triazin-2-yl)ethylcarbamate Bromine (90 µL, 1.76 mmol) was added dropwise to a solution of triphenylphosphine (460 mg, 1.75 mmol) in dichloromethane (4 mL) under nitrogen. The solution was stirred for 30 min, and triethylamine (700 µL, 7.02 mmol) and a solution of tert-butyl (S)-1-(3-bromo-2-((R)-1-phenylethylcarbamoyl)-1H-pyrrol-1-ylamino)-1-oxopropan-2-ylcarbamate (0.60 g, 1.25 mmol) in 10 ml of dichloromethane were added. The reaction mixture was stirred at 60° C. for 2 h, poured onto 4% sodium bicarbonate solution and extracted with dichloromethane. The organic phase is passed through a phase separator and the solvent removed under reduced pressure. The residue was redissolved in DMF (10 ml) and sodium thiomethoxide (263 mg, 3.75 mmol) was added. The reaction mixture was stirred for 2 h, poured onto 4% sodium bicarbonate solution and extracted with ethyl acetate (x3). The organic mixture was washed with water and brine, dried ($Mg_2SO_4$) and concentrated to give 1.18 g of a crude which was purified by flash chromatography (0% to 20% AcOEt/hexanes) to yield 470 mg (81% yield) of the title compound.

LRMS (m/z): 462 (M+1)$^+$.

Preparation 55

2-((S)-1-Aminoethyl)-4-oxo-3,4(R)-1-phenylethyl)-3,4-dihydropyrrolo[1,2-f][1,2,4]triazine-5-carbonitrile a) tert-Butyl (S)-1-(5-iodo-4-oxo-3-((R)-1-phenylethyl)-3,4-dihydropyrrolo[1,2-f][1,2,4]triazin-2-yl)ethylcarbamate The title compound was prepared from tert-butyl (S)-1-(5-bromo-4-oxo-3-((R)-1-phenylethyl)-3,4-dihydropyrrolo[1,2-f][1,2,4]triazin-2-yl)ethylcarbamate (470 mg, 1 mmol) following the experimental procedure described in Preparation 53a. 507 mg (90% yield) of the desired compound were obtained.

LRMS (m/z): 509 (M+1)$^+$.

b) tert-Butyl (S)-1-(5-cyano-4-oxo-3-((R)-1-phenylethyl)-3,4-dihydropyrrolo[1,2-f][1,2,4]triazin-2-yl)ethylcarbamate The title compound was prepared from tert-butyl (S)-1-(5-iodo-4-oxo-3-((R)-1-phenylethyl)-3,4-dihydropyrrolo[1,2-f][1,2,4]triazin-2-yl)ethylcarbamate (0.51 g, 1 mmol) following the experimental procedure described in Preparation 53b. 410 mg (100% yield) of the desired compound were obtained.

LRMS (m/z): 408 (M+1)$^+$.

c) 2-((S)-1-Aminoethyl)-4-oxo-3-((R)-1-phenylethyl)-3,4-dihydropyrrolo[1,2-f][1,2,4]triazine-5-carbonitrile The title compound was prepared from tert-butyl (S)-1-(5-cyano-4-oxo-3-((R)-1-phenylethyl)-3,4-dihydropyrrolo[1,2-f][1,2,4]triazin-2-yl)ethylcarbamate (498 mg, 1.22 mmol) following the experimental procedure described in Preparation 46c. 241 mg (53% yield) of the desired compound were obtained.

LRMS (m/z): 308 (M+1)$^+$.

Preparation 56

(S)-2-(1-Aminoethyl)-3-(5-methyl-1H-pyrazol-3-yl)pyrrolo[1,2-f][1,2,4]triazin-4(3H)-one a) (S)-tert-Butyl 1-(2-(5-methyl-1H-pyrazol-3-ylcarbamoyl)-1H-pyrrol-1-ylamino)-1-oxopropan-2-ylcarbamate The title compound was prepared from (S)-methyl 1-(2-(tert-butoxycarbonylamino)propanamido)-1H-pyrrole-2-carboxylate (900 mg, 2.89 mmol) following the experimental procedure described in Preparation 27a. 188 mg (15% yield) of the desired compound were obtained.

LRMS (m/z): 377 (M+1)$^+$.

b) (S)-tert-Butyl 1-(3-(5-methyl-1H-pyrazol-3-yl)-4-oxo-3,4-dihydropyrrolo[1,2-f][1,2,4]triazin-2-yl)ethylcarbamate The title compound was prepared from (S)-tert-butyl 1-(2-(5-methyl-1H-pyrazol-3-ylcarbamoyl)-1H-pyrrol-1- ylamino)-1-oxopropan-2-ylcarbamate (180 mg, 0.41 mmol) following the experimental procedure described in Preparation 54b. 64 mg (44% yield) of the desired compound were obtained.

LRMS (m/z): 359 (M+1)$^+$.

c) (S)-2-(1-Aminoethyl)-3-(5-methyl-1H-pyrazol-3-yl)pyrrolo[1,2-f][1,2,4]triazin-4(3H)-one The title compound was prepared from (S)-tert-butyl 1-(3-(5-methyl-1H-pyrazol-3-yl)-4-oxo-3,4-dihydropyrrolo[1,2f][1,2,4]triazin-2-yl)ethylcarbamate (64 mg, 0.18 mmol) following the experimental procedure described in Preparation 46c. 46 mg (100% yield) of the desired compound were obtained.

LRMS (m/z): 259 (M+1)$^+$.

Preparation 57

(S)-2-(1-Aminoethyl)-3-(1H-pyrazol-3-yl)pyrrolo[1,2-f][1,2,4]triazin-4(3H)-one a) (S)-tert-Butyl 1-(2-(1H-pyrazol-3-ylcarbamoyl)-1H-pyrrol-1-ylamino)-1-oxopropan-2-yl carbamate The title compound was prepared from (S)-methyl 1-(2-(tert-butoxycarbonylamino)propanamido)-1H-pyrrole-2-carboxylate (900 mg, 2.89 mmol) following the experimental procedure described in Preparation 27a. 247 mg (17% yield) of the desired compound were obtained.

LRMS (m/z): 363 (M+1)$^+$.

b) (S)-tert-Butyl 1-(4-oxo-3-(1H-pyrazol-3-yl)-3,4-di hydropyrrolo[1,2-f][1,2,4]triazin-2-yl)ethylcarbamate The title compound was prepared from (S)-tert-butyl 1-(2-(1H-pyrazol-3-ylcarbamoyl)-1H-pyrrol-1-ylamino)-1-oxopropan-2-ylcarbamate (247 mg, 0.49 mmol) following the experimental procedure described in Preparation 54b. 220 mg (46% yield) of the desired compound were obtained.

LRMS (m/z): 345 (M+1)$^+$.

c) (S)-2-(1-Aminoethyl)-3-(1H-pyrazol-3-yl)pyrrolo[1,2-f][1,2,4]triazin-4(3H)-one The title compound was prepared from (S)-tert-butyl 1-(4-oxo-3-(1H-pyrazol-3-yl)-3,4-dihydropyrrolo[1,2-f][1,2,4]triazin-2-yl)ethylcarbamate (220 mg, 0.22 mmol) following the experimental procedure described in Preparation 46c. 54 mg (100% yield) of the desired compound were obtained.

LRMS (m/z): 245 (M+1)$^+$.

Preparation 58

(S)-3-((1H-Pyrazol-3-yl)methyl)-2-(1-aminoethyl) pyrrolo[1,2-f][1,2,4]triazin-4(3H)-one a) (S)-tert-Butyl 1-(2-((1H-pyrazol-3-yl)methylcarbamoyl)-1H-pyrrol-1-ylamino)-1-oxopropan-2-yl-carbamate The title compound was prepared from (S)-methyl 1-(2-(tert-butoxycarbonylamino)propanamido)-1H-pyrrole-2-carboxylate (900 mg, 2.89 mmol) following the experimental procedure described in Preparation 27a. 370 mg (14% yield) of the desired compound were obtained.

LRMS (m/z): 377 (M+1)$^+$.

b) (S)-tert-Butyl 1-(3-((1H-pyrazol-3-yl)methyl)-4-oxo-3,4-dihydropyrrolo[1,2-f][1,2,4]triazin-2-yl) ethylcarbamate The title compound was prepared from (S)-tert-butyl 1-(2-((1H-pyrazol-3-yl)methylcarbamoyl)-1H-pyrrol-1-ylamino)-1-oxopropan-2-ylcarbamate (370 mg, 0.41 mmol) following the experimental procedure described in Preparation 54b. 784 mg (37% yield) of the desired compound were obtained.

LRMS (m/z): 359 (M+1)$^+$.

c) (S)-3-((1H-Pyrazol-3-yl)methyl)-2-(1-aminoethyl) pyrrolo[1,2-f][1,2,4]triazin-4(3H)-one The title compound was prepared from (S)-tert-butyl 1-(3-((1H-pyrazol-3-yl)methyl)-4-oxo-3,4-dihydropyrrolo[1,2-f][1,2,4]triazin-2-yl)ethylcarbamate (794 mg, 0.16 mmol) following the experimental procedure described in Preparation 46c. 41 mg (100% yield) of the desired compound were obtained.

LRMS (m/z): 259 (M+1)$^+$.

Preparation 59

(S)-2-(1-Aminoethyl)-3-phenylimidazo[1,2-f][1,2,4] triazin-4(3H)-one a) (S)-tert-Butyl 1-oxo-1-(2-(phenylcarbamoyl)-1H-imidazol-1-ylamino)propan-2-ylcarbamate The title compound was prepared following the experimental procedure described in preparation 20a, from 1.12 g (5.54 mmol) of 1-amino-N-phenyl-1H-imidazole-2-carboxamide, 1.26 g (6.65 mmol) of (S)-2-(tert-butoxycarbonylamino)propanoic acid and 1.03 g (6.65 mmol) of EDC.HCl. The solid obtained was triturated in diisopropylether to give 1.51 g (67% yield) of the title compound.

LRMS (m/z): 374 (M+1)$^+$.

b) (S)-tert-Butyl 1-(4-oxo-3-phenyl-3,4-dihydroimidazo[1,2-f][1,2,4]triazin-2-yl)ethylcarbamate A solution of bromine (370 µl, 7.39 mmol) in 10 mL of dichloromethane was added dropwise to a solution of triphenylphosphine (1.94 g, 7.39 mmol) in 10 mL of dichloromethane. The resulting solution was stirred for 10 min., and triethylamine (2.58 mL, 18.48 mmol) and (S)-tert-butyl 1-oxo-1-(2-(phenylcarbamoyl)-1H-imidazol-1-ylamino) propan-2-ylcarbamate (1.50 g, 3.70 mmol) in 30 mL of dichloromethane were added. The reaction mixture was refluxed under nitrogen for 2 hours, cooled and concentrated to dryness. The solid thus obtained was dissolved in a mixture of tetrahydrofurane/dimethylformamide (90:10) and 0.78 g (11.09 mmol) of sodium methanethiolate was added. The mixture was heated at 60° C. for 2 hours and then partitioned between a saturated aqueous solution of sodium bicarbonate and ethyl acetate. The organic layer was washed with brine, dried over magnesium sulphate, filtered and the solvent was removed in vacuum. The product was purified by flash chromatography (20% to 100% hexane/AcOEt) to yield 0.72 g (55% yield) of the title compound.

LRMS (m/z): 356 (M+1)$^+$.

c) (S)-2-(1-Aminoethyl)-3-phenylimidazo[1,2-f][1,2,4]triazin-4(3H)-one 0.72 g (2.21 mmol) of (S)-tert-butyl 1-(4-oxo-3-phenyl-3,4-dihydroimidazo[1,2-f][1,2,4]triazin-2-yl)ethylcarbamate were dissolved in 3 mL of dichloromethane and 3 mL of trifluoroacetic acid were added. The mixture was stirred at room temperature for 1 hour. The solvents were evaporated to dryness and the residue was partitioned between ethyl acetate and an aqueous solution of sodium bicarbonate. The organic layer was washed with brine, dried over magnesium sulphate, filtered and the solvent was removed in vacuum. 372 mg (66% yield) of the title compound were obtained.

LRMS (m/z): 256 (M+1)$^+$.

$^1$H NMR (400 MHz, DMSO) δ 8.06 (d, 1H), 7.57 (d, 6H), 3.46-3.37 (m, 1H), 1.87 (s, 2H), 1.18 (d, 3H).

Preparation 60

2-(tert-Butoxycarbonylamino)-4,4,4-trifluorobutanoic acid 350 mg (2.23 mmol) of 2-amino-4,4,4-trifluorobutanoic acid (purchased from Alfa Aesar® cat. no. L13131) were suspended in 10 mL of dichloromethane and cooled in an ice bath. 534 mg (2.45 mmol) of di-tert-butyl dicarbonate and 621 µl (4.46 mmol) of triethylamine were added and the resulting solution was stirred at room temperature overnight. The solution was extracted with water and the aqueous layer was acidified to pH=3 with 2N hydrochloric acid and extracted with dichloromethane (x3). The combined organic layers were washed with brine, dried over magnesium sulphate, filtered and evaporated to yield 425 mg (74% yield) of a white solid.

LRMS (m/z): 258 (M+1)$^+$.

$^1$H NMR (400 MHz, DMSO) δ 13.05 (s, 1H), 7.36 (d, 1H), 4.20 (td, 1H), 2.84-2.53 (m, 2H), 1.38 (s, 9H).

Preparation 61

2-(1-Amino-3,3,3-trifluoropropyl)-3-phenylpyrrolo[1,2-f][1,2,4]triazin-4(3H)-one a) tert-Butyl 4,4,4-trifluoro-1-oxo-1-(2-(phenylcarbamoyl)-1H-pyrrol-1-ylamino)butan-2-ylcarbamate 421 mg (1.64 mmol) of 2-(tert-butoxycarbonylamino)-4,4,4-trifluorobutanoic acid were suspended in a mixture of N,N-dimethylformamide (5 mL) and dichloromethane (5 mL) and HATU (624 mg, 1.64 mmol) and DIEA (286 µl, 1.64 mmol) were added. The resulting suspension was stirred at room temperature for 2 hours and then 1-amino-N-phenyl-1H-pyrrole-2-carboxamide (300 mg, 1.49 mmol) was added. The resulting solution was stirred at room temperature overnight and the dichloromethane was removed in vacuum. 25 mL of water were added to the remaining solution and, after vigorous stirring, the solid that formed was filtered and washed with water. 582 mg (89% yield) of the title compound were obtained as a white solid.

LRMS (m/z): 441 (M+1)$^+$.

b) tert-Butyl 3,3,3-trifluoro-1-(4-oxo-3-phenyl-3,4-dihydropyrrolo[1,2-f][1,2,4]triazin-2-yl)propylcarbamate A solution of bromine (81 µl, 1.58 mmol) in dichloromethane (5 mL) was added dropwise to a solution of triphenylphosphine (415 mg, 1.58 mmol) in dichloromethane (10 mL) under nitrogen. The solution was stirred for 15 min, and triethylamine (552 µL, 3.97 mmol) and a solution of tert-butyl 4,4,4-trifluoro-1-oxo-1-(2-(phenylcarbamoyl)-1H-pyrrol-1-ylamino)butan-2-ylcarbamate (582 mg, 1.32 mmol) were added. The reaction mixture was stirred at room temperature for 4 hours, and then the volatiles were removed under reduced pressure. The residue was redissolved in 80 mL of a 7M methanolic solution of ammonia and stirred overnight at 80° C. in a sealed vessel. The solvent was then evaporated and the residue was purified by flash chromatography (0% to 50% AcOEt/hexanes) to yield 228 mg (41% yield) of the title compound as a white solid.

LRMS (m/z): 423 (M+1)$^+$.

c) 2-(1-Amino-3,3,3-trifluoropropyl)-3-phenylpyrrolo[1,2-f][1,2,4]triazin-4(3H)-one 228 mg (0.54 mmol) of tert-butyl 3,3,3-trifluoro-1-(4-oxo-3-phenyl-3,4-dihydropyrrolo[1,2-f][1,2,4]triazin-2 11)propylcarbamate were dissolved in 5 mL of dichloromethane and 125 µl (1.62 mmol) of trifluoroacetic acid were added. The solvent was evaporated and the residue was partitioned between water and ethyl acetate. The organic layer was washed three times with a diluted aqueous solution of potassium carbonate and brine, dried over magnesium sulphate, filtered and the solvent was removed under vacuum to yield 139 mg (80%) of the title product as a white solid.

LRMS (m/z): 323 (M+1)$^+$.

Preparation 62

(S)-2-(1-Aminoethyl)-5-methyl-3-phenylpyrrolo[1,2-f][1,2,4]triazin-4(3H)-one a) (S)-tert-Butyl 1-(3-methyl-2-(phenylcarbamoyl)-1H-pyrrol-1-ylamino)-1-oxopropan-2-ylcarbamate Prepared from 2.00 g (9.29 mmol) of 1-amino-3-methyl-N-phenyl-1H-pyrrole-2-carboxamide and 2.11 g (11.15 mmol) of (S)-2-(tert-butoxycarbonylamino)propanoic acid following the experimental procedure described in Preparation 22a. After purification by flash chromatography (0 to 10% methanol in dichloromethane), 825 mg (23% yield) of the title product were obtained.

LRMS (m/z): 387 (M+1)$^+$.

b) (S)-tert-Butyl 1-(5-methyl-4-oxo-3-phenyl-3,4-dihydropyrrolo[1,2-f][1,2,4]triazin-2-yl)ethylcarbamate The title compound was obtained from 825 mg (2.13 mmol) of (S)-tert-butyl 1-(3-methyl-2-(phenylcarbamoyl)-1H-pyrrol-1-ylamino)-1-oxopropan-2-ylcarbamate following the experimental procedure described in Preparation 61b. After purification by flash chromatography (0 to 50% AcOEt/hexanes), 330 mg (42% yield) of the title compound were obtained.

LRMS (m/z): 368 (M+1)$^+$.

c) (S)-2-(1-Aminoethyl)-5-methyl-3-phenylpyrrolo[1,2-f][1,2,4]triazin-4(3H)-one Prepared from 330 mg (0.90 mmol) of (S)-tert-butyl 1-(5-methyl-4-oxo-3-phenyl-3,4-dihydropyrrolo[1,2-f][1,2,4]triazin-2-yl)ethylcarbamate following the experimental procedure described in Preparation 61c. 201 mg (84% yield) of the title compound were obtained as a white solid.

LRMS (m/z): 268 (M+1)$^+$.

$^1$H NMR (400 MHz, DMSO) δ 7.59-7.38 (m, 6H), 6.41 (d, 1H), 3.41-3.35 (m, 1H), 2.39 (s, 3H), 1.15 (d, 3H).

Preparation 63

(S)-1-(tert-Butoxycarbonyl)-4,4-difluoropyrrolidine-2-carboxylic acid 1.08 g (4.08 mmol) of (S)-1-tert-butyl 2-methyl 4,4-difluoropyrrolidine-1,2-dicarboxylate (purchased from Aldrich®; cat. no. 702463) were dissolved in a mixture of 10 mL of methanol and 10 mL of tetrahydrofurane and 6.12 mL of a 2M aqueous solution of sodium hydroxide were added. The solution was stirred at room temperature for 1 hour and then the organic solvents were removed. The remaining solution was diluted with water and 6.12 mL of 2M hydrochloric acid were added. The product that precipitated was extracted with dichloromethane (×3), the combined organic layers were washed with brine, dried over magnesium sulphate, filtered and the solvent was removed. 1.01 g (99% yield) of the title compound were obtained as a white solid.

LRMS (m/z): 250 (M–1)$^+$.

Preparation 64

(S)-2-(4,4-Difluoropyrrolidin-2-yl)-3-phenyl pyrrolo[1,2-f][1,2,4]triazin-4(3H)-one a) (S)-tert-Butyl 4,4-difluoro-2-(2-(phenylcarbamoyl)-1H-pyrrol-1-ylcarbamoyl)pyrrolidine-1-carboxylate 1-Amino-N-phenyl-1H-pyrrole-2-carboxamide (500 mg, 2.48 mmol), (S)-1-(tert-butoxycarbonyl)-4,4-difluoropyrrolidine-2-carboxylic acid (687 mg, 2.73 mmol), HATU (1.04 g, 2.73 mmol) and diisopropylethylamine (476 µl, 2.73 mmol) were dissolved in a mixture of 6 mL of dichloromethane and 6 mL of DMF and stirred at room temperature overnight. The dichloromethane was removed under vacuum and 25 mL of water were poured over the remaining solution. A precipitated appeared and the suspension was stirred overnight. The solid was filtered and washed with water to furnish 1.05 g (97% yield) of the title compound.

LRMS (m/z): 435 (M+1)$^+$.

b) (S)-tert-Butyl 4,4-difluoro-2-(4-oxo-3-phenyl-3,4-dihydropyrrolo[1,2-f][1,2,4]triazin-2-Apyrrolidine-1-carboxylate To a solution of 760 mg (1.20 mmol) of triphenylphosphine in 20 mL of dichloromethane was added a solution of 150 µl (1.18 mmol) of bromine in 10 mL of dichloromethane dropwise under nitrogen atmosphere. At the end of the addition the colourless solution was stirred for 10 minutes and then 1.34 mL (9.61 mmol) of triethylamine and 1.05 g (2.42 mmol) of (S)-tert-butyl 4,4-difluoro-2-(2-(phenylcarbamoyl)-1H-pyrrol-1-ylcarbamoyl)pyrrolidine-1-carboxylate were added. The reaction mixture was then stirred at 40° C. for 3 hours. In a separate vessel, an additional 760 mg (1.20 mmol) of triphenylphosphine in 20 mL of dichloromethane was added a solution of 150 µl (1.18 mmol) of bromine in 10 mL of dichloromethane dropwise under nitrogen atmosphere and stirred for 15 minutes. Then this solution was added to the reaction mixture and 1.34 mL of triethylamine were also added. After 3 hours at 40° C., the solvent was evaporated and the residue was redissolved in a mixture of N,N-dimethylformamide (20 mL) and methanol (20 mL) and 500 mg (7.13 mmol) of sodium methanethiolate was added. The solution was stirred at room temperature overnight. The solvents were evaporated and the residue was partitioned between water and ethyl acetate. The organic layer was washed with water and brine, dried over magnesium sulphate, filtered and evaporated under vacuum. The product was purified by flash chromatography (0% to 30% hexane/AcOEt) to yield 823 mg (82%) of the title compound.

LRMS (m/z): 417 (M+1)$^+$.

c) (S)-2-(4,4-Difluoropyrrolidin-2-yl)-3-phenylpyrrolo[1,2-f][1,2,4]triazin-4(3H)-one 580 mg (1.39 mmol) of (S)-tert-butyl 4,4-difluoro-2-(4-oxo-3-phenyl-3,4-dihydropyrrolo[1,2-f][1,2,4]triazin-2-yl)pyrrolidine-1-carboxylate were dissolved in dichloromethane (5 mL) and 536 µl (6.96 mmol) of trifluoroacetic acid were added. The solution was stirred at room temperature overnight and then the volatiles were removed in vacuum. The residue was partitioned between ethyl acetate and a diluted aqueous solution of potassium carbonate, and the organic layer was washed twice with water and brine, dried over magnesium sulphate, filtered and the solvent was removed under vacuum. 418 mg (95% yield) of the title compound were obtained as a yellowish solid.

LRMS (m/z): 317 (M+1)$^+$.

$^1$H NMR (400 MHz, DMSO) δ 7.78-7.46 (m, 5H), 7.46-7.20 (m, 1H), 7.06-6.85 (m, 1H), 6.71-6.56 (m, 1H), 4.47 (ddd, 1H), 3.93-3.67 (m, 2H), 2.87 (m, 1H), 2.47-2.27 (m, 1H).

Preparation 65

1-Amino-N-(3,5-difluorophenyl)-1H-imidazole-2-carboxamide a)
N-(3,5-Difluorophenyl)-1H-imidazole-2-carboxamide To a solution of 1H-imidazole-2-carboxylic acid (2.50 g, 22.3 mmol) in DMF (30 mL) were added 3,5-difluoroaniline (2.23 mL, 22.3 mmol), EDCHCl (6.41 g, 33.46 mmol) and HOBt (4.52 g, 33.46 mmol). The reaction mixture was stirred at room temperature overnight. The solvent was removed in vacuum and the crude was dissolved in dichloromethane. The solution was washed with a diluted aqueous solution of potassium carbonate, dried over sodium sulphate, filtered and concentrated. 2.75 g (55% yield) of the title compound were obtained as a solid.

LRMS (m/z): 224 (M+1)$^+$.

b) 1-Amino-N-(3,5-difluorophenyl)-1H-imidazole-2-carboxamide

Prepared following the experimental procedure described in Preparation 33b from 2.68 g (12.01 mmol) of N-(3,5-difluorophenyl)-1H-imidazole-2-carboxamide. The product was purified by flash chromatography (dichloromethane/ methanol/ammonium hydroxide, 100/8/1) to yield 1.50 g (52% yield) of the title compound as a pale yellow solid.
LRMS (m/z): 239 (M+1)$^+$.

Preparation 66

(S)-2-(1-Aminoethyl)-3-(3,5-difluorophenyl)imidazo[1,2-f][1,2,4]triazin-4(3H)-one a) (S)-tert-Butyl 1-(2-(3,5-difluorophenylcarbamoyl)-1H-imidazol-1-ylamino)-1-oxopropan-2-ylcarbamate 1.60 g (6.18 mmol) of 1-amino-N-(3,5-difluorophenyl)-1H-imidazole-2-carboxamide, 1.64 g (8.65 mmol) of (S)-2-(tert-butoxycarbonylamino)butanoic acid and 1.34 g (8.65 mmol) of EDCHCl were dissolved in 45 mL of THF and stirred at 55° C. overnight and at room temperature for 2 days. Then the solvent was evaporated and the crude residue was taken up in ethyl acetate and washed with brine. The organic layer was dried over magnesium sulphate, filtered and the solvent was evaporated. The solid obtained was redissolved in the minimum amount of ethyl acetate and diisopropylether was added until a solid precipitated, which was filtered to furnish 1.51 g (57% yield) of the title compound.
LRMS (m/z): 410 (M+1)$^+$.

b) (S)-tert-Butyl 1-(3-(3,5-difluorophenyl)-4-oxo-3,4-dihydroimidazo[1,2-f][1,2,4]triazin-2-yl)ethylcarbamate Prepared following the experimental procedure described in Preparation 64b from 1.51 g (3.28 mmol) of (S)-tert-butyl 1-(2-(3,5-difluorophenylcarbamoyl)-1H-imidazol-1-ylamino)-1-oxopropan-2-ylcarbamate, using 1.05 g (6.57 mmol) of bromine, 1.72 g (6.57 mmol) of triphenylphosphine, 2.29 mL (16.41 mmol) of triethylamine. After 3 hours, the dichloromethane was removed and 0.69 g (9.85 mmol) of sodium methanethiolate was used in a mixture of N,N-dimethylformamide and methanol at 55° C. for 5 hours. The product was purified by flash chromatography (20% to 60% hexane/AcOEt) to yield 2.46 g (40% purity) of a mixture of the title compound and triphenylphosphine oxide, which was used without further purification in the next step.
LRMS (m/z): 392 (M+1)$^+$.

c) (S)-2-(1-Aminoethyl)-3-(3,5-difluorophenyl)imidazo[1,2-f][1,2,4]triazin-4(3H)-one The mixture of (S)-tert-butyl 1-(3-(3,5-difluorophenyl)-4-oxo-3,4-dihydroimidazo[1,2-f][1,2,4]triazin-2-yl)ethylcarbamate and triphenylphosphine oxide obtained in Preparation 66b was dissolved in 20 mL of dichloromethane and 2 mL of trifluoroacetic acid were added. The solution was stirred at room temperature for 1.2 hours and the solvent was removed. The residue was partitioned between water and diethylether, the two layers were separated and the aqueous layer was washed twice more with diethylether. Then the aqueous layer was basified with a diluted aqueous solution of sodium hydroxide and the product was extracted 3 times with ethyl acetate. The combined organic layers were washed with brine, dried over magnesium sulphate, filtered and the solvent removed under vacuum. 0.26 g of the title compound were obtained as a solid. Yield=24% in two steps.
LRMS (m/z): 292 (M+1)$^+$.

Preparation 67

2-(tert-Butoxycarbonylamino)-3,3,3-trifluoropropanoic acid 650 mg (4.54 mmol) of 2-amino-3,3,3-trifluoropropanoic acid (purchased from Aldrich®; cat. no. 307556) and 866 mg (9.50 mmol) of tetramethylammonium were suspended in 30 mL acetonitrile. The mixture was stirred for 30 minutes until a clear solution was observed. Then 1.98 g (9.09 mmol) of di-tert-butyl dicarbonate were added and the resulting solution was stirred for 2 hours at room temperature. The solvent was removed in vacuum and the residue was dissolved in water and this solution was washed twice with diethylether. The aqueous layer was acidified with 2M hydrochloric acid and the product was extracted with ethyl acetate (x3). The combined organic layers were washed with brine, dried over magnesium sulphate, filtered and the solvent was removed in vacuum to furnish 830 mg (75% yield) of a white solid.
LRMS (m/z): 242 (M−1)$^+$.
$^1$H NMR (400 MHz, DMSO) δ 13.83 (s, 1H), 8.07 (d, 1H), 5.10-4.76 (m, 1H), 1.41 (s, 9H).

Preparation 68

2-(1-Amino-2,2,2-trifluoroethyl)-3-phenylpyrrolo[1,2-f][1,2,4]triazin-4(3H)-one a) tert-Butyl 1,1,1-trifluoro-3-oxo-3-(2-(phenylcarbamoyl)-1H-pyrrol-1-ylamino)propan-2-ylcarbamate 1-Amino-N-phenyl-1H-pyrrole-2-carboxamide (570 mg, 2.83 mmol), 2-(tert-butoxycarbonylamino)-3,3,3-trifluoropropanoic acid (826 mg, 3.40 mmol), HATU (1.29 g, 3.40 mmol) and N-methylmorpholine (685 µl, 6.23 mmol) were suspended in 20 mL of dichloromethane and stirred overnight. The reaction mixture was diluted with more dichloromethane and the solution was washed with water and brine, dried over magnesium sulphate, filtered and the solvent was removed in vacuum. The product was purified by reverse phase chromatography (C-18 silica from Waters®, water/1:1 acetonitrile-methanol as eluents [0.1% v/v formic acid buffered] 0% to 100%) to obtain the title compound in a 47% yield (562 mg) as a white solid.
LRMS (m/z): 427 (M+1)$^+$.

b) tert-Butyl 2,2,2-trifluoro-1-(4-oxo-3-phenyl-3,4-dihydropyrrolo[1,2-f][1,2,4]triazin-2-yl)ethylcarbamate To a solution of 414 mg (1.58 mmol) of triphenylphosphine in 10 mL of dichloromethane was added a solution of 81 µl (1.58 mmol) of bromine in 5 mL of dichloromethane dropwise under nitrogen atmosphere. At the end of the addition the colourless solution was stirred for 15 minutes and then 735 µl (5.27 mmol) of triethylamine and 562 mg (1.32 mmol) of tert-butyl 1,1,1-trifluoro-3-oxo-3-(2-(phenylcarbamoyl)-1H-pyrrol-1-ylamino)propan-2-ylcarbamate were added. The reaction mixture was then stirred at 40° C. for 3 days. In a separate vessel, an additional 414 mg (1.58 mmol) of triphenylphosphine in 10 mL of dichloromethane was added a solution of 81 µl (1.58 mmol) of bromine in 5 mL of dichloromethane dropwise under nitrogen atmosphere and stirred for 15 minutes. Then this solution was added to the reaction mixture and 734 µl of triethylamine were also added. After 3 hours at 40° C., the solvent was evaporated and the residue was redissolved in a mixture of N,N-dimethylformamide (10 mL) and methanol (10 mL) and 277 mg (3.95 mmol) of sodium methanethiolate was added. The solution was stirred at 60° C. for 4 hours and at room temperature overnight. Then the solvents were evaporated and the residue was partitioned between water and ethyl acetate. The organic layer was washed with water and brine, dried over magnesium sulphate, filtered and evaporated under vacuum. The product was purified by flash chromatography (0% to 40% hexane/AcOEt) to yield 218 mg (41%) of the title compound.

LRMS (m/z): 409 (M+1)$^+$.

c) 2-(1-Amino-2,2,2-trifluoroethyl)-3-phenylpyrrolo[1,2-f][1,2,4]triazin-4(3H)-one 218 mg (0.53 mmol) of tert-butyl 2,2,2-trifluoro-1-(4-oxo-3-phenyl-3,4-dihydropyrrolo[1,2-f][1,2,4]triazin-2-yl)ethylcarbamate were dissolved in dichloromethane (2 mL) and 205 µl of trifluoroacetic acid were added. The solution was stirred at room temperature for 3 hours and then the solvent was removed to dryness. The residue was partitioned between ethyl acetate and a diluted aqueous solution of potassium carbonate, and the organic layer was washed twice with water and brine, dried over magnesium sulphate, filtered and the solvent was removed under vacuum. 155 mg (94% yield) of the title compound were obtained as a brownish solid.

LRMS (m/z): 309 (M+1)$^+$.
$^1$H NMR (400 MHz, DMSO) δ 7.74 (s, 1H), 7.65-7.50 (m, 4H), 7.40 (d, 1H), 7.05-6.99 (m, 1H), 6.70-6.64 (m, 1H), 4.00-3.86 (m, 1H), 2.63 (d, 2H).

Preparation 69

6-Bromo-9-(4-methoxybenzyl)-9H-purine 1.00 g (5.02 mmol) of 6-bromo-9H-purine (purchased from Aldrich; cat. no. 104981) was suspended in 10 mL of DMF and potassium carbonate (2.08 g, 15.05 mmol) was added. The mixture was stirred at room temperature for 20 minutes and then 1-(chloromethyl)-4-methoxybenzene (1.40 mL, 10.06 mmol) were added. The reaction mixture was stirred at 45° C. overnight. Then the mixture was evaporated to dryness and the residue was partitioned between water and dichloromethane. The organic layer was washed with water and brine, dried over magnesium sulphate, filtered and the solvent was removed in vacuum. The product was purified by flash chromatography (0% to 50% hexane/AcOEt) to yield 447 mg (28%) of the title compound.

LRMS (m/z): 320 (M+1)$^+$.
$^1$H NMR (400 MHz, DMSO) δ 8.83 (s, 1H), 8.75 (s, 1H), 7.35 (d, 2H), 6.90 (d, 2H), 5.44 (s, 2H), 3.71 (s, 3H).

Preparation 70

3-Phenyl-2-(2,2,2-trifluoro-1-(9-(4-methoxybenzyl)-9H-purin-6-ylamino)ethyl)pyrrolo[1,2-f][1,2,4]triazin-4(3H)-one 2-(1-Amino-2,2,2-trifluoroethyl)-3-phenylpyrrolo[1,2-f][1,2,4]triazin-4(3H)-one (120 mg, 0.39 mmol), 6-bromo-9-(4-methoxybenzyl)-9H-purine (150 mg, 0.47 mmol), BINAP (73 mg, 0.12 mmol), caesium carbonate (190 mg, 0.58 mmol) and palladium (II) acetate (9 mg, 0.04 mmol) were suspended in toluene (2 mL) and stirred at 120° C. under nitrogen atmosphere overnight. The solvent was removed in vacuum and the residue was partitioned between water and dichloromethane. The organic layer was washed with water and brine, dried over magnesium sulphate, filtered and the solvent was evaporated to dryness. The product was purified by flash chromatography (0% to 30% hexane/AcOEt) to give 138 mg (65%) of the title compound as a white solid.

LRMS (m/z): 547 (M+1)$^+$.

Preparation 71

(S)-2-(1-Aminoethyl)-3-benzylpyrrolo[1,2-f][1,2,4]triazin-4(3H)-one a) (S)-tert-Butyl 1-(3-benzyl-4-oxo-3,4-dihydropyrrolo[1,2-f][1,2,4]triazin-2-yl)ethylcarbamate (S)-tert-Butyl 1-(4-oxo-3,4-dihydropyrrolo[1,2-f][1,2,4]triazin-2-yl)ethylcarbamate (150 mg, 0.43 mmol) was suspended in hexane (2 mL) and benzyl bromide (110 µl, 0.92 mmol) and silver (I) carbonate (150 mg, 0.54 mmol) were added. The mixture was heated at 150° C. for 20 minutes using microwave irradiation. The reaction mixture was filtered through Celite® and the solvent was evaporated. The product was isolated from the mixture of by-products by flash chromatography (0% to 40% hexane/AcOEt) to give 20 mg (13%) of the title compound as a white solid.

LRMS (m/z): 369 (M+1)$^+$.

b) (S)-2-(1-Aminoethyl)-3-benzylpyrrolo[1,2-f][1,2,4]triazin-4(3H)-one 20 mg (0.05 mmol) of (S)-tert-butyl 1-(3-benzyl-4-oxo-3,4-dihydropyrrolo[1,2-f][1,2,4]triazin-2-yl)ethylcarbamate were dissolved in 1 mL of dichloromethane and 1 mL of trifluoroacetic acid were added. The reaction mixture was stirred at room temperature for 1.5 hours and the volatiles were removed in vacuum to furnish 21 mg (100% yield) of (S)-2-(1-Aminoethyl)-3-benzylpyrrolo[1,2-f][1,2,4]triazin-4(3H)-one as its trifluoroacetate salt.

LRMS (m/z): 269 (M+1)$^+$.

Preparation 72

1-Amino-3-bromo-N-(3,5-dichlorophenyl)-1H-pyrrole-2-carboxamide a) 3-Bromo-N-(3,5-dichlorophenyl)-1-(phenylsulfonyl)-1H-pyrrole-2-carboxamide Prepared from 2.00 g (5.81 mmol) of methyl 3-bromo-1-(phenylsulfonyl)-1H-pyrrole-2-carboxylate and 2.82 g (17.41 mmol) of 3,5-dichloroaniline following the experimental procedure described in Preparation 44a. The product was purified by flash chromatography (0% to 40% hexane/AcOEt) to give 2.64 g (96% yield) of the title compound as a beige solid.

LRMS (m/z): 474 (M+1)$^+$. BrCl$_2$ isotopic pattern.

b) 3-Bromo-N-(3,5-dichlorophenyl)-1H-pyrrole-2-carboxamide

Prepared from 2.64 g (5.57 mmol) of 3-bromo-N-(3,5-dichlorophenyl)-1-(phenylsulfonyl)-1H-pyrrole-2-carboxamide following the experimental procedure described in Preparation 44b. 1.51 g (81% yield) of the title compound were obtained as a white solid.

LRMS (m/z): 334 (M+1)$^+$. BrCl$_2$ isotopic pattern.

c) 1-Amino-3-bromo-N-(3,5-dichlorophenyl)-1H-pyrrole-2-carboxamide

This compound was prepared starting from 3-Bromo-N-(3,5-dichlorophenyl)-1H-pyrrole-2-carboxamide (1.51 g, 4.52 mmol) and following the experimental procedure described in Preparation 1b to afford 1.58 g (100% yield) of the title compound that was used in the next step without any further purification.

LRMS (m/z): 350 (M+1)$^+$. BrCl$_2$ isotopic pattern.

$^1$H NMR (400 MHz, DMSO) δ 11.23 (s, 1H), 7.78 (d, 2H), 7.32 (t, 1H), 7.02 (d, 1H), 6.54 (s, 2H), 6.21 (d, 1H).

Preparation 73

(S)-tert-Butyl 1-(5-bromo-3-(3,5-dichlorophenyl)-4-oxo-3,4-dihydropyrrolo[1,2-f][1,2,4]triazin-2-yl) ethylcarbamate a) (S)-tert-Butyl 1-(3-bromo-2-(3,5-dichlorophenyl-carbamoyl)-1H-pyrrol-1-ylamino)-1-oxopropan-2-ylcarbamate To a solution of 1.58 g (4.53 mmol) of 1-amino-3-bromo-N-(3,5-dichlorophenyl)-1H-pyrrole-2-carboxamide in 30 mL DMF were added 2.60 mL (14.93 mmol) of DIEA and 0.94 g (4.97 mmol) of (S)-2-(tert-butoxycarbonylamino)propanoic acid. The solution was cooled to 0° C. and 4 mL of T3P® (50% solution in DMF, 6.78 mmol) were added dropwise. The mixture was stirred at room temperature overnight and an additional 2.60 mL (14.93 mmol) of DIEA, 0.94 g (4.97 mmol) of (S)-2-(tert-butoxycarbonylamino)propanoic acid and 4 mL of T3P® (50% solution in DMF, 6.78 mmol) were added. The stirring was kept for 24 hours more and water was added to the reaction mixture. The product was extracted three times with ethyl acetate and the combined organic extracts were washed with water and brine, dried over magnesium sulphate, filtered and the solvents evaporated in vacuum. The product was purified by flash chromatography (0% to 50% hexane/AcOEt) to give 1.11 g (47% yield) of the title compound as a beige solid.

LRMS (m/z): 521 (M+1)$^+$. BrCl$_2$ isotopic pattern.

b) (S)-tert-Butyl 1-(5-bromo-3-(3,5-dichlorophenyl)-4-oxo-3,4-dihydropyrrolo[1,2-f][1,2,4]triazin-2-yl) ethylcarbamate A solution of bromine (130 µl, 2.56 mmol) in dichloromethane (3 mL) was added dropwise to a solution of triphenylphosphine (670 mg, 2.55 mmol) in dichloromethane (20 mL) under nitrogen. The solution was stirred for 10 min, and triethylamine (1.2 mL, 2.56 mmol) and a solution of (S)-tert-butyl 1-(3-bromo-2-(3,5-dichlorophenylcarbamoyl)-1H-pyrrol-1-ylamino)-1-oxopropan-2-ylcarbamate (1.11 g, 2.13 mmol) were added. The reaction mixture was stirred at room temperature for 3 hours. In a separate vessel, an additional 670 mg (2.55 mmol) of triphenylphosphine in 20 mL of dichloromethane was added a solution of 130 µl (2.56 mmol) of bromine in 5 mL of dichloromethane dropwise under nitrogen atmosphere and stirred for 15 minutes. Then this solution was added to the reaction mixture and an additional 1.2 mL of triethylamine was also added. The reaction mixture was stirred overnight at 40° C. and then the volatiles were removed under reduced pressure. The residue was redissolved in 40 mL of a 7M methanolic solution of ammonia and stirred overnight at 100° C. in a sealed vessel. The solvent was then evaporated and the residue was purified by flash chromatography (0% to 30% AcOEt/hexanes) to yield 576 mg (54% yield) of the title compound as a white solid.

LRMS (m/z): 503 (M+1)$^+$. BrCl$_2$ isotopic pattern.

Preparation 74

(S)-2-(1-Aminoethyl)-3-(3,5-dichlorophenyl)-4-oxo-3,4-dihydropyrrolo[1,2-f][1,2,4]triazine-5-carbonitrile a) (S)-tert-Butyl 1-(5-cyano-3-(3,5-dichlorophenyl)-4-oxo-3,4-dihydropyrrolo[1,2-f][1,2,4]triazin-2-yl) ethylcarbamate Prepared according to the experimental procedure described in Preparation 47a from 570 mg (1.14 mmol) of (S)-tert-butyl 1-(5-bromo-3-(3,5-dichlorophenyl)-4-oxo-3,4-dihydropyrrolo[1,2-f][1,2,4]triazin-2-yl)ethylcarbamate. The product was purified by flash chromatography (0% to 30% AcOEt/hexanes) to give 418 mg (82% yield) of the title compound as a white solid.

LRMS (m/z): 509 (M+1)$^+$. Cl$_2$ isotopic pattern.

b) (S)-2-(1-Aminoethyl)-3-(3,5-dichlorophenyl)-4-oxo-3,4-dihydropyrrolo[1,2-f][1,2,4]triazine-5-carbonitrile 418 mg (0.93 mmol) of (S)-tert-butyl 1-(5-cyano-3-(3,5-dichlorophenyl)-4-oxo-3,4-dihydropyrrolo[1,2-f][1,2,4]triazin-2-yl)ethylcarbamate were dissolved in 5 mL of dichloromethane and 431 µl of trifluoroacetic acid were added. The reaction mixture was stirred at room temperature for 5 hours and the volatiles were removed in vacuum. The residue was partitioned between water and dichloromethane and 2M aqueous solution of sodium hydroxide was added until pH=9 was reached. Then the organic layer was washed with brine, dried over magnesium sulphate, filtered and the solvent was evaporated in vacuum. The product was purified by reverse phase chromatography (C-18 silica from Waters®, water/1:1 acetonitrile-methanol as eluents [0.1% v/v formic acid buffered] 0% to 100%) to obtain the title compound in a 58% yield (188 mg) as a white solid.

LRMS (m/z): 349 (M+1)$^+$. Cl$_2$ isotopic pattern.

$^1$H NMR (400 MHz, DMSO) δ 7.91-7.82 (m, 2H), 7.78 (s, 2H), 7.21 (d, 1H), 3.53-3.41 (m, 1H), 1.87 (s, 2H), 1.22 (d, 3H).

Preparation 75

(R)-tert-Butyl 1-(5-bromo-3-(3,5-difluorophenyl)-4-oxo-3,4-dihydropyrrolo[1,2-f][1,2,4]triazin-2-yl)-2-tert-butoxyethylcarbamate a) (S)-tert-Butyl 1-(3-bromo-2-(3,5-difluorophenyl-carbamoyl)-1H-pyrrol-1-ylamino)-3-tert-butoxy-1-oxopropan-2-ylcarbamate Prepared according to the experimental procedure described in Preparation 61a from 1.07 g (3.39 mmol) of 1-amino-3-bromo-N-(3,5-difluorophenyl)-1H-pyrrole-2-carboxamide and 1.65 g (3.73 mmol) of (S)-3-tert-butoxy-2-(tert-butoxycarbonylamino)propanoic acid. After stirring the reaction mixture overnight, an excess of an additional 1.65 g (3.73 mmol) of the acid was added and the reaction stirred for yet 24 hours more. After precipitation and filtration of the product, two purification steps were needed. First by flash chromatography (70% to 100% DCM/hexanes) and a second purification by reverse phase chromatography (C-18 silica from Waters®, water/1:1 acetonitrile-methanol as eluents [0.1% v/v formic acid buffered] 0% to 100%). 494 mg (26% yield) of the title compound were isolated as a white solid.

LRMS (m/z): 559, 561 (M+H)$^+$. Br isotopic pattern.

b) (R)-tert-Butyl 1-(5-bromo-3-(3,5-difluorophenyl)-4-oxo-3,4-dihydropyrrolo[1,2-f][1,2,4]triazin-2-yl)-2-tert-butoxyethylcarbamate Prepared according to the experimental procedure described in Preparation 68b from 494 mg (0.88 mmol) of (S)-tert-butyl 1-(3-bromo-2-(3,5-difluorophenylcarbamoyl)-1H-pyrrol-1-ylamino)-3-tert-butoxy-1-oxopropan-2-ylcarbamate. The reaction was stirred overnight and then after a second addition of reagents for 2 hours more. The final product was purified by flash chromatography (0% to 40% AcOEt/hexanes) to give 313 mg (66% yield) of the title compound as a white solid.

LRMS (m/z): 541, 543 (M+1)$^+$. Br isotopic pattern.

$^1$H NMR (400 MHz, CDCl3) δ 7.32 (d, 1H), 7.05-6.87 (m, 3H), 6.62 (d, 1H), 5.01 (s, 1H), 4.58-4.45 (m, 1H), 3.57-3.38 (m, 2H), 1.41 (s, 9H), 1.10 (s, 9H).

Preparation 76

(R)-2-(1-Amino-2-hydroxyethyl)-3-(3,5-difluorophenyl)-4-oxo-3,4-dihydropyrrolo[1,2-f][1,2,4]triazine-5-carbonitrile a) (R)-tert-Butyl 2-tert-butoxy-1-(5-cyano-3-(3,5-difluorophenyl)-4-oxo-3,4-dihydropyrrolo[1,2-f][1,2,4]triazin-2-yl)ethylcarbamate Prepared from 150 mg (0.28 mmol) of (R)-tert-butyl 1-(5-bromo-3-(3,5-difluorophenyl)-4-oxo-3,4-dihydropyrrolo[1,2-f][1,2,4]triazin-2-yl)-2-tert-butoxyethylcarbamate following the experimental procedure described in Preparation 47a. The product was purified by flash chromatography (0% to 40% AcOEt/hexanes) to give 105 mg (78% yield) of the title compound as a white solid.

LRMS (m/z): 488 (M+1)$^+$.

$^1$H NMR (400 MHz, CDCl$_3$) δ 7.38 (d, 1H), 7.08-6.92 (m, 3H), 6.90 (d, 1H), 5.03 (d, 1H), 4.63-4.52 (m, 1H), 3.57-3.41 (m, 2H), 1.40 (s, 9H), 1.10 (s, 9H).

b) (R)-2-(1-Amino-2-hydroxyethyl)-3-(3,5-difluorophenyl)-4-oxo-3,4-dihydropyrrolo[1,2-f][1,2,4]triazine-5-carbonitrile 105 mg (0.22 mmol) of (R)-tert-butyl 2-tert-butoxy-1-(5-cyano-3-(3,5-difluorophenyl)-4-oxo-3,4-dihydropyrrolo[1,2-f][1,2,4]triazin-2-yl)ethylcarbamate were stirred in 5.5 mL of a 4M solution of hydrogen chloride in dioxane overnight at room temperature and then 2 hours at 50° C. The volatiles were evaporated under reduced pressure and the residue was partitioned between water and dichloromethane and 2M aqueous solution of sodium hydroxide was added until pH=8 was reached. Then the organic layer was washed with brine, dried over magnesium sulphate, filtered and the solvent was evaporated. 71 mg (100% yield) of the title product were obtained.

LRMS (m/z): 332 (M+1)$^+$.

Preparation 77

(R)-tert-Butyl 2-tert-butoxy-1-(3-(3,5-difluorophenyl)-5-iodo-4-oxo-3,4-dihydropyrrolo[1,2-f][1,2,4]triazin-2-yl)ethylcarbamate A solution of (R)-tert-butyl 1-(5-bromo-3-(3,5-difluorophenyl)-4-oxo-3,4-dihydropyrrolo[1,2-f][1,2,4]triazin-2-yl)-2-tert-butoxyethylcarbamate (150 mg, 0.28 mmol), trans-1,2-bis(methylamino)cyclohexane (24 mg, 0.17 mmol), sodium iodide (165, 1.11 mmol) and copper (I) iodide (16 mg, 0.08 mmol) in 1,4-dioxane (2 mL) was stirred under argon atmosphere at 120° C. overnight. The crude was allowed to reach room temperature and filtered thought Celite® washing with ethyl acetate. The organic solution was washed with water (×3) and brine, dried over magnesium sulphate and concentrated to give 148 mg (91% yield) of the title compound, which was used without further purification.

LRMS (m/z): 589 (M+1)$^+$.

Preparation 78

(R)-2-(1-Amino-2-hydroxyethyl)-3-(3,5-difluorophenyl)-5-(trifluoromethyl)pyrrolo[1,2-f][1,2,4]triazin-4(3H)-one a) (R)-tert-Butyl 2-tert-butoxy-1-(3-(3,5-difluorophenyl)-4-oxo-5-(trifluoromethyl)-3,4-dihydropyrrolo[1,2-f][1,2,4]triazin-2-yl)ethylcarbamate Prepared following the experimental procedure described in Preparation 26b from 148 mg (0.25 mmol) of (R)-tert-butyl 2-tert-butoxy-1-(3-(3,5-difluorophenyl)-5-iodo-4-oxo-3,4-dihydropyrrolo[1,2-f][1,2,4]triazin-2-yl)ethylcarbamate. 133 mg (100% yield) of the title compound were obtained.

LRMS (m/z): 531 (M+1)$^+$.

b) (R)-2-(1-Amino-2-hydroxyethyl)-3-(3,5-difluorophenyl)-5-(trifluoromethyl)-pyrrolo[1,2-f][1,2,4]triazin-4(3H)-one Prepared from (R)-tert-butyl 2-tert-butoxy-1-(3-(3,5-difluorophenyl)-4-oxo-5-(trifluoromethyl)-3,4-dihydropyrrolo[1,2-f][1,2,4]triazin-2-yl)ethylcarbamate (134 mg, 0.25 mmol) following the method described in Preparation 76b. 61 mg (65% yield) of the title compound were obtained and used directly in the next step.

LRMS (m/z): 375 (M+1)$^+$.

Preparation 79

(S)-tert-Butyl 1-(7-bromo-4-oxo-3-phenyl-3,4-dihydropyrrolo[1,2-f][1,2,4]triazin-2-yl)ethylcarbamate To a solution of (S)-tert-butyl 1-(4-oxo-3-phenyl-3,4-dihydropyrrolo[1,2-f][1,2,4]triazin-2-yl)ethylcarbamate (500 mg, 1.41 mmol) in a mixture of methanol (5 mL) and tetrahydrofurane (5 mL), N-bromosuccinimide (252 mg, 1.42 mmol) were added. The reaction mixture was stirred at room temperature for 40 hours and then an excess of N-br omosuccinimide (252 mg, 1.42 mmol) was added. After 2 hours at room temperature the solvents were removed in vacuum and the residue was partitioned between water and dichloromethane. The organic layer was washed with brine, dried over magnesium sulphate, filtered and the solvent was evaporated. Purification by flash chromatography (0% to 15% AcOEt/hexanes) yielded 233 mg (38% yield) of the title compound as a white solid.

LRMS (m/z): 433, 435 (M+1)$^+$. Br isotopic pattern.

Preparation 80

(S)-tert-Butyl 1-(7-iodo-4-oxo-3-phenyl-3,4-dihydropyrrolo[1,2-f][1,2,4]triazin-2-yl)ethylcarbamate Prepared from 233 mg (0.54 mmol) of (S)-tert-butyl 1-(7-bromo-4-oxo-3-phenyl-3,4-dihydropyrrolo[1,2-f][1,2,4]triazin-2-yl)ethylcarbamate following the experimental procedure described in Preparation 77. The product was purified by reverse phase chromatography (C-18 silica from Waters®, water/1:1 acetonitrile-methanol as eluents [0.1% v/v formic acid buffered] 0% to 100%) to furnish 130 mg (50% yield) of the title compound.

LRMS (m/z): 481 (M+1)+.

1H NMR (400 MHz, CDCl3) δ 7.61-7.47 (m, 4H), 7.39 (d, 1H), 7.28 (t, 1H), 7.12 (d, 1H), 6.75 (d, 1H), 5.19 (d, 1H), 4.58-4.45 (m, 1H), 1.43 (s, 9H), 1.29 (d, 3H).

Preparation 81

(S)-2-(1-Aminoethyl)-3-phenyl-7-(trifluoromethyl)pyrrolo[1,2-f][1,2,4]triazin-4(3H)-one a) (S)-tert-Butyl 1-(4-oxo-3-phenyl-7-(trifluoromethyl)-3,4-dihydropyrrolo[1,2-f][1,2,4]triazin-2-yl)ethylcarbamate Prepared following the experimental procedure described in Preparation 26b from 22 mg (0.05 mmol) of (S)-tert-butyl 1-(7-iodo-4-oxo-3-phenyl-3,4-dihydropyrrolo[1,2-f][1,2,4]triazin-2-yl)ethylcarbamate. After purification by flash chromatography (0% to 50% AcOEt/hexanes), 17 mg (87% yield) of the title compound were obtained.

LRMS (m/z): 423 (M+1)+.

b) (S)-2-(1-Aminoethyl)-3-phenyl-7-(trifluoromethyl)pyrrolo[1,2-f][1,2,4]triazin-4(3H)-one (S)-tert-Butyl 1-(4-oxo-3-phenyl-7-(trifluoromethyl)-3,4-dihydropyrrolo[1,2-f][1,2,4]triazin-2-yl)ethylcarbamate (17 mg, 0.04 mmol) was stirred in 5 mL of a 4M solution of hydrogen chloride in dioxane at room temperature for 4 hours. The volatiles were evaporated under reduced pressure and 14 mg (100% yield) of the title compound, isolated as the hydrochloric salt form, were obtained and used directly in the next step.

LRMS (m/z): 323 (M+1)+.

Preparation 82

(S)-2-(1-Aminoethyl)-4-oxo-3-phenyl-3,4-dihydropyrrolo[1,2-f][1,2,4]triazine-7-carbonitrile a) (S)-tert-Butyl 1-(7-cyano-4-oxo-3-phenyl-3,4-di hydropyrrolo[1,2-f][1,2,4]triazin-2-yl)ethylcarbamate A mixture of (S)-tert-butyl 1-(7-iodo-4-oxo-3-phenyl-3,4-dihydropyrrolo[1,2-f][1,2,4]triazin-2-yl)ethylcarbamate (130 mg, 0.27 mmol), dicyanozinc (64 mg, 0.55 mmol) and tetrakis(triphenylphosphine)palladium (0) (31 mg, 0.03 mmol) in DMF, was heated at 120° C. in a sealed tub with stirring. Additional amounts of dicyanozinc (64 mg, 0.55 mmol) and tetrakis(triphenylphosphine)palladium (0) (31 mg, 0.03 mmol) were added after 16 hours and 40 hours. After 64 hours of reaction, the mixture was allowed to cool to room temperature and ethyl acetate was added. The resulting suspension was filtered thought Celite®, the two phases were separated and the aqueous layer extracted with more ethyl acetate. The combined organic layer were dried over magnesium sulphate and concentrated in vacuum. The product was purified by flash chromatography (0% to 50% AcOEt/hexanes) to obtain 37 mg (36% yield) of the title compound.

LRMS (m/z): 380 (M+1)+.

b) (S)-2-(1-Aminoethyl)-4-oxo-3-phenyl-3,4-dihydropyrrolo[1,2-f][1,2,4]triazine-7-carbonitrile (S)-tert-Butyl 1-(7-cyano-4-oxo-3-phenyl-3,4-dihydropyrrolo[1,2-f][1,2,4]triazin-2-yl)ethylcarbamate (37 mg, 0.20 mmol) was stirred in 5 mL of a 4M solution of hydrogen chloride in dioxane at room temperature for 4 hours. The volatiles were evaporated under reduced pressure and the residue was partitioned between dichloromethane and diluted aqueous solution of potassium carbonate. The organic layer was washed with brine, dried over magnesium sulphate, filtered and the solvent was removed in vacuum to give 53 mg (100% yield) of the title compound which was used directly in the next step.

LRMS (m/z): 280 (M+1)+.

Preparation 83

(S)-2-(1-Aminoethyl)-4-oxo-3-(pyridin-2-ylmethyl)-3,4-di hydropyrrolo[1,2-f][1,2,4]triazine-5-carbonitrile a) (S)-tert-Butyl 1-(3-bromo-2-(pyridin-2-ylmethylcarbamoyl)-1H-pyrrol-1-ylamino)-1-oxopropan-2-ylcarbamate Same procedure as described in preparation 133a was used from (S)-methyl 3-bromo-1-(2-(tert-butoxycarbonylamino)propanamido)-1H-pyrrole-2-carboxylate (374 mg, 0.96 mmols) and pyridine-2-ylmethanamine (0.30 ml, 2.87 mmols). After reverse phase chromatography the title compound was obtained (74 mg, 17%).

LRMS (m/z): 467 (M+1)+ b) (S)-tert-Butyl 1-(5-bromo-4-oxo-3-(pyridin-2-ylmethyl)-3,4-dihydropyrrolo[1,2-f][1,2,4]triazin-2-yl)ethylcarbamate Same procedure as described in preparation 133b was used from (S)-tert-butyl 1-(3-bromo-2-(pyridin-2-ylmethylcarbamoyl)-1H-pyrrol-1-ylamino)-1-oxopropan-2-ylcarbamate (271 mg, 0.41 mmols). After reverse phase chromatography the title compound was obtained (50 mg, 27%)

LRMS (m/z): 449 (M+1)+ c) (S)-tert-Butyl 1-(5-iodo-4-oxo-3-(pyridin-2-ylmethyl)-3,4-dihydropyrrolo[1,2-f][1,2,4]triazin-2-yl)ethylcarbamate Sodium iodide (67 mg, 0.45 mmols), Copper (I) iodide (11 mg, 0.06 mmols) and (1S,2S)—N1,N2-dimethylcyclohexane-1,2-diamine (10 mg, 0.07 mmols) were added to a solution of (S)-tert-butyl 1-(5-bromo-4-oxo-3-(pyridin-2-ylmethyl)-3,4-dihydropyrrolo[1,2-f][1,2,4]triazin-2-yl)ethylcarbamate (50 mg, 0.11 mmols) in dioxane (5.4 ml). It was stirred at 120° C. in a sealed tube for 5 days. It was concentrated in vacuum. Ethyl acetate was added and it was washed with water and brine. The title compound was obtained (59 mg, 88%).

LRMS (m/z): 496 (M+1)+ d) (S)-tert-Butyl 1-(5-cyano-4-oxo-3-(pyridin-2-ylmethyl)-3,4-dihydropyrrolo[1,2-f][1,2,4]triazin-2-yl)ethylcarbamate Copper (I) cyanide (98 mg, 1.09 mmols) was added to a solution of (S)-tert-butyl 1-(5-iodo-4-oxo-3-(pyridin-2-ylmethyl)-3,4-dihydropyrrolo[1,2-f][1,2,4]triazin-2-yl)ethylcarbamate (59 mg, 0.01 mmols) in pyridine (5 ml). It was stirred at 115° C. in a sealed tube overnight. It was concentrated in vacuum. Ethyl acetate and water were added and it was filtered through celite. The organic phase was washed, dried, filtered and concentrated in vacuum. The title compound was obtained (59 mg, 87% purity, 100%).

LRMS (m/z): 395 (M+1)+ e) (S)-2-(1-Aminoethyl)-4-oxo-3-(pyridin-2-ylmethyl)-3,4-dihydropyrrolo[1,2-f][1,2,4]triazine-5-carbonitrile Same procedure as described in preparation 133c was used from (S)-tert-butyl 1-(5-cyano-4-oxo-3-(pyridin-2-ylmethyl)-3,4-dihydropyrrolo[1,2-f][1,2,4]triazin-2-yl)ethylcarbamate (49 mg, 0.11 mmols). The title compound was obtained (39 mg, 45% purity, 4%) pure enough to be used in the next synthetic step without further purification.

LRMS (m/z): 295 (M+1)+

Preparation 84

2-((S)-1-Aminoethyl)-4-oxo-3-(tetrahydro-2H-pyran-3-yl)-3,4-dihydropyrrolo[1,2-f][1,2,4]triazine-5-carbonitrile a) tert-Butyl (2S)-1-(3-bromo-2-(tetrahydro-2H-pyran-3-ylcarbamoyl)-1H-pyrrol-1-ylamino)-1-oxopropan-2-ylcarbamate Same procedure as described in preparation 137a was used from (S)-methyl 3-bromo-1-(2-(tert-butoxycarbonylamino)propanamido)-1H-pyrrole-2-carboxylate (4.00 g, 10.25 mmols) and tetrahydro-2H-pyran-3-amine.HCl (2.12 g, 15.41 mmols). The title compound was obtained (2.24 g, 48%).

LRMS (m/z): 460 (M+1)+ b) tert-Butyl (1S)-1-(5-bromo-4-oxo-3-(tetrahydro-2H-pyran-3-yl)-3,4-dihydropyrrolo[1,2-f][1,2,4]triazin-2-yl)ethylcarbamate Same procedure as described in preparation 137b was used from tert-butyl (2S)-1-(3-bromo-2-(tetrahydro-2H-pyran-3-ylcarbamoyl)-1H-pyrrol-1-ylamino)-1-oxopropan-2-ylcarbamate (2.14 g, 4.66 mmols). The title compound was obtained (3.91 g, 50% purity, 95%) pure enough to be used in the next reaction step without further purification.

LRMS (m/z): 442 (M+1)+ c) tert-Butyl (1S)-1-(5-iodo-4-oxo-3-(tetrahydro-2H-pyran-3-yl)-3,4-dihydropyrrolo[1,2-f][1,2,4]triazin-2-yl)ethylcarbamate Same procedure as described in Preparation 83c was used from tert-butyl (1S)-1-(5-bromo-4-oxo-3-(tetrahydro-2H-pyran-3-yl)-3,4-dihydropyrrolo[1,2-f][1,2,4]triazin-2-yl)ethylcarbamate (3.91 g, 4.43 mmols). After reverse phase chromatography the title compound was obtained (0.60 g, 28%)

LRMS (m/z): 489 (M+1)+ d) tert-Butyl (1S)-1-(5-cyano-4-oxo-3-(tetrahydro-2H-pyran-3-yl)-3,4-dihydropyrrolo[1,2-f][1,2,4]triazin-2-yl)ethylcarbamate Same procedure as described in Preparation 83d was used from tert-butyl (1S)-1-(5-iodo-4-oxo-3-(tetrahydro-2H-pyran-3-yl)-3,4-dihydropyrrolo[1,2-f][1,2,4]triazin-2-yl)ethylcarbamate (280 mg, 0.57 mmols). The title compound was obtained (0.33 g, 60% purity, 88%) pure enough to be used in the next synthetic step without further purification.

LRMS (m/z): 388 (M+1)+ e) 2-((S)-1-Aminoethyl)-4-oxo-3-(tetrahydro-2H-pyran-3-yl)-3,4-dihydropyrrolo[1,2-f][1,2,4]triazine-5-carbonitrile Same procedure as described in preparation 133c was used from tert-butyl (1S)-1-(5-cyano-4-oxo-3-(tetrahydro-2H-pyran-3-yl)-3,4-dihydropyrrolo[1,2-t][1,2,4]triazin-2-yl)ethylcarbamate (329 mg, 0.50 mmols). The title compound was obtained (0.12 g, 57% purity, 47%) pure enough to be used in the next synthetic step without further purification.

LRMS (m/z): 288 (M+1)+

Preparation 85

2-((S)-1-Aminoethyl)-3-(tetrahydro-2H-pyran-3-yl)-5-(trifluoromethyl)pyrrolo[1,2-f][1,2,4]triazin-4(3H)-one a) tert-Butyl (1S)-1-(4-oxo-3-(tetrahydro-2H-pyran-3-yl)-5-(trifluoromethyl)-3,4-dihydropyrrolo[1,2-f][1,2,4]triazin-2-yl)ethylcarbamate Copper (I) iodide (131 mg, 0.69 mmols), Hexamethylphosphoramide (HMPA) (0.5 ml, 2.87 mmols) and methyl 2,2-difluoro-2-(fluorosulfonyl)acetate (0.37 ml, 2.87 mmols) were added to a solution of tert-butyl (1S)-1-(5-iodo-4-oxo-3-(tetrahydro-2H-pyran-3-yl)-3,4-dihydropyrrolo[1,2-f][1,2,4]triazin-2-yl)ethylcarbamate (280 mg, 0.57m mols) in dimethylformamide (5.5 ml). It was stirred at 80° C. overnight in a sealed tube. It was concentrated in vacuum, ethyl acetate was added and it was filtered through celite. It was washed with water and brine. The title compound was obtained (303 mg, 51% purity, 63%) pure enough to be used in the next synthetic step without further purification.

LRMS (m/z): 431 (M+1)+ b) 2-((S)-1-Aminoethyl)-3-(tetrahydro-2H-pyran-3-yl)-5-(trifluoromethyl)pyrrolo[1,2-f][1,2,4]triazin-4(3H)-one Same procedure as described in preparation 133c was used from tert-butyl (1S)-1-(4-oxo-3-(tetrahydro-2H-pyran-3-yl)-5-(trifluoromethyl)-3,4-dihydropyrrolo[1,2-f][1,2,4]triazin-2-yl)ethylcarbamate (303 mg, 0.36 mmols). The title compound was obtained (0.16 g, 41% purity, 55%) pure enough to be used in the next synthetic step without further purification.

LRMS (m/z): 331 (M+1)+

Preparation 86

2-(1-Aminoethyl)-3-((5-methylisoxazol-3-yl)methyl)pyrrolo[1,2-f][1,2,4]triazin-4(3H)-one a) (S)-tert-Butyl 1-(2-((5-methylisoxazol-3-yl)methylcarbamoyl)-1H-pyrrol-1-ylamino)-1-oxopropan-2-ylcarbamate The title compound was prepared from (S)-methyl 1-(2-(tert-butoxycarbonylamino)propanamido)-1H-pyrrole-2-carboxylate (750 mg, 2.41 mmol) and (5-methylisoxazol-3-yl)methanamine bromhydrate (698 mg, 3.62 mmol)

following the experimental procedure described in Preparation 27a. 613 mg (63% yield) of the desired compound were obtained.
LRMS (m/z): 392 (M+1)+.

b) (S)-tert-Butyl 1-(34(5-methylisoxazol-3-yl)methyl)-4-oxo-3,4-dihydropyrrolo[1,2-f][1,2,4]triazin-2-yl)ethylcarbamate The title compound was prepared from (S)-tert-butyl 1-(2-((5-methylisoxazol-3-yl)methylcarbamoyl)-1H-pyrrol-1-ylamino)-1-oxopropan-2-ylcarbamate (613 mg, 1.57 mmol) following the experimental procedure described in Preparation 54b. 1.07 g (62% yield) of the desired compound were obtained.
LRMS (m/z): 374 (M+1)+.

c) 2-(1-Aminoethyl)-3-((5-methylisoxazol-3-yl)methyl)pyrrolo[1,2-f][1,2,4]triazin-4(3H)-one The title compound was prepared from (S)-tert-butyl 1-(34(5-methylisoxazol-3-yl)methyl)-4-oxo-3,4-dihydropyrrolo[1,2-f][1,2,4]triazin-2-yl)ethylcarbamate (1.07, 0.97 mmol) following the experimental procedure described in Preparation 46c. 300 mg (93% yield) of the desired compound were obtained.
LRMS (m/z): 274 (M+1)+.

Preparation 87

2-(1-Aminoethyl)-3-(1-methyl-1H-pyrazol-3-yl)pyrrolo[1,2-f][1,2,4]triazin-4(3H)-one a) tert-Butyl 1-(2-(1-methyl-1H-pyrazol-3-ylcarbamoyl)-1H-pyrrol-1-ylamino)-1-oxopropan-2-ylcarbamate The title compound was prepared from (S)-methyl 1-(2-(tert-butoxycarbonylamino)propanamido)-1H-pyrrole-2-carboxylate (900 mg, 2.89 mmol) and 1-methyl-1H-pyrazol-3-amine (421 mg, 4.33 mmol) following the experimental procedure described in Preparation 27a. 680 mg (36% yield) of the desired compound were obtained.
LRMS (m/z): 377 (M+1)+.

b) (S)-tert-Butyl 1-(3-(1-methyl-1H-pyrazol-3-yl)-4-oxo-3,4-dihydropyrrolo[1,2-f][1,2,4]triazin-2-yl)ethylcarbamate The title compound was prepared from (S)-tert-butyl 1-(2-(1-methyl-1H-pyrazol-3-ylcarbamoyl)-1H-pyrrol-1-ylamino)-1-oxopropan-2-ylcarbamate (680 mg, 1.05 mmol) following the experimental procedure described in Preparation 54b. 750 mg (50% yield) of the desired compound were obtained.
LRMS (m/z): 359 (M+1)+.

c) 2-(1-Aminoethyl)-3-(1-methyl-1H-pyrazol-3-yl)pyrrolo[1,2-f][1,2,4]triazin-4(3H)-one The title compound was prepared from (S)-tert-butyl 1-(3-(1-methyl-1H-pyrazol-3-yl)-4-oxo-3,4-dihydropyrrolo[1,2-f][1,2,4]triazin-2-yl)ethylcarbamate (750 mg, 0,52 mmol) following the experimental procedure described in Preparation 46c. 100 mg (72% yield) of the desired compound were obtained.
LRMS (m/z): 259 (M+1)+.

Preparation 88

(S)-2-(1-Aminoethyl)-7-methyl-3-phenylpyrrolo[1,2-f][1,2,4]triazin-4(3H)-one a) 5-Methyl-N-phenyl-1H-pyrrole-2-carboxamide The title compound was prepared from ethyl 5-methyl-1H-pyrrole-2-carboxylate (1 g, 6.53 mmol, purchased from Matrix) following the experimental procedure described in Preparation 44a. Trituration with diisopropyl ether gave the title compound as a beige solid (0.65 g, 98% yield).
LRMS (m/z): 201 (M+1)+.

b) 1-Amino-5-methyl-N-phenyl-1H-pyrrole-2-carboxamide

This compound was prepared starting from 5-methyl-N-phenyl-1H-pyrrole-2-carboxamide (0.64 g, 3.20 mmol) and following the experimental procedure described in Preparation 1b to afford 0.68 g (50% yield) of the title compound that was used in the next step without any further purification.
LRMS (m/z): 216 (M+1)+.

c) (S)-tert-Butyl 1-(2-methyl-5-(phenylcarbamoyl)-1H-pyrrol-1-ylamino)-1-oxopropan-2-ylcarbamate The title compound was prepared following the experimental procedure described in preparation 20a from 380 mg (1.77 mmol) of 1-amino-5-methyl-N-phenyl-1H-pyrrole-2-carboxamide and 334 mg (1.77 mmol) of (S)-2-(tert-butoxycarbonylamino)propanoic acid (purchased from Aldrich). The crude product was purified by flash chromatography in hexane/ethyl acetate to afford 500 mg (59% yield) of the title compound.
LRMS (m/z): 387 (M+1)+.

d) (S)-tert-Butyl 1-(7-methyl-4-oxo-3-phenyl-3,4-dihydropyrrolo[1,2-f][1,2,4]triazin-2-yl)ethylcarbamate This compound was prepared starting from (S)-tert-butyl 1-(2-methyl-5-(phenylcarbamoyl)-1H-pyrrol-1-ylamino)-1-oxopropan-2-ylcarbamate (500 mg, 1.04 mmol) and following the experimental procedure described in Preparation 42b. The residue was purified by flash chromatography in hexane/ethyl acetate to afford 95 mg (24% yield) of the title compound were obtained.
LRMS (m/z): 369 (M+1)+.

e) (S)-2-(1-Aminoethyl)-7-methyl-3-phenylpyrrolo[1,2-f][1,2,4]triazin-4(3H)-one

The title compound was prepared from (S)-tert-butyl 1-(7-methyl-4-oxo-3-phenyl-3,4-dihydropyrrolo[1,2-f][1,2,4]triazin-2-yl)ethylcarbamate (95 mg, 0.26 mmol) following the experimental procedure described in Preparation 46c. 70 mg (97% yield) of the desired compound were obtained.
LRMS (m/z): 269 (M+1)+.

Preparation 89

7-Chloropyrazolo[1,5-a]pyrimidine

Pyrazolo[1,5-a]pyrimidin-7(4H)-one (0.50 g, 3.70 mmols), phosphorus oxychloride (0.88 ml, 9.62 mmols) and diisopropylethylamine (DIEA, 0.13 ml, 0.74 mmols) were mixed and stirred at 90° C. overnight. It was poured onto water/ice, extracted with dichloromethane and washed with brine. It was dried, filtered and concentrated in vacuum. It was purified by chromatography (Silica gel, Hexane/Ethyl acetate 9:1) to afford the expected compound (83 mg, 71%).

LRMS (m/z): 154 (M+1)$^+$.

$^1$H NMR (400 MHz, DMSO-d$_6$) d ppm 6.93 (d, 1H) 7.43 (d, 1H) 8.37 (d, 1H) 8.52 (d, 1H)

Preparation 90

(S)-2-(1-(methylamino)ethyl)-3-phenylpyrrolo[1,2-f][1,2,4]triazin-4(3H)-one a) (S)-tert-butyl 1-(4-oxo-3-phenyl-3,4-dihydropyrrolo[1,2-f][1,2,4]triazin-2-yl)ethyl carbamate To a solution of (S)-2-(1-aminoethyl)-3-phenylpyrrolo[1,2-f][1,2,4]triazin-4(3H)-one (300 mg, 0.87 mmol) and triethylamine (302 μl, 2.17 mmol) in DCM (15 ml) was added di-tert-butyl dicarbonate (227 mg, 1.04 mmol) and the reaction mixture stirred overnight at room temperature. Ethyl acetate was added and the organic phase washed with water, then dried, filtered and concentrated in vacuum to yield the title compound as an oil (99% yield).

LRMS (m/z): 355 (M+1)$^+$.

b) (S)-tert-Butyl methyl(1-(4-oxo-3-phenyl-3,4-dihydropyrrolo[1,2-f][1,2,4]triazin-2-yl)ethyl)carbamate To a solution of (S)-tert-butyl 1-(4-oxo-3-phenyl-3,4-dihydropyrrolo[1,2-f][1,2,4]triazin-2-yl)ethylcarbamate (415 mg, 1.17 mmol) in tetrahydrofurane (20 mL), sodium tedbutoxide (169 mg, 1.75 mmol) was added. The reaction mixture was stirred at room temperature for 1 hour and then methyl iodide (109 μl, 1.75 mmol) was added. After overnight stirring at room temperature ethyl acetate was added and the organic layer washed with water and brine. The organic layer was then dried over magnesium sulphate, filtered and concentrated. Purification by reverse phase flash chromatography (0% to 50% ACN/water) yielded 225 mg (52% yield) of the title compound as a white solid.

LRMS (m/z): 369 (M+1)$^+$.

c) (S)-2-(1-(Methylamino)ethyl)-3-phenylpyrrolo[1,2-f][1,2,4]triazin-4(3H)-one

The title compound was prepared from (S)-tert-butyl methyl(1-(4-oxo-3-phenyl-3,4-dihydropyrrolo[1,2-f][1,2,4]triazin-2-yl)ethyl)carbamate (225 mg, 0,61 mmol) following the experimental procedure described in Preparation 46c. 170 mg (87% yield) of the desired compound were obtained.

LRMS (m/z): 305 (M+1)$^+$.

Preparation 91

1-Amino-3-bromo-N-(3,5-difluorophenyl)-1H-pyrrole-2-carboxamide a) 3-Bromo-N-(3,5-difluorophenyl)-1-(phenylsulfonyl)-1H-pyrrole-2-carboxamide The title compound was prepared from methyl 3-bromo-1-(phenylsulfonyl)-1H-pyrrole-2-carboxylate[2] (18 g, 52.2 mmol) following the experimental procedure described in Preparation 44a. 23 g (100% yield) of the desired compound were obtained.

LRMS (m/z): 441, 443 (M+1)$^+$.

b) 3-Bromo-N-(3,5-difluorophenyl)-1H-pyrrole-2-carboxamide

The title compound was prepared from 3-bromo-N-(3,5-difluorophenyl)-1-(phenylsulfonyl)-1H-pyrrole-2-carboxamide (23 g, 52.2 mmol) following the experimental procedure described in Preparation 44b. 14.6 g (93% yield) of the desired compound were obtained.

LRMS (m/z): 301, 303 (M+1)$^+$.

c) 1-Amino-3-bromo-N-(3,5-difluorophenyl)-1H-pyrrole-2-carboxamide

The title compound was prepared from 3-bromo-N-(3,5-difluorophenyl)-1H-pyrrole-2-carboxamide (14.6 g, 48.6 mmol) following the experimental procedure described in Preparation 44c. 8.9 g (58% yield) of the desired compound were obtained.

LRMS (m/z): 316, 318 (M+1)$^+$.

Preparation 92

(S)-tert-Butyl 1-(5-bromo-3-(3,5-difluorophenyl)-4-oxo-3,4-dihydropyrrolo[1,2-f][1,2,4]triazin-2-yl)ethylcarbamate a) (S)-tert-Butyl 1-(3-bromo-2-(3,5-difluorophenylcarbamoyl)-1H-pyrrol-1-ylamino)-1-oxopropan-2-ylcarbamate The title compound was prepared from 1-amino-3-bromo-N-(3,5-difluorophenyl)-1H-pyrrole-2-carboxamide (7.87 g, 24.9 mmol) and (S)-2-(tert-butoxycarbonylamino)propanoic acid (purchased from Aldrich, 5.65 g, 29.9 mmol) following the experimental procedure described in Preparation 45a. 6.6 g (51% yield) of the desired compound were obtained.

LRMS (m/z): 487, 489 (M+1)$^+$.

b) (S)-tert-Butyl 1-(5-bromo-3-(3,5-difluorophenyl)-4-oxo-3,4-dihydropyrrolo[1,2-f][1,2,4]triazin-2-yl)ethylcarbamate The title compound was prepared from (S)-tert-butyl 1-(3-bromo-2-(3,5-difluorophenylcarbamoyl)-1H-pyrrol-1-ylamino)-1-oxopropan-2-ylcarbamate (6.12 g, 12.6 mmol) following the experimental procedure described in Preparation 45b. 2.6 g (44% yield) of the desired compound were obtained.

LRMS (m/z): 469, 471 (M+1)$^+$.

Preparation 93

(S)-2-(1-Aminoethyl)-3-(3,5-difluorophenyl)-5-(trifluoromethyl)pyrrolo[1,2-f][1,2,4]triazin-4(3H)-one a) (S)-tert-Butyl 1-(3-(3,5-difluorophenyl)-5-iodo-4-oxo-3,4-dihydropyrrolo[1,2-f][1,2,4]triazin-2-yl)ethylcarbamate The title compound was prepared from (S)-tert-butyl 1-(5-bromo-3-(3,5-difluorophenyl)-4-oxo-3,4-dihydropyrrolo[1,2-f][1,2,4]triazin-2-yl)ethylcarbamate (500 mg, 1.07 mmol)

following the experimental procedure described in Preparation 46a. 578 mg (77.5% yield) of the desired compound were obtained.

LRMS (m/z): 517 (M+1)+.

b) (S)-tert-Butyl 1-(3-(3,5-difluorophenyl)-4-oxo-5-(trifluoromethyl)-3,4-dihydropyrrolo[1,2-f][1,2,4]triazin-2-yl)ethylcarbamate The title compound was prepared from (S)-tert-butyl 1-(3-(3,5-difluorophenyl)-5-iodo-4-oxo-3,4-dihydropyrrolo[1,2-f][1,2,4]triazin-2-yl)ethylcarbamate (578 mg, 0.83 mmol) following the experimental procedure described in Preparation 46b. 342 mg (87.5% yield) of the desired compound were obtained.

LRMS (m/z): 459 (M+1)+.

c) (S)-2-(1-Aminoethyl)-3-(3,5-difluorophenyl)-5-(trifluoromethyl)pyrrolo[1,2-f][1,2,4]triazin-4(3H)-one The title compound was prepared from (S)-tert-butyl 1-(3-(3,5-difluorophenyl)-4-oxo-5-(trifluoromethyl)-3,4-dihydropyrrolo[1,2-f][1,2,4]triazin-2-yl)ethylcarbamate (342 mg, 0.75 mmol) following the experimental procedure described in Preparation 46c. 132 mg (47% yield) of the desired compound were obtained.

LRMS (m/z): 359 (M+1)+.

Preparation 94

(S)-2-(1-Aminoethyl)-3-(3,5-difluorophenyl)-4-oxo-3,4-di hydropyrrolo[1,2-f][1,2,4]triazine-5-carbonitrile a) (S)-tert-Butyl 1-(5-cyano-3-(3,5-difluorophenyl)-4-oxo-3,4-dihydropyrrolo[1,2-f][1,2,4]triazin-2-yl)ethylcarbamate The title compound was prepared from (S)-tert-butyl 1-(5-bromo-3-(3,5-difluorophenyl)-4-oxo-3,4-dihydropyrrolo[1,2-f][1,2,4]triazin-2-yl)ethylcarbamate (500 mg, 1.07 mmol) following the experimental procedure described in Preparation 47a. 326 mg (73.7% yield) of the desired compound were obtained.

LRMS (m/z): 416 (M+1)+.

b) (S)-2-(1-Aminoethyl)-3-(3,5-difluorophenyl)-4-oxo-3,4-dihydropyrrolo[1,2-f][1,2,4]triazine-5-carbonitrile The title compound was prepared from (S)-tert-butyl 1-(5-cyano-3-(3,5-difluorophenyl)-4-oxo-3,4-dihydropyrrolo[1,2-f][1,2,4]triazin-2-yl)ethylcarbamate (326 mg, 0.78 mmol) following the experimental procedure described in Preparation 47b. 250 mg (90% yield) of the desired compound were obtained.

LRMS (m/z): 352 (M+1)+.

Preparation 95

(S)-2-(1-Aminopropyl)-3-(3,5-difluorophenyl)-4-oxo-3,4-dihydropyrrolo[1,2-f][1,2,4]triazine-5-carbonitrile a) (S)-tert-Butyl 1-(3-bromo-2-(3,5-difluorophenylcarbamoyl)-1H-pyrrol-1-ylamino)-1-oxobutan-2-ylcarbamate The title compound was prepared from 1-amino-3-bromo-N-(3,5-difluorophenyl)-1H-pyrrole-2-carboxamide (1 g, 3.16 mmol) and (S)-2-(tert-butoxycarbonylamino)butanoic acid following the experimental procedure described in Preparation 45a. 0.26 g (14% yield) of the desired compound were obtained.

LRMS (m/z): 501, 503 (M+1)+.

b) (S)-tert-Butyl 1-(5-bromo-3-(3,5-difluorophenyl)-4-oxo-3,4-dihydropyrrolo[1,2-f][1,2,4]triazin-2-yl)propylcarbamate The title compound was prepared from (S)-tert-butyl 1-(3-bromo-2-(3,5-difluorophenylcarbamoyl)-1H-pyrrol-1-ylamino)-1-oxobutan-2-ylcarbamate (263 mg, 0.52 mmol) following the experimental procedure described in Preparation 45b. 113 mg (44% yield) of the desired compound were obtained.

LRMS (m/z): 483, 485 (M+1)+.

c) (S)-tert-Butyl 1-(5-cyano-3-(3,5-difluorophenyl)-4-oxo-3,4-dihydropyrrolo[1,2-f][1,2,4]triazin-2-yl)propylcarbamate The title compound was prepared from (S)-tert-butyl 1-(5-bromo-3-(3,5-difluorophenyl)-4-oxo-3,4-dihydropyrrolo[1,2-f][1,2,4]triazin-2-yl)propylcarbamate (113 mg, 0.23 mmol) following the experimental procedure described in Preparation 47a. 73 mg (71% yield) of the desired compound were obtained.

LRMS (m/z): 430 (M+1)+.

d) (S)-2-(1-Aminopropyl)-3-(3,5-difluorophenyl)-4-oxo-3,4-dihydropyrrolo[1,2-f][1,2,4]triazine-5-carbonitrile The title compound was prepared from (S)-tert-butyl 1-(5-cyano-3-(3,5-difluorophenyl)-4-oxo-3,4-dihydropyrrolo[1,2-f][1,2,4]triazin-2-yl)propylcarbamate (73 mg, 0.17 mmol) following the experimental procedure described in Preparation 47b. 62 mg (100% yield) of the desired compound were obtained.

LRMS (m/z): 330 (M+1)+.

Preparation 96

(S)-2-(1-Aminoethyl)-3-(3,5-difluorophenyl)-4-oxo-3,4-di hydropyrrolo[1,2-f][1,2,4]triazine-5-carboxamide A suspension of 60 mg (0.17 mmol) of (S)-2-(1-aminoethyl)-3-(3,5-difluorophenyl)-4-oxo-3,4-dihydropyrrolo[1,2-f][1,2,4]triazine-5-carbonitrile in sulphuric acid (2 ml) was stirred at room temperature overnight. The reaction mixture was slowly poured into a mixture of ice/water, neutralized with a 2N solution of NaHCO3 and extracted with ethyl acetate. The organic layer was then washed with brine, dried over magnesium sulphate and concentrated. The title compound was obtained as a white solid (38 mg, 64% yield).

LRMS (m/z): 334 (M+1)+.

Preparation 97

2-Amino-4-chloropyrimidine-5-carbonitrile

To a solution of 2,4-dichloropyrimidine-5-carbonitrile (600 mg, 3.45 mmol) in dioxane (20 ml) was added a 0.5M solution of NH3 in dioxane (20 ml, 10 mmol) and the mixture stirred at room temperature for 4 h. A mixture of two isomers were obtained and separated by column chromatography using a mixture of hexane/ethyl acetate (from 0% to 45% of ethyl acetate). The title compound (304 mg, 56% yield) was found to be the less polar isomer.

LRMS (m/z): 153 (M−1)⁻.

Preparation 98

2,4-Diamino-6-Chloropyrimidine-5-Carbonitrile

A mixture of 2,4,6-trichloropyrimidine-5-carbonitrile (200 mg, 0.96 mmol) and a 0.5M solution of $NH_3$ in dioxane (12 ml, 6 mmol) and the mixture stirred at room temperature for 2 h. The monosubstituted intermediate was obtained and 10 ml more of NH3 in dioxane were added and the mixture stirred at 80° C. over the weekend. A suspension was obtained, the solid filtered off and the filtrate concentrated to give a solid which was triturated in diethyl ether. The title compound was obtained as a beige solid (156 mg, 78% yield).

LRMS (m/z): 170 (M+1)⁺.

Preparation 99

(S)-2-(1-Aminoethyl)-3-phenyl-5-(thiazol-2-yl)pyrrolo[1,2-f][1,2,4]triazin-4(3H)-one a) (S)-tert-Butyl 1-(4-oxo-3-phenyl-5-(thiazol-2-yl)-3,4-dihydropyrrolo[1,2-f][1,2,4]triazin-2-yl)ethylcarbamate 100 mg (0.23 mmol) of (S)-tert-butyl 1-(5-bromo-4-oxo-3-phenyl-3,4-dihydropyrrolo[1,2-f][1,2,4]triazin-2-yl)ethylcarbamate, 95 µl (0.3 mmol) of 2-(tribuylstannyl)thiazole and 8 mg (0.01 mmol) of tetrakis(triphenylphosphine)palladium (0) under argon were stirred in dimethylformamide (2 ml) at 100° C. overnight. Then 95 µl (0.3 mmol) of 2-(tribuylstannyl)thiazole and 8 mg (0.01 mmol) of tetrakis(triphenylphosphine) palladium (0) were added and the mixture was stirred at 100° C. for 2 more days. The crude was filtered over celite washing with ethyl acetate. Then the organic phase was washed with water and brine, dried over magnesium sulphate and the solvent evaporated. The crude product was purified by normal phase chromatography (hexane-diethyl eter, 0-60% in 30CV) to obtain the title compound (48 mg, 45% yield) as a white solid.

LRMS (m/z): 438(M+1)⁺.

b) (S)-2-(1-Aminoethyl)-3-phenyl-5-(thiazol-2-yl) pyrrolo[1,2-f][1,2,4]triazin-4(3H)-one This compound was prepared starting from (S)-tert-Butyl 1-(4-oxo-3-phenyl-5-(thiazol-2-yl)-3,4-dihydropyrrolo[1,2-f][1,2,4]triazin-2-yl)ethylcarbamate (48 mg, 0.11 mmol) and following the experimental procedure described in Preparation 46c to afford 26 mg (70% yield) of the title compound that was used in the next step without any further purification.

LRMS (m/z): 338 (M+1)⁺.

Preparation 100

(S)-tert-Butyl 1-(4-oxo-3-phenyl-5-vinyl-3,4-dihydropyrrolo[1,2-f][1,2,4]triazin-2-yl)ethylcarbamate The title compound was prepared from (S)-tert-butyl 1-(5-bromo-4-oxo-3-phenyl-3,4-dihydropyrrolo[1,2-f][1,2,4]triazin-2-yl)ethylcarbamate (245 mg, 0.57 mmol) and ethenyl (tributyl)tin (214 µl, 0.74 mmol) following the experimental procedure described in Preparation 99a. 144 mg (65% yield) of the desired compound were obtained.

LRMS (m/z): 381 (M+1)⁺.

Preparation 101

(S)-tert-Butyl 1-(5-formyl-4-oxo-3-phenyl-3,4-dihydropyrrolo[1,2-f][1,2,4]triazin-2-yl)ethylcarbamate (S)-tert-butyl 1-(4-oxo-3-phenyl-5-vinyl-3,4-dihydropyrrolo[1,2-f][1,2,4]triazin-2-yl)ethylcarbamate (120 mg, 0.32 mmol) in a mixture of acetone/water (25 ml, 95/5) was ozonolysed in a Sander Labor-Ozonisator (300.5) at −20° C. with an air flow of 20l/h and 40 mA for 20 min. Reaction mixture was concentrated and the crude was purified by reverse phase chromatography to yield the final compound as a white solid (93 mg, 77% yield).

LRMS (m/z): 383 (M+1)⁺.

Preparation 102

(S)-2-(1-Aminoethyl)-5-(morpholinomethyl)-3-phenylpyrrolo[1,2-f][1,2,4]triazin-4(3H)-one a) (S)-tert-Butyl 1-(5-(morpholinomethyl)-4-oxo-3-phenyl-3,4-dihydropyrrolo[1,2-f][1,2,4]triazin-2-yl) ethylcarbamate To a solution of (S)-tert-butyl 1-(5-formyl-4-oxo-3-phenyl-3,4-dihydropyrrolo[1,2-f][1,2,4]triazin-2-yl)ethylcarbamate (93 mg, 0.24 mmol) in methanol (9 ml), was added morpholine (27 µl, 0.31 mmol) and acetic acid (58 µl, 1.01 mmol) and the reaction mixture was stirred 3 h at room temperature. Then sodium cyanoborohydride (10 mg, 0.16 mmol) was added and the reaction mixture stirred overnight at room temperature. The solvents were evaporated and the residue was partitioned between water and ethyl acetate. The organic layer was washed with 4% NaHCO3 and brine, dried over magnesium sulphate, filtered and evaporated under vacuum. The product was obtained as an oil (125 mg, 99% yield)

LRMS (m/z): 454 (M+1)⁺.

b) (S)-2-(1-Aminoethyl)-5-(morpholinomethyl)-3-phenylpyrrolo[1,2-f][1,2,4]triazin-4(3H)-one This compound was prepared starting from (S)-tert-butyl 1-(5-(morpholinomethyl)-4-oxo-3-phenyl-3,4-dihydropyrrolo[1,2-f][1,2,4]triazin-2-yl)ethylcarbamate (125 mg, 0.24 mmol) and following the experimental procedure described in Preparation 46c to afford 95 mg (86% yield) of the title compound as a dihydrochloride salt that was used in the next step without any further purification.

LRMS (m/z): 354 (M+1)⁺.

Preparation 103

(S)-2-(1-(tert-Butoxycarbonylamino)ethyl)-4-oxo-3-phenyl-3,4-dihydropyrrolo[1,2-f][1,2,4]triazine-5-carboxylic acid (S)-tert-Butyl 1-(4-oxo-3-phenyl-5-vinyl-3,4-dihydropyrrolo[1,2-f][1,2,4]triazin-2-yl)ethylcarbamate (108 mg, 0.28 mmol) in a mixture of ethyl acetate/pyridine (15 mL, 80/20) was ozonolysed in a Sander Labor-Ozonisator (300.5) at −25° C. with an air flow of 15 I/h and 30 mA for 10 h. Reaction mixture was concentrated and the crude was purified by normal phase chromatography (hexane/ethyl acetate) to yield the final compound (26 mg, 23% yield).
LRMS (m/z): 399 (M+1)+.

Preparation 104

(S)-2-(1-Aminoethyl)-5-(1-methyl-1H-pyrazol-4-yl)-3-phenyl pyrrolo[1,2-f][1,2,4]triazin-4(3H)-one a) (S)-tert-Butyl 1-(5-(1-methyl-1H-pyrazol-4-yl)-4-oxo-3-phenyl-3,4-dihydropyrrolo[1,2-f][1,2,4]triazin-2-yl)ethylcarbamate 50 mg (0.12 mmol) of (S)-tert-butyl 1-(5-bromo-4-oxo-3-phenyl-3,4-dihydropyrrolo[1,2-f][1,2,4]triazin-2-yl)ethylcarbamate, 48 mg (0.23 mmol) of 1-methyl-4-(4,4,5,5-tetramethyl-1,3,2-dioxaborolan-2-yl)-1H-pyrazole, 8 mg (0.01 mmol) of tetrakis(triphenylphosphine)palladium(0) and 184 µl of sodium carbonate 2M in water under argon were stirred in dimethylformamide (1 ml) at 120° C. for 2 h. The crude was filtered over celite washing with ethyl acetate. Then the organic phase was washed with water and brine, dried over magnesium sulphate and the solvent evaporated. The crude product was purified by reverse phase chromatography (C-18 silica from Waters, water/1:1 acetonitrile-methanol as eluents 0% to 100%) to obtain the title compound (50 mg, 87% yield) as a white solid.
LRMS (m/z): 435 (M+1)+.

b) (S)-2-(1-Aminoethyl)-5-(1-methyl-1H-pyrazol-4-yl)-3-phenyl pyrrolo[1,2-f][1,2,4]triazin-4(3H)-one This compound was prepared starting from (S)-tert-butyl 1-(5-(1-methyl-1H-pyrazol-4-yl)-4-oxo-3-phenyl-3,4-dihydropyrrolo[1,2-f][1,2,4]triazin-2-yl)ethylcarbamate (50 mg, 0.1 mmol) and following the experimental procedure described in Preparation 46c to afford 50 mg (100% yield) of the title compound that was used in the next step without any further purification.
LRMS (m/z): 335 (M+1)+.

Preparation 105

(S)-2-(1-Aminoethyl)-5-(2-hydroxyethyl)-3-phenylpyrrolo[1,2-f][1,2,4]triazin-4(3H)-one a) (S)-tert-Butyl 1-(5-(2-hydroxyethyl)-4-oxo-3-phenyl-3,4-dihydropyrrolo[1,2-f][1,2,4]triazin-2-yl) ethylcarbamate 100 mg (0.26 mmol) of (S)-tert-butyl 1-(4-oxo-3-phenyl-5-vinyl-3,4-dihydropyrrolo[1,2-f][1,2,4]triazin-2-yl)ethylcarbamate in tetrahydrofurane (8 ml) were cooled to 0° C. in an ice bath. Then 3.15 ml (1.58 mmol) of 9-BBN (0.5M in THF) were slowly added. The reaction mixture was led at 0° C. for an additional hour and then 4 h at room temperature. Then it was cooled at 0° C. and 1.7 ml (3.4 mmol) of sodium hydroxide 2M and 3.8 ml (0.03 mmol) of hydrogen peroxide (35% in water) were added. The reaction mixture was stirred at room temperature for 2 h.
LRMS (m/z): 399 (M+1)+.

b) (S)-2-(1-aminoethyl)-5-(2-hydroxyethyl)-3-phenylpyrrolo[1,2-f][1,2,4]triazin-4(3H)-one This compound was prepared starting from (S)-tert-butyl 1-(5-(2-hydroxyethyl)-4-oxo-3-phenyl-3,4-dihydropyrrolo [1,2-f][1,2,4]triazin-2-yl)ethylcarbamate (160 mg, 0.2 mmol) and following the experimental procedure described in Preparation 46c to afford 160 mg (100% yield) of the title compound that was used in the next step without any further purification.
LRMS (m/z): 299 (M+1)+.

Preparation 106

(S)-2-(1-Aminoethyl)-5-bromo-3-phenylpyrrolo[1,2-f][1,2,4]triazin-4(3H)-one

This compound was prepared starting from (S)-tert-butyl 1-(5-bromo-4-oxo-3-phenyl-3,4-dihydropyrrolo[1,2-f][1,2,4]triazin-2-yl)ethylcarbamate (50 mg, 0.12 mmol) and following the experimental procedure described in Preparation 46c to afford 42 mg (100% yield) of the title compound that was used in the next step without any further purification.
LRMS (m/z): 333, 335 (M+1)+.

Preparation 107

(S)-2-(1-Aminoethyl)-5-(2-methoxyethyl)-3-phenylpyrrolo[1,2-f][1,2,4]triazin-4(3H)-one a) (S)-tert-Butyl 1-(5-(2-methoxyethyl)-4-oxo-3-phenyl-3,4-d i hydropyrrolo[1,2-f][1,2,4]triazin-2-yl) ethylcarbamate To a solution of (S)-tert-butyl 1-(5-(2-hydroxyethyl)-4-oxo-3-phenyl-3,4-dihydropyrrolo[1,2-f][1,2,4]triazin-2-yl) ethylcarbamate (47 mg, 0.12 mmol) in tetrahydrofurane (1 mL), sodium hydride (6 mg, 0.15 mmol) was added. The reaction mixture was stirred at room temperature for 10 min and then methyl iodide (11 µl, 0.18 mmol) was added. After overnight stirring at room temperature ethyl acetate was added and the organic layer washed with water and brine. The organic layer was then dried over magnesium sulphate, filtered and concentrated. The crude was used without further purification
LRMS (m/z): 413 (M+1)+.

b) (S)-2-(1-Aminoethyl)-5-(2-methoxyethyl)-3-phenyl pyrrolo[1,2-f][1,2,4]triazin-4(3H)-one This compound was prepared starting from (S)-tert-butyl 1-(5-(2-methoxyethyl)-4-oxo-3-phenyl-3,4-dihydropyrrolo [1,2-f][1,2,4]triazin-2-yl)ethylcarbamate (50 mg, 0.08 mmol) and following the experimental procedure described in Preparation 46c to afford 50 mg (100% yield) of the hydrochloride salt of the title compound, that was used in the next step without any further purification.
LRMS (m/z): 313 (M+1)+.

Preparation 108

(S)-tert-Butyl 1-(5-bromo-4-oxo-3-(3-(trifluoromethyl)phenyl)-3,4-dihydropyrrolo[1,2-f][1,2,4]triazin-2-yl)ethylcarbamate a) (S)-tert-Butyl 1-(3-bromo-2-(3-(trifluoromethyl) phenyl carbamoyl)-1H-pyrrol-1-ylamino)-1-oxopropan-2-ylcarbamate The title compound was prepared from (S)-methyl 3-bromo-1-(2-(tert-butoxycarbonylamino)propanamido)-1H-pyrrole-2-carboxylate (2 g, 5.13 mmol) following the experimental procedure described in Preparation 27a. 2.35 g (81% yield) of the desired compound were obtained.
LRMS (m/z): 520 (M+1)$^+$.

b) (S)-tert-Butyl 1-(5-bromo-4-oxo-3-(3-(trifluoromethyl)phenyl)-3,4-dihydropyrrolo[1,2-f][1,2,4]triazin-2-yl)ethylcarbamate The title compound was prepared from (S)-tert-butyl 1-(3-bromo-2-(3-(trifluoromethyl)phenylcarbamoyl)-1H-pyrrol-1-ylamino)-1-oxopropan-2-ylcarbamate (2.30 g, 4.43 mmol) following the experimental procedure described in Preparation 54b. 1.40 g (63% yield) of the desired compound were obtained.
LRMS (m/z): 502 (M+1)$^+$.

Preparation 109

Methyl 1-(2-(tert-butoxycarbonylamino)propanamido)-1H-pyrrole-2-carboxylate a) Methyl 1-amino-1H-pyrrole-2-carboxylate Sodium hydride (4.40 g, 0.11 mol, 60% in hexanes) was suspended in DMF (550 ml) under nitrogen atmosphere. Once cooled at −5° C., methyl 1H-pyrrole-2-carboxylate (11.0 g, 0.09 mol) dissolved in DMF (182 ml) was dropwise added and vigorously stirred for 30. 277 ml more of DMF was added and then 0-(diphenylphosphoryl)hydroxylamine (32.8 g, 0.14 mol) was introduced into the reaction mixture. The reaction mixture was stirred at room temperature for 4 h. Once the reaction is over, 1l of saturated sodium thiosulfate solution (×5H$_2$O) was added and the mixture was warmed to 80° C. for 1 h. Once at room temperature, 1l of ethyl ether was added and the phases separated. The aqueous phase was twice extracted with ethyl ether. The organic phase was washed with water and brine, dried over magnesium sulphate, filtered and the solvent evaporated under reduced pressure. 10.41 g (81.1% yield) of the final compound were obtained.
LRMS (m/z): 141 (M+1)$^+$.

b) Methyl 1-(2-(tert-butoxycarbonylamino)propanamido)-1H-pyrrole-2-carboxylate

Methyl 1-amino-1H-pyrrole-2-carboxylate (6 g, 48.1 mmol) and (S)-2-(tert-butoxycarbonylamino)propanoic acid (8.10 g, 48.1 mmol) were dissolved in ethyl acetate (40 ml) and cooled in an ice-bath. Under an argon atmosphere, diisopropylethylamine (24.6 ml, 141.2 mmol) was added and, after stirring for 15 min, T3P solution (35.7 ml, 60 mmol, 50% in ethyl acetate) was dropwise added. After stirring for 20 min at 0° C., the reaction was left overnight at room temperature. The reaction mixture was poured onto water and extracted with ethyl ether. The organic phase was washed with water and brine, dried over magnesium sulphate and the solvent evaporated under reduced pressure. 8.6 g (83% yield) of the final product was obtained and use in the next synthetic step without further purification.
LRMS (m/z): 312 (M+1)$^+$.

Preparation 110

(S)-tert-Butyl 1-(5-bromo-3-(3-methoxyphenyl)-4-oxo-3,4-d hydropyrrolo[1,2-f][1,2,4]triazin-2-yl)ethylcarbamate a) (S)-tert-Butyl 1-(3-bromo-2-(3-methoxyphenyl-carbamoyl)-1H-pyrrol-1-ylamino)-1-oxopropan-2-yl carbamate The title compound was prepared from (S)-methyl 3-bromo-1-(2-(tert-butoxycarbonylamino)propanamido)-1H-pyrrole-2-carboxylate (2 g, 5.13 mmol) following the experimental procedure described in Preparation 27a. 2.10 g (83% yield) of the desired compound were obtained.
LRMS (m/z): 481, 483 (M+1)$^+$.

b) (S)-tert-Butyl 1-(5-bromo-3-(3-methoxyphenyl)-4-oxo-3,4-dihydropyrrolo[1,2-f][1,2,4]triazin-2-yl)ethylcarbamate The title compound was prepared from (S)-tert-butyl 1-(3-bromo-2-(3-methoxyphenylcarbamoyl)-1H-pyrrol-1-ylamino)-1-oxopropan-2-ylcarbamate (2.10 g, 4.36 mmol) following the experimental procedure described in Preparation 54b. 1.00 g (50% yield) of the desired compound were obtained.
LRMS (m/z): 463, 465 (M+1)$^+$.

Preparation 111

(S)-2-(1-Aminoethyl)-4-oxo-3-(3-(trifluoromethyl)phenyl)-3,4-dihydropyrrolo[1,2-f][1,2,4]triazine-5-carbonitrile a) (S)-tert-Butyl 1-(5-cyano-4-oxo-3-(3-(trifluoromethyl)phenyl)-3,4-dihydropyrrolo[1,2-f][1,2,4]triazin-2-yl)ethylcarbamate The title compound was prepared from (S)-tert-butyl 1-(5-bromo-4-oxo-3-(3-(trifluoromethyl)phenyl)-3,4-dihydropyrrolo[1,2-f][1,2,4]triazin-2-yl)ethylcarbamate (400 mg, 0.80 mmol) following the experimental procedure described in Preparation 47a. 228 mg (64% yield) of the desired compound were obtained.
LRMS (m/z): 448 (M+1)$^+$.

b) (S)-2-(1-Aminoethyl)-4-oxo-3-(3-(trifluoromethyl)phenyl)-3,4-dihydropyrrolo[1,2-f][1,2,4]triazine-5-carbonitrile The dihydrochloride salt of the title compound was prepared from (S)-tert-butyl 1-(5-cyano-4-oxo-3-(3-(trifluoromethyl)phenyl)-3,4-dihydropyrrolo[1,2-f][1,2,4]triazin-2-yl)ethylcarbamate (228 mg, 0.51 mmol) following the experimental procedure described in Preparation 47b. 229 mg (100% yield) of the desired compound were obtained.
LRMS (m/z): 348 (M+1)$^+$.

Preparation 112

(S)-2-(1-Aminoethyl)-3-(3-methoxyphenyl)-4-oxo-3,4-d hydropyrrolo[1,2-f][1,2,4]triazine-5-carbonitrile a) (S)-tert-Butyl 1-(5-cyano-3-(3-methoxyphenyl)-4-oxo-3,4-dihydropyrrolo[1,2-f][1,2,4]triazin-2-yl)ethylcarbamate The title compound was prepared from (S)-tert-butyl 1-(5-bromo-3-(3-methoxyphenyl)-4-oxo-3,4-dihydropyrrolo[1,2-f][1,2,4]triazin-2-yl)ethylcarbamate (453 mg, 0.98 mmol) following the experimental procedure described in Preparation 47a. 197 mg (49% yield) of the desired compound were obtained.
LRMS (m/z): 410 (M+1)$^+$.

b) (S)-2-(1-Aminoethyl)-3-(3-methoxyphenyl)-4-oxo-3,4-d i hydropyrrolo[1,2-f][1,2,4]triazine-5-carbonitrile The dihydrochloride salt of the title compound was prepared from (S)-tert-butyl 1-(5-cyano-3-(3-methoxyphenyl)-

4-oxo-3,4-dihydropyrrolo[1,2-f][1,2,4]triazin-2-yl)ethylcarbamate (195 mg, 0.48 mmol) following the experimental procedure described in Preparation 47b. 250 mg (100% yield) of the desired compound were obtained.

LRMS (m/z): 310 (M+1)$^+$.

Preparation 113

2-(Chloromethyl)-5-(difluoromethyl)-3-phenylpyrrolo[1,2-f][1,2,4]triazin-4(3H)-one a) Methyl 1-(phenylsulfonyl)-3-vinyl-1H-pyrrole-2-carboxylate Tetrakis(triphenylphosphane) palladium(0) (170 mg, 0.15 mmol) was added to a solution of 3-bromo-1-(phenylsulfonyl)-1H-pyrrole-2-carboxylate[2] (2 g, 5.8 mmol) and ethenyl(tributyl)tin (2.3 ml, 7.6 mmol) in N,N-dimethylformamide (60 mL). The resulting mixture was stirred for 23 h under Ar at 100° C., cooled and evaporated in vacuum. The residue was dissolved in a saturated solution of potassium fluoride in methanol and stirred for 2 hours. The mixture was evaporated in vacuum and the product was purified by flash chromatography silica (hexane/ethyl acetate) to give a 1640 mg (97% yield) of the title compound.

b) Methyl 3-formyl-1-(phenylsulfonyl)-1H-pyrrole-2-carboxylate

To a solution of methyl 1-(phenylsulfonyl)-3-vinyl-1H-pyrrole-2-carboxylate (1640 mg, 5.63 mmol) in 45 ml of tetrahydrofurane were added 4-methylmorpholine 4-oxide (1.36 g, 11.3 mmol) and 2,4 ml (0.39 mmol) of a 4% aqueous solution of osmium tetraoxide and the reaction was leaved with stirring at room temperature overnight. Afterwards, the starting material was completely consumed and the reaction mixture was filtered through a pad of Celite® using tetrahydrofurane. The filtrate was evaporated to dryness, taken up with ethyl acetate and washed with water and brine. The organic layer was dried (Na$_2$SO$_4$) and concentrated to give a brown residue that was immediately submitted to the next step. In this sense, this residue was dissolved in tetrahydrofurane (28 ml) and water (3,4 ml) and solid sodium periodate (1.8 g, 8.4 mmol) was added stirring the reaction vigorously at room temperature overnight. Next day, a suspension was formed and reaction was finished. The work-up was done by adding 4% aqueous solution of sodium bicarbonate (200 ml) and extracting with ethyl acetate (3x). The organic mixture was washed with water and brine, dried (Na$_2$SO$_4$) and concentrated to dryness to give a residue that was purified by flash chromatography silica (hexane/ethyl acetate) to give a 1.46 g (88% yield) of the title compound.

c) Methyl 3-(difluoromethyl)-1-(phenylsulfonyl)-1H-pyrrole-2-carboxylate

To a solution of methyl 3-formyl-1-(phenylsulfonyl)-1H-pyrrole-2-carboxylate (1.46 g, mmol) in dry dichloromethane (25 ml) in a schlenck flask at −75° C. under Ar was added diethylaminosulfur trifluoride (DAST) (1.64 ml, 12.5 mmol) and the mixture was allowed to warm-up to room temperature during 3 h and then stirred a this temperature overnight. Next day, the reaction was finished and 200 ml of 4% aqueous solution of sodium bicarbonate were added carefully maintaining a vigorous stirring during 20 minutes. Afterwards, the mixture was extracted with ethyl acetate (3x) and the organic layers were washed with brine, dried (Na$_2$SO$_4$) and concentrated in vacuum to give a residue that was purified by flash chromatography silica (hexane/ethyl acetate) to give a 1.4 g (85% yield) of the title compound.

d) 3-(Difluoromethyl)-N-phenyl-1-(phenylsulfonyl)-1H-pyrrole-2-carboxamide

The title compound was prepared from methyl 3-(difluoromethyl)-1-(phenylsulfonyl)-1H-pyrrole-2-carboxylate (1.16 g, 3.7 mmol) following the experimental procedure described in Preparation 44a. 0.96 g (70% yield) of the desired compound were obtained.

LRMS (m/z): 377 (M+1)$^+$.

e) 3-(Difluoromethyl)-N-phenyl-1H-pyrrole-2-carboxamide

The title compound was prepared from 3-(difluoromethyl)-N-phenyl-1-(phenylsulfonyl)-1H-pyrrole-2-carboxamide (0.96 g, 2.6 mmol) following the experimental procedure described in Preparation 44b. 0.6 g (98% yield) of the desired compound were obtained.

LRMS (m/z): 237 (M+1)$^+$.

f) 1-Amino-3-(difluoromethyl)-N-phenyl-1H-pyrrole-2-carboxamide 1.1 ml (1.1 mmol) of a 1M solution of lithium bis(trimethylsilyl)amide was added to a solution of 3-(difluoromethyl)-N-phenyl-1H-pyrrole-2-carboxamide (100 mg, 0.42 mmol) and DPPONH$_2$ (P,P-diphenylphosphinic amide, available from Sigma Aldrich®, cat. no. 5994-87-6) (250 mg, 1,1 mmol) in DMF (4 mL) at room temperature. A thick suspension formed and additional 4 mL of DMF were added. The mixture was stirred at room temperature for 1 hour and then it was poured into 50 mL of water and extracted with ethyl acetate. The aqueous layer was further extracted with ethyl acetate (2x). The combined organic layer was washed with water and brine and was dried over sodium sulphate, filtered and concentrated. The crude product was purified by flash chromatography (0% to 33% AcOEt/Hexanes) to yield 40 mg (38% yield) of the title compound.

LRMS (m/z): 252 (M+1)$^+$.

g) 2-(Chloromethyl)-5-(difluoromethyl)-3-phenylpyrrolo[1,2-f][1,2,4]triazin-4(3H)-one The title compound was prepared from 1-amino-3-(difluoromethyl)-N-phenyl-1H-pyrrole-2-carboxamide (0.167 g, 0.66 mmol) following the experimental procedure described in Preparation 2. 57 mg (28% yield) of the desired compound were obtained.

LRMS (m/z): 310 (M+1)$^+$.

Preparation 114

(S)-2-(1-Aminoethyl)-5-(difluoromethyl)-3-phenylpyrrolo[1,2-f][1,2,4]triazin-4(3H)-one a) (S)-tert-Butyl 1-(4-oxo-3-phenyl-5-vinyl-3,4-dihydropyrrolo[1,2-f][1,2,4]triazin-2-yl)ethylcarbamate Tetrakis(triphenylphosphane) palladium(0) (90 mg, 0.01 mmol) was added to a solution of (S)-tert-butyl 1-(5-bromo-4-oxo-3-phenyl-3,4-dihydropyrrolo[1,2-f][1,2,4]triazin-2-yl)ethylcarbamate (100 mg, 0.23 mmol) and ethenyl(tributyl)tin (90 μl, 0.31 mmol) in N,N-dimethylformamide (2.4 mL).

The resulting mixture was stirred for 24 h under Ar at 100° C., cooled and evaporated in vacuum. The residue was dissolved in a saturated solution of potassium fluoride in methanol and stirred for 1 hour. The mixture was evaporated in vacuum and the product was purified by flash chromatography silica (hexane/ethyl acetate) to give a 65 mg (74% yield) of the title compound.

b) (S)-tert-Butyl 1-(5-formyl-4-oxo-3-phenyl-3,4-dihydropyrrolo[1,2-f][1,2,4]triazin-2-yl)ethylcarbamate To a solution of tert-butyl 1-(4-oxo-3-phenyl-5-vinyl-3,4-dihydropyrrolo[1,2-f][1,2,4]triazin-2-yl)ethylcarbamate (37 mg, 0.1 mmol) in 0.8 ml of tetrahydrofurane were added 4-methylmorpholine 4-oxide (23 mg, 0.2 mmol) and 42 µl (0.01 mmol) of a 4% aqueous solution of osmium tetraoxide and the reaction was leaved with stirring at room temperature overnight. Afterwards, the starting material was completely consumed and the reaction mixture was filtered through a pad of Celite® using tetrahydrofurane. The filtrate was evaporated to dryness, taken up with ethyl acetate and washed with water and brine. The organic layer was dried ($Na_2SO_4$) and concentrated to give a brown residue that was immediately submitted to the next step. In this sense, this residue was dissolved in tetrahydrofurane (0.5 ml) and water (60 µl) and solid sodium periodate (31 mg, 0.14 mmol) was added stirring the reaction vigorously at room temperature overnight. Next day, a suspension was formed and reaction was finished. The work-up was done by adding 4% aqueous solution of sodium bicarbonate and extracting with ethyl acetate (3×). The organic mixture was washed with water and brine, dried ($Na_2SO_4$) and concentrated to dryness to give a residue that was purified by flash chromatography silica (hexane/ethyl acetate) to give a 26 g (70% yield) of the title compound.

c) (S)-tert-Butyl 1-(5-(difluoromethyl)-4-oxo-3-phenyl-3,4-dihydropyrrolo[1,2-f][1,2,4]triazin-2-yl)ethylcarbamate To a solution of tert-butyl 1-(5-formyl-4-oxo-3-phenyl-3,4-dihydropyrrolo[1,2-f][1,2,4]triazin-2-yl)ethylcarbamate (400 mg, 1.05 mmol) in dry dichloromethane (10 ml) in a schlenck flask at −75° C. under Ar was added diethylaminosulfur trifluoride (DAST) (1 ml, 7.63 mmol) and the mixture was allowed to warm-up till room temperature during 3 h and then stirred a this temperature overnight. Next day, the reaction was finished and 4% aqueous solution of sodium bicarbonate were added carefully maintaining a vigorous stirring during 20 minutes. Afterwards, the mixture was extracted with ethyl acetate (3×) and the organic layers were washed with brine, dried ($Na_2SO_4$) and concentrated in vacuum to give a residue that was purified by flash chromatography silica (hexane/ethyl acetate) to give a 316 mg (75% yield) of the title compound.

d) (S)-2-(1-Aminoethyl)-5-(difluoromethyl)-3-phenylpyrrolo[1,2-f][1,2,4]triazin-4(3H)-one The title compound was prepared from tert-butyl 1-(5-(difluoromethyl)-4-oxo-3-phenyl-3,4-dihydropyrrolo[1,2-f][1,2,4]triazin-2-yl)ethylcarbamate (316 mg, 0.78 mmol) following the experimental procedure described in Preparation 46c. 219 mg (92% yield) of the desired compound were obtained.

LRMS (m/z): 305 (M+1)$^+$.

Preparation 115

(R)-2-(1-Amino-2-hydroxyethyl)-3-phenylpyrrolo[1,2-f][1,2,4]triazin-4(3H)-one a) (R)-tert-Butyl 3-tert-butoxy-1-oxo-1-(2-(phenylcarbamoyl)-1H-pyrrol-1-ylamino)propan-2-ylcarbamate The title compound was prepared from 1-amino-N-phenyl-1H-pyrrole-2-carboxamide (1 g, 5 mmol) following the experimental procedure described in Preparation 42a. 0.72 g (32% yield) of the desired compound was obtained.

LRMS (m/z): 445 (M+1)$^+$.

b) (R)-tert-Butyl 2-tert-butoxy-1-(4-oxo-3-phenyl-3,4-dihydropyrrolo[1,2-f][1,2,4]triazin-2-yl)ethylcarbamate The title compound was prepared from (R)-tert-butyl 3-tert-butoxy-1-oxo-1-(2-(phenylcarbamoyl)-1H-pyrrol-1-ylamino)propan-2-ylcarbamate (0.62 g, 1.4 mmol) following the experimental procedure described in Preparation 42b. 0.12 g (20% yield) of the desired compound was obtained.

LRMS (m/z): 427 (M+1)$^+$.

c) (R)-2-(1-Amino-2-hydroxyethyl)-3-phenylpyrrolo[1,2-f][1,2,4]triazin-4(3H)-one 110 mg (0.26 mmol) of (R)-tert-butyl 2-tert-butoxy-1-(4-oxo-3-phenyl-3,4-dihydropyrrolo[1,2-f][1,2,4]triazin-2-yl)ethylcarbamate were dissolved in 40 µl of methylene chloride and 40 µl of trifluoroacetic acid were added. The resulting solution was stirred at room temperature overnight and the reaction mixture was evaporated to dryness. The residue was then redissolved in dioxane (2 ml) and the solution was treated with 4M HCl solution in dioxane (0.5 ml) stirring 10 minutes at this temperature and evaporated to dryness to obtain the corresponding hydrochloride 75 mg (91%) of the title compound.

LRMS (m/z): 271 (M+1)$^+$.

Preparation 116

(S)-2-(1-Aminoethyl)-6-fluoro-3-phenylpyrrolo[1,2-f][1,2,4]triazin-4(3H)-one a) 4-Fluoro-N-phenyl-1H-pyrrole-2-carboxamide The title compound was prepared from methyl 4-fluoro-1H-pyrrole-2-carboxylate[3] (1.14 g, 8.0 mmol) and aniline (2.2 ml, 24.0 mmol) following the experimental procedure described in Preparation 44a. 1.09 g (64% yield) of the desired compound were obtained.

LRMS (m/z): 205 (M+1)$^+$.

b) 1-Amino-4-fluoro-N-phenyl-1H-pyrrole-2-carboxamide

This compound was prepared starting from 4-fluoro-N-phenyl-1H-pyrrole-2-carboxamide (1.05 g, 5.1 mmol) and following the experimental procedure described in Preparation 1b to afford 1.14 g (84% yield) of the title compound.

LRMS (m/z): 220 (M+1)$^+$.

c) (S)-tert-Butyl 1-(4-fluoro-2-(phenylcarbamoyl)-1H-pyrrol-1-ylamino)-1-oxopropan-2-ylcarbamate The title compound was prepared from 1-amino-4-fluoro-N-phenyl-1H-pyrrole-2-carboxamide (0.95 g, 3.6 mmol) and (S)-2-(tert-butoxycarbonylamino)propanoic acid following the experimental procedure described in Preparation 47b. 1.28 g (91% yield) of the desired compound were obtained.
LRMS (m/z): 391 (M+1)$^+$.

d) (S)-tert-Butyl 1-(6-fluoro-4-oxo-3-phenyl-3,4-dihydropyrrolo[1,2-f][1,2,4]triazin-2-yl)ethylcarbamate This compound was prepared starting from (S)-tert-butyl 1-(4-fluoro-2-(phenylcarbamoyl)-1H-pyrrol-1-ylamino)-1-oxopropan-2-ylcarbamate (1.15 g, 2.95 mmol) and following the experimental procedure described in Preparation 73b to afford 0.68 g (62% yield) of the title compound.
LRMS (m/z): 373 (M+1)$^+$.

e) (S)-2-(1-Aminoethyl)-6-fluoro-3-phenylpyrrolo[1,2-f][1,2,4]triazin-4(3H)-one

This compound was prepared starting from (S)-tert-butyl 1-(6-fluoro-4-oxo-3-phenyl-3,4-dihydropyrrolo[1,2-f][1,2,4]triazin-2-yl)ethylcarbamate (0.64 g, 1.64 mmol) and following the experimental procedure described in Preparation 71b but heating the reaction mixture at 35° C. during 5 hours to afford 0.59 g (96% yield) of the title compound, isolated as the trifluoroacetate salt form.
LRMS (m/z): 273 (M+1)$^+$.

Preparation 117

2-((S)-1-Aminoethyl)-3-((S)-1-phenylethyl)pyrrolo[1,2-f][1,2,4]triazin-4(3H)-one a) (S)—N-(1-Phenylethyl)-1H-pyrrole-2-carboxamide The title compound was prepared from methyl 1H-pyrrole-2-carboxylate (8.0 g, 0.06 mol) and (S)-1-phenylethanamine (24.7 ml, 0.19 mol) following the experimental procedure described in Preparation 44a. 10.4 g (75% yield) of the desired compound were obtained.
LRMS (m/z): 215 (M+1)$^+$.

b) (S)-1-Amino-N-(1-phenylethyl)-1H-pyrrole-2-carboxamide

This compound was prepared starting from (S)—N-(1-phenylethyl)-1H-pyrrole-2-carboxamide (11.5 g, 0.05 mol) and following the experimental procedure described in Preparation 1b to afford 9.8 g (79% yield) of the title compound.
LRMS (m/z): 230 (M+1)$^+$.

c) tert-Butyl (S)-1-oxo-1-(2-((S)-1-phenylethylcarbamoyl)-1H-pyrrol-1-ylamino)propan-2-ylcarbamate The title compound was prepared from (S)-1-amino-N-(1-phenylethyl)-1H-pyrrole-2-carboxamide (3.50 g, 15.3 mmol) and (S)-2-(tert-butoxycarbonylamino)propanoic acid (2.89 g, 15.3 mmol) following the experimental procedure described in Preparation 73a. 5.78 g (92% yield) of the desired compound were obtained.

d) tert-Butyl (S)-1-(4-oxo-3-((S)-1-phenylethyl)-3,4-dihydropyrrolo[1,2-f][1,2,4]triazin-2-yl)ethylcarbamate This compound was prepared starting from tert-butyl (S)-1-oxo-1-(2-((S)-1-phenylethylcarbamoyl)-1H-pyrrol-1-ylamino)propan-2-ylcarbamate (5.23 g, 13.1 mmol) and following the experimental procedure described in Preparation 68b to afford 4.40 g (85% yield) of the title compound.
LRMS (m/z): 383 (M+1)$^+$.

e) 2-((S)-1-Aminoethyl)-3-((S)-1-phenylethyl)pyrrolo[1,2-f][1,2,4]triazin-4(3H)-one This compound was prepared starting from tert-butyl (S)-1-(4-oxo-3-((S)-1-phenylethyl)-3,4-dihydropyrrolo[1,2-f][1,2,4]triazin-2-yl)ethylcarbamate (4.34 g, 11.4 mmol) and following the experimental procedure described in Preparation 71b but heating the reaction mixture at 35° C. during 5 hours to afford 4.27 g (95% yield) of the title compound, isolated as the trifluoroacetate salt form.
LRMS (m/z): 283 (M+1)$^+$.

Preparation 118

(S)-2-(1-Aminoethyl)-3-(2,6-dimethylphenyl)pyrrolo[1,2-f][1,2,4]triazin-4(3H)-one a)
N-(2,6-Dimethylphenyl)-1H-pyrrole-2-carboxamide The title compound was prepared from 1H-pyrrole-2-carboxylic acid (2 g, 18 mmol) and 2,6-dimethylaniline (2.75 g, 22.7 mmol) following the experimental procedure described in Preparation 44a. 900 mg (23% yield) of the desired compound were obtained.
LRMS (m/z): 215 (M+1)$^+$.

b) 1-Amino-N-(2,6-dimethylphenyl)-1H-pyrrole-2-carboxamide

This compound was prepared starting from N-(2,6-dimethylphenyl)-1H-pyrrole-2-carboxamide (1080 mg, 5.04 mmol) and following the experimental procedure described in Preparation 1b to afford 324 mg (25% yield) of the title compound.
LRMS (m/z): 230 (M+1)$^+$.

c) (S)-Benzyl 1-(2-(2,6-dimethylphenylcarbamoyl)-1H-pyrrol-1-ylamino)-1-oxopropan-2-ylcarbamate The title compound was prepared from 1-amino-N-(2,6-dimethylphenyl)-1H-pyrrole-2-carboxamide (324 mg, 1.41 mmol) and (S)-2-(benzyloxycarbonylamino)propanoic acid (347 g, 1.55 mmol) following the experimental procedure described in Preparation 73a. 458 mg (75% yield) of the desired compound were obtained.
LRMS (m/z): 435 (M+1)$^+$.

d) (S)-Benzyl 1-(3-(2,6-dimethylphenyl)-4-oxo-3,4-dihydropyrrolo[1,2-f][1,2,4]triazin-2-yl)ethylcarbamate This compound was prepared starting from (S)-benzyl 1-(2-(2,6-dimethylphenyl-carbamoyl)-1H-pyrrol-1-ylamino)-1-oxopropan-2-ylcarbamate (458 mg, 1.05 mmol) and following the experimental procedure described in Preparation 68b to afford 252 mg (58% yield) of the title compound that was used in the next step without any further purification.
LRMS (m/z): 417 (M+1)$^+$.

e) (S)-2-(1-Aminoethyl)-3-(2,6-dimethylphenyl) pyrrolo[1,2-f][1,2,4]triazin-4(3H)-one This compound was prepared starting from (S)-benzyl 1-(3-(2,6-dimethylphenyl)-4-oxo-3,4-dihydropyrrolo[1,2-f][1,2,4]triazin-2-yl)ethylcarbamate (126 mg, 0.3 mmol) and following the experimental procedure described in Preparation 128c to afford 85 mg (100% yield) of the title compound that was used in the next step without any further purification.
LRMS (m/z): 283 (M+1)$^+$.

Preparation 119

(S)-2-(Aminomethyl)-3-(1-phenylethyl)pyrrolo[1,2-f][1,2,4]triazin-4(3H)-one a) (S)-tert-Butyl 2-oxo-2-(2-(1-phenylethylcarbamoyl)-1H-pyrrol-1-ylamino)ethylcarbamate The title compound was prepared from (S)-1-amino-N-(1-phenylethyl)-1H-pyrrole-2-carboxamide (3.50 g, 15.3 mmol) and 2-(tert-butoxycarbonylamino)acetic acid (2.67 g, 15.3 mmol) following the experimental procedure described in Preparation 73a. 5.79 g (89% yield) of the desired compound were obtained.
LRMS (m/z): 387 (M+1)$^+$.

b) (S)-tert-Butyl (4-oxo-3-(1-phenylethyl)-3,4-dihydropyrrolo[1,2-f][1,2,4]triazin-2-yl)methylcarbamate This compound was prepared starting from (S)-tert-butyl 2-oxo-2-(2-(1-phenylethylcarbamoyl)-1H-pyrrol-1-ylamino)ethylcarbamate (5.75 g, 14.9 mmol) and following the experimental procedure described in Preparation 68b to afford 2.34 g (35% yield, 81% purity) of the title compound that was used in the next step without any further purification.
LRMS (m/z): 369 (M+1)$^+$.

c) (S)-2-(Aminomethyl)-3-(1-phenylethyl)pyrrolo[1,2-f][1,2,4]triazin-4(3H)-one

This compound was prepared starting from (S)-tert-butyl (4-oxo-3-(1-phenylethyl)-3,4-dihydropyrrolo[1,2-f][1,2,4]triazin-2-yl)methylcarbamate (2.30 g, 81% purity, 5.1 mmol) and following the experimental procedure described in Preparation 71b but heating the reaction mixture at 35° C. during 4 hours to afford 2.22 g (75% yield, 65% purity) of the title compound, isolated as the trifluoroacetate salt form.
LRMS (m/z): 269 (M+1)$^+$.

Preparation 120

(S)-2-(1-Aminoethyl)-5-fluoro-3-phenylpyrrolo[1,2-f][1,2,4]triazin-4(3H)-one a) (S)-tert-Butyl 1-(5-fluoro-4-oxo-3-phenyl-3,4-dihydropyrrolo[1,2-f][1,2,4]triazin-2-yl)ethylcarbamate To a solution of (S)-tert-Butyl 1-(5-bromo-4-oxo-3-phenyl-3,4-dihydropyrrolo[1,2-f][1,2,4]triazin-2-yl)ethylcarbamate (500 mg, 1.15 mmol) in anhydrous THF (5 ml) placed in a schlenk tube under Ar was added dropwise a 1.6 M solution of n-BuLi in hexanes (1.8 ml, 2.88 mmol) at −78° C. This mixture was stirred during 30 min. at −78° C. in order to accomplish the halogen-metal exchange. After this period, a solution of N-fluoro-N-(phenylsulfonyl)-benzenesulfonamide (475 mg, 1.5 mmol) in THF (4 ml) was added dropwise and the reaction mixture was allowed to warm up overnight till room temperature and then it was quenched by addition of a saturated solution of ammonium chloride (15 ml). Some additional water was added and the mixture was extracted with ethyl acetate (3×). The total organic phase was washed with brine, dried (sodium sulphate) and concentrated in vacuum to get 606 mg of a residue. This crude material was purified by flash chromatography (0% to 20% dichloromethane/AcOEt) to yield 78 mg (18% yield) of the title compound.
LRMS (m/z): 373 (M+1)$^+$.

b) 2-(1-Aminoethyl)-5-fluoro-3-phenylpyrrolo[1,2-f][1,2,4]triazin-4(3H)-one

This compound was prepared starting from (S)-tert-butyl 1-(5-fluoro-4-oxo-3-phenyl-3,4-dihydropyrrolo[1,2-f][1,2,4]triazin-2-yl)ethylcarbamate (78 mg, 0.21 mmol) and following the experimental procedure described in Preparation 81b to afford 65 mg (quantitative yield) of the title compound, isolated as the hydrochloric salt form.
LRMS (m/z): 273 (M+1)$^+$.

Preparation 121

2-((S)-1-Aminoethyl)-5-(1,2-dihydroxyethyl)-3-phenylpyrrolo[1,2-f][1,2,4]triazin-4(3H)-one a) tert-Butyl (1S)-1-(5-(1,2-dihydroxyethyl)-4-oxo-3-phenyl-3,4-dihydropyrrolo[1,2-f][1,2,4]triazin-2-yl)ethylcarbamate To a solution of (S)-tert-butyl 1-(4-oxo-3-phenyl-5-vinyl-3,4-dihydropyrrolo[1,2-f][1,2,4]triazin-2-yl)ethylcarbamate (1.85 g, 4.9 mmol) in 40 ml of tetrahydrofurane were added 4-methylmorpholine 4-oxide (1.15 g, 9.8 mmol) and 4% aqueous solution of osmium tetraoxide (2.1 ml, 0.3 mmol) and the reaction was leaved with stirring at room temperature overnight. Afterwards, the starting material was completely consumed and the reaction mixture was filtered through a pad of Celite® using tetrahydrofurane. The filtrate was evaporated to dryness, taken up with ethyl acetate and washed with water and brine. The organic layer was dried (Na$_2$SO$_4$) and concentrated to afford 1.98 g (98% yield) of the title compound.
LRMS (m/z): 415 (M+1)$^+$.

b) 2-((S)-1-Aminoethyl)-5-(1,2-dihydroxyethyl)-3-phenylpyrrolo[1,2-f][1,2,4]triazin-4(3H)-one This compound was prepared starting from tert-butyl (1S)-1-(5-(1,2-dihydroxyethyl)-4-oxo-3-phenyl-3,4-dihydropyrrolo[1,2-f][1,2,4]triazin-2-yl)ethylcarbamate (200 mg, 0.5 mmol) and following the experimental procedure described in Preparation 81b to afford 112 mg (66% yield) of the title compound, isolated as the hydrochloric salt form.
LRMS (m/z): 315 (M+1)$^+$.

Preparation 122

(S)-2-(1-Aminoethyl)-5-(hydroxymethyl)-3-phenylpyrrolo[1,2-f][1,2,4]triazin-4(3H)-one a) (S)-tert-Butyl 1-(5-(hydroxymethyl)-4-oxo-3-phenyl-3,4-dihydropyrrolo[1,2-f][1,2,4]triazin-2-yl)ethylcarbamate To a solution of (S)-tert-butyl 1-(5-formyl-4-oxo-3-phenyl-3,4-dihydropyrrolo[1,2-f][1,2,4]triazin-2-yl)ethylcarbamate (400 mg, 1.1 mmol) in 20 mL of methanol was added NaBH₄ (30 mg, 0.8 mmol) and the mixture was stirred at room temperature during 3.5 h. The solvent was evaporated and the residue was partitioned between ammonium chloride saturated aqueous solution and ethyl acetate. The organic layer was washed with water and brine, dried over magnesium sulphate, filtered and evaporated under vacuum. The product was purified by flash chromatography (0% to 30% hexane/AcOEt) to yield 301 mg (75%) of the title compound.
LRMS (m/z): 385 (M+1)⁺.

b) (S)-2-(1-Aminoethyl)-5-(hydroxymethyl)-3-phenylpyrrolo[1,2-f][1,2,4]triazin-4(3H)-one This compound was prepared starting from (S)-tert-butyl 1-(5-(hydroxymethyl)-4-oxo-3-phenyl-3,4-dihydropyrrolo[1,2-f][1,2,4]triazin-2-yl)ethylcarbamate (300 mg, 0.8 mmol) and following the experimental procedure described in Preparation 81b to afford 233 mg (93% yield) of the title compound, isolated as the hydrochloric salt form.
LRMS (m/z): 285 (M+1)⁺.

Preparation 123

(S)-2-(1-Aminoethyl)-5-(difluoromethyl)-3-(3,5-difluorophenyl)pyrrolo[1,2-f][1,2,4]triazin-4(3H)-one a) (S)-tert-Butyl 1-(3-(3,5-difluorophenyl)-4-oxo-5-vinyl-3,4-dihydropyrrolo[1,2-f][1,2,4]triazin-2-yl)ethylcarbamate This compound was prepared starting from (S)-tert-butyl 1-(5-bromo-3-(3,5-difluorophenyl)-4-oxo-3,4-dihydropyrrolo[1,2-f][1,2,4]triazin-2-yl)ethylcarbamate (1.00 g, 2.1 mmol) and following the experimental procedure described in Preparation 114a to afford 0.71 g (76%) of the title compound.
LRMS (m/z): 417 (M+1)⁺.

b) (S)-tert-Butyl 1-(3-(3,5-difluorophenyl)-5-formyl-4-oxo-3,4-dihydropyrrolo[1,2-f][1,2,4]triazin-2-yl)ethylcarbamate This compound was prepared starting from (S)-tert-butyl 1-(3-(3,5-difluorophenyl)-4-oxo-5-vinyl-3,4-dihydropyrrolo[1,2-f][1,2,4]triazin-2-yl)ethylcarbamate (0.70 g, 1.7 mmol) and following the experimental procedure described in Preparation 114b to afford 0.62 g (88% yield) of the title compound.
LRMS (m/z): 419 (M+1)⁺.

c) (S)-tert-Butyl 1-(5-(difluoromethyl)-3-(3,5-difluorophenyl)-4-oxo-3,4-dihydropyrrolo[1,2-f][1,2,4]triazin-2-yl)ethylcarbamate This compound was prepared starting from (S)-tert-butyl 1-(3-(3,5-difluorophenyl)-5-formyl-4-oxo-3,4-dihydropyrrolo[1,2-f][1,2,4]triazin-2-yl)ethylcarbamate (0.62 g, 1.5 mmol) and following the experimental procedure described in Preparation 114c to afford 0.45 g (68% yield) of the title compound.
LRMS (m/z): 441 (M+1)⁺.

d) (S)-2-(1-Aminoethyl)-5-(difluoromethyl)-3-(3,5-difluorophenyl)pyrrolo[1,2-f][1,2,4]triazin-4(3H)-one This compound was prepared starting from (S)-tert-butyl 1-(5-(difluoromethyl)-3-(3,5-difluorophenyl)-4-oxo-3,4-dihydropyrrolo[1,2-f][1,2,4]triazin-2-yl)ethylcarbamate (0.45 g, 1.0 mmol) and following the experimental procedure described in Preparation 81b to afford 0.36 g (94% yield) of the title compound, isolated as the hydrochloric salt form.
LRMS (m/z): 341 (M+1)⁺.

Preparation 124

(S)-2-(1-Aminoethyl)-3-(2-chlorobenzyl)-4-oxo-3,4-dihydropyrrolo[1,2-f][1,2,4]triazine-5-carbonitrile a) (S)-tert-Butyl 1-(3-bromo-2-(2-chlorobenzylcarbamoyl)-1H-pyrrol-1-ylamino)-1-oxopropan-2-ylcarbamate The title compound was prepared from (S)-Methyl 3-bromo-1-(2-(tert-butoxycarbonylamino)propanamido)-1H-pyrrole-2-carboxylate (310 mg, 0.8 mmol) and (2-chlorophenyl)methanamine (385 µL, 3.2 mmol) following the experimental procedure described in Preparation 44a. 259 mg (65% yield) of the desired compound were obtained.
LRMS (m/z): 499, 501 (M+1)⁺.

b) (S)-tert-Butyl 1-(5-bromo-3-(2-chlorobenzyl)-4-oxo-3,4-dihydropyrrolo[1,2-f][1,2,4]triazin-2-yl)ethylcarbamate This compound was prepared starting from (S)-tert-butyl 1-(3-bromo-2-(2-chlorobenzylcarbamoyl)-1H-pyrrol-1-ylamino)-1-oxopropan-2-ylcarbamate (296 mg, 0.6 mmol) and following the experimental procedure described in Preparation 73b to afford 38 mg (13% yield) of the title compound.
LRMS (m/z): 481, 483 (M+1)⁺.

c) (S)-tert-Butyl 1-(3-(2-chlorobenzyl)-5-cyano-4-oxo-3,4-d hydropyrrolo[1,2-f][1,2,4]triazin-2-yl)ethylcarbamate This compound was prepared starting from (S)-tert-butyl 1-(5-bromo-3-(2-chlorobenzyl)-4-oxo-3,4-dihydropyrrolo[1,2-f][1,2,4]triazin-2-yl)ethylcarbamate (38 mg, 0.08 mmol) and following the experimental procedure described in Preparation 47a to afford 20 mg (59% yield) of the title compound.
LRMS (m/z): 428 (M+1)⁺.

d) (S)-2-(1-Aminoethyl)-3-(2-chlorobenzyl)-4-oxo-3,4-d hydropyrrolo[1,2-f][1,2,4]triazine-5-carbonitrile This compound was prepared starting from (S)-tert-butyl 1-(5-bromo-3-(2-chlorobenzyl)-4-oxo-3,4-dihydropyrrolo[1,2-f][1,2,4]triazin-2-yl)ethylcarbamate (16 mg, 0.04 mmol) and following the experimental procedure described in Preparation 81b to afford 13 mg (95% yield) of the title compound, isolated as the hydrochloric salt form.
LRMS (m/z): 328 (M+1)$^+$.

Preparation 125

(S)-Methyl 1-(2-(benzyloxycarbonylamino)propanamido)-3-bromo-1H-pyrrole-2-carboxylate a) Methyl 3-bromo-1H-pyrrole-2-carboxylate To a solution of methyl 3-bromo-1-(phenylsulfonyl)-1H-pyrrole-2-carboxylate[2] (6.59 g, 19.2 mmol) in 132 mL of methanol was added MeONa (1.55 g, 28.7 mmol) and the mixture was stirred at room temperature during 4 h. The solvent was evaporated and the residue was partitioned between ammonium chloride saturated aqueous solution and ethyl acetate. The organic layer was washed with water and brine, dried over magnesium sulphate, filtered and evaporated under vacuum. The product was purified by flash chromatography (0% to 30% hexane/AcOEt) to yield 3.32 g (85%) of the title compound.
LRMS (m/z): 203, 205 (M+1)$^+$.

b) Methyl 1-amino-3-bromo-1H-pyrrole-2-carboxylate

This compound was prepared starting from methyl 3-bromo-1H-pyrrole-2-carboxylate (3.30 g, 16.2 mmol) and following the experimental procedure described in Preparation 35b to afford 3.42 g (48% yield, 50% purity) of the title compound.
LRMS (m/z): 218, 220 (M+1)$^+$.

c) (S)-Methyl 1-(2-(benzyloxycarbonylamino)propanamido)-3-Bromo-1H-Pyrrole-2-carboxylate The title compound was prepared from methyl 1-amino-3-bromo-1H-pyrrole-2-carboxylate (9.05 g, 25.6 mmol) and (S)-2-(benzyloxycarbonylamino)propanoic acid (5.72 g, 25.6 mmol) following the experimental procedure described in Preparation 73a. 9.73 g (84% yield) of the desired compound were obtained.
LRMS (m/z): 424, 426 (M+1)$^+$.

Preparation 126

(S)-2-(1-Aminoethyl)-3-(5-fluoropyridin-3-yl)pyrrolo[1,2-f][1,2,4]triazin-4(3H)-one a) (S)-Benzyl 1-(3-bromo-2-(5-fluoropyridin-3-ylcarbamoyl)-1H-pyrrol-1-ylamino)-1-oxopropan-2-ylcarbamate The title compound was prepared from (S)-methyl 1-(2-(benzyloxycarbonylamino)propanamido)-3-bromo-1H-pyrrole-2-carboxylate (2.00 g, 4.7 mmol) and 5-fluoropyridin-3-amine (4.23 g, 37.6 mmol) following the experimental procedure described in Preparation 44a. 1.65 g (69% yield) of the desired compound were obtained.
LRMS (m/z): 504, 506 (M+1)$^+$.

b) (S)-Benzyl 1-(5-bromo-3-(5-fluoropyridin-3-yl)-4-oxo-3,4-dihydropyrrolo[1,2-f][1,2,4]triazin-2-yl)ethylcarbamate This compound was prepared starting from (S)-benzyl 1-(3-bromo-2-(5-fluoropyridin-3-ylcarbamoyl)-1H-pyrrol-1-ylamino)-1-oxopropan-2-ylcarbamate (1.50 g, 3.0 mmol) and following the experimental procedure described in Preparation 73b to afford 0.40 g (28% yield) of the title compound.
LRMS (m/z): 486, 488 (M+1)$^+$.

c) (S)-2-(1-Aminoethyl)-3-(5-fluoropyridin-3-yl)pyrrolo[1,2-f][1,2,4]triazin-4(3H)-one This compound was prepared starting from (S)-benzyl 1-(5-bromo-3-(5-fluoropyridin-3-yl)-4-oxo-3,4-dihydropyrrolo[1,2-f][1,2,4]triazin-2-yl)ethylcarbamate (100 mg, 0.21 mmol) and following the experimental procedure described in Preparation 127c to afford 53 mg (95% yield) of the title compound.
LRMS (m/z): 274 (M+1)$^+$.

Preparation 127

(S)-2-(1-Aminoethyl)-3-(pyrimidin-5-yl)pyrrolo[1,2-f][1,2,4]triazin-4(3H)-one a) (S)-Benzyl 1-(3-bromo-2-(pyrimidin-5-ylcarbamoyl)-1H-pyrrol-1-ylamino)-1-oxopropan-2-ylcarbamate The title compound was prepared from (S)-methyl 1-(2-(benzyloxycarbonylamino)propanamido)-3-bromo-1H-pyrrole-2-carboxylate (0.81 g, 1.91 mmol) and pyrimidin-5-amine (1.45 g, 15.3 mmol) following the experimental procedure described in Preparation 44a. 0.58 g (62% yield) of the desired compound were obtained.
LRMS (m/z): 487, 489 (M+1)$^+$.

b) (S)-Benzyl 1-(5-bromo-4-oxo-3-(pyrimidin-5-yl)-3,4-dihydropyrrolo[1,2-f][1,2,4]triazin-2-yl)ethylcarbamate This compound was prepared starting from (S)-benzyl 1-(3-bromo-2-(pyrimidin-5-ylcarbamoyl)-1H-pyrrol-1-ylamino)-1-oxopropan-2-ylcarbamate (0.57 g, 1.17 mmol) and following the experimental procedure described in Preparation 73b to afford 0.33 g (61% yield) of the title compound.
LRMS (m/z): 469, 471 (M+1)$^+$.

c) (S)-2-(1-Aminoethyl)-3-(pyrimidin-5-yl)pyrrolo[1,2-f][1,2,4]triazin-4(3H)-one To a solution of (S)-benzyl 1-(5-bromo-4-oxo-3-(pyrimidin-5-yl)-3,4-dihydropyrrolo[1,2-f][1,2,4]triazin-2-yl)ethylcarbamate (40 mg, 0.09 mmol) in 4 mL of methanol were added Et$_3$N (24 µL, 0.18 mmol) and Pd/C, 10% (20 mg). The reaction was stirred at room temperature under hydrogen (30 psi) for 15 hours. The reaction mixture was filtered through Celite® and the filtrate was evaporated to dryness to give 20 mg (89%) of the title compound.
LRMS (m/z): 257 (M+1)$^+$.

Preparation 128

(S)-2-(1-Amino-3-hydroxypropyl)-3-phenylpyrrolo[1,2-f][1,2,4]triazin-4(3H)-one a) (S)-tert-Butyl 4-(benzyloxy)-1-oxo-1-(2-(phenylcarbamoyl)-1H-pyrrol-1-ylamino)butan-2-ylcarbamate The title compound was prepared from 1-amino-N-phenyl-1H-pyrrole-2-carboxamide (0.65 g, 3.2 mmol) and (S)-4-

(benzyloxy)-2-(tert-butoxycarbonylamino)butanoic acid (1.0 g, 3.2 mmol) following the experimental procedure described in Preparation 73a. 1.57 g (96% yield) of the desired compound were obtained.
LRMS (m/z): 493 (M+1)⁺.

b) (S)-tert-Butyl 3-(benzyloxy)-1-(4-oxo-3-phenyl-3,4-dihydropyrrolo[1,2-f][1,2,4]triazin-2-yl)propylcarbamate This compound was prepared starting from (S)-tert-butyl 4-(benzyloxy)-1-oxo-1-(2-(phenylcarbamoyl)-1H-pyrrol-1-ylamino)butan-2-ylcarbamate (1.57 g, 3.2 mmol) and following the experimental procedure described in Preparation 73b to afford 0.81 g (53% yield) of the title compound.
LRMS (m/z): 475 (M+1)⁺.

c) (S)-tert-Butyl 3-hydroxy-1-(4-oxo-3-phenyl-3,4-dihydropyrrolo[1,2-f][1,2,4]triazin-2-yl)propylcarbamate To a solution of (S)-tert-butyl 3-(benzyloxy)-1-(4-oxo-3-phenyl-3,4-dihydropyrrolo[1,2-f][1,2,4]triazin-2-yl)propylcarbamate (0.65 g, 1.37 mmol) in 33 mL of methanol was added Pd/C 10% (0.65 g). The reaction was stirred at room temperature under hydrogen (30 psi) for 15 hours. The reaction mixture was filtered through Celite® and the filtrate was evaporated to dryness to give 0.52 g (99%) of the title compound.
LRMS (m/z): 385 (M+1)⁺.

d) (S)-2-(1-Amino-3-hydroxypropyl)-3-phenylpyrrolo[1,2-f][1,2,4]triazin-4(3H)-one This compound was prepared starting from (S)-tert-butyl 3-hydroxy-1-(4-oxo-3-phenyl-3,4-dihydropyrrolo[1,2-f][1,2,4]triazin-2-yl)propylcarbamate (0.30 g, 0.8 mmol) and following the experimental procedure described in Preparation 81b to afford 0.24 g (85% yield) of the title compound, isolated as the hydrochloric salt form.
LRMS (m/z): 285 (M+1)⁺.

Preparation 129

(S)-2-(1-Amino-3-hydroxypropyl)pyrrolo[1,2-f][1,2,4]triazin-4(3H)-one a) (S)-tert-Butyl 3-(benzyloxy)-1-(4-oxo-3,4-dihydropyrrolo[1,2-f][1,2,4]triazin-2-yl)propylcarbamate This compound was obtained as subproduct in preparation 128b.
LRMS (m/z): 399 (M+1)⁺.

b) (S)-tert-Butyl 3-hydroxy-1-(4-oxo-3,4-dihydropyrrolo[1,2-f][1,2,4]triazin-2-yl)propylcarbamate This compound was prepared starting from (S)-tert-butyl 3-(benzyloxy)-1-(4-oxo-3,4-dihydropyrrolo[1,2-f][1,2,4]triazin-2-yl)propylcarbamate (200 mg, 0.5 mmol) and following the experimental procedure described in Preparation 128c to afford 152 mg (93% yield) of the title compound.
LRMS (m/z): 309 (M+1)⁺.

c) (S)-2-(1-Amino-3-hydroxypropyl)pyrrolo[1,2-f][1,2,4]triazin-4(3H)-one

This compound was prepared starting from (S)-tert-butyl 3-hydroxy-1-(4-oxo-3,4-dihydropyrrolo[1,2-f][1,2,4]triazin-2-yl)propylcarbamate (150 mg, 0.5 mmol) and following the experimental procedure described in Preparation 81b to afford 96 mg (73% yield, 91% purity) of the title compound, isolated as the hydrochloric salt form.
LRMS (m/z): 245 (M+1)⁺.

Preparation 130

(S)-2-(1-Aminoethyl)-3-(6-(trifluoromethyl)pyridin-2-yl)pyrrolo[1,2-f][1,2,4]triazin-4(3H)-one a) (S)-Benzyl 1-(3-bromo-2-(6-(trifluoromethyl)pyridin-2-ylcarbamoyl)-1H-pyrrol-1-ylamino)-1-oxopropan-2-ylcarbamate The title compound was prepared from (S)-methyl 1-(2-(benzyloxycarbonylamino)propanamido)-3-bromo-1H-pyrrole-2-carboxylate (2.00 g, 4.7 mmol) and 6-(trifluoromethyl)pyridin-2-amine (3.00 g, 18.5 mmol) following the experimental procedure described in Preparation 44a. 1.32 g (51% yield) of the desired compound were obtained.
LRMS (m/z): 554, 556 (M+1)⁺.

b) (S)-Benzyl 1-(5-bromo-4-oxo-3-(6-(trifluoromethyl)pyridin-2-yl)-3,4-dihydropyrrolo[1,2-f][1,2,4]triazin-2-yl)ethylcarbamate This compound was prepared starting from (S)-benzyl 1-(3-bromo-2-(6-(trifluoromethyl)pyridin-2-ylcarbamoyl)-1H-pyrrol-1-ylamino)-1-oxopropan-2-ylcarbamate (1.32 g, 2.4 mmol) and following the experimental procedure described in Preparation 68b to afford 0.71 g (55% yield) of the title compound.
LRMS (m/z): 536, 538 (M+1)⁺.

c) (S)-2-(1-Aminoethyl)-3-(6-(trifluoromethyl)pyridin-2-yl)pyrrolo[1,2-f][1,2,4]triazin-4(3H)-one This compound was prepared starting from (S)-benzyl 1-(5-bromo-4-oxo-3-(6-(trifluoromethyl)pyridin-2-yl)-3,4-dihydropyrrolo[1,2-f][1,2,4]triazin-2-yl)ethylcarbamate (1.00 mg, 1.9 mmol) and following the experimental procedure described in Preparation 127c to afford 0.55 g (92% yield) of the title compound.
LRMS (m/z): 324 (M+1)⁺.

Preparation 131

(S)-2-(1-Aminoethyl)-3-(5-fluoropyridin-3-yl)-4-oxo-3,4-dihydropyrrolo[1,2-f][1,2,4]triazine-5-carbonitrile a) (S)-Benzyl 1-(5-cyano-3-(5-fluoropyridin-3-yl)-4-oxo-3,4-dihydropyrrolo[1,2-f][1,2,4]triazin-2-yl)ethylcarbamate This compound was prepared starting from (S)-benzyl 1-(5-bromo-3-(5-fluoropyridin-3-yl)-4-oxo-3,4-dihydropyrrolo[1,2-f][1,2,4]triazin-2-yl)ethylcarbamate (240 mg, 0.5 mmol) and following the experimental procedure described in Preparation 47a to afford 170 mg (71% yield, 90% purity) of the title compound.
LRMS (m/z): 433 (M+1)⁺.

b) (S)-2-(1-Aminoethyl)-3-(5-fluoropyridin-3-yl)-4-oxo-3,4-dihydropyrrolo[1,2-f][1,2,4]triazine-5-carbonitrile This compound was prepared starting from (S)-benzyl 1-(5-cyano-3-(5-fluoropyridin-3-yl)-4-oxo-3,4-dihydropyrrolo[1,2-f][1,2,4]triazin-2-yl)ethylcarbamate (170 g, 0.4 mmol) and following the experimental procedure described in Preparation 128c but the mixture was hydrogenated at 14 psi to afford 114 mg (97% yield) of the title compound.

LRMS (m/z): 299 (M+1)+.

Preparation 132

2-(1-Aminocyclopropyl)-3-phenylpyrrolo[1,2-f][1,2,4]triazin-4(3H)-one a) tert-Butyl 1-(2-(phenylcarbamoyl)-1H-pyrrol-1-ylcarbamoyl)cyclopropylcarbamate The title compound was prepared from 1-amino-N-phenyl-1H-pyrrole-2-carboxamide (0.30 g, 1.5 mmol) and 1-(tert-butoxycarbonylamino)cyclopropanecarboxylic acid (0.30 g, 1.5 mmol) following the experimental procedure described in Preparation 73a. 0.55 g (91% yield) of the desired compound were obtained.

LRMS (m/z): 385 (M+1)+.

b) tert-Butyl 1-(4-oxo-3-phenyl-3,4-dihydropyrrolo[1,2-f][1,2,4]triazin-2-yl)cyclopropylcarbamate This compound was prepared starting from tert-butyl 1-(2-(phenylcarbamoyl)-1H-pyrrol-1-ylcarbamoyl)cyclopropylcarbamate (0.54 g, 1.4 mmol) and following the experimental procedure described in Preparation 68b to afford 0.42 g (74% yield) of the title compound.

LRMS (m/z): 367 (M+1)+.

c) 2-(1-Aminocyclopropyl)-3-phenylpyrrolo[1,2-f][1,2,4]triazin-4(3H)-one

This compound was prepared starting from tert-butyl 1-(4-oxo-3-phenyl-3,4-dihydropyrrolo[1,2-f][1,2,4]triazin-2-yl)cyclopropylcarbamate (0.41 g, 1.1 mmol) and following the experimental procedure described in Preparation 81b to afford 0.33 g (98% yield) of the title compound, isolated as the hydrochloric salt form.

LRMS (m/z): 267 (M+1)+.

Preparation 133

(S)-2-(1-Aminoethyl)-3-(tetrahydro-2H-pyran-4-yl)pyrrolo[1,2-f][1,2,4]triazin-4(3H)-one a) (S)-tert-Butyl 1-oxo-1-(2-(tetrahydro-2H-pyran-4-yl carbamoyl)-1H-pyrrol-1-ylamino)propan-2-ylcarbamate Tetrahydro-2H-pyran-4-amine (900 microl, 8.69 mmols) was added to a solution of (S)-methyl 1-(2-(tert-butoxycarbonylamino)propanamido)-1H-pyrrole-2-carboxylate (900 mg, 2.89 mmols, preparation 109) in toluene (36 ml). A 2M solution of Trimethyl aluminium in toluene (7 ml, 14.00 mmols) was added and it was stirred at 80° C. overnight. Water (50 ml) and a 0.5M solution of sodium tartrate (25 ml) were added. It was extracted with ethylacetate. The combined organic layers were washed with water and brine. It was dried, filtered and concentrated in vacuum. The title compound was obtained (617 mg, 56%).

LRMS (m/z): 381 (M+1)+ b) (S)-tert-Butyl 1-(4-oxo-3-(tetrahydro-2H-pyran-4-yl)-3,4-dihydropyrrolo[1,2-f][1,2,4]triazin-2-yl)ethylcarbamate Bromine (200 µl, 3.905 mmols) was added to a solution of triphenylphosphine (500 mg, 1.91 mmols) in dry dichloromethane (10 ml) and it was stirred under inert atmosphere at room temperature for 30 min. Triethylamine (1.14 ml, 8.179 mmols) was added and it was stirred under inert atmosphere at room temperature for 5 min. A solution of (S)-tert-butyl 1-oxo-1-(2-(tetrahydro-2H-pyran-4-ylcarbamoyl)-1H-pyrrol-1-ylamino)propan-2-ylcarbamate (517 mg, 1.36 mmols) in dry dichloromethane (5 ml) was added to the previous solution and it was stirred under inert atmosphere at 60° C. for 1 h. A 4% aqueous solution of NaHCO3 (100 ml) and dichloromethane (75 ml) were added to the reaction crude. The organic layer was passed through a phase separator cartridge and it was concentrated in vacuum. The residue was dissolved in 10 ml of THF/DMF 9:1 and sodium methanethiolate (172 mg, 2.45 mmols) was added. It was stirred under inert atmosphere at room temperature overnight. A 4% aqueous solution of NaHCO$_3$ and ethylacetate were added to the reaction crude. The organic phase was washed with water and brine. It was dried, filtered and concentrated in vacuum. The title compound was obtained (1180 mg, 60% approx purity, 100%) pure enough to be used in the next synthetic step without further purification.

LRMS (m/z): 363 (M+1)+ c) (S)-2-(1-Aminoethyl)-3-(tetrahydro-2H-pyran-4-yl)pyrrolo[1,2-f][1,2,4]triazin-4(3H)-one HCl 4M dioxane (24 ml, 96 mmols) was added to (S)-tert-butyl 1-(4-oxo-3-(tetrahydro-2H-pyran-4-yl)-3,4-dihydropyrrolo[1,2-f][1,2,4]triazin-2-yl)ethylcarbamate (1180 mg, 60% purity, 1.95 mmols) and it was stirred at room temperature for 1 h. It was concentrated in vacuum. Water was added and it was washed with dichloromethane. A saturated aqueous solution of potassium carbonate was added to the aqueous phase and it was extracted with dichloromethane. The organic phase was dried, filtered and concentrated in vacuum. The title compound (287 mg, 85% purity, 48%) was obtained.

LRMS (m/z): 263 (M+1)+

$^1$H NMR (400 MHz, DMSO-d$_6$) d ppm 1.41 (d, 3 H) 1.55-1.82 (m, 2 H) 2.13 (s, 2 H) 2.64-2.89 (m, 2 H) 3.34-3.45 (m, 2 H) 3.80-4.01 (m, 2 H) 4.10-4.27 (m, 1 H) 4.58-4.75 (m, 1 H) 6.52 (dd, 1 H) 6.82 (dd, 1 H) 7.41-7.55 (m, 1 H)

Preparation 134

(S)-2-(1-Aminoethyl)-3-(2,2,2-trifluoroethyl)pyrrolo[1,2-f][1,2,4]triazin-4(3H)-one a) (S)-tert-Butyl 1-oxo-1-(2-(2,2,2-trifluoroethylcarbamoyl)-1H-pyrrol-1-ylamino)propan-2-ylcarbamate 2,2,2-Trifluoroethanamine (680 microl, 8.66 mmols) was added to a solution of (S)-methyl 1-(2-(tert-butoxycarbonylamino)propanamido)-1H-pyrrole-2-carboxylate (900 mg, 2.89 mmols) in toluene (36 ml). A 2M solution of trimethyl aluminium in toluene (7 ml, 14.00 mmols) was added and it was stirred at 80° C. overnight. Water (50 ml) and a 0.5M solution of sodium tartrate (25 ml) were added. It was extracted with ethylacetate. The combined organic layers were washed with water and brine. It was dried, filtered and concentrated in vacuum. The title compound was obtained (1.021 g, 93%).

LRMS (m/z): 379 (M+1)+

¹H NMR (400 MHz, DMSO-d₆) d ppm 1.20-1.30 (d, 3 H) 1.34-1.43 (s, 9 H) 3.80-4.03 (m, 2 H) 4.03-4.17 (m, 1 H) 6.00-6.20 (m, 1 H) 6.80-6.93 (m, 2 H) 6.96-7.17 (m, 1 H) 8.39-8.56 (m, 1 H) 11.09-11.27 (s, 1 H)

b) (S)-tert-Butyl 1-(4-oxo-3-(2,2,2-trifluoroethyl)-3,4-dihydropyrrolo[1,2-f][1,2,4]triazin-2-yl)ethylcarbamate Bromine (350 µl, 6.83 mmols) was added to a solution of triphenylphosphine (895 mg, 3.41 mmols) in dry dichloromethane (18 ml) and it was stirred under inert atmosphere at room temperature for 30 min. Triethylamine (2.00 ml, 14.35 mmols) was added and it was stirred under inert atmosphere at room temperature for 5 min. A solution of (S)-tert-butyl 1-oxo-1-(2-(2,2,2-trifluoroethylcarbamoyl)-1H-pyrrol-1-ylamino)propan-2-ylcarbamate (921 mg, 2.43 mmols) in dry dichloromethane (9 ml) was added to the previous solution and it was stirred under inert atmosphere at 60° C. for 1 h. A 4% aqueous solution of NaHCO3 (180 ml) and dichloromethane (135 ml) were added to the reaction crude. The organic layer was passed through a phase separator cartridge and it was concentrated in vacuum. The residue was dissolved in 18 ml of THF/DMF 9:1 and sodium methanethiolate (307 mg, 4.38 mmols) was added. It was stirred under inert atmosphere at room temperature overnight. A 4% aqueous solution of NaHCO3 and ethylacetate were added to the reaction crude. The organic phase was washed with water and brine. It was dried, filtered and concentrated in vacuum. The title compound was obtained (2300 mg, 50% approx purity, 100%) pure enough to be used in the next synthetic step without further purification.

LRMS (m/z): 361 (M+1)+ c) (S)-2-(1-Aminoethyl)-3-(2,2,2-trifluoroethyl)pyrrolo[1,2-f][1,2,4]triazin-4(3H)-one HCl 4M dioxane (37 ml, 148 mmols) was added to (S)-tert-butyl 1-(4-oxo-3-(2,2,2-trifluoroethyl)-3,4-dihydropyrrolo[1,2-t][1,2,4]triazin-2-yl)ethylcarbamate (2.30 g, 50% purity, 3.19 mmols) and it was stirred at room temperature for 1 h. It was concentrated in vacuum. Water was added and it was washed with dichloromethane. A saturated aqueous solution of potassium carbonate (50 ml) was added to the aqueous phase and it was extracted with dichloromethane. The organic phase was dried, filtered and concentrated in vacuum. The title compound (526 mg, 58% yield) was obtained.

LRMS (m/z): 261 (M+1)+

¹H NMR (400 MHz, DMSO-d₆) d ppm 1.42 (d, 3 H) 2.20 (s, 2 H) 3.86-4.16 (q, 1 H) 4.88-5.40 (m, 2 H) 6.60 (dd, 1 H) 6.99 (dd, 1 H) 7.47-7.81 (m, 1 H)

Preparation 135

(S)-2-(1-Aminoethyl)-3-cyclobutylpyrrolo[1,2-f][1,2,4]triazin-4(3H)-one a) (S)-tert-Butyl 1-(2-(cyclobutylcarbamoyl)-1H-pyrrol-1-ylamino)-1-oxopropan-2-yl carbamate Same procedure as described in preparation 133a was used from (S)-methyl 1-(2-(tert-butoxycarbonylamino)propanamido)-1H-pyrrole-2-carboxylate (900 mg, 2.66 mmols) and cyclobutanamine (0.68 ml, 7.98 mmols). After reverse phase chromatography the title compound was obtained (229 mg, 25%).

LRMS (m/z): 351 (M+1)+ b) (S)-tert-Butyl 1-(3-cyclobutyl-4-oxo-3,4-dihydropyrrolo[1,2-f][1,2,4]triazin-2-yl)ethylcarbamate Same procedure as described in preparation 133b was used from (S)-tert-butyl 1-(2-(cyclobutylcarbamoyl)-1H-pyrrol-1-ylamino)-1-oxopropan-2-ylcarbamate (204 mg, 0.58 mmols). The title compound was obtained (424 mg, 25% purity, 50%) pure enough to be used in the next synthetic step without further purification.

LRMS (m/z): 333 (M+1)+ c) (S)-2-(1-Aminoethyl)-3-cyclobutylpyrrolo[1,2-f][1,2,4]triazin-4(3H)-one

Same procedure as described in preparation 133c was used from (S)-tert-butyl 1-(3-cyclobutyl-4-oxo-3,4-dihydropyrrolo[1,2-f][1,2,4]triazin-2-yl)ethylcarbamate (424 mg, 25% purity, 0.32 mmols). The title compound was obtained (107 mg, 83% purity, 100%)

LRMS (m/z): 233 (M+1)+

Preparation 136

(S)-2-(1-Aminoethyl)-3-cyclopropylpyrrolo[1,2-f][1,2,4]triazin-4(3H)-one a) (S)-tert-Butyl 1-(2-(cyclopropylcarbamoyl)-1H-pyrrol-1-ylamino)-1-oxopropan-2-ylcarbamate Same procedure as described in preparation 133a was used from (S)-methyl 1-(2-(tert-butoxycarbonylamino)propanamido)-1H-pyrrole-2-carboxylate (900 mg, 80% purity, 2.28 mmols) and cyclopropanamine (0.48 ml, 6.86 mmols). After 3.5 h stirring at 80° C. the title compound was obtained (589 mg, 77%).

LRMS (m/z): 337 (M+1)+ b) (S)-tert-Butyl 1-(3-cyclopropyl-4-oxo-3,4-dihydropyrrolo[1,2-f][1,2,4]triazin-2-yl)ethylcarbamate Same procedure as described in preparation 133b was used from (S)-tert-butyl 1-(2-(cyclopropylcarbamoyl)-1H-pyrrol-1-ylamino)-1-oxopropan-2-ylcarbamate (589 mg, 1.75 mmols). The title compound was obtained (1.18 g, 100%)

LRMS (m/z): 319 (M+1)+ c) (S)-2-(1-Aminoethyl)-3-cyclopropylpyrrolo[1,2-f][1,2,4]triazin-4(3H)-one

Same procedure as described in preparation 133c was used from (S)-tert-butyl 1-(3-cyclopropyl-4-oxo-3,4-dihydropyrrolo[1,2-f][1,2,4]triazin-2-yl)ethylcarbamate (1.18 g, 3.37 mmols). The title compound was obtained (311 mg, 69% purity, 29%)

LRMS (m/z): 219 (M+1)+

Preparation 137

2-((S)-1-Aminoethyl)-3-(tetrahydro-2H-pyran-3-yl)pyrrolo[1,2-f][1,2,4]triazin-4(3H)-one a) tert-Butyl (2S)-1-oxo-1-(2-(tetrahydro-2H-pyran-3-ylcarbamoyl)-1H-pyrrol-1-ylamino)propan-2-ylcarbamate Anhydrous triethylamine (600 µl, 4.31 mmols) was added to a solution of tetrahydro-2H-pyran-3-amine.HCl (600 mg, 4.36 mmols) in toluene (10 ml) and it was stirred at room temperature for 30 min. A solution of (S)-methyl 1-(2-(tert-butoxycarbonylamino)propanamido)-1H-pyrrole-2-carboxylate (900 mg, 2.90 mmols) in toluene (36 ml) and a 2M solution of trimethylaluminium in toluene (7 ml, 14 mmols) were added. The solution obtained was stirred at 80° C. for 2 h. Water (70 ml) and a 0.5M sodium tartrate solution (35 ml) were added. It was extracted with ethylacetate. The combined organic layers were washed with water and brine. It was dried, filtered and concentrated in vacuum. The title compound was obtained (750 mg, 68%).
LRMS (m/z): 381 (M+1)+ b) tert-Butyl (1S)-1-(4-oxo-3-(tetrahydro-2H-pyran-3-yl)-3,4-dihydropyrrolo[1,2-f][1,2,4]triazin-2-yl)ethylcarbamate Bromine (283 µl, 5.52 mmols) was added to a solution of triphenylphosphine (727 mg, 2.77 mmols) in dry dichloromethane (15 ml) and it was stirred under inert atmosphere at room temperature for 30 min. Triethylamine (1.65 ml, 11.83 mmols) was added and it was stirred under inert atmosphere at room temperature for 5 min. A solution of ted-butyl (2S)-1-oxo-1-(2-(tetrahydro-2H-pyran-3-ylcarbamoyl)-1H-pyrrol-1-ylamino)propan-2-ylcarbamate (750 mg, 1.97 mmols) in dry dichloromethane (7 ml) was added to the previous solution and it was stirred under inert atmosphere at 60° C. for 1 h. A 4% aqueous solution of NaHCO3 (145 ml) and dichloromethane (110 ml) were added to the reaction crude. The organic layer was passed through a phase separator cartridge and it was concentrated in vacuum. The residue was dissolved in 15 ml of THF/DMF 9:1 and sodium methanethiolate (250 mg, 3.57 mmols) was added. It was stirred under inert atmosphere at room temperature overnight. A 4% aqueous solution of NaHCO$_3$ and ethylacetate were added to the reaction crude. The organic phase was washed with water and brine. It was dried, filtered and concentrated in vacuum. The title compound was obtained (1163 mg, 60% approx purity, 100%) pure enough to be used in the next synthetic step without further purification.
LRMS (m/z): 363 (M+1)+ c) 2-((S)-1-Aminoethyl)-3-(tetrahydro-2H-pyran-3-yl)pyrrolo[1,2-f][1,2,4]triazin-4(3H)-one HCl 4M dioxane (24 ml, 96 mmols) was added to tert-butyl (1S)-1-(4-oxo-3-(tetrahydro-2H-pyran-3-yl)-3,4-dihydropyrrolo[1,2-f][1,2,4]triazin-2-yl)ethylcarbamate (1163 mg, 1.93 mmols, 60% purity) and it was stirred at room temperature for 1 h. It was concentrated in vacuum. Water was added and it was washed with dichloromethane. A saturated aqueous solution of potassium carbonate (50 ml) was added to the aqueous phase and it was extracted with dichloromethane. The organic phase was dried, filtered and concentrated in vacuum. The title compound (278 mg, 55%) was obtained.
LRMS (m/z): 263 (M+1)+

Preparation 138

(S)-2-(1-Aminoethyl)-3-(isoxazol-3-yl)pyrrolo[1,2-f][1,2,4]triazin-4(3H)-one a) (S)-tert-Butyl 1-(2-(isoxazol-3-yl carbamoyl)-1H-pyrrol-1-ylamino)-1-oxopropan-2-ylcarbamate Same procedure as described in preparation 133a was used from (S)-methyl 1-(2-(tert-butoxycarbonylamino)propanamido)-1H-pyrrole-2-carboxylate (854 mg, 2.17 mmols) and isoxazol-3-amine (0.48 ml, 6.50 mmols). The title compound was obtained (919 mg, 55% purity, 64%).
LRMS (m/z): 364 (M+1)+ b) (S)-tert-Butyl 1-(3-(isoxazol-3-yl)-4-oxo-3,4-dihydropyrrolo[1,2-f][1,2,4]triazin-2-yl)ethylcarbamate Same procedure as described in preparation 133b was used from (S)-tert-butyl 1-(2-(isoxazol-3-ylcarbamoyl)-1H-pyrrol-1-ylamino)-1-oxopropan-2-ylcarbamate (919 mg, 55% purity, 1.39 mmols). The title compound was obtained (1.34 g, 17% purity, 47%)
LRMS (m/z): 346 (M+1)+ c) (S)-2-(1-Aminoethyl)-3-(isoxazol-3-yl)pyrrolo[1,2-f][1,2,4]triazin-4(3H)-one Same procedure as described in preparation 133c was used from (S)-tert-butyl 1-(3-(isoxazol-3-yl)-4-oxo-3,4-dihydropyrrolo[1,2-f][1,2,4]triazin-2-yl)ethylcarbamate (1.34 g, 17% purity, 0.66 mmols). The title compound was obtained (188 mg, 100%)
LRMS (m/z): 246 (M+1)+

Preparation 139

(S)-tert-Butyl 3-(benzyloxy)-1-(5-bromo-3-(3,5-difluorophenyl)-4-oxo-3,4-dihydropyrrolo[1,2-f][1,2,4]triazin-2-yl)propylcarbamate a) (S)-Methyl 1-(4-(benzyloxy)-2-(tert-butoxycarbonylamino)butanamido)-3-bromo-1H-pyrrole-2-carboxylate The title compound was prepared from methyl 1-amino-3-bromo-1H-pyrrole-2-carboxylate (2.83 g, 12.9 mmol) and (S)-4-(benzyloxy)-2-(tert-butoxycarbonylamino)butanoic acid (4.0 g, 12.9 mmol) following the experimental procedure described in Preparation 73a. 6.12 g (93% yield) of the desired compound were obtained.
LRMS (m/z): 510, 512 (M+1)+.

b) (S)-tert-Butyl 4-(benzyloxy)-1-(3-bromo-2-(3,5-difluorophenylcarbamoyl)-1H-pyrrol-1-ylamino)-1-oxobutan-2-ylcarbamate The title compound was prepared from (S)-methyl 1-(4-(benzyloxy)-2-(tert-butoxycarbonylamino)butanamido)-3-bromo-1H-pyrrole-2-carboxylate (4.0 g, 7.8 mmol) and 3,5-difluoroaniline (5.1 g, 39.0 mmol) following the experimental procedure described in Preparation 44a. 3.2 g (66% yield) of the desired compound were obtained.
LRMS (m/z): 607, 609 (M+1)+.

c) (S)-tert-Butyl 3-(benzyloxy)-1-(5-bromo-3-(3,5-difluorophenyl)-4-oxo-3,4-dihydropyrrolo[1,2-f][1,2,4]triazin-2-yl)propylcarbamate This compound was prepared starting from (S)-tert-butyl 4-(benzyloxy)-1-(3-bromo-2-(3,5-difluorophenylcarbamoyl)-1H-pyrrol-1-ylamino)-1-oxobutan-2-ylcarbamate (2.14 g, 3.52 mmol) and following the experimental procedure described in Preparation 68b to afford 1.66 g (80% yield) of the title compound.

LRMS (m/z): 589, 591 (M+1)$^+$.

Preparation 140

(S)-2-(1-Amino-3-hydroxypropyl)-3-(3,5-difluorophenyl)-5-(trifluoromethyl)pyrrolo[1,2-f][1,2,4]triazin-4(3H)-one a) (S)-tert-Butyl 3-(benzyloxy)-1-(3-(3,5-difluorophenyl)-5-iodo-4-oxo-3,4-dihydropyrrolo[1,2-f][1,2,4]triazin-2-yl)propylcarbamate This compound was prepared starting from (S)-tert-butyl 3-(benzyloxy)-1-(5-bromo-3-(3,5-difluorophenyl)-4-oxo-3,4-dihydropyrrolo[1,2-f][1,2,4]triazin-2-yl)propylcarbamate (0.81 g, 1.37 mmol) and following the experimental procedure described in Preparation 26a to afford 0.80 g (54% yield, 59% purity) of the title compound.

LRMS (m/z): 637 (M+1)$^+$.

b) (S)-tert-Butyl 3-(benzyloxy)-1-(3-(3,5-difluorophenyl)-4-oxo-5-(trifluoromethyl)-3,4-dihydropyrrolo[1,2-f][1,2,4]triazin-2-yl)propylcarbamate This compound was prepared starting from (S)-tert-butyl 3-(benzyloxy)-1-(3-(3,5-difluorophenyl)-5-iodo-4-oxo-3,4-dihydropyrrolo[1,2-f][1,2,4]triazin-2-yl)propylcarbamate (0.40 g, 0.63 mmol) and following the experimental procedure described in Preparation 26b to afford 0.32 g (87% yield) of the title compound.

LRMS (m/z): 579 (M+1)$^+$.

c) (S)-tert-Butyl 1-(3-(3,5-difluorophenyl)-4-oxo-5-(trifluoromethyl)-3,4-dihydropyrrolo[1,2-f][1,2,4]triazin-2-yl)-3-hydroxypropylcarbamate This compound was prepared starting from (S)-tert-butyl 3-(benzyloxy)-1-(3-(3,5-difluorophenyl)-4-oxo-5-(trifluoromethyl)-3,4-dihydropyrrolo[1,2-f][1,2,4]triazin-2-yl)propylcarbamate (0.32 g, 0.55 mmol) and following the experimental procedure described in Preparation 128c to afford 0.26 g (98% yield) of the title compound.

LRMS (m/z): 489 (M+1)$^+$.

d) (S)-2-(1-Amino-3-hydroxypropyl)-3-(3,5-difluorophenyl)-5-(trifluoromethyl)pyrrolo[1,2-f][1,2,4]triazin-4(3H)-one This compound was prepared starting from (S)-tert-butyl 1-(3-(3,5-difluorophenyl)-4-oxo-5-(trifluoromethyl)-3,4-dihydropyrrolo[1,2-f][1,2,4]triazin-2-yl)-3-hydroxypropylcarbamate (0.25 g, 0.51 mmol) and following the experimental procedure described in Preparation 81b to afford 0.21 g (95% yield) of the title compound, isolated as the hydrochloric salt form.

LRMS (m/z): 389 (M+1)$^+$.

Preparation 141 a) (S)-tert-Butyl 3-(benzyloxy)-1-(5-cyano-3-(3,5-difluorophenyl)-4-oxo-3,4-dihydropyrrolo[1,2-f][1,2,4]triazin-2-yl)propylcarbamate This compound was prepared starting from (S)-tert-butyl 3-(benzyloxy)-1-(5-bromo-3-(3,5-difluorophenyl)-4-oxo-3,4-dihydropyrrolo[1,2-f][1,2,4]triazin-2-yl)propylcarbamate (0.81 g, 1.37 mmol) and following the experimental procedure described in Preparation 47a to afford 0.57 g (77% yield) of the title compound.

LRMS (m/z): 536 (M+1)$^+$.

b) (S)-2-(1-Amino-3-hydroxypropyl)-3-(3,5-difluorophenyl)-4-oxo-3,4-dihydropyrrolo[1,2-f][1,2,4]triazine-5-carbonitrile Under a nitrogen atmosphere, to a solution of (S)-tert-butyl 3-(benzyloxy)-1-(5-cyano-3-(3,5-difluorophenyl)-4-oxo-3,4-dihydropyrrolo[1,2-f][1,2,4]triazin-2-yl)propylcarbamate (0.25 g, 0.47 mmol) in 1.9 mL of dichloromethane, boron tribromide 1.0 M methylene chloride solution (1.41 ml, 1.41 mmol) was added at −78° C., and the mixture was stirred at the same temperature for 1 hour. After saturated aqueous NaHCO$_3$ was added and the mixture was extracted three times with ethyl acetate. The combined organic extracts were washed with water and brine, dried over magnesium sulphate, filtered and the solvent evaporated in vacuum to afford 0.17 g (77% yield, 73% purity) of the title compound that was used in the next step without any further purification.

LRMS (m/z): 346 (M+1)$^+$.

Preparation 142

(S)-4-Amino-6-(1-(3-(1-(4-methoxybenzyl)-1H-pyrazol-4-yl)-4-oxo-3,4-dihydropyrrolo[1,2-f][1,2,4]triazin-2-yl)ethylamino)pyrimidine-5-carbonitrile a) (S)-tert-Butyl 1-(2-(1-(4-methoxybenzyl)-1H-pyrazol-4-ylcarbamoyl)-1H-pyrrol-1-ylamino)-1-oxopropan-2-ylcarbamate This compound was prepared starting from (S)-methyl 1-(2-(tert-butoxycarbonylamino)propanamido)-1H-pyrrole-2-carboxylate (900 mg, 2.89 mmol) and 1-(4-methoxybenzyl)-1H-pyrazol-4-amine (1.24 g, 6.10 mmol) following the experimental procedure described in Preparation 27a to afford 1.02 g (100% purity, 73% yield) of the title compound after purification by flash chromatography (0% to 100% AcOEt/hexanes).

LRMS (m/z): 483 (M+1)$^+$.

b) (S)-tert-Butyl 1-(3-(1-(4-methoxybenzyl)-1H-pyrazol-4-yl)-4-oxo-3,4-dihydropyrrolo[1,2-f][1,2,4]triazin-2-yl)ethylcarbamate Bromine (151 µl, 2.95 mmol) was added dropwise to a solution of triphenylphosphine (780 mg, 2.97 mmol) in dichloromethane (8 ml) under nitrogen. The solution was stirred for 30 min, and triethylamine (1.18 ml, 8.47 mmol) and a solution of (S)-tert-butyl 1-(2-(1-(4-methoxybenzyl)-1H-pyrazol-4-ylcarbamoyl)-1H-pyrrol-1-ylamino)-1-oxopropan-2-ylcarbamate (1.02 g, 2.11 mmol) in 16 ml of dichloromethane was added. The reaction mixture was stirred at 60°

C. for 2 h, and then poured onto 4% NaHCO$_3$. After extraction with dichloromethane, the organic phase was dried over magnesium sulphate and the volatiles were removed under reduced pressure. The residue was redissolved in a mixture of 40 ml of tetrahydrofurane and 4 ml of dimethylformamide, sodium thiomethoxide (0.44 g, 6.28 mmol) was added and the mixture was stirred at room temperature for 2 h. After pouring onto 4% NaHCO$_3$, it was extracted with dichloromethane, the organic phase was dried over magnesium sulphate and the volatiles were removed under reduced pressure. The residue was purified by flash chromatography (0% to 70% AcOEt/hexanes) to yield 0.86 g (88% yield) of the title compound.

LRMS (m/z): 465 (M+1)$^+$.

c) (S)-2-(1-Aminoethyl)-3-(1-(4-methoxybenzyl)-1H-pyrazol-4-yl)pyrrolo[1,2-f][1,2,4]triazin-4(3H)-one The title compound was prepared from (S)-tert-butyl 1-(3-(1-(4-methoxybenzyl)-1H-pyrazol-4-yl)-4-oxo-3,4-dihydropyrrolo[1,2-f][1,2,4]triazin-2-yl)ethylcarbamate (860 mg, 1.85 mmol) following the experimental procedure described in Preparation 46c. 540 mg (75% yield) of the desired compound were obtained.

LRMS (m/z): 365 (M+1)$^+$.

d) (S)-4-Amino-6-(1-(3-(1-(4-methoxybenzyl)-1H-pyrazol-4-yl)-4-oxo-3,4-dihydropyrrolo[1,2-f][1,2,4]triazin-2-yl)ethylamino)pyrimidine-5-carbonitrile The title compound (290 mg, 39% yield) was obtained from (S)-2-(1-Aminoethyl)-3-(1-(4-methoxybenzyl)-1H-pyrazol-4-yl)pyrrolo[1,2-f][1,2,4]triazin-4(3H)-one and 4-amino-6-chloropyrimidine-5-carbonitrile following the experimental procedure described in example 23.

LRMS (m/z): 483 (M+1)$^+$.

Preparation 143

(2S,4R)-4-(Benzyloxy)-1-(tert-butoxycarbonyl)pyrrolidine-2-carboxylic acid

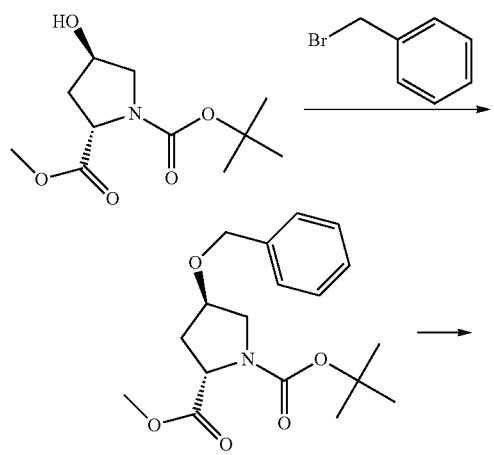

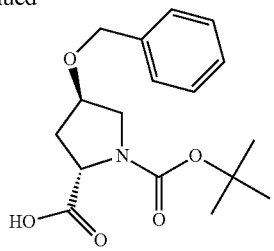

a) (2S,4R)-1-tert-Butyl 2-methyl 4-(benzyloxy)pyrrolidine-1,2-dicarboxylate (2S,4R)-1-tert-Butyl 2-methyl 4-hydroxypyrrolidine-1,2-dicarboxylate (2.65 g, 10.80 mmol) was dissolved in dimethylformamide (75 ml) and cooled in an ice bath. Sodium hydride (60% in hexanes, 0.57 g, 23.75 mmol) was added and stirred for 10 min. To this solution, benzyl bromide (1.39 ml, 11.69 mmol) dissolved in dichloromethane (9 ml) was dropwise added and the reaction mixture was overnight stirred at room temperature. The solvent was evaporated under reduced pressure and the residue redissolved in ethyl acetate. This organic phase was washed with water, dried over magnesium sulphate, filtered and the solvent evaporated under reduced pressure. 3.93 g (77% yield) of the final product were obtained, pure enough to perform the next synthetic step.

LRMS (m/z): 336 (M+1)$^+$ b) (2S,4R)-4-(Benzyloxy)-1-(tert-butoxycarbonyl)pyrrolidine-2-carboxylic acid (2S,4R)-1-tert-Butyl 2-methyl 4-(benzyloxy)pyrrolidine-1,2-dicarboxylate (2.78 g, 8.29 mmol) was dissolved in a 1:1 mixture of MeOH and THF (30 ml) and 2N NaOH (12.5 ml, 26 mmol) was added. After stirring at room temperature for 2 h, the organic solvents were evaporated under reduced pressure and the aqueous phase was extracted twice with dichloromethane. The aqueous phase was then cooled at 0° C. and then acidified with concentrated chlorhydric acid. This phase was extracted twice with dichloromethane. The organic phase was dried over magnesium sulphate, filtered and the solvent evaporated under reduced pressure. 2.01 g (76% yield) of the final compound were obtained, pure enough to perform the next synthetic step.

LRMS (m/z): 322 (M+1)$^+$

Preparation 144

(2S,4R)-tert-Butyl 4-(benzyloxy)-2-(5-bromo-3-(3,5-difluorophenyl)-4-oxo-3,4-dihydropyrrolo[1,2-f][1,2,4]triazin-2-yl)pyrrolidine-1-carboxylate a) (2S,4R)-tert-Butyl 4-(benzyloxy)-2-(3-bromo-2-(3,5-difluorophenylcarbamoyl)-1H-pyrrol-1-ylcarbamoyl)pyrrolidine-1-carboxylate 1-Amino-3-bromo-N-(3,5-difluorophenyl)-1H-pyrrole-2-carboxamide (1.5 g, 4.75 mmol), (2S,4R)-4-(benzyloxy)-1-(tert-butoxycarbonyl)pyrrolidine-2-carboxylic acid (0.99 g, 3.08 mmol) and diisopropylethylamine (2.8 ml, 16.08 mmol) were dissolved in dimethylformamide (30 ml) and the mixture cooled at 0° C. To this mixture, T3P (50% solution in ethyl acetate, 2.1 ml, 7.19 mmol) dissolved in DMF (5 ml) was dropwise added. Once the addition is over, the mixture was stirred at room temperature for 48 h. To this mixture, water was added and extracted twice with ethyl acetate. The organic phase was washed with water and brine, dried over sodium sulphate, filtered and the solvents evaporated under reduced pressure. The residue was purified by flash chromatography (0% to 25% hexanes/AcOEt) to yield 1.42 g (74% yield) of the title compound.

LRMS (m/z): 620 (M+1)$^+$.

b) (2S,4R)-tert-Butyl 4-(benzyloxy)-2-(5-bromo-3-(3,5-difluorophenyl)-4-oxo-3,4-dihydropyrrolo[1,2-f][1,2,4]triazin-2-yl)pyrrolidine-1-carboxylate The title compound was prepared from (2S,4R)-tert-butyl 4-(benzyloxy)-2-(3-bromo-2-(3,5-difluorophenylcarbamoyl)-1H-pyrrol-1-ylcarbamoyl)pyrrolidine-1-carboxylate (1.42 g, 2.29 mmol) following the experimental procedure described in Preparation 142b. 648 mg (47% yield) of the desired compound were obtained.

LRMS (m/z): 602 (M+1)$^+$.

Preparation 145

(2S,4R)-tert-Butyl 4-(benzyloxy)-2-(5-cyano-3-(3,5-difluorophenyl)-4-oxo-3,4-dihydropyrrolo[1,2-f][1,2,4]triazin-2-yl)pyrrolidine-1-carboxylate a) (2S,4R)-tert-Butyl 4-(benzyloxy)-2-(3-(3,5-difluorophenyl)-5-iodo-4-oxo-3,4-dihydropyrrolo[1,2-f][1,2,4]triazin-2-yl)pyrrolidine-1-carboxylate This compound was prepared starting from (2S,4R)-tert-butyl 4-(benzyloxy)-2-(5-bromo-3-(3,5-difluorophenyl)-4-oxo-3,4-dihydropyrrolo[1,2-f][1,2,4]triazin-2-yl)pyrrolidine-1-carboxylate (648 mg, 1.08 mmol) and following the experimental procedure described in Preparation 26a to afford 326 mg (47% yield) of the title compound.

LRMS (m/z): 649 (M+1)$^+$.

b) (2S,4R)-tert-Butyl 4-(benzyl oxy)-2-(5-cyano-3-(3,5-difluorophenyl)-4-oxo-3,4-dihydropyrrolo[1,2-f][1,2,4]triazin-2-yl)pyrrolidine-1-carboxylate (2S,4R)-tert-Butyl 4-(benzyloxy)-2-(3-(3,5-difluorophenyl)-5-iodo-4-oxo-3,4-dihydropyrrolo[1,2-f][1,2,4]triazin-2-yl)pyrrolidine-1-carboxylate (125 mg, 0.19 mmol) was dissolved in pyridine (10 ml) and copper (I) cyanide (210 mg, 2.32 mmol) was added. The reaction vessel was closed, purged with nitrogen and heated at 120° C. for 5 h in a microwave apparatus. The reaction mixture was filtered through Celite®, and the solvents evaporated under reduced pressure. The residue was redissolved in water and extracted with ethyl acetate. The organic phase was washed with water and brine, dried over magnesium sulphate, filtered and the solvent evaporated under reduced pressure. 105 mg (100% yield) of the final compound were obtained, pure enough to perform the next synthetic step.

LRMS (m/z): 548 (M+1)+

Preparation 146

2-((2S,4R)-1-(6-Amino-5-cyanopyrimidin-4-yl)-4-(benzyloxy)pyrrolidin-2-yl)-3-(3,5-difluorophenyl)-4-oxo-3,4-dihydropyrrolo[1,2-f][1,2,4]triazine-5-carbonitrile a) 2-((2S,4R)-4-(Benzyloxy)pyrrolidi n-2-yl)-3-(3,5-difluorophenyl)-4-oxo-3,4-dihydropyrrolo[1,2-f][1,2, 4]triazine-5-carbonitrile This compound was prepared starting from (2S,4R)-tert-butyl 4-(benzyloxy)-2-(5-cyano-3-(3,5-difluorophenyl)-4-oxo-3,4-dihydropyrrolo[1,2-f][1,2,4]triazin-2-yl)pyrrolidine-1-carboxylate (105 mg, 0.19 mmol) and following the experimental procedure described in Preparation 46c to afford 37 mg (43% yield) of the title compound.

LRMS (m/z): 448 (M+1)$^+$.

b) 2-((2S,4R)-1-(6-Amino-5-cyanopyrimidin-4-yl)-4-(benzyloxy)pyrrolidi n-2-yl)-3-(3,5-difluorophenyl)-4-oxo-3,4-dihydropyrrolo[1,2-f][1,2,4]triazine-5-carbonitrile 2-((2S,4R)-4-(Benzyloxy)pyrrolidin-2-yl)-3-(3,5-difluorophenyl)-4-oxo-3,4-dihydropyrrolo[1,2-f][1,2,4]triazine-5-carbonitrile (37 mg, 0.08 mmol), 23 mg (0.12 mmol) of 4-amino-6-chloropyrimidine-5-carbonitrile (prepared according to the procedure described in WO2010151735A2) and 60 µL (0.34 mmol) of diisopropylamine in 5 mL of tert-butanol was heated with stirring at 100° C. overnight. Then the solvent was removed under vacuum and the product was purified by reverse phase chromatography (C-18 silica from Waters®, water/1:1 acetonitrile-methanol as eluents [0.1% v/v formic acid buffered] 0% to 100%) to obtain the title compound (20 mg, 43% yield) as a white solid.

LRMS (m/z): 566 (M+1)$^+$.

Example 1

2-((6-Amino-9H-purin-9-yl)methyl)-5-chloro-3-o-tolylpyrrolo[1,2-f][1,2,4]triazin-4(3H)-one A mixture of 5-chloro-2-(chloromethyl)-3-o-tolylpyrrolo[1,2-f][1,2,4]triazin-4(3H)-one (90 mg, 0.25 mmol) and adenine (43 mg, 0.32 mmol) was suspended in N,N-dimethylformamide (2 mL) and potassium carbonate (44 mg, 0.32 mmol) was added stirring the reaction at room temperature overnight. At the end of this period, dichloromethane was added and the insolubles were filtered out. The filtrate was concentrated to dryness and macerated with dimethylsulphoxyde affording 57 mg (51% yield) of a solid corresponding to the title compound.

LRMS (m/z): 407 (M+1)$^+$.
$^1$H NMR (400 MHz, DMSO) δ 8.06 (s, 1H), 7.92 (s, 1H), 7.61 (d, J=3.0 Hz, 1H), 7.54-7.33 (m, 4H), 7.25 (s, 2H), 6.67 (d, J=3.0 Hz, 1H), 5.03 (d, J=17.1 Hz, 1H), 4.79 (d, J=17.1 Hz, 1H), 2.11 (s, 3H).

Example 2

2-((6-Aminopyrimidin-4-ylamino)methyl)-5-chloro-3-o-tolylpyrrolo[1,2-f][1,2,4]triazin-4(3H)-one In a microwave tub, a mixture of 2-(aminomethyl)-5-chloro-3-o-tolylpyrrolo[1,2-f][1,2,4]triazin-4(3H)-one (85 mg, 0.29 mmol), 6-bromopyrimidin-4-amine (102 mg, 0.59 mmol), and DIEA (205 µL, 1.2 mmol) was dissolved in tert-butanol (3 mL) and was heated at 140° C. with stirring during 20 hours. Next day, ethyl acetate was added and the organic phase was washed with water and brine, dried (Na$_2$SO$_4$) and concentrated to give 180 mg of a residue that was purified using a Bond Elut 5 g silica cartridge eluting with dichloromethane/methanol mixtures obtain 5 mg of the title compound (4% yield).

LRMS (m/z): 382 (M+1)$^+$.

Example 3

2-((6-Amino-9H-purin-9-yl)methyl)-5-cyclopropyl-3-o-tolylpyrrolo[1,2-f][1,2,4]triazin-4(3H)-one This compound was prepared starting from 2-(chloromethyl)-5-cyclopropyl-3-O—tolylpyrrolo[1,2-f][1,2,4]triazin-4(3H)-one (107 mg, 0.29 mmol) and following the experimental procedure described in Example 1. Isolation of the compound was done by reverse phase chromatography (C-18 silica from Waters, water/1:1 acetonitrile-methanol as eluents [0.1% v/v formic acid buffered] 0% to 100%) to afford 12 mg (10% yield) of the title compound.

LRMS (m/z): 413 (M+1)$^+$.

$^1$H NMR (400 MHz, DMSO) δ 8.05 (s, 1H), 7.47-7.38 (m, 5H), 7.22 (s, 2H), 6.14 (d, J=2.8 Hz, 1H), 5.01 (d, J=16.9 Hz, 1H), 4.78 (d, J=16.9 Hz, 1H), 2.50 (m, 1H), 2.10 (s, 3H), 0.94 (d, J=8.6 Hz, 2H), 0.70-0.56 (m, 2H).

Example 4

2-((6-Amino-9H-purin-9-yl)methyl)-3-o-tolylpyrrolo[1,2-f][1,2,4]triazin-4(3H)-one To a solution of 2-(chloromethyl)-3-o-tolylpyrrolo[1,2-f][1,2,4]triazin-4(3H)-one (90 mg, 0.23 mmol) in dry N,N-dimethylformamide (4 mL), 9H-purin-6-amine (38 mg, 0.28 mmol) and potassium carbonate (38 mg, 0.27 mmol) were added. It was stirred at room temperature overnight. It was filtered through Celite® and it was concentrated in vacuum. The residue obtained was purified by flash chromatography silica (dichloromethane/methanol). The expected product was obtained (25 mg, 29% yield).

LRMS (m/z): 373 (M+1)$^+$.

$^1$H NMR (400 MHz, DMSO) δ 8.06 (s, 1 H), 7.92 (s, 1 H), 7.53-7.62 (m, 1 H), 7.50 (d, J=7.42 Hz, 1 H), 7.34-7.48 (m, 3 H), 7.25 (s, 2 H), 7.00 (dd, J=4.30, 1.56 Hz, 1 H), 6.58 (dd, J=4.30, 2.74 Hz, 1 H), 5.07 (d, J=16.80 Hz, 1 H), 4.82 (d, J=16.80 Hz, 1 H), 2.09 (s, 3 H).

Example 5

2-((6-Aminopyrimidin-4-ylamino)methyl)-3-o-tolylpyrrolo[1,2-f][1,2,4]triazin-4(3H)-one 100 mg (0.39 mmol) of 2-(aminomethyl)-3-o-tolylpyrrolo[1,2-f][1,2,4]triazin-4(3H)-one, 76 mg (0.44 mmol) of 6-bromopyrimidin-4-amine and 140 µL (0.80 mmol) of DIEA were suspended in 2 mL of tert-butanol and the resulting mixture was stirred at 80° C. overnight. After an extra addition of 76 mg (0.44 mmol) of 6-bromopyrimidin-4-amine and 140 µL (0.80 mmol) of DIEA the reaction was heated at 80° C. for 70 hours. Then the solvents were evaporated under vacuum and the crude product was purified by reverse phase chromatography (C-18 silica from Waters®, water/1:1 acetonitrile-methanol as eluents [0.1% v/v formic acid buffered] 0% to 100%) and then by preparative HPLC (Symmetry Prep O$_{18}$ column, mixture of eluents NB from 20% B to 20% B, in a 10 min. gradient) to give 18 mg (13% yield) of the title compound.

LRMS (m/z): 348 (M+1)$^+$.

Example 6

4-((4-oxo-3-o-tolyl-3,4-dihydropyrrolo[1,2-f][1,2,4]triazin-2-yl)methylamino)picolinamide A mixture of 2-(aminomethyl)-3-o-tolylpyrrolo[1,2-f][1,2,4]triazin-4(3H)-one (102 mg, 0.4 mmol), 4-bromopicolinamide (105 mg, 0.52 mmol) and DIEA (200 µL, 1.13 mmol) in n-butanol (2.2 mL) was reacted under microwave irradiation at 190° C. during 22 h. After cooled to room temperature, the mixture was concentrated in vacuum and was purified by reverse phase chromatography (C-18 silica from Waters, water/1:1 acetonitrile-methanol as eluents [0.1% v/v formic acid buffered] 0% to 100%) to obtain 7 mg of the title compound (4,6%).

LRMS (m/z): 375 (M+1)$^+$.

$^1$H NMR (400 MHz, DMSO) δ 8.38 (s, 2 H), 8.01 (d, J=5.86 Hz, 1 H), 7.90 (m, 1H), 7.61-7.73 (m, 1 H), 7.48-7.58 (m, 1 H), 7.39-7.48 (m, 1 H), 7.23-7.40 (m, 2 H), 7.03-7.14 (m, 1 H), 6.93-7.04 (m, 1 H), 6.62 (dd, J=4.30, 2.74 Hz, 1H), 6.38-6.53 (m, 1 H), 3.86-3.99 (m, 2 H), 2.08 (s, 3 H)

Example 7

2-((2-Aminopyridin-4-ylamino)methyl)-3-o-tolylpyrrolo[1,2-f][1,2,4]triazin-4(3H)-one 150 mg (0.59 mmol) of 2-(aminomethyl)-3-o-tolylpyrrolo[1,2-f][1,2,4]triazin-4(3H)-one, 104 mg (0.60 mmol) of 4-bromopyridin-2-amine and 105 µL (0.60 mmol) DIEA were dissolved in 2 mL of tert-butanol and stirred at 180° C. under microwave irradiation for 5.5 hours. Then the solvent was evaporated in vacuum and the crude product was purified by flash chromatography (dichloromethane to dichloromethane/MeOH/NH4OH, 100:8:1) to give 57 mg (28% yield) of the title compound.

LRMS (m/z): 347 (M+1)$^+$.

$^1$H NMR (400 MHz, DMSO) δ 7.69 (s, 1H), 7.55-7.29 (m, 5H), 6.99 (s, 1H), 6.62 (s, 1H), 6.37 (s, 1H), 5.76 (s, 1H), 5.54 (s, 2H), 5.40 (s, 1H), 3.85-3.66 (m, 2H), 2.08 (s, 3H).

Example 8

2-((9H-Purin-6-ylamino)methyl)-3-o-tolylpyrrolo[1,2-f][1,2,4]triazin-4(3H)-one 100 mg (0.39 mmol) of 2-(aminomethyl)-3-o-tolylpyrrolo[1,2-f][1,2,4]triazin-4(3H)-one, 86 mg (0.43 mmol) of 6-bromo-9H-purine and 151 µL (0.87 mmol) DIEA were dissolved in 5 mL of tert-butanol and stirred at 80° C. overnight. Then the solvent was evaporated in vacuum and the residue was dissolved in ethyl acetate and washed with a saturated aqueous solution of sodium bicarbonate and brine. It was dried over magnesium sulphate, filtered and the solvent was evaporated. The crude product was purified by reverse phase chromatography (C-18 silica from Waters®, water/1:1 acetonitrile-methanol as eluents [0.1% v/v formic acid buffered] 0% to 100%) to give 42 mg (29% yield) of the title compound.

LRMS (m/z): 373 (M+1)$^+$.

$^1$H NMR (400 MHz, DMSO) δ 12.95 (s, 1H), 8.14 (s, 1H), 8.08 (s, 1H), 7.87 (s, 1H), 7.62 (s, 1H), 7.46 (d, J=7.1 Hz, 1H), 7.42-7.22 (m, 3H), 6.97 (dd, J=4.3, 1.6 Hz, 1H), 6.57 (dd, J=4.3, 2.7 Hz, 1H), 4.20 (br s, 2H), 2.19 (s, 3H).

Example 9

2-((6-Amino-9H-purin-9-yl)methyl)-3-cyclohexylpyrrolo[1,2-f][1,2,4]triazin-4(3H)-one 2-(Chloromethyl)-3-cyclohexylpyrrolo[1,2-f][1,2,4]triazin-4(3H)-one (140 mg, 0,53 mmol), 9H-purin-6-amine (91 mg, 0.67 mmol) and potassium carbonate (93 mg, 0.67 mmol) were suspended in N,N-dimethylformamide under argon atmosphere and the reaction was stirred overnight at room temperature. Next day, dichloromethane was added and the resulting solid was filtered off. The filtrate was concentrated to dryness giving a residue of 176 mg that was purified by flash chromatography silica (dichloromethane/methanol) to obtain 7 mg of the title compound (3,4% yield).

LRMS (m/z): 365 (M+1)$^+$.

$^1$H NMR (400 MHz, DMSO) δ 8.19 (s, 1H), 8.21 (s, 1H), 7.46 (br s, 1H), 7.32 (brs, 2H), 6.90-6.77 (m, 1H), 6.57-6.47 (m, 1H), 5.58 (s, 2H), 3.86 (s, 1H), 1.63-0.96 (m, 10H).

Example 10

2-((6-Amino-9H-purin-9-yl)methyl)-5-methyl-3-o-tolylpyrrolo[1,2-f][1,2,4]triazin-4(3H)-one 50 mg (0.17 mmol) of 2-(chloromethyl)-5-methyl-3-o-tolylpyrrolo[1,2-f][1,2,4]triazin-4(3H)-one, 25.8 mg (0.19 mmol) of 9H-purin-6-amine and 26.4 mg of potassium carbonate were dissolved in 2.5 mL of DMF and stirred at room temperature for 3 hours. Then the reaction mixture was diluted with dichloromethane, filtered and evaporated to dryness. The oil that resulted was purified by flash chromatography (DCM to 5% MeOH/DCM) to give 52 mg (77% yield) of the title compound.

LRMS (m/z): 387 (M+1)$^+$.

Example 11

2-((9H-Purin-6-ylthio)methyl)-5-methyl-3-o-tolylpyrrolo[1,2-f][1,2,4]triazin-4(3H)-one To a solution of 2-(chloromethyl)-5-methyl-3-o-tolylpyrrolo[1,2-f][1,2,4]triazin-4(3H)-one (108 mg, 0.38 mmol) in 7,5 mL of N,N-dimethylformamide was added 9H-purine-6-thiol (57 mg, 0.37 mmol) and potassium carbonate (52 mg, 0.38 mmol) and the stirring was continued overnight at room temperature. Next day, the reaction was concentrated to dryness and the residue was purified by reverse phase chromatography (C-18 silica from Waters, water/1:1 acetonitrile-methanol as eluents [0.1% v/v formic acid buffered] 0% to 100%) to obtain 35 mg of the title compound (23%).

LRMS (m/z): 404 (M+1)$^+$.

$^1$H NMR (400 MHz, DMSO) δ 8.46 (s, 1H), 8.39 (s, 1H), 7.53 (d, J=2.7 Hz, 1H), 7.44 (m, 1H), 7.24 (m, 3H), 6.42 (d, J=2.7 Hz, 1H), 4.38 (d, J=15.2 Hz, 1H), 4.26 (d, J=15.2 Hz, 1H), 2.39 (s, 3H), 2.15 (s, 3H).

Example 12

2-((6-Amino-9H-purin-9-yl)methyl)-6-methyl-3-o-tolylpyrrolo[1,2-f][1,2,4]triazin-4(3H)-one 289 mg (1.00 mmol) of 2-(chloromethyl)-6-methyl-3-o-tolylpyrrolo[1,2-f][1,2,4]triazin-4(3H)-one, 163 mg (1.21 mmol) of 9H-purin-6-amine and 278 mg (2.01 mmol) of potassium carbonate were dissolved in 8 mL of DMF and stirred at room temperature overnight. The solvent was removed in vacuum and the residue was taken up in ethyl acetate, washed with brine, filtered and evaporated to dryness. The product was purified by preparative HPLC (Symmetry Prep C$_{18}$ column, mixture of eluents A/B from 40% B to 52% B, in a 12 min. gradient) to give 116 mg (29% yield) of the title compound.

LRMS (m/z): 387 (M+1)$^+$.

$^1$H NMR (400 MHz, DMSO) b 8.04 (s, 1H), 7.88 (s, 1H), 7.52-7.29 (m, 5H), 7.24 (s, 2H), 6.80 (s, 1H), 5.04 (d, J=17.0 Hz, 1H), 4.80 (d, J=16.9 Hz, 1H), 2.13 (s, 3H), 2.04 (s, 3H).

Example 13

2-((9H-Purin-6-ylthio)methyl)-6-methyl-3-o-tolylpyrrolo[1,2-f][1,2,4]triazin-4(3H)-one 289 mg (1.00 mmol) of 2-(chloromethyl)-6-methyl-3-o-tolylpyrrolo[1,2-f][1,2,4]triazin-4(3H)-one, 183 mg (1.21 mmol) of 7H-purine-6-thiol and 277 mg (2.01 mmol) of potassium carbonate were dissolved in 8 mL of DMF and stirred at room temperature overnight. The solvent was removed in vacuum and the product was purified by preparative HPLC (Symmetry Prep C$_{18}$ column, mixture of eluents NB from 50% B to 63% B, in a 13 min. gradient) to give 133 mg (50% yield) of the title compound.

LRMS (m/z): 404 (M+1)$^+$.

$^1$H NMR (400 MHz, DMSO) δ 8.47 (s, 1H), 8.43 (s, 1H), 7.51-7.16 (m, 5H), 6.79 (s, 1H), 4.41 (d, J=15.2 Hz, 1H), 4.29 (d, J=15.2 Hz, 1H), 2.16 (s, 3H), 2.11 (s, 3H).

Example 14

2-(1-(6-Amino-9H-purin-9-yl)ethyl)-3-phenylpyrrolo[1,2-f][1,2,4]triazin-4(3H)-one To a solution of 100 mg (0.37 mmol) of 2-(1-chloroethyl)-3-phenylpyrrolo[1,2-f][1,2,4]triazin-4(3H)-one in 5 mL of DMF, 55 mg (0.41 mmol) of 9H-purin-6-amine and 55 mg (0.40 mmol) of potassium carbonate were added. It was stirred at 60° C. overnight. It was then filtered through Celite® and it was concentrated in vacuum. The residue that was obtained was purified by flash chromatography (5% MeOH in dichloromethane). 20 mg (15% yield) of the title product were obtained.

LRMS (m/z): 373 (M+1)+.

$^1$H NMR (400 MHz, DMSO) δ ppm 8.27-7.80 (m, 2H), 7.82-6.88 (d, J=7.03 Hz, 1H), 6.64 (m, 1H), 5.49 (q, J=6.25 Hz, 1H), 1.71 (d, J=5.86 Hz, 3H).

Example 15

(S)-2-(1-(9H-Purin-6-ylamino)propyl)-3-phenylpyrrolo[1,2-f][1,2,4]triazin-4(3H)-one 90 mg (0.34 mmol) of (S)-2-(1-aminopropyl)-3-phenylpyrrolo[1,2-f][1,2,4]triazin-4(3H)-one, 134 mg (0.67 mmol) of 6-bromo-9H-purine and 174 mg (1.35 mmol) of DIEA were suspended in 3 mL of tert-butanol and the mixture was heated to 100° C. for 40 hours. Then the solvent was removed in vacuum and the residue was taken up in AcOEt, washed with water and brine, dried over magnesium sulphate and the solvent evaporated. The crude product was purified by reverse phase chromatography (C-18 silica from Waters®, water/1:1 acetonitrile-methanol as eluents [0.1% v/v formic acid buffered] 0% to 100%) to obtain the title compound (59 mg, 45% yield) as a white solid.

LRMS (m/z): 387 (M+1)$^+$.

$^1$H NMR (400 MHz, DMSO) δ 12.92 (s, 1H), 8.10 (m, 2H), 7.94 (s, 1H), 7.60 (s, 1H), 7.53-7.34 (m, 4H), 6.93 (dd, 1H), 6.64-6.54 (m, 1H), 4.65 (s, 1H), 1.98 (m, 2H), 0.77 (t, 3H).

Example 16

(S)-2-(1-(6-Aminopyrimidin-4-ylamino)propyl)-3-phenylpyrrolo[1,2-f][1,2,4]triazin-4(3H)-one 100 mg (0.37 mmol) of (S)-2-(1-aminopropyl)-3-phenylpyrrolo[1,2-f][1,2,4]triazin-4(3H)-one, 130 mg (0.75 mmol) of 6-bromopyrimidine-4-amine and 130 µL (0.75 mmol) of diisopropylethylamine were suspended in 2 mL tert-butanol and the mixture was heated to 190° C. for 3 hours under microwave irradiation. Then the solvent was evaporated and the product was purified by preparative HPLC (Symmetry Prep $C_{18}$ column, mixture of eluents A/B from 5% B to 45% B, in a 30 min. gradient). 10 mg (7% yield) were obtained as a white solid.

LRMS (m/z): 362 (M+1)$^+$.

$^1$H NMR (400 MHz, DMSO) δ 8.52 (s, 1H), 7.80 (s, 1H), 7.67-7.38 (m, 5H), 7.04 (d, J=6.9 Hz, 1H), 6.93 (d, J=2.7 Hz, 1H), 6.64-6.49 (m, 1H), 6.05 (s, 2H), 5.43 (s, 1H), 4.28 (s, 1H), 1.90-1.71 (m, 2H), 0.70 (t, J=7.2 Hz, 3H).

Example 17

(S)-2-(1-(2-Amino-9H-purin-6-ylamino)propyl)-3-phenylpyrrolo[1,2-f][1,2,4]triazin-4(3H)-one 60 mg (0.34 mmol) of (S)-2-(1-aminopropyl)-3-phenylpyrrolo[1,2-f][1,2,4]triazin-4(3H)-one, 76 mg (0.45 mmol) of 6-chloro-9H-purin-2-amine and 78 µL (0.45 mmol) of diisopropylethylamine were suspended in 2 mL tert-butanol and the mixture was heated to 150° C. for 1.5 hours under microwave irradiation. Then the solvent was evaporated and the product was purified by preparative HPLC (Symmetry Prep $C_{18}$ column, mixture of eluents A/B from 10% B to 40% B, in a 25 min. gradient). 12 mg (13% yield) were obtained as a white solid.

LRMS (m/z): 402 (M+1)$^+$.

$^1$H NMR (400 MHz, DMSO) δ 12.11 (s, 1H), 8.27 (s, 1H), 7.69 (s, 2H), 7.62-7.42 (m, 4H), 7.34 (s, 1H), 6.92 (dd, J=4.2, 1.6 Hz, 1H), 6.56 (dd, J=4.3, 2.7 Hz, 1H), 5.59 (s, 2H), 4.55 (s, 1H), 1.83 (m, 2H), 0.65 (t, J=7.2 Hz, 3H).

Example 18

(S)-4-Amino-6-(1-(4-oxo-3-phenyl-3,4-dihydropyrrolo[1,2-f][1,2,4]triazin-2-yl)propylamino)pyrimidine-5-carbonitrile A suspension of 125 mg (0.33 mmol) of (S)-2-(1-aminopropyl)-3-phenylpyrrolo[1,2-f][1,2,4]triazin-4(3H)-one, 56 mg (0.36 mmol) of 4-amino-6-chloropyrimidine-5-carbonitrile (prepared according to the procedure described in WO2010151735A2) and 170 µL (0.98 mmol) of diisopropylamine in 4 mL of tert-butanol was heated with stirring at 120° C. overnight. Then the solvent was removed under vacuum and the product was purified by flash chromatography (dichloromethane to dichloromethane/MeOH/NH4OH, 100:8:1) followed by a second purification by reverse phase chromatography (C-18 silica from Waters®, water/1:1 acetonitrile-methanol as eluents [0.1% v/v formic acid buffered] 0% to 100%) to obtain the title compound (58 mg, 45% yield) as a white solid.

LRMS (m/z): 387 (M+1)$^+$.

$^1$H NMR (400 MHz, DMSO) δ 7.79 (s, 1H), 7.67 (s, 1H), 7.60 (d, J=7.2 Hz, 1H), 7.48 (d, J=3.5 Hz, 2H), 7.40-7.29 (m, 3H), 7.23 (s, 2H), 6.95 (d, J=2.8 Hz, 1H), 6.64-6.57 (m, 1H), 4.68 (dd, J=13.3, 7.3 Hz, 1H), 1.86 (ddt, J=28.8, 13.9, 7.1 Hz, 2H), 0.75 (t, J=7.2 Hz, 3H).

Example 19

(R)-2-(1-(9H-Purin-6-ylamino)propyl)-3-phenylpyrrolo[1,2-f][1,2,4]triazin-4(3H)-one 70 mg (0.26 mmol) of racemic 2-(1-aminopropyl)-3-phenylpyrrolo[1,2-f][1,2,4]triazin-4(3H)-one, 106 mg (0.53 mmol) of 6-bromo-9H-purine and 134 mg (1.04 mmol) of DIEA were suspended in 4 mL of tert-butanol and the mixture was heated to 80° C. for 40 hours. Then the solvent was removed in vacuum and the crude product was purified by reverse phase chromatography (C-18 silica from Waters®, water/1:1 acetonitrile-methanol as eluents [0.1% v/v formic acid buffered] 0% to 100%) to obtain 50 mg (50% yield) of racemic 2-(1-(9H-purin-6-ylamino)propyl)-3-phenylpyrrolo[1,2-f][1,2,4]triazin-4(3H)-one.

The two enantiomers were separated by chiral HPLC with a Chiralpack IA column (5 µm, 20×250 mm), eluting with a mixture of heptane/isopropanol/diethylamine (85/15/0.1) and 15 mg (15% yield) of the title enantiomer were obtained, corresponding to the second peak to elute (e.e. >99.5%).

LRMS (m/z): 387 (M+1)$^+$.

$^1$H NMR (400 MHz, DMSO) δ 12.88 (s, 1H), 8.11 (m, 2H), 7.97 (s, 1H), 7.62-7.56 (m, 1H), 7.56-7.41 (m, 3H), 7.40 (s, 1H), 7.29 (s, 1H), 6.92 (dd, J=4.2, 1.4 Hz, 1H), 6.56 (dd, J=4.2, 2.7 Hz, 1H), 4.65 (s, 1H), 1.95 (m, 2H), 0.75 (t, J=7.0 Hz, 3H).

Example 20

(S)-2-(1-(9H-Purin-6-ylamino)ethyl)-3-phenylpyrrolo[1,2-f][1,2,4]triazin-4(3H)-one 90 mg (0.34 mmol) of (S)-2-(1-Aminoethyl)-3-phenylpyrrolo[1,2-f][1,2,4]triazin-4(3H)-one, 134 mg (0.67 mmol) of 6-bromo-9H-purine and 174 µL (1.35 mmol) of diisopropylethylamine were suspended in 3 mL tert-butanol and the mixture was heated to 100° C. for 40 hours. Then the solvent was removed in vacuum and the residue was taken up in AcOEt, washed with water and brine, dried over magnesium sulphate and the solvent evaporated. The crude product was purified by reverse phase chromatography (C-18 silica from Waters®, water/1:1 acetonitrile-methanol as eluents [0.1% v/v formic acid buffered] 0% to 100%) to obtain the title compound (59 mg, 45% yield) as a white solid.

LRMS (m/z): 373 (M+1)$^+$.

$^1$H NMR (400 MHz, DMSO) δ 12.92 (s, 1H), 8.19-7.95 (m, 3H), 7.68-7.42 (m, 4H), 7.29 (d, J=17.2 Hz, 1H), 7.17 (s, 1H), 6.93 (dd, J=4.3, 1.6 Hz, 1H), 6.58 (dd, J=4.2, 2.7 Hz, 1H), 4.95-4.69 (m, 1H), 1.45 (d, J=6.7 Hz, 3H).

Example 21

(S)-2-(1-(2-Amino-9H-purin-6-ylamino)ethyl)-3-phenylpyrrolo[1,2-f][1,2,4]triazin-4(3H)-one 75 mg (0.29 mmol) of (S)-2-(1-aminoethyl)-3-phenylpyrrolo[1,2-f][1,2,4]triazin-4(3H)-one, 100 mg (0.59 mmol) of 6-chloro-9H-purin-2-amine and 154 µL (0.88 mmol) of diisopropylethylamine were suspended in 2 mL of 2-propanol and the mixture was heated at 170° C. for 1 hour under microwave irradiation. Then the solvent was removed in vacuum and the residue was taken up in AcOEt, washed with water and brine, dried over magnesium sulphate and the solvent evaporated. The crude product was purified by reverse phase chromatography (C-18 silica from Waters®, water/1:1 acetonitrile-methanol as eluents [0.1% v/v formic acid buffered] 0% to 100%) to obtain the title compound (26 mg, 23% yield) as a white solid.

LRMS (m/z): 388 (M+1)$^+$.

$^1$H NMR (400 MHz, DMSO) δ 12.07 (s, 1H), 8.17 (s, 1H), 7.67 (s, 1H), 7.63-7.56 (m, 2H), 7.51 (s, 2H), 7.46-7.28 (m, 2H), 6.93 (dd, J=4.3, 1.6 Hz, 1H), 6.57 (dd, J=4.3, 2.7 Hz, 1H), 5.57 (s, 2H), 4.77 (s, 1H), 1.37 (d, J=6.8 Hz, 3H).

Example 22

(S)-2-(1-(6-Aminopyrimidin-4-ylamino)ethyl)-3-phenylpyrrolo[1,2-f][1,2,4]triazin-4(3H)-one 100 mg (0.39 mmol) of (S)-2-(1-aminoethyl)-3-phenylpyrrolo[1,2-f][1,2,4]triazin-4(3H)-one, 136 mg (0.78 mmol) of 6-bromopyrimidin-4-amine and 274 µL (1.57 mmol) of diisopropylethylamine were suspended in 2 mL of N-methylpirrolidone and the mixture was heated at 170° C. for 1 hour under microwave irradiation, then at 180° C. for 2 hours and then at 200° C. for 4 hours. Then water was added to the reaction mixture and the product was extracted with dichloromethane. The organic layer was washed with water and brine, dried over MgSO4, filtered and the solvent was evaporated under vacuum. The product was purified by preparative HPLC (Symmetry Prep $C_{18}$ column, mixture of eluents A/B from 5% B to 45% B, in a 30 min. gradient). 23 mg (17% yield) were obtained as a solid.

LRMS (m/z): 348 (M+1)$^+$.

$^1$H NMR (400 MHz, DMSO) δ 7.80 (s, 1H), 7.64-7.57 (m, 1H), 7.55-7.47 (m, 3H), 7.47-7.38 (m, 2H), 7.19 (s, 1H), 6.93 (dd, J=4.2, 1.5 Hz, 1H), 6.58 (dd, J=4.3, 2.7 Hz, 1H), 6.12 (s, 2H), 5.39 (s, 1H), 4.48 (s, 1H), 1.30 (d, J=6.8 Hz, 3H).

Example 23

(S)-4-Amino-6-(1-(4-oxo-3-phenyl-3,4-dihydropyrrolo[1,2-f][1,2,4]triazin-2-yl)ethylamino)pyrimidine-5-carbonitrile 35 mg (0.14 mmol) of (S)-2-(1-aminoethyl)-3-phenylpyrrolo[1,2-f][1,2,4]triazin-4(3H)-one, 23 mg (0.15 mmol) of 4-amino-6-chloropyrimidine-5-carbonitrile (prepared according to the procedure described in WO2010151735A2) and 72 µL (0.41 mmol) of diisopropylethylamine were heated in tert-butanol (2 mL) for 21 hours. Then the solvent was removed under vacuum and the crude product was purified by flash chromatography (0-10% methanol in dichloromethane) to give 26 mg (51% yield) of the title compound as a white solid.

LRMS (m/z): 348 (M+1)$^+$.

$^1$H NMR (400 MHz, DMSO) δ 7.76 (s, 1H), 7.73-7.64 (m, 2H), 7.52-7.46 (m, 1H), 7.43 (ddd, J=8.0, 4.6, 2.3 Hz, 1H), 7.38-7.26 (m, 3H), 7.20 (s, 2H), 6.95 (dd, J=4.3, 1.7 Hz, 1H), 6.61 (dd, J=4.3, 2.7 Hz, 1H), 4.99-4.77 (m, 1H), 1.37 (d, J=6.7 Hz, 3H).

Example 24

2-(1-(6-Amino-9H-purin-9-yl)ethyl)-5-methyl-3-phenylpyrrolo[1,2-f][1,2,4]triazin-4(3H)-one 340 mg (0.90 mmol) of 2-(1-iodoethyl)-5-methyl-3-phenylpyrrolo[1,2-f][1,2,4]triazin-4(3H)-one, 194 mg (1.44 mmol) of 9H-purin-6-amine and 310 mg (2.24 mmol) of potassium carbonate were heated in DMF (10 mL) at 50° C. overnight. Then the solvent was removed under vacuum and water was added to the residue. A white solid precipitated and was stirred in water overnight. Then the solid was filtered and washed with water and the product was purified by flash chromatography (dichloromethane to dichloromethane/MeOH/NH4OH, 100:8:1) to give 116 mg (34% yield) of the title compound as a white solid.

LRMS (m/z): 387 (M+1)$^+$.

$^1$H NMR (400 MHz, DMSO) δ 8.03 (s, 1H), 7.94 (s, 1H), 7.61 (dd, J=6.7, 1.8 Hz, 1H), 7.55 (d, J=2.7 Hz, 1H), 7.49 (td, J=7.6, 1.3 Hz, 1H), 7.30 (tt, J=7.5, 1.2 Hz, 1H), 7.19 (s, 2H), 7.09 (td, J=7.7, 1.4 Hz, 1H), 6.76 (d, J=8.0 Hz, 1H), 6.45 (dd, J=2.7, 0.7 Hz, 1H), 5.44 (q, J=6.8 Hz, 1H), 2.39 (s, 3H), 1.68 (d, J=6.8 Hz, 3H).

Example 25

2-((6-Amino-9H-purin-9-yl)methyl)-3-o-tolyl-5-(trifluoromethyl)pyrrolo[1,2-f][1,2,4]triazin-4(3H)-one This compound was prepared starting from 2-(chloromethyl)-3-o-tolyl-5-(trifluoromethyl)pyrrolo[1,2-f][1,2,4]triazin-4(3H)-one (2 mg, 0.006 mmol) and following the experimental procedure described in Example 1. Isolation of the compound was done by purification on a 5 g Bond Elut silica cartridge eluting with a mixture of dichloromethane/methanol to afford 1 mg (50% yield) of the pure title compound.

LRMS (m/z): 441 (M+1)$^+$.

Example 26

2-((6-Amino-9H-purin-9-yl)methyl)-5-chloro-3-phenylpyrrolo[1,2-f][1,2,4]triazin-4(3H)-one a) To a solution of di-tert-butyl 9-((5-chloro-4-oxo-4H-pyrrolo[1,2-d][1,3,4]oxadiazin-2-yl)methyl)-9H-purin-6-ylimidodicarbonate (125 mg, 0.2 mmol) in 2.5 mL of dry 1,4-dioxane under argon atmosphere 132 µL of aniline (1.45 mmol) were added and the mixture was heated to reflux with stirring overnight. At the end of this period, the reaction mixture was poured into 50 mL of a 4% aqueous solution of sodium bicarbonate and extracted with ethyl acetate (2×40 mL). The organic layers were mixed and washed with more 4% aqueous solution of sodium bicarbonate, water and brine, and were dried (MgSO$_4$) and concentrated under reduced pressure to give 187 mg of a solid that was purified by flash chromatography silica (hexane/ethyl acetate). After purification were obtained 136 mg of di-tert-butyl [9-(2-{[2-(anilinocarbonyl)-3-chloro-1H-pyrrol-1-yl]amino}-2-oxoethyl)-9H-purin-6-yl]imidodicarbonate (91% yield).

b) To a solution of di-tert-butyl [9-(2-{[2-(anilinocarbonyl)-3-chloro-1H-pyrrol-1-yl]amino}-2-oxoethyl)-9H-purin-6-yl]imidodicarbonate (120 mg, 0.2 mmol) in 1.6 mL of dry 1,4-dioxane under argon atmosphere 179 µL of phosphorous oxychloride (2 mmol) in 0.8 mL of dry 1,4-dioxane were added and the mixture was heated to reflux with stirring during 2 hours. Afterwards, the reaction mixture was concentrated to dryness co-evaporating with toluene to remove traces of phosphorous oxychloride and the residue was suspended in 1.2 mL of 7N ammonia in methanol heating the reaction at 60° C. overnight. At the end of this period, the cooled reaction mixture was poured into 25 mL of a 1/1 mixture of water/brine and extracted with ethyl acetate (2×20 mL). The organic layers were mixed and washed brine, dried (MgSO$_4$) and concentrated under reduced pressure to give 45 mg of a solid that was purified by flash chromatography silica (dichloromethane/methanol). After purification were obtained 14 mg of the title compound of this example (18% yield).

LRMS (m/z): 393 (M+1)$^+$.

$^1$H NMR (600 MHz, DMSO) δ 8.04 (s, 1H), 7.95 (s, 1H), 7.59 (d, J=3.1 Hz, 1H), 7.53-7.46 (m, 5H), 7.23 (s, 2H), 6.66 (d, J=3.1 Hz, 1H), 4.97 (s, 2H).

Example 27

2-((6-Amino-9H-purin-9-yl)methyl)-5-chloro-3-(3-methoxyphenyl)pyrrolo[1,2-f][1,2,4]triazin-4(3H)-one a) To a solution of di-tert-butyl 94(5-chloro-4-oxo-4H-pyrrolo[1,2-d][1,3,4]oxadiazin-2-yl)methyl)-9H-purin-6-ylimidodicarbonate (110 mg, 0.21 mmol) in 2 mL of dry 1,4-dioxane under argon atmosphere 160 µL of 3-methoxyaniline (1.25 mmol) were added and the mixture was heated to reflux with stirring overnight. At the end of this period, the reaction mixture was poured into 50 mL of a 4% aqueous solution of sodium bicarbonate and extracted with ethyl acetate (2×40 mL). The organic layers were mixed and washed with more 4% aqueous solution of sodium bicarbonate, water and brine, and were dried (MgSO$_4$) and concentrated under reduced pressure to give a residue of 280 mg that was submitted to purification using a 10 g Bond Elut silica cartridge eluting with a mixture of hexane/ethyl acetate. After purification were obtained 65 mg of di-tert-butyl [9-(2-{[2-(3-methoxyphenylcarbamoyl)-3-chloro-1H-pyrrol-1-yl]amino}-2-oxoethyl)-9H-purin-6-yl]imidodicarbonate (42% yield).

b) To a solution of di-tert-butyl [9-(2-{[2-(3-methoxyphenylcarbamoyl)-3-chloro-1H-pyrrol-1-yl]amino}-2-oxoethyl)-9H-purin-6-yl]imidodicarbonate (65 mg, 0.09 mmol) in 1 mL of dry 1,4-dioxane under argon atmosphere 100 µL of phosphorous oxychloride (1.1 mmol) in 0.5 mL of dry 1,4-dioxane were added and the mixture was heated to reflux with stirring during 2 hours. Afterwards, the reaction mixture was concentrated to dryness co-evaporating with toluene to remove traces of phosphorous oxychloride and the residue was suspended in 1 mL of 7N ammonia in methanol heating the reaction at 60° C. overnight. At the end of this period, the cooled reaction mixture was poured into 25 mL of a 4% aqueous solution of sodium bicarbonate and extracted with ethyl acetate (3×25 mL). The organic layers were mixed and washed brine, dried (MgSO$_4$) and concentrated under reduced pressure to give a residue that was purified by flash chromatography silica (dichloromethane/methanol). After purification were obtained 12 mg of the title compound of this example (30% yield).

LRMS (m/z): 423 (M+1)$^+$.

$^1$H NMR (400 MHz, DMSO) δ 12.02 (s, 1H), 8.03 (s, 1H), 7.95 (s, 1H), 7.60 (d, J=3.0 Hz, 1H), 7.39 (dd, J=9.1, 7.7 Hz, 1H), 7.22 (s, 2H), 7.06-6.96 (m, 3H), 6.66 (d, J=3.0 Hz, 1H), 5.07 (d, J=16.8 Hz, 1H), 4.99 (d, J=16.8 Hz, 1H), 3.73 (s, 3H).

Example 28

2-((6-Amino-9H-purin-9-yl)methyl)-5-chloro-3-(2,4-difluorophenyl)pyrrolo-[1,2-f][1,2,4]triazin-4(3H)-one a) Sodium hexamethyldisilazide (1M solution in tetrahydrofurane, 965 µL, 0.97 mmol) was added to a solution of 2,4-difluoroaniline (118 µL, 1.16 mmol) in 0.5 mL of dry tetrahydrofurane under argon and the mixture was stirred at room temperature during 15 minutes. At the end of this period, the mixture was put in an ice-water bath and a solution of di-tert-butyl 9-((5-chloro-4-oxo-4H-pyrrolo[1,2-d][1,3,4]oxadiazin-2-yl)methyl)-9H-purin-6-ylimidodicarbonate (100 mg, 0.19 mmol) in 2 mL of tetrahydrofurane was added maintaining the stirring during 30 minutes at room temperature. Next, the reaction mixture was poured into 25 mL of a saturated aqueous solution of ammonium chloride and extracted with ethyl acetate (2×20 mL). The organic layers were mixed and washed water and brine, dried (MgSO$_4$) and concentrated under reduced pressure to give 145 mg of an oil that was purified by flash chromatography silica (dichloromethane/methanol). After purification were obtained 68 mg of tert-butyl 9-(2-(3-chloro-2-(2,4-difluorophenylcarbamoyl)-1H-pyrrol-1-ylamino)-2-oxoethyl)-9H-purin-6-ylcarbamate (65% yield).

b) To a solution of tert-butyl 9-(2-(3-chloro-2-(2,4-difluorophenylcarbamoyl)-1H-pyrrol-1-ylamino)-2-oxoethyl)-9H-purin-6-ylcarbamate (60 mg, 0.09 mmol) in 0.8 mL of dry 1,4-dioxane under argon atmosphere 85 µL of phosphorous oxychloride (0.93 mmol) in 0,4 mL of dry 1,4-dioxane were added and the mixture was heated to reflux with stirring during 2 hours. Afterwards, the reaction mixture was concentrated to dryness co-evaporating with toluene to remove traces of phosphorous oxychloride and the residue was suspended in 2.4 mL of 7N ammonia in methanol heating the reaction at 60° C. overnight. At the end of this period, the cooled reaction mixture was poured into 25 mL of a 1/1 mixture of water/brine and extracted with chloroform (3×25 mL). The organic layers were mixed and washed brine, dried (MgSO$_4$) and concentrated under reduced pressure to give 41 mg of a solid that was purified by flash chromatography silica (dichloromethane/methanol). After purification were obtained 9 mg of the title compound of this example (23% yield).

LRMS (m/z): 429 (M+1)$^+$.

$^1$H NMR (600 MHz, DMSO) δ 7.95 (s, 1H), 7.89 (s, 1H), 7.70 (m, 1H), 7.64 (d, J=3.0 Hz, 1H), 7.34 (m, 1H), 7.22 (m, 1H), 7.20 (s, 2H), 6.67 (d, J=3.0 Hz, 1H), 5.04 (dd, J=16.7 Hz, 2H).

Example 29

24(6-Amino-9H-purin-9-yl)methyl)-3-benzyl-5-chloropyrrolo[1,2-f][1,2,4]-triazin-4(3H)-one a) To a solution di-tert-butyl 9-((5-chloro-4-oxo-4H-pyrrolo[1,2-d][1,3,4]oxadiazin-2-yl)methyl)-9H-purin-6-ylimidodicarbonate (100 mg, 0.2 mmol) in 2 mL of dry 1,4-dioxane under argon atmosphere 127 µL of benzylamine (1.16 mmol) were added and the mixture was stirred at 30° C. during 2 hours. At the end of this period, the reaction mixture was concentrated to dryness under reduced pressure and the residue was purified by flash chromatography silica (dichloromethane/methanol). After purification were obtained 95 mg of tert-butyl 9-(2-(2-(benzylcarbamoyl)-3-chloro-1H-pyrrol-1-ylamino)-2-oxoethyl)-9H-purin-6-ylcarbamate (92% yield).

b) To a solution of tert-butyl 9-(2-(2-(benzylcarbamoyl)-3-chloro-1H-pyrrol-1-ylamino)-2-oxoethyl)-9H-purin-6-ylcarbamate (95 mg, 0.18 mmol) in 1.32 mL of dry 1,4-dioxane under argon atmosphere 165 µL of phosphorous oxychloride (1.8 mmol) in 0.6 mL of dry 1,4-dioxane were added and the mixture was heated to reflux with stirring during 2 h. Afterwards, the reaction mixture was concentrated to dryness coevaporating with toluene to remove traces of phosphorous oxychloride and the residue was suspended in 3,8 mL of 7N ammonia in methanol heating the reaction at 60° C. overnight. At the end of this period, the cooled reaction mixture was poured into 25 mL of a 1/1 mixture of water/brine and extracted with chloroform (3×25 mL). The organic layers were mixed and washed brine, dried (MgSO$_4$) and concentrated under reduced pressure to give 57 mg of a solid that was purified by reverse phase chromatography (C-18 silica from Waters, water/1:1 acetonitrile-methanol as eluents [0.1% v/v formic acid buffered] 0% to 100%). After purification were obtained 11 mg of the title compound of this example (15% yield).

LRMS (m/z): 407 (M+1)$^+$.

$^1$H NMR (600 MHz, DMSO) δ 8.13 (s, 1H), 8.08 (s, 1H), 7.51 (d, J=3.0 Hz, 1H), 7.49-7.28 (m, 5H), 7.25 (s, 2H), 6.64 (d, J=3.0 Hz, 1H), 5.46 (s, 2H), 5.33 (s, 2H).

Example 30

2-((6-Amino-9H-purin-9-yl)methyl)-3-phenylimidazo[1,2-f][1,2,4]triazin-4(3H)-one 9H-purin-6-amine (85 mg, 0.63 mmol) and potassium carbonate (87 mg, 0.63 mmol) were added to a solution of 2-(chloromethyl)-3-phenylimidazo[1,2-f][1,2,4]triazin-4 (3H)-one (137 mg, 0.53 mmol) in 10 mL of DMF. The mixture was stirred at room temperature for 21 hours. The solvent was evaporated to dryness and the crude product was purified by flash chromatography (10% to 20% MeOH/DCM) to yield 100 mg (53% yield) of the title compound as a white solid.

LRMS (m/z): 360 (M+1)$^+$.

$^1$H NMR (250 MHz, DMSO) δ 8.05 (s, 1H), 7.98 (m, 2H), 7.53 (m, 6H), 7.25 (br s, 2H), 5.04 (s, 2H).

Example 31

2-((6-amino-9H-purin-9-yl)methyl)-3-o-tolylimidazo[1,2-f][1,2,4]triazin-4(3H)-one 9H-purin-6-amine (207 mg, 1.53 mmol) and potassium carbonate (211 mg, 1.53 mmol) were added to a solution of 2-(chloromethyl)-3-o-tolylimidazo[1,2-f][1,2,4]triazin-4 (3H)-one (350 mg, 1.27 mmol) in 20 mL of DMF. The mixture was stirred at room temperature for 5 hours and poured into water. A 10% aqueous solution of sodium hydroxide was added until the solution reached pH=11 and then the product was extracted with dichloromethane. The combined organic layers were dried over sodium sulphate, filtered and the solvent was evaporated. The crude product was triturated with dichloromethane (5 mL) and methanol (5 mL) and 130 mg (27% yield) of the title compound ere obtained as a white solid.

LRMS (m/z): 374 (M+1)$^+$.

$^1$H NMR (250 MHz, DMSO) δ 8.02 (m, 3H), 7.51 (m, 5H), 7.24 (br s, 2H), 5.12 (s, J=16.0 Hz, 1H), 4.86 (s, J=16.0 Hz, 1H), 2.13 (s, 3H)

Example 32

2-((6-Amino-9H-purin-9-yl)methyl)-5-chloro-3-(pyridin-4-yl)pyrrolo[1,2-f][1,2,4]triazin-4(3H)-one a) To a suspension of 4-aminopyridine (164 mg, 1.74 mmol) in 3.3 mL of dichloromethane under inert atmosphere was added a 2M solution of trimethyl aluminium in toluene (0.87 mL, 1.74 mmol) and the mixture was stirred during 20 minutes at room temperature. Next, this mixture was cooled in an ice-water bath and a solution of di-tert-butyl 9-((5-chloro-4-oxo-4H-pyrrolo[1,2-d][1,3,4]oxadiazin-2-yl)methyl)-9H-purin-6-ylimidodicarbonate (150 mg, 0.29 mmol) in 2.2 mL of dry dichloromethane was added stirring the mixture during 3 days at room temperature. At the end of this period, the reaction mixture was cooled-down with an ice-water bath and mL of water were added followed by a 5% aqueous solution disodium tartrate dihydrate. The resulting mixture was purified directly by reverse phase chromatography (C-18 silica from Waters, water/1:1 acetonitrile-methanol as eluents 0% to 100%). After purification were obtained 139 mg of tert-butyl 9-(2-(3-chloro-2-(pyridin-4-ylcarbamoyl)-1H-pyrrol-1-ylamino)-2-oxoethyl)-9H-purin-6-ylcarbamate (93% yield).

b) Starting from tert-butyl 9-(2-(3-chloro-2-(pyridin-4-yl-carbamoyl)-1H-pyrrol-1-ylamino)-2-oxoethyl)-9H-purin-6-ylcarbamate (131 mg, 0.26 mmol) and following the experimental procedure described in Example 26b were obtained 4.2 mg (3.5% yield) of the title compound of this example.

LRMS (m/z): 394 (M+1)$^+$.

$^1$H NMR (600 MHz, DMSO) δ 8.61 (dd, J=4.5, 1.6 Hz, 2H), 7.95 (s, 1H), 7.90 (s, 1H), 7.59 (d, J=3.0 Hz, 1H), 7.44 (dd, J=4.5, 1.6 Hz, 2H), 7.18 (s, 2H), 6.64 (d, J=3.1 Hz, 1H), 4.97 (s, 2H).

Example 33

2-((6-Amino-9H-purin-9-yl)methyl)-5-chloro-3-(tetrahydro-2H-pyran-4-yl)pyrrolo-[1,2-f][1,2,4]triazin-4(3H)-one a) Starting from di-tert-butyl 9-((5-chloro-4-oxo-4H-pyrrolo[1,2-d][1,3,4]oxadiazin-2-yl)methyl)-9H-purin-6-ylimidodicarbonate (131 mg, 0.26 mmol) and following the experimental procedure described in Example 26a but heating the reaction mixture at 80° C. during 4 hours were obtained 170 mg (70% yield) of di-tert-butyl {9-[2-oxo-2-({2-[(tetrahydro-2H-pyran-4-ylamino)carbonyl]-1H-pyrrol-1-yl}amino)ethyl]-9H-purin-6-yl}imidodicarbonate.

b) Starting from di-tert-butyl {9-[2-oxo-2-({2-[(tetrahydro-2H-pyran-4-ylamino)carbonyl]-1H-pyrrol-1-yl}amino)ethyl]-9H-purin-6-yl}imidodicarbonate (131 mg, 0.26 mmol) and using the conditions described in Example 26b but isolating the product in the following way: the crude was concentrated to dryness and the residue obtained was precipitated from a 1/1 mixture of dimethylsulfoxide/4% aqueous solution of sodium bicarbonate to afford 43 mg after filtration (36% yield) of the title compound of this example.

LRMS (m/z): 401 (M+1)$^+$.

$^1$H NMR (600 MHz, DMSO) δ 8.22 (s, 1H), 8.21 (s, 1H), 7.51 (d, J=3.0 Hz, 1H), 7.38 (s, 2H), 6.62 (d, J=3.0 Hz, 1H), 5.62 (s, 2H), 4.18-4.09 (m, 1H), 3.84-3.76 (m, 2H), 3.08-2.99 (m, 2H), 2.67-2.57 (m, 2H), 1.35-1.26 (m, 2H).

Example 34

2-((6-Amino-9H-purin-9-yl)methyl)-5-chloro-3-(1-methylpiperidin-4-yl)pyrrolo[1,2-f][1,2,4]triazin-4(3H)-one a) Starting from di-tert-butyl 9-((5-chloro-4-oxo-4H-pyrrolo[1,2-d][1,3,4]oxadiazin-2-yl)methyl)-9H-purin-6-ylimidodicarbonate (150 mg, 0.29 mmol) and following the experimental procedure described in Example 26a but heating the reaction mixture at 100° C. during 4 hours were obtained 136 mg (86% yield) of tert-butyl 9-(2-(3-chloro-2-(1-methylpiperidin-4-ylcarbamoyl)-1H-pyrrol-1-ylamino)-2-oxoethyl)-9H-purin-6-ylcarbamate.

b) Starting from tert-butyl 9-(2-(3-chloro-2-(1-methylpiperidin-4-ylcarbamoyl)-1H-pyrrol-1-ylamino)-2-oxoethyl)-9H-purin-6-ylcarbamate (128 mg, 0.24 mmol) and following the experimental procedure described in Example 33b were obtained 21 mg (21% yield) of the title compound of this example.

LRMS (m/z): 414 (M+1)$^+$.

$^1$H NMR (600 MHz, DMSO) δ 8.21 (s, 1H), 8.21 (s, 1H), 7.52 (d, J=2.4 Hz, 1H), 7.36 (s, 2H), 6.62 (d, J=2.5 Hz, 1H), 5.55 (s, 2H), 3.90-3.67 (m, 1H), 2.74-2.54 (m, 4H), 2.05 (s, 3H), 1.63-1.44 (m, 2H), 1.31-1.13 (m, 2H).

Example 35

(S)-2-(1-(9H-Purin-6-ylamino)ethyl)-3-(3-fluorophenyl)pyrrolo[1,2-f][1,2,4]triazin-4(3H)-one Starting from (S)-2-(1-aminoethyl)-3-(3-fluorophenyl)pyrrolo[1,2-f][1,2,4]triazin-4(3H)-one (23 mg, 0.08 mmol) and following the experimental procedure described in Example 20 were obtained 18 mg (50% yield) of the title compound of this example.

LRMS (m/z): 391 (M+1)$^+$.

$^1$H NMR (400 MHz, DMSO) δ 12.92 (s, 1H), 8.11-8.00 (2s, 1H), 7.68 (m, 1H), 7.58-7.07 (m, 2H), 6.95 (m, 1H), 6.60 (m, 1H), 4.95 (m, 1H), 4.84 (m, 1H), 1.47 (d, J=6.6 Hz, 3H).

Example 36

(S)-4-Amino-6-(1-(3-(3-fluorophenyl)-4-oxo-3,4-dihydropyrrolo[1,2-f][1,2,4]triazin-2-yl)ethylamino)pyrimidine-5-carbonitrile Starting from (S)-2-(1-aminoethyl)-3-(3-fluorophenyl)pyrrolo[1,2-f][1,2,4]triazin-4(3H)-one (23 mg, 0.08 mmol) and following the experimental procedure described in Example 23 were obtained 13 mg (36% yield) of the title compound of this example.

LRMS (m/z): 391 (M+1)$^+$.

$^1$H NMR (400 MHz, DMSO) δ 7.78, 7.74 (2s, 1H), 7.73-7.67 (m, 1H), 7.55-7.27 (m, 2H), 7.22 (br s, 2H), 7.17-7.11 (m, 2H), 6.97 (m, 1H), 6.63 (m, 1H), 5.07-4.92 (m, 1H), 4.84 (m, 1H), 1.38 (d, J=6.5 Hz, 3H).

Example 37

(S)-2-(1-(9H-Purin-6-ylamino)ethyl)-3-(3,5-difluorophenyl)pyrrolo[1,2-f][1,2,4]triazin-4(3H)-one Starting from (S)-2-(1-aminoethyl)-3-(3,5-difluorophenyl)pyrrolo[1,2-f][1,2,4]triazin-4(3H)-one (17 mg, 0.06 mmol) and following the experimental procedure described in Example 20 were obtained 18 mg (71% yield) of the title compound of this example.

LRMS (m/z): 409 (M+1)$^+$.

$^1$H NMR (600 MHz, DMSO) δ 12.92 (s, 1H), 8.15-7.95 (m, 3H), 7.71 (s, 1H), 7.48 (m, 1H), 7.10-7.01 (m, 1H), 6.99-6.94 (m, 1H), 6.66-6.58 (m, 1H), 5.15-5.04 (m, 1H), 4.64 (m, 1H), 1.48 (d, J=6.7 Hz, 2H).

Example 38

(S)-4-Amino-6-(1-(3-(3,5-difluorophenyl)-4-oxo-3,4-dihydropyrrolo[1,2-f][1,2,4]triazin-2-yl)ethylamino)pyrimidine-5-carbonitrile Starting from (S)-2-(1-aminoethyl)-3-(3,5-difluorophenyl)pyrrolo[1,2-f][1,2,4]triazin-4(3H)-one (17 mg, 0.06 mmol) and following the experimental procedure described in Example 23 were obtained 13 mg (41% yield) of the title compound of this example.

LRMS (m/z): 409 (M+1)$^+$.

$^1$H NMR (600 MHz, DMSO) δ 7.78 (s, 1H), 7.75 (dd, J=2.7, 1.7 Hz, 1H), 7.66 (d, J=7.4 Hz, 1H), 7.47 (m, 1H), 7.25 (br s, 2H), 7.18 (m, 1H), 6.99 (dd, J=4.2, 1.7 Hz, 1H), 6.64 (dd, J=4.3, 2.7 Hz, 1H), 5.15-5.04 (m, 1H), 4.68-4.61 (m, 1H), 1.39 (d, J=6.6 Hz, 2H).

Example 39

2-((6-Amino-9H-purin-9-yl)methyl)-5-chloro-3-methylpyrrolo[1,2-f][1,2,4]triazin-4(3H)-one a) Starting from di-tert-butyl 9-((5-chloro-4-oxo-4H-pyrrolo[1,2-d][1,3,4]oxadiazin-2-yl)methyl)-9H-purin-6-ylimidodicarbonate (150 mg, 0.29 mmol) and following the experimental procedure described in Example 26a but using tetrahydrofurane as solvent and stirring the reaction mixture at room temperature during 2 hours were obtained 126 mg (97% yield) of tert-butyl 9-(2-(3-chloro-2-(methylcarbamoyl)-1H-pyrrol-1-ylamino)-2-oxoethyl)-9H-purin-6-ylcarbamate.

b) Starting from tert-butyl 9-(2-(3-chloro-2-(methylcarbamoyl)-1H-pyrrol-1-ylamino)-2-oxoethyl)-9H-purin-6-ylcarbamate (125 mg, 0.28 mmol) and following the experimental procedure described in Example 26b were obtained 46 mg (48% yield) of the title compound of this example.

LRMS (m/z): 331 (M+1)$^+$.

$^1$H NMR (400 MHz, DMSO) δ 8.15 (s, 1H), 8.15 (s, 1H), 7.42 (d, J=3 Hz, 1H), 7.32 (s, 2H), 6.57 (d, J=3 Hz, 1H), 5.58 (s, 2H), 3.46 (s, 3H).

Example 40

2-((6-Amino-9H-purin-9-yl)methyl)-3-((1r,4r)-4-aminocyclohexyl)-5-chloropyrrolo[1,2-f][1,2,4]triazin-4(3H)-one a) Starting from di-tert-butyl 9-((5-chloro-4-oxo-4H-pyrrolo[1,2-d][1,3,4]oxadiazin-2-yl)methyl)-9H-purin-6-ylimidodicarbonate (150 mg, 0.29 mmol) and following the experimental procedure described in Example 26a but heating the reaction mixture at 50° C. during 2 hours were obtained 138 mg (82% yield) of tert-butyl 9-(2-(2-((1r,4r)-4-aminocyclohexylcarbamoyl)-3-chloro-1H-pyrrol-1-ylamino)-2-oxoethyl)-9H-purin-6-ylcarbamate.

b) Starting from tert-butyl 9-(2-(2-((1r,4r)-4-aminocyclohexylcarbamoyl)-3-chloro-1H-pyrrol-1-ylamino)-2-oxoethyl)-9H-purin-6-ylcarbamate (130 mg, 0.24 mmol) and using the conditions described in Example 26b but isolating the product in the following way: the crude was concentrated to dryness and the residue obtained was purified by reverse phase chromatography (C-18 silica from Waters, water/1:1 acetonitrile-methanol as eluents 0% to 100%). After purification were obtained 14 mg (13% yield) of the title compound of this example.

LRMS (m/z): 414 (M+1)$^+$.

¹H NMR (600 MHz, DMSO) δ 8.20 (s, 1H), 8.20 (s, 1H), 7.50 (d, J=3.0 Hz, 1H), 7.35 (s, 2H), 6.61 (d, J=3.0 Hz, 1H), 5.55 (s, 2H), 3.88-3.79 (m, 1H), 2.40-2.37 (m, 1H), 1.67-1.58 (m, 4H), 1.35-1.27 (m, 2H), 0.83-0.74 (m, 4H).

Example 41

(R)-2-((6-Amino-9H-purin-9-yl)methyl)-5-chloro-3-(1-phenylethyl)pyrrolo[1,2-f][1,2,4]triazin-4(3H)-one a) Starting from di-tert-butyl 9-((5-chloro-4-oxo-4H-pyrrolo[1,2-d][1,3,4]oxadiazin-2-yl)methyl)-9H-purin-6-ylimidodicarbonate (150 mg, 0.29 mmol) and following the experimental procedure described in Example 26a but heating the reaction mixture at 40° C. during 1.5 hours were obtained 138 mg (78% yield) of tert-butyl [9-(2-{[3-chloro-2-({[(1R)-1-phenylethyl]amino}carbonyl)-1H-pyrrol-1-yl]amino}-2-oxoethyl)-9H-purin-6-yl]carbamate.

b) A solution of bromine (37 mg, 0.24 mmol) in dichloromethane (100 μL) was added dropwise to a solution of triphenylphosphine (63 mg, 0.24 mmol) in dichloromethane (1 ml) under nitrogen. The solution was stirred for 30 min, and triethylamine (78 μL, 0.56 mmol) and tert-butyl [9-(2-{[3-chloro-2-({[(1R)-1-phenylethyl]amino}carbonyl)-1H-pyrrol-1-yl]amino}-2-oxoethyl)-9H-purin-6-yl]carbamate (100 mg, 0.19 mmol) were added. The reaction mixture was refluxed for 1.5 h, and quenched with 10% aqueous sodium bicarbonate solution. The organic phase was separated, dried (sodium sulphate) and concentrated to obtain an oil that was treated with 6 ml of a 7M methanolic solution of ammonia at 60° C. in a sealed vessel. The solvent was then evaporated to obtain 66 mg (34% yield, 48% purity) of tert-butyl [9-({5-chloro-4-oxo-3-[(1R)-1-phenylethyl]-3,4-dihydropyrrolo[2,1-f][1,2,4]triazin-2-yl}methyl)-9H-purin-6-yl]carbamate.

c) tert-Butyl [9-({5-chloro-4-oxo-3-[(1R)-1-phenylethyl]-3,4-dihydropyrrolo[2,1-f][1,2,4]triazin-2-yl}methyl)-9H-purin-6-yl]carbamate (66 mg, 48% purity, 0.061 mmol) were dissolved in 4 ml of a 4M hydrogen chloride solution in dioxane and heated to 45° C. for 1 hour. Then, the crude was concentrated to dryness and the residue obtained was purified by flash chromatography silica (dichloromethane/methanol). After purification were obtained 22 mg of the title compound of this example (85% yield).

LRMS (m/z): 421 (M+1)⁺.

¹H NMR (400 MHz, DMSO) δ 8.21 (s, 1H), 8.11 (s, 1H), 7.47 (d, J=3.0 Hz, 1H), 7.40-7.21 (m, 7H), 6.58 (d, J=3.0 Hz, 1H), 5.80 (m, 1H), 5.58 (m, 2H), 1.81 (d, J=6.6 Hz, 3H).

Example 42

(S)-2-((6-Amino-9H-purin-9-yl)methyl)-5-chloro-3-(1-phenylethyl)pyrrolo[1,2-f][1,2,4]triazin-4(3H)-one a) Starting from di-tert-butyl 9-((5-chloro-4-oxo-4H-pyrrolo[1,2-d][1,3,4]oxadiazin-2-yl)methyl)-9H-purin-6-ylimidodicarbonate (150 mg, 0.29 mmol) and following the experimental procedure described in Example 26a but heating the reaction mixture at 40° C. during 1.5 hours were obtained 132 mg (75% yield) of tert-butyl [9-(2-{[3-chloro-2-({[(1S)-1-phenylethyl]amino}carbonyl)-1H-pyrrol-1-yl]amino}-2-oxoethyl)-9H-purin-6-yl]carbamate.

b) Starting from tert-butyl [9-(2-{[3-chloro-2-({[(1S)-1-phenylethyl]amino}carbonyl)-1H-pyrrol-1-yl]amino}-2-oxoethyl)-9H-purin-6-yl]carbamate (132 mg, 0.24 mmol) and following the experimental procedure described in Example 41b were obtained 132 mg (55% yield, 52% purity) of tert-butyl [9-({5-chloro-4-oxo-3-[(1S)-1-phenylethyl]-3,4-dihydropyrrolo[2,1-f][1,2,4]triazin-2-yl}methyl)-9H-purin-6-yl]carbamate.

c) Starting from tert-butyl tert-butyl [9-({5-chloro-4-oxo-3-[(1S)-1-phenylethyl]-3,4-dihydropyrrolo[2,1-f][1,2,4]triazin-2-yl}methyl)-9H-purin-6-yl]carbamate (132 mg, 52% purity, 0.13 mmol) and following the experimental procedure described in Example 41c were obtained 48 mg of the title compound of this example (87% yield).

LRMS (m/z): 421 (M+1)⁺.

¹H NMR (400 MHz, DMSO) δ 8.21 (s, 1H), 8.11 (s, 1H), 7.47 (d, J=3.0 Hz, 1H), 7.39-7.20 (m, 7H), 6.59 (d, J=3.0 Hz, 1H), 5.80 (s, 1H), 5.53 (m, 2H), 1.81 (d, J=6.7 Hz, 3H).

Example 43

(S)-4-Amino-6-(1-(4-oxo-3-(pyridin-2-yl)-3,4-dihydropyrrolo[1,2-f][1,2,4]triazin-2-yl)ethylamino)pyrimidine-5-carbonitrile Starting from (S)-2-(1-aminoethyl)-3-(pyridin-2-yl)pyrrolo[1,2-f][1,2,4]triazin-4(3H)-one dihydrochloride (60 mg, 0.13 mmol) and following the experimental procedure described in Example 23 were obtained 8 mg (9% yield) of the title compound of this example.

LRMS (m/z): 374 (M+1)⁺.

¹H NMR (400 MHz, DMSO) δ 8.47 (d, J=4.0 Hz, 1H), 7.83 (t, J=7.8 Hz, 1H), 7.75 (m, 2H), 7.69 (d, J=7.4 Hz, 1H), 7.44 (d, J=6.6 Hz, 1H), 7.37-7.29 (m, 1H), 7.21 (bs, 2H), 7.01 (dd, J=4.3, 1.6 Hz, 1H), 6.65 (dd, J=4.3, 2.7 Hz, 1H), 5.10 (m, 1H), 1.40 (d, J=6.7 Hz, 4H).

Example 44

(S)-2-(1-(9H-Purin-6-yl)pyrrolidin-2-yl)-3-phenylpyrrolo[1,2-f][1,2,4]triazin-4(3H)-one 45 mg (0.16 mmol) of (S)-3-phenyl-2-(pyrrolidin-2-yl)pyrrolo[1,2-f][1,2,4]triazin-4(3H)-one, 35 mg (0.17 mmol) of 6-bromo-9H-purine and 25 μl (0.17 mmol) of diisopropylethylamine were stirred in tert-butanol (5 ml) at 80° C. overnight. Then the solvent was removed in vacuum and the residue was taken up in AcOEt, washed with water and brine, dried over magnesium sulphate and the solvent evaporated. The crude product was purified by reverse phase chromatography (C-18 silica from Waters®, water/1:1 acetonitrile-methanol as eluents [0.1% v/v formic acid buffered] 0% to 100%) to obtain the title compound (22 mg, 80% yield) as a white solid.

LRMS (m/z): 399 (M+1)⁺.

Example 45

(S)-4-Amino-6-(1-(4-oxo-3-phenyl-5-(trifluoromethyl)-3,4-dihydropyrrolo[1,2-f][1,2,4]triazin-2-yl)ethylamino)pyrimidine-5-carbonitrile The title compound (53 mg, 58% yield) was obtained from (S)-2-(1-aminoethyl)-3-phenyl-5-(trifluoromethyl)pyrrolo[1,2-f][1,2,4]triazin-4(3H)-one and 4-amino-6-chloropyrimidine-5-carbonitrile following the experimental procedure described in example 23.

LRMS (m/z): 441 (M+1)⁺.

¹H NMR (400 MHz, DMSO) δ 7.83 (d, J=2.8 Hz, 1H), 7.75 (s, 1H), 7.62 (d, J=6.8 Hz, 1H), 7.53 (d, J=7.9 Hz, 1H), 7.44

(m, 1H), 7.37-7.17 (m, 5H), 6.99 (d, J=2.8 Hz, 1H), 4.89 (p, J=6.5 Hz, 1H), 1.36 (d, J=6.6 Hz, 3H).

Example 46

(S)-2-(1-(9H-Purin-6-ylamino)ethyl)-3-phenyl-5-(trifluoromethyl)pyrrolo[1,2-f][1,2,4]triazin-4(3H)-one The title compound (53 mg, 58% yield) was obtained from (S)-2-(1-aminoethyl)-3-phenyl-5-(trifluoromethyl)pyrrolo[1,2-f][1,2,4]triazin-4(3H)-one and 6-bromo-9H-purine following the experimental procedure described in example 20.
LRMS (m/z): 441 (M+1)$^+$.
$^1$H NMR (400 MHz, DMSO) δ 12.95 (s, 1H), 8.19-8.02 (m, 3H), 7.78 (d, J=2.7 Hz, 1H), 7.59 (m, 1H), 7.49 (d, J=7.5 Hz, 2H), 7.34 (m, 1H), 7.15 (t, J=7.8 Hz, 1H), 6.98 (d, J=2.8 Hz, 1H), 4.85 (m, 1H), 1.47 (d, J=6.7 Hz, 3H).

Example 47

(S)-4-Amino-6-(1-(5-(difluoromethyl)-4-oxo-3-phenyl-3,4-dihydropyrrolo[1,2-f][1,2,4]triazin-2-yl)ethylamino)pyrimidine-5-carbonitrile The title compound (67 mg, 59% yield) was obtained from (S)-2-(1-Aminoethyl)-5-(difluoromethyl)-3-phenylpyrrolo[1,2-f][1,2,4]triazin-4(3H)-one and 4-amino-6-chloropyrimidine-5-carbonitrile following the experimental procedure described in example 18.
LRMS (m/z): 423 (M+1)$^+$.
$^1$H NMR (400 MHz, DMSO) δ 7.81 (d, 1H), 7.77 (s, 1H), 7.66 (d, 1H), 7.54 (d, 1H), 7.50-7.41 (m, 1H), 7.40-7.12 (m, 6H), 6.91 (s, 1H), 4.97-4.85 (m, 1H), 1.38 (d, 3H).

Example 48

(S)-2-(1-(9H-Purin-6-ylamino)ethyl)-5-(difluoromethyl)-3-phenylpyrrolo[1,2-f][1,2,4]triazin-4(3H)-one The title compound (42 mg, 60% yield) was obtained from (S)-2-(1-Aminoethyl)-5-(difluoromethyl)-3-phenylpyrrolo[1,2-f][1,2,4]triazin-4(3H)-one and 6-bromo-9H-purine following the experimental procedure described in example 20.
LRMS (m/z): 423 (M+1)$^+$.
$^1$H NMR (400 MHz, DMSO) δ 12.94 (s, 1H), 8.20-7.99 (m, 2H), 7.86-6.80 (m, 9H), 4.86 (s, 1H), 1.46 (d, 3H).

Example 49

(S)-2-(1-(9H-Purin-6-ylamino)ethyl)-3-phenylimidazo[1,2-f][1,2,4]triazin-4(3H)-one (S)-2-(1-Aminoethyl)-3-phenylimidazo[1,2-f][1,2,4]triazin-4(3H)-one (80 mg, 0.31 mmol), 6-bromo-9H-purine (125 mg, 0.63 mmol) and DIPEA (162 μl, 1.25 mmol) were stirred in tert-butanol at 100° C. for 24 hours. The solvent was removed in vacuum and the residue was dissolved in dichloromethane. The organic solution was washed with water and brine, dried and the solvent was removed under reduced pressure. The product was purified by reverse phase chromatography (C-18 silica from Waters®, water/1:1 acetonitrile-methanol as eluents [0.1% v/v formic acid buffered] 0% to 100%) to furnish 47 mg (40% yield) of the title compound.
LRMS (m/z): 374 (M+1)$^+$.
$^1$H RMN (400 MHz, DMSO) δ 8.14 (s, 1H), 8.13-8.00 (m, 1H), 7.70-7.42 (m, 4H), 7.27 (m, 2H), 4.83 (q, 1H), 1.47 (d, J=6.7 Hz, 3H).

Example 50

(S)-4-amino-6-(1-(4-oxo-3-phenyl-3,4-dihydroimidazo[1,2-f][1,2,4]triazin-2-yl)ethylamino)pyrimidine-5-carbonitrile Prepared according to the experimental procedure described in Example 48 from (S)-2-(1-Aminoethyl)-3-phenylimidazo[1,2-f][1,2,4]triazin-4(3H)-one (70 mg, 0.27 mmol), and 4-amino-6-chloropyrimidine-5-carbonitrile (51 mg, 0.33 mmol). The product was purified by reverse phase chromatography (C-18 silica from Waters®, water/1:1 acetonitrile-methanol as eluents [0.1% v/v formic acid buffered] 0% to 100%) to furnish 43 mg (42% yield) of the title compound.
LRMS (m/z): 374 (M+1)$^+$.
$^1$H RMN (400 MHz, DMSO) δ 8.14 (s, 1H), 7.78 (s, 1H), 7.64 (d, 1H), 7.60 (s, 1H), 7.55 (d, 1H), 7.47 (dd, 1H), 7.40-7.28 (m, 2H), 7.25 (s, 2H), 4.90 (m, 1H), 1.39 (d, 3H).

Example 51

2-(1-(9H-Purin-6-ylamino)-3,3,3-trifluoropropyl)-3-phenylpyrrolo[1,2-f][1,2,4]triazin-4(3H)-one 2-(1-Amino-3,3,3-trifluoropropyl)-3-phenylpyrrolo[1,2-f][1,2,4]triazin-4(3H)-one (70 mg, 0.22 mmol), 6-bromo-9H-purine (86 mg, 0.43 mmol) and DIEA (151 μl, 0.87 mmol) were stirred in tert-butanol at 100° C. for 16 hours. An excess of 150 μl of DIEA was added and the mixture was stirred at 100° C. for 24 hours more. The solvent was removed in vacuum and the residue was dissolved in ethyl acetate. The organic solution was washed with water and brine, dried and the solvent was removed under reduced pressure. The product was purified by flash chromatography (dichloromethane to dichloromethane/MeOH/NH4OH, 100:8:1) to give 24 mg (25% yield) of the title compound as a white solid.
LRMS (m/z): 441 (M+1)$^+$.
$^1$H RMN (400 MHz, DMSO) δ 13.02 (s, 1H), 8.39 (d, 1H), 8.17 (s, 1H), 8.14 (s, 1H), 7.60 (dd, 2H), 7.54 (t, 2H), 7.42 (t, 1H), 7.32 (t, 1H), 6.96 (dd, 1H), 6.59 (dd, 1H), 5.22 (s, 1H), 3.17-2.97 (m, 2H).

Example 52

4-Amino-6-(3,3,3-trifluoro-1-(4-oxo-3-phenyl-3,4-dihydropyrrolo[1,2-f][1,2,4]triazin-2-yl)propylamino)pyrimidine-5-carbonitrile 2-(1-Amino-3,3,3-trifluoropropyl)-3-phenylpyrrolo[1,2-f][1,2,4]triazin-4(3H)-one (70 mg, 0.22 mmol), 4-amino-6-chloropyrimidine-5-carbonitrile (67 mg, 0.43 mmol) and DIEA (151 μl, 0.87 mmol) were stirred in tert-butanol at 100° C. for 16 hours. An excess of 150 μl of DIEA was added and the mixture was stirred at 100° C. for 24 hours more. The solvent was removed in vacuum and the residue was dissolved in ethyl acetate. The organic solution was washed with water and brine, dried and the solvent was removed under reduced pressure. The product was purified by flash chromatography (0% to 5% MeOH/DCM) to give 40 mg (42% yield) of the title compound as a white solid.
LRMS (m/z): 441 (M+1)$^+$.

¹H RMN (400 MHz, DMSO) δ 7.94 (d, 1H), 7.84 (s, 1H), 7.69 (dd, 1H), 7.57-7.46 (m, 2H), 7.38 (ddd, 4H), 6.97 (dd, 1H), 6.63 (dd, 1H), 5.22 (dd, 1H), 3.09-2.91 (m, 2H).

Example 53

(S)-4-Amino-6-(2-(4-oxo-3-phenyl-3,4-dihydropyrrolo[1,2-f][1,2,4]triazin-2-yl)pyrrolidin-1-yl)pyrimidine-5-carbonitrile (S)-3-Phenyl-2-(pyrrolidin-2-yl)pyrrolo[1,2-f][1,2,4]triazin-4(3H)-one (50 mg, 0.18 mmol), 4-amino-6-chloropyrimidine-5-carbonitrile (61 mg, 0.40 mmol) and DIEA (150 µl, 0.86 mmol) were stirred in tert-butanol at 120° C. for 16 hours. An excess of 50 mg of 4-amino-6-chloropyrimidine-5-carbonitrile was added and the mixture was stirred at 100° C. for 24 hours more. The solvent was removed in vacuum and the residue was dissolved in dichloromethane. The organic solution was washed with water and brine, dried and the solvent was removed under reduced pressure. The product was purified by flash chromatography (0% to 3% MeOH/DCM) to give 30 mg (41% yield) of the title compound as a white solid.
LRMS (m/z): 399 (M+1)⁺.
¹H NMR (400 MHz, DMSO) δ 8.03 (s, 1H), 7.69-7.46 (m, 6H), 7.28 (s, 2H), 6.91 (dd, 1H), 6.53 (m, 1H), 2.26-2.08 (m, 3H), 2.00-1.90 (m, 2H), 1.86-1.74 (m, 2H).

Example 54

(S)-3-Phenyl-2-(1-(pyrazolo[1,5-a]pyrimidin-7-ylamino)ethyl)pyrrolo[1,2-f][1,2,4]triazin-4(3H)-one The title compound (38 mg, 35% yield) was obtained from (S)-2-(1-aminoethyl)-3-phenylpyrrolo[1,2-f][1,2,4]triazin-4 (3H)-one (preparation 22) and 7-Chloropyrazolo[1,5-a]pyrimidine (preparation 89) following the experimental procedure described in example 26.
LRMS (m/z): 372 (M+1)⁺.
¹H NMR (400 MHz, DMSO) δ 8.22 (d, J=7.9 Hz, 1H), 8.09 (d, J=2.1 Hz, 1H), 7.93 (d, J=5.2 Hz, 1H), 7.76-7.70 (m, 1H), 7.55 (d, J=7.9 Hz, 1H), 7.45 (t, J=7.5 Hz, 1H), 7.22 (dd, J=12.8, 7.2 Hz, 2H), 6.97 (dd, J=4.2, 1.5 Hz, 1H), 6.87 (t, J=7.5 Hz, 1H), 6.63 (dd, J=4.1, 2.8 Hz, 1H), 6.41 (d, J=2.1 Hz, 1H), 5.59 (d, J=5.3 Hz, 1H), 4.62-4.47 (m, 1H), 1.53 (d, J=6.5 Hz, 3H).

Example 55

2-((6-Amino-9H-purin-9-yl)methyl)-5-(difluoromethyl)-3-phenylpyrrolo[1,2-f][1,2,4]triazin-4(3H)-one The title compound (36 mg, 52% yield) was obtained from 2-(chloromethyl)-5-(difluoromethyl)-3-phenylpyrrolo[1,2-f][1,2,4]triazin-4(3H)-one and adenine following the experimental procedure described in example 1.
LRMS (m/z): 409 (M+1)⁺.
¹H NMR (400 MHz, DMSO) δ 8.04 (s, 1H), 7.96 (s, 1H), 7.66 (d, 1H), 7.58-7.42 (m, 5H), 7.35-7.11 (m, 3H), 6.86 (d, 1H), 5.03 (s, 2H).

Example 56

(S)-2-(1-(2-Amino-9H-purin-6-yl)pyrrolidin-2-yl)-3-phenyl pyrrolo[1,2-f][1,2,4]triazin-4(3H)-one (S)-3-Phenyl-2-(pyrrolidin-2-yl)pyrrolo[1,2-f][1,2,4]triazin-4(3H)-one (70 mg, 0.25 mmol), 6-bromo-9H-purin-2-amine (169 mg, 1.00 mmol) and DIEA (174 µl, 1.00 mmol) were stirred in tert-butanol at 150° C. for 1.5 hours under microwave irradiation. The solvent was removed in vacuum and the residue was dissolved in dichloromethane. The organic solution was washed with brine, dried and the solvent was removed under reduced pressure. The product was purified by reverse phase chromatography (C-18 silica from Waters®, water/1:1 acetonitrile-methanol as eluents [0.1% v/v formic acid buffered] 0% to 100%) to furnish 104 mg (100% yield) of the title compound.
LRMS (m/z): 414 (M+1)⁺.

Example 57

(S)-2-(1-(4,6-diamino-1,3,5-triazin-2-ylamino)ethyl)-3-phenylpyrrolo[1,2-f][1,2,4]triazin-4(3H)-one The title compound (26 mg, 24% yield) was obtained from (S)-2-(1-aminoethyl)-3-phenylpyrrolo[1,2-f][1,2,4]triazin-4 (3H)-one (preparation 22) and 6-chloro-1,3,5-triazine-2,4-diamine (purchased from Aldrich) following the experimental procedure described in example 26.
LRMS (m/z): 364 (M+1)⁺.
¹H NMR (400 MHz, DMSO) δ 7.65-7.57 (m, 2H), 7.45 (m, 4H), 6.91 (dd, J=4.3, 1.7 Hz, 1H), 6.83 (d, J=7.4 Hz, 1H), 6.56 (dd, J=4.3, 2.7 Hz, 1H), 5.99 (br s, 4H), 4.48 (p, J=6.6 Hz, 1H), 1.20 (d, J=6.8 Hz, 3H).

Example 58

(S)-2-((6-Amino-9H-purin-9-yl)methyl)-5-chloro-3-(1-(5-fluoropyridin-2-yl)ethyl)pyrrolo[1,2-f][1,2,4]triazin-4(3H)-one a) Starting from di-tert-butyl 9-((5-chloro-4-oxo-4H-pyrrolo[1,2-d][1,3,4]oxadiazin-2-yl)methyl)-9H-purin-6-ylimidodicarbonate (150 mg, 0,29 mmol) and following the experimental procedure described in Example 26a but heating the reaction mixture at 30° C. during 2 hours were obtained 188 mg (81% yield) of di-tert-butyl [9-(2-{[3-chloro-2-({[(1S)-1-(5-fluoropyridin-2-yl)ethyl]amino}carbonyl)-1H-pyrrol-1-yl]amino}-2-oxoethyl)-9H-purin-6-yl]imidodicarbonate.
b) Starting from di-tert-butyl [9-(2-{[3-chloro-2-({[(1S)-1-(5-fluoropyridin-2-yl)ethyl]amino}carbonyl)-1H-pyrrol-1-yl]amino}-2-oxoethyl)-9H-purin-6-yl]imidodicarbonate (185 mg, 0,28 mmol) and following the experimental procedure described in Example 41b were obtained 232 mg (47% yield, 31% purity) of (S)-tert-butyl 9-((5-chloro-3-(1-(5-fluoropyridin-2-yl)ethyl)-4-oxo-3,4-dihydropyrrolo[1,2-f][1,2,4]triazin-2-yl)methyl)-9H-purin-6-ylcarbamate.
c) Starting from (S)-tert-butyl 9-((5-chloro-3-(1-(5-fluoropyridin-2-yl)ethyl)-4-oxo-3,4-dihydropyrrolo[1,2-f][1,2,4]triazin-2-yl)methyl)-9H-purin-6-ylcarbamate (232 mg, 31% purity, 0.13 mmol) and following the experimental procedure described in Example 41c were obtained 44 mg of the title compound of this example (75% yield).
LRMS (m/z): 440 (M+1)⁺.
¹H NMR (400 MHz, DMSO) δ 8.41 (s, 1H), 8.19 (s, 1H), 8.11 (s, 1H), 7.80-7.63 (m, 1H), 7.61-7.45 (m, 2H), 7.30 (s, 2H), 6.59 (d, 1H), 5.91-5.44 (m, 3H), 1.85 (d, 3H).

Example 59

(S)-2-(1-(2-Amino-9H-purin-6-ylamino)ethyl)-3-(3,5-difluorophenyl)pyrrolo[1,2-f][1,2,4]triazin-4(3H)-one The title compound (11 mg, 20% yield) was obtained from (S)-2-(1-aminoethyl)-3-(3,5-difluorophenyl)pyrrolo[1,2-f]

[1,2,4]triazin-4(3H)-one and 6-chloro-9H-purin-2-amine following the experimental procedure described in example 21.

LRMS (m/z): 424 (M+1)$^+$.

$^1$H NMR (400 MHz, DMSO) δ 12.04 (d, 1H), 7.69 (dd, 1H), 7.67-7.65 (m, 1H), 7.53-7.38 (m, 2H), 7.20-7.09 (m, 2H), 6.99-6.93 (dd, 1H), 6.61 (dd, 1H), 5.57 (s, 2H), 4.95-4.85 (m, 1H), 1.43 (d, 3H).

Example 60

(S)-2-(1-(6-Amino-5-cyanopyrimidin-4-ylamino)ethyl)-4-oxo-3-phenyl-3,4-dihydropyrrolo[1,2-f][1,2,4]triazine-5-carbonitrile The title compound (35 mg, 74% yield) was obtained from (S)-2-(1-aminoethyl)-4-oxo-3-phenyl-3,4-dihydropyrrolo[1,2-f][1,2,4]triazine-5-carbonitrile and 4-amino-6-chloropyrimidine-5-carbonitrile following the experimental procedure described in example 23.

LRMS (m/z): 398 (M+1)$^+$.

$^1$H NMR (400 MHz, DMSO) δ 7.89 (d, J=2.9 Hz, 1H), 7.78 (s, 1H), 7.62 (d, J=6.8 Hz, 1H), 7.54 (d, J=7.9 Hz, 1H), 7.50-7.44 (m, 1H), 7.39-7.30 (m, 3H), 7.24 (br s, 1H), 7.21 (d, J=2.9 Hz, 1H), 4.91 (p, J=6.6 Hz, 1H), 1.38 (d, J=6.7 Hz, 3H).

Example 61

(S)-2-(1-(9H-Purin-6-ylamino)ethyl)-4-oxo-3-phenyl-3,4-dihydropyrrolo[1,2-f][1,2,4]triazine-5-carbonitrile The title compound (35 mg, 74% yield) was obtained from (S)-2-(1-aminoethyl)-4-oxo-3-phenyl-3,4-dihydropyrrolo[1,2-f][1,2,4]triazine-5-carbonitrile and 6-bromo-9H-purine following the experimental procedure described in example 20.

LRMS (m/z): 398 (M+1)$^+$.

$^1$H NMR (400 MHz, DMSO) δ 12.96 (s, 1H), 8.10 (m, 3H), 7.83 (d, J=2.8 Hz, 1H), 7.64-7.45 (m, 3H), 7.42-7.29 (m, 1H), 7.18 (d, J=3.0 Hz, 2H), 4.92-4.74 (m, 1H), 1.46 (d, J=6.7 Hz, 3H).

Example 62

(R)-2-(1-(9H-Purin-6-ylamino)-2-hydroxyethyl)-3-phenylpyrrolo[1,2-f][1,2,4]triazin-4(3H)-one The title compound (25 mg, 50% yield) was obtained from (R)-2-(1-amino-2-hydroxyethyl)-3-phenylpyrrolo[1,2-f][1,2,4]triazin-4(3H)-one and 6-bromo-9H-purine following the experimental procedure described in example 20.

LRMS (m/z): 389 (M+1)$^+$.

$^1$H NMR (400 MHz, DMSO) δ 12.98 (s, 1H), 8.17 (br s, 1H), 8.07 (s, 1H), 7.62 (dd, 1H), 7.52-7.21 (m, 6H), 6.92 (dd, 1H), 6.56 (dd, 1H), 5.04 (t, 1H), 4.84-4.74 (m, 1H), 3.86 (td, 1H), 3.69 (td, 1H).

Example 63

(R)-4-Amino-6-(2-hydroxy-1-(4-oxo-3-phenyl-3,4-dihydropyrrolo[1,2-f][1,2,4]triazin-2-yl)ethylamino)pyrimidine-5-carbonitrile The title compound (20 mg, 39% yield) was obtained from (R)-2-(1-amino-2-hydroxyethyl)-3-phenylpyrrolo[1,2-f][1,2,4]triazin-4(3H)-one and 4-amino-6-chloropyrimidine-5-carbonitrile following the experimental procedure described in example 23.

LRMS (m/z): 389 (M+1)$^+$.

$^1$H NMR (400 MHz, DMSO) δ 7.82 (s, 1H), 7.67 (dd, 1H), 7.50-7.24 (m, 8H), 6.93 (dd, 1H), 6.59 (dd, 1H), 4.95 (t, 1H), 4.80-4.74 (m, 1H), 3.79 (dt, 1H), 3.55 (dt, 1H).

Example 64

(S)-2-(1-(2-Amino-9H-purin-6-ylamino)ethyl)-3-phenylimidazo[1,2-f][1,2,4]triazin-4(3H)-one (S)-2-(1-Aminoethyl)-3-phenylimidazo[1,2-f][1,2,4]triazin-4(3H)-one (80 mg, 0.31 mmol), 6-chloro-9H-purin-2-amine (106 mg, 0.63 mmol) and DIEA (109 µl, 0.63 mmol) were stirred in 1-butanol (2 mL) at 150° C. for 2 hours under microwave irradiation. The solvent was removed in vacuum and the residue was dissolved in ethyl acetate. The organic solution was washed with water and brine, dried and the solvent was removed under reduced pressure. The product was purified by flash chromatography (dichloromethane to dichloromethane/MeOH/NH4OH, 100:8:1) to give 25 mg (20% yield) of the title compound as a white solid.

LRMS (m/z): 389 (M+1)$^+$.

$^1$H RMN (400 MHz, DMSO) δ 12.10 (s, 1H), 8.02 (d, 1H), 7.75-7.27 (m, 7H), 5.59 (s, 2H), 4.71 (s, 1H), 2.48 (m, 1H), 1.36 (d, 3H).

Example 65

(S)-2-(1-(7H-Pyrrolo[2,3-d]pyrimidin-4-ylamino)ethyl)-3-phenylpyrrolo[1,2-f][1,2,4]triazin-4(3H)-one The title compound (17 mg, 13% yield) was obtained from (S)-2-(1-aminoethyl)-3-phenylpyrrolo[1,2-f][1,2,4]triazin-4(3H)-one (preparation 22) and 4-Chloropyrrolo[2,3-D]pyrimidine (purchased from Alfa Aesar) following the experimental procedure described in example 26.

LRMS (m/z): 372 (M+1)$^+$.

$^1$H NMR (400 MHz, DMSO) δ 11.53 (s, 1H), 7.99 (s, 1H), 7.88 (br s, 1H), 7.62 (m, 1H), 7.57-7.46 (m, 3H), 7.34 (t, J=7.2 Hz, 1H), 7.20 (t, J=7.4 Hz, 1H), 7.10 (s, 1H), 6.95 (dd, J=4.2, 1.6 Hz, 1H), 6.59 (dd, J=4.9, 2.1 Hz, 2H), 4.93-4.69 (m, 1H), 1.45 (d, J=6.7 Hz, 3H).

Example 66

(S)-4-Amino-6-(methyl(1-(4-oxo-3-phenyl-3,4-dihydropyrrolo[1,2-f][1,2,4]triazin-2-yl)ethyl)amino)pyrimidine-5-carbonitrile The title compound (24 mg, 22% yield) was obtained from (S)-2-(1-(methylamino)ethyl)-3-phenylpyrrolo[1,2-f][1,2,4]triazin-4(3H)-one and 4-amino-6-chloropyrimidine-5-carbonitrile following the experimental procedure described in example 23.

LRMS (m/z): 387 (M+1)$^+$.

$^1$H NMR (400 MHz, DMSO) δ 7.74 (dd, J=2.6, 1.7 Hz, 1H), 7.64 (s, 1H), 7.50 (dd, J=6.9, 1.1 Hz, 1H), 7.35 (td, J=7.7, 1.7 Hz, 1H), 7.24-7.11 (m, 4H), 6.97 (dd, J=4.3, 1.6 Hz, 1H), 6.64 (dd, J=4.3, 2.7 Hz, 1H), 5.79 (q, J=6.6 Hz, 1H), 3.02 (s, 3H), 1.38 (d, J=6.6 Hz, 3H).

Example 67

(S)-2-(1-(Methyl(9H-purin-6-yl)amino)ethyl)-3-phenylpyrrolo[1,2-f][1,2,4]triazin-4(3H)-one The title compound (35 mg, 32% yield) was obtained from (S)-2-(1-(methylamino)ethyl)-3-phenylpyrrolo[1,2-f][1,2,4]triazin-4(3H)-one and 6-bromo-9H-purine following the experimental procedure described in example 20.
LRMS (m/z): 387 (M+1)$^+$.

Example 68

(S)-2-(1-(9H-Purin-6-ylamino)ethyl)-5-methyl-3-phenyl pyrrolo[1,2-f][1,2,4]triazin-4(3H)-one 100 mg (0.37 mmol) of (S)-2-(1-aminoethyl)-5-methyl-3-phenylpyrrolo[1,2-f][1,2,4]triazin-4(3H)-one, 148 mg (0.74 mmol) of 6-bromo-9H-purine and 260 µL (1.49 mmol) of diisopropylethylamine were heated at 100° C. in tert-butanol (2 mL) for 16 hours. Then the solvent was removed under vacuum and the crude product was purified by flash chromatography (dichloromethane to dichloromethane/MeOH/NH4OH, 100:8:1) to give 94 mg (65% yield) of the title compound as a white solid.
LRMS (m/z): 387 (M+1)$^+$.
$^1$H NMR (400 MHz, DMSO) δ 12.92 (s, 1H), 8.13 (s, 1H), 8.08 (s, 1H), 8.01 (s, 1H), 7.48 (t, 4H), 7.33 (s, 1H), 7.20 (s, 1H), 6.39 (d, 1H), 4.88-4.73 (m, 1H), 2.38 (s, 3H), 1.43 (d, 3H).

Example 69

(S)-4-Amino-6-(1-(5-methyl-4-oxo-3-phenyl-3,4-dihydropyrrolo[1,2-f][1,2,4]triazin-2-yl)ethylamino)pyrimidine-5-carbonitrile The title compound was prepared following the experimental procedure described in Example 68 from (S)-2-(1-aminoethyl)-5-methyl-3-phenylpyrrolo[1,2-f][1,2,4]triazin-4(3H)-one (100 mg, 0.37 mmol) and 4-amino-6-chloropyrimidine-5-carbonitrile (115 mg, 0.74 mmol). The product was purified by flash chromatography (0% to 5% MeOH/DCM) to give 94 mg (65% yield) of the title compound as a white solid.
LRMS (m/z): 387 (M+1)$^+$.
$^1$H NMR (400 MHz, DMSO) δ 13.02 (s, 1H), 8.39 (d, 1H), 8.17 (s, 1H), 8.14 (s, 1H), 7.60 (dd, 2H), 7.54 (t, 2H), 7.42 (t, 1H), 7.32 (t, 1H), 6.96 (dd, 1H), 6.59 (dd, 1H), 5.22 (s, 1H), 3.17-2.97 (m, 2H).

Example 70

(S)-2-(1-(9H-Purin-6-ylamino)ethyl)-7-methyl-3-phenylpyrrolo[1,2-f][1,2,4]triazin-4(3H)-one The title compound (35 mg, 68% yield) was obtained from (S)-2-(1-aminoethyl)-7-methyl-3-phenylpyrrolo[1,2-f][1,2,4]triazin-4(3H)-one and 6-bromo-9H-purine following the experimental procedure described in example 20.
LRMS (m/z): 387 (M+1)$^+$.
$^1$H NMR (400 MHz, DMSO) δ 12.92 (s, 1H), 8.12 (s, 1H), 8.07-7.98 (m, 2H), 7.49 (m, 2H), 7.41 (d, J=7.8 Hz, 1H), 7.33-7.24 (m, 1H), 7.15-7.05 (m, 1H), 6.87 (d, J=4.2 Hz, 1H), 6.41 (d, J=4.1 Hz, 1H), 4.94 (m, 1H), 2.41 (s, 3H), 1.47 (d, J=6.6 Hz, 3H).

Example 71

(S)-4-Amino-6-(1-(7-methyl-4-oxo-3-phenyl-3,4-dihydropyrrolo[1,2-f][1,2,4]triazin-2-yl)ethylamino)pyrimidine-5-carbonitrile The title compound (35 mg, 68% yield) was obtained from (S)-2-(1-aminoethyl)-7-methyl-3-phenylpyrrolo[1,2-f][1,2,4]triazin-4(3H)-one and 4-amino-6-chloropyrimidine-5-carbonitrile following the experimental procedure described in example 23.
LRMS (m/z): 387 (M+1)$^+$.
$^1$H NMR (400 MHz, DMSO) δ 7.75 (s, 1H), 7.63 (d, J=7.1 Hz, 1H), 7.49-7.38 (m, 2H), 7.27 (m, 5H), 6.88 (d, J=4.1 Hz, 1H), 6.44 (d, J=3.9 Hz, 1H), 5.02-4.90 (m, 1H), 2.47 (s, 3H).

Example 72

(S)-2-(4,4-Difluoro-1-(9H-purin-6-yl)pyrrolidin-2-yl)-3-phenylpyrrolo[1,2-f][1,2,4]triazin-4(3H)-one The title compound was prepared following the experimental procedure described in Example 68 from (S)-2-(4,4-difluoropyrrolidin-2-yl)-3-phenylpyrrolo[1,2-f][1,2,4]triazin-4(3H)-one (100 mg, 0.32 mmol) and 6-bromo-9H-purine (126 mg, 0.63 mmol). The product was purified by flash chromatography (DCM to DCM/MeOH/NH4OH, 100:8:1) to give 109 mg (85% yield) of the title compound as a white solid.
LRMS (m/z): 435 (M+1)$^+$.
$^1$H NMR (400 MHz, DMSO) δ (mixture of 2 conformers) 13.18 (s, 1H), 8.40-8.01 (m, 3H), 7.80-7.36 (m, 5H), 6.99-6.82 (m, 1H), 6.58-6.38 (m, 1H), 5.02-3.98 (m, 3H), 3.11-2.85 (m, 2H).

Example 73

(S)-4-Amino-6-(4,4-difluoro-2-(4-oxo-3-phenyl-3,4-dihydropyrrolo[1,2-f][1,2,4]triazin-2-yl)pyrrolidin-1-yl)pyrimidine-5-carbonitrile The title compound was prepared following the experimental procedure described in Example 68 from (S)-2-(4,4-difluoropyrrolidin-2-yl)-3-phenylpyrrolo[1,2-f][1,2,4]triazin-4(3H)-one (100 mg, 0.32 mmol) and 4-amino-6-chloropyrimidine-5-carbonitrile (59 mg, 0.38 mmol). The product was purified by flash chromatography (0% to 7% MeOH/DCM) to give 57 mg (42% yield) of the title compound as a white solid.
LRMS (m/z): 435 (M+1)$^+$.
$^1$H NMR (400 MHz, DMSO) δ 8.14 (s, 1H), 7.80-7.40 (m, 7H), 6.95 (dd, 1H), 6.57 (dd, 1H), 4.91 (s, 1H), 4.53-4.21 (m, 2H), 3.01-2.74 (m, 1H), 2.48-2.40 (m, 1H).

Example 74

(S)-2-(1-(9H-Purin-6-ylamino)ethyl)-6-fluoro-3-phenylpyrrolo[1,2-f][1,2,4]triazin-4(3H)-one The title compound (136 mg, 47% yield) was obtained from (S)-2-(1-aminoethyl)-6-fluoro-3-phenylpyrrolo[1,2-f]

[1,2,4]triazin-4(3H)-one and 6-bromo-9H-purine following the experimental procedure described in example 20 but using n-butanol as solvent.

LRMS (m/z): 391 (M+1)⁺.

¹H NMR (400 MHz, DMSO) δ 12.83 (s, 1H), 8.14 (br s, 1H), 8.07 (s, 1H), 7.78 (d, 1H), 7.59-7.11 (m, 6H), 6.83 (d, 1H), 4.91-4.77 (m, 1H), 1.45 (d, 3H).

Example 75

(S)-4-Amino-6-(1-(6-fluoro-4-oxo-3-phenyl-3,4-dihydropyrrolo[1,2-f][1,2,4]triazin-2-yl)ethylamino) pyrimidine-5-carbonitrile The title compound (241 mg, 75% yield) was obtained from (S)-2-(1-aminoethyl)-6-fluoro-3-phenylpyrrolo[1,2-f][1,2,4]triazin-4(3H)-one and 4-amino-6-chloropyrimidine-5-carbonitrile following the experimental procedure described in example 23 but using n-butanol as solvent.

LRMS (m/z): 391 (M+1)⁺.

¹H NMR (400 MHz, DMSO) δ 7.85 (d, 1H), 7.76 (s, 1H), 7.68 (d, 1H), 7.55-7.09 (m, 7H), 6.85 (d, 1H), 4.95-4.83 (m, 1H), 1.36 (d, 3H).

Example 76

2-((S)-1-(9H-Purin-6-ylamino)ethyl)-3-((S)-1-phenylethyl)pyrrolo[1,2-f][1,2,4]triazin-4(3H)-one The title compound (238 mg, 64% yield) was obtained from 2-((S)-1-aminoethyl)-3-((S)-1-phenylethyl)pyrrolo[1,2f][1,2,4]triazin-4(3H)-one and 6-bromo-9H-purine following the experimental procedure described in example 20 but using n-butanol as solvent and heating the reaction mixture at 120° C. during 15 hours.

LRMS (m/z): 401 (M+1)⁺.

¹H NMR (400 MHz, DMSO) δ 12.98 (s, 1H), 8.45-8.03 (m, 3H), 8.13 (s, 1H), 7.53 (dd, 1H), 7.48-7.01 (m, 5H), 6.74 (dd, 1H), 6.51 (dd, 1H), 5.95-5.55 (m, 2H), 1.91 (d, 3H), 1.72-1.42 (m, 3H).

Example 77

4-Amino-6-((S)-1-(4-oxo-3-((S)-1-phenylethyl)-3,4-dihydropyrrolo[1,2-f][1,2,4]triazin-2-yl)ethylamino) pyrimidine-5-carbonitrile The title compound (247 mg, 70% yield) was obtained from 2-(S)-1-aminoethyl)-3-(S)-1-phenylethyl)pyrrolo[1,2-f][1,2,4]triazin-4(3H)-one and 4-amino-6-chloropyrimidine-5-carbonitrile following the experimental procedure described in example 23 but using n-butanol as solvent and heating the reaction mixture at 120° C. during 15 hours.

LRMS (m/z): 401 (M+1)⁺.

¹H NMR (400 MHz, DMSO) δ 8.18-7.88 (m, 2H), 7.60 (dd, 1H), 7.46-7.00 (m, 7H), 6.77 (dd, 1H), 6.54 (dd, 1H), 5.83-5.59 (m, 1H), 5.59-5.25 (m, 1H), 1.87 (d, 3H), 1.67-1.37 (m, 3H).

Example 78

(S)-4-Amino-6-(1-(3-(2,6-dimethylphenyl)-4-oxo-3,4-dihydropyrrolo[1,2-f][1,2,4]triazin-2-yl)ethylamino)pyrimidine-5-carbonitrile The title compound (27 mg, 22% yield) was obtained from (S)-2-(1-aminoethyl)-3-(2,6-dimethylphenyl)pyrrolo[1,2-f][1,2,4]triazin-4(3H)-one and 4-amino-6-chloropyrimidine-5-carbonitrile following the experimental procedure described in example 23 but using n-butanol as solvent and heating the reaction mixture at 130° C. during 15 hours.

LRMS (m/z): 401 (M+1)⁺.

¹H NMR (400 MHz, DMSO) δ 7.87 (d, 1H), 7.79 (dd, 1H), 7.56 (s, 1H), 7.27-7.10 (m, 3H), 7.06 (t, 1H), 7.01 (dd, 1H), 6.83 (d, 1H), 6.66 (dd, 1H), 5.09-4.97 (m, 1H), 2.04 (s, 3H), 2.00 (s, 3H), 1.38 (d, 3H).

Example 79

(S)-2-(9H-Purin-6-ylamino)methyl)-3-(1-phenylethyl)pyrrolo[1,2-f][1,2,4]triazin-4(3H)-one The title compound (116 mg, 41% yield) was obtained from (S)-2-(aminomethyl)-3-(1-phenylethyl)pyrrolo[1,2-f][1,2,4]triazin-4(3H)-one and 6-bromo-9H-purine following the experimental procedure described in example 20 but using n-butanol as solvent and heating the reaction mixture at 80° C. during 15 hours.

LRMS (m/z): 387 (M+1)⁺.

¹H NMR (400 MHz, DMSO) δ 12.95 (s, 1H), 8.38-7.94 (m, 3H), 7.54 (dd, 1H), 7.44-7.06 (m, 5H), 6.77 (dd, 1H), 6.51 (dd, 1H), 5.99-5.53 (m, 1H), 4.90-4.80 (bm, 2H), 1.86 (d, 3H).

Example 80

(S)-4-Amino-6-((4-oxo-3-(1-phenylethyl)-3,4-dihydropyrrolo[1,2-f][1,2,4]triazin-2-yl)methylamino) pyrimidine-5-carbonitrile The title compound (107 mg, 38% yield) was obtained from (S)-2-(aminomethyl)-3-(1-phenylethyl)pyrrolo[1,2-f][1,2,4]triazin-4(3H)-one and 4-amino-6-chloropyrimidine-5-carbonitrile following the experimental procedure described in example 23 but using n-butanol as solvent and heating the reaction mixture at 50° C. during 15 hours.

LRMS (m/z): 387 (M+1)⁺.

¹H NMR (400 MHz, DMSO) δ 8.00 (s, 1H), 7.95-7.83 (m, 1H), 7.58 (dd, 1H), 7.47-7.18 (m, 7H), 6.79 (dd, 1H), 6.53 (dd, 1H), 5.83-5.49 (bm, 1H), 4.81-4.46 (bm, 2H), 1.85 (d, 3H).

Example 81

(S)-2-(1-(5-Fluoro-7H-pyrrolo[2,3-d]pyrimidin-4-ylamino)ethyl)-3-phenylpyrrolo[1,2-f][1,2,4]triazin-4(3H)-one The title compound (10 mg, 13% yield) was obtained from (S)-2-(1-aminoethyl)-3-phenylpyrrolo[1,2-f][1,2,4]triazin-4(3H)-one (preparation 22) and 4-chloro-5-fluoro-7H-pyrrolo[2,3-d]pyrimidine (purchased from Matrix Scientific) following the experimental procedure described in example 26.

LRMS (m/z): 390 (M+1)⁺.

¹H NMR (400 MHz, DMSO) δ 11.39 (s, 1H), 7.94 (s, 1H), 7.68-7.64 (m, 1H), 7.52 (d, J=8.4 Hz, 1H), 7.43 (m, 2H), 7.25 (m, 2H), 7.14 (td, J=7.8, 0.8 Hz, 1H), 7.06 (t, J=2.4 Hz, 1H), 6.94 (dd, J=4.3, 1.6 Hz, 1H), 6.60 (dd, J=4.2, 2.7 Hz, 1H), 4.97 (p, J=6.7 Hz, 1H), 1.45 (d, J=6.7 Hz, 3H

Example 82

(S)-2-(1-(9H-Purin-6-ylamino)ethyl)-3-(2,6-dimethylphenyl)pyrrolo[1,2-f][1,2,4]triazin-4(3H)-one The title compound (25 mg, 20% yield) was obtained from (S)-2-(1-aminoethyl)-3-(2,6-dimethylphenyl)pyrrolo[1,2-f]

[1,2,4]triazin-4(3H)-one and 6-bromo-9H-purine following the experimental procedure described in example 20 but using n-butanol as solvent and heating the reaction mixture at 130° C. during 15 hours.

LRMS (m/z): 401 (M+1)⁺

¹H NMR (400 MHz, DMSO) δ 12.68 (s, 1H), 8.16-7.80 (m, 3H), 7.77 (dd, 1H), 7.24-7.11 (m, 1H), 7.09-6.96 (m, 2H), 6.66 (dd, 1H), 6.60-6.48 (m, 1H), 5.19-5.01 (m, 1H), 2.05 (s, 3H), 1.90 (s, 3H), 1.45 (d, 3H).

Example 83

(S)-4-Amino-6-(1-(5-fluoro-4-oxo-3-phenyl-3,4-dihydropyrrolo[1,2-f][1,2,4]triazin-2-yl)ethylamino)pyrimidine-5-carbonitrile The title compound (24 mg, 42% yield) was obtained from (S)-2-(1-aminoethyl)-5-fluoro-3-phenylpyrrolo[1,2-f][1,2,4]triazin-4(3H)-one and 4-amino-6-chloropyrimidine-5-carbonitrile following the experimental procedure described in example 23 but heating the reaction mixture at 110° C. during 15 hours.

LRMS (m/z): 391 (M+1)⁺.

¹H NMR (400 MHz, CDCl3) δ 10.73 (s, 1H), 8.33 (s, 1H), 7.98 (br s, 1H), 7.57-7.41 (m, 5H), 7.38-7.31 (m, 1H), 7.14 (dd, 1H), 6.52 (m, 1H), 5.18 (s, 1H), 1.50 (d, 3H).

Example 84

(S)-2-(1-(9H-Purin-6-ylamino)ethyl)-5-fluoro-3-phenylpyrrolo[1,2-f][1,2,4]triazin-4(3H)-one The title compound (17 mg, 35% yield) was obtained from (S)-2-(1-aminoethyl)-5-fluoro-3-phenylpyrrolo[1,2-f][1,2,4]triazin-4(3H)-one and 6-bromo-9H-purine following the experimental procedure described in example 20 but heating the reaction mixture at 110° C. during 15 hours.

LRMS (m/z): 391 (M+1)⁺.

¹H NMR (400 MHz, CDCl3) δ 10.73 (s, 1H), 8.33 (s, 1H), 7.98 (br s, 1H), 7.57-7.41 (m, 5H), 7.38-7.31 (m, 1H), 7.14 (dd, 1H), 6.52 (m, 1H), 5.18 (s, 1H), 1.50 (d, 3H).

Example 85

(S)-2-(1-(6-Amino-5-cyanopyrimidin-4-ylamino)ethyl)-3-(3,5-difluorophenyl)-4-oxo-3,4-dihydropyrrolo[1,2-f][1,2,4]triazine-5-carbonitrile The title compound (84 mg, 54% yield) was obtained from (S)-2-(1-aminoethyl)-3-(3,5-difluorophenyl)-4-oxo-3,4-dihydropyrrolo[1,2-f][1,2,4]triazine-5-carbonitrile and 4-amino-6-chloropyrimidine-5-carbonitrile following the experimental procedure described in example 23.

LRMS (m/z): 434 (M+1)⁺.

¹H NMR (400 MHz, DMSO) δ 7.96 (d, J=3.0 Hz, 1H), 7.80 (s, 1H), 7.57 (d, J=7.3 Hz, 1H), 7.47 (d, J=8.5 Hz, 1H), 7.37 (m, 2H), 7.31-7.18 (m, 2H), 7.05 (d, J=8.8 Hz, 1H), 5.10 (p, J=6.5 Hz, 1H), 1.40 (d, J=6.6 Hz, 3H)

Example 86

(S)-4-Amino-6-(1-(3-(3,5-difluorophenyl)-4-oxo-3,4-dihydroimidazo[1,2-f][1,2,4]triazin-2-yl)ethylamino)pyrimidine-5-carbonitrile 75 mg (0.26 mmol) of (S)-2-(1-aminoethyl)-3-(3,5-difluorophenyl)imidazo[1,2-f][1,2,4]triazin-4(3H)-one, 52 mg (0.33 mmol) of 4-amino-6-chloropyrimidine-5-carbonitrile and 134 μL (0.77 mmol) of diisopropylethylamine were heated at 120° C. in tert-butanol (3 mL) for 48 hours. The solvent was removed in vacuum and the residue was dissolved in dichloromethane. The organic solution was washed with water and brine, dried and the solvent was removed under reduced pressure. The product was purified by reverse phase chromatography (C-18 silica from Waters®, water/1:1 acetonitrile-methanol as eluents [0.1% v/v formic acid buffered] 0% to 100%) to furnish 30 mg (28% yield) of the title compound.

LRMS (m/z): 410 (M+1)⁺.

¹H NMR (400 MHz, DMSO) δ 8.19 (d, 1H), 8.19 (d, 1H), 7.80 (s, 1H), 7.63 (d, 1H), 7.57 (d, 1H), 7.48 (dd, 1H), 7.30 (s, 2H), 7.08-7.00 (m, 1H), 5.09 (m, 1H), 1.43 (d, 3H).

Example 87

(S)-2-(1-(9H-Purin-6-ylamino)ethyl)-3-(3,5-difluorophenyl)-4-oxo-3,4-dihydropyrrolo[1,2-f][1,2,4]triazine-5-carbonitrile The title compound (31 mg, 20% yield) was obtained from (S)-2-(1-aminoethyl)-3-(3,5-difluorophenyl)-4-oxo-3,4-dihydropyrrolo[1,2-f][1,2,4]triazine-5-carbonitrile and 6-bromo-9H-purine following the experimental procedure described in example 20.

LRMS (m/z): 434 (M+1)⁺.

¹H NMR (400 MHz, DMSO) δ 12.96 (br s, 1H), 8.14 (m, 1H), 8.01 (m, 2H), 7.92 (d, J=2.9 Hz, 1H), 7.50 (m, 1H), 7.23 (d, J=3.0 Hz, 1H), 7.13 (t, J=9.0 Hz, 1H), 7.04 (d, J=8.9 Hz, 1H), 5.20-4.97 (m, 1H), 1.50 (d, J=6.1 Hz, 3H).

Example 88

4-Amino-6-(1S)-1-(5-(1,2-dihydroxyethyl)-4-oxo-3-phenyl-3,4-dihydropyrrolo[1,2-f][1,2,4]triazin-2-Aethylamino)pyrimidine-5-carbonitrile The title compound (14 mg, 10% yield) was obtained from 2-((S)-1-aminoethyl)-5-(1,2-dihydroxyethyl)-3-phenylpyrrolo[1,2-f][1,2,4]triazin-4(3H)-one and 4-amino-6-chloropyrimidine-5-carbonitrile following the experimental procedure described in example 23 but using n-butanol as solvent and heating the reaction mixture at 110° C. during 15 hours.

LRMS (m/z): 433 (M+1)⁺.

¹H NMR (400 MHz, DMSO) δ 7.78 (d, 1H), 7.73-7.67 (m, 1H), 7.61-7.56 (m, 1H), 7.52-7.16 (m, 7H), 6.66-6.57 (m, 1H), 5.18-5.04 (m, 2H), 4.93-4.81 (m, 1H), 4.69-4.60 (m, 1H), 1.34 (d, 3H).

Example 89

(S)-4-amino-6-(1-(3-(3,5-difluorophenyl)-4-oxo-5-(trifluoromethyl)-3,4-dihydropyrrolo[1,2-f][1,2,4]triazin-2-yl)ethylamino)pyrimidine-5-carbonitrile The title compound (60 mg, 68% yield) was obtained from (S)-2-(1-aminoethyl)-3-(3,5-difluorophenyl)-5-(trifluoromethyl)pyrrolo[1,2-f][1,2,4]triazin-4(3H)-one and 4-amino-6-chloropyrimidine-5-carbonitrile following the experimental procedure described in example 23.

LRMS (m/z): 477 (M+1)⁺.

¹H NMR (400 MHz, DMSO) δ 7.91 (d, J=2.9 Hz, 1H), 7.80 (s, 1H), 7.57 (d, J=7.3 Hz, 1H), 7.49 (d, J=9.2 Hz, 1H), 7.30

(br s, 2H), 7.27-7.21 (m, 1H), 7.06 (d, J=3.0 Hz, 1H), 7.04 (d, J=11.7 Hz, 1H), 5.10 (p, J=6.5 Hz, 1H), 1.41 (d, J=6.6 Hz, 3H).

Example 90

(S)-2-(1-(9H-Purin-6-ylamino)ethyl)-3-(3,5-difluorophenyl)-5-(trifluoromethyl)pyrrolo[1,2-f][1,2,4]triazin-4(3H)-one The title compound (58 mg, 65% yield) was obtained from (S)-2-(1-aminoethyl)-3-(3,5-difluorophenyl)-5-(trifluoromethyl)pyrrolo[1,2-f][1,2,4]triazin-4(3H)-one and 6-bromo-9H-purine following the experimental procedure described in example 20.

LRMS (m/z): 477 (M+1)$^+$.

$^1$H NMR (400 MHz, DMSO) δ 12.95 (br s, 1H), 8.15 (m, 1H), 8.02 (m, 2H), 7.87 (d, J=2.8 Hz, 1H), 7.51 (d, J=9.0 Hz, 1H), 7.11 (t, J=8.9 Hz, 1H), 7.07-6.99 (m, 2H), 5.25-4.96 (m, 1H), 1.50 (d, J=6.2 Hz, 3H).

Example 91

(S)-4-Amino-6-(1-(5-(hydroxymethyl)-4-oxo-3-phenyl-3,4-dihydropyrrolo[1,2-f][1,2,4]triazin-2-yl)ethylamino)pyrimidine-5-carbonitrile The title compound (5 mg, 44% yield) was obtained from (S)-2-(1-aminoethyl)-5-(hydroxymethyl)-3-phenylpyrrolo[1,2-f][1,2,4]triazin-4(3H)-one and 4-amino-6-chloropyrimidine-5-carbonitrile following the experimental procedure described in example 23 but using n-butanol as solvent and heating the reaction mixture at 110° C. during 15 hours.

LRMS (m/z): 403 (M+1)$^+$.

$^1$H NMR (400 MHz, DMSO) δ 8.08 (s, 1H), 7.64-7.53 (m, 3H), 7.51-7.45 (m, 1H), 7.38-7.30 (m, 2H), 6.48 (d, 1H), 5.76 (d, 1H), 5.50 (br s, 2H), 5.11-4.98 (m, 1H), 4.81 (s, 2H), 1.42 (d, 3H).

Example 92

(S)-2-(1-(6-Amino-5-(trifluoromethyl)pyrimidin-4-ylamino)ethyl)-3-phenylpyrrolo[1,2-f][1,2,4]triazin-4(3H)-one The title compound (17 mg, 16% yield) was obtained from (S)-2-(1-aminoethyl)-3-phenylpyrrolo[1,2-f][1,2,4]triazin-4(3H)-one (preparation 22) and 6-chloro-5-(trifluoromethyl)pyrimidine-4-amine (prepared as described at WO2005047279) following the experimental procedure described in example 26.

LRMS (m/z): 416 (M+1)$^+$.

$^1$H NMR (400 MHz, DMSO) δ 7.79 (s, 1H), 7.68-7.62 (m, 1H), 7.53-7.44 (m, 2H), 7.41-7.30 (m, 3H), 6.94 (dd, J=4.2, 1.6 Hz, 1H), 6.74 (br s, 2H), 6.65 (dd, J=6.8, 1.7 Hz, 1H), 6.60 (dd, J=4.2, 2.7 Hz, 1H), 5.02-4.85 (m, 1H), 1.35 (d, J=6.6 Hz, 3H).

Example 93

(S)-2-(1-(6-Amino-5-cyanopyrimidin-4-ylamino)ethyl)-4-oxo-3-(pyridin-2-ylmethyl)-3,4-dihydropyrrolo[1,2-f][1,2,4]triazine-5-carbonitrile To a solution of (S)-2-(1-aminoethyl)-4-oxo-3-(pyridin-2-ylmethyl)-3,4-dihydropyrrolo[1,2-f][1,2,4]triazine-5-carbonitrile (39 mg, 0.06 mmols) in butan-1-ol (1.5 ml), 4-amino-6-chloropyrimidine-5-carbonitrile (9 mg, 0.06 mmols) and DIEA (73 μl, 0.42 mmols) were added. It was stirred at 120° C. overnight. It was concentrated in vacuum and it was purified by reverse phase chromatography. The title compound was obtained (3 mg, 6%).

LRMS (m/z): 413 (M+1)+

Example 94

(S)-2-(1-(9H-Purin-6-ylamino)ethyl)-5-(difluoromethyl)-3-(3,5-difluorophenyl)pyrrolo[1,2-f][1,2,4]triazin-4(3H)-one The title compound (95 mg, 64% yield) was obtained from (S)-2-(1-aminoethyl)-5-(difluoromethyl)-3-(3,5-difluorophenyl)pyrrolo[1,2-f][1,2,4]triazin-4(3H)-one and 6-bromo-9H-purine following the experimental procedure described in example 20 but using n-butanol as solvent and heating the reaction mixture at 110° C. during 15 hours.

LRMS (m/z): 459 (M+1)$^+$.

$^1$H NMR (400 MHz, DMSO) δ 12.94 (s, 1H), 8.15 (s, 1H), 8.09-7.95 (m, 2H), 7.83 (d, 1H), 7.50 (d, 1H), 7.32 (t, 2H), 7.16-6.96 (m, 2H), 6.91 (d, 1H), 5.18-4.99 (m, 1H), 1.50 (d, 3H).

Example 95

(S)-2-(1-(9H-Purin-6-ylamino)ethyl)-3-(3,5-difluorophenyl)imidazo[1,2-f][1,2,4]triazin-4(3H)-one The title compound was prepared following the experimental procedure described in Example 86 from (S)-2-(1-aminoethyl)-3-(3,5-difluorophenyl)imidazo[1,2-f][1,2,4]triazin-4(3H)-one (67 mg, 0.23 mmol) and 6-bromo-9H-purine (100 mg, 0.50 mmol). The product was purified by reverse phase chromatography (C-18 silica from Waters®, water/1:1 acetonitrile-methanol as eluents [0.1% v/v formic acid buffered] 0% to 100%) to furnish 28 mg (30% yield) of the title compound.

LRMS (m/z): 410 (M+1)$^+$.

$^1$H NMR (400 MHz, DMSO) δ 12.91 (s, 1H), 8.36-6.86 (m, 7H), 5.07 (s, 1H), 1.51 (d, 3H).

Example 96

(S)-4-Amino-6-(1-(5-(difluoromethyl)-3-(3,5-difluorophenyl)-4-oxo-3,4-dihydropyrrolo[1,2-f][1,2,4]triazin-2-yl)ethylamino)pyrimidine-5-carbonitrile The title compound (111 mg, 74% yield) was obtained from (S)-2-(1-aminoethyl)-5-(difluoromethyl)-3-(3,5-difluorophenyl)pyrrolo[1,2-f][1,2,4]triazin-4(3H)-one and 4-amino-6-chloropyrimidine-5-carbonitrile following the experimental procedure described in example 23 but heating the reaction mixture at 110° C. during 15 hours.

LRMS (m/z): 459 (M+1)$^+$.

$^1$H NMR (400 MHz, DMSO) δ 7.86 (d, 1H), 7.79 (s, 1H), 7.59 (d, 1H), 7.54-7.45 (m, 1H), 7.39-7.14 (m, 4H), 7.03 (d, 1H), 6.94 (d, 1H), 5.16-5.03 (m, 1H), 1.39 (d, 3H).

Example 97

(S)-2-(1-(2-Amino-9H-purin-6-ylamino)ethyl)-5-(difluoromethyl)-3-(3,5-difluorophenyl)pyrrolo[1,2-f][1,2,4]triazin-4(3H)-one The title compound (44 mg, 28% yield) was obtained from (S)-2-(1-aminoethyl)-5-(difluoromethyl)-3-(3,5-difluororophenyl)pyrrolo[1,2-f][1,2,4]triazin-4(3H)-one and 6-chloro-9H-purin-2-amine following the experimental procedure described in example 21 but heating the reaction mixture at 110° C. during 15 hours.

LRMS (m/z): 474 (M+1)$^+$.

$^1$H NMR (400 MHz, DMSO) δ 12.07 (s, 1H), 8.17 (s, 1H), 7.80 (d, 1H), 7.68 (s, 1H), 7.57-7.41 (m, 2H), 7.32 (t, 1H), 7.17 (m, 1H), 6.90 (d, 1H), 5.59 (br s, 2H), 4.99-4.81 (m, 1H), 1.44 (d, 3H).

Example 98

(S)-2-(1-(2-Amino-9H-purin-6-ylamino)ethyl)-3-(3,5-difluorophenyl)-4-oxo-3,4-dihydropyrrolo[1,2-f][1,2,4]triazine-5-carbonitrile The title compound (45 mg, 35% yield) was obtained from (S)-2-(1-aminoethyl)-3-(3,5-difluorophenyl)-4-oxo-3,4-dihydropyrrolo[1,2-f][1,2,4]triazine-5-carbonitrile and 6-chloro-9H-purin-2-amine following the experimental procedure described in example 21.

LRMS (m/z): 449 (M+1)$^+$.

$^1$H NMR (400 MHz, DMSO) δ 12.07 (br s, 1H), 7.87 (d, J=2.9 Hz, 1H), 7.67 (s, 1H), 7.46 (d, J=7.7 Hz, 2H), 7.23-7.16 (m, 3H), 5.60 (bs, 2H), 4.88 (m, 1H), 1.44 (d, J=6.6 Hz, 3H).

Example 99

2-(1-(9H-Purin-6-ylamino)-2,2,2-trifluoroethyl)-3-phenylpyrrolo[1,2-f][1,2,4]triazin-4(3H)-one 3-Phenyl-2-(2,2,2-trifluoro-1-(9-(4-methoxybenzyl)-9H-purin-6-ylamino)ethyl)pyrrolo[1,2-f][1,2,4]triazin-4(3H)-one (138 mg, 0.25 mmol) were dissolved in trifluoroacetic acid (2 mL). The solution was stirred at 60° C. overnight and at 80° C. for 4 hours. The volatiles were removed under reduced pressure and the residue was partitioned between ethyl acetate and a diluted aqueous solution of potassium carbonate. The organic layer was washed with water and brine, dried over magnesium sulphate, filtered and the solvent was removed in vacuum. The product was purified by reverse phase chromatography (C-18 silica from Waters®, water/1:1 acetonitrile-methanol as eluents [0.1% v/v formic acid buffered] 0% to 100%) to furnish 17 mg (16% yield) of the title compound.

LRMS (m/z): 427 (M+1)$^+$.

$^1$H NMR (400 MHz, DMSO) δ 13.01 (s, 1H), 8.51 (s, 1H), 8.23 (s, 1H), 7.92-7.73 (m, 2H), 7.56 (s, 1H), 7.41 (s, 1H), 7.14-6.83 (m, 3H), 6.69 (dd, 1H), 6.53 (s, 1H), 6.07 (s, 1H).

Example 100

(S)-4-Amino-6-(1-(3-benzyl-4-oxo-3,4-dihydropyrrolo[1,2-f][1,2,4]triazin-2-yl)ethylamino)pyrimidine-5-carbonitrile The title compound was prepared following the experimental procedure described in Example 68 from (S)-2-(1-aminoethyl)-3-benzylpyrrolo[1,2-f][1,2,4]triazin-4(3H)-one (obtained as a by-product of Preparation 22) (30 mg, 0.11 mmol) and 4-amino-6-chloropyrimidine-5-carbonitrile (34 mg, 0.22 mmol). The product was purified by reverse phase chromatography (C-18 silica from Waters®, water/1:1 acetonitrile-methanol as eluents [0.1% v/v formic acid buffered] 0% to 100%) to furnish 19 mg (44% yield) of the title compound as a white solid.

LRMS (m/z): 387 (M+1)$^+$.

$^1$H NMR (400 MHz, DMSO) δ 11.49 (s, 1H), 8.04 (s, 1H), 7.45 (d, 1H), 7.38 (d, 3H), 7.26 (s, 2H), 7.25 (d, 2H), 7.15 (m, 1H), 6.32 (d, 1H), 5.13 (p, 1H), 4.20 (s, 2H), 1.52 (d, 3H).

Example 101

(S)-2-(1-(6-Amino-5-fluoropyrimidin-4-ylamino)ethyl)-3-phenyl pyrrolo[1,2-f][1,2,4]triazin-4(3H)-one The title compound (20 mg, 37% yield) was obtained from (S)-2-(1-aminoethyl)-3-phenylpyrrolo[1,2-f][1,2,4]triazin-4(3H)-one and 5,6-difluoropyrimidin-4-amine following the experimental procedure described in example 20 but using n-butanol as solvent and heating the reaction mixture at 120° C. during 24 hours.

LRMS (m/z): 366 (M+1)$^+$.

$^1$H NMR (400 MHz, DMSO) δ 7.70-7.29 (m, 7H), 7.18 (d, 1H), 6.94 (dd, 1H), 6.59 (dd, 1H), 6.36 (br s, 2H), 4.71-4.55 (m, 1H), 1.36 (d, 3H).

Example 102

(S)-2-(1-(6-Amino-5-fluoropyrimidin-4-ylamino)ethyl)-5-(difluoromethyl)-3-(3,5-difluorophenyl)pyrrolo[1,2-f][1,2,4]triazin-4(3H)-one The title compound (11 mg, 33% yield) was obtained from (S)-2-(1-aminoethyl)-5-(difluoromethyl)-3-(3,5-difluorophenyl)pyrrolo[1,2-f][1,2,4]triazin-4(3H)-one and 5,6-difluoropyrimidin-4-amine following the experimental procedure described in example 20 but using n-butanol as solvent and heating the reaction mixture at 120° C. during 6 hours.

LRMS (m/z): 452 (M+1)$^+$.

$^1$H NMR (400 MHz, DMSO) δ 7.86 (d, 1H), 7.37 (d, 1H), 7.26 (t, 2H), 7.23-7.16 (m, 1H), 7.06-6.97 (m, 1H), 6.95-6.88 (m, 1H), 6.86-6.81 (m, 1H), 5.00-4.90 (m, 1H), 4.74 (br s, 2H), 1.48 (d, 3H).

Example 103

(S)-2-(1-(6-Amino-5-cyanopyrimidin-4-ylamino)propyl)-3-(3,5-difluorophenyl)-4-oxo-3,4-dihydropyrrolo[1,2-f][1,2,4]triazine-5-carbonitrile The title compound (84 mg, 54% yield) was obtained from (S)-2-(1-aminopropyl)-3-(3,5-difluorophenyl)-4-oxo-3,4-dihydropyrrolo[1,2-f][1,2,4]triazine-5-carbonitrile and 4-amino-6-chloropyrimidine-5-carbonitrile following the experimental procedure described in example 23.

LRMS (m/z): 448 (M+1)$^+$.

$^1$H NMR (400 MHz, DMSO) δ 7.93 (d, J=2.8 Hz, 1H), 7.78 (s, 1H), 7.47 (d, J=7.6 Hz, 1H), 7.37-7.26 (m, 2H), 7.25 (d, J=2.8 Hz, 1H), 7.05 (d, J=8.5 Hz, 1H), 4.91 (m, 1H), 2.07-1.89 (m, 1H), 1.80 (m, 1H), 0.84 (t, J=7.1 Hz, 3H).

Example 104

(S)-2-(1-(6-Amino-5-cyanopyrimidin-4-ylamino)ethyl)-3-(3,5-dichlorophenyl)-4-oxo-3,4-dihydropyrrolo[1,2-f][1,2,4]triazine-5-carbonitrile The title compound was prepared following the experimental procedure described in Example 68 from (S)-2-(1-aminoethyl)-3-(3,5-dichlorophenyl)-4-oxo-3,4-dihydropyrrolo[1,2-f][1,2,4]triazine-5-carbonitrile (100 mg, 0.29 mmol) and 4-amino-6-chloropyrimidine-5-carbonitrile (54 mg, 0.35 mmol). The product was purified by reverse phase chromatography (C-18 silica from Waters®, water/1:1 acetonitrile-methanol as eluents [0.1% v/v formic acid buffered] 0% to 100%) to furnish 91 mg (68% yield) of the title compound as a white solid.

LRMS (m/z): 467 (M+1)+.

$^1$H NMR (400 MHz, DMSO) δ 7.97 (d, 1H), 7.83-7.69 (m, 2H), 7.56-7.48 (m, 2H), 7.39-7.19 (m, 3H), 5.23-5.02 (m, 2H), 1.39 (d, 3H).

Example 105

(S)-2-(1-(6-Amino-5-fluoropyrimidin-4-ylamino) ethyl)-3-(3,5-difluorophenyl)-4-oxo-3,4-dihydropyrrolo[1,2-f][1,2,4]triazine-5-carbonitrile The title compound (49 mg, 69% yield) was obtained from (S)-2-(1-aminoethyl)-3-(3,5-difluorophenyl)-4-oxo-3,4-dihydropyrrolo[1,2-f][1,2,4]triazine-5-carbonitrile and 5,6-difluoropyrimidin-4-amine following the experimental procedure described in example 20 but using n-butanol as solvent and heating the reaction mixture at 120° C. during 72 hours.

LRMS (m/z): 427 (M+1)+.

$^1$H NMR (400 MHz, DMSO) δ 7.92 (s, 1H), 7.59-7.40 (m, 2H), 7.34-7.02 (m, 4H), 6.43 (br s, 2H), 4.92-4.74 (m, 1H), 1.41 (d, 3H).

Example 106

(S)-2-(1-(6-Amino-5-(trifluoromethyl)pyrimidin-4-ylamino)ethyl)-4-oxo-3-phenyl-3,4-dihydropyrrolo [1,2-f][1,2,4]triazine-5-carbonitrile The title compound (12 mg, 16% yield) was obtained from (S)-2-(1-aminoethyl)-4-oxo-3-phenyl-3,4-dihydropyrrolo[1,2-f][1,2,4]triazine-5-carbonitrile (preparation 47) and 6-chloro-5-(trifluoromethyl)pyrimidine-4-amine (prepared as described at WO2005047279) following the experimental procedure described in example 26.

LRMS (m/z): 441 (M+1)+.

$^1$H NMR (400 MHz, DMSO) δ 7.85 (d, J=2.9 Hz, 1H), 7.78 (s, 1H), 7.55 (d, J=7.8 Hz, 1H), 7.49 (t, J=7.0 Hz, 1H), 7.36 (m, 3H), 7.20 (d, J=2.9 Hz, 1H), 6.76 (br s, 2H), 6.62 (d, J=5.2 Hz, 1H), 5.03-4.89 (m, 1H), 1.36 (d, J=6.5 Hz, 3H).

Example 107

(R)-2-(1-(6-Amino-5-cyanopyrimidin-4-ylamino)-2-hydroxyethyl)-3-(3,5-difluorophenyl)-4-oxo-3,4-dihydropyrrolo[1,2-f][1,2,4]triazine-5-carbonitrile The title compound was prepared following the experimental procedure described in Example 86 from (R)-2-(1-amino-2-hydroxyethyl)-3-(3,5-difluorophenyl)-4-oxo-3,4-dihydropyrrolo[1,2-f][1,2,4]triazine-5-carbonitrile (71 mg, 0.21 mmol) and 4-amino-6-chloropyrimidine-5-carbonitrile (40 mg, 0.26 mmol). The product was purified by flash chromatography (0% to 10% MeOH/DCM) to give 32 mg (33% yield) of the title compound as a white solid.

LRMS (m/z): 450 (M+1)+.

$^1$H NMR (400 MHz, DMSO) δ 7.92 (d, 1H), 7.83 (s, 1H), 7.66-7.51 (m, 1H), 7.46-7.28 (m, 4H), 7.24 (d, 1H), 7.15 (d, 1H), 5.04-4.90 (m, 2H), 3.94-3.80 (m, 1H), 3.70-3.54 (m, 1H).

Example 108

(S)-2-(1-(6-Amino-5-carbamoylpyrimidin-4-ylamino)ethyl)-3-(3,5-difluorophenyl)-4-oxo-3,4-dihydropyrrolo[1,2-f][1,2,4]triazine-5-carboxamide A suspension of 30 mg (0.07 mmol) of (S)-2-(1-(6-amino-5-cyanopyrimidin-4-ylamino)ethyl)-3-(3,5-difluorophenyl)-4-oxo-3,4-dihydropyrrolo[1,2-f][1,2,4]triazine-5-carbonitrile (Example 85) in sulphuric acid (2 ml) was heated to 60° C. for 2 h. The reaction mixture was slowly poured into a mixture of ice/water, neutralized with a 2N solution of NaHCO3 and extracted with ethyl acetate. The organic layer was then washed with brine, dried over magnesium sulphate and concentrated. The title compound was obtained as a white solid (29 mg, 88% yield).

LRMS (m/z): 470 (M+1)+.

$^1$H NMR (400 MHz, DMSO) δ 9.16 (d, J=2.2 Hz, 1H), 7.78 (d, J=2.8 Hz, 1H), 7.77 (s, 1H), 7.62 (d, J=7.5 Hz, 1H), 7.54 (d, J=8.7 Hz, 1H), 7.46 (d, J=2.2 Hz, 1H), 7.43-7.36 (m, 3H), 7.33 (d, J=8.8 Hz, 1H), 7.09 (d, J=2.9 Hz, 1H), 6.65 (s, 2H), 4.95-4.76 (m, 1H), 1.38 (d, J=6.7 Hz, 3H).

Example 109

(S)-2-(1-(6-Amino-5-cyanopyrimidin-4-ylamino) ethyl)-3-(3,5-difluorophenyl)-4-oxo-3,4-dihydropyrrolo[1,2-f][1,2,4]triazine-5-carboxamide The title compound (25 mg, 49% yield) was obtained from (S)-2-(1-aminoethyl)-3-(3,5-difluorophenyl)-4-oxo-3,4-dihydropyrrolo[1,2-f][1,2,4]triazine-5-carboxamide and 4-amino-6-chloropyrimidine-5-carbonitrile following the experimental procedure described in example 23.

LRMS (m/z): 452 (M+1)+.

$^1$H NMR (400 MHz, DMSO) δ 9.16 (d, J=2.4 Hz, 1H), 7.87 (d, J=2.9 Hz, 1H), 7.79 (s, 1H), 7.60 (d, J=7.4 Hz, 1H), 7.55-7.45 (m, 2H), 7.30 (br s, 2H), 7.25 (m, 1H), 7.13 (d, J=2.8 Hz, 1H), 7.06 (d, J=8.6 Hz, 1H), 5.10 (p, J=6.6 Hz, 1H), 1.41 (d, J=6.5 Hz, 3H).

Example 110

(S)-2-(1-(6-Amino-5-cyanopyrimidin-4-ylamino) ethyl)-3-(2-chlorobenzyl)-4-oxo-3,4-dihydropyrrolo [1,2-f][1,2,4]triazine-5-carbonitrile The title compound (6 mg, 36% yield) was obtained from (S)-2-(1-aminoethyl)-3-(2-chlorobenzyl)-4-oxo-3,4-dihydropyrrolo[1,2-f][1,2,4]triazine-5-carbonitrile and 4-amino-6-chloropyrimidine-5-carbonitrile following the experimental procedure described in example 23 but using n-butanol as solvent and heating the reaction mixture at 120° C. during 15 hours.

LRMS (m/z): 446 (M+1)+.

Example 111

2-((S)-1-(6-Amino-5-cyanopyrimidin-4-ylamino) ethyl)-4-oxo-3-(tetrahydro-2H-pyran-3-yl)-3,4-dihydropyrrolo[1,2-f][1,2,4]triazine-5-carbonitrile first diastereomer Same procedure as described in Example 93 was used from 2-((S)-1-aminoethyl)-4-oxo-3-(tetrahydro-2H-pyran-3-yl)-3,4-dihydropyrrolo[1,2-f][1,2,4]triazine-5-carbonitrile (118 mg, 0.23 mmols). The title compound (first eluting diastereomer) was obtained (64 mg, 68%)

LRMS (m/z): 406 (M+1)+

$^1$H NMR (400 MHz, DMSO-d$_6$) d ppm 0.88-1.03 (m, 1 H) 1.46 (d, 3 H) 1.52-1.64 (m, 1 H) 1.67-1.86 (m, 1 H) 2.55-2.78 (m, 1 H) 2.57-2.75 (m, 1 H) 3.09-3.30 (m, 1 H) 3.60-3.78 (m, 1 H) 3.87 (d, 1 H) 4.10-4.31 (m, 1 H) 5.64-5.92 (m, 1 H) 7.05-7.22 (m, 1 H) 7.40 (m, 1 H) 7.80 (d, 1 H) 8.00 (m, 1 H) 8.17 (s, 1 H) 8.40 (s, 1 H)

Example 112

(R)-4-Amino-6-(1-(3-(3,5-difluorophenyl)-4-oxo-5-(trifluoromethyl)-3,4-dihydropyrrolo[1,2-f][1,2,4] triazin-2-yl)-2-hydroxyethylamino)pyrimidine-5-carbonitrile Prepared from (R)-2-(1-amino-2-hydroxyethyl)-3-(3,5-difluorophenyl)-5-(trifluoromethyl)pyrrolo[1,2-f][1,2,4]triazin-4(3H)-one (61 mg, 0.16 mmol) and 4-amino-6-chloropyrimidine-5-carbonitrile (30 mg, 0.19 mmol) following the experimental procedure described in Example 86, but heating at 120° C. only for 16 hours. The product was purified by reverse phase chromatography (C-18 silica from Waters®, water/1:1 acetonitrile-methanol as eluents [0.1% v/v formic acid buffered] 0% to 100%) to furnish 8 mg (10% yield) of the title compound as a white solid.

LRMS (m/z): 493 (M+1)$^+$.

$^1$H NMR (400 MHz, DMSO) δ 7.87 (d, 1H), 7.84 (s, 1H), 7.48-7.25 (m, 5H), 7.15 (d, 1H), 7.04 (d, 1H), 5.05-4.84 (m, 2H), 4.00-3.79 (m, 2H), 3.72-3.52 (m, 1H).

Example 113

(S)-2-(1-(2-Amino-5-fluoropyrimidin-4-ylamino) ethyl)-3-(3,5-difluorophenyl)-4-oxo-3,4-dihydropyrrolo[1,2-f][1,2,4]triazine-5-carbonitrile The title compound (22 mg, 33% yield) was obtained from (S)-2-(1-aminoethyl)-3-(3,5-difluorophenyl)-4-oxo-3,4-dihydropyrrolo[1,2-f][1,2,4]triazine-5-carbonitrile and 4-chloro-5-fluoropyrimidin-2-amine (purchased from Ark Pharm) following the experimental procedure described in example 20.

LRMS (m/z): 427 (M+1)$^+$.

$^1$H NMR (400 MHz, DMSO) δ 7.91 (d, J=3.0 Hz, 1H), 7.64 (d, J=3.7 Hz, 1H), 7.48 (d, J=9.0 Hz, 1H), 7.42 (d, J=6.8 Hz, 1H), 7.29 (tt, J=9.3, 2.3 Hz, 1H), 7.22 (m, 2H), 5.87 (s, 2H), 4.76 (p, J=6.6 Hz, 1H), 1.39 (d, J=6.7 Hz, 3H).

Example 114

(S)-2-(1-(2-Amino-5-cyanopyrimidin-4-ylamino) ethyl)-3-(3,5-difluorophenyl)-4-oxo-3,4-dihydropyrrolo[1,2-f][1,2,4]triazine-5-carbonitrile The title compound (34 mg, 50% yield) was obtained from (S)-2-(1-aminoethyl)-3-(3,5-difluorophenyl)-4-oxo-3,4-dihydropyrrolo[1,2-f][1,2,4]triazine-5-carbonitrile and 2-amino-4-chloropyrimidine-5-carbonitrile following the experimental procedure described in example 20.

LRMS (m/z): 427 (M+1)$^+$.

$^1$H NMR (400 MHz, DMSO) δ 8.12 (s, 1H), 7.96 (d, J=3.0 Hz, 1H), 7.55 (d, J=7.2 Hz, 1H), 7.46 (d, J=9.0 Hz, 1H), 7.26 (d, J=3.0 Hz, 1H), 7.25-7.18 (m, 1H), 7.05 (m, 2H), 6.97 (br s, 1H), 5.05 (p, J=6.5 Hz, 1H), 1.39 (d, J=6.6 Hz, 3H).

Example 115

((S)-2-(1-(9H-Purin-6-ylamino)ethyl)-3-(3,5-difluorophenyl)-5-(2H-tetrazol-5-yl)pyrrolo[1,2-f][1,2,4] triazin-4(3H)-one 40 mg (0.1 mmol, Example 87) of (S)-2-(1-(9H-purin-6-ylamino)ethyl)-3-(3,5-difluorophenyl)-4-oxo-3,4-dihydropyrrolo[1,2-f][1,2,4]triazine-5-carbonitrile and 31 mg (0.15 mmol) of azidotrimethylstannane were stirred in toluene (2 ml) at 100° C. for 3 days in a sealed reactor. Then the solvent was removed in vacuum and the residue was taken up in AcOEt, washed with water and brine, dried over magnesium sulphate and the solvent evaporated. The crude product was purified by normal phase chromatography (DCM-AcOEt, 0-100% in 40CV) to obtain the title compound (19 mg, 43% yield) as a white solid.

LRMS (m/z): 477(M+1)$^+$.

$^1$H NMR (400 MHz, DMSO) δ ppm 1.53 (d, J=6.64 Hz, 3H), 5.13 (q, 1H), 6.98-7.15 (m, 2H), 7.20 (s, 1H), 7.54 (d, 1H), 7.89-8.27 (m, 4H), 12.94 (s, 1H)

Example 116

(S)-4-Amino-6-(1-(3-((5-methylisoxazol-3-yl)methyl)-4-oxo-3,4-dihydropyrrolo[1,2-f][1,2,4]triazin-2-yl)ethylamino)pyrimidine-5-carbonitrile The title compound (120 mg, 34% yield) was obtained from (S)-2-(1-aminoethyl)-3-((5-methylisoxazol-3-yl)methyl)pyrrolo[1,2-f][1,2,4]triazin-4(3H)-one (preparation 59) and 4-amino-6-chloropyrimidine-5-carbonitrile following the experimental procedure described in example 18.

LRMS (m/z): 392 (M+1)$^+$.

$^1$H NMR (400 MHz, CDCl3) δ 8.15 (s, 1H), 7.35 (dd, 1H), 7.06 (dd, 1H), 6.54 (dd, 1H), 6.04 (d, 1H), 5.82 (d, 1H), 5.73 (m, 1H), 5.52 (d, 1H), 5.47-5.33 (m, 3H), 2.39 (d, 3H), 1.53 (d, 3H).

Example 117

(S)-4-Amino-6-(1-(4-oxo-3-phenyl-7-(trifluoromethyl)-3,4-dihydropyrrolo[1,2-f][1,2,4]triazin-2-yl) ethylamino)pyrimidine-5-carbonitrile Prepared following the experimental procedure described in Example 112 from 14.5 mg (0.04 mmol) of (S)-2-(1-aminoethyl)-3-phenyl-7-(trifluoromethyl)pyrrolo[1,2-f][1,2,4] triazin-4(3H)-one hydrochloric acid salt and 7 mg (0.05 mmol) of 4-amino-6-chloropyrimidine-5-carbonitrile. The product was purified first by flash chromatography (0% to 10% MeOH/DCM) and then preparative HPLC (Waters XBridge C18 OBD column, mixture of eluents A/B from 80% B to 100% B, in a 10 min. gradient) to give 10 mg (56% yield) of the title compound as a white solid.

LRMS (m/z): 441 (M+1)$^+$.

Example 118

(S)-2-(1-(6-Amino-5-cyanopyrimidin-4-ylamino) ethyl)-4-oxo-3-phenyl-3,4-dihydropyrrolo[1,2-f][1,2, 4]triazine-7-carbonitrile Prepared following the experimental procedure described in Example 112 from (S)-2-(1-aminoethyl)-4-oxo-3-phenyl-3,4-dihydropyrrolo[1,2-f][1,2,4]triazine-7-carbonitrile (27 mg, 0.10 mmol) and 4-amino-6-chloropyrimidine-5-carbonitrile (33 mg, 0.21 mmol). The product was purified first by preparative HPLC (Waters SymmetryPrep C18 column, mixture of eluents NB from 45% B to 75% B, in a 20 min. gradient) to give 15 mg (39% yield) of the title compound as a white solid.
LRMS (m/z): 398 (M+1)+.

Example 119

(S)-2-(1-(6-Amino-5-cyanopyrimidin-4-ylamino) ethyl)-3-(1-(4-methoxybenzyl)-1H-pyrazol-4-yl)-4-oxo-3,4-dihydropyrrolo[1,2-f][1,2,4]triazine-5-carbonitrile The title compound (9 mg, 10% yield) was obtained from (S)-2-(1-aminoethyl)-3-(1-(4-methoxybenzyl)-1H-pyrazol-4-yl)-4-oxo-3,4-dihydropyrrolo[1,2-f][1,2,4]triazine-5-carbonitrile and 4-amino-6-chloropyrimidine-5-carbonitrile following the experimental procedure described in example 18.
LRMS (m/z): 508 (M+1)+.
$^1$H NMR (400 MHz, CDCl3) δ 8.00 (s, 1H), 7.69 (d, J=0.7 Hz, 1H), 7.52 (d, J=0.7 Hz, 1H), 7.31 (d, J=2.9 Hz, 1H), 7.26-7.21 (m, 1H), 6.94-6.87 (m, 2H), 6.84 (d, J=2.9 Hz, 1H), 5.68 (d, J=8.0 Hz, 1H), 5.39 (s, 1H), 5.31 (s, 1H), 5.26 (dq, J=13.8, 7.0 Hz, 1H), 3.81 (d, J=3.0 Hz, 3H), 1.58 (s, 4H), 1.43 (d, J=6.9 Hz, 2H).

Example 120

(S)-4-amino-6-(1-(4-oxo-3-phenyl-5-(thiazol-2-yl)-3,4-dihydropyrrolo[1,2-f][1,2,4]triazin-2-yl)ethylamino)pyrimidine-5-carbonitrile Starting from (S)-2-(1-aminoethyl)-3-phenyl-5-(thiazol-2-yl)pyrrolo[1,2-f][1,2,4]triazin-4(3H)-one (26 mg, 0,08 mmol) and following the experimental procedure described in Example 23 were obtained 12 mg (34% yield) of the title compound of this example.
LRMS (m/z): 491 (M+1)+.
$^1$H NMR (400 MHz, CDCl$_3$) δ ppm 1.44 (d, J=7.03 Hz, 3 H) 5.04 (q, 1 H) 5.35 (s, 2 H) 5.73 (d, J=7.82 Hz, 1 H) 7.31 (d, J=3.13 Hz, 1 H) 7.33-7.39 (m, J=2.74 Hz, 2 H) 7.43 (d, J=2.74 Hz, 1 H) 7.47-7.63 (m, 4 H) 7.77-7.89 (m, J=3.13 Hz, 1 H) 8.11 (s, 1 H)

Example 121

(S)-2-(1-(2,6-Diamino-5-cyanopyrimidin-4-ylamino) ethyl)-3-(3,5-difluorophenyl)-4-oxo-3,4-dihydropyrrolo[1,2-f][1,2,4]triazine-5-carbonitrile The title compound (20 mg, 29% yield) was obtained from (S)-2-(1-aminoethyl)-3-(3,5-difluorophenyl)-4-oxo-3,4-dihydropyrrolo[1,2-f][1,2,4]triazine-5-carbonitrile and 2,4-diamino-6-chloropyrimidine-5-carbonitrile following the experimental procedure described in example 20.
LRMS (m/z): 449(M+1)+.
$^1$H NMR (400 MHz, DMSO) δ 7.94 (dd, J=2.9, 1.7 Hz, 1H), 7.44 (d, J=9.1 Hz, 1H), 7.30-7.19 (m, 2H), 7.10 (d, J=9.1 Hz, 1H), 6.93 (d, J=6.7 Hz, 1H), 6.53 (s, 2H), 6.28 (s, 2H), 5.05-4.89 (m, 1H), 1.36 (d, J=6.4 Hz, 3H).

Example 122

(S)-4-Amino-6-(1-(5-(morpholinomethyl)-4-oxo-3-phenyl-3,4-dihydropyrrolo[1,2-f][1,2,4]triazin-2-yl) ethylamino)pyrimidine-5-carbonitrile The formate salt of the title compound (63 mg, 53% yield) was obtained from (S)-2-(1-aminoethyl)-5-(morpholinomethyl)-3-phenylpyrrolo[1,2-f][1,2,4]triazin-4(3H)-one and 4-amino-6-chloropyrimidine-5-carbonitrile following the experimental procedure described in example 23.
LRMS (m/z): 472 (M+1)+.
$^1$H NMR (400 MHz, DMSO) δ 8.21 (s, 1H), 7.77 (s, 1H), 7.69 (d, J=7.0 Hz, 1H), 7.62 (s, 1H), 7.49 (d, J=8.1 Hz, 1H), 7.42 (t, J=7.1 Hz, 1H), 7.28 (m, 4H), 6.56 (s, 1H), 4.96-4.79 (m, 1H), 3.78 (s, 2H), 3.55 (s, 4H), 2.39 (s, 4H), 1.36 (d, J=6.4 Hz, 3H).

Example 123

24(S)-1-(6-Amino-5-cyanopyrimidin-4-ylamino) ethyl)-4-oxo-3-((R)-1-phenylethyl)-3,4-dihydropyrrolo[1,2-f][1,2,4]triazine-5-carbonitrile The title compound (27 mg, 9% yield) was obtained from 24S)-1-aminoethyl)-4-oxo-3-((R)-1-phenylethyl)-3,4-dihydropyrrolo[1,2-f][1,2,4]triazine-5-carbonitrile and 4-amino-6-chloropyrimidine-5-carbonitrile following the experimental procedure described in example 18.
LRMS (m/z): 426 (M+1)+.
$^1$H NMR (400 MHz, CDCl3) δ 8.02 (s, 1H), 7.33 (s, 1H), 7.18 (s, 1H), 6.87 (s, 1H), 5.62 (d, J=26.3 Hz, 2H), 5.36 (s, 2H), 2.01 (d, J=7.0 Hz, 3H), 1.60 (d, J=6.2 Hz, 7H).

Example 124

(S)-4-Amino-6-(1-(4-oxo-3-(1H-pyrazol-4-yl)-3,4-dihydropyrrolo[1,2-f][1,2,4]triazin-2-yl)ethylamino) pyrimidine-5-carbonitrile The title compound (60 mg, 28% yield) was obtained from (S)-4-amino-6-(1-(3-(1-(4-methoxybenzyl)-1H-pyrazol-4-yl)-4-oxo-3,4-dihydropyrrolo[1,2-f][1,2,4]triazin-2-yl)ethylamino)pyrimidine-5-carbonitrile (290 mg, 0.6 mmol) by heating with TFA (1.40 ml, 18.17 mmol) in dichloromethane (15 ml) and further purification.
LRMS (m/z): 363 (M+1)+.
$^1$H NMR (400 MHz, CDCl3) δ 13.02 (br s, 1H), 7.95 (s, 1H), 7.90 (bs, 1H), 7.73 (d, 1H), 7.65 (d, 1H), 7.50 (bs, 1H), 7.30 (bs, 2H), 6.95 (d, 1H), 6.65 (d, 1H), 5.10 (m, 1H), 1.40 (d, 3H).

Example 125

(S)-2-(1-(9H-Purin-6-ylamino)ethyl)-3-(3,5-difluorophenyl)-5-(5-methyl-1,2,4-oxadiazol-3-yl)pyrrolo [1,2-f][1,2,4]triazin-4(3H)-one a) 45 mg (0.1 mmol) of (S)-2-(1-(9H-purin-6-ylamino) ethyl)-3-(3,5-difluorophenyl)-4-oxo-3,4-dihydropyrrolo[1, 2-f][1,2,4]triazine-5-carbonitrile (Example 87), 14 mg (0.21 mmol) of hydroxylamine hydrochloride and 28 mg (0.21 mmol) of potassium carbonate were stirred in ethanol (2 ml) at 80° C. for 48 h. Then the precipitate is filtrated, washed with ethanol and diethylether obtaining (S,Z)-2-(1-(9H-purin-6-ylamino)ethyl)-3-(3,5-difluorophenyl)-N'-hydroxy-4-oxo-3,4-dihydropyrrolo[1,2-f][1,2,4]triazine-5-carboximidamide (70 mg, >100% yield) as a white solid.
LRMS (m/z): 467 (M+1)+.
b) 70 mg (0.1 mmol) of (S,Z)-2-(1-(9H-purin-6-ylamino) ethyl)-3-(3,5-difluorophenyl)-N'-hydroxy-4-oxo-3,4-dihydropyrrolo[1,2-f][1,2,4]triazine-5-carboximidamide in acetic acid (0.5 ml) was cooled to 0° C. in an under pressure reactor. Then 507 µl of acetic anhydride (5.37 mmol) were added and the crude was heated at 90° C. for 2 h to obtain the acetylated title compound. The solvent was removed and methanol (2 ml) and HCl 4M in dioxane (2 ml) is added and the resulting mixture is heated at 70° C. for 5 h. The solvent was removed in vacuum and the residue was purified directly by reverse phase chromatography (C-18 silica from Waters, water/1:1 acetonitrile-methanol as eluents 0% to 100%) obtaining (S)-2-(1-(9H-purin-6-ylamino)ethyl)-3-(3,5-difluorophenyl)-5-(5-methyl-1,2,4-oxadiazol-3-yl)pyrrolo[1,2-f][1,2,4]triazin-4(3H)-one (10 mg, 13% yield).

LRMS (m/z): 491 (M+1)$^+$.

$^1$H NMR (400 MHz, DMSO) δ ppm 1.25 (s, 3 H) 1.59 (d, J=6.25 Hz, 3 H) 5.06-5.35 (m, 1 H) 6.44 (s, 1 H) 6.88-6.99 (m, 2 H) 7.04 (s, 1 H) 7.10-7.25 (m, 1 H) 7.28-7.44 (m, 1 H) 8.01 (s, 1 H) 8.36 (s, 1 H) 12.22-12.76 (m, 1 H)

Example 126

4-Amino-6-((1S)-1-(4-oxo-3-(tetrahydro-2H-pyran-3-yl)-5-(trifluoromethyl)-3,4-dihydropyrrolo[1,2-f][1,2,4]triazin-2-yl)ethylamino)pyrimidine-5-carbonitrile—first diastereomer Same procedure as describes in Example 93 was used from 2-((S)-1-aminoethyl)-3-(tetrahydro-2H-pyran-3-yl)-5-(trifluoromethyl)pyrrolo[1,2-f][1,2,4]triazin-4(3H)-one (158 mg, 0.20 mmols). The title compound (first eluting diastereomer) was obtained (36 mg, 41%)

LRMS (m/z): 449 (M+1)+

$^1$H NMR (400 MHz, DMSO-d$_6$) d ppm 0.82 (d, 1 H) 1.45 (d, 3 H) 1.50-1.64 (m, 1 H) 1.66-1.81 (m, 1 H) 2.60-2.77 (m, 1 H) 3.02-3.23 (m, 2 H) 3.60-3.75 (m, 1 H) 3.76-3.94 (m, 1 H) 4.11-4.30 (m, 1 H) 5.69-5.90 (m, 1 H) 6.95 (d, 1 H) 7.42 (s, 1 H) 7.74 (d, 1 H) 8.03 (s, 1 H) 8.12-8.23 (m, 1 H) 8.37 (s, 1 H)

Example 127

(S)-4-Amino-6-(1-(3-(5-methyl-1H-pyrazol-3-yl)-4-oxo-3,4-dihydropyrrolo[1,2-f][1,2,4]triazin-2-yl)ethylamino)pyrimidine-5-carbonitrile The title compound (9 mg, 12% yield) was obtained from (S)-2-(1-aminoethyl)-3-(5-methyl-1H-pyrazol-3-yl)pyrrolo[1,2-f][1,2,4]triazin-4(3H)-one and 4-amino-6-chloropyrimidine-5-carbonitrile following the experimental procedure described in example 18.

LRMS (m/z): 377 (M+1)$^+$.

$^1$H NMR (400 MHz, CDCl$_3$) δ 8.00 (s, 1H), 7.34 (dd, J=2.6, 1.7 Hz, 1H), 7.04 (dd, J=4.3, 1.7 Hz, 1H), 6.49 (dd, J=4.3, 2.7 Hz, 1H), 6.09 (s, 1H), 5.93 (d, J=8.2 Hz, 1H), 5.52 (s, 2H), 5.19 (dq, J=13.7, 6.8 Hz, 1H), 3.58 (q, J=7.1 Hz, 1H), 2.30 (s, 3H), 1.41 (d, J=6.8 Hz, 3H).

Example 128

(S)-2-(1-(6-Amino-5-cyanopyrimidin-4-ylamino) ethyl)-4-oxo-3-phenyl-3,4-dihydropyrrolo[1,2-f][1,2,4]triazine-5-carboxylic acid a) (S)-2-(1-Aminoethyl)-4-oxo-3-phenyl-3,4-d i hydropyrrolo[1,2-f][1,2,4]triazine-5-carboxylic acid This compound was prepared starting from (S)-2-(1-(tert-butoxycarbonylamino)ethyl)-4-oxo-3-phenyl-3,4-dihydropyrrolo[1,2-f][1,2,4]triazine-5-carboxylic acid (26 mg, 0.07 mmol, Preparation 103) and following the experimental procedure described in Preparation 46c to afford 28 mg (99% yield) of the title compound as a dihydrocloride salt that was used in the next step without any further purification.

LRMS (m/z): 299 (M+1)$^+$.

b) (S)-2-(1-(6-Amino-5-cyanopyrimidin-4-ylamino) ethyl)-4-oxo-3-phenyl-3,4-dihydropyrrolo[1,2-f][1,2,4]triazine-5-carboxylic acid The formate salt of the title compound (21 mg, 67% yield) was obtained from (S)-2-(1-aminoethyl)-4-oxo-3-phenyl-3,4-dihydropyrrolo[1,2-f][1,2,4]triazine-5-carboxylic acid (Example 128a) and 4-amino-6-chloropyrimidine-5-carbonitrile following the experimental procedure described in example 18.

LRMS (m/z): 417 (M+1)$^+$.

$^1$H NMR (400 MHz, DMSO) δ 7.78 (s, 1H), 7.65 (d, J=6.8 Hz, 1H), 7.61 (d, J=8.6 Hz, 1H), 7.50 (td, J=7.7, 1.6 Hz, 1H), 7.44-7.38 (m, 1H), 7.38-7.30 (m, 2H), 7.27 (br s, 2H), 7.18 (d, J=2.9 Hz, 1H), 4.95 (p, J=6.6 Hz, 1H), 1.41 (d, J=6.6 Hz, 3H).

Example 129

2-((S)-1-(6-Amino-5-cyanopyrimidin-4-ylamino) ethyl)-4-oxo-3-(tetrahydro-2H-pyran-3-yl)-3,4-dihydropyrrolo[1,2-f][1,2,4]triazine-5-carbonitrile—second diastereomer Same procedure as described in Example 93 was used from 2-((S)-1-aminoethyl)-4-oxo-3-(tetrahydro-2H-pyran-3-yl)-3,4-dihydropyrrolo[1,2-f][1,2,4]triazine-5-carbonitrile (118 mg, 0.23 mmols). The title compound (second eluting diastereomer) was obtained (3 mg, 3%)

LRMS (m/z): 406 (M+1)+

Example 130

(S)-4-Amino-6-(1-(3-(5-fluoropyridin-3-yl)-4-oxo-3, 4-dihydropyrrolo[1,2-f][1,2,4]triazin-2-yl)ethylamino)pyrimidine-5-carbonitrile The title compound (39 mg, 39% yield) was obtained from (S)-2-(1-Aminoethyl)-3-(5-fluoropyridin-3-yl)pyrrolo[1,2-f][1,2,4]triazin-4(3H)-one and 4-amino-6-chloropyrimidine-5-carbonitrile following the experimental procedure described in example 23 but using n-butanol as solvent and heating the reaction mixture at 100° C. during 5 hours.

LRMS (m/z): 392 (M+1)$^+$.

$^1$H NMR (400 MHz, DMSO) δ 8.53 (d, 1H), 8.42 (d, 1H), 8.17 (d, 1H), 7.82-7.57 (m, 3H), 7.26 (br s, 2H), 7.02 (dd, 1H), 6.71-6.61 (dd, 1H), 5.13-4.95 (m, 1H), 1.39 (d, 3H).

Example 131

(S)-4-Amino-6-(1-(4-oxo-3-(1H-pyrazol-3-yl)-3,4-dihydropyrrolo[1,2-f][1,2,4]triazin-2-yl)ethylamino) pyrimidine-5-carbonitrile The title compound (8 mg, 10% yield) was obtained from (S)-2-(1-aminoethyl)-3-(1H-pyrazol-3-yl)pyrrolo[1,2-f][1,2,4]triazin-4(3H)-one and 4-amino-6-chloropyrimidine-5-carbonitrile following the experimental procedure described in example 18.

LRMS (m/z): 363 (M+1)$^+$.

$^1$H NMR (400 MHz, CDCl$_3$) δ 8.04 (s, 1H), 7.69 (d, J=2.4 Hz, 1H), 7.43 (dd, J=2.7, 1.7 Hz, 1H), 7.12 (dd, J=4.4, 1.7 Hz, 1H), 6.58 (dd, J=4.4, 2.7 Hz, 1H), 6.45 (d, J=2.4 Hz, 1H), 5.90

(d, J=8.3 Hz, 1H), 5.76 (s, 1H), 5.23 (dq, J=13.6, 6.8 Hz, 1H), 3.56-3.42 (m, 1H), 2.62 (s, 1H), 1.49 (d, J=6.8 Hz, 3H).

Example 132

(S)-4-Amino-6-(1-(4-oxo-3-(pyrimidin-5-yl)-3,4-dihydropyrrolo[1,2-f][1,2,4]triazin-2-yl)ethylamino)pyrimidine-5-carbonitrile The title compound (4 mg, 14% yield) was obtained from (S)-2-(1-aminoethyl)-3-(pyrimidin-5-yl)pyrrolo[1,2-f][1,2,4]triazin-4(3H)-one and 4-amino-6-chloropyrimidine-5-carbonitrile following the experimental procedure described in example 23 but using n-butanol as solvent and heating the reaction mixture at 110° C. during 15 hours.
LRMS (m/z): 375 (M+1)$^+$.

Example 133

4-Amino-6-((1S)-1-(4-oxo-3-(tetrahydro-2H-pyran-3-yl)-5-(trifluoromethyl)-3,4-dihydropyrrolo[1,2-f][1,2,4]triazin-2-yl)ethylamino)pyrimidine-5-carbonitrile second diastereomer Same procedure as describes in Example 93 was used from 2-((S)-1-aminoethyl)-3-(tetrahydro-2H-pyran-3-yl)-5-(trifluoromethyl)pyrrolo[1,2-f][1,2,4]triazin-4(3H)-one (158 mg, 0.20 mmols). The title compound (second eluting diastereomer) was obtained (10 mg, 11%)
LRMS (m/z): 449 (M+1)+
$^1$H NMR (400 MHz, DMSO-d$_6$) d ppm 1.46 (d, 3 H) 1.55-1.77 (m, 1 H) 1.83-2.03 (m, 1 H) 2.33 (d, 1 H) 2.53-2.79 (m, 2 H) 3.01-3.25 (m, 1 H) 3.55-3.78 (m, 1 H) 3.80-4.02 (m, 1 H) 4.24 (t, 1 H) 5.58-5.87 (m, 1 H) 6.95 (d, 1 H) 7.37 (s, 2 H) 7.74 (d, 1 H) 7.95 (d, 1 H) 8.05-8.21 (m, 1 H)

Example 134

(S)-2,4-Diamino-6-(1-(4-oxo-3-phenyl-3,4-dihydropyrrolo[1,2-f][1,2,4]triazin-2-yl)ethylamino)pyrimidine-5-carbonitrile The title compound (17 mg, 33% yield) was obtained from (S)-2-(1-aminoethyl)-3-phenylpyrrolo[1,2-f][1,2,4]triazin-4(3H)-one (preparation 22) and 2,4-diamino-6-chloropyrimidine-5-carbonitrile following the experimental procedure described in example 20.
LRMS (m/z): 388 (M+1)$^+$.
$^1$H NMR (400 MHz, DMSO) δ 7.67 (dd, J=2.6, 1.7 Hz, 1H), 7.46 (m, 3H), 7.35 (m, 2H), 6.99-6.90 (m, 2H), 6.60 (dd, J=4.3, 2.7 Hz, 1H), 6.49 (br s, 2H), 6.20 (bs, 2H), 4.80 (p, J=6.7 Hz, 1H), 1.31 (d, J=6.7 Hz, 3H).

Example 135

(S)-4-(1-(3-((1H-Pyrazol-3-yl)methyl)-4-oxo-3,4-dihydropyrrolo[1,2-f][1,2,4]triazin-2-yl)ethylamino)-6-aminopyrimidine-5-carbonitrile The title compound (8 mg, 10% yield) was obtained from (S)-3-((1H-pyrazol-3-yl)methyl)-2-(1-aminoethyl)pyrrolo[1,2-f][1,2,4]triazin-4(3H)-one and 4-amino-6-chloropyrimidine-5-carbonitrile following the experimental procedure described in example 18.
LRMS (m/z): 377 (M+1)$^+$.
$^1$H NMR (400 MHz, CDCl$_3$) δ 8.22 (s, 1H), 7.51 (d, J=2.2 Hz, 1H), 7.34 (dt, J=16.1, 8.1 Hz, 1H), 7.05 (dd, J=4.3, 1.6 Hz, 1H), 6.54 (dd, J=4.4, 2.6 Hz, 1H), 6.39 (d, J=2.2 Hz, 1H), 5.82 (dq, J=13.4, 6.7 Hz, 1H), 5.58 (s, 1H), 5.49 (d, J=15.8 Hz, 1H), 5.34 (d, J=15.8 Hz, 1H), 3.83-3.74 (m, 2H), 1.52 (d, J=6.6 Hz, 3H).

Example 136

(S)-4-Amino-6-(1-(4-oxo-3-(tetrahydro-2H-pyran-4-yl)-3,4-dihydropyrrolo[1,2-f][1,2,4]triazin-2-yl)ethylamino)pyrimidine-5-carbonitrile To a solution of (S)-2-(1-aminoethyl)-3-(tetrahydro-2H-pyran-4-yl)pyrrolo[1,2-f][1,2,4]triazin-4(3H)-one (100 mg, 0.38 mmols, Preparation 133) in butan-1-ol (4 ml), 4-amino-6-chloropyrimidine-5-carbonitrile (61 mg, 0.39 mmols) and DIEA (200 µl, 1.14 mmols) were added. It was stirred at 120° C. for 8 h. It was concentrated in vacuum and it was purified by reverse phase chromatography. The title compound was obtained (70 mg, 48% yield).
LRMS (m/z): 381 (M+1)+
$^1$H NMR (400 MHz, DMSO-d$_6$) d ppm 1.38-1.44 (m, 1 H) 1.62-1.75 (m, 1 H) 2.62-2.84 (m, 2 H) 3.03-3.17 (m, 1 H) 3.23-3.30 (m, 1 H) 3.71-3.83 (m, 1 H) 3.83-3.95 (m, 2 H) 5.81 (q, 1 H) 6.49-6.63 (m, 1 H) 6.79-6.91 (m, 1 H) 7.31-7.54 (s, 2 H) 7.52-7.66 (m, 1 H) 8.08-8.24 (m, 2 H)

Example 137

(S)-4-Amino-6-(1-(4-oxo-3-(2,2,2-trifluoroethyl)-3,4-dihydropyrrolo[1,2-f][1,2,4]triazin-2-yl)ethylamino)pyrimidine-5-carbonitrile To a solution of (S)-2-(1-aminoethyl)-3-(2,2,2-trifluoroethyl)pyrrolo[1,2-f][1,2,4]triazin-4(3H)-one (100 mg, 0.38 mmols, preparation 134) in butan-1-ol (4 ml), 4-amino-6-chloropyrimidine-5-carbonitrile (60 mg, 0.38 mmols) and DIEA (200 µl, 1.14 mmols) were added. It was stirred at 120° C. for 8 h. It was concentrated in vacuum and it was purified by reverse phase chromatography. The title compound was obtained (81 mg, 56% yield).
LRMS (m/z): 379 (M+1)+
$^1$H NMR (400 MHz, DMSO-d$_6$) d ppm 1.52 (d, 3 H) 4.45-4.65 (m, 1 H) 5.05-5.25 (m, 1 H) 5.53 (q, 1 H) 6.64 (dd, 1 H) 7.03 (dd, 1 H) 7.34-7.56 (m, 2 H) 7.67-7.82 (m, 1 H) 7.95 (d,1 H) 8.11 (s, 1 H)

Example 138

(S)-4-Amino-6-(1-(3-cyclobutyl-4-oxo-3,4-dihydropyrrolo[1,2-f][1,2,4]triazin-2-yl)ethylamino)pyrimidine-5-carbonitrile To a solution of (S)-2-(1-aminoethyl)-3-cyclobutylpyrrolo[1,2-f][1,2,4]triazin-4(3H)-one (107 mg, 0.38 mmols, preparation 135) in butan-1-ol (4 ml), 4-amino-6-chloropyrimidine-5-carbonitrile (59 mg, 0.38 mmols) and DIEA (466 µl, 2.68 mmols) were added. It was stirred at 120° C. for 12 h. It was concentrated in vacuum and it was purified by reverse phase chromatography. The title compound was obtained (70 mg, 53% yield).
LRMS (m/z): 351 (M+1)+
$^1$H NMR (400 MHz, DMSO-d$_6$) d ppm 1.26-1.56 (m, 4 H) 1.66-1.95 (m, 2 H) 1.97-2.22 (m, 1 H) 2.82-3.05 (m, 1 H) 3.04-3.22 (m, 1 H) 4.28-4.64 (m, 1 H) 5.56-5.79 (m, 1 H) 6.54 (dd, 1 H) 6.86 (dd, 1 H) 7.39 (s, 2 H) 7.46-7.64 (m, 1 H) 7.99 (d, 1 H) 8.15 (s, 1 H)

Example 139

(S)-2-Amino-4-(1-(4-oxo-3-phenyl-3,4-dihydropyrrolo[1,2-f][1,2,4]triazin-2-yl)ethylamino)pyrimidine-5-carbonitrile The title compound (29 mg, 35% yield) was obtained from (S)-2-(1-aminoethyl)-3-phenylpyrrolo[1,2-f][1,2,4]triazin-4(3H)-one (preparation 22) and 2-amino-4-chloropyrimidine-5-carbonitrile (preparation 97) following the experimental procedure described in example 26.

LRMS (m/z): 373 (M+1)$^+$.

$^1$H NMR (400 MHz, DMSO) δ 8.06 (s, 1H), 7.73-7.64 (m, 2H), 7.48 (d, J=7.7 Hz, 1H), 7.43 (m, 1H), 7.34 (m, 1H), 7.30-7.21 (m, 2H), 6.97 (m, 2H), 6.76 (br s, 1H), 6.65-6.58 (m, 1H), 5.03-4.76 (m, 1H), 1.36 (d, J=6.5 Hz, 3H).

Example 140

4-Amino-6-(1-(5-(1-methyl-1H-pyrazol-4-yl)-4-oxo-3-phenyl-3,4-dihydropyrrolo[1,2-f][1,2,4]triazin-2-yl)ethylamino)pyrimidine-5-carbonitrile Starting from (S)-2-(1-aminoethyl)-5-(1-methyl-1H-pyrazol-4-yl)-3-phenylpyrrolo[1,2-f][1,2,4]triazin-4(3H)-one (78 mg, 0,16 mmol) and following the experimental procedure described in Example 23 were obtained 27 mg (36% yield) of the title compound of this example.

LRMS (m/z): 453 (M+1)$^+$.

$^1$H NMR (400 MHz, CDCl$_3$) δ ppm 1.63 (s, 3 H) 3.85 (s, 3 H) 4.94-5.10 (m, 1 H) 5.37 (s, 2 H) 5.78 (d, J=7.82 Hz, 1 H) 6.74 (d, J=2.74 Hz, 1 H) 7.34 (d, J=7.82 Hz, 1 H) 7.38 (d, J=2.74 Hz, 1 H) 7.42-7.49 (m, 1 H) 7.49-7.64 (m, 3 H) 7.85 (s, 1 H) 8.09 (s, 1 H) 8.35 (s, 1 H)

Example 141

(S)-4-Amino-6-(1-(3-cyclopropyl-4-oxo-3,4-dihydropyrrolo[1,2-f][1,2,4]triazin-2-yl)ethylamino)pyrimidine-5-carbonitrile To a solution of (S)-2-(1-aminoethyl)-3-cyclopropylpyrrolo[1,2-f][1,2,4]triazin-4(3H)-one (311 mg, 1.28 mmols, preparation 136) in butan-1-ol (11.5 ml), 4-amino-6-chloropyrimidine-5-carbonitrile (198 mg, 1.28 mmols) and DIEA (1.5 ml, 8.61 mmols) were added. It was stirred at 120° C. for 6 h. It was concentrated in vacuum and it was purified by reverse phase chromatography. The title compound was obtained (246 mg, 57% yield).

LRMS (m/z): 337 (M+1)+

$^1$H NMR (400 MHz, DMSO-d$_6$) d ppm 0.75-1.06 (m, 3 H) 1.07-1.22 (m, 1 H) 2.70-2.84 (m, 1 H) 5.63-6.06 (m, 1 H) 6.51 (dd, 1 H) 6.83 (dd, 1 H) 7.33 (s, 2 H) 7.45-7.58 (m, 1 H) 7.81 (d, 1 H) 8.07 (s, 1 H)

Example 142

(S)-4-Amino-6-(1-(5-bromo-4-oxo-3,4-dihydropyrrolo[1,2-f][1,2,4]triazin-2-yl)ethylamino)pyrimidine-5-carbonitrile a) (S)-2-(1-Aminoethyl)-5-bromopyrrolo[1,2-f][1,2,4]triazin-4(3H)-one 837 mg (2.34 mmol) of (S)-tert-butyl 1-(5-bromo-4-oxo-3,4-dihydropyrrolo[1,2-f][1,2,4]triazin-2-yl)ethylcarbamate (obtained as a by-product in Preparation 45b) was stirred in a 4M solution of hydrochloric acid in dioxane at room temperature for 4 hours. The volatiles were removed in vacuum and the residue was partitioned between ethyl acetate and a diluted aqueous solution of potassium carbonate. The organic layers were washed with water and brine, dried over magnesium sulphate, filtered and the solvent was removed.

LRMS (m/z): 258 (M+1)$^+$.

b) (S)-4-Amino-6-(1-(5-bromo-4-oxo-3,4-dihydropyrrolo[1,2-f][1,2,4]triazin-2-yl)ethylamino)pyrimidine-5-carbonitrile Prepared from (S)-2-(1-Aminoethyl)-5-bromopyrrolo[1,2-f][1,2,4]triazin-4(3H)-one (570 mg, 2.22 mmol) and 4-amino-6-chloropyrimidine-5-carbonitrile (377 mg, 2.44 mmol) following the experimental procedure described in Example 68 at a temperature of 120° C. The product was purified by flash chromatography (0% to 10% MeOH/DCM) to give 563 mg (68% yield) of the title compound as a white solid.

LRMS (m/z): 376 (M+1)$^+$.

$^1$H NMR (400 MHz, DMSO) δ 11.79 (s, 1H), 8.03 (s, 1H), 7.62 (d, 1H), 7.49-7.18 (m, 3H), 6.66 (d, 1H), 5.17-5.02 (m, 1H), 1.51 (d, 3H).

Example 143

4-Amino-6-((1S)-1-(4-oxo-3-(tetrahydro-2H-pyran-3-yl)-3,4-dihydropyrrolo[1,2-f][1,2,4]triazin-2-Aethylamino)pyrimidine-5-carbonitrile—first diastereomer To a solution of 2-((S)-1-aminoethyl)-3-(tetrahydro-2H-pyran-3-yl)pyrrolo[1,2-f][1,2,4]triazin-4(3H)-one (100 mg, 0.38 mmols) in butan-1-ol (4 ml), 4-amino-6-chloropyrimidine-5-carbonitrile (60 mg, 0.38 mmols) and DIEA (200 μl, 1.14 mmols) were added. It was stirred at 120° C. for 12 h. It was concentrated in vacuum and it was purified by reverse phase chromatography. The title compound (first eluting diastereomer) was obtained (34 mg, 23%).

LRMS (m/z): 381 (M+1)$^+$.

$^1$H NMR (400 MHz, DMSO-d$_6$) d ppm 0.77-0.94 (m, 1 H) 1.06-1.20 (m, 1 H) 1.46 (d, 3 H) 1.52-1.62 (m, 1 H) 1.70-1.82 (m, 1 H) 2.66 (d, 1 H) 3.07-3.24 (m, 1 H) 3.68 (d, 1 H) 3.71-3.91 (m, 1 H) 4.17-4.34 (m, 1 H) 5.65-5.86 (m, 1 H) 6.56 (dd, 1 H) 6.84 (dd, 1 H) 7.41 (s, 2 H) 7.52-7.64 (m, 1 H) 8.06-8.22 (m, 2 H)

Example 144

(S)-4-Amino-6-(1-(5-bromo-4-oxo-3-phenyl-3,4-dihydropyrrolo[1,2-f][1,2,4]triazin-2-yl)ethylamino)pyrimidine-5-carbonitrile Starting from (S)-2-(1-aminoethyl)-5-bromo-3-phenylpyrrolo[1,2-f][1,2,4]triazin-4(3H)-one (213 mg, 0,58 mmol) and following the experimental procedure described in Example 23 were obtained 203 mg (78% yield) of the title compound of this example.

LRMS (m/z): 451, 453 (M+1)$^+$.

$^1$H NMR (400 MHz, DMSO) δ 7.77 (s, 1H), 7.74 (d, J=2.9 Hz, 1H), 7.64 (d, J=6.9 Hz, 1H), 7.50 (m, 1H), 7.44 (m, 1H), 7.37-7.32 (m, 1H), 7.32-7.27 (m, 2H), 7.27-7.17 (br s, 2H), 6.76 (d, J=2.9 Hz, 1H), 4.85 (p, J=6.6 Hz, 1H), 1.35 (d, J=6.7 Hz, 3H).

Example 145

2-((3-Iodo-1H-pyrazolo[3,4-d]pyrimidin-4-ylamino)methyl)-5-methyl-3-O— tolylpyrrolo[1,2-f][1,2,4]triazin-4(3H)-one To a solution of 317 mg (1.10 mmol) of 2-(chloromethyl)-5-methyl-3-o-tolylpyrrolo[1,2-f][1,2,4]triazin-4(3H)-one in DMF (10 ml), 3-iodo-1H-pyrazolo[3,4-d]pyrimidin-4-amine (316 mg, 1.21 mmol) and potassium carbonate (167 mg, 1.21 mmol) were added. The solution was stirred at room temperature for 2 h and the solvent was removed under vacuum. The residue was partitioned between water and dichloromethane and the organic layer was washed with water and brine, dried over magnesium sulphate, filtered and the solvent was evaporated. The product was purified first by flash chromatography (0% to 10% MeOH/DCM) and then by reverse phase chromatography (C-18 silica from Waters®, water/1:1 acetonitrile-methanol as eluents [0.1% v/v formic acid buffered] 0% to 100%) to obtain 30 mg (6% yield) of the title compound, which was the minor isomer of the reaction.

LRMS (m/z): 513 (M+1)+.

Example 146

(S)-2-(1-(6-Amino-5-cyanopyrimidin-4-ylamino)ethyl)-3-(5-fluoropyridin-3-yl)-4-oxo-3,4-dihydropyrrolo[1,2-f][1,2,4]triazine-5-carbonitrile The title compound (15 mg, 10% yield) was obtained from (S)-2-(1-aminoethyl)-3-(5-fluoropyridin-3-yl)-4-oxo-3,4-dihydropyrrolo[1,2-f][1,2,4]triazine-5-carbonitrile and 4-amino-6-chloropyrimidine-5-carbonitrile following the experimental procedure described in example 23 but using n-butanol as solvent and heating the reaction mixture at 110° C. during 15 hours.

LRMS (m/z): 417 (M+1)+.

$^1$H NMR (400 MHz, DMSO) δ 8.59 (d, 1H), 8.50 (d, 1H), 8.16 (d, 1H), 7.76 (d, 1H), 7.71-7.49 (m, 2H), 7.45-7.12 (m, 3H), 5.16-4.93 (m, 1H), 1.40 (d, 3H).

Example 147

4-Amino-6-((1S)-1-(4-oxo-3-(tetrahydro-2H-pyran-3-yl)-3,4-d hydropyrrolo[1,2-f][1,2,4]triazin-2-yl)ethylamino)pyrimidine-5-carbonitrile—second diastereomer To a solution of 2-((S)-1-aminoethyl)-3-(tetrahydro-2H-pyran-3-yl)pyrrolo[1,2-f][1,2,4]triazin-4(3H)-one (100 mg, 0.38 mmols) in butan-1-ol (4 ml), 4-amino-6-chloropyrimidine-5-carbonitrile (60 mg, 0.38 mmols) and DI EA (200 µl, 1.14 mmols) were added. It was stirred at 120° C. for 12 h. It was concentrated in vacuum and it was purified by reverse phase chromatography. The title compound (second eluting diastereomer) was obtained (14 mg, 10%).

LRMS (m/z): 381 (M+1)+.

$^1$H NMR (400 MHz, DMSO-d$_6$) d ppm 1.47 (d, 3 H) 1.60-1.79 (m, 1 H) 1.81-1.97 (m, 1 H) 2.66 (d, 1 H) 3.06-3.21 (m, 2 H) 3.56-3.72 (m, 2 H) 3.73-3.91 (m, 1H) 4.17-4.34 (m, 1H) 5.60-5.81 (m, 1H) 6.56 (dd, 1H) 6.84 (d, 1H) 7.36 (s, 2 H) 7.60 (s, 1 H) 8.02-8.20 (m, 2 H)

Example 148

(S)-4-Amino-6-(1-(4-oxo-3-phenyl-5-(1H-pyrazol-4-yl)-3,4-dihydropyrrolo[1,2-f][1,2,4]triazin-2-yl)ethylamino)pyrimidine-5-carbonitrile 40 mg (0.09 mmol) of (S)-4-amino-6-(1-(5-bromo-4-oxo-3-phenyl-3,4-dihydropyrrolo[1,2-f][1,2,4]triazin-2-yl)ethylamino)pyrimidine-5-carbonitrile, 33 mg (0.17 mmol, Example 144) of 4-(4,4,5,5-tetramethyl-1,3,2-dioxaborolan-2-yl)-1H-pyrazole, 6 mg (0.01 mmol) of tetrakis(triphenylphosphine)palladium(0) and 136 µl of sodium carbonate 2M in water under argon were stirred in dimethylformamide (1 ml) at 120° C. overnight. The crude was filtered over Celite washing with ethyl acetate. Then the organic phase was washed with water and brine, dried over magnesium sulphate and the solvent evaporated. The crude product was purified by reverse phase chromatography (C-18 silica from Waters, water/1:1 acetonitrile-methanol as eluents 0% to 100%) to obtain the title compound (10 mg, 27% yield) as a white solid.

LRMS (m/z): 439 (M+1)+.

$^1$H NMR (400 MHz, CDCl3) δ ppm 1.41 (d, J=6.64 Hz, 3 H) 2.00 (s, 1 H) 4.95-5.08 (m, 1 H) 5.47 (s, 2 H) 5.83 (d, J=8.21 Hz, 1 H) 6.74 (d, J=2.74 Hz, 1 H) 7.33 (d, J=7.42 Hz, 1 H) 7.39 (d, J=2.74 Hz, 1 H) 7.42-7.48 (m, 1 H) 7.49-7.62 (m, 3 H) 8.07 (s, 1 H) 8.23 (s, 2 H)

Example 149

(S)-4-Amino-6-(1-(3-(isoxazol-3-yl)-4-oxo-3,4-dihydropyrrolo[1,2-f][1,2,4]triazin-2-Aethylamino)pyrimidine-5-carbonitrile To a solution of (S)-2-(1-aminoethyl)-3-(isoxazol-3-yl)pyrrolo[1,2-f][1,2,4]triazin-4(3H)-one (188 mg, 0.77 mmols) in butan-1-ol (7 ml), 4-amino-6-chloropyrimidine-5-carbonitrile (118 mg, 0.77 mmols) and DIEA (0.94 ml, 5.37 mmols) were added. It was stirred at 120° C. for 8 h. It was concentrated in vacuum and it was purified by reverse phase chromatography. The title compound was obtained (82 mg, 29%).

LRMS (m/z): 364 (M+1)+

$^1$H NMR (400 MHz, DMSO-d$_6$) d ppm 1.43 (d, 3 H) 4.98-5.24 (m, 1 H) 6.58-6.83 (m, 2 H) 7.07 (dd, 1 H) 7.26 (s, 2 H) 7.67-7.85 (m, 2 H) 7.93 (s, 1 H) 8.98 (d, 1 H)

Example 150

(S)-2-(1-(6-Amino-5-cyanopyrimidin-4-ylamino)ethyl)-N,N-dimethyl-4-oxo-3-phenyl-3,4-dihydropyrrolo[1,2-f][1,2,4]triazine-5-carboxamide The title compound (24 mg, 72% yield) was obtained from (S)-2-(1-(6-amino-5-cyanopyrimidin-4-ylamino)ethyl)-4-oxo-3-phenyl-3,4-dihydropyrrolo[1,2-f][1,2,4]triazine-5-carboxylic acid (30 mg, 0.07 mmol, Example 128) and dimethylamine (2M solution in Methanol, 0.09 mmol) following the experimental procedure described in Preparation 20a.

LRMS (m/z): 444 (M+1)+.

$^1$H NMR (400 MHz, DMSO) δ 7.77 (s, 1H), 7.71 (d, J=2.6 Hz, 1H), 7.64 (d, J=7.0 Hz, 1H), 7.49 (d, J=7.8 Hz, 1H), 7.43 (m, 1H), 7.30 (m, 3H), 7.19 (br s, 2H), 6.63 (d, J=2.6 Hz, 1H), 5.02-4.83 (m, 1H), 2.92 (s, 3H), 2.83 (s, 3H), 1.38 (d, J=6.6 Hz, 3H).

Example 151

(S)-4-Amino-6-(1-(3-(1-methyl-1H-pyrazol-3-yl)-4-oxo-3,4-dihydropyrrolo[1,2-f][1,2,4]triazin-2-yl)ethylamino)pyrimidine-5-carbonitrile The title compound (50 mg, 33% yield) was obtained from (S)-2-(1-aminoethyl)-3-(1-methyl-1H-pyrazol-3-yl)pyrrolo[1,2-f][1,2,4]triazin-4(3H)-one and 4-amino-6-chloropyrimidine-5-carbonitrile following the experimental procedure described in example 18.

LRMS (m/z): 377 (M+1)$^+$.

$^1$H NMR (400 MHz, CDCl3) δ 8.10 (s, 1H), 7.50 (t, 1H), 7.40 (dd, 1H), 7.09 (dd, 1H), 6.54 (dd, 1H), 6.36 (d, 1H), 6.08 (d, 1H), 5.40 (s, 2H), 5.25 (dq, 1H), 3.95 (s, 3H), 1.49-1.46 (m, 3H).

Example 152

(S)-2-(1-(6-Amino-5-cyanopyrimidin-4-ylamino)ethyl)-4-oxo-3-phenyl-N-propyl-3,4-dihydropyrrolo[1,2-f][1,2,4]triazine-5-carboxamide The title compound (24 mg, 72% yield) was obtained from (S)-2-(1-(6-amino-5-cyanopyrimidin-4-ylamino)ethyl)-4-oxo-3-phenyl-3,4-dihydropyrrolo[1,2-f][1,2,4]triazine-5-carboxylic acid (30 mg, 0.07 mmol, Example 128) and propan-1-amine (7 µl, 0.09 mmol) following the experimental procedure described in Example 150.

LRMS (m/z): 458 (M+1)$^+$.

$^1$H NMR (400 MHz, DMSO) δ 9.87 (t, J=5.5 Hz, 1H), 7.81 (d, J=2.9 Hz, 1H), 7.77 (s, 1H), 7.63 (d, J=6.8 Hz, 1H), 7.60-7.55 (m, 1H), 7.50-7.43 (m, 1H), 7.42-7.38 (m, 1H), 7.37-7.29 (m, 2H), 7.22 (br s, 2H), 7.12 (d, J=2.9 Hz, 1H), 4.90 (p, J=6.6 Hz, 1H), 3.21 (q, J=6.5 Hz, 2H), 1.46 (q, J=7.1 Hz, 2H), 1.39 (d, J=6.7 Hz, 3H) 0.84 (t, J=7.4 Hz, 3H).

Example 153

2-((S)-1-(9H-Purin-6-ylamino)ethyl)-3-(tetrahydro-2H-pyran-3-yl)pyrrolo[1,2-f][1,2,4]triazin-4(3H)-one—first diastereomer To a solution of 2-((S)-1-aminoethyl)-3-(tetrahydro-2H-pyran-3-yl)pyrrolo[1,2-f][1,2,4]triazin-4(3H)-one (89 mg, 0.34 mmols) in tert-butanol (4 ml), 6-bromo-9H-purine (68 mg, 0.34 mmols) and DIEA (415 µl, 2.38 mmols) were added. It was stirred at 80° C. for 18 h. It was concentrated in vacuum and it was purified by reverse phase chromatography. The title compound (first eluting diastereomer) was obtained (37 mg, 29%).

LRMS (m/z): 381 (M+1)$^+$

1H NMR (400 MHz, DMSO-d$_6$) d ppm 0.92-1.06 (m, 1 H) 1.15-1.30 (m, 1 H) 1.57 (d, 3 H) 1.60-1.75 (m, 1 H) 2.96-3.15 (m, 2 H) 3.49-3.66 (m, 1 H) 3.75-3.91 (m, 1 H) 3.93-4.11 (m, 1 H) 4.23 (d, 1 H) 5.75-5.97 (m, 1 H) 6.41-6.62 (m, 1 H) 6.83 (dd, 1 H) 7.58 (s, 1 H) 8.14 (s, 1 H) 8.24 (s, 1 H) 8.28-8.49 (m, 1 H)

Example 154

24(S)-1-(9H-Purin-6-ylamino)ethyl)-3-(tetrahydro-2H-pyran-3-yl)pyrrolo[1,2-f][1,2,4]triazin-4(3H)-one-second diastereomer To a solution of 2-((S)-1-aminoethyl)-3-(tetrahydro-2H-pyran-3-yl)pyrrolo[1,2-f][1,2,4]triazin-4(3H)-one (89 mg, 0.34 mmols) in tert-butanol (4 ml), 6-bromo-9H-purine (68 mg, 0.34 mmols) and DIEA (415 µl, 2.38 mmols) were added. It was stirred at 80° C. for 18 h. It was concentrated in vacuum and it was purified by reverse phase chromatography. The title compound (second eluting diastereomer) was obtained (13 mg, 10%).

LRMS (m/z): 381 (M+1)+

$^1$H NMR (400 MHz, DMSO-d$_6$) d ppm 1.34-1.75 (m, 4 H) 1.81-1.99 (m, 1 H) 2.22-2.39 (m, 1 H) 2.58-2.79 (m, 1 H) 2.86-3.17 (m, 2 H) 3.47-3.68 (m, 1 H) 4.00-4.33 (m, 2 H) 5.65-5.89 (m, 1 H) 6.54 (dd, 1 H) 6.75-6.85 (m, 1 H) 7.57 (s, 1 H) 8.14 (s, 1 H) 8.20-8.42 (m, 2 H)

Example 155

(S)-4-Amino-6-(3-hydroxy-1-(4-oxo-3-phenyl-3,4-dihydropyrrolo[1,2-f][1,2,4]triazin-2-yl)propylamino)pyrimidine-5-carbonitrile The title compound (92 mg, 61% yield) was obtained from (S)-2-(1-Amino-3-hydroxypropyl)-3-phenylpyrrolo[1,2-f][1,2,4]triazin-4(3H)-one and 4-amino-6-chloropyrimidine-5-carbonitrile following the experimental procedure described in example 20 but using n-butanol as solvent and heating the reaction mixture at 120° C. during 15 hours.

LRMS (m/z): 403 (M+1)$^+$.

$^1$H NMR (400 MHz, DMSO) δ 7.84 (s, 1H), 7.74-7.57 (m, 2H), 7.53-7.32 (m, 5H), 7.24 (br s, 2H), 6.94 (dd, 1H), 6.60 (dd, 1H), 4.92-4.79 (m, 1H), 4.53 (t, 1H), 3.46-3.34 (m, 2H), 2.12-1.99 (m, 1H), 1.98-1.87 (m, 1H).

Example 156

(S)-2-(1-(9H-Purin-6-ylamino)-3-hydroxypropyl)-3-phenylpyrrolo[1,2-f][1,2,4]triazin-4(3H)-one The title compound (28 mg, 18% yield) was obtained from (S)-2-(1-Amino-3-hydroxypropyl)-3-phenylpyrrolo[1,2-f][1,2,4]triazin-4(3H)-one and 6-bromo-9H-purine following the experimental procedure described in example 20 but using n-butanol as solvent and heating the reaction mixture at 120° C. during 15 hours.

LRMS (m/z): 403 (M+1)$^+$.

$^1$H NMR (400 MHz, DMSO) δ 12.89 (s, 1H), 8.22-8.04 (m, 2H), 7.96 (s, 1H), 7.60 (dd, 1H), 7.55-7.13 (m, 5H), 6.93 (dd, 1H), 6.57 (dd, 1H), 5.00-4.78 (m, 1H), 4.51 (t, 1H), 3.49-3.34 (m, 2H), 2.19-2.06 (m, 1H), 2.06-1.93 (m, 1H).

Example 157

(R)-4-Amino-6-(1-(3-(3,5-difluorophenyl)-4-oxo-3,4-dihydropyrrolo[1,2-f][1,2,4]triazin-2-yl)-2-hydroxyethylamino)pyrimidine-5-carbonitrile The title compound (9.2 mg) was obtained as a by-product during the synthesis of Example 112.

LRMS (m/z): 425 (M+1)$^+$.

Example 158

4-Amino-6-((4-oxo-3-o-tolyl-3,4-dihydropyrrolo[1,2-f][1,2,4]triazin-2-yl)methylamino)pyrimidine-5-carbonitrile The title compound (34 mg, 45% yield) was obtained from 2-(aminomethyl)-3-O— tolylpyrrolo[1,2-f][1,2,4]triazin-4

(3H)-one (preparation 9) and 4-amino-6-chloropyrimidine-5-carbonitrile following the experimental procedure described in example 18.

LRMS (m/z): 373 (M+1)+.

$^1$H NMR (400 MHz, CDCl3) δ 8.09 (s, 1H), 7.49-7.34 (m, 4H), 7.20 (d, 1H), 7.11 (dd, 1H), 6.66-6.53 (m, 1H), 5.95 (s, 1H), 5.34 (s, 2H), 4.23 (ddd, 2H), 2.21 (s, 3H).

Example 159

(S)-4-Amino-6-(1-(5-(2-hydroxyethyl)-4-oxo-3-phenyl-3,4-dihydropyrrolo[1,2-f][1,2,4]triazin-2-yl)ethylamino)pyrimidine-5-carbonitrile Starting from (S)-2-(1-aminoethyl)-5-(2-hydroxyethyl)-3-phenylpyrrolo[1,2-f][1,2,4]triazin-4(3H)-one (35 mg, 0,08 mmol) and following the experimental procedure described in Example 23 were obtained 12 mg (32% yield) of the title compound of this example.

LRMS (m/z): 417 (M+1)+.

$^1$H NMR (400 MHz, CDCl3) δ ppm 1.40 (d, J=7.03 Hz, 3 H) 3.16 (t, J=6.06 Hz, 2 H) 3.87 (t, J=5.86 Hz, 2 H) 4.97-5.12 (m, 1 H) 5.38 (s, 2 H) 5.77 (d, J=8.21 Hz, 1 H) 6.44 (d, J=2.74 Hz, 1 H) 7.29-7.36 (m, 2 H) 7.44 (d, J=7.03 Hz, 1 H) 7.48-7.64 (m, 3 H) 8.08 (s, 1 H)

Example 160

(S)-2-(1-(6-Amino-5-cyanopyrimidin-4-ylamino)-3-hydroxypropyl)-3-(3,5-difluorophenyl)-4-oxo-3,4-dihydropyrrolo[1,2-f][1,2,4]triazine-5-carbonitrile The title compound (41 mg, 25% yield) was obtained from (S)-2-(1-amino-3-hydroxypropyl)-3-(3,5-difluorophenyl)-4-oxo-3,4-dihydropyrrolo[1,2-f][1,2,4]triazine-5-carbonitrile and 4-amino-6-chloropyrimidine-5-carbonitrile following the experimental procedure described in example 23 but using n-butanol as solvent and heating the reaction mixture at 120° C. during 15 hours.

LRMS (m/z): 464 (M+1)+.

$^1$H NMR (400 MHz, DMSO) δ 7.89 (d, 1H), 7.87 (s, 1H), 7.58 (d, 1H), 7.43 (d, 1H), 7.39-7.27 (m, 3H), 7.22 (d, 1H), 7.18 (d, 1H), 5.04-4.95 (m, 1H), 4.49 (t, 1H), 3.46-3.37 (m, 2H), 2.16-2.04 (m, 1H), 2.01-1.90 (m, 1H).

Example 161

(S)-2-(1-(9H-Purin-6-ylamino)ethyl)-3-(5-fluoropyridin-3-yl)-4-oxo-3,4-dihydropyrrolo[1,2-f][1,2,4]triazine-5-carbonitrile The title compound (2 mg, 3% yield) was obtained from (S)-2-(1-aminoethyl)-3-(5-fluoropyridin-3-yl)-4-oxo-3,4-dihydropyrrolo[1,2-f][1,2,4]triazine-5-carbonitrile and 6-bromo-9H-purine following the experimental procedure described in example 20 but using n-butanol as solvent and heating the reaction mixture at 120° C. during 15 hours.

LRMS (m/z): 417 (M+1)+.

Example 162

(S)-4-Amino-6-(1-(5-(2-methyloxazol-5-yl)-4-oxo-3-phenyl-3,4-dihydropyrrolo[1,2-f][1,2,4]triazin-2-yl)ethylamino)pyrimidine-5-carbonitrile The title compound (18 mg, 34% yield) was obtained from (S)-4-amino-6-(1-(5-bromo-4-oxo-3-phenyl-3,4-dihydropyrrolo[1,2-f][1,2,4]triazin-2-yl)ethylamino)pyrimidine-5-carbonitrile (52 mg, 0.12 mmol, Example 144) and 2-methyl-5-(4,4,5,5-tetramethyl-1,3,2-dioxaborolan-2-yl)oxazole (48 mg, 0.23 mmol) following the experimental procedure described in Example 148.

LRMS (m/z): 454 (M+1)+.

$^1$H NMR (400 MHz, CDCl$_3$) δ ppm 1.43 (d, J=6.64 Hz, 3 H) 2.50 (s, 3 H) 4.98-5.08 (m, 1 H) 5.35 (s, 2 H) 5.75 (d, J=8.21 Hz, 1 H) 6.86 (d, J=3.13 Hz, 1 H) 7.34 (d, J=7.42 Hz, 1 H) 7.39 (d, J=3.13 Hz, 1 H) 7.44-7.51 (m, 1 H) 7.52-7.64 (m, 3 H) 7.85 (s, 1 H) 8.09 (s, 1 H)

Example 163

(S)-4-Amino-6-(1-(5-(2-methoxyethyl)-4-oxo-3-phenyl-3,4-dihydropyrrolo[1,2-f][1,2,4]triazin-2-yl)ethylamino)pyrimidine-5-carbonitrile Starting from (S)-2-(1-aminoethyl)-5-(2-methoxyethyl)-3-phenylpyrrolo[1,2-f][1,2,4]triazin-4(3H)-one (40 mg, 0,10 mmol) and following the experimental procedure described in Example 23 were obtained 8 mg (18% yield) of the title compound.

LRMS (m/z): 431 (M+1)+.

$^1$H NMR (400 MHz, CDCl3) δ ppm 1.40 (d, J=7.03 Hz, 3 H) 3.19 (t, J=6.64 Hz, 2 H) 3.34 (s, 3 H) 3.66 (t, J=6.64 Hz, 2 H) 4.99-5.08 (m, 1 H) 5.40 (s, 2 H) 5.80 (d, J=7.82 Hz, 1 H) 6.46 (d, J=2.74 Hz, 1 H) 7.29-7.34 (m, 2 H) 7.38-7.45 (m, 1 H) 7.46-7.59 (m, 3 H) 8.07 (s, 1 H)

Example 164

(S)-Propyl 2-(1-(6-amino-5-cyanopyrimidin-4-ylamino)ethyl)-4-oxo-3-phenyl-3,4-dihydropyrrolo[1,2-f][1,2,4]triazine-5-carboxylate To a solution of (S)-2-(1-(6-amino-5-cyanopyrimidin-4-ylamino)ethyl)-4-oxo-3-phenyl-3,4-dihydropyrrolo[1,2-f][1,2,4]triazine-5-carboxylic acid (55 mg, 0.08 mmol, Example 128) in DMF (2 ml) was added potassium carbonate (22 mg, 0.16 mmol) and 1-bromopropane (14.4 μl, 0.16 mmol). The reaction mixture was stirred overnight at 50° C. The crude product was purified by reverse phase chromatography (C-18 silica from Waters, water/1:1 acetonitrile-methanol as eluents 0% to 100%) to obtain the title compound (15 mg, 40% yield) as a white solid.

LRMS (m/z): 459 (M+1)+.

$^1$H NMR (400 MHz, CDCl3) δ ppm 0.90-1.03 (m, 3 H) 1.41 (d, J=6.64 Hz, 3 H) 1.71-1.80 (m, 2 H) 4.24 (t, J=6.84 Hz, 2 H) 4.95-5.09 (m, 1 H) 5.38 (s, 2 H) 5.72 (d, J=7.82 Hz, 1 H) 7.04 (d, J=3.13 Hz, 1 H) 7.29-7.37 (m, 2 H) 7.43-7.60 (m, 4 H) 8.08 (s, 1 H)

Example 165

(S)-4-Amino-6-(3-hydroxy-1-(4-oxo-3,4-dihydropyrrolo[1,2-f][1,2,4]triazin-2-yl)propylamino)pyrimidine-5-carbonitrile The title compound (16 mg, 27% yield) was obtained from (S)-2-(1-amino-3-hydroxypropyl)pyrrolo[1,2-f][1,2,4]triazin-4(3H)-one and 4-amino-6-chloropyrimidine-5-carbonitrile following the experimental procedure described in example 23 but using n-butanol as solvent and heating the reaction mixture at 120° C. during 15 hours.

LRMS (m/z): 327 (M+1)+.

¹H NMR (400 MHz, DMSO) δ 11.68 (s, 1H), 8.88 (br s, 2H), 8.02 (s, 1H), 7.58 (dd, 1H), 7.36 (d, 1H), 6.86 (dd, 1H), 6.52 (dd, 1H), 5.26-5.17 (m, 1H), 4.77 (t, 1H), 3.55-3.45 (m, 2H), 2.13-1.99 (m, 2H).

Example 166

(S)-2-(1-(9H-Purin-6-ylamino)-3-hydroxypropyl) pyrrolo[1,2-f][1,2,4]triazin-4(3H)-one The title compound (11 mg, 18% yield) was obtained from (S)-2-(1-amino-3-hydroxypropyl)pyrrolo[1,2-f][1,2,4]triazin-4(3H)-one and 6-bromo-9H-purine following the experimental procedure described in example 20 but using n-butanol as solvent and heating the reaction mixture at 120° C. during 15 hours.
LRMS (m/z): 327 (M+1)⁺.
¹H NMR (400 MHz, DMSO) δ 12.94 (s, 1H), 11.93 (s, 1H), 8.21 (s, 1H), 8.18 (s, 1H), 7.72 (d, 1H), 7.54 (dd, 1H), 6.82 (dd, 1H), 6.49 (dd, 1H), 5.50-5.24 (m, 1H), 4.71 (t, 1H), 3.63-3.46 (m, 2H), 2.19-2.04 (m, 2H).

Example 167

(S)-4-Amino-6-(1-(3-(3,5-difluorophenyl)-4-oxo-5-(trifluoromethyl)-3,4-dihydropyrrolo[1,2-f][1,2,4] triazin-2-yl)-3-hydroxypropylamino)pyrimidine-5-carbonitrile The title compound (131 mg, 33% yield) was obtained from (S)-2-(1-amino-3-hydroxypropyl)-3-(3,5-difluorophenyl)-5-(trifluoromethyl)pyrrolo[1,2-f][1,2,4]triazin-4(3H)-one and 4-amino-6-chloropyrimidine-5-carbonitrile following the experimental procedure described in example 23 but using n-butanol as solvent and heating the reaction mixture at 120° C. during 15 hours.
LRMS (m/z): 507 (M+1)⁺.
¹H NMR (400 MHz, DMSO) δ 7.86 (s, 1H), 7.85 (d, 1H), 7.57 (d, 1H), 7.46 (d, 1H), 7.41-7.23 (m, 3H), 7.15 (d, 1H), 7.03 (d, 1H), 5.07-4.93 (m, 1H), 4.49 (t, 1H), 3.48-3.37 (m, 2H), 2.18-2.06 (m, 1H), 2.01-1.89 (m, 1H).

Example 168

(S)-4-Amino-6-(1-(4-oxo-3-(6-(trifluoromethyl)pyridin-2-yl)-3,4-dihydropyrrolo[1,2-f][1,2,4]triazin-2-yl)ethylamino)pyrimidine-5-carbonitrile The title compound (21 mg, 16% yield) was obtained from (S)-2-(1-aminoethyl)-3-(6-(trifluoromethyl)pyridin-2-yl) pyrrolo[1,2-f][1,2,4]triazin-4(3H)-one and 4-amino-6-chloropyrimidine-5-carbonitrile following the experimental procedure described in example 23 but using n-butanol as solvent and heating the reaction mixture at 110° C. during 15 hours.
LRMS (m/z): 442 (M+1)⁺.
¹H NMR (400 MHz, DMSO) δ 8.22-8.09 (m, 1H), 7.83 (d, 1H), 7.79 (dd, 1H), 7.73-7.60 (m, 3H), 7.20 (br s, 2H), 7.06 (dd, 1H), 6.67 (dd, 1H), 5.28-5.15 (m, 1H), 1.42 (d, 3H).

Example 169

(S)-4-Amino-6-(1-(5-bromo-4-oxo-3-(3-(trifluoromethyl)phenyl)-3,4-dihydropyrrolo[1,2-f][1,2,4]triazin-2-yl)ethylamino)pyrimidine-5-carbonitrile a) (S)-2-(1-Aminoethyl)-5-bromo-3-(3-(trifluoromethyl)phenyl)pyrrolo[1,2-f][1,2,4]triazin-4(3H)-one This compound was prepared starting from ((S)-tert-butyl 1-(5-bromo-4-oxo-3-(3-(trifluoromethyl)phenyl)-3,4-dihydropyrrolo[1,2-f][1,2,4]triazin-2-yl)ethylcarbamate (200 mg, 0.40 mmol) and following the experimental procedure described in Preparation 46c to afford 230 mg (99% yield) of the title compound as a dihydrochloride salt that was used in the next step without any further purification.
LRMS (m/z): 401, 403 (M+1)⁺.

b) (S)-4-Amino-6-(1-(5-bromo-4-oxo-3-(3-(trifluoromethyl)phenyl)-3,4-dihydropyrrolo[1,2-f][1,2,4] triazin-2-yl)ethylamino)pyrimidine-5-carbonitrile The title compound (21 mg, 67% yield) was obtained from (S)-2-(1-aminoethyl)-5-bromo-3-(3-(trifluoromethyl)phenyl)pyrrolo[1,2-f][1,2,4]triazin-4(3H)-one and 4-amino-6-chloropyrimidine-5-carbonitrile following the experimental procedure described in example 18.
LRMS (m/z): 519, 521 (M+1)⁺.
¹H NMR (400 MHz, DMSO, 1/1 mixture of isomers) δ 8.05 (s, 0.5H), 7.87 (d, J=7.6 Hz, 0.5H), 7.79 (t, J=3.3 Hz, 1H), 7.62 (m, 4.5H), 7.49 (t, J=7.8 Hz, 0.5H), 7.17 (br s, 2H), 6.79 (dd, J=3.4, 1.9 Hz, 1H), 5.08-4.88 (m, 1H), 1.36 (d, J=6.5 Hz, 3H).

Example 170

(S)-2-(2-(1-(6-Amino-5-cyanopyrimidin-4-ylamino) ethyl)-4-oxo-3-phenyl-3,4-dihydropyrrolo[1,2-f][1,2,4]triazin-5-yl)ethyl acetate A mixture of (S)-4-amino-6-(1-(5-(2-hydroxyethyl)-4-oxo-3-phenyl-3,4-dihydropyrrolo[1,2-f][1,2,4]triazin-2-yl) ethylamino)pyrimidine-5-carbonitrile (11 mg, 0.03 mmol, Example 159) in acetic acid was heated overnight at 100° C. Removal of the solvent yielded the title compound as a solid (13 mg, 100% yield).
LRMS (m/z): 459 (M+1)⁺.
¹H NMR (400 MHz, CDCl3-d) δ ppm 1.41 (d, 3 H) 2.01 (s, 3 H) 3.25 (t, J=6.64 Hz, 2 H) 4.31 (t, J=6.84 Hz, 2 H) 5.07 (d, J=6.25 Hz, 1 H) 5.45 (s, 2 H) 5.80 (d, J=8.21 Hz, 1 H) 6.43 (d, J=2.74 Hz, 1 H) 7.28-7.35 (m, 2 H) 7.42 (d, J=5.86 Hz, 1 H) 7.47-7.61 (m, 3 H) 8.08 (s, 1 H)

Example 171

(S)-2-(1-(9H-Purin-6-ylamino)ethyl)-3-(6-(trifluoromethyl)pyridin-2-yl)pyrrolo[1,2-f][1,2,4]triazin-4 (3H)-one The title compound (7 mg, 5% yield) was obtained from (S)-2-(1-aminoethyl)-3-(6-(trifluoromethyl)pyridin-2-yl) pyrrolo[1,2-f][1,2,4]triazin-4(3H)-one and 6-bromo-9H-purine following the experimental procedure described in example 20 but using n-butanol as solvent and heating the reaction mixture at 110° C. during 15 hours.
LRMS (m/z): 442 (M+1)⁺.
¹H NMR (400 MHz, DMSO) δ 12.87 (s, 1H), 8.14-7.97 (m, 3H), 7.88 (br s, 2H), 7.82-7.74 (dd, 1H), 7.74-7.65 (m, 1H), 7.04 (dd, 1H), 6.66 (dd, 1H), 5.26-5.13 (m, 1H), 1.52 (d, 3H).

Example 172

2-((2S,4R)-1-(6-Amino-5-cyanopyrimidin-4-yl)-4-hydroxypyrrolidin-2-yl)-3-(3,5-difluorophenyl)-4-oxo-3,4-dihydropyrrolo[1,2-f][1,2,4]triazine-5-carbonitrile 2-((2S,4R)-1-(6-Amino-5-cyanopyrimidin-4-yl)-4-(benzyloxy)pyrrolidin-2-yl)-3-(3,5-difluorophenyl)-4-oxo-3,4- dihydropyrrolo[1,2-f][1,2,4]triazine-5-carbonitrile (20 mg, 0.04 mmol) was dissolved in methanol (2 ml) and 10 drops of concentrated acetic acid were added. This mixture was hydrogenated in an H-Cube apparatus (1 ml/min, 30° C., full H2) using Pd/C 10% as catalyst. Then the solvent was removed under vacuum and the product was purified by reverse phase chromatography (C-18 silica from Waters®, water/1:1 acetonitrile-methanol as eluents [0.1% v/v formic acid buffered] 0% to 100%) to obtain the title compound (7 mg, 42% yield) as a white solid.

LRMS (m/z): 476 (M+1)+.

$^1$H NMR (400 MHz, DMSO) δ 8.06 (s, 1H), 7.28 (d, 1H), 7.26-7.24 (m, 1H), 7.06 (ddd, 1H), 6.86-6.82 (m, 2H), 5.48 (s, 2H), 4.95 (t, 1H), 4.84-4.73 (m, 1H), 4.31 (dd, 1H), 4.07 (d, 1H), 2.26 (ddd, 1H), 2.18 (ddd, 1H).

Example 173

4-Amino-6-((2S,4R)-2-(5-(aminomethyl)-3-(3,5-difluorophenyl)-4-oxo-3,4-dihydropyrrolo[1,2-f][1,2,4]triazin-2-yl)-4-hydroxypyrrolidin-1-yl)pyrimidine-5-carbonitrile The title compound was obtained and isolated as a by-product of the reaction described in Example 172.

LRMS (m/z): 480 (M+1)$^+$.

$^1$H NMR (600 MHz, cdcl3) δ 8.09 (s, 1H), 7.20 (d, 1H), 7.02 (t, 2H), 6.83 (d, 1H), 6.46 (d, 1H), 5.42 (s, 2H), 4.94 (t, 1H), 4.79 (s, 1H), 4.33 (dd, 2H), 4.04 (s, 3H), 2.28-2.20 (m, 2H), 2.18-2.10 (m, 2H).

Example 174

(S)-4-Amino-6-(1-(5-(4-methyl-1H-imidazol-1-yl)-4-oxo-3-phenyl-3,4-dihydropyrrolo[1,2-f][1,2,4]triazin-2-yl)ethylamino)pyrimidine-5-carbonitrile In a sealed tube a mixture of (S)-4-amino-6-(1-(5-bromo-4-oxo-3-phenyl-3,4-dihydropyrrolo[1,2-f][1,2,4]triazin-2-yl)ethylamino)pyrimidine-5-carbonitrile (50 mg, 0.11 mmol, Example 144), 4-methyl-1H-imidazole (14 mg, 0.17 mmol), L-proline (3 mg, 0.03 mmol), copper iodide (2 mg, 0.01 mmol) and K3PO4 (59 mg, 0.28 mmol) in DMSO (2 ml) was heated at 140° C. overnight. The same amount of 4-methyl-1H-imidazole, L-proline, copper iodide and K3PO4 were added and the mixture stirred at 140° C. overnight. The crude product was purified by reverse phase chromatography (C-18 silica from Waters, water/1:1 acetonitrile-methanol as eluents 0% to 100%) to obtain the title compound (10 mg, 20% yield) as a white solid.

LRMS (m/z): 453 (M+1)$^+$.

Example 175

(S)-4-Amino-6-(1-(5-bromo-3-(3-methoxyphenyl)-4-oxo-3,4-dihydropyrrolo[1,2-f][1,2,4]triazin-2-yl)ethylamino)pyrimidine-5-carbonitrile a) (S)-2-(1-Aminoethyl)-5-bromo-3-(3-methoxyphenyl)pyrrolo[1,2-f][1,2,4]triazin-4(3H)-one This compound was prepared starting from (S)-tert-butyl 1-(5-bromo-3-(3-methoxyphenyl)-4-oxo-3,4-dihydropyrrolo[1,2-f][1,2,4]triazin-2-yl)ethylcarbamate (453 mg, 0.98 mmol) and following the experimental procedure described in Preparation 46c to afford 414 mg (99% yield) of the title compound as a dihydrochloride salt that was used in the next step without any further purification.

LRMS (m/z): 363, 365 (M+1)$^+$.

b) (S)-4-Amino-6-(1-(5-bromo-3-(3-methoxyphenyl)-4-oxo-3,4-dihydropyrrolo[1,2-f][1,2,4]triazin-2-yl)ethylamino)pyrimidine-5-carbonitrile The title compound (178 mg, 75% yield) was obtained from (S)-2-(1-aminoethyl)-5-bromo-3-(3-methoxyphenyl)pyrrolo[1,2-f][1,2,4]triazin-4(3H)-one and 4-amino-6-chloropyrimidine-5-carbonitrile following the experimental procedure described in example 18.

LRMS (m/z): 481, 483 (M+1)$^+$.

$^1$H NMR (400 MHz, DMSO) δ 7.79 (s, 0.5H), 7.77-7.70 (m, 1.5H), 7.59 (m, 1H), 7.32 (t, J=8.1 Hz, 0.5H), 7.25-7.13 (m, 2.5H), 7.05 (d, J=7.8 Hz, 0.5H), 6.88 (m, 2.5H), 6.75 (s, 1H), 5.05-4.86 (m, 1H), 3.75 (s, 1.5H), 3.66 (s, 1.5H), 1.36 (t, J=6.5 Hz, 3H).

Example 176

(S)-2-(1-(6-Amino-5-cyanopyrimidin-4-ylamino)ethyl)-4-oxo-3-(3-(trifluoromethyl)phenyl)-3,4-dihydropyrrolo[1,2-f][1,2,4]triazine-5-carbonitrile The title compound (85 mg, 71% yield) was obtained from (S)-2-(1-aminoethyl)-4-oxo-3-(3-(trifluoromethyl)phenyl)-3,4-dihydropyrrolo[1,2-f][1,2,4]triazine-5-carbonitrile and 4-amino-6-chloropyrimidine-5-carbonitrile following the experimental procedure described in example 18.

LRMS (m/z): 466 (M+1)$^+$.

$^1$H NMR (400 MHz, DMSO, 1/1 mixture of isomers) δ 8.07 (s, 0.5H), 7.95 (dd, J=2.9, 2.2 Hz, 1H), 7.90 (d, J=7.6 Hz, 0.5H), 7.76-7.64 (m, 3H), 7.60 (m, 1H), 7.57-7.50 (m, 1H), 7.24 (d, J=3.0 Hz, 1H), 7.22 (br s, 2H), 5.08-4.90 (m, 1H), 1.39 (d, J=6.6 Hz, 3H).

Example 177

(S)-4-Amino-6-(1-(5-bromo-3-(3-hydroxyphenyl)-4-oxo-3,4-dihydropyrrolo[1,2-f][1,2,4]triazin-2-yl)ethylamino)pyrimidine-5-carbonitrile To a mixture of (S)-4-amino-6-(1-(5-bromo-3-(3-methoxyphenyl)-4-oxo-3,4-dihydropyrrolo[1,2-f][1,2,4]triazin-2-yl)ethylamino)pyrimidine-5-carbonitrile (100 mg, 0.21 mmol, Example 175) in anhydrous DCM (5 ml) at 0° C., was added dropwise 1M solution of boron tribromide in DCM (623 µl, 0.62 mmol). The reaction mixture was then stirred at room temperature overnight. Ethyl acetate was added and the organic phase washed with water and brine, dried over magnesium sulphate and the solvent evaporated. The title compound (91 mg, 90% yield) was obtained as a beige solid.

LRMS (m/z): 467, 469 (M+1)$^+$.

$^1$H NMR (400 MHz, DMSO, 1/1 mixture of isomers) δ 9.67 (2s, 1H), 7.85 (2s, 1H), 7.69 (2d, J=5.6, 1H), 7.59 (t, J=6.9 Hz, 1H), 7.23 (t, J=8.0 Hz, 0.5H), 7.19 (br s, 2H), 7.07 (t, J=8.0 Hz, 0.5H), 6.86 (m, 1H), 6.81-6.67 (m, 3H), 4.96-4.75 (2q, J=6.5 Hz, 1H), 1.36 (2d, J=6.5 Hz, 3H)

Example 178

(S)-4-Amino-6-(1-(3-(3-methoxyphenyl)-4-oxo-3,4-dihydropyrrolo[1,2-f][1,2,4]triazin-2-yl)ethylamino)pyrimidine-5-carbonitrile To a mixture of (S)-4-amino-6-(1-(5-bromo-3-(3-methoxyphenyl)-4-oxo-3,4-dihydropyrrolo[1,2-f][1,2,4]triazin-2- yl)ethylamino)pyrimidine-5-carbonitrile (50 mg, 0.10 mmol, Example 175) and triethylamine (0.30 mmol) in MeOH (10 ml), was added Pd/C (10%) and the reaction mixture was hydrogenated at 4 psi for 2 h. The catalyst was filtered off and the filtrate concentrated. Ethyl acetate was added and the organic phase washed with water and brine, dried over magnesium sulphate and the solvent evaporated. The title compound (30 mg, 71% yield) was obtained as a white solid.

LRMS (m/z): 403 (M+1)$^+$.

$^1$H NMR (400 MHz, DMSO, 1/1 mixture of isomers) δ 7.77 (2s, 1H), 7.69 (dd, J=4.5, 3.1 Hz, 1H), 7.65 (dd, J=9.5, 7.3 Hz, 1H), 7.32 (t, J=8.0 Hz, 0.5H), 7.23-7.12 (m, 3H), 7.04 (d, J=7.6 Hz, 0.5H), 6.95 (dd, J=4.2, 1.5 Hz, 1H), 6.90 (m, 1H), 6.85 (m, 1H), 6.65-6.59 (m, 1H), 5.09-4.94 (m, 1H), 3.71 (2sd, 3H), 1.39 (2d, J=6.6 Hz, 3H).

Example 179

(S)-4-Amino-6-(1-(3-(3-hydroxyphenyl)-4-oxo-3,4-dihydropyrrolo[1,2-f][1,2,4]triazin-2-Aethylamino)pyrimidine-5-carbonitrile The title compound (35 mg, 82% yield) was obtained from (S)-4-amino-6-(1-(5-bromo-3-(3-hydroxyphenyl)-4-oxo-3,4-dihydropyrrolo[1,2-f][1,2,4]triazin-2-yl)ethylamino)pyrimidine-5-carbonitrile (Example 177) following the experimental procedure described in Example 178.

LRMS (m/z): 389 (M+1)$^+$.

$^1$H NMR (400 MHz, DMSO, 1/1 mixture of isomers) δ 9.66 (2s, 1H), 7.84 (2s, 1H), 7.65 (m, 2H), 7.23 (t, J=8.0 Hz, 0.5H), 7.18 (br s, 2H), 7.07 (t, J=8.0 Hz, 0.5H), 6.93 (dd, J=4.3, 1.6 Hz, 1H), 6.86 (m, 0.5H), 6.82 (dt, J=7.5, 2.0 Hz, 1H), 6.76 (m, 1H), 6.69 (m, 0.5H), 6.59 (2t, J=4.4 Hz, 1H), 5.00-4.93 (m, 0.5H), 4.92-4.85 (m, 0.5H), 1.38 (2d, J=6.6 Hz, 3H).

Example 180

(S)-2-(1-(6-Amino-5-cyanopyrimidin-4-ylamino)ethyl)-3-(3-methoxyphenyl)-4-oxo-3,4-dihydropyrrolo[1,2-f][1,2,4]triazine-5-carbonitrile The title compound (177 mg, 87% yield) was obtained from (S)-2-(1-aminoethyl)-3-(3-methoxyphenyl)-4-oxo-3,4-dihydropyrrolo[1,2-f][1,2,4]triazine-5-carbonitrile and 4-amino-6-chloropyrimidine-5-carbonitrile following the experimental procedure described in example 18.

LRMS (m/z): 428 (M+1)$^+$.

$^1$H NMR (400 MHz, DMSO, 1/1 mixture of isomers) δ 7.89 (2d, J=2.8 Hz, 1H), 7.77 (2s, 1H), 7.56 (m, 1H), 7.35 (m, 0.5H), 7.28-7.17 (m, 3.5H), 7.12-7.06 (m, 0.5H), 6.90 (m, 2.5H), 5.03 (2q, J=6.6 Hz, 1H), 3.71 (2s, 3H), 1.39 (2d, J=6.2 Hz, 3H).

Example 181

4-Amino-6-(1-(4-oxo-3-phenyl-3,4-dihydropyrrolo[1,2-f][1,2,4]triazin-2-yl)cyclopropylamino)pyrimidine-5-carbonitrile The title compound (73 mg, 36% yield) was obtained from 2-(1-aminocyclopropyl)-3-phenylpyrrolo[1,2-f][1,2,4]triazin-4(3H)-one and 4-amino-6-chloropyrimidine-5-carbonitrile following the experimental procedure described in example 23 but using n-butanol as solvent and heating the reaction mixture at 120° C. during 15 hours.

LRMS (m/z): 385 (M+1)$^+$.

$^1$H NMR (400 MHz, DMSO) δ 7.99 (s, 1H), 7.68 (s, 1H), 7.59-7.45 (m, 3H), 7.39-7.15 (m, 4H), 6.90 (dd, 1H), 6.58 (dd, 1H), 5.38 (dd, 1H), 1.83-1.69 (m, 2H), 1.15-1.03 (m, 2H).

Example 182

2-(1-(9H-Purin-6-ylamino)cyclopropyl)-3-phenylpyrrolo[1,2-f][1,2,4]triazin-4(3H)-one The title compound (18 mg, 9% yield) was obtained from 2-(1-aminocyclopropyl)-3-phenylpyrrolo[1,2-f][1,2,4]triazin-4(3H)-one and 6-bromo-9H-purine following the experimental procedure described in example 20 but using n-butanol as solvent and heating the reaction mixture at 120° C. during 15 hours.

LRMS (m/z): 385 (M+1)$^+$.

$^1$H NMR (400 MHz, DMSO) δ 12.96 (s, 1H), 8.17 (s, 1H), 8.06 (s, 1H), 7.71 (s, 1H), 7.53-7.31 (m, 3H), 7.20-7.02 (m, 2H), 6.90 (dd, 1H), 6.60 (dd, 1H), 5.91 (dd, 1H), 1.87-1.75 (m, 2H), 1.16-1.05 (m, 2H).

Example 183

(S)-4-Amino-6-(1-(4-oxo-3-(3-(trifluoromethyl)phenyl)-3,4-dihydropyrrolo[1,2-f][1,2,4]triazin-2-yl)ethylamino)pyrimidine-5-carbonitrile The title compound (35 mg, 82% yield) was obtained from (S)-4-amino-6-(1-(5-bromo-4-oxo-3-(3-(trifluoromethyl)phenyl)-3,4-dihydropyrrolo[1,2-f][1,2,4]triazin-2-yl)ethylamino)pyrimidine-5-carbonitrile (Example 169) following the experimental procedure described in Example 178.

LRMS (m/z): 441 (1M+1)$^+$.

$^1$H NMR (600 MHz, DMSO, 1/1 mixture of isomers) δ 8.06 (s, 0.5H), 7.88 (d, J=7.8 Hz, 0.5H), 7.76 (m, 1H), 7.71-7.55 (m, 4.5H), 7.48 (t, J=7.9 Hz, 0.5H), 7.20 (br s, 2H), 6.98 (m, 1H), 6.65 (m, 1H), 5.09-5.02 (p, J=6.6 Hz, 0.5H), 4.99 (p, J=6.6 Hz, 0.5H), 1.42-1.33 (m, 3H).

Example 184

(S)-2-(1-(6-Amino-5-cyanopyrimidin-4-ylamino)ethyl)-3-(3-hydroxyphenyl)-4-oxo-3,4-dihydropyrrolo[1,2-f][1,2,4]triazine-5-carbonitrile The title compound (25 mg, 17% yield) was obtained from (S)-2-(1-(6-amino-5-cyanopyrimidin-4-ylamino)ethyl)-3-(3-methoxyphenyl)-4-oxo-3,4-dihydropyrrolo[1,2-f][1,2,4]triazine-5-carbonitrile (Example 180) following the experimental procedure described in example 177.

LRMS (m/z): 414 (M+1)$^+$.

$^1$H NMR (400 MHz, DMSO, 1/1 mixture of isomers) δ 9.73 (2s, 1H), 7.85 (m, 2H), 7.64-7.54 (m, 1H), 7.29-7.06 (m, 4H), 6.91 (m, 1H), 6.85-6.69 (m, 2H), 5.05-4.84 (m, 1H), 1.39 (m, 3H).

Following a similar procedure to that described above, the following compounds were obtained:

Example 185

(S)-2-(1-(9H-Purin-6-ylamino)ethyl)-3-(pyridin-2-yl)pyrrolo[1,2-f][1,2,4]triazin-4(3H)-one

Example 186

(S)-2-(1-(9H-Purin-6-ylamino)propyl)-3-phenylimidazo[1,2-f][1,2,4]triazin-4(3H)-one

Example 187

(S)-4-Amino-6-(1-(4-oxo-3-phenyl-3,4-dihydroimidazo[1,2-f][1,2,4]triazin-2-yl)propylamino)pyrimidine-5-carbonitrile References
1.—Tehrani, A. K.; Borremans D.; De Kimpe N. *Tetrahedron* 1999, 55, 4133-4152
2.—Ohta, T.; Fukuda, T.; Ishibashi, F., Iwao, M. *J. Org. Chem.* 2009, 74, 8143-8153
3.—Leroy, J.; Porthiel, E.; Bondon, A. *Tetrahedron* 2002, 58, 6713-6722

Pharmacological Activity

PI3K α, β, δ and γ Enzymatic Inhibition Assays

Compounds were screened for their ability to inhibit PI3Kα (PI3Kα), PI3Kβ (PI3 Kb), PI3Kδ (PI3 Kd) and PI3Kγ (PI3 Kg) using a cell-free based PI3K HTRF™ assay (Millipore, ref. #33-017) All reagents to perform the reactions were prepared according to the manufacturer protocol. All PI3K enzymes were recombinant and were purchased at Millipore.

All four assays were performed according to the following procedure:
1) Dilution curves of compounds were done in 100% DMSO and dispensed in a reservoir plate, typically from column 2 to 11. Column 1 and 12 were used for the negative controls (100% inhibition using a reference PI3K inhibitor for the four isoforms) and the positive controls (0% inhibition using dimethyl sulfoxide (DMSO) only).
2) Mix of Phosphoinositide 3-kinase (PI3K)+Phosphatidylinositol 4,5-bisphosphate (PIP2) was diluted in buffer (supplied with the kit) and plated in a medium binding black 96-well plate (Greiner ref. #675076) PI3Ka was diluted at 0.25 nM with PIP2 at 2 μM; PI3 Kb was diluted at 0.50 nM with PIP2 at 5 μM; PI3 Kd was diluted at 0.60 nM with PIP2 at 2 μM and PI3 Kg was diluted at 0.30 nM with PIP2 at 10 μM. These concentrations were final in the assay.
3) A reservoir plate containing Adenosine TriPhosphate (ATP) diluted in the Millipore kit buffer was prepared for each isoform. The final concentration of ATP in the assay was 10 μM, 15 μM, 20 μM and 10 μM for PI3Ka, PI3 Kb, PI3 Kd and PI3 Kg respectively.
4) Reactions were started by addition to the PI3+PIP2 plates of the ATP and compounds simultaneously. Incubation was done for 8 minutes (for all four isoforms) then the reaction was stopped by addition of the Stop solution. The Detection solution was added. These solutions were prepared previously according to the kit specifications. The plates were then incubated overnight at RT before reading the signal in an Envision (PerkinElmer), with excitation at 340 nm and emissions at 620 and 665 nm.
5) Data obtained from the compound curves were normalized in respect to the negative and positive controls, and then fitted by a 4-parameter log curve in ActivityBase (IDBS) in order to determine their potency.

The results are shown in Table 1.

| Example | IC$_{50}$ PI3Kd HTRF (nM) |
| --- | --- |
| 1 | 120 |
| 11 | 119 |
| 15 | 18 |
| 17 | 9 |
| 20 | 11 |
| 21 | 5 |
| 23 | 4 |
| 25 | 347 |
| 29 | 376 |
| 31 | 6566 |
| 37 | 15 |
| 43 | 11 |
| 44 | 29 |
| 47 | 1 |
| 50 | 57 |
| 54 | 60 |
| 56 | 15 |
| 61 | 6 |
| 62 | 73 |
| 64 | 69 |
| 68 | 1 |
| 71 | 9 |
| 73 | 31 |
| 75 | 17 |
| 81 | 9 |
| 90 | 7 |
| 102 | 42 |
| 104 | 36 |
| 122 | 2928 |
| 124 | 11 |
| 125 | 90 |
| 127 | 89 |
| 129 | 38 |
| 133 | 11 |
| 136 | 24 |
| 138 | 8 |
| 142 | 5 |
| 144 | 1 |
| 152 | 747 |
| 157 | 66 |
| 158 | 43 |
| 159 | 35 |
| 164 | 67 |
| 165 | 670 |
| 169 | 6 |
| 176 | 32 |
| 179 | 7 |

It can be seen from Table 1 that the compounds of formula (I) are potent inhibitors of Phosphoinositide 3-kinase delta (PI3 kd). Preferred compounds of the invention possess an IC$_{50}$ value for the inhibition of PI3 Kd (determined as defined above) of less than 10 μM (10,000 nM), preferably less than 1 μM (1,000 nM), even more preferably of less than 0.2 μM (200 nM), most preferably less than 0.05 μM (50 nM)

The invention is also directed to a compound of the invention as described herein for use in the treatment of the human or animal body by therapy. Compounds of the invention intended for pharmaceutical use may be administered as crystalline or amorphous products, or mixtures thereof. They may be obtained, for example, as solid plugs, powders, or films by methods such as precipitation, crystallization, freeze drying, spray drying, or evaporative drying. Microwave or radio frequency drying may be used for this purpose.

Combinations

The pyrrolotriazinone derivatives defined herein may also be combined with other active compounds in the treatment of a pathological condition or disease susceptible to amelioration by inhibition of PI3Ks.

The combinations of the invention can optionally comprise one or more additional active substances which are known to be useful in the treatment of respiratory diseases; allergic diseases; inflammatory or autoimmune-mediated diseases; function disorders and neurological disorders; cardiovascular diseases; viral infection; metabolism/endocrine function disorders; neurological disorders and pain; bone marrow and organ transplant rejection; myelo-dysplastic syndrome; myeloproliferative disorders (MPDs); cancer and hematologic malignancies, leukemia, lymphomas and solid tumors.

Particularly, the combinations of the invention can optionally comprise one or more additional active substances which are known to be useful in the treatment of neoplastic diseases (e.g. leukemia, lymphomas, solid tumors); transplant rejection, bone marrow transplant applications (e.g., graft—versus-host disease); autoimmune diseases (e.g. rheumatoid arthritis, multiple sclerosis, amyotrophic lateral sclerosis, Crohn's disease, ulcerative colitis, systemic lupus erythematosis, autoimmune hemolytic anemia, type I diabetes, cutaneous vasculitis, cutaneous lupus erythematosus, dermatomyositis and blistering diseases including but not limited to pemphigus vulgaris, bullous pemphigoid and epidermolysis bullosa; respiratory inflammation diseases (e.g. asthma, chronic obstructive pulmonary disease, cystic fibrosis, idiopathic pulmonary fibrosis, sarcoidosis); skin inflammatory diseases (e.g., atopic dermatitis, contact dermatitis, eczema or psoriasis); premalignant and malignant skin conditions (e.g. basal cell carcinoma (BCC), squamous cell carcinoma (SCC) or actinic keratosis (AK)); neurological disorders and pain (such as pain associated with rheumatoid arthritis or osteoarthritis, back pain, general inflammatory pain, inflammatory neuropathic pain, trigeminal neuralgia or central pain).

Preferably, the combinations of the invention can optionally comprise one or more additional active substances which are known to be useful in the treatment of neoplastic diseases leukemia, lymphomas and solid tumors, rheumatoid arthritis, multiple sclerosis, amyotrophic lateral sclerosis, Crohn's disease, ulcerative colitis, systemic lupus erythematosis, autoimmune hemolytic anemia, type I diabetes, type I diabetes, cutaneous vasculitis, cutaneous lupus erythematosus, dermatomyositis, blistering diseases including but not limited to pemphigus vulgaris, bullous pemphigoid and epidermolysis bullosa, chronic obstructive pulmonary disease, cystic fibrosis, idiopathic pulmonary fibrosis, sarcoidosis, allergic rhinitis, atopic dermatitis, contact dermatitis, eczema, psoriasis, basal cell carcinoma, squamous cell carcinoma and actinic keratosis.

In particular, the combinations of the invention can optionally comprise one or more additional active substances which are known to be useful in the treatment of neoplastic diseases leukemia, lymphomas and solid tumors, rheumatoid arthritis, multiple sclerosis, amyotrophic lateral sclerosis, Crohn's disease, ulcerative colitis, systemic lupus erythematosis, autoimmune hemolytic anemia, type I diabetes, type I diabetes, asthma, chronic obstructive pulmonary disease, cystic fibrosis, idiopathic pulmonary fibrosis, sarcoidosis, allergic rhinitis, atopic dermatitis, contact dermatitis, eczema, psoriasis, basal cell carcinoma, squamous cell carcinoma and actinic keratosis The combinations of the invention comprise (i) a compound of the invention as defined above; and (ii) another compound selected from the group consisting of an Adenoside $A_{2A}$ agonist, an agent for treating cardiovascular disorders, an agent for treating diabetes, and an agent for treating liver disease, an anti-allergic agent, an anti-cholinergic agent, an anti-inflammatory agent, an anti-infective agent, a β2-adrenergic agonist, a Chemoattractant receptor homologous molecule expressed on $TH_2$ cells (CRTH2) inhibitor, a chemotherapeutic agent, a corticosteroid, an IKKβ/IKBKB (IkB kinase beta or IKK2) inhibitor, an immunosuppressant, a Janus kinase (JAK) inhibitor, a topically acting p38 Mitogen-Activated Protein Kinase (p38 MAPK) inhibitor, a Phosphosdiesterase (PDE) IV inhibitor, and a Spleen tyrosine kinase (Syk) inhibitor, for simultaneous, separate or sequential use in the treatment of the human or animal body.

In a particular embodiment, the combinations of the invention can optionally comprise one or more additional active substances selected from a) Dyhydrofolate reductase inhibitors, such as Methotrexate or CH-1504;

b) Dihydroorotate dehydrogenase (DHODH) inhibitors such as leflunomide, teriflunomide, or the compounds described in the International Patent Application Nos. WO2008/077639 and WO2009/021696;

c) Immunomodulators such as Glatiramer acetate (Copaxone), Laquinimod or Imiquimod;

d) Inhibitors of DNA synthesis and repair, such as Mitoxantrone or Cladribine;

e) Immunosuppressants, such as Imuran (azathioprine) or Purinethol (6-mercaptopurine or 6-MP);

f) Anti-alpha 4 integrin antibodies, such as Natalizumab (Tysabri);

g) Alpha 4 integrin antagonists such as R-1295, TBC-4746, CDP-323, ELND-002, Firategrast or TMC-2003;

h) Corticoids and glucocorticoids such as prednisone or methylprednisolone, fluticasone, mometasone, budesonide, ciclesonide or beta-metasone;

i) Fumaric acid esters, such as BG-12;

j) Anti-tumor necrosis factor-alpha (Anti-TNF-alpha) monoclonal antibodies such as Infliximab, Adalimumab or Certolizumab pegol;

k) Soluble Tumor necrosis factor-alpha (TNF-alpha) Antagonists such as Ethanercept;

l) Anti-CD20 (lymphocyte protein) monoclonal antibodies such as Rituximab, Ocrelizumab Ofatumumab or TRU-015;

m) Anti-CD52 (lymphocyte protein) monoclonal antibodies such as alemtuzumab;

n) Anti-CD25 (lymphocyte protein) such as daclizumab;

o) Anti-CD88 (lymphocyte protein), such as eculizumab or pexilizumab;

p) Anti-Interleukin 6 Receptor (IL-6R), such as tocilizumab;

q) Anti-Interleukin 12 Receptor (IL-12R)/Interleukin 23 Receptor (IL-23R), such as ustekinumab;

r) Calcineurin inhibitors such as cyclosporine A or tacrolimus;

s) Inosine-monophosphate dehydrogenase (IMPDH) inhibitors, such as mycophenolate mophetyl, ribavirin, mizoribine or mycophenolic acid;

t) Cannabinoid receptor agonists such as Sativex;

u) Chemokine CCR1 antagonists such as MLN-3897 or PS-031291;

v) Chemokine CCR2 antagonists such as INCB-8696;

w) Necrosis factor-kappaB (NF-kappaB or NFKB) Activation Inhibitors such as Sulfasalazine, Iguratimod or MLN-0415;

x) Adenosine $A_{2A}$ agonists, such as ATL-313, ATL-146e, CGS-21680, Regadenoson or UK-432,097;

y) Sphingosine-1 (S1P) phosphate receptor agonists such as fingolimod, BAF-312, or ACT128800;

z) Sphingosine-1 (S1P) liase inhibitors such as LX2931;

aa) Spleen tyrosine kinase (Syk) inhibitors, such as R-112;

bb) Protein Kinase Inhibitors (PKC) inhibitors, such as NVP-AEB071;
cc) Anti-cholinergic agents such as tiotropium or aclidinium;
dd) Beta adrenergic agonists such as formoterol, indacaterol or LAS100977 (abediterol);
ee) MABA (molecules with dual activity: beta-adrenergic agonists and muscarinic receptor antagonists)
ff) Histamine 1 (H1) receptor antagonists, such as azelastine or ebastine;
gg) Cysteinyl leukotriene (CysLT) receptor antagonists, such as montelukast;
hh) Mast cell stabilizers, such as nedocromil or chromoglycate;
ii) 5-lipoxygenase-activating protein (FLAP) inhibitors, such as MK886 or BAY X 1005;
jj) 5-lipoxygenase (5-LO) inhibitors, such as WY-50295T;
kk) Chemoattractant receptor homologous molecule expressed on $TH_2$ cells (CRTH2) inhibitors, such as OC-459, AZD-1981, ACT-129968, QAV-680;
ll) Vitamin D derivatives like calcipotriol (Daivonex);
mm) Anti-inflammatory agents, such as non-steroidal anti-inflammatory drugs (NSAIDs) or selective cyclooxygenase-2 (COX-2) inhibitors such as aceclofenac, diclofenac, ibuprofen, naproxen, apricoxib, celecoxib, cimicoxib, deracoxib, etoricoxib, lumiracoxib, parecoxib sodium, rofecoxib, selenocoxib-1 or valdecoxib;
nn) Anti-allergic agents;
oo) Anti-viral agents;
pp) Phosphodiestearase (PDE) III inhibitors;
qq) Phosphosdiesterase (PDE) IV inhibitors such as roflumilast or GRC-4039;
rr) Dual Phosphodiestearase (PDE) III/IV inhibitors;
ss) Xanthine derivatives, such as theophylline or theobromine;
tt) p38 Mitogen-Activated Protein Kinase (p38 MAPK) Inhibitors such as ARRY-797;
uu) Mitogen-activated extracellular signal regulated kinase kinase (MEK) inhibitor, such as ARRY-142886 or ARRY-438162;
vv) Janus kinase (JAK) inhibitors, such as tofacitinib (previously known as tasocitinib or CP-690,550) from Pfizer and INCB-18424, from Incyte;
ww) Interferons comprising Interferon beta 1a such as Avonex from Biogen Idec, CinnoVex from CinnaGen and Rebif from EMD Serono, and Interferon beta 1b such as Betaferon from Schering and Betaseron from Berlex;
xx) Interferon alpha such as Sumiferon MP;
YY) Epidermal Growth Factor Receptor (EGFR) inhibitors such as erlotinib, Trastuzumab, Herceptin, Avastin, Platins (cisplatin, carboplatin) or Temazolamide;
zz) Antineoplastic agents such as Docetaxel, Estramustine, Anthracyc lines, (doxorubicin (Adriamycin), epirubicin (Ellence), and liposomal doxorubicin (Doxil)), Taxanes (docetaxel (Taxotere), paclitaxel (Taxol), and protein-bound paclitaxel (Abraxane)), Cyclophosphamide (Cytoxan), Capecitabine (Xeloda), 5 fluorouracil (5 FU), Gemcitabine (Gemzar) or Vinorelbine (Navelbine);

Specific examples of suitable corticoids and glucocorticoids that can be combined with the PI3K inhibitors of the present invention are prednisolone, methylprednisolone, dexamethasone, dexamethasone cipecilate, naflocort, deflazacort, halopredone acetate, budesonide, beclomethasone dipropionate, hydrocortisone, triamcinolone acetonide, fluocinolone acetonide, fluocinonide, clocortolone pivalate, methylprednisolone aceponate, dexamethasone palmitoate, tipredane, hydrocortisone aceponate, prednicarbate, alclometasone dipropionate, halometasone, methylprednisolone suleptanate, mometasone furoate, rimexolone, prednisolone farnesylate, ciclesonide, butixocort propionate, RPR-106541, deprodone propionate, fluticasone propionate, fluticasone furoate, halobetasol propionate, loteprednol etabonate, betamethasone butyrate propionate, flunisolide, prednisone, dexamethasone sodium phosphate, triamcinolone, betamethasone 17-valerate, betamethasone, betamethasone dipropionate, hydrocortisone acetate, hydrocortisone sodium succinate, prednisolone sodium phosphate and hydrocortisone probutate.

Specific examples of suitable Syk kinase inhibitors that can be combined with the PI3K inhibitors of the present invention are fosfamatinib (from Rigel), R-348 (from Rigel), R-343 (from Rigel), R-112 (from Rigel), piceatannol, 2-(2-Aminoethylamino)-4-[3-(trifluoromethyl)phenylamino]pyrimidine-5-carboxamide, R-091 (from Rigel), 6-[5-Fluoro-2-(3,4,5-trimethoxyphenylamino)pyrimidin-4-ylamino]-2,2-dimethyl-3,4-dihydro-2H-pyrido[3,2-b][1,4]oxazin-3-one benzenesulfonate (R-406 from Rigel), 1-(2,4,6-Trihydroxyphenyl)-2-(4-methoxyphenyl)ethan-1-one, N-[4-[6-(Cyclobutylamino)-9H-purin-2-ylamino]phenyl]-N-methylacetamide (QAB-205 from Novartis), 2-[7-(3,4-Dimethoxyphenyl)imidazo[1,2-c]pyrimidin-5-ylamino]pyridine-3-carboxamide dihydrochloride (BAY-61-3606 from Bayer) and AVE-0950 (from Sanofi-Aventis).

Specific examples of suitable M3 antagonists (anticholinergics) that can be combined with the PI3K inhibitors of the present invention are tiotropium salts, oxitropium salts, flutropium salts, ipratropium salts, glycopyrronium salts, trospium salts, zamifenacin, revatropate, espatropate, darotropium bromide, CI-923, NPC-14695, BEA-2108, 3-[2-Hydroxy-2,2-bis(2-thienyl)acetoxy]-1-(3-phenoxypropyl)-1-azoniabicyclo[2.2.2]octane salts (in particular aclidinium salts, more preferably aclidinium bromide), 1-(2-Phenylethyl)-3-(9H-xanthen-9-ylcarbonyloxy)-1-azoniabicyclo[2.2.2]octane salts, 2-oxo-1,2,3,4-tetrahydroquinazoline-3-carboxylic acid endo-8-methyl-8-azabicyclo[3.2.1]oct-3-yl ester salts (DAU-5884), 3-(4-Benzylpiperazin-1-yl)-1-cyclobutyl-1-hydroxy-1-phenylpropan-2-one (NPC-14695), N-[1-(6-Aminopyridin-2-ylmethyl)piperidin-4-yl]-2(R)-[3,3-difluoro-1(R)-cyclopentyl]-2-hydroxy-2-phenylacetamide (J-104135), 2(R)-Cyclopentyl-2-hydroxy-N-[1-[4(S)-methylhexyl]piperidin-4-yl]-2-phenylacetamide (J-106366), 2(R)-Cyclopentyl-2-hydroxy-N-[1-(4-methyl-3-pentenyl)-4-piperidinyl]-2-phenylacetamide (J-104129), 1-[4-(2-Aminoethyl)piperidin-1-yl]-2(R)-[3,3-difluorocyclopent-1(R)-yl]-2-hydroxy-2-phenylethan-1-one (Banyu-280634), N—[N-[2-[N-[1-(Cyclohexylmethyl)piperidin-3(R)-ylmethyl]carbamoyl]ethyl]carbamoylmethyl]-3,3,3-triphenylpropionamide (Banyu CPTP), 2(R)-Cyclopentyl-2-hydroxy-2-phenylacetic acid 4-(3-azabicyclo[3.1.0]hex-3-yl)-2-butynyl ester (Ranbaxy 364057), 3(R)-[4,4-Bis(4-fluorophenyl)-2-oxoimidazolidin-1-yl]-1-methyl-1s-[2-oxo-2-(3-thienyl)ethyl]pyrrolidinium iodide, N-[1-(3-Hydroxybenzyl)-1-methylpiperidinium-3(S)-yl]-N-[N-[4-(isopropoxycarbonyl)phenyl]carbamoyl]-tyrosinamide trifluoroacetate, UCB-101333, Merck's OrM3, 7-endo-(2-hydroxy-2,2-diphenylacetoxy)-9,9-dimethyl-3-oxa-9-azoniatricyclo[3.3.1.0(2,4)]nonane salts, 3(R)-[4,4-Bis(4-fluorophenyl)-2-oxoimidazolidin-1-yl]-1-methyl-1-(2-phenylethyl)pyrrolidinium iodide, trans-4-[2-[Hydroxy-2,2-(dithien-2-yl)acetoxy]-1-methyl-1-(2-phenoxyethyl) piperidinium bromide from Novartis (412682), 7-(2,2-diphenylpropionyloxy)-7,9,9-trimethyl-3-oxa-9-azoniatricyclo[3.3.1.0*2,4*]nonane salts, 7-hydroxy-7,9,9- trimethyl-3-oxa-9-azoniatricyclo[3.3.1.0*2,4*]nonane 9-methyl-9H-fluorene-9-carboxylic acid ester salts, all of them optionally in the form of their racemates, their enantiomers, their diastereomers and mixtures thereof, and optionally in the form of their pharmacologically-compatible acid addition salts. Among the salts chlorides, bromides, iodides and methanesulphonates are preferred.

Specific examples of suitable beta adrenergic agonists (β2-agonists) that can be combined with the PI3K inhibitors of the present invention are terbutaline sulphate, eformoterol fumarate, formoterol fumarate, bambuterol, ibuterol, isoprenaline hydrochloride, dopexamine, metaprotenerol, tulobuterol, procaterol hydrochloride, sibenadet hydrochloride, mabuterol hydrochloride, albuterol sulphate, salbutamol sulphate, salmefamol, salmeterol xinafoate, carmoterol hydrochloride, (R)-albuterol hydrochloride, Levalbuterol hydrochloride; Levosalbutamol hydrochloride; (−)-Salbutamol hydrochloride, formoterol, (R,R)-Formoterol tartrate; Arformoterol tartrate, sulfonterol, Bedoradrine sulphate, Indacaterol, Trantinterol hydrochloride, Milveterol hydrochloride, Olodaterol, fenoterol hydrobromide, rimoterol hydrobromide, riproterol hydrochloride, Vilanterol broxaterol, pirbuterol hydrochloride, bitolterol mesylate, clenbuterol hydrochloride, AZD-3199, GSK-159802; GSK-597901, GSK-678007, GSK-961081; 4-[2-[3-(1H-Benzimidazol-1-yl)-1,1-dimethylpropylamino]-1-hydroxyethyl]-2-(4-methoxybenzylamino)phenol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl-]-2-[3-(4-domethoxyphenyl)-2-methyl-2-propylamino]ethanol, 1-[2H-5-hydroxy-3-oxo-4H-1,4-benzoxazin-8-yl]-2-[3-(4-n-butyloxyhenyl)-2-methyl-2-propylamino]ethanol, KUL-1248, HOKU-81, SM-110444, RP-58802B, LAS100977 (abediterol) and compounds described in PCT patent applications Nos. WO 2007/124898, WO 2006/122788A1, WO 2008/046598, WO 2008095720, WO 2009/068177 and WO 2010/072354.

Specific examples of suitable anti-allergic agents that can be combined with the PI3K inhibitors of the present invention are anti-histamines (e.g. Methapyrilene, Mequitazine, Azelastine hydrochloride, Acrivastine, Emedastine difumarate, Emedastine fumarate, Loratadine, Cyproheptadine hydrochloride, Diphenhydramine hydrochloride, Doxepin hydrochloride, Promethazine hydrochloride, Levocabastine hydrochloride, Desloratadine, Cinnarizine, Setastine hydrochloride, Mizolastine, Ebastine, Cetirizine hydrochloride, Epinastine hydrochloride, Olopatadine hydrochloride, Bepotastine besilate, Triprolidine hydrochloride, Rupatadine fumarate, Fexofenadine hydrochloride, Levocetirizine dihydrochloride, Ketotifen, Azatadine maleate, Dimethindene maleate, Clemastine fumarate, Alcaftadine, Bilastine, Vapitadine hydrochloride, AZD-1744, GSK-1004723D, GSK-835726 or SUN-1334H.

Specific examples of suitable Phosphosdiesterase IV (PDE IV) inhibitors that can be combined with the PI3K inhibitors of the present invention are benafentrine dimaleate, etazolate, denbufylline, rolipram, cipamfylline, zardaverine, arofylline, filaminast, tipelukast, tofimilast, piclamilast, tolafentrine, mesopram, drotaverine hydrochloride, lirimilast, roflumilast, cilomilast, oglemilast, apremilast, tetomilast, filaminast, (R)-(+)-4-[2-(3-Cyclopentyloxy-4-methoxyphenyl)-2-phenylethyl]pyridine (CDP-840), N-(3,5-Dichloro-4-pyridinyl)-2-[1-(4-fluorobenzyl)-5-hydroxy-1H-indol-3-yl]-2-oxoacetamide (GSK-842470), 9-(2-Fluorobenzyl)-N-6-methyl-2-(trifluoromethyl)adenine (NCS-613), N-(3,5-Dichloro-4-pyridinyl)-8-methoxyquinoline-5-carboxamide (D-4418), 3-[3-(Cyclopentyloxy)-4-methoxybenzyl]-6-(ethylamino)-8-isopropyl-3H-purine hydrochloride (V-11294A), 6-[3-(N,N-Dimethylcarbamoyl)phenylsulfonyl]-4-(3-methoxyphenylamino)-8-methylquinoline-3-carboxamide hydrochloride (GSK-256066), 4-[6,7-Diethoxy-2,3-bis(hydroxymethyl)naphthalen-1-yl]-1-(2-methoxyethyl)pyridin-2(1H)-one (T-440), (−)-trans-2-[3'-[3-(N-Cyclopropylcarbamoyl)-4-oxo-1,4-dihydro-1,8-naphthyridin-1-yl]-3-fluorobiphenyl-4-yl]cyclopropanecarboxylic acid, MK-0873, CDC-801, UK-500001, BLX-914, 2-carbomethoxy-4-cyano-4-(3-cyclopropylmethoxy-4-difluororomethoxyphenyl)cyclohexan1-one, cis [4-cyano-4-(3-cyclopropylmethoxy-4-difluoromethoxyphenyl)cyclohexan-1-ol, 5(S)-[3-(Cyclopentyloxy)-4-methoxyphenyl]-3(S)-(3-methylbenzyl)piperidin-2-one (IPL-455903), ONO-6126 (Eur Respir J 2003, 22(Suppl. 45): Abst 2557) and the compounds claimed in the PCT patent applications number WO 03/097613, WO 2004/058729, WO 2005/049581, WO 2005/123693, WO 2005/123692, and WO 2010/069504.

Specific examples of suitable immunosupressants that can be combined with the PI3K inhibitors of the present invention are picremolimus, tacrolimus, cyclosporine A, leflunomide, teriflunomide, vidofludimus, laquinimod, methotrexate, 5-fluorouracil (5-FU), anti-TNF agents and compounds described in PCT patent applications Nos. WO 2008/077639, WO 2009/021696, WO 2009/153043, and WO2010083975 (in particular amino(iso)nicotinic acid derivatives selected from the group consisting of 2-(3'-ethoxy-3-(trifluoromethoxy)biphenyl-4-ylamino)nicotinic acid, 2-(3,5-difluoro-3'-methoxybiphenyl-4-ylamino)nicotinic acid and 2-(3,5-difluoro-2-methylbiphenyl-4-ylamino)nicotinic acid; and azabiphenylaminobenzoic acid derivatives selected from the group consisting of 5-cyclopropyl-2-(2-(2,6-difluorophenyl)pyrimidin-5-ylamino)benzoic acid, 5-cyclopropyl-2-((2-(2-(trifluoromethyl)phenyl)pyrimidin-5-yl)amino)benzoic acid and 5-methyl-2-((6-(2,3-difluorophenyl)pyridin-3-yl)amino)benzoic acid)

Specific examples of suitable anti-infectives that can be combined with the PI3K inhibitors of the present invention are aclarubicin, actinomycin D, amrubicin, annamycin, adhamycin, bleomycin, daunorubicin, doxorubicin, elsamitrucin, epirubicin, galarubicin, idarubicin, mitomycin C, mupiricin, nemorubicin, neocarzinostatin, peplomycin, pirarubicin, rebeccamycin, retapamulin, stimalamer, streptozocin, valrubicin, zinostatin, amphotericin B, bifonazole, caspofungin, clotrimazole, echinocandin B, econazole, fluconazole, flucytosine, itraconazole, ketoconazole, miconazole, posaconazole, ravuconazole, terbinafine, tioconazole, voriconazole and combinations thereof.

Particularly preferred combination products according to the invention comprise a compound of formula (I) and a therapeutically effective amount of one or more additional therapeutic agents selected from the group consisting of mometasone furoate, ciclesonide, budesonide, fluticasone propionate, fluticasone furoate, betamethasone valerate, clobetasol propionate, tiotropium salts, glycopyrronium salts, 3-[2-Hydroxy-2,2-bis(2-thienyl)acetoxy]-1-(3-phenoxypropyl)-1-azoniabicyclo[2.2.2]octane salts (in particular aclidinium salts, preferably aclidinium bromide), 1-(2-Phenylethyl)-3-(9H-xanthen-9-ylcarbonyloxy)-1-azoniabicyclo[2.2.2]octane salts, formoterol, salmeterol, indacaterol, carmoterol, LAS 100977 (abediterol), compounds described in PCT patent applications Nos. WO 2008/077639, WO 2009/021696, WO 2009/153043, and WO 2010/083975 (in particular amino(iso)nicotinic acid derivatives selected from the group consisting of 2-(3'-ethoxy-3-(trifluoromethoxy)biphenyl-4-ylamino)nicotinic acid, 2-(3,5-difluoro-3'-methoxybiphenyl-4-ylamino)nicotinic acid and 2-(3,5-difluoro-2-methylbiphenyl-4-ylamino)nicotinic acid; and azabiphenylaminobenzoic acid derivatives selected from the group consisting of 5-cyclopropyl-2-(2-(2,6-difluorophenyl) pyrimidin-5-ylamino)benzoic acid, 5-cyclopropyl-2-((2-(2-(trifluoromethyl)phenyl)pyrimidin-5-yl)amino)benzoic acid and 5-methyl-2((6-(2,3-difluorophenyl)pyridin-3-yl)amino) benzoic acid), methapyrilene, cetirizine, loratadine, ebastine, desloratadine, fexofenadine, azelastine, levocabastine, olopatadine, Montelukast, picremolimus, tacrolimus, mupiricin, retapamulin, clotrimazole, ketoconazole and terbinafine.

The compounds of formula (I) and the combinations of the invention may be used in the treatment of respiratory diseases; allergic diseases; inflammatory or autoimmune-mediated diseases; function disorders and neurological disorders; cardiovascular diseases; viral infection; metabolism/endocrine function disorders; neurological disorders and pain; bone marrow and organ transplant rejection; myelo-dysplastic syndrome; myeloproliferative disorders (MPDs such as polycythemia vera, essential thrombocythemia or mielofibrosis); cancer and hematologic malignancies, leukemia, lymphomas and solid tumors, wherein the use of a PI3K inhibitor is expected to have a beneficial effect, for example leukemia, lymphomas and solid tumors, rheumatoid arthritis, multiple sclerosis, amyotrophic lateral sclerosis, Crohn's disease, ulcerative colitis, systemic lupus erythematosis, autoimmune hemolytic anemia, type I diabetes, cutaneous vasculitis, cutaneous lupus erythematosus, dermatomyositis, blistering diseases including but not limited to pemphigus vulgaris, bullous pemphigoid and epidermolysis bullosa, asthma, chronic obstructive pulmonary disease, cystic fibrosis, idiopathic pulmonary fibrosis, sarcoidosis, allergic rhinitis, atopic dermatitis, contact dermatitis, eczema, psoriasis, basal cell carcinoma, squamous cell carcinoma and actinic keratosis.

In particular the pathological condition or disease is selected from leukemia, lymphomas and solid tumors, rheumatoid arthritis, multiple sclerosis, amyotrophic lateral sclerosis, Crohn's disease, ulcerative colitis, systemic lupus erythematosis, autoimmune hemolytic anemia, type I diabetes, asthma, chronic obstructive pulmonary disease, cystic fibrosis, idiopathic pulmonary fibrosis, sarcoidosis, allergic rhinitis, atopic dermatitis, contact dermatitis, eczema, psoriasis, basal cell carcinoma, squamous cell carcinoma and actinic keratosis.

The active compounds in the combination product may be administered together in the same pharmaceutical composition or in different compositions intended for separate, simultaneous, concomitant or sequential administration by the same or a different route.

It is contemplated that all active agents would be administered at the same time, or very close in time. Alternatively, one or two actives could be administered in the morning and the other (s) later in the day. Or in another scenario, one or two actives could be administered twice daily and the other (s) once daily, either at the same time as one of the twice-a-day dosing occurred, or separately. Preferably at least two, and more preferably all, of the actives would be administered together at the same time. Preferably, at least two, and more preferably all actives would be administered as an admixture.

The invention is also directed to a combination product of the compounds of the invention together with one or more other therapeutic agents for use in the treatment of a pathological condition or disease susceptible to amelioration by inhibiton of Phosphoinositide 3-Kinases (PI3Ks), in particular wherein the pathological condition or disease is selected from respiratory diseases; allergic diseases; inflammatory or autoimmune-mediated diseases; function disorders and neurological disorders; cardiovascular diseases; viral infection; metabolism/endocrine function disorders; neurological disorders and pain; bone marrow and organ transplant rejection; myelo-dysplastic syndrome; myeloproliferative disorders (MPDS such as polycythemia vera, essential thrombocythemia or mielofibrosis); cancer and hematologic malignancies, leukemia, lymphomas and solid tumors; more in particular wherein the pathological condition or disease is selected from leukemia, lymphomas and solid tumors, rheumatoid arthritis, multiple sclerosis, amyotrophic lateral sclerosis, Crohn's disease, ulcerative colitis, systemic lupus erythematosis, autoimmune hemolytic anemia, type I diabetes, cutaneous vasculitis, cutaneous lupus erythematosus, dermatomyositis, blistering diseases including but not limited to pemphigus vulgaris, bullous pemphigoid and epidermolysis bullosa, asthma, chronic obstructive pulmonary disease, cystic fibrosis, idiopathic pulmonary fibrosis, sarcoidosis, allergic rhinitis, atopic dermatitis, contact dermatitis, eczema, psoriasis, basal cell carcinoma, squamous cell carcinoma and actinic keratosis.

In particular the pathological condition or disease is selected from leukemia, lymphomas and solid tumors, rheumatoid arthritis, multiple sclerosis, amyotrophic lateral sclerosis, Crohn's disease, ulcerative colitis, systemic lupus erythematosis, autoimmune hemolytic anemia, type I diabetes, asthma, chronic obstructive pulmonary disease, cystic fibrosis, idiopathic pulmonary fibrosis, sarcoidosis, allergic rhinitis, atopic dermatitis, contact dermatitis, eczema, psoriasis, basal cell carcinoma, squamous cell carcinoma and actinic keratosis.

The invention also encompasses the use of a combination of the compounds of the invention together with one or more other therapeutic agents for the manufacture of a formulation or medicament for treating these diseases.

The invention also provides a method of treatment of a pathological condition or disease susceptible to amelioration by inhibiton of Phosphoinositide 3-Kinases (PI3Ks), in particular wherein the pathological condition or disease is selected from respiratory diseases; allergic diseases; inflammatory or autoimmune-mediated diseases; function disorders and neurological disorders; cardiovascular diseases; viral infection; metabolism/endocrine function disorders; neurological disorders and pain; bone marrow and organ transplant rejection; myelo-dysplastic syndrome; myeloproliferative disorders (MPDs such as polycythemia vera, essential thrombocythemia or mielofibrosis); cancer and hematologic malignancies, leukemia, lymphomas and solid tumors; more in particular wherein the pathological condition or disease is selected from leukemia, lymphomas and solid tumors, rheumatoid arthritis, multiple sclerosis, amyotrophic lateral sclerosis, Crohn's disease, ulcerative colitis, systemic lupus erythematosis, autoimmune hemolytic anemia, type I diabetes, cutaneous vasculitis, cutaneous lupus erythematosus, dermatomyositis, blistering diseases including but not limited to pemphigus vulgaris, bullous pemphigoid and epidermolysis bullosa, asthma, chronic obstructive pulmonary disease, cystic fibrosis, idiopathic pulmonary fibrosis, sarcoidosis, allergic rhinitis, atopic dermatitis, contact dermatitis, eczema, psoriasis, basal cell carcinoma, squamous cell carcinoma and actinic keratosis.

In particular the pathological condition or disease is selected from leukemia, lymphomas and solid tumors, rheumatoid arthritis, multiple sclerosis, amyotrophic lateral sclerosis, Crohn's disease, ulcerative colitis, systemic lupus erythematosis, autoimmune hemolytic anemia, type I diabetes, asthma, chronic obstructive pulmonary disease, cystic fibrosis, idiopathic pulmonary fibrosis, sarcoidosis, allergic rhinitis, atopic dermatitis, contact dermatitis, eczema, psoriasis, basal cell carcinoma, squamous cell carcinoma and actinic keratosis.

The active compounds in the combinations of the invention may be administered by any suitable route, depending on the nature of the disorder to be treated, e.g. orally (as syrups, tablets, capsules, lozenges, controlled-release preparations, fast-dissolving preparations, etc); topically (as creams, ointments, lotions, nasal sprays or aerosols, etc); by injection (subcutaneous, intradermic, intramuscular, intravenous, etc.) or by inhalation (as a dry powder, a solution, a dispersion, etc).

The active compounds in the combination, i.e. the pyrrolotriazinone derivatives of the invention, and the other optional active compounds may be administered together in the same pharmaceutical composition or in different compositions intended for separate, simultaneous, concomitant or sequential administration by the same or a different route.

One execution of the present invention consists of a kit of parts comprising a imidazopyridine derivative of the invention together with instructions for simultaneous, concurrent, separate or sequential use in combination with another active compound useful in the treatment of respiratory diseases; allergic diseases; inflammatory or autoimmune-mediated diseases; function disorders and neurological disorders; cardiovascular diseases; viral infection; metabolism/endocrine function disorders; neurological disorders and pain; bone marrow and organ transplant rejection; myelo-dysplastic syndrome; myeloproliferative disorders (MPDS such as polycythemia vera, essential thrombocythemia or mielofibrosis); cancer and hematologic malignancies, leukemia, lymphomas and solid tumors; more in particular wherein the pathological condition or disease is selected from leukemia, lymphomas and solid tumors, rheumatoid arthritis, multiple sclerosis, amyotrophic lateral sclerosis, Crohn's disease, ulcerative colitis, systemic lupus erythematosis, autoimmune hemolytic anemia, type I diabetes, cutaneous vasculitis, cutaneous lupus erythematosus, dermatomyositis, blistering diseases including but not limited to pemphigus vulgaris, bullous pemphigoid and epidermolysis bullosa, asthma, chronic obstructive pulmonary disease, cystic fibrosis, idiopathic pulmonary fibrosis, sarcoidosis, allergic rhinitis, atopic dermatitis, contact dermatitis, eczema, psoriasis, basal cell carcinoma, squamous cell carcinoma and actinic keratosis.

In particular the pathological condition or disease is selected from leukemia, lymphomas and solid tumors, rheumatoid arthritis, multiple sclerosis, amyotrophic lateral sclerosis, Crohn's disease, ulcerative colitis, systemic lupus erythematosis, autoimmune hemolytic anemia, type I diabetes, asthma, chronic obstructive pulmonary disease, cystic fibrosis, idiopathic pulmonary fibrosis, sarcoidosis, allergic rhinitis, atopic dermatitis, contact dermatitis, eczema, psoriasis, basal cell carcinoma, squamous cell carcinoma and actinic keratosis.

Another execution of the present invention consists of a package comprising a imidazopyridine derivative of the invention and another active compound useful in the treatment of respiratory diseases; allergic diseases; inflammatory or autoimmune-mediated diseases; function disorders and neurological disorders; cardiovascular diseases; viral infection; metabolism/endocrine function disorders; neurological disorders and pain; bone marrow and organ transplant rejection; myelo-dysplastic syndrome; myeloproliferative disorders (MPDS such as polycythemia vera, essential thrombocythemia or mielofibrosis); cancer and hematologic malignancies, leukemia, lymphomas and solid tumors; more in particular wherein the pathological condition or disease is selected from leukemia, lymphomas and solid tumors, rheumatoid arthritis, multiple sclerosis, amyotrophic lateral sclerosis, Crohn's disease, ulcerative colitis, systemic lupus erythematosis, autoimmune hemolytic anemia, type I diabetes, cutaneous vasculitis, cutaneous lupus erythematosus, dermatomyositis, blistering diseases including but not limited to pemphigus vulgaris, bullous pemphigoid and epidermolysis bullosa, asthma, chronic obstructive pulmonary disease, cystic fibrosis, idiopathic pulmonary fibrosis, sarcoidosis, allergic rhinitis, atopic dermatitis, contact dermatitis, eczema, psoriasis, basal cell carcinoma, squamous cell carcinoma and actinic keratosis.

In particular the pathological condition or disease is selected from leukemia, lymphomas and solid tumors, rheumatoid arthritis, multiple sclerosis, amyotrophic lateral sclerosis, Crohn's disease, ulcerative colitis, systemic lupus erythematosis, autoimmune hemolytic anemia, type I diabetes, asthma, chronic obstructive pulmonary disease, cystic fibrosis, idiopathic pulmonary fibrosis, sarcoidosis, allergic rhinitis, atopic dermatitis, contact dermatitis, eczema, psoriasis, basal cell carcinoma, squamous cell carcinoma and actinic keratosis.

Pharmaceutical Compositions

Pharmaceutical compositions according to the present invention comprise the compounds of the invention in association with a pharmaceutically acceptable diluent or carrier.

As used herein, the term pharmaceutical composition refers to a mixture of one or more of the compounds described herein, or physiologically/pharmaceutically acceptable salts, solvates, N-oxides, stereoisomers, deuterated derivatives thereof or prodrugs thereof, with other chemical components, such as physiologically/pharmaceutically acceptable carriers and excipients. The purpose of a pharmaceutical composition is to facilitate administration of a compound to an organism.

As used herein, a physiologically/pharmaceutically acceptable diluent or carrier refers to a carrier or diluent that does not cause significant irritation to an organism and does not abrogate the biological activity and properties of the administered compound.

The invention further provides pharmaceutical compositions comprising the compounds of the invention in association with a pharmaceutically acceptable diluent or carrier together with one or more other therapeutic agents for use in the treatment of a pathological condition or disease susceptible to amelioration by inhibiton of Phosphoinositide 3-Kinases (PI3Ks), such as the ones previously described.

The invention is also directed to pharmaceutical compositions of the invention for use in the treatment of a pathological condition or disease susceptible to amelioration by inhibiton of Phosphoinositide 3-Kinases (PI3Ks), in particular wherein the pathological condition or disease is selected from respiratory diseases; allergic diseases; inflammatory or autoimmune-mediated diseases; function disorders and neurological disorders; cardiovascular diseases; viral infection; metabolism/endocrine function disorders; neurological disorders and pain; bone marrow and organ transplant rejection; myelodysplastic syndrome; myeloproliferative disorders (MPDs such as polycythemia vera, essential thrombocythemia or mielofibrosis); cancer and hematologic malignancies, leukemia, lymphomas and solid tumors; more in particular wherein the pathological condition or disease is selected from leukemia, lymphomas and solid tumors, rheumatoid arthritis, multiple sclerosis, amyotrophic lateral sclerosis, Crohn's disease, ulcerative colitis, systemic lupus erythematosis, autoimmune hemolytic anemia, type I diabetes, cutaneous vasculitis, cutaneous lupus erythematosus, dermatomyositis, blistering diseases including but not limited to pemphigus vulgaris, bullous pemphigoid and epidermolysis bullosa, asthma, chronic obstructive pulmonary disease, cystic fibrosis, idiopathic pulmonary fibrosis, sarcoidosis, allergic rhinitis, atopic dermatitis, contact dermatitis, eczema, psoriasis, basal cell carcinoma, squamous cell carcinoma and actinic keratosis.

In particular the pathological condition or disease is selected from leukemia, lymphomas and solid tumors, rheumatoid arthritis, multiple sclerosis, amyotrophic lateral sclerosis, Crohn's disease, ulcerative colitis, systemic lupus erythematosus, autoimmune hemolytic anemia, type I diabetes, asthma, chronic obstructive pulmonary disease, cystic fibrosis, idiopathic pulmonary fibrosis, sarcoidosis, allergic rhinitis, atopic dermatitis, contact dermatitis, eczema, psoriasis, basal cell carcinoma, squamous cell carcinoma and actinic keratosis. The invention also encompasses the use of a pharmaceutical composition of the invention for the manufacture of a medicament for treating these diseases.

The invention also provides a method of treatment of a pathological condition or disease susceptible to amelioration by inhibiton of Phosphoinositide 3-Kinases (PI3Ks), in particular wherein the pathological condition or disease is selected from respiratory diseases; allergic diseases; inflammatory or autoimmune-mediated diseases; function disorders and neurological disorders; cardiovascular diseases; viral infection; metabolism/endocrine function disorders; neurological disorders and pain; bone marrow and organ transplant rejection; myelo-dysplastic syndrome; myeloproliferative disorders (MPDS such as polycythemia vera, essential thrombocythemia or mielofibrosis); cancer and hematologic malignancies, leukemia, lymphomas and solid tumors; more in particular wherein the pathological condition or disease is selected from leukemia, lymphomas and solid tumors, rheumatoid arthritis, multiple sclerosis, amyotrophic lateral sclerosis, Crohn's disease, ulcerative colitis, systemic lupus erythematosus, autoimmune hemolytic anemia, type I diabetes, cutaneous vasculitis, cutaneous lupus erythematosus, dermatomyositis, blistering diseases including but not limited to pemphigus vulgaris, bullous pemphigoid and epidermolysis bullosa, asthma, chronic obstructive pulmonary disease, cystic fibrosis, idiopathic pulmonary fibrosis, sarcoidosis, allergic rhinitis, atopic dermatitis, contact dermatitis, eczema, psoriasis, basal cell carcinoma, squamous cell carcinoma and actinic keratosis; more in particular the pathological condition or disease is selected from leukemia, lymphomas and solid tumors, rheumatoid arthritis, multiple sclerosis, amyotrophic lateral sclerosis, Crohn's disease, ulcerative colitis, systemic lupus erythematosus, autoimmune hemolytic anemia, type I diabetes, asthma, chronic obstructive pulmonary disease, cystic fibrosis, idiopathic pulmonary fibrosis, sarcoidosis, allergic rhinitis, atopic dermatitis, contact dermatitis, eczema, psoriasis, basal cell carcinoma, squamous cell carcinoma and actinic keratosis; comprising administering a therapeutically effective amount of a pharmaceutical composition of the invention.

The present invention also provides pharmaceutical compositions which comprise, as an active ingredient, at least a compound of formula (I) or a pharmaceutically acceptable salt thereof in association with a pharmaceutically acceptable excipient such as a carrier or diluent. The active ingredient may comprise 0.001% to 99% by weight, preferably 0.01% to 90% by weight, of the composition depending upon the nature of the formulation and whether further dilution is to be made prior to application. Preferably the compositions are made up in a form suitable for oral, inhalation, topical, nasal, rectal, percutaneous or injectable administration.

Pharmaceutical compositions suitable for the delivery of compounds of the invention and methods for their preparation will be readily apparent to those skilled in the art. Such compositions and methods for their preparation can be found, for example, in Remington: The Science and Practice of Pharmacy, 21st Edition, Lippincott Williams & Wilkins, Philadelphia, Pa., 2001.

The pharmaceutically acceptable excipients which are admixed with the active compound or salts of such compound, to form the compositions of this invention are well-known per se and the actual excipients used depend inter alia on the intended method of administering the compositions. Examples, without limitation, of excipients include calcium carbonate, calcium phosphate, various sugars and types of starch, cellulose derivatives, gelatin, vegetable oils and polyethylene glycols.

Additional suitable carriers for formulations of the compounds of the present invention can be found in Remington: The Science and Practice of Pharmacy, 21st Edition, Lippincott Williams & Wilkins, Philadelphia, Pa., 2001.

i) Oral Administration

The compounds of the invention may be administered orally (peroral administration; per os (latin)). Oral administration involve swallowing, so that the compound is absorbed from the gut and delivered to the liver via the portal circulation (hepatic first pass metabolism) and finally enters the gastrointestinal (GI) tract.

Compositions for oral administration may take the form of tablets, retard tablets, sublingual tablets, capsules, inhalation aerosols, inhalation solutions, dry powder inhalation, or liquid preparations, such as mixtures, solutions, elixirs, syrups or suspensions, all containing the compound of the invention; such preparations may be made by methods well-known in the art. The active ingredient may also be presented as a bolus, electuary or paste.

Where the composition is in the form of a tablet, any pharmaceutical carrier routinely used for preparing solid formulations may be used. Examples of such carriers include magnesium stearate, talc, gelatine, acacia, stearic acid, starch, lactose and sucrose.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent.

Moulded tablets may be made by moulding in a suitable machine a mixture of the powdered compound moistened with an inert liquid diluent. The tablets may optionally be coated or scored and may be formulated so as to provide slow or controlled release of the active ingredient therein.

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant will comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate. Tablets may also optionally include surface active agents, such as sodium lauryl sulfate and polysorbate 80, and glidants such as silicon dioxide and talc. When present, surface active agents are typically in amounts of from 0.2 wt % to 5 wt % of the tablet, and glidants typically from 0.2 wt % to 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally are present in amounts from 0.25 wt % to 10 wt %, preferably from 0.5 wt % to 3 wt % of the tablet. Other conventional ingredients include antioxidants, colorants, flavoring agents, preservatives and taste-masking agents.

Exemplary tablets contain up to about 80 wt % drug, from about 10 wt % to about 90 wt % binder, from about 0 wt % to about 85 wt % diluent, from about 2 wt % to about 10 wt % disintegrant, and from about 0.25 wt % to about 10 wt % lubricant. Tablet blends may be compressed directly or by roller to form tablets. Tablet blends or portions of blends may alternatively be wet-, dry-, or melt-granulated, melt congealed, or extruded before tabletting. The final formulation may include one or more layers and may be coated or uncoated; or encapsulated.

The formulation of tablets is discussed in detail in "Pharmaceutical Dosage Forms: Tablets, Vol. 1", by H. Lieberman and L. Lachman, Marcel Dekker, N.Y., 1980.

Where the composition is in the form of a capsule, any routine encapsulation is suitable, for example using the aforementioned carriers in a hard gelatine capsule. Where the composition is in the form of a soft gelatine capsule any pharmaceutical carrier routinely used for preparing dispersions or suspensions may be considered, for example aqueous gums, celluloses, silicates or oils, and are incorporated in a soft gelatine capsule.

Solid formulations for oral administration may be formulated to be immediate and/or modified release. Modified release formulations include delayed-, sustained-, pulsed-, controlled-, targeted and programmed release.

Suitable modified release formulations are described in U.S. Pat. No. 6,106,864. Details of other suitable release technologies such as high energy dispersions and osmotic and coated particles can be found in Verma et al, Pharmaceutical Technology On-line, 25(2), 1-14 (2001). The use of chewing gum to achieve controlled release is described in WO 00/35298. The disclosures of these references are incorporated herein by reference in their entireties.

Liquid formulations include suspensions, solutions, syrups and elixirs. Such formulations may be used as fillers in soft or hard capsules and typically include a carrier, for example, water, ethanol, polyethylene glycol, propylene glycol, methylcellulose, or a suitable oil, and one or more emulsifying agents and/or suspending agents. The solutions may be aqueous solutions of a soluble salt or other derivative of the active compound in association with, for example, sucrose to form a syrup. The suspensions may comprise an insoluble active compound of the invention or a pharmaceutically acceptable salt thereof in association with water, together with a suspending agent or flavouring agent. Liquid formulations may also be prepared by the reconstitution of a solid, for example, from a sachet.

ii) Oral Mucosal Administration

The compounds of the invention can also be administered via the oral mucosal. Within the oral mucosal cavity, delivery of drugs is classified into three categories: (a) sublingual delivery, which is systemic delivery of drugs through the mucosal membranes lining the floor of the mouth, (b) buccal delivery, which is drug administration through the mucosal membranes lining the cheeks (buccal mucosa), and (c) local delivery, which is drug delivery into the oral cavity.

Pharmaceutical products to be administered via the oral mucosal can be designed using mucoadhesive, quick dissolve tablets and solid lozenge formulations, which are formulated with one or more mucoadhesive (bioadhesive) polymers (such as hydroxy propyl cellulose, polyvinyl pyrrolidone, sodium carboxymethyl cellulose, hydroxy propyl methyl cellulose, hydroxy ethyl cellulose, polyvinyl alcohol, polyisobutylene or polyisoprene); and oral mucosal permeation enhancers (such as butanol, butyric acid, propranolol, sodium lauryl sulphate and others)

iii) Inhaled Administration

The compounds of the invention can also be administered by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may include a bioadhesive agent, for example, chitosan or cyclodextrin.

Dry powder compositions for topical delivery to the lung by inhalation may, for example, be presented in capsules and cartridges of for example gelatine or blisters of for example laminated aluminium foil, for use in an inhaler or insufflator. Formulations generally contain a powder mix for inhalation of the compound of the invention and a suitable powder base (carrier substance) such as lactose or starch. Use of lactose is preferred. Each capsule or cartridge may generally contain between 0.001-50 mg, more preferably 0.01-5 mg of active ingredient or the equivalent amount of a pharmaceutically acceptable salt thereof. Alternatively, the active ingredient (s) may be presented without excipients.

Packaging of the formulation may be suitable for unit dose or multi-dose delivery. In the case of multi-dose delivery, the formulation can be pre-metered or metered in use. Dry powder inhalers are thus classified into three groups: (a) single dose, (b) multiple unit dose and (c) multi dose devices.

For inhalers of the first type, single doses have been weighed by the manufacturer into small containers, which are mostly hard gelatine capsules. A capsule has to be taken from a separate box or container and inserted into a receptacle area of the inhaler. Next, the capsule has to be opened or perforated with pins or cutting blades in order to allow part of the inspiratory air stream to pass through the capsule for powder entrainment or to discharge the powder from the capsule through these perforations by means of centrifugal force during inhalation. After inhalation, the emptied capsule has to be removed from the inhaler again. Mostly, disassembling of the inhaler is necessary for inserting and removing the capsule, which is an operation that can be difficult and burdensome for some patients.

Other drawbacks related to the use of hard gelatine capsules for inhalation powders are (a) poor protection against moisture uptake from the ambient air, (b) problems with opening or perforation after the capsules have been exposed previously to extreme relative humidity, which causes fragmentation or indenture, and (c) possible inhalation of capsule fragments. Moreover, for a number of capsule inhalers, incomplete expulsion has been reported (e.g. Nielsen et al, 1997).

Some capsule inhalers have a magazine from which individual capsules can be transferred to a receiving chamber, in which perforation and emptying takes place, as described in WO 92/03175. Other capsule inhalers have revolving magazines with capsule chambers that can be brought in line with the air conduit for dose discharge (e. g. WO91/02558 and GB 2242134). They comprise the type of multiple unit dose inhalers together with blister inhalers, which have a limited number of unit doses in supply on a disk or on a strip.

Blister inhalers provide better moisture protection of the medicament than capsule inhalers. Access to the powder is obtained by perforating the cover as well as the blister foil, or by peeling off the cover foil. When a blister strip is used instead of a disk, the number of doses can be increased, but it is inconvenient for the patient to replace an empty strip. Therefore, such devices are often disposable with the incorporated dose system, including the technique used to transport the strip and open the blister pockets.

Multi-dose inhalers do not contain pre-measured quantities of the powder formulation. They consist of a relatively large container and a dose measuring principle that has to be operated by the patient. The container bears multiple doses that are isolated individually from the bulk of powder by volumetric displacement. Various dose measuring principles exist, including rotatable membranes (Ex. EP0069715) or disks (Ex. GB 2041763; EP 0424790; DE 4239402 and EP 0674533), rotatable cylinders (Ex. EP 0166294; GB 2165159 and WO 92/09322) and rotatable frustums (Ex. WO 92/00771), all having cavities which have to be filled with powder from the container. Other multi dose devices have measuring slides (Ex. U.S. Pat. No. 5,201,308 and WO 97/00703) or measuring plungers with a local or circumferential recess to displace a certain volume of powder from the container to a delivery chamber or an air conduit (Ex. EP 0505321, WO 92/04068 and WO 92/04928), or measuring slides such as the Genuair® (formerly known as Novolizer SD2FL), which is described the following patent applications Nos: WO97/000703, WO03/000325 and WO2006/008027.

Reproducible dose measuring is one of the major concerns for multi dose inhaler devices.

The powder formulation has to exhibit good and stable flow properties, because filling of the dose measuring cups or cavities is mostly under the influence of the force of gravity.

For reloaded single dose and multiple unit dose inhalers, the dose measuring accuracy and reproducibility can be guaranteed by the manufacturer. Multi dose inhalers on the other hand, can contain a much higher number of doses, whereas the number of handlings to prime a dose is generally lower.

Because the inspiratory air stream in multi-dose devices is often straight across the dose measuring cavity, and because the massive and rigid dose measuring systems of multi dose inhalers can not be agitated by this inspiratory air stream, the powder mass is simply entrained from the cavity and little de-agglomeration is obtained during discharge.

Consequently, separate disintegration means are necessary. However in practice, they are not always part of the inhaler design. Because of the high number of doses in multi-dose devices, powder adhesion onto the inner walls of the air conduits and the de-agglomeration means must be minimized and/or regular cleaning of these parts must be possible, without affecting the residual doses in the device. Some multi dose inhalers have disposable drug containers that can be replaced after the prescribed number of doses has been taken (Ex. WO 97/000703). For such semi-permanent multi dose inhalers with disposable drug containers, the requirements to prevent drug accumulation are even more strict.

Apart from applications through dry powder inhalers the compositions of the invention can be administered in aerosols which operate via propellant gases or by means of so-called atomisers, via which solutions of pharmacologically-active substances can be sprayed under high pressure so that a mist of inhalable particles results. The advantage of these atomisers is that the use of propellant gases can be completely dispensed with. Such atomiser is the Respimat® which is described, for example, in PCT Patent Applications Nos. WO 91/14468 and WO 97/12687, reference here is being made to the contents thereof.

Spray compositions for topical delivery to the lung by inhalation may for example be formulated as aqueous solutions or suspensions or as aerosols delivered from pressurised packs, such as a metered dose inhaler, with the use of a suitable liquefied propellant. Aerosol compositions suitable for inhalation can be either a suspension or a solution and generally contain the active ingredient (s) and a suitable propellant such as a fluorocarbon or hydrogen-containing chlorofluorocarbon or mixtures thereof, particularly hydrofluoroalkanes, e.g. dichlorodifluoromethane, trichlorofluoromethane, dichlorotetra-fluoroethane, especially 1,1, 1, 2-tetrafluoroethane, 1,1, 1,2, 3,3, 3-heptafluoro-n-propane or a mixture thereof. Carbon dioxide or other suitable gas may also be used as propellant.

The aerosol composition may be excipient free or may optionally contain additional formulation excipients well known in the art such as surfactants (eg oleic acid or lecithin) and cosolvens (eg ethanol). Pressurised formulations will generally be retained in a canister (eg an aluminium canister) closed with a valve (eg a metering valve) and fitted into an actuator provided with a mouthpiece.

Medicaments for administration by inhalation desirably have a controlled particle size. The optimum particle size for inhalation into the bronchial system is usually 1-10 µm, preferably 2-5 µm. Particles having a size above 20 µm are generally too large when inhaled to reach the small airways. To achieve these particle sizes the particles of the active ingredient as produced may be size reduced by conventional means eg by micronisation. The desired fraction may be separated out by air classification or sieving. Preferably, the particles will be crystalline.

Achieving high dose reproducibility with micronised powders is difficult because of their poor flowability and extreme agglomeration tendency. To improve the efficiency of dry powder compositions, the particles should be large while in the inhaler, but small when discharged into the respiratory tract. Thus, an excipient such as lactose or glucose is generally employed. The particle size of the excipient will usually be much greater than the inhaled medicament within the present invention. When the excipient is lactose it will typically be present as milled lactose, preferably crystalline alpha lactose monohydrate.

Pressurized aerosol compositions will generally be filled into canisters fitted with a valve, especially a metering valve. Canisters may optionally be coated with a plastics material e.g. a fluorocarbon polymer as described in WO96/32150. Canisters will be fitted into an actuator adapted for buccal delivery.

iv) Nasal Mucosal Administration

The compounds of the invention may also be administered via the nasal mucosal. Typical compositions for nasal mucosa administration are typically applied by a metering, atomizing spray pump and are in the form of a solution or suspension in an inert vehicle such as water optionally in combination with conventional excipients such as buffers, anti-microbials, tonicity modifying agents and viscosity modifying agents.

v) Parenteral Administration

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilization, may readily be accomplished using standard pharmaceutical techniques well known to those skilled in the art. The solubility of compounds of the invention used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a solid, semisolid, or thixotropic liquid for administration as an implanted depot providing modified release of the active compound. Examples of such formulations include drug-coated stents and PGLA microspheres.

vi) Topical Administration

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated; see, for example, J Pharm Sci, 88 (10), 955-958 by Finnin and Morgan (October 1999). Other means of topical administration include delivery by electroporation, iontophoresis, phonophoresis, sonophoresis and microneedle or needle-free injection.

Formulations for topical administration may be formulated to be immediate and/or modified release. Modified release formulations include delayed-, sustained-, pulsed-, controlled-, targeted and programmed release.

vii) Rectal/Intravaginal Administration

Compounds of the invention may be administered rectally or vaginally, for example, in the form of a suppository, pessary, or enema. Cocoa butter is a traditional suppository base, but various alternatives may be used as appropriate. Formulations for rectal/vaginal administration may be formulated to be immediate and/or modified release. Modified release formulations include delayed-, sustained-, pulsed-, controlled-, targeted and programmed release.

viii) Ocular Administration

Compounds of the invention may also be administered directly to the eye or ear, typically in the form of drops of a micronized suspension or solution in isotonic, pH-adjusted, sterile saline. Other formulations suitable for ocular and aural administration include ointments, biodegradable (e.g. absorbable gel sponges, collagen) and nonbiodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

ix) Other Technologies

Compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

The amount of the active compound administered will be dependent on the subject being treated, the severity of the disorder or condition, the rate of administration, the disposition of the compound and the discretion of the prescribing physician. However, an effective dosage is typically in the range of 0.01-3000 mg, more preferably 0.5-1000 mg of active ingredient or the equivalent amount of a pharmaceutically acceptable salt thereof per day. Daily dosage may be administered in one or more treatments, preferably from 1 to 4 treatments, per day.

Preferably, the pharmaceutical compositions of the invention are made up in a form suitable for oral, inhalation or topical administration, being particularly preferred oral or inhalation administration.

The pharmaceutical formulations may conveniently be presented in unit dosage form and may be prepared by any of the methods well known in the art of pharmacy.

Preferably the composition is in unit dosage form, for example a tablet, capsule or metered aerosol dose, so that the patient may administer a single dose.

The amount of each active which is required to achieve a therapeutic effect will, of course, vary with the particular active, the route of administration, the subject under treatment, and the particular disorder or disease being treated.

The following preparations forms are cited as formulation examples:

FORMULATION EXAMPLES

Formulation Example 1

Oral Suspension

| Ingredient | Amount |
| --- | --- |
| Active Compound | 3 mg |
| Citric acid | 0.5 g |
| Sodium chloride | 2.0 g |
| Methyl paraben | 0.1 g |
| Granulated sugar | 25 g |
| Sorbitol (70% solution) | 11 g |
| Veegum K | 1.0 g |
| Flavoring | 0.02 g |
| Dye | 0.5 mg |
| Distilled water | q.s. to 100 mL |

Formulation Example 2

Hard Gelatine Capsule for Oral Administration

| Ingredient | Amount |
| --- | --- |
| Active Compound | 1 mg |
| Lactose | 150 mg |
| Magnesium stearate | 3 mg |

Formulation Example 3

Gelatin Cartridge for Inhalation

| Ingredient | Amount |
| --- | --- |
| Active Compound (micronized) | 0.2 mg |
| Lactose | 25 mg |

Formulation Example 4

Formulation for Inhalation with a DPI

| Ingredient | Amount |
| --- | --- |
| Active Compound (micronized) | 15 mg |
| Lactose | 3000 mg |

Formulation Example 5

Formulation for a MDI

| Ingredient | Amount |
| --- | --- |
| Active Compound (micronized) | 10 g |
| 1,1,1,2,3,3,3-heptafluoro-n-propane | q.s. to 200 mL |

In all the formulation examples, active compound is (S)-2-(1-(2-amino-9H-purin-6-ylamino)propyl)-3-phenylpyrrolo[1,2-f][1,2,4]triazin-4(3H)-one.

Modifications, which do not affect, alter, change or modify the essential aspects of the compounds, combinations or pharmaceutical compositions described, are included within the scope of the present invention.

The invention claimed is:

1. A compound of formula (I), or a pharmaceutically acceptable salt, or solvate, or N-oxide, or stereoisomer thereof;

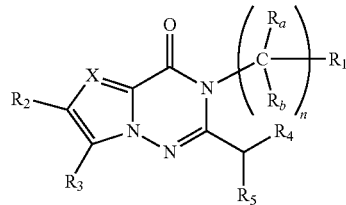

wherein,

X is chosen from a nitrogen atom or a —$CR_6$ group;

n is chosen from 0, 1, 2 or 3;

$R_a$ and $R_b$ independently are chosen from a hydrogen atom, a $C_1$-$C_4$ haloalkyl group, a $C_1$-$C_4$ hydroxyalkyl group or a linear or branched $C_1$-$C_4$ alkyl group;

$R_1$ is chosen from a hydrogen atom, a linear or branched $C_1$-$C_4$ alkyl group, a $C_1$-$C_4$ haloalkyl group, a $C_3$-$C_{10}$ cycloalkyl group, a $C_3$-$C_{10}$ cycloalkenyl group, a monocyclic or bicyclic $C_6$-$C_{14}$ aryl group, a 5- to 14-membered monocyclic or bicyclic heteroaryl group containing at least one heteroatom chosen from O, S and N, or a 5- to 14-membered monocyclic or bicyclic heterocyclyl group containing at least one heteroatom chosen from O, S and N, wherein the cycloalkyl, cycloalkenyl, aryl, heteroaryl, and heterocyclyl groups are unsubstituted or substituted by at least one substituent chosen from a halogen atom, a hydroxyl group, a cyano group, a linear or branched $C_1$-$C_4$ alkyl group, a $C_1$-$C_4$ haloalkyl group, a $C_1$-$C_4$ hydroxyalkyl group, a $C_3$-$C_4$ cycloalkyl group, a —$(CH_2)_{1-3}CN$ group, a —$(CH_2)_{0-3}OR_8$ group, a —$(CH_2)_{0-3}NR_7R_8$ group, a —$C(O)$—$(CH_2)_{1-3}$—$CN$ group, a —$C(O)$—$(CH_2)_{0-3}$—$R_8$ group, a —$C(O)$—$(CH_2)_{0-3}$—$NR_7R_8$ group, a —$S(O)_2(CH_2)_{0-3}R_8$ group, a —$S(O)_2(CH_2)_{0-3}NR_7R_8$ group or a —$(CH_2)_{0-3}(phenyl)$-$OR_8$ group;

$R_2$ and $R_3$ independently are chosen from a hydrogen atom, a halogen atom, a hydroxyl group, a cyano group, a $C_1$-$C_4$ alkoxy group, a $C_1$-$C_4$ haloalkyl group, a $C_1$-$C_4$ hydroxyalkyl group, a $C_3$-$C_7$ cycloalkyl group, a —$NR'R''$ group, or a linear or branched $C_1$-$C_6$ alkyl group, wherein the alkyl group is unsubstituted or substituted by at least one substituent chosen from a $C_1$-$C_4$ alkoxy group, a cyano group or a $C_3$-$C_7$ cycloalkyl group;

$R_4$ is chosen from a hydrogen atom, a $C_1$-$C_4$ alkoxy group, a $C_1$-$C_4$ haloalkyl group, a $C_1$-$C_4$ hydroxyalkyl group, a $C_3$-$C_7$ cycloalkyl group, a —$(CH_2)_{1-4}$NR'R" group, or a linear or branched $C_1$-$C_4$ alkyl group, wherein the alkyl group is unsubstituted or substituted by at least one substituent chosen from a $C_1$-$C_4$ alkoxy group, a cyano group, a $C_3$-$C_4$ cycloalkyl group, a —C(O)—$(CH_2)_{0-3}$—R' group or a —C(O)—$(CH_2)_{0-3}$—NR'R" group;

$R_6$ is chosen from a hydrogen atom, halogen atom, a hydroxyl group, a cyano group, a $C_1$-$C_4$ alkoxy group, a $C_1$-$C_4$ haloalkyl group, a linear or branched $C_1$-$C_4$ hydroxyalkyl group, a $C_3$-$C_7$ cycloalkyl group, a —$(CH_2)_{0-3}$NR'R" group, a —$(CH_2)_{1-3}$O($C_1$-$C_4$ alkyl group), a —$(CH_2)_{0-3}$OC(O)—($C_1$-$C_4$ alkyl group), a —$(CH_2)_{0-3}$C(O)O—($C_1$-$C_4$ alkyl group), a —C(O)—$(CH_2)_{0-3}$—NR'R" group, a —$(CH_2)_{0-3}$C(O)OH group, a —$(CH_2)_{0-3}$-(5- to 14-membered monocyclic or bicyclic heteroaryl group containing at least one heteroatom chosen from O, S and N), a —$(CH_2)_{0-3}$—(5- to 14-membered monocyclic or bicyclic heterocyclyl group containing at least one heteroatom chosen from O, S and N), or a linear or branched $C_1$-$C_4$ alkyl group, wherein the alkyl group is unsubstituted or substituted by at least one substituent chosen from a $C_1$-$C_4$ alkoxy group, a cyano group or a $C_3$-$C_4$ cycloalkyl group,
wherein the heteroaryl and heterocyclyl groups are unsubstituted or substituted by at least one substituents chosen from a halogen atom, a hydroxyl group, a cyano group, a linear or branched $C_1$-$C_4$ alkyl group or a $C_1$-$C_4$ haloalkyl group;

$R_7$ and $R_8$ independently are chosen from a hydrogen atom, a $C_1$-$C_4$ haloalkyl group, a $C_1$-$C_4$ hydroxyalkyl group or a linear or branched $C_1$-$C_4$ alkyl group, wherein the alkyl group is unsubstituted or substituted by at least one substituent chosen from a $C_1$-$C_4$ alkoxy group, a cyano group or a $C_3$-$C_4$ cycloalkyl group;

R' and R" independently are chosen from a hydrogen atom, a hydroxyl group, a $C_1$-$C_4$ alkoxy group or a linear or branched $C_1$-$C_4$ alkyl group;

$R_5$ is chosen from:

i) a group of formula (IIb-1),

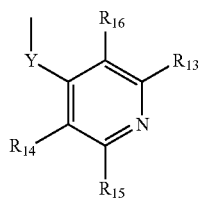

ii) a group of formula (IIb-2),

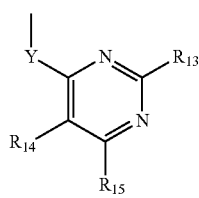

iii) a group of formula (IIb-3),

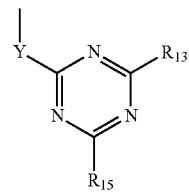

iv) a group of formula (IIb-4), and

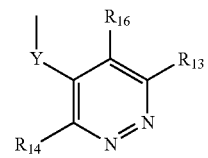

v) a group of formula (IIb-5),

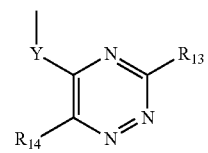

wherein
Y is chosen from a —NR'— group, —O— or —S—;
(*) represents a point of attachment of $R_5$ to the remainder of formula (I); and
$R_{13}$, $R_{14}$, $R_{15}$ and $R_{16}$ independently are chosen from a hydrogen atom, a halogen atom, a $C_1$-$C_4$ alkoxy group, a $C_1$-$C_4$ haloalkyl group, a $C_1$-$C_4$ hydroxyalkyl group, a $C_3$-$C_4$ cycloalkyl group, a —$(CH_2)_{0-3}$CN group, a —C(O)—$(CH_2)_{1-3}$—CN group, a —C(O)—$(CH_2)_{0-3}$—R' group, a —C(O)—$(CH_2)_{0-3}$—NR'R", a —$(CH_2)_{0-3}$NR'R" group, or a linear or branched $C_1$-$C_4$ alkyl group, wherein the alkyl group is unsubstituted or substituted by at least one substituent chosen from a $C_1$-$C_4$ alkoxy group, a cyano group or a $C_3$-$C_4$ cycloalkyl group.

2. The compound according to claim 1, wherein
$R_1$ is chosen from a linear or branched $C_1$-$C_4$ alkyl group, a $C_3$-$C_{10}$ cycloalkyl group, a $C_3$-$C_{10}$ cycloalkenyl group, a monocyclic or bicyclic $C_6$-$C_{14}$ aryl group, a 5- to 14-membered monocyclic or bicyclic heteroaryl group containing at least one heteroatom chosen from O, S and N, or a 5- to 14-membered monocyclic or bicyclic heterocyclyl group containing at least one heteroatom chosen from O, S and N,
wherein the cycloalkyl, cycloalkenyl, aryl, heteroaryl, and heterocyclyl groups are unsubstituted or substituted by at least one substituents chosen from a halogen atom, a hydroxyl group, a cyano group, a linear or branched $C_1$-$C_4$ alkyl group, a $C_1$-$C_4$ haloalkyl group, a $C_1$-$C_4$ hydroxyalkyl group, a $C_3$-$C_4$ cycloalkyl group, a —$(CH_2)_{1-3}$CN group, a —$(CH_2)_{0-3}$OR$_8$ group, a —$(CH_2)_{0-3}$NR$_7$R$_8$ group, a —C(O)—$(CH_2)_{1-3}$—CN group, a —C(O)—$(CH_2)_{0-3}$—R$_8$ group, a —C(O)—$(CH_2)_{0-3}$—NR$_7$R$_8$ group, a —S(O)$_2$$(CH_2)_{0-3}$R$_8$ group or a —S(O)$_2$CH$_2$)$_{0-3}$NR$_7$R$_8$ group;

$R_6$ is chosen from a hydrogen atom, a halogen atom, a hydroxyl group, a cyano group, a $C_1$-$C_4$ alkoxy group, a $C_1$-$C_4$ haloalkyl group, a $C_1$-$C_4$ hydroxyalkyl group, a $C_3$-$C_7$ cycloalkyl group, a —$(CH_2)_{0-3}$NR'R" group, or a linear or branched $C_1$-$C_4$ alkyl group, wherein the alkyl group is unsubstituted or substituted by at least one substituent chosen from a $C_1$-$C_4$ alkoxy group, a cyano group or a $C_3$-$C_4$ cycloalkyl group;

$R_{13}$, $R_{14}$, $R_{15}$ and $R_{16}$ independently are chosen from a hydrogen atom, a $C_1$-$C_4$ alkoxy group, a $C_1$-$C_4$ haloalkyl group, a $C_1$-$C_4$ hydroxyalkyl group, a $C_3$-$C_4$ cycloalkyl group, a —$(CH_2)_{0-3}$CN group, a —$C(O)$—$(CH_2)_{1-3}$—CN group, a —$C(O)$—$(CH_2)_{0-3}$—R' group, a —$C(O)$—$(CH_2)_{0-3}$—NR'R", a —$(CH_2)_{0-3}$NR'R" group, or a linear or branched $C_1$-$C_4$ alkyl group, wherein the alkyl group is unsubstituted or substituted by at least one substituent chosen from a $C_1$-$C_4$ alkoxy group, a cyano group or a $C_3$-$C_4$ cycloalkyl group.

3. The compound according to claim 1, wherein $R_1$ is chosen from a hydrogen atom, $C_1$-$C_3$ alkyl group, a $C_1$-$C_3$ haloalkyl group, a $C_3$-$C_7$ cycloalkyl group, a phenyl group, a naphthyl group, a 5- to 10-membered monocyclic or bicyclic heteroaryl group containing one, two or three heteroatoms chosen from O, S and N, or a 5- to 10-membered monocyclic or bicyclic heterocyclyl group containing one, two or three heteroatoms chosen from O, S and N, wherein the cycloalkyl, phenyl, naphthyl, heteroaryl and heterocyclyl groups are unsubstituted or substituted by at least one substituents chosen from a halogen atom, a hydroxyl group, a cyano group, a linear or branched $C_1$-$C_4$ alkyl group, a $C_1$-$C_4$ haloalkyl group, a $C_1$-$C_4$ hydroxyalkyl group, a $C_3$-$C_4$ cycloalkyl group, a —$(CH_2)_{0-3}$OR$_8$ group, a —$(CH_2)_{0-3}$NR$_7$R$_8$ group, a —$C(O)$—$(CH_2)_{0-3}$—R$_8$ group, a —$C(O)$—$(CH_2)_{0-3}$—NR$_7$R$_8$ group or a —$(CH_2)_{0-3}$(phenyl)-OR$_8$ group.

4. The compound according to claim 1, wherein $R_1$ is chosen from a $C_1$-$C_3$ alkyl group, a $C_3$-$C_7$ cycloalkyl group, a phenyl group, a naphthyl group, a 5- to 10-membered monocyclic or bicyclic heteroaryl group containing one, two or three heteroatoms chosen from O, S and N, or a 5- to 10-membered monocyclic or bicyclic heterocyclyl group containing one, two or three heteroatoms chosen from O, S and N, wherein the cycloalkyl, phenyl, naphthyl, heteroaryl and heterocyclyl groups are unsubstituted or substituted by at least one substituents chosen from a halogen atom, a hydroxyl group, a cyano group, a linear or branched $C_1$-$C_4$ alkyl group, a $C_1$-$C_4$ haloalkyl group, a $C_1$-$C_4$ hydroxyalkyl group, a $C_3$-$C_4$ cycloalkyl group, a —$(CH_2)_{0-3}$OR$_8$ group, a —$(CH_2)_{0-3}$NR$_7$R$_8$ group, a —$C(O)$—$(CH_2)_{0-3}$—R$_8$ group or a —$C(O)$—$(CH_2)_{0-3}$—NR$_7$R$_8$ group.

5. The compound according to claim 1, wherein $R_2$ is chosen from a hydrogen atom, a halogen atom, a hydroxyl group, a cyano group, a $C_1$-$C_4$ alkoxy group, a $C_1$-$C_4$ haloalkyl group, a $C_1$-$C_4$ hydroxyalkyl group, a $C_3$-$C_4$ cycloalkyl group, a NR'R" group, or a linear or branched $C_1$-$C_4$ alkyl group, wherein the alkyl group is unsubstituted or substituted by a $C_1$-$C_3$ alkoxy group; wherein R' and R" independently are chosen from a hydrogen atom, a hydroxyl group, or a linear or branched $C_1$-$C_3$ alkyl group.

6. The compound according to claim 1, wherein $R_3$ is chosen from a hydrogen atom, a halogen atom, a hydroxyl group, a cyano group, a $C_1$-$C_4$ alkoxy group, a $C_1$-$C_4$ haloalkyl group, a $C_1$-$C_4$ hydroxyalkyl group, a $C_3$-$C_4$ cycloalkyl group, a NR'R" group, or a linear or branched $C_1$-$C_4$ alkyl group, wherein the alkyl group is unsubstituted or substituted by a $C_1$-$C_3$ alkoxy group; wherein R' and R" independently are chosen from a hydrogen atom, a hydroxy group, or a linear or branched $C_1$-$C_3$ alkyl group.

7. A The compound according to claim 1, wherein $R_4$ is chosen from a hydrogen atom, a $C_1$-$C_4$ haloalkyl group, a $C_1$-$C_4$ hydroxyalkyl group, a $C_3$-$C_4$ cycloalkyl group, a —$(CH_2)_{1-4}$NR'R" group, or a linear or branched $C_1$-$C_4$ alkyl group, wherein the alkyl group is unsubstituted or substituted by a $C_1$-$C_3$ alkoxy group, a —$C(O)$—$(CH_2)_{0-3}$—R' group or a —$C(O)$—$(CH_2)_{0-3}$—NR'R" group; wherein R' and R" independently are chosen from a hydrogen atom, a hydroxyl group, or a linear or branched $C_1$-$C_3$ alkyl group.

8. The compound according to claim 1, wherein $R_6$ is chosen from a hydrogen atom; a halogen atom; a hydroxyl group; a cyano group; a $C_1$-$C_4$ alkoxy group; a $C_1$-$C_4$ haloalkyl group; a linear or branched $C_1$-$C_4$ hydroxyalkyl group; a $C_3$-$C_7$ cycloalkyl group; a —$(CH_2)_{0-3}$NR'R" group; a —$(CH_2)_{1-3}$O($C_1$-$C_4$ alkyl group); a —$(CH_2)_{0-3}$OC(O)—($C_1$-$C_4$ alkyl group); a —$(CH_2)_{0-3}$C(O)O—($C_1$-$C_4$ alkyl group); a —$C(O)$—$(CH_2)_{0-3}$—NR'R" group; a —$(CH_2)_{0-3}$C(O)OH group; a —$(CH_2)_{0-3}$-(5- to 10-membered monocyclic or bicyclic heteroaryl group containing at least one heteroatom chosen from O, S and N); a —$(CH_2)_{0-3}$-(5- to 10-membered monocyclic or bicyclic heterocyclyl group containing at least one heteroatom chosen from O, S and N); or a linear or branched $C_1$-$C_3$ alkyl group, wherein the alkyl group is unsubstituted or substituted by at least one substituent chosen from a $C_1$-$C_4$ alkoxy group, a cyano group or a $C_3$-$C_4$ cycloalkyl group; wherein R' and R" independently are chosen from a hydrogen atom, a hydroxyl group, or a linear or branched $C_1$-$C_3$ alkyl group; and wherein the heteroaryl and heterocyclyl groups are unsubstituted or substituted by at least one substituent chosen from a halogen atom, a hydroxyl group, a cyano group, a linear or branched $C_1$-$C_3$ alkyl group or a $C_1$-$C_3$ haloalkyl group.

9. The compound according to claim 1, wherein $R_6$ is chosen from a hydrogen atom, a halogen atom, a hydroxyl group, a cyano group, a $C_1$-$C_4$ alkoxy group, a $C_1$-$C_4$ haloalkyl group, a $C_1$-$C_4$ hydroxyalkyl group, a $C_3$-$C_4$ cycloalkyl group, a —$(CH_2)_{0-3}$NR'R" group, or a linear or branched $C_1$-$C_4$ alkyl group, wherein the alkyl group is unsubstituted or substituted by a $C_1$-$C_3$ alkoxy group; wherein R' and R" independently are chosen from a hydrogen atom, a hydroxyl group, or a linear or branched $C_1$-$C_3$ alkyl group.

10. The compound of according to claim 1, wherein X represents a —CR$_6$ group.

11. The compound according to claim 1, wherein X represents a nitrogen atom.

12. The compound according to claim 1, chosen from:
2-((6-aminopyrimidin-4-ylamino)methyl)-5-chloro-3-o-tolylpyrrolo[1,2-f][1,2,4]triazin-4(3H)-one;
2-((6-aminopyrimidin-4-ylamino)methyl)-3-o-tolylpyrrolo[1,2-f][1,2,4]triazin-4(3H)-one;
4-((4-oxo-3-o-tolyl-3,4-dihydropyrrolo[1,2-f][1,2,4]triazin-2-yl)methylamino)picolinamide;
2-((2-aminopyridin-4-ylamino)methyl)-3-o-tolylpyrrolo[1,2-f][1,2,4]triazin-4(3H)-one;
(S)-2-(1-(6-aminopyrimidin-4-ylamino)propyl)-3-phenylpyrrolo[1,2-f][1,2,4]triazin-4(3H)-one;
(S)-4-amino-6-(1-(4-oxo-3-phenyl-3,4-dihydropyrrolo[1,2-f][1,2,4]triazin-2-yl)propylamino)pyrimidine-5-carbonitrile;
(S)-2-(1-(6-aminopyrimidin-4-ylamino)ethyl)-3-phenylpyrrolo[1,2-f][1,2,4]triazin-4(3H)-one;

(S)-4-amino-6-(1-(4-oxo-3-phenyl-3,4-dihydropyrrolo[1,2-f][1,2,4]triazin-2-yl)ethylamino)pyrimidine-5-carbonitrile;

(S)-4-amino-6(1-(3-(3-fluorophenyl)-4-oxo-3,4-dihydropyrrolo[1,2-f][1,2,4]triazin-2-yl)ethylamino)pyrimidine-5-carbonitrile;

(S)-4-amino-6-(1-(3-(3,5-difluorophenyl)-4-oxo-3,4-dihydropyrrolo[1,2-f][1,2,4]triazin-2-yl)ethylamino)pyrimidine-5-carbonitrile;

(S)-4-amino-6-(1-(4-oxo-3-(pyridin-2-yl)-3,4-dihydropyrrolo[1,2-f][1,2,4]triazin-2-yl)ethylamino)pyrimidine-5-carbonitrile;

(S)-4-amino-6-(1-(4-oxo-3-phenyl-5-(trifluoromethyl)-3,4-dihydropyrrolo[1,2-f][1,2,4]triazin-2-yl)ethylamino)pyrimidine-5-carbonitrile;

(S)-4-amino-6-(1-(5-(difluoromethyl)-4-oxo-3-phenyl-3,4-dihydropyrrolo[1,2-f][1,2,4]triazin-2-yl)ethylamino)pyrimidine-5-carbonitrile;

(S)-4-amino-6-(1-(4-oxo-3-phenyl-3,4-dihydroimidazo[1,2-f][1,2,4]triazin-2-yl)ethylamino)pyrimidine-5-carbonitrile;

4-amino-6-(3,3,3-trifluoro-1-(4-oxo-3-phenyl-3,4-dihydropyrrolo[1,2-f][1,2,4]triazin-2-yl)propylamino)pyrimidine-5-carbonitrile;

(S)-4-amino-6-(2-(4-oxo-3-phenyl-3,4-dihydropyrrolo[1,2-f][1,2,4]triazin-2-yl)pyrrolidin-1-yl)pyrimidine-5-carbonitrile;

(S)-2-(1-(4,6-diamino-1,3,5-triazin-2-ylamino)ethyl)-3-phenylpyrrolo[1,2-f][1,2,4]triazin-4(3H)-one;

(S)-2-(1-(6-amino-5-cyanopyrimidin-4-ylamino)ethyl)-4-oxo-3-phenyl-3,4-dihydropyrrolo[1,2-f][1,2,4]triazine-5-carbonitrile;

(R)-4-amino-6-(2-hydroxy-1-(4-oxo-3-phenyl-3,4-dihydropyrrolo[1,2-f][1,2,4]triazin-2-yl)-ethylamino)pyrimidine-5-carbonitrile;

(S)-4-amino-6-(methyl(1-(4-oxo-3-phenyl-3,4-dihydropyrrolo[1,2-f][1,2,4]triazin-2-yl)ethyl)amino)pyrimidine-5-carbonitrile;

(S)-4-amino-6-(1-(5-methyl-4-oxo-3-phenyl-3,4-dihydropyrrolo[1,2-f][1,2,4]triazin-2-yl)ethylamino)pyrimidine-5-carbonitrile;

(S)-4-amino-6-(1-(7-methyl-4-oxo-3-phenyl-3,4-dihydropyrrolo[1,2-f][1,2,4]triazin-2-yl)ethylamino)pyrimidine-5-carbonitrile;

(S)-4-amino-6-(4,4-difluoro-2-(4-oxo-3-phenyl-3,4-dihydropyrrolo[1,2-f][1,2,4]triazin-2-yl)pyrrolidin-1-yl)pyrimidine-5-carbonitrile;

(S)-4-amino-6-(1-(6-fluoro-4-oxo-3-phenyl-3,4-dihydropyrrolo[1,2-f][1,2,4]triazin-2-yl)ethylamino)pyrimidine-5-carbonitrile;

4-amino-6-((S)-1-(4-oxo-3-((S)-1-phenylethyl)-3,4-dihydropyrrolo[1,2-f][1,2,4]triazin-2-yl)ethylamino)pyrimidine-5-carbonitrile;

(S)-4-amino-6-(1-(3-(2,6-dimethylphenyl)-4-oxo-3,4-dihydropyrrolo[1,2-f][1,2,4]triazin-2-yl)ethylamino)pyrimidine-5-carbonitrile;

(S)-4-amino-6-((4-oxo-3-(1-phenylethyl)-3,4-dihydropyrrolo[1,2-f][1,2,4]triazin-2-yl)methylamino)pyrimidine-5-carbonitrile;

(S)-4-amino-6-(1-(5-fluoro-4-oxo-3-phenyl-3,4-dihydropyrrolo[1,2-f][1,2,4]triazin-2-yl)ethylamino)pyrimidine-5-carbonitrile;

(S)-2-(1-(6-amino-5-cyanopyrimidin-4-ylamino)ethyl)-3-(3,5-difluorophenyl)-4-oxo-3,4-dihydropyrrolo[1,2-f][1,2,4]triazine-5-carbonitrile;

(S)-4-amino-6-(1-(3-(3,5-difluorophenyl)-4-oxo-3,4-dihydroimidazo[1,2-f][1,2,4]triazin-2-yl)ethylamino)pyrimidine-5-carbonitrile;

4-amino-6-((1S)-1-(5-(1,2-dihydroxyethyl)-4-oxo-3-phenyl-3,4-dihydropyrrolo[1,2-f][1,2,4]triazin-2-yl)ethylamino)pyrimidine-5-carbonitrile;

(S)-4-amino-6-(1-(3-(3,5-difluorophenyl)-4-oxo-5-(trifluoromethyl)-3,4-dihydropyrrolo[1,2-f][1,2,4]triazin-2-yl)ethylamino)pyrimidine-5-carbonitrile;

(S)-4-amino-6-(1-(5-(hydroxymethyl)-4-oxo-3-phenyl-3,4-dihydropyrrolo[1,2-f][1,2,4]triazin-2-yl)ethylamino)pyrimidine-5-carbonitrile;

(S)-2-(1-(6-amino-5-(trifluromethyl)pyrimidin-4-ylamino)ethyl)-3-phenylpyrrolo[1,2-f][1,2,4]triazin-4(3H)-one;

(S)-2-(1-(6-amino-5-cyanopyrimidin-4-ylamino)ethyl)-4-oxo-3-(pyridin-2-ylmethyl)-3,4-dihydropyrrolo[1,2-f][1,2,4]triazine-5-carbonitrile;

(S)-4-amino-6-(1-(5-(difluoromethyl)-3-(3,5-difluorophenyl)-4-oxo-3,4-dihydropyrrolo[1,2-f][1,2,4]triazin-2-yl)ethylamino)pyrimidine-5-carbonitrile;

(S)-4-amino-6-(1-(3-benzyl-4-oxo-3,4-dihydropyrrolo[1,2-f][1,2,4]triazin-2-yl)ethylamino)pyrimidine-5-carbonitrile;

(S)-2-(1-(6-amino-5-fluoropyrimidin-4-ylamino)ethyl)-3-phenylpyrrolo[1,2-f][1,2,4]triazin-4(3H)-one;

(S)-2-(1-(6-amino-5-fluoropyrimidin-4-ylamino)ethyl)-5-(difluoromethyl)-3-(3,5-difluorophenyl)pyrrolo[1,2-f][1,2,4]triazin-4(3H)-one;

(S)-2-(1-(6-amino-5-cyanopyrimidin-4-ylamino)propyl)-3-(3,5-difluorophenyl)-4-oxo-3,4-dihydropyrrolo[1,2-f][1,2,4]triazine-5-carbonitrile;

(S)-2-(1-(6-amino-5-cyanopyrimidin-4-ylamino)ethyl)-3-(3,5-dichlorophenyl)-4-oxo-3,4-dihydropyrrolo[1,2-f][1,2,4]triazine-5-carbonitrile;

(S)-2-(1-(6-amino-5-fluoropyrimidin-4-ylamino)ethyl)-3-(3,5-difluorophenyl)-4-oxo-3,4-dihydropyrrolo[1,2-f][1,2,4]triazine-5-carbonitrile;

(S)-2-(1-(6-amino-5-(trifluoromethyl)pyrimidin-4-ylamino)ethyl)-4-oxo-3-phenyl-3,4-dihydropyrrolo[1,2-f][1,2,4]triazine-5-carbonitrile;

(R)-2-(1-(6-amino-5-cyanopyrimidin-4-ylamino)-2-hydroxyethyl)-3-(3,5-difluorophenyl)-4-oxo-3,4-dihydropyrrolo[1,2-f][1,2,4]triazine-5-carbonitrile;

(S)-2-(1-(6-amino-5-carbamoylpyrimidin-4-ylamino)ethyl)-3-(3,5-difluorophenyl)-4-oxo-3,4-dihydropyrrolo[1,2-f][1,2,4]triazine-5-carboxamide;

(S)-2-(1-(6-amino-5-cyanopyrimidin-4-ylamino)ethyl)-3-(3,5-difluorophenyl)-4-oxo-3,4-dihydropyrrolo[1,2-f][1,2,4]triazine-5-carboxamide;

(S)-2-(1-(6-amino-5-cyanopyrimidin-4-ylamino)ethyl)-3-(2-chlorobenzyl)-4-oxo-3,4-dihydropyrrolo[1,2-f][1,2,4]triazine-5-carbonitrile;

2-((S)-1-(6-amino-5-cyanopyrimidin-4-ylamino)ethyl)-4-oxo-3-((S)-tetrahydro-2H-pyran-3-yl)-3,4-dihydropyrrolo[1,2-f][1,2,4]triazine-5-carbonitrile;

(R)-4-amino-6-(1-(3-(3,5-difluorophenyl)-4-oxo-5-(trifluoromethyl)-3,4-dihydropyrrolo[1,2-f][1,2,4]triazin-2-yl)-2-hydroxyethylamino)pyrimidine-5-carbonitrile;

(S)-2-(1-(2-amino-5-fluoropyrimidin-4-ylamino)ethyl)-3-(3,5-difluoraphenyl)-4-oxo-3,4-dihydropyrrolo[1,2-f][1,2,4]triazine-5-carbonitrile;

(S)-2-(1-(2-amino-5-cyanopyrimidin-4-ylamino)ethyl)-3-(3,5-difluorophenyl)-4-oxo-3,4-dihydropyrrolo[1,2-f][1,2,4]triazine-5-carbonitrile;

(S)-4-amino-6-(1-(3-((5-methylisoxazol-3-yl)methyl)-4-oxo-3,4-dihydropyrrolo[1,2-f][1,2,4]triazin-2-yl)ethylamino)pyrimidine-5-carbonitrile;

(S)-4-amino-6-(1-(4-oxo-3-phenyl-7-(trifluoromethyl)-3,4-dihydropyrrolo[1,2-f][1,2,4]triazin-2-yl)ethylamino)pyrimidine-5-carbonitrile;

(S)-2-(1-(6-amino-5-cyanopyrimidin-4-ylamino)ethyl)-4-oxo-3-phenyl-3,4-dihydropyrrolo[1,2-f][1,2,4]triazine-7-carbonitrile;

(S)-2-(1-(6-amino-5-cyanopyrimidin-4-ylamino)ethyl)-3-(1-(4-methoxybenzyl)-1H-pyrazol-4-yl)-4-oxo-3,4-dihydropyrrolo[1,2-f][1,2,4]triazine-5-carbonitrile;

(S)-4-amino-6-(1-(4-oxo-3-phenyl-5-(thiazol-2-yl)-3,4-dihydropyrrolo[1,2-f][1,2,4]triazin-2-yl)ethylamino)pyrimidine-5-carbonitrile;

(S)-2-(1-(2,6-diamino-5-cyanopyrimidin-4-ylamino)ethyl)-3-(3,5-difluorophenyl)-4-oxo-3,4-dihydropyrrolo[1,2-f][1,2,4]triazine-5-carbonitrile;

(S)-4-amino-6-(1-(5-(morpholinomethyl)-4-oxo-3-phenyl-3,4-dihydropyrrolo[1,2-f][1,2,4]triazin-2-yl)ethylamino)pyrimidine-5-carbonitrile;

2-((S)-1-(6-amino-5-cyanopyrimidin-4-ylamino)ethyl)-4-oxo-3-R)-1-phenylethyl)-3,4-dihydropyrrolo[1,2-f][1,2,4]triazine-5-carbonitrile;

(S)-4-amino-6-(1-(4-oxo-3-(1H-pyrazol-4-yl)-3,4-dihydropyrrolo[1,2-f][1,2,4]triazin-2-yl)ethylamino)pyrimidine-5-carbonitrile;

4-amino-6-((S)-1-(4-oxo-3-((S)-tetrahydro-2H-pyran-3-yl)-5-(trifluoromethyl)-3,4-dihydropyrrolo[1,2-f][1,2,4]triazin-2-yl)ethylamino)pyrimidine-5-carbonitrile;

(S)-4-amino-6-(1-(3-(5-methyl-1H-pyrazol-3-yl)-4-oxo-3,4-dihydropyrrolo[1,2-f][1,2,4]-triazin-2-yl)ethylamino)pyrimidine-5-carbonitrile;

(S)-2-(1-(6-amino-5-cyanopyrimidin-4-ylamino)ethyl)-4-oxo-3-phenyl-3,4-dihydropyrrolo[1,2-f][1,2,4]triazine-5-carboxylic acid;

2-((S)-1-(6-amino-5-cyanopyrimidin-4-ylamino)ethyl)-4-oxo-3-((R)-tetrahydro-2H-pyran-3-yl)-3,4-dihydropyrrolo[1,2-f][1,2,4]triazine-5-carbonitrile;

(S)-4-amino-6-(1-(3-(5-fluoropyridin-3-yl)-4-oxo-3,4-dihydropyrrolo[1,2-f][1,2,4]triazin-2-yl)ethylamino)pyrimidine-5-carbonitrile;

(S)-4-amino-6-(1-(4-oxo-3-(1H-pyrazol-3-yl)-3,4-dihydropyrrolo[1,2-f][1,2,4]triazin-2-yl)ethylamino)pyrimidine-5-carbonitrile;

(S)-4-amino-6-(1-(4-oxo-3-(pyrimidin-5-yl)-3,4-dihydropyrrolo[1,2-f][1,2,4]triazin-2-yl)ethylamino)pyrimidine-5-carbonitrile;

4-amino-6-((S)-1-(4-oxo-3-((R)-tetrahydro-2H-pyran-3-yl)-5-(trifluoromethyl)-3,4-dihydropyrrolo[1,2-f][1,2,4]triazin-2-yl)ethylamino)pyrimidine-5-carbonitrile;

(S)-2,4-diamino-6-(1-(4-oxo-3-phenyl-3,4-dihydropyrrolo[1,2-f][1,2,4]triazin-2-yl)ethylamino)pyrimidine-5-carbonitrile;

(S)-4-(1-(3-((1H-pyrazol-3-yl)methyl)-4-oxo-3,4-dihydropyrrolo[1,2-f][1,2,4]triazin-2-yl)ethylamino)-6-aminopyrimidine-5-carbonitrile;

(S)-4-amino-6-(1-(4-oxo-3-(tetrahydro-2H-pyran-4-yl)-3,4-dihydropyrrolo[1,2-f][1,2,4]thazin-2-yl)ethylamino)pyrimidine-5-carbonithle;

(S)-4-amino-6-(1-(4-oxo-3-(2,2,2-trifluoroethyl)-3,4-dihydropyrrolo[1,2-f][1,2,4]thazin-2-yl)ethylamino)pyrimidine-5-carbonitrile;

(S)-4-amino-6-(1-(3-cyclobutyl-4-oxo-3,4-dihydropyrrolo[1,2-f][1,2,4]triazin-2-yl)ethylamino)pyrimidine-5-carbonitrile;

(S)-2-amino-4-(1-(4-oxo-3-phenyl-3,4-dihydropyrrolo[1,2-f][1,2,4]triazin-2-yl)ethylamino)pyrimidine-5-carbonitrile;

4-amino-6-(1-(5-(1-methyl-1H-pyrazol-4-yl)-4-oxo-3-phenyl-3,4-dihydropyrrolo[1,2-f][1,2,4]triazin-2-yl)ethylamino)pyrimidine-5-carbonitrile;

(S)-4-amino-6-(1-(3-cyclopropyl-4-oxo-3,4-dihydropyrrolo[1,2-f][1,2,4]triazin-2-yl)ethylamino)pyrimidine-5-carbonitrile;

(S)-4-amino-6-(1-(5-bromo-4-oxo-3,4-dihydropyrrolo[1,2-f][1,2,4]triazin-2-yl)ethylamino)pyrimidine-5-carbonitrile;

4-amino-6-((S)-1-(4-oxo-3-((R)-tetrahydro-2H-pyran-3-yl)-3,4-dihydropyrrolo[1,2-f][1,2,4]triazin-2-yl)ethylamino)pyrimidine-5-carbonitrile;

(S)-4-amino-6-(1-(5-bromo-4-oxo-3-phenyl-3,4-dihydropyrrol[1,2-f][1,2,4]triazin-2-yl)ethylamino)pyrimidine-5-carbonitrile;

(S)-2-(1-(6-amino-5-cyanopyrimidin-4-ylamino)ethyl-3-(5-fluoropyridin-3-yl)-4-oxo-3,4-dihydropyrrolo[1,2-f][1,2,4]triazine-5-carbonitrile;

4-amino-6-((S)-1-(4-oxo-3-((S)-tetrahydro-2H-pyran-3-yl)-3,4-dihydropyrrolo[1,2-f][1,2,4]triazin-2-yl)ethylamino)pyrimidine-5-carbonitrile;

(S)-4-amino-6-(1-(4-oxo-3-phenyl-5-(1H-pyrazol-4-yl)-3,4-dihydropyrrolo[1,2-f][1,2,4]triazin-2-yl)ethylamino)pyrimidine-5-carbonitrile;

(S)-4-amino-6-(1-(3-(isoxazol-3-yl)-4-oxo-3,4-dihydropyrrolo[1,2-f][1,2,4]triazin-2-yl)ethylamino)pyrimidine-5-carbonitrile;

(S)-2-(1-(6-amino-5-cyanopyrimidin-4-ylamino)ethyl)-N,N-dimethyl-4-oxo-3-phenyl-3,4-dihydropyrrolo[1,2-f][1,2,4]triazine-5-carboxamide;

(S)-4-amino-6-(1-(3-(1-methyl-1H-pyrazol-3-yl)-4-oxo-3,4-dihydropyrrolo[1,2-f][1,2,4]triazin-2-yl)ethylamino)pyrimidine-5-carbonitrile;

(S)-2-(1-(6-amino-5-cyanopyrimidin-4-ylamino)ethyl)-4-oxo-3-phenyl-N-propyl-3,4-dihydropyrrolo[1,2-f][1,2,4]triazine-5-carboxamide;

(S)-4-amino-6-(3-hydroxy-1-(4-oxo-3-phenyl-3,4-dihydropyrrolo[1,2-f][1,2,4]triazin-2-yl)propylamino)pyrimidine-5-carbonitrile;

(R)-4-amino-6-(1-(3-(3,5-difluorophenyl)-4-oxo-3,4-dihydropyrrolo[1,2-f][1,2,4]triazin-2-yl)-2-hydroxyethylamino)pyrimidine-5-carbonitrile;

4-amino-6-((4-oxo-3-o-tolyl-3,4-dihydropyrrolo[1,2-f][1,2,4]triazin-2-yl)methylamino)pyrimidine-5-carbonitrile;

(S)-4-amino-6-(1-(5-(2-hydroxyethyl)-4-oxo-3-phenyl-3,4-dihydropyrrolo[1,2-f][1,2,4]triazin-2-yl)ethylamino)pyrimidine-5-carbonitrile;

(S)-2-(1-(6-amino-5-cyanopyrimidin-4-ylamino)-3-hydroxypropyl)-3-(3,5-difluorophenyl)-4-oxo-3,4-dihydropyrrolo[1,2-f][1,2,4]triazine-5-carbonitrile;

(S)-4-amino-6(1-(5-(2-methyloxazol-5-yl)-4-oxo-3-phenyl-3,4-dihydropyrrolo[1,2-f][1,2,4]triazin-2-yl)ethylamino)pyrimidine-5-carbonitrile;

(S)-4-amino-6-(1-(5-(2-methoxyethyl)-4-oxo-3-phenyl-3,4-dihydropyrrolo[1,2-f][1,2,4]triazin-2-yl)ethylamino)pyrimidine-5-carbonitrile;

(S)-propyl 2-(1-(6-amino-5-cyanopyrimidin-4-ylamino)ethyl)-4-oxo-3-phenyl-3,4-dihydropyrrolo[1,2-f][1,2,4]triazine-5-carboxylate;

(S)-4-amino-6-(3-hydroxy-1-(4-oxo-3,4-dihydropyrrolo[1,2-f][1,2,4]triazin-2-yl)propylamino)pyrimidine-5-carbonitrile;

(S)-4-amino-6-(1-(3-(3,5-difluorophenyl)-4-oxo-5-(trifluoromethyl)-3,4-dihydropyrrolo[1,2-f][1,2,4]triazin-2-yl)-3-hydroxypropylamino)pyrimidine-5-carbonitrile;

(S)-4-amino-6-(1-(4-oxo-3-(6-(trifluoromethyl)pyridin-2-yl)-3,4-dihydropyrrolo[1,2-f][1,2,4]triazin-2-yl)ethylamino)pyrimidine-5-carbonitrile;

(S)-2-(2-(1-(6-amino-5-cyanopyrimidin-4-ylamino)ethyl)-4-oxo-3-phenyl-3,4-dihydropyrrolo[1,2-f][1,2,4]triazin-5-yl)ethyl acetate;

(S)-2-(1-(9H-purin-6-ylamino)ethyl)-3-(6-(trifluoromethyl)pyridin-2-yl)pyrrolo[1,2-f][1,2,4]triazin-4(3H)-one;

2-((2S,4R)-1-(6-amino-5-cyanopyrimidin-4-yl)-4-hydroxypyrrolidin-2-yl)-3-(3,5-difluorophenyl)-4-oxo-3,4-dihydropyrrolo[1,2-f][1,2,4]triazine-5-carbonitrile;

4-amino-6-((2S,4R)-2-(5-(aminomethyl)-3-(3,5-difluorophenyl)-4-oxo-3,4-dihydropyrrolo[1,2-f][1,2,4]triazin-2-0)-4-hydroxypyrrolidin-1-yl)pyrimidine-5-carbonitrile;

(S)-4-amino-6-(1-(5-(4-methyl-1H-imidazol-1-yl)-4-oxo-3-phenyl-3,4-dihydropyrrolo[1,2-f][1,2,4]triazin-2-yl)ethylamino)pyrimidine-5-carbonitrile;

(S)-4-amino-6-(1-(5-bromo-3-(3-methoxyphenyl)-4-oxo-3,4-dihydropyrrolo[1,2-f][1,2,4]triazin-2-yl)ethylamino)pyrimidine-5-carbonitrile;

(S)-2-(1-(6-amino-5-cyanopyrimidin-4-ylamino)ethyl)-4-oxo-3-(3-(trifluoromethyl)phenyl)-3,4-dihydropyrrolo[1,2-f][1,2,4]triazine-5-carbonitrile;

(S)-4-amino-6-(1-(5-bromo-3-(3-hydroxyphenyl)-4-oxo-3,4-dihydropyrrolo[1,2-f][1,2,4]triazin-2-yl)ethylamino)pyrimidine-5-carbonitrile;

(S)-4-amino-6-(1-(3-(3-methoxyphenyl)-4-oxo-3,4-dihydropyrrolo[1,2-f][1,2,4]triazin-2-yl)ethylamino)pyrimidine-5-carbonitrile;

(S)-4-amino-6-(1-(3-(3-hydroxyphenyl)-4-oxo-3,4-dihydropyrrolo[1,2-f][1,2,4]triazin-2-yl)ethylamino)pyrimidine-5-carbonitrile;

(S)-2-(1-(6-amino-5-cyanopyrimidin-4-ylamino)ethyl)-3-(3-methoxyphenyl)-4-oxo-3,4-dihydropyrrolo[1,2-f][1,2,4]triazine-5-carbonitrile;

4-amino-6-(1-(4-oxo-3-phenyl-3,4-dihydropyrrolo[1,2-f][1,2,4]triazin-2-yl)cyclopropylamino)pyrimidine-5-carbonitrile;

(S)-4-amino-6-(1-(4-oxo-3-(3-(trifluoromethyl)phenyl)-3,4-dihydropyrrolo[1,2-f][1,2,4]triazin-2-yl)ethylamino)pyrimidine-5-carbonitrile;

(S)-2-(1-(6-amino-5-cyanopyrimidin-4-ylamino)ethyl)-3-(3-hydroxyphenyl)-4-oxo-3,4-dihydropyrrolo[1,2-f][1,2,4]triazine-5-carbonitrile;

(S)-4-amino-6-(1-(4-oxo-3-phenyl-3,4-dihydroimidazo[1,2-f][1,2,4]triazin-2-yl)propylamino)pyrimidine-5-carbonitrile;

or a pharmaceutically acceptable salt, or solvate, or N-oxide, or stereoisomer thereof.

13. A pharmaceutical composition comprising a compound according to claim 1, and a pharmaceutically acceptable diluent or carrier.

14. A method for treating asthma, chronic obstructive pulmonary disease, cystic fibrosis and idiopathic pulmonary fibrosis in a subject in need thereof, comprising:
administering to the subject a therapeutically effective amount of a compound according to claim 1.

15. A combination product comprising (i) a compound according to claim 1; and (ii) at least one other compound chosen from the group consisting of an Adenoside $A_{2A}$ agonist, an agent for treating cardiovascular disorders, an agent for treating diabetes, and an agent for treating liver disease, an anti-allergic agent, an anti-cholinergic agent, an anti-inflammatory agent, an anti-infective agent, a β2-adrenergic agonist, a Chemoattractant receptor homologous molecule expressed on $TH_2$ cells (CRTH2) inhibitor, a chemotherapeutic agent, a corticosteroid, an IKKβ/IKBKB (IkB kinase beta or IKK2) inhibitor, an immunosuppressant, a Janus kinase (JAK) inhibitor, a topically acting p38 Mitogen-Activated Protein Kinase (p38 MAPK) inhibitor, a Phosphosdiesterase (PDE) IV inhibitor, and a Spleen tyrosine kinase (Syk) inhibitor, for simultaneous, separate or sequential use in the treatment of the human or animal body.

16. The compound according to compound claim 4, wherein $R_1$ is chosen from a $C_3$-$C_7$ cycloalkyl group, a phenyl group, a 5- to 10-membered monocyclic or bicyclic heteroaryl group containing one, two or three heteroatoms chosen from O, S and N, a pyrrolidinyl group, a piperidinyl group, a piperazinyl group, a tetrahydropyranyl group or a morpholinyl group,
wherein the cycloalkyl, phenyl, heteroaryl, pyrrolidinyl, piperidinyl, piperazinyl, tetrahydropyranyl or morpholinyl groups are unsubstituted or substituted by at least one substituent chosen from a halogen atom, a linear or branched $C_1$-$C_4$ alkyl group, a $C_1$-$C_4$ haloalkyl group, a $C_1$-$C_4$ hydroxyalkyl group, a $C_3$-$C_4$ cycloalkyl group, a —$(CH_2)_{0-3}OR_6$ group, a —$(CH_2)_{0-3}NR_7R_8$ group, a —$C(O)$—$(CH_2)_{0-3}$—$R_8$ group or a —$C(O)$—$(CH_2)_{0-3}$—$NR_7R_8$ group; wherein $R_7$ and $R_8$ independently are chosen from a hydrogen atom or a $C_1$-$C_4$ alkyl group.

17. The compound according to compound claim 16, wherein $R_1$ is chosen from a phenyl group or a pyridinyl group, wherein the phenyl or a pyridinyl groups are unsubstituted or substituted by one, two or three substituents chosen from a halogen atom, a linear or branched $C_1$-$C_3$ alkyl group or a —$(CH_2)_{0-3}OCH_3$ group.

18. The compound according to claim 17, wherein the phenyl and pyridinyl groups are directly bonded to the pyrrolotriazinone group.

19. The compound according to claim 5, wherein $R_2$ is chosen from a hydrogen atom, a halogen atom, a hydroxyl group, a $C_1$-$C_3$ alkoxy group, a $C_1$-$C_3$ haloalkyl group, a $C_3$-$C_4$ cycloalkyl group, a —$NH_2$ group, a —$N(CH_3)H$ group, a —$N(CH_3)_2$ group, or a linear or branched $C_1$-$C_4$ alkyl group, wherein the alkyl group is unsubstituted or substituted by a $C_1$-$C_2$ alkoxy group.

20. The compound according to claim 6, wherein $R_3$ is chosen from a hydrogen atom, a halogen atom, a hydroxyl group, a cyano group, a $C_1$-$C_3$ alkoxy group, a $C_1$-$C_3$ haloalkyl group, a $C_3$-$C_4$ cycloalkyl group, a —$NH_2$ group, a —$N(CH_3)H$ group, a —$N(CH_3)_2$ group, or a linear or branched $C_1$-$C_4$ alkyl group, wherein the alkyl group is unsubstituted or substituted by a $C_1$-$C_2$ alkoxy group.

21. The compound according to claim 7, wherein $R_4$ is chosen from a hydrogen atom, a $C_1$-$C_3$ haloalkyl group, a $C_1$-$C_3$ hydroxyalkyl group, a $C_3$-$C_4$ cycloalkyl group, or a linear or branched $C_1$-$C_3$ alkyl group.

22. The compound according to claim 1, wherein the compound is (S)-2-(1-(6-amino-5-cyanopyrimidin-4-ylamino)ethyl)-4-oxo-3-phenyl-3,4-dihydropyrrolo[1,2-f][1,2,4]triazine-5-carbonitrile or a pharmaceutically acceptable salt, or a solvate, or N-oxide, or stereoisomer thereof.

* * * * *

UNITED STATES PATENT AND TRADEMARK OFFICE
CERTIFICATE OF CORRECTION

PATENT NO.      : 9,340,547 B2
APPLICATION NO. : 14/114541
DATED           : May 17, 2016
INVENTOR(S)     : Francisco Javier Bernal Anchuela et al.

Page 1 of 1

It is certified that error appears in the above-identified patent and that said Letters Patent is hereby corrected as shown below:

Title Page, Item (54), and in the Specification, Col. 1, line 1, "PYRROLOTRIAZINONE DERIVATIVES AS INHIBITORS PI3K", should read as -- PYRROLOTRIAZINONE DERIVATIVES AS PI3K INHIBITORS --.

In the Claims,

Claim 7, Col. 244, Line 44, "A The", should read as -- The --.

Signed and Sealed this
Nineteenth Day of July, 2016

Michelle K. Lee
*Director of the United States Patent and Trademark Office*